United States Patent
Furukawa et al.

(10) Patent No.: US 8,017,610 B2
(45) Date of Patent: Sep. 13, 2011

(54) PHENYLPYRROLE DERIVATIVE

(75) Inventors: Akihiro Furukawa, Kanagawa (JP);
Takehiro Fukuzaki, Tokyo (JP); Yukari Onishi, Kanagawa (JP); Hideki Kobayashi, Tokyo (JP); Takeshi Honda, Tokyo (JP); Yumi Matsui, Tokyo (JP); Masahiro Konishi, Tokyo (JP); Kenjiro Ueda, Chiba (JP); Tetsuyoshi Matsufuji, Kanagawa (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 12/843,348

(22) Filed: Jul. 26, 2010

(65) Prior Publication Data
US 2011/0003787 A1    Jan. 6, 2011

Related U.S. Application Data

(63) Continuation of application No. PCT/JP2009/051834, filed on Feb. 4, 2009.

(30) Foreign Application Priority Data

Feb. 6, 2008    (JP) .................... 2008-026519
Dec. 10, 2008   (JP) .................... 2008-314479

(51) Int. Cl.
  A61K 31/501    (2006.01)
  A61K 31/497    (2006.01)
  A61K 31/443    (2006.01)
  A61K 31/421    (2006.01)
  C07D 403/14    (2006.01)
  C07D 413/14    (2006.01)
  C07D 265/08    (2006.01)

(52) U.S. Cl. ............ 514/252.05; 514/255.05; 514/343; 514/374; 544/238; 544/405; 546/271.4; 548/238

(58) Field of Classification Search .............. None
See application file for complete search history.

(56) References Cited

U.S. PATENT DOCUMENTS

| | | |
|---|---|---|
| 2001/0039344 A1 | 11/2001 | Bizzarro et al. |
| 2005/0250769 A1 | 11/2005 | Mayweg et al. |
| 2005/0282815 A1 | 12/2005 | Nishimura et al. |
| 2006/0167053 A1 | 7/2006 | Ilno et al. |
| 2007/0054897 A1 | 3/2007 | Murray et al. |
| 2007/0078168 A1 | 4/2007 | Caulkett |
| 2007/0099936 A1 | 5/2007 | Bian et al. |
| 2007/0117808 A1 | 5/2007 | Urbanski et al. |
| 2008/0032996 A1 | 2/2008 | Mitsuya et al. |
| 2008/0132479 A1 | 6/2008 | Sugawara et al. |
| 2009/0118304 A1 | 5/2009 | Takahashi et al. |
| 2009/0156603 A1 | 6/2009 | Aicher et al. |
| 2009/0247746 A1 | 10/2009 | Yasuma et al. |

FOREIGN PATENT DOCUMENTS

| | | |
|---|---|---|
| EP | 1 702 919 | 9/2006 |
| EP | 2 149 550 | 2/2010 |
| WO | WO 2004-076420 | 9/2004 |

(Continued)

OTHER PUBLICATIONS

Garfinkel, David et al. "Computer modeling identifies glucokinase as glucose sensor of pancreatic β-cells," *American Physiological Society*, 247, pp. R527-R536 (Sep. 1984).
Bedoya, F.J. et al. "The Glucokinase Glucose Sensor in Human Pancreatic Islet Tissue," *Diabetes*, vol. 35, pp. 61-67 (Jan. 1986).
Meglasson, M.D. et al. "Identification of Glucokinase as an Alloxan-Sensitive Glucose Sensor of the Pancreatic β-Cell," *Diabetes*, vol. 35, pp. 1163-1173 (Oct. 1986).

(Continued)

*Primary Examiner* — Rebecca Anderson
*Assistant Examiner* — Alicia L Otton
(74) *Attorney, Agent, or Firm* — Dorsey & Whitney LLP

(57) ABSTRACT

The present invention relates to a compound or a pharmacologically acceptable salt thereof having superior glucokinase activating activity, and is a compound represented by general formula (I), or pharmacologically acceptable salt thereof:

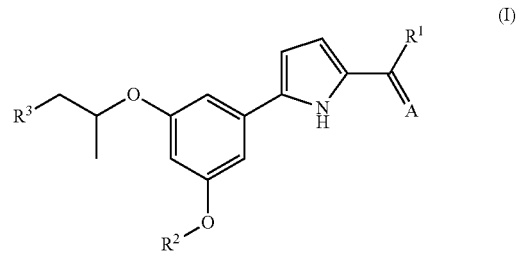

(I)

[wherein,
A represents, for example, an oxygen atom or sulfur atom, $R^1$ represents, for example, a $C_1$-$C_6$ alkyl group, a $C_1$-$C_6$ alkoxy group or a $C_1$-$C_6$ halogenated alkyl group, A and $R^1$ together with the carbon atom bonded thereto form a heterocyclic group that may be substituted with 1 to 3 group(s) independently selected from Substituent Group α, $R^2$ represents a phenyl group that may be substituted with 1 to 5 group(s) independently selected from Substituent Group α or a heterocyclic group that may be substituted with 1 to 3 group(s) independently selected from Substituent Group α, $R^3$ represents a hydroxy group or a $C_1$-$C_6$ alkoxy group, and Substituent Group α consists of, for example, a halogen atom, a $C_1$-$C_6$ alkyl group, a $C_1$-$C_6$ alkyl group substituted with 1 or 2 hydroxy group(s), a $C_1$-$C_6$ alkylsulfonyl group, and a group represented by the formula —V—$NR^5R^6$ (wherein, V represents a carbonyl group or a sulfonyl group, and $R^5$ and $R^6$ may be the same or different and respectively represent a hydrogen atom or a $C_1$-$C_6$ alkyl group, or $R^5$ and $R^6$ together with the nitrogen atom bonded thereto form a 4- to 6-membered saturated heterocycle that may be substituted with 1 or 2 group(s) independently selected from a $C_1$-$C_6$ alkyl group and a hydroxy group, and the 4- to 6-membered saturated heterocycle may further contain one oxygen atom or nitrogen atom)].

52 Claims, No Drawings

FOREIGN PATENT DOCUMENTS

| | | | |
|---|---|---|---|
| WO | WO 2005/080359 | | 9/2005 |
| WO | WO 2007/031739 | * | 3/2007 |
| WO | WO 2007/061923 | | 5/2007 |

OTHER PUBLICATIONS

Grupe, Andrew et al. "Transgenic Knockouts Reveal a Critical Requirement for Pancreatic β Cell Glucokinase in Maintaining Glucose Homeostatis," *Cell*, vol. 83, pp. 69-78 (Oct. 1995).

Ferre, Tura et al. "Correction of diabetic alterations by glucokinase," *Proc. Natl. Acad. Sci*, vol. 93, pp. 7225-7230 (Jul. 1996).

Vionnet, N. et al. "Nonsense mutation in the glucokinase gene causes early-onset non-insulin-dependent diabetes mellitus," *Nature*, vol. 356, pp. 721-722 (Apr. 1992).

Glaser, Benjamin, et al. "Familial Hyperinsulinism Caused by an Activating Glucokinase Mutation," *New Engl. J. Med.*, vol. 338, No. 4, pp. 226-230 (Jan. 1998).

Fujimoto, Kazuma et al. "Administration of D-Glucosamine Into the Third Cerebroventricle Induced Feeding Accompanied by Hyperglycemia in Rats," *Life Sciences*, vol. 37, pp. 2475-2482 (Dec. 1985).

Kang, Ling et al. "Glucokinase is a Critical Regulator of Ventromedial Hypothalamic Neuronal Glucosensing," *Diabetes*, vol. 55, pp. 412-420 (Mar. 2006).

Grimsby, Joseph et al. "Allosteric Activators of Glucokinase: Potential Role in Diabetes Therapy," *Science*, vol. 301, pp. 370-373 (Jul. 2003).

Futamura, Mayumi et al. "An Allosteric Activator of Glucokinase Impairs the Interaction of Glucokinase and Glucokinase Regulatory Protein and Regulates Glucose Metabolism," *Jour. of Biol. Chem.*, vol. 281, No. 49, pp. 27668-37674 (Dec. 2006).

\* cited by examiner

PHENYLPYRROLE DERIVATIVE

This application is a Continuation of PCT Patent Application No. PCT/JP2009/051834 filed Feb. 4, 2009, which claims priority to Japanese Patent Application Nos. 2008-026519 filed Feb. 6, 2008, and 2008-314479 filed Dec. 10, 2008, the contents of all of which are hereby incorporated herein by reference in their entirety.

TECHNICAL FIELD

The present invention relates to a phenylpyrrole compound, or a pharmacologically acceptable salt thereof, that has superior glucokinase activating activity and is useful as a therapeutic for diabetes and the like.

BACKGROUND ART

Glucokinase (abbreviated as GK in the present description; EC 2.7.1.1) is one of the four types of hexokinases (hexokinase IV) found in mammals. Hexokinases are enzymes that catalyze the conversion of glucose to glucose-6-phosphate in the first stage of the glycolysis system in cells, and the expression of GK is localized mainly in the liver and pancreatic beta cells. In pancreatic beta cells, GK functions as a detection mechanism of extracellular glucose concentration that regulates glucose-stimulated insulin secretion, while in the liver, the enzymatic reaction of GK serves as the rate-limiting step to regulate subsequent reactions such as glycolysis and glycogen synthesis. Although GK found in the liver and that found in pancreatic beta cells differ in the sequence consisting of 15 amino acids from the N-terminal due to a difference in splicing, their enzymatic properties are identical. In contrast to the enzymatic activities of the three types of hexokinases other than GK (types I, II and III) becoming saturated at a glucose concentration of 1 mM or less, GK exhibits low affinity for glucose, and the Km value thereof is near that of the physiological level of glucose in the blood at 8 to 15 mM. Thus, acceleration of GK-mediated intracellular glucose metabolism occurs in response to changes in blood glucose levels ranging from normal blood glucose levels (about 5 mM) to postprandial blood glucose levels (10 to 15 mM).

The hypothesis that GK functions as a glucose sensor in the liver and pancreatic beta cells has long been advocated (Non-Patent Documents 1 to 3). Recent research findings have demonstrated that GK actually plays an important role in maintaining systemic glucose homeostasis, thereby verifying this hypothesis. For example, mice in which glucokinase gene had been disrupted exhibited prominent hyperglycemia symptoms and died soon after birth, while GK hetero-deficient mice were observed to have defective glucose tolerance and impaired glucose-stimulated insulin secretion (Non-Patent Document 4). On the other hand, normal mice excessively expressing GK were observed to demonstrate decreased blood glucose levels and increased glycogen content in the liver, and these phenomena were similar to those in mice in which diabetes was artificially induced (Non-Patent Document 5).

In addition, GK also functions as a glucose sensor in humans, and has been demonstrated by recent research to play an important role in maintaining glucose homeostasis. Abnormalities have been discovered in the GK genes of family lineages exhibiting a form of juvenile-onset diabetes referred to as maturity onset diabetes of the young (MODY2), and a correlation was clearly observed between these cases and GK activity (Non-Patent Document 6). On the other hand, family lineages have also been found that possess a mutation that increases GK activity, and symptoms of fasting hypoglycemia accompanied by elevated plasma insulin concentrations have been observed in such family lineages (Non-Patent Document 7). On the basis of these reports, GK plays an important role in blood glucose regulation by functioning as a glucose sensor in mammals, including humans. Thus, substances having GK activating activity are considered to be useful as drugs for treatment of glycometabolic diseases including type II diabetes mellitus. Since GK activating substances can be expected to simultaneously demonstrate glucose uptake promoting activity and glucose release inhibitory activity in the liver as well as insulin secretion promoting activity in pancreatic beta cells in particular, they are predicted to be able to demonstrate potent therapeutic effects unable to be attained with existing drugs.

Pancreatic beta cell type GK has recently been determined to be expressed, being localized in the ventromedial hypothalamus (VMH) of the rat brain. The VMH has been conventionally known to be the site of neurons that respond to glucose concentration. In contrast to food intake decreasing when glucose is administered to rat ventricle, food intake is accelerated when glucose metabolism is inhibited by administration of the glucose analogue, glucosamine (Non-Patent Document 8). Electrophysiological experiments have demonstrated that glucose-responsive neurons are activated by responding to physiological changes in glucose concentrations (5 to 20 mM), and glucokinase has been determined to similarly function as a glucose sensor in peripheral tissue (Non-Patent Document 9). Thus, substances that give rise to glucokinase activation not only in the liver and pancreatic beta cells, but also in the VMH can be expected to demonstrate blood glucose lowering activity as well as activity that corrects obesity, which is considered to be a problem associated with numerous patients of type II diabetes mellitus.

On the basis of the aforementioned descriptions, substances having GK activating activity are useful as diabetes therapeutics and preventives, or as therapeutics and preventives of chronic complications of diabetes, including diabetic retinopathy, diabetic nephropathy, diabetic neuropathy, ischemic heart disease and arteriosclerosis.

Furthermore, although a plurality of compounds having GK activating activity have been reported in the past, all of these have different structures from that of the compound of the present invention. For example, although Patent Document 1 describes a compound having an amide structure as an essential constituent thereof, the compound of the present invention has a pyrrole structure instead of an amide structure as an essential constituent thereof. In addition, although Patent Document 2 describes a compound having a condensed pyrrole, the compound of the present invention has a non-condensed pyrrole as an essential constituent thereof. Moreover, although Patent Document 3 describes a compound having a 3,5-di-substituted pyrazole or 1,2,4-triazole moiety, this differs from the 2,5-di-substituted pyrrole structure of the present invention. Although a plurality of compounds having GK activating activity have been reported in addition to those described in the above publications, all of these have different structures from that of the compound of the present invention (see, for example, Patent Documents 4 to 15 and Non-Patent Documents 10 and 11).

[Patent Document 1] International Publication No. WO2005/080359 Pamphlet

[Patent Document 2] International Publication No. WO2007/031739 Pamphlet

[Patent Document 3] International Publication No. WO2007/061923 Pamphlet

[Patent Document 4] International Publication No. WO2000/058293 Pamphlet
[Patent Document 5] International Publication No. WO2003/080585 Pamphlet
[Patent Document 6] International Publication No. WO2005/066145 Pamphlet
[Patent Document 7] International Publication No. WO2005/090332 Pamphlet
[Patent Document 8] International Publication No. WO2006/112549 Pamphlet
[Patent Document 9] International Publication No. WO2007/007886 Pamphlet
[Patent Document 10] International Publication No. WO2007/037534 Pamphlet
[Patent Document 11] International Publication No. WO2007/053765 Pamphlet
[Patent Document 12] International Publication No. WO2007/117381 Pamphlet
[Patent Document 13] International Publication No. WO2005/044801 Pamphlet
[Patent Document 14] International Publication No. WO2007/053662 Pamphlet
[Patent Document 15] International Publication No. WO2008/136428 Pamphlet
[Non-Patent Document 1] Am J. Physiol. 1984 September; 247(3 Pt 2):R527-36.
[Non-Patent Document 2] Diabetes. 1986 January; 35(1): 61-7.
[Non-Patent Document 3] Diabetes. 1986 October; 35(10): 1163-73.
[Non-Patent Document 4] Cell. 1995 Oct. 6; 83(1):69-78.
[Non-Patent Document 5] Proc Natl Acad Sci USA. 1996 Jul. 9; 93(14):7225-30.
[Non-Patent Document 6] Nature. 1992 Apr. 23; 356(6371):721-2.
[Non-Patent Document 7] N Engl J. Med. 1998 Jan. 22; 338(4):226-30.
[Non-Patent Document 8] Life Sci. 1985 Dec. 30; 37(26): 2475-82.
[Non-Patent Document 9] Diabetes. 2006 February; 55(2): 412-20. Erratum in: Diabetes. 2006 March; 55(3):862.
[Non-Patent Document 10] Science. 2003 Jul. 18; 301 (5631):370-3.
[Non-Patent Document 11] J Biol. Chem. 2006 Dec. 8; 281(49):37668-74. Epub 2006 Oct. 6.

DISCLOSURE OF THE INVENTION

Problems to be Solved by the Invention

An object of the present invention is to provide a novel phenylpyrrole derivative and a GK activator that uses this novel phenylpyrrole derivative, and particularly to provide a therapeutic and preventive of diabetes and impaired glucose tolerance. As a result of conducting extensive studies on compounds having GK activating activity, the inventors of the present invention found that a phenylpyrrole compound having a specific chemical structure has superior GK activating activity. In addition, the compound of the present invention has superior GK selectivity, low toxicity and few adverse side effects. The inventors of the present invention also found that this phenylpyrrole compound is useful as an active ingredient of a pharmaceutical for the treatment and/or prevention of diseases selected from the group consisting of diabetes, impaired glucose tolerance, gestational diabetes, chronic complications of diabetes (including diabetic peripheral neuropathy, diabetic nephropathy, diabetic retinopathy and diabetic macroangiopathy) and metabolic syndrome. The present invention was completed based on the aforementioned findings.

Means for Solving the Problems

The present invention relates to:
(1) a compound having the general formula (I):

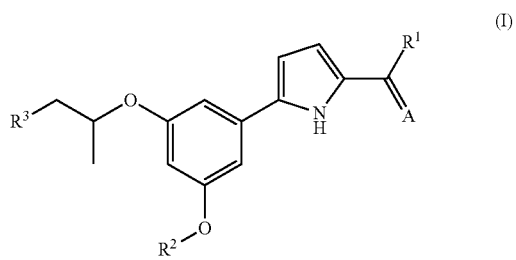

[wherein,
A represents a group represented by the formula =NOR$^4$, an oxygen atom or a sulfur atom,
R$^4$ represents a hydrogen atom or a $C_1$-$C_6$ alkyl group,
R$^1$ represents a $C_1$-$C_6$ alkyl group, a $C_1$-$C_6$ alkoxy group, a $C_1$-$C_6$ halogenated alkyl group, a $C_1$-$C_6$ halogenated alkoxy group, an amino group, a mono-$C_1$-$C_6$ alkylamino group, a mono-$C_1$-$C_6$ halogenated alkylamino group, a di($C_1$-$C_6$ alkyl)amino group or a di-($C_1$-$C_6$ halogenated alkyl)amino group, or
A and R$^1$ together with the carbon atom bonded thereto form a heterocyclic group that may be substituted with 1 to 3 group(s) independently selected from Substituent Group α,
R$^2$ represents a phenyl group that may be substituted with 1 to 5 group(s) independently selected from Substituent Group α or a heterocyclic group that may be substituted with 1 to 3 group(s) independently selected from Substituent Group α,
R$^3$ represents a hydroxy group or a $C_1$-$C_6$ alkoxy group, and
Substituent Group α represents the group of substituents selected from a halogen atom, a $C_1$-$C_6$ alkyl group, a $C_1$-$C_6$ halogenated alkyl group, a $C_2$-$C_6$ alkenyl group, a $C_2$-$C_6$ alkynyl group, a hydroxy group, a $C_1$-$C_6$ alkyl group substituted with 1 or 2 hydroxy group(s), a $C_1$-$C_6$ alkoxy group, a $C_1$-$C_6$ halogenated alkoxy group, a ($C_1$-$C_6$ alkoxy)-($C_1$-$C_6$ alkyl) group, a ($C_1$-$C_6$ alkoxy)-($C_1$-$C_6$ alkoxy) group, a formyl group, a carboxyl group, a $C_2$-$C_7$ alkylcarbonyl group, a $C_2$-$C_7$ alkoxycarbonyl group, a $C_2$-$C_7$ alkylcarbonyloxy group, a $C_2$-$C_7$ alkoxycarbonyloxy group, a nitro group, an amino group, a mono-$C_1$-$C_6$ alkylamino group, a di-($C_1$-$C_6$ alkyl)amino group, a $C_1$-$C_6$ alkylthio group, a $C_1$-$C_6$ alkylsulfonyl group, a $C_3$-$C_6$ cycloalkylsulfonyl group, a $C_1$-$C_6$ hydroxyalkylsulfonyl group, a ($C_1$-$C_6$ alkoxy)-($C_1$-$C_6$ alkylsulfonyl) group, a group represented by the formula —V—NR$^5$R$^6$ (wherein V represents a carbonyl group or a sulfonyl group, and R$^5$ and R$^6$ may be the same or different and respectively represent a hydrogen atom or a $C_1$-$C_6$ alkyl group, or R$^5$ and R$^6$ together with the nitrogen atom bonded thereto form a 4- to 6-membered saturated heterocycle that may be substituted with 1 or 2 group(s) independently selected from a $C_1$-$C_6$ alkyl group and a hydroxy group, and the 4- to 6-membered saturated heterocycle may further contain one oxygen atom or nitrogen atom), a mono-$C_2$-$C_7$ alkylcarbonylamino group, a mono-$C_1$-$C_6$ alkylaminocarbonyloxy group, a di-($C_1$-$C_6$ alkyl)aminocarbonyloxy group, a mono-$C_2$-$C_7$ alkoxycarbonylamino group, a mono-$C_1$-$C_6$ alkylsulfonylamino group, a cyano group, a 1,3,4-oxadiazol-2-yl group optionally substituted with a $C_1$-$C_6$ alkyl group at the 5-position, a 1,3,4-thiadiazol-2-yl group optionally substituted with a $C_1$-$C_6$ alkyl group at the 5-position, and an oxo group]

or a pharmacologically acceptable salt thereof;

(2) the compound or pharmacologically acceptable salt thereof in (1) above, wherein Substituent Group α represents the group of substituents selected from a halogen atom, a $C_1$-$C_6$ alkyl group, a $C_1$-$C_6$ halogenated alkyl group, a $C_2$-$C_6$ alkenyl group, a $C_2$-$C_6$ alkynyl group, a hydroxy group, a $C_1$-$C_6$ alkyl group substituted with 1 or 2 hydroxy group(s), a $C_1$-$C_6$ alkoxy group, a $C_1$-$C_6$ halogenated alkoxy group, a ($C_1$-$C_6$ alkoxy)-($C_1$-$C_6$ alkyl) group, a ($C_1$-$C_6$ alkoxy)-($C_1$-$C_6$ alkoxy) group, a formyl group, a carboxyl group, a $C_2$-$C_7$ alkylcarbonyl group, a $C_2$-$C_7$ alkoxycarbonyl group, a $C_2$-$C_7$ alkylcarbonyloxy group, a $C_2$-$C_7$ alkoxycarbonyloxy group, a nitro group, an amino group, a mono-$C_1$-$C_6$ alkylamino group, a di-($C_1$-$C_6$ alkyl)amino group, a $C_1$-$C_6$ alkylthio group, a $C_1$-$C_6$ alkylsulfonyl group, a $C_3$-$C_6$ cycloalkylsulfonyl group, a $C_1$-$C_6$ hydroxyalkylsulfonyl group, a ($C_1$-$C_6$ alkoxy)-($C_1$-$C_6$ alkylsulfonyl) group, a group represented by the formula —V—NR$^5$R$^6$ (wherein V represents a carbonyl group or a sulfonyl group, and R$^5$ and R$^6$ may be the same or different and respectively represent a hydrogen atom or a $C_1$-$C_6$ alkyl group, or R$^5$ and R$^6$ together with the nitrogen atom bonded thereto form a 4- to 6-membered saturated heterocycle that may be substituted with 1 or 2 group(s) independently selected from a $C_1$-$C_6$ alkyl group and a hydroxy group, and the 4- to 6-membered saturated heterocycle may further contain one oxygen atom or nitrogen atom), a mono-$C_2$-$C_7$ alkylcarbonylamino group, a mono-$C_1$-$C_6$ alkylaminocarbonyloxy group, a di-($C_1$-$C_6$ alkyl)aminocarbonyloxy group, a mono-$C_2$-$C_7$ alkoxycarbonylamino group, a mono-$C_1$-$C_6$ alkylsulfonylamino group, a cyano group, a 1,3,4-oxadiazol-2-yl group optionally substituted with a $C_1$-$C_6$ alkyl group at the 5-position, and a 1,3,4-thiadiazol-2-yl group optionally substituted with a $C_1$-$C_6$ alkyl group at the 5-position;

(3) the compound or pharmacologically acceptable salt thereof in (1) or (2) above, wherein the general formula (I) is a general formula (Ia);

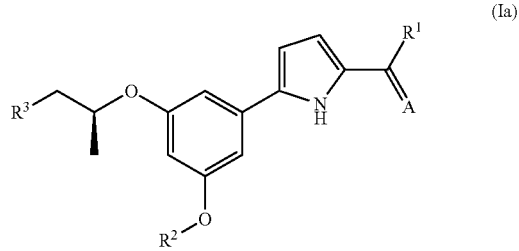

(Ia)

(4) the compound or pharmacologically acceptable salt thereof in any one selected from (1) to (3) above, wherein A is an oxygen atom;

(5) the compound or pharmacologically acceptable salt thereof in any one selected from (1) to (4) above, wherein R$^1$ is a $C_1$-$C_6$ alkyl group, a $C_1$-$C_6$ alkoxy group or a mono-$C_1$-$C_6$ halogenated alkylamino group;

(6) the compound or pharmacologically acceptable salt thereof in any one selected from (1) to (4) above, wherein R$^1$ is a methyl group or a 2-chloroethylamino group;

(7) the compound or pharmacologically acceptable salt thereof in any one selected from (1) to (4) above, wherein the heterocyclic group formed by A and R$^1$ together with the carbon atom bonded thereto and which may be substituted with 1 to 3 group(s) independently selected from Substituent Group α is a 2-pyridyl group, 5,6-dihydro-4H-1,3-oxazin-2-yl group, 1,3-thiazol-2-yl group, 1,3-oxazol-2-yl group, 1,3,4-oxadiazol-2-yl group, 1,3,4-thiadiazol-2-yl group, 4,5-dihydro-1,3-thiazol-2-yl group, 4,5-dihydro-1,3-oxazol-2-yl group or 1,3-benzothiazol-2-yl group that may be substituted with 1 to 3 group(s) independently selected from Substituent Group γ, and Substituent Group γ indicates the group consisting of a halogen atom, a $C_1$-$C_6$ alkyl group, a $C_1$-$C_6$ halogenated alkyl group, a $C_1$-$C_6$ alkyl group substituted with 1 or 2 hydroxy group(s), a $C_1$-$C_6$ alkoxy group, a carboxyl group, a mono-$C_1$-$C_6$ alkylaminocarbonyl group, a di-($C_1$-$C_6$ alkyl)aminocarbonyl group and a hydroxy group;

(8) the compound or pharmacologically acceptable salt thereof in any one selected from (1) to (3) above, wherein the heterocyclic group formed by A and R$^1$ together with the carbon atom bonded thereto and which may be substituted with 1 to 3 group(s) independently selected from Substituent Group α is a 1,3-thiazol-2-yl group, a 5-methyl-1,3-thiazol-2-yl group, a 5-methyl-1,3,4-oxadiazol-2-yl group, a 4,5-dihydro-1,3-thiazol-2-yl group, a 4,5-dihydro-1,3-oxazol-2-yl group, a (5S)-5-methyl-4,5-dihydro-1,3-oxazol-2-yl group, a (5R)-5-methyl-4,5-dihydro-1,3-oxazol-2-yl group, a 5-hydroxymethyl-4,5-dihydro-1,3-oxazol-2-yl group, a (5R)-5-hydroxymethyl-4,5-dihydro-1,3-oxazol-2-yl group, a (4R)-4-methyl-4,5-dihydro-1,3-oxazol-2-yl group, a (4R)-4-ethyl-4,5-dihydro-1,3-oxazol-2-yl group, a (4R)-4-hydroxymethyl-4,5-dihydro-1,3-oxazol-2-yl group, a (4S)-4-[(1R)-1-hydroxyethyl]-4,5-dihydro-1,3-oxazol-2-yl group, a (4S)-4-[(1S)-1-hydroxyethyl]-4,5-dihydro-1,3-oxazol-2-yl group, a (4R,5S)-4,5-dimethyl-4,5-dihydro-1,3-oxazol-2-yl group, a (5S)-4-hydroxy-5-methyl-4,5-dihydro-1,3-oxazol-2-yl group, a (4R,5S)-4-hydroxymethyl-5-methyl-4,5-dihydro-1,3-oxazol-2-yl group, a (4R,5R)-5-hydroxymethyl-4-methyl-4,5-dihydro-1,3-oxazol-2-yl group, a 5-carboxyl-1,3-thiazol-2-yl group, a 5-dimethylaminocarbonyl-1,3-thiazol-2-yl group, a 5-methyl-1,3,4-thiadiazol-2-yl group or a 5,6-dihydro-4H-1,3-oxazin-2-yl group;

(9) the compound or pharmacologically acceptable salt thereof in any one selected from (1) to (3) above, wherein the heterocyclic group formed by A and R$^1$ together with the carbon atom bonded thereto and which may be substituted with 1 to 3 group(s) independently selected from Substituent Group α is a 4,5-dihydro-1,3-oxazol-2-yl group, a (4R)-4-methyl-4,5-dihydro-1,3-oxazol-2-yl group, a (4R)-4-ethyl-4,5-dihydro-1,3-oxazol-2-yl group, a (5S)-5-methyl-4,5-dihydro-1,3-oxazol-2-yl group, a (4R)-4-hydroxymethyl-4,5-dihydro-1,3-oxazol-2-yl group, a (5R)-5-hydroxymethyl-4,5-dihydro-1,3-oxazol-2-yl group, a (4S)-4-[(1R)-1-hydroxyethyl]-4,5-dihydro-1,3-oxazol-2-yl group, a (4S)-4-[(1S)-1-hydroxyethyl]-4,5-dihydro-1,3-oxazol-2-yl group, a (4R,5S)-4,5-dimethyl-4,5-dihydro-1,3-oxazol-2-yl group, a (4R,5S)-4-hydroxymethyl-5-methyl-4,5-dihydro-1,3-oxazol-2-yl group, a (4R,5R)-5-hydroxymethyl-4-methyl-4,5-dihydro-1,3-oxazol-2-yl group, a 1,3-thiazol-2-yl group, a 5-carboxyl-1,3-thiazol-2-yl group, a 5-dimethylaminocarbonyl-1,3-thiazol-2-yl group, a 5-methyl-1,3,4-thiadiazol-2-yl group, a 5-methyl-1,3,4-oxadiazol-2-yl group, a 4,5-dihydro-1,3-thiazol-2-yl group or a 5,6-dihydro-4H-1,3-oxazin-2-yl group;

(10) the compound or pharmacologically acceptable salt thereof in any one selected from (1) to (3) above, wherein the heterocyclic group formed by A and $R^1$ together with the carbon atom bonded thereto and which may be substituted with 1 to 3 group(s) independently selected from Substituent Group α is a 4,5-dihydro-1,3-oxazol-2-yl group, a (4R)-4-methyl-4,5-dihydro-1,3-oxazol-2-yl group, a (4R)-4-ethyl-4,5-dihydro-1,3-oxazol-2-yl group, a (5S)-5-methyl-4,5-dihydro-1,3-oxazol-2-yl group, a (4R)-4-hydroxymethyl-4,5-dihydro-1,3-oxazol-2-yl group, a (5R)-5-hydroxymethyl-4,5-dihydro-1,3-oxazol-2-yl group, a (4S)-4-[(1R)-1-hydroxyethyl]-4,5-dihydro-1,3-oxazol-2-yl group, a (4S)-4-[(1S)-1-hydroxyethyl]-4,5-dihydro-1,3-oxazol-2-yl group, a (4R,5S)-4,5-dimethyl-4,5-dihydro-1,3-oxazol-2-yl group, a (4R,5S)-4-hydroxymethyl-5-methyl-4,5-dihydro-1,3-oxazol-2-yl group or a (4R,5R)-5-hydroxymethyl-4-methyl-4,5-dihydro-1,3-oxazol-2-yl group;

(11) the compound or pharmacologically acceptable salt thereof in any one selected from (1) to (10) above, wherein $R^2$ is a phenyl group that may be substituted with 1 to 5 group(s) independently selected from Substituent Group δ or a 2-pyridyl group, 3-pyridyl group or 2-pyrazinyl group that may be substituted with 1 to 3 group(s) independently selected from Substituent Group δ, and Substituent Group δ indicates the group consisting of a halogen atom, a $C_1$-$C_6$ alkyl group, a $C_1$-$C_6$ halogenated alkyl group, a $C_1$-$C_6$ alkyl group substituted with 1 or 2 hydroxy group(s), a $C_2$-$C_7$ alkylcarbonyl group, a $C_2$-$C_7$ alkoxycarbonyl group, a $C_1$-$C_6$ alkylsulfonyl group, a group represented by the formula —V—$NR^5R^6$ (wherein V represents a carbonyl group or a sulfonyl group, and $R^5$ and $R^6$ may be the same or different and respectively represent a hydrogen atom or a $C_1$-$C_6$ alkyl group, or $R^5$ and $R^6$ together with the nitrogen atom bonded thereto form a 4- to 6-membered saturated heterocycle that may be substituted with 1 or 2 group(s) independently selected from a $C_1$-$C_6$ alkyl group and a hydroxy group, and the 4- to 6-membered saturated heterocycle may further contain one oxygen atom or nitrogen atom), a 1,3,4-oxadiazol-2-yl group optionally substituted with a $C_1$-$C_6$ alkyl group at the 5-position, and a 1,3,4-thiadiazol-2-yl group optionally substituted with a $C_1$-$C_6$ alkyl group at the 5-position;

(12) the compound or pharmacologically acceptable salt thereof in any one selected from (1) to (10) above, wherein $R^2$ is a 4-methylsulfonylphenyl group, a 4-(1-azetidinyl)carbonyl-2-fluorophenyl group, a 2-fluoro-4-(1-pyrrolidinyl)carbonylphenyl group, a 5-(1-azetidinyl)carbonyl-3-chloro-2-pyridyl group, a 2-methylsulfonyl-5-pyridyl group, a 5-(4-methyl-1-piperazinyl)carbonyl-2-pyrazinyl group, a 2-methylaminocarbonyl-5-pyridyl group, a 2-methylaminosulfonyl-5-pyridyl group or a 5-methylsulfonyl-2-pyrazinyl group;

(13) the compound or pharmacologically acceptable salt thereof selected from any of (1) to (10) above, wherein $R^2$ is a 4-methylsulfonylphenyl group, a 2-methylsulfonyl-5-pyridyl group, a 5-methylsulfonyl-2-pyrazinyl group or a 5-(1-azetidinyl)carbonyl-3-chloro-2-pyridyl group;

(14) the compound or pharmacologically acceptable salt thereof in any one selected from (1) to (13) above, wherein $R^3$ is a hydroxy group or a methoxy group;

(15) the compound or pharmacologically acceptable salt thereof in (1) above, wherein the general formula (I) is the general formula (Ia), A is an oxygen atom, $R^1$ is a $C_1$-$C_6$ alkyl group, a $C_1$-$C_6$ alkoxy group or a mono-$C_1$-$C_6$ halogenated alkylamino group, $R^2$ is a phenyl group that may be substituted with 1 to 5 group(s) independently selected from Substituent Group δ or a 2-pyridyl group, 3-pyridyl group or 2-pyrazinyl group that may be substituted with 1 to 3 group(s) independently selected from Substituent Group δ, and $R^3$ is a hydroxy group or a methoxy group;

(16) the compound or pharmacologically acceptable salt thereof in (1) above, wherein the general formula (I) is the general formula (Ia), A is an oxygen atom, $R^1$ is a methyl group or a 2-chloroethylamino group, $R^2$ is a 4-methylsulfonylphenyl group, a 4-(1-azetidinyl)carbonyl-2-fluorophenyl group, a 2-fluoro-4-(1-pyrrolidinyl)carbonylphenyl group, a 5-(1-azetidinyl)carbonyl-3-chloro-2-pyridyl group, a 2-methylsulfonyl-5-pyridyl group, a 5-(4-methyl-1-piperazinyl)carbonyl-2-pyrazinyl group, a 2-methylaminocarbonyl-5-pyridyl group, a 2-methylaminosulfonyl-5-pyridyl group or a 5-methylsulfonyl-2-pyrazinyl group, and $R^3$ is a hydroxy group or a methoxy group;

(17) the compound or pharmacologically acceptable salt thereof in (1) above, wherein the general formula (I) is the general formula (Ia), A is an oxygen atom, $R^1$ is a methyl group or a 2-chloroethylamino group, $R^2$ is a 4-methylsulfonylphenyl group, a 2-methylsulfonyl-5-pyridyl group, a 5-methylsulfonyl-2-pyrazinyl group or a 5-(1-azetidinyl)carbonyl-3-chloro-2-pyridyl group, and $R^3$ is a hydroxy group or a methoxy group;

(18) the compound or pharmacologically acceptable salt thereof in (1) above, wherein the general formula (I) is the general formula (Ia), the heterocyclic group formed by A and $R^1$ together with the carbon atom bonded thereto and which may be substituted with 1 to 3 group(s) independently selected from Substituent Group α is a 2-pyridyl group, 5,6-dihydro-4H-1,3-oxazin-2-yl group, 1,3-thiazol-2-yl group, 1,3-oxazol-2-yl group, 1,3,4-oxadiazol-2-yl group, 1,3,4-thiadiazol-2-yl group, 4,5-dihydro-1,3-thiazol-2-yl group, 4,5-dihydro-1,3-oxazol-2-yl group or 1,3-benzothiazol-2-yl group that may be substituted with 1 to 3 group(s) independently selected from Substituent Group γ, $R^2$ is a phenyl group that may be substituted with 1 to 5 group(s) independently selected from Substituent Group δ or a 2-pyridyl group, 3-pyridyl group or 2-pyrazinyl group that may be substituted with 1 to 3 group(s) independently selected from Substituent Group δ, and $R^3$ is a hydroxy group or a methoxy group;

(19) the compound or pharmacologically acceptable salt thereof in (1) above, wherein the general formula (I) is the general formula (Ia), the heterocyclic group formed by A and $R^1$ together with the carbon atom bonded thereto and which may be substituted with 1 to 3 group(s) independently selected from Substituent Group α is a 1,3-thiazol-2-yl group, a 5-methyl-1,3-thiazol-2-yl group, a 5-methyl-1,3,4-oxadiazol-2-yl group, a 4,5-dihydro-1,3-thiazol-2-yl group, a 4,5-dihydro-1,3-oxazol-2-yl group, a (5S)-5-methyl-4,5-dihydro-1,3-oxazol-2-yl group, a (5R)-5-methyl-4,5-dihydro-1,3-oxazol-2-yl group, a 5-hydroxymethyl-4,5-dihydro-1,3-oxazol-2-yl group, a (5R)-5-hydroxymethyl-4,5-dihydro-1,3-oxazol-2-yl group, a (4R)-4-methyl-4,5-dihydro-1,3-oxazol-2-yl group, a (4R)-4-ethyl-4,5-dihydro-1,3-oxazol-2-yl group, a (4R)-4-hydroxymethyl-4,5-dihydro-1,3-oxazol-2-yl group, a (4S)-4-[(1R)-1-hydroxyethyl]-4,5-dihydro-1,3-oxazol-2-yl group, a (4S)-4-[(1S)-1-hydroxyethyl]-4,5-dihydro-1,3-oxazol-2-yl group, a (4R,5S)-4,5-dimethyl-4,5-dihydro-1,3-oxazol-2-yl group, a (5S)-4-hydroxy-5-methyl-4,5-dihydro-1,3-oxazol-2-yl group, a (4R,5S)-4-hydroxymethyl-5-methyl-4,5-dihydro-1,3-oxazol-2-yl group, a (4R,5R)-5-hydroxymethyl-4-methyl-4,5-dihydro-1,3-oxazol-2-yl group, a 5-carboxyl-1,3-thiazol-2-yl group, a 5-dimethylaminocarbonyl-1,3-thiazol-2-yl group, a 5-methyl-1,3,4-thiadiazol-2-yl group or a 5,6-dihydro-4H-1,3-oxazin-2-yl group, $R^2$ is a 4-methylsulfonylphenyl group, a 4-(1-azetidinyl)carbonyl-2-fluorophenyl group, a 2-fluoro-4-

(1-pyrrolidinyl)carbonylphenyl group, a 5-(1-azetidinyl)carbonyl-3-chloro-2-pyridyl group, a 2-methylsulfonyl-5-pyridyl group, a 5-(4-methyl-1-piperazinyl)carbonyl-2-pyrazinyl group, a 2-methylaminocarbonyl-5-pyridyl group, a 2-methylaminosulfonyl-5-pyridyl group or a 5-methylsulfonyl-2-pyrazinyl group, and $R^3$ is a hydroxy group or a methoxy group;

(20) the compound or pharmacologically acceptable salt thereof in (1) above, wherein the general formula (I) is the general formula (Ia), the heterocyclic group formed by A and $R^1$ together with the carbon atom bonded thereto and which may be substituted with 1 to 3 group(s) independently selected from Substituent Group α is a 4,5-dihydro-1,3-oxazol-2-yl group, a (4R)-4-methyl-4,5-dihydro-1,3-oxazol-2-yl group, a (4R)-4-ethyl-4,5-dihydro-1,3-oxazol-2-yl group, a (5S)-5-methyl-4,5-dihydro-1,3-oxazol-2-yl group, a (4R)-4-hydroxymethyl-4,5-dihydro-1,3-oxazol-2-yl group, a (5R)-5-hydroxymethyl-4,5-dihydro-1,3-oxazol-2-yl group, a (4S)-4-[(1R)-1-hydroxyethyl]-4,5-dihydro-1,3-oxazol-2-yl group, a (4S)-4-[(1S)-1-hydroxyethyl]-4,5-dihydro-1,3-oxazol-2-yl group, a (4R,5S)-4,5-dimethyl-4,5-dihydro-1,3-oxazol-2-yl group, a (4R,5S)-4-hydroxymethyl-5-methyl-4,5-dihydro-1,3-oxazol-2-yl group, a (4R,5R)-5-hydroxymethyl-4-methyl-4,5-dihydro-1,3-oxazol-2-yl group, a 1,3-thiazol-2-yl group, a 5-carboxyl-1,3-thiazol-2-yl group, a 5-dimethylaminocarbonyl-1,3-thiazol-2-yl group, a 5-methyl-1,3,4-thiadiazol-2-yl group, a 5-methyl-1,3,4-oxadiazol-2-yl group, a 4,5-dihydro-1,3-thiazol-2-yl group or a 5,6-dihydro-4H-1,3-oxazin-2-yl group, $R^2$ is a 4-methylsulfonylphenyl group, a 2-methylsulfonyl-5-pyridyl group, a 5-methylsulfonyl-2-pyrazinyl group or a 5-(1-azetidinyl)carbonyl-3-chloro-2-pyridyl group, and $R^3$ is a hydroxy group or a methoxy group;

(21) the compound or pharmacologically acceptable salt thereof in (1) above,
wherein the general formula (I) is the general formula (Ia), the heterocyclic group formed by A and $R^1$ together with the carbon atom bonded thereto and which may be substituted with 1 to 3 group(s) independently selected from Substituent Group α is a 4,5-dihydro-1,3-oxazol-2-yl group, a (4R)-4-methyl-4,5-dihydro-1,3-oxazol-2-yl group, a (4R)-4-ethyl-4,5-dihydro-1,3-oxazol-2-yl group, a (5S)-5-methyl-4,5-dihydro-1,3-oxazol-2-yl group, a (4R)-4-hydroxymethyl-4,5-dihydro-1,3-oxazol-2-yl group, a (5R)-5-hydroxymethyl-4,5-dihydro-1,3-oxazol-2-yl group, a (4S)-4-[(1R)-1-hydroxyethyl]-4,5-dihydro-1,3-oxazol-2-yl group, a (4S)-4-[(1S)-1-hydroxyethyl]-4,5-dihydro-1,3-oxazol-2-yl group, a (4R,5S)-4,5-dimethyl-4,5-dihydro-1,3-oxazol-2-yl group, a (4R,5S)-4-hydroxymethyl-5-methyl-4,5-dihydro-1,3-oxazol-2-yl group or a (4R,5R)-5-hydroxymethyl-4-methyl-4,5-dihydro-1,3-oxazol-2-yl group, $R^2$ is a 4-methylsulfonylphenyl group, a 2-methylsulfonyl-5-pyridyl group, a 5-methylsulfonyl-2-pyrazinyl group or a 5-(1-azetidinyl)carbonyl-3-chloro-2-pyridyl group, and $R^3$ is a hydroxy group or a methoxy group;

(22) the compound or pharmacologically acceptable salt thereof described in (1) above, wherein the compound represented by the general formula (I) is:
2-(5-{3-[(1S)-2-methoxy-1-methylethoxy]-5-[4-(methylsulfonyl)phenoxy]phenyl}-1H-pyrrol-2-yl)-1,3-thiazole,
(2S)-2-{3-[4-(methylsulfonyl)phenoxy]-5-[5-(1,3-thiazol-2-yl)-1H-pyrrol-2-yl]phenoxy}propan-1-ol,
2-(5-{3-[(1S)-2-methoxy-1-methylethoxy]-5-[4-(methylsulfonyl)phenoxy]phenyl}-1H-pyrrol-2-yl)-1,3-thiazole-5-carboxylic acid,
2-(5-{3-[(1S)-2-methoxy-1-methylethoxy]-5-[4-(methylsulfonyl)phenoxy]phenyl}-1H-pyrrol-2-yl)-N,N-dimethyl-1,3-thiazole-5-carboxamide,
1-(5-{3-[(1S)-2-methoxy-1-methylethoxy]-5-[4-(methylsulfonyl)phenoxy]phenyl}-1H-pyrrol-2-yl)ethanone,
(2S)-2-{3-[5-(4,5-dihydro-1,3-oxazol-2-yl)-1H-pyrrol-2-yl]-5-[4-(methylsulfonyl)phenoxy]phenoxy}propan-1-ol,
2-(5-{3-[(1S)-2-methoxy-1-methylethoxy]-5-[4-(methylsulfonyl)phenoxy]phenyl}-1H-pyrrol-2-yl)-5-methyl-1,3,4-thiadiazole,
2-(5-{3-[(1S)-2-methoxy-1-methylethoxy]-5-[4-(methylsulfonyl)phenoxy]phenyl}-1H-pyrrol-2-yl)-4,5-dihydro-1,3-thiazole,
(2S)-2-{3-[5-(4,5-dihydro-1,3-thiazol-2-yl)-1H-pyrrol-2-yl]-5-[4-(methylsulfonyl)phenoxy]phenoxy}propan-1-ol,
(2S)-2-(3-{5-[(5S)-5-methyl-4,5-dihydro-1,3-oxazol-2-yl]-1H-pyrrol-2-yl}-5-[4-(methylsulfonyl)phenoxy]phenoxy)propan-1-ol,
2-(5-{3-[(1S)-2-methoxy-1-methylethoxy]-5-[4-(methylsulfonyl)phenoxy]phenyl}-1H-pyrrol-2-yl)-5,6-dihydro-4H-1,3-oxazine,
(2S)-2-(3-{[5-(azetidin-1-ylcarbonyl)-3-chloropyridin-2-yl]oxy}-5-[5-(5-methyl-1,3,4-oxadiazol-2-yl)-1H-pyrrol-2-yl]phenoxy)propan-1-ol,
(2S)-2-(3-{[5-(azetidin-1-ylcarbonyl)-3-chloropyridin-2-yl]oxy}-5-{5-[(5S)-5-methyl-4,5-dihydro-1,3-oxazol-2-yl]-1H-pyrrol-2-yl}phenoxy)propan-1-ol,
(2S)-2-(3-{5-[(5S)-5-methyl-4,5-dihydro-1,3-oxazol-2-yl]-1H-pyrrol-2-yl}-5-{[6-(methylsulfonyl)pyridin-3-yl]oxy}phenoxy)propan-1-ol,
(2S)-2-(3-[5-(5-methyl-1,3,4-oxadiazol-2-yl)-1H-pyrrol-2-yl]-5-{[6-(methylsulfonyl)pyridin-3-yl]oxy}phenoxy)propan-1-ol,
{(5R)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-5-yl}methanol,
(2S)-2-(3-{5-[(4R)-4-methyl-4,5-dihydro-1,3-oxazol-2-yl]-1H-pyrrol-2-yl}-5-{[6-(methylsulfonyl)pyridin-3-yl]oxy}phenoxy)propan-1-ol,
(2S)-2-(3-{5-[(4R)-4-ethyl-4,5-dihydro-1,3-oxazol-2-yl]-1H-pyrrol-2-yl}-5-{[6-(methylsulfonyl)pyridin-3-yl]oxy}phenoxy)propan-1-ol,
{(4R)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-4-yl}methanol,
(2S)-2-(3-{5-[(4R,5S)-4,5-dimethyl-4,5-dihydro-1,3-oxazol-2-yl]-1H-pyrrol-2-yl}-5-{[6-(methylsulfonyl)pyridin-3-yl]oxy}phenoxy)propan-1-ol,
{(4R,5R)-2-[5-(3-[(1S)-2-methoxy-1-methylethoxy]-5-{[6-(methylsulfonyl)pyridin-3-yl]oxy}phenyl)-1H-pyrrol-2-yl]-4-methyl-4,5-dihydro-1,3-oxazol-5-yl}methanol,
{(4R,5S)-2-[5-(3-[(1S)-2-methoxy-1-methylethoxy]-5-{[6-(methylsulfonyl)pyridin-3-yl]oxy}phenyl)-1H-pyrrol-2-yl]-5-methyl-4,5-dihydro-1,3-oxazol-4-yl}methanol,
(1S)-1-{(4S)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-4-yl}ethanol,
(1R)-1-{(4S)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-4-yl}ethanol,
(2S)-2-(3-[5-(5-methyl-1,3,4-oxadiazol-2-yl)-1H-pyrrol-2-yl]-5-{[5-(methylsulfonyl)pyrazin-2-yl]oxy}phenoxy)propan-1-ol,
(2S)-2-(3-{5-[(5S)-5-methyl-4,5-dihydro-1,3-oxazol-2-yl]-1H-pyrrol-2-yl}-5-{[5-(methylsulfonyl)pyrazin-2-yl]oxy}phenoxy)propan-1-ol, {(5R)-2-[5-(3-[(1S)-2-methoxy-1-methylethoxy]-5-{[5-(methylsulfonyl)pyrazin-2-yl]oxy}phenyl)-1H-pyrrol-2-yl]-4,5-dihydro-1,3-oxazol-5-yl}methanol,
(2S)-2-(3-{5-[(4R)-4-methyl-4,5-dihydro-1,3-oxazol-2-yl]-1H-pyrrol-2-yl}-5-{[5-(methylsulfonyl)pyrazin-2-yl]oxy}phenoxy)propan-1-ol,
(2S)-2-(3-{5-[(4R)-4-ethyl-4,5-dihydro-1,3-oxazol-2-yl]-1H-pyrrol-2-yl}-5-{[5-(methylsulfonyl)pyrazin-2-yl]oxy}phenoxy)propan-1-ol,
(2S)-2-(3-{5-[(4R,5S)-4,5-dimethyl-4,5-dihydro-1,3-oxazol-2-yl]-1H-pyrrol-2-yl}-5-{[5-(methylsulfonyl)pyrazin-2-yl]oxy}phenoxy)propan-1-ol,
{(4R,5S)-2-[5-(3-{[(2S)-1-methoxypropan-2-yl]oxy}-5-{[5-(methylsulfonyl)pyrazin-2-yl]oxy}phenyl)-1H-pyrrol-2-yl]-5-methyl-4,5-dihydro-1,3-oxazol-4-yl}methanol,
(1S)-1-{(4S)-2-[5-(3-{[(2S)-1-methoxypropan-2-yl]oxy}-5-{[5-(methylsulfonyl)pyrazin-2-yl]oxy}phenyl)-1H-pyrrol-2-yl]-4,5-dihydro-1,3-oxazol-4-yl}ethanol, or
(1R)-1-{(4S)-2-[5-(3-{[(2S)-1-methoxypropan-2-yl]oxy}-5-{[5-(methylsulfonyl)pyrazin-2-yl]oxy}phenyl)-1H-pyrrol-2-yl]-4,5-dihydro-1,3-oxazol-4-yl}ethanol.

(23) the compound or pharmacologically acceptable salt thereof described in (1) above, wherein the compound represented by the general formula (I) is:
(2S)-2-{3-[5-(4,5-dihydro-1,3-oxazol-2-yl)-1H-pyrrol-2-yl]-5-[4-(methylsulfonyl)phenoxy]phenoxy}propan-1-ol,
(2S)-2-(3-{5-[(5S)-5-methyl-4,5-dihydro-1,3-oxazol-2-yl]-1H-pyrrol-2-yl}-5-[4-(methylsulfonyl)phenoxy]phenoxy)propan-1-ol,
(2S)-2-(3-{5-[(5S)-5-methyl-4,5-dihydro-1,3-oxazol-2-yl]-1H-pyrrol-2-yl}-5-{[6-(methylsulfonyl)pyridin-3-yl]oxy}phenoxy)propan-1-ol,
{(5R)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-5-yl}methanol,
(2S)-2-(3-{5-[(4R)-4-methyl-4,5-dihydro-1,3-oxazol-2-yl]-1H-pyrrol-2-yl}-5-{[6-(methylsulfonyl)pyridin-3-yl]oxy}phenoxy)propan-1-ol,
(2S)-2-(3-{5-[(4R)-4-ethyl-4,5-dihydro-1,3-oxazol-2-yl]-1H-pyrrol-2-yl}-5-{[6-(methylsulfonyl)pyridin-3-yl]oxy}phenoxy)propan-1-ol,
{(4R)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-4-yl}methanol,
(2S)-2-(3-{5-[(4R,5S)-4,5-dimethyl-4,5-dihydro-1,3-oxazol-2-yl]-1H-pyrrol-2-yl}-5-{[6-(methylsulfonyl)pyridin-3-yl]oxy}phenoxy)propan-1-ol,
{(4R,5R)-2-[5-(3-[(1S)-2-methoxy-1-methylethoxy]-5-{[6-(methylsulfonyl)pyridin-3-yl]oxy}phenyl)-1H-pyrrol-2-yl]-4-methyl-4,5-dihydro-1,3-oxazol-5-yl}methanol,
{(4R,5S)-2-[5-(3-[(1S)-2-methoxy-1-methylethoxy]-5-{[6-(methylsulfonyl)pyridin-3-yl]oxy}phenyl)-1H-pyrrol-2-yl]-5-methyl-4,5-dihydro-1,3-oxazol-4-yl}methanol,
(1S)-1-{(4S)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-4-yl}ethanol,
(1R)-1-{(4S)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-4-yl}ethanol,
(2S)-2-(3-{5-[(5S)-5-methyl-4,5-dihydro-1,3-oxazol-2-yl]-1H-pyrrol-2-yl}-5-{[5-(methylsulfonyl)pyrazin-2-yl]oxy}phenoxy)propan-1-ol,
{(5R)-2-[5-(3-[(1S)-2-methoxy-1-methylethoxy]-5-{[5-(methylsulfonyl)pyrazin-2-yl]oxy}phenyl)-1H-pyrrol-2-yl]-4,5-dihydro-1,3-oxazol-5-yl}methanol,
(2S)-2-(3-{5-[(4R)-4-methyl-4,5-dihydro-1,3-oxazol-2-yl]-1H-pyrrol-2-yl}-5-{[5-(methylsulfonyl)pyrazin-2-yl]oxy}phenoxy)propan-1-ol,
(2S)-2-(3-{5-[(4R)-4-ethyl-4,5-dihydro-1,3-oxazol-2-yl]-1H-pyrrol-2-yl}-5-{[5-(methylsulfonyl)pyrazin-2-yl]oxy}phenoxy)propan-1-ol,

(24) the compound described in (1) above, wherein the compound represented by the general formula (I) is:
(2S)-2-{3-[5-(4,5-dihydro-1,3-oxazol-2-yl)-1H-pyrrol-2-yl]-5-[4-(methylsulfonyl)phenoxy]phenoxy}propan-1-ol,
(2S)-2-(3-{5-[(5S)-5-methyl-4,5-dihydro-1,3-oxazol-2-yl]-1H-pyrrol-2-yl}-5-[4-(methylsulfonyl)phenoxy]phenoxy)propan-1-ol,
(2S)-2-(3-{5-[(5S)-5-methyl-4,5-dihydro-1,3-oxazol-2-yl]-1H-pyrrol-2-yl}-5-{[6-(methylsulfonyl)pyridin-3-yl]oxy}phenoxy)propan-1-ol,
{(5R)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-5-yl}methanol,
(2S)-2-(3-{5-[(4R)-4-methyl-4,5-dihydro-1,3-oxazol-2-yl]-1H-pyrrol-2-yl}-5-{[6-(methylsulfonyl)pyridin-3-yl]oxy}phenoxy)propan-1-ol,
(2S)-2-(3-{5-[(4R)-4-ethyl-4,5-dihydro-1,3-oxazol-2-yl]-1H-pyrrol-2-yl}-5-{[6-(methylsulfonyl)pyridin-3-yl]oxy}phenoxy)propan-1-ol,
{(4R)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-4-yl}methanol,
(2S)-2-(3-{5-[(4R,5S)-4,5-dimethyl-4,5-dihydro-1,3-oxazol-2-yl]-1H-pyrrol-2-yl}-5-{[6-(methylsulfonyl)pyridin-3-yl]oxy}phenoxy)propan-1-ol,
{(4R,5R)-2-[5-(3-[(1S)-2-methoxy-1-methylethoxy]-5-{[6-(methylsulfonyl)pyridin-3-yl]oxy}phenyl)-1H-pyrrol-2-yl]-4-methyl-4,5-dihydro-1,3-oxazol-5-yl}methanol,
{(4R,5S)-2-[5-(3-[(1S)-2-methoxy-1-methylethoxy]-5-{[6-(methylsulfonyl)pyridin-3-yl]oxy}phenyl)-1H-pyrrol-2-yl]-5-methyl-4,5-dihydro-1,3-oxazol-4-yl}methanol,
(1S)-1-{(4S)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-4-yl}ethanol,
(1R)-1-{(4S)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-4-yl}ethanol,
(2S)-2-(3-{5-[(5S)-5-methyl-4,5-dihydro-1,3-oxazol-2-yl]-1H-pyrrol-2-yl}-5-{[5-(methylsulfonyl)pyrazin-2-yl]oxy}phenoxy)propan-1-ol,
{(5R)-2-[5-(3-[(1S)-2-methoxy-1-methylethoxy]-5-{[5-(methylsulfonyl)pyrazin-2-yl]oxy}phenyl)-1H-pyrrol-2-yl]-4,5-dihydro-1,3-oxazol-5-yl}methanol,
(2S)-2-(3-{5-[(4R)-4-methyl-4,5-dihydro-1,3-oxazol-2-yl]-1H-pyrrol-2-yl}-5-{[5-(methylsulfonyl)pyrazin-2-yl]oxy}phenoxy)propan-1-ol,
(2S)-2-(3-{5-[(4R)-4-ethyl-4,5-dihydro-1,3-oxazol-2-yl]-1H-pyrrol-2-yl}-5-{[5-(methylsulfonyl)pyrazin-2-yl]oxy}phenoxy)propan-1-ol, (2S)-2-(3-{5-[(4R,5S)-4,5-dimethyl-4,5-dihydro-1,3-oxazol-2-yl]-1H-pyrrol-2-yl}-5-{[5-(methylsulfonyl)pyrazin-2-yl]oxy}phenoxy)propan-1-ol,
{(4R,5S)-2-[5-(3-{[(2S)-1-methoxypropan-2-yl]oxy}-5-{[5-(methylsulfonyl)pyrazin-2-yl]oxy}phenyl)-1H-pyrrol-2-yl]-5-methyl-4,5-dihydro-1,3-oxazol-4-yl}methanol,
(1S)-1-{(4S)-2-[5-(3-{[(2S)-1-methoxypropan-2-yl]oxy}-5-{[5-(methylsulfonyl)pyrazin-2-yl]oxy}phenyl)-1H-pyrrol-2-yl]-4,5-dihydro-1,3-oxazol-4-yl}ethanol, or
(1R)-1-{(4S)-2-[5-(3-{[(2S)-1-methoxypropan-2-yl]oxy}-5-{[5-(methylsulfonyl)pyrazin-2-yl]oxy}phenyl)-1H-pyrrol-2-yl]-4,5-dihydro-1,3-oxazol-4-yl}ethanol.

(25) the compound or pharmacologically acceptable salt thereof described in (1) above, wherein the compound represented by the general formula (I) is:

1-(4-{3-[(1S)-2-methoxy-1-methylethoxy]-5-[5-(1,3-thiazol-2-yl)-1H-pyrrol-2-yl]phenoxy}phenyl)ethanone,
1-(4-{3-[(1S)-2-methoxy-1-methylethoxy]-5-[5-(1,3-thiazol-2-yl)-1H-pyrrol-2-yl]phenoxy}phenyl)ethanol,
1-(5-{3-[(1S)-2-methoxy-1-methylethoxy]-5-[4-(methylsulfonyl)phenoxy]phenyl}-1H-pyrrol-2-yl)ethanone,
N-(2-chloroethyl)-5-{3-[(1S)-2-methoxy-1-methylethoxy]-5-[4-(methylsulfonyl)phenoxy]phenyl}-1H-pyrrol-2-carboxamide,
6-(5-{3-[(1S)-2-methoxy-1-methylethoxy]-5-[4-(methylsulfonyl)phenoxy]phenyl}-1H-pyrrol-2-yl)nicotinic acid,
2-(5-{3-[(1S)-2-methoxy-1-methylethoxy]-5-[4-(methylsulfonyl)phenoxy]phenyl}-1H-pyrrol-2-yl)-5,6-dihydro-4H-1,3-oxazine,
2-(5-{3-[(1S)-2-methoxy-1-methylethoxy]-5-[4-(methylsulfonyl)phenoxy]phenyl}-1H-pyrrol-2-yl)-1,3-thiazole,
2-(5-{3-[(1S)-2-methoxy-1-methylethoxy]-5-[4-(methylsulfonyl)phenoxy]phenyl}-1H-pyrrol-2-yl)-5-methyl-1,3-thiazole,
[2-(5-{3-[(1S)-2-methoxy-1-methylethoxy]-5-[4-(methylsulfonyl)phenoxy]phenyl}-1H-pyrrol-2-yl)-1,3-thiazol-5-yl]methanol,
2-(5-{3-[(1S)-2-methoxy-1-methylethoxy]-5-[4-(methylsulfonyl)phenoxy]phenyl}-1H-pyrrol-2-yl)-1,3-thiazole-5-carboxylic acid,
2-(5-{3-[(1S)-2-methoxy-1-methylethoxy]-5-[4-(methylsulfonyl)phenoxy]phenyl}-1H-pyrrol-2-yl)-N,N-dimethyl-1,3-thiazol-5-carboxamide,
2-(5-{3-[(1S)-2-methoxy-1-methylethoxy]-5-[4-(methylsulfonyl)phenoxy]phenyl}-1H-pyrrol-2-yl)-1,3-oxazole,
5-methoxy-2-(5-{3-[(1S)-2-methoxy-1-methylethoxy]-5-[4-(methylsulfonyl)phenoxy]phenyl}-1H-pyrrol-2-yl)-1,3-oxazole,
2-(5-{3-[(1S)-2-methoxy-1-methylethoxy]-5-[4-(methylsulfonyl)phenoxy]phenyl}-1H-pyrrol-2-yl)-5-methyl-1,3,4-oxadiazole,
2-(5-{3-[(1S)-2-methoxy-1-methylethoxy]-5-[4-(methylsulfonyl)phenoxy]phenyl}-1H-pyrrol-2-yl)-5-methyl-1,3,4-thiadiazole,
2-(5-{3-[(1S)-2-methoxy-1-methylethoxy]-5-[4-(methylsulfonyl)phenoxy]phenyl}-1H-pyrrol-2-yl)-4,5-dihydro-1,3-thiazole,
2-(5-{3-[(1S)-2-methoxy-1-methylethoxy]-5-[4-(methylsulfonyl)phenoxy]phenyl}-1H-pyrrol-2-yl)-4,5-dihydro-1,3-oxazole,
(5S)-2-(5-{3-[(1S)-2-methoxy-1-methylethoxy]-5-[4-(methylsulfonyl)phenoxy]phenyl}-1H-pyrrol-2-yl)-5-methyl-4,5-dihydro-1,3-oxazole,
(5R)-2-(5-{3-[(1S)-2-methoxy-1-methylethoxy]-5-[4-(methylsulfonyl)phenoxy]phenyl}-1H-pyrrol-2-yl)-5-methyl-4,5-dihydro-1,3-oxazole,
2-(5-{3-[(1S)-2-methoxy-1-methylethoxy]-5-[4-(methylsulfonyl)phenoxy]phenyl}-1H-pyrrol-2-yl)-5,5-dimethyl-4,5-dihydro-1,3-oxazole,
[2-(5-{3-[(1S)-2-methoxy-1-methylethoxy]-5-[4-(methylsulfonyl)phenoxy]phenyl}-1H-pyrrol-2-yl)-4,5-dihydro-1,3-oxazol-5-yl]methanol,
2-(5-{3-[(1S)-2-methoxy-1-methylethoxy]-5-[4-(methylsulfonyl)phenoxy]phenyl}-1H-pyrrol-2-yl)-1,3-benzothiazole,
2-(5-{3-[4-(azetidin-1-ylsulfonyl)phenoxy]-5-[(1S)-2-methoxy-1-methylethoxy]phenyl}-1H-pyrrol-2-yl)-1,3-thiazole,
Methyl 3-fluoro-4-{3-[(1S)-2-methoxy-1-methylethoxy]-5-[5-(1,3-thiazol-2-yl)-1H-pyrrol-2-yl]phenoxyl}benzoate,
3-fluoro-4-{3-[(1S)-2-methoxy-1-methylethoxy]-5-[5-(1,3-thiazol-2-yl)-1H-pyrrol-2-yl]phenoxy}benzamide,
3-fluoro-4-{3-[(1S)-2-methoxy-1-methylethoxy]-5-[5-(1,3-thiazol-2-yl)-1H-pyrrol-2-yl]phenoxy}-N-methylbenzamide,
3-fluoro-4-{3-[(1S)-2-methoxy-1-methylethoxy]-5-[5-(1,3-thiazol-2-yl)-1H-pyrrol-2-yl]phenoxy}-N,N-dimethylbenzamide,
2-(5-{3-[4-(azetidin-1-ylcarbonyl)-2-fluorophenoxy]-5-[(1S)-2-methoxy-1-methylethoxy]phenyl}-1H-pyrrol-2-yl)-1,3-thiazole,
2-(5-{3-[4-(azetidin-1-ylcarbonyl)-2-fluorophenoxy]-5-[(1S)-2-methoxy-1-methylethoxy]phenyl}-1H-pyrrol-2-yl)-5-methyl-1,3,4-oxadiazole,
2-(5-{3-[4-(azetidin-1-ylcarbonyl)-2-fluorophenoxy]-5-[(1S)-2-methoxy-1-methylethoxy]phenyl}-1H-pyrrol-2-yl)-4,5-dihydro-1,3-oxazole,
(5S)-2-(5-{3-[4-(azetidin-1-ylcarbonyl)-2-fluorophenoxy]-5-[(1S)-2-methoxy-1-methylethoxy]phenyl}-1H-pyrrol-2-yl)-5-methyl-4,5-dihydro-1,3-oxazole,
2-(5-{3-[2-fluoro-4-(pyrrolidin-1-ylcarbonyl)phenoxy]-5-[(1S)-2-methoxy-1-methylethoxy]phenyl}-1H-pyrrol-2-yl)-1,3-thiazole,
4-(3-fluoro-4-{3-[(1S)-2-methoxy-1-methylethoxy]-5-[5-(1,3-thiazol-2-yl)-1H-pyrrol-2-yl]phenoxy}benzoyl)morpholine,
3-fluoro-4-{3-[(1S)-2-methoxy-1-methylethoxy]-5-[5-(1,3-thiazol-2-yl)-1H-pyrrol-2-yl]phenoxy}-N-methylbenzenesulfonamide,
2-(5-{3-[4-(azetidin-1-ylsulfonyl)-2-fluorophenoxy]-5-[(1S)-2-methoxy-1-methylethoxy]phenyl}-1H-pyrrol-2-yl)-1,3-thiazole,
2-(3-fluoro-4-{3-[(1S)-2-methoxy-1-methylethoxy]-5-[5-(1,3-thiazol-2-yl)-1H-pyrrol-2-yl]phenoxy}phenyl)-5-methyl-1,3,4-oxadiazole,
2-(3-fluoro-4-{3-[(1S)-2-methoxy-1-methylethoxy]-5-[5-(1,3-thiazol-2-yl)-1H-pyrrol-2-yl]phenoxy}phenyl)-5-methyl-1,3,4-thiadiazole,
2-(5-{3-[4-(azetidin-1-ylcarbonyl)-2-methylphenoxy]-5-[(1S)-2-methoxy-1-methylethoxy]phenyl}-1H-pyrrol-2-yl)-1,3-thiazole,
2-(5-{3-[4-(azetidin-1-ylcarbonyl)-2-(trifluoromethyl)phenoxy]-5-[(1S)-2-methoxy-1-methylethoxy]phenyl}-1H-pyrrol-2-yl)-1,3-thiazole,
5-(azetidin-1-ylcarbonyl)-2-{3-[(1S)-2-methoxy-1-methylethoxy]-5-[5-(1,3-thiazol-2-yl)-1H-pyrrol-2-yl]phenoxyl}pyridine,
5-(azetidin-1-ylcarbonyl)-3-chloro-2-{3-[(1S)-2-methoxy-1-methylethoxy]-5-[5-(1,3-thiazol-2-yl)-1H-pyrrol-2-yl]phenoxy}pyridine,
5-(azetidin-1-ylcarbonyl)-3-chloro-2-{3-[(1S)-2-methoxy-1-methylethoxy]-5-[5-(5-methyl-1,3,4-oxadiazol-2-yl)-1H-pyrrol-2-yl]phenoxyl}pyridine, 5-(azetidin-1-ylcarbonyl)-3-chloro-2-{3-[5-(4,5-dihydro-1,3-oxazol-2-yl)-1H-pyrrol-2-yl]-5-[(1S)-2-methoxy-1-methylethoxy]phenoxyl}pyridine,
5-(azetidin-1-ylcarbonyl)-3-chloro-2-(3-[(1S)-2-methoxy-1-methylethoxy]-5-{5-[(5S)-5-methyl-4,5-dihydro-1,3-oxazol-2-yl]-1H-pyrrol-2-yl}phenoxy)pyridine,
5-(azetidin-1-ylcarbonyl)-2-{3-[[(1S)-2-methoxy-1-methylethoxy]-5-[5-(1,3-thiazol-2-yl)-1H-pyrrol-2-yl]phenoxy}-3-methylpyridine,
5-{3-[(1S)-2-methoxy-1-methylethoxy]-5-[5-(1,3-thiazol-2-yl)-1H-pyrrol-2-yl]phenoxy}-2-(methylsulfonyl)pyridine,
5-(3-[(1S)-2-methoxy-1-methylethoxy]-5-{5-[(5S)-5-methyl-4,5-dihydro-1,3-oxazol-2-yl]-1H-pyrrol-2-yl}phenoxy)-2-(methylsulfonyl)pyridine,
2-{3-[(1S)-2-methoxy-1-methylethoxy]-5-[5-(1,3-thiazol-2-yl)-1H-pyrrol-2-yl]phenoxy}-5-[(4-methylpiperazin-1-yl)carbonyl]pyrazine,
5-(fluoromethyl)-2-(5-{3-[(1S)-2-methoxy-1-methylethoxy]-5-[4-(methylsulfonyl)phenoxy]phenyl}-1H-pyrrol-2-yl)-4,5-dihydro-1,3-oxazole,
(5R)-2-(5-{3-[(1S)-2-methoxy-1-methylethoxy]-5-[4-(methylsulfonyl)phenoxy]phenyl}-1H-pyrrol-2-yl)-5-(trifluoromethyl)-4,5-dihydro-1,3-oxazole,
[(5R)-2-(5-{3-[(1S)-2-methoxy-1-methylethoxy]-5-[4-(methylsulfonyl)phenoxy]phenyl}-1H-pyrrol-2-yl)-4,5-dihydro-1,3-oxazol-5-yl]methanol,
2-(5-{3-[(1S)-2-methoxy-1-methylethoxy]-5-[4-(methylsulfonyl)phenoxy]phenyl}-1H-pyrrol-2-yl)-N,N-dimethyl-4,5-dihydro-1,3-oxazole-5-carboxamide,
N-(2-chloroethyl)-5-{3-[(1S)-2-hydroxy-1-methylethoxy]-5-[4-(methylsulfonyl)phenoxy]phenyl}-1H-pyrrole-2-carboxamide,
(2S)-2-{3-[4-(methylsulfonyl)phenoxy]-5-[5-(1,3-thiazol-2-yl)-1H-pyrrol-2-yl]phenoxy}propan-1-ol,
(2S)-2-{3-[5-(4,5-dihydro-1,3-thiazol-2-yl)-1H-pyrrol-2-yl]-5-[4-(methylsulfonyl)phenoxy]phenoxy}propan-1-ol,
(2S)-2-{3-[5-(4,5-dihydro-1,3-oxazol-2-yl)-1H-pyrrol-2-yl]-5-[4-(methylsulfonyl)phenoxy]phenoxy}propan-1-ol,
(2S)-2-(3-{5-[(5S)-5-methyl-4,5-dihydro-1,3-oxazol-2-yl]-1H-pyrrol-2-yl}-5-[4-(methylsulfonyl)phenoxy]phenoxy)propan-1-ol,
(2S)-2-{3-[4-(azetidin-1-ylcarbonyl)-2-fluorophenoxy]-5-[5-(5-methyl-1,3,4-oxadiazol-2-yl)-1H-pyrrol-2-yl]phenoxy}propan-1-ol,
(2S)-2-(3-[4-(azetidin-1-ylcarbonyl)-2-fluorophenoxy]-5-{5-[(5S)-5-methyl-4,5-dihydro-1,3-oxazol-2-yl]-1H-pyrrol-2-yl}phenoxy)propan-1-ol,
(2S)-2-(3-{[5-(azetidin-1-ylcarbonyl)-3-chloropyridin-2-yl]oxy}-5-[5-(5-methyl-1,3,4-oxadiazol-2-yl)-1H-pyrrol-2-yl]phenoxy)propan-1-ol,
(2S)-2-(3-{[5-(azetidin-1-ylcarbonyl)-3-chloropyridin-2-yl]oxy}-5-{5-[(5S)-5-methyl-4,5-dihydro-1,3-oxazol-2-yl]-1H-pyrrol-2-yl}phenoxy)propan-1-ol, or
(2S)-2-(3-{5-[(5S)-5-methyl-4,5-dihydro-1,3-oxazol-2-yl]-1H-pyrrol-2-yl}-5-{[6-(methylsulfonyl)pyridin-3-yl]oxy}phenoxy)propan-1-ol.

(26) the compound or pharmacologically acceptable salt thereof described in (1) above, wherein the compound represented by the general formula (I) is:
1-(5-{3-[(1S)-2-methoxy-1-methylethoxy]-5-[4-(methylsulfonyl)phenoxy]phenyl}-1H-pyrrol-2-yl)ethanone,
2-(5-{3-[(1S)-2-methoxy-1-methylethoxy]-5-[4-(methylsulfonyl)phenoxy]phenyl}-1H-pyrrol-2-yl)-1,3-thiazole,
2-(5-{3-[(1S)-2-methoxy-1-methylethoxy]-5-[4-(methylsulfonyl)phenoxy]phenyl}-1H-pyrrol-2-yl)-5-methyl-1,3-thiazole,
2-(5-{3-[(1S)-2-methoxy-1-methylethoxy]-5-[4-(methylsulfonyl)phenoxy]phenyl}-1H-pyrrol-2-yl)-4,5-dihydro-1,3-thiazole,
2-(5-{3-[(1S)-2-methoxy-1-methylethoxy]-5-[4-(methylsulfonyl)phenoxy]phenyl}-1H-pyrrol-2-yl)-4,5-dihydro-1,3-oxazole,
(5S)-2-(5-{3-[(1S)-2-methoxy-1-methylethoxy]-5-[4-(methylsulfonyl)phenoxy]phenyl}-1H-pyrrol-2-yl)-5-methyl-4,5-dihydro-1,3-oxazole,
(5R)-2-(5-{3-[(1S)-2-methoxy-1-methylethoxy]-5-[4-(methylsulfonyl)phenoxy]phenyl}-1H-pyrrol-2-yl)-5-methyl-4,5-dihydro-1,3-oxazole,
[2-(5-{3-[(1S)-2-methoxy-1-methylethoxy]-5-[4-(methylsulfonyl)phenoxy]phenyl}-1H-pyrrol-2-yl)-4,5-dihydro-1,3-oxazol-5-yl]methanol,
2-(5-{3-[4-(azetidin-1-ylcarbonyl)-2-fluorophenoxy]-5-[(1S)-2-methoxy-1-methylethoxy]phenyl}-1H-pyrrol-2-yl)-1,3-thiazole,
2-(5{-3-[4-(azetidin-1-ylcarbonyl)-2-fluorophenoxy]-5-[(1S)-2-methoxy-1-methylethoxy]phenyl}-1H-pyrrol-2-yl)-4,5-dihydro-1,3-oxazole,
(5S)-2-(5-{3-[4-(azetidin-1-ylcarbonyl)-2-fluorophenoxy]-5-[(1S)-2-methoxy-1-methylethoxy]phenyl}-1H-pyrrol-2-yl)-5-methyl-4,5-dihydro-1,3-oxazole,
2-(5-{3-[2-fluoro-4-(pyrrolidin-1-ylcarbonyl)phenoxy]-5-[(1S)-2-methoxy-1-methylethoxy]phenyl}-1H-pyrrol-2-yl)-1,3-thiazole,
5-(azetidin-1-ylcarbonyl)-3-chloro-2-{3-[(1S)-2-methoxy-1-methylethoxy]-5-[5-(1,3-thiazol-2-yl)-1H-pyrrol-2-yl]phenoxy}pyridine,
5-(azetidin-1-ylcarbonyl)-3-chloro-2-{3-[5-(4,5-dihydro-1,3-oxazol-2-yl)-1H-pyrrol-2-yl]-5-[(1S)-2-methoxy-1-methylethoxy]phenoxyl}pyridine,
5-(azetidin-1-ylcarbonyl)-3-chloro-2-(3-[(1S)-2-methoxy-1-methylethoxy]-5-{5-[(5S)-5-methyl-4,5-dihydro-1,3-oxazol-2-yl]-1H-pyrrol-2-yl}phenoxy)pyridine,
5-{3-[(1S)-2-methoxy-1-methylethoxy]-5-[5-(1,3-thiazol-2-yl)-1H-pyrrol-2-yl]phenoxy}-2-(methylsulfonyl)pyridine,
5-(3-[(1S)-2-methoxy-1-methylethoxy]-5-{5-[(5S)-5-methyl-4,5-dihydro-1,3-oxazol-2-yl]-1H-pyrrol-2-yl}phenoxy)-2-(methylsulfonyl)pyridine,
2-{3-[(1S)-2-methoxy-1-methylethoxy]-5-[5-(1,3-thiazol-2-yl)-1H-pyrrol-2-yl]phenoxy}-5-[(4-methylpiperazin-1-yl)carbonyl]pyrazine,
[(5R)-2-(5-{3-[(1S)-2-methoxy-1-methylethoxy]-5-[4-(methylsulfonyl)phenoxy]phenyl}-1H-pyrrol-2-yl)-4,5-dihydro-1,3-oxazol-5-yl]methanol,
(2S)-2-{3-[4-(methylsulfonyl)phenoxy]-5-[5-(1,3-thiazol-2-yl)-1H-pyrrol-2-yl]phenoxy}propan-1-ol,
(2S)-2-{3-[5-(4,5-dihydro-1,3-thiazol-2-yl)-1H-pyrrol-2-yl]-5-[4-(methylsulfonyl)phenoxy]phenoxy}propan-1-ol,
(2S)-2-{3-[5-(4,5-dihydro-1,3-oxazol-2-yl)-1H-pyrrol-2-yl]-5-[4-(methylsulfonyl)phenoxy]phenoxy}propan-1-ol,
(2S)-2-(3-{5-[(5S)-5-methyl-4,5-dihydro-1,3-oxazol-2-yl]-1H-pyrrol-2-yl}-5-[4-(methylsulfonyl)phenoxy]phenoxy)propan-1-ol,
(2S)-2-{3-[4-(azetidin-1-ylcarbonyl)-2-fluorophenoxy]-5-[5-(5-methyl-1,3,4-oxadiazol-2-yl)-1H-pyrrol-2-yl]phenoxy}propan-1-ol,
(2S)-2-(3-[4-(azetidin-1-ylcarbonyl)-2-fluorophenoxy]-5-{5-[(5S)-5-methyl-4,5-dihydro-1,3-oxazol-2-yl]-1H-pyrrol-2-yl}phenoxy)propan-1-ol,
(2S)-2-(3-{[5-(azetidin-1-ylcarbonyl)-3-chloropyridin-2-yl]oxy}-5-{5-[(5S)-5-methyl-4,5-dihydro-1,3-oxazol-2-yl]-1H-pyrrol-2-yl}phenoxy)propan-1-ol, or (2S)-2-(3-{5-[(5S)-5-methyl-4,5-dihydro-1,3-oxazol-2-yl]-1H-pyrrol-2-yl}-5-{[6-(methylsulfonyl)pyridin-3-yl]oxy}phenoxy)propan-1-ol.

(27) the compound described in (1) above, wherein the compound represented by the general formula (I) is:

1-(5-{3-[(1S)-2-methoxy-1-methylethoxy]-5-[4-(methylsulfonyl)phenoxy]phenyl}-1H-pyrrol-2-yl)ethanone, 2-(5-{3-[(1S)-2-methoxy-1-methylethoxy]-5-[4-(methylsulfonyl)phenoxy]phenyl}-1H-pyrrol-2-yl)-1,3-thiazole, 2-(5-{3-[(1S)-2-methoxy-1-methylethoxy]-5-[4-(methylsulfonyl)phenoxy]phenyl}-1H-pyrrol-2-yl)-5-methyl-1,3-thiazole, 2-(5-{3-[(1S)-2-methoxy-1-methylethoxy]-5-[4-(methylsulfonyl)phenoxy]phenyl}-1H-pyrrol-2-yl)-4,5-dihydro-1,3-thiazole, 2-(5-{3-[(1S)-2-methoxy-1-methylethoxy]-5-[4-(methylsulfonyl)phenoxy]phenyl}-1H-pyrrol-2-yl)-4,5-dihydro-1,3-oxazole, (5S)-2-(5-{3-[(1S)-2-methoxy-1-methylethoxy]-5-[4-(methylsulfonyl)phenoxy]phenyl}-1H-pyrrol-2-yl)-5-methyl-4,5-dihydro-1,3-oxazole, (5R)-2-(5-{3-[(1S)-2-methoxy-1-methylethoxy]-5-[4-(methylsulfonyl)phenoxy]phenyl}-1H-pyrrol-2-yl)-5-methyl-4,5-dihydro-1,3-oxazole,

[2-(5-{3-[(1S)-2-methoxy-1-methylethoxy]-5-[4-(methylsulfonyl)phenoxy]phenyl}-1H-pyrrol-2-yl)-4,5-dihydro-1,3-oxazol-5-yl]methanol, 2-(5-{3-[4-(azetidin-1-ylcarbonyl)-2-fluorophenoxy]-5-[(1S)-2-methoxy-1-methylethoxy]phenyl}-1H-pyrrol-2-yl)-1,3-thiazole, 2-(5-{3-[4-(azetidin-1-ylcarbonyl)-2-fluorophenoxy]-5-[(1S)-2-methoxy-1-methylethoxy]phenyl}-1H-pyrrol-2-yl)-4,5-dihydro-1,3-oxazole, (5S)-2-(5-{3-[4-(azetidin-1-ylcarbonyl)-2-fluorophenoxy]-5-[(1S)-2-methoxy-1-methylethoxy]phenyl}-1H-pyrrol-2-yl)-5-methyl-4,5-dihydro-1,3-oxazole, 2-(5-{3-[2-fluoro-4-(pyrrolidin-1-ylcarbonyl)phenoxy]-5-[(1S)-2-methoxy-1-methylethoxy]phenyl}-1H-pyrrol-2-yl)-1,3-thiazole, 5-(azetidin-1-ylcarbonyl)-3-chloro-2-{3-[(1S)-2-methoxy-1-methylethoxy]-5-[5-(1,3-thiazol-2-yl)-1H-pyrrol-2-yl]phenoxyl}pyridine, 5-(azetidin-1-ylcarbonyl)-3-chloro-2-{3-[5-(4,5-dihydro-1,3-oxazol-2-yl)-1H-pyrrol-2-yl]-5-[(1S)-2-methoxy-1-methylethoxy]phenoxyl}pyridine, 5-(azetidin-1-ylcarbonyl)-3-chloro-2-(3-[(1S)-2-methoxy-1-methylethoxy]-5-{5-[(5S)-5-methyl-4,5-dihydro-1,3-oxazol-2-yl]-1H-pyrrol-2-yl}phenoxy)pyridine, 5-{3-[(1S)-2-methoxy-1-methylethoxy]-5-[5-(1,3-thiazol-2-yl)-1H-pyrrol-2-yl]phenoxy}-2-(methylsulfonyl)pyridine, 5-(3-[(1S)-2-methoxy-1-methylethoxy]-5-{5-[(5S)-5-methyl-4,5-dihydro-1,3-oxazol-2-yl]-1H-pyrrol-2-yl}phenoxy)-2-(methylsulfonyl)pyridine, 2-{3-[(1S)-2-methoxy-1-methylethoxy]-5-[5-(1,3-thiazol-2-yl)-1H-pyrrol-2-yl]phenoxy}-5-[(4-methylpiperazin-1-yl)carbonyl]pyrazine,

[(5R)-2-(5-{3-[(1S)-2-methoxy-1-methylethoxy]-5-[4-(methylsulfonyl)phenoxy]phenyl}-1H-pyrrol-2-yl)-4,5-dihydro-1,3-oxazol-5-yl]methanol, (2S)-2-{3-[4-(methylsulfonyl)phenoxy]-5-[5-(1,3-thiazol-2-yl)-1H-pyrrol-2-yl]phenoxy}propan-1-ol, (2S)-2-{3-[5-(4,5-dihydro-1,3-oxazol-2-yl)-1H-pyrrol-2-yl]-5-[4-(methylsulfonyl)phenoxy]phenoxy}propan-1-ol, (2S)-2-{3-[5-(4,5-dihydro-1,3-oxazol-2-yl)-1H-pyrrol-2-yl]-5-[4-(methylsulfonyl)phenoxy]phenoxy}propan-1-ol, (2S)-2-(3-{5-[(5S)-5-methyl-4,5-dihydro-1,3-oxazol-2-yl]-1H-pyrrol-2-yl}-5-[4-(methylsulfonyl)phenoxy]phenoxy)propan-1-ol, (2S)-2-(3-{4-(azetidin-1-ylcarbonyl)-2-fluorophenoxy]-5-[5-(5-methyl-1,3,4-oxadiazol-2-yl)-1H-pyrrol-2-yl]phenoxy}propan-1-ol, (2S)-2-(3-{4-(azetidin-1-ylcarbonyl)-2-fluorophenoxy]-5-{5-[(5S)-5-methyl-4,5-dihydro-1,3-oxazol-2-yl]-1H-pyrrol-2-yl}phenoxy)propan-1-ol, (2S)-2-(3-{[5-(azetidin-1-ylcarbonyl)-3-chloropyridin-2-yl]oxy}-5-{5-[(5S)-5-methyl-4,5-dihydro-1,3-oxazol-2-yl]-1H-pyrrol-2-yl}phenoxy)propan-1-ol, or (2S)-2-(3-{5-[(5S)-5-methyl-4,5-dihydro-1,3-oxazol-2-yl]-1H-pyrrol-2-yl}-5-{[6-(methylsulfonyl)pyridin-3-yl]oxy}phenoxy)propan-1-ol.

(28) a compound or pharmacologically acceptable salt thereof described in (1) above, wherein the compound represented by the general formula (I) is:

(2S)-2-(3-[5-(5-methyl-1,3,4-oxadiazol-2-yl)-1H-pyrrol-2-yl]-5-{[6-(methylsulfonyl)pyridin-3-yl]oxy}phenoxy)propan-1-ol, {(5R)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-5-yl}methanol, (2S)-2-(3-{5-[(4R)-4-methyl-4,5-dihydro-1,3-oxazol-2-yl]-1H-pyrrol-2-yl}-5-{[6-(methylsulfonyl)pyridin-3-yl]oxy}phenoxy)propan-1-ol, (2S)-2-(3-{5-[(4R)-4-ethyl-4,5-dihydro-1,3-oxazol-2-yl]-1H-pyrrol-2-yl}-5-{[6-(methylsulfonyl)pyridin-3-yl]oxy}phenoxy)propan-1-ol, {(4R)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-4-yl}methanol, (2S)-2-(3-{5-[(4R,5S)-4,5-dimethyl-4,5-dihydro-1,3-oxazol-2-yl]-1H-pyrrol-2-yl}-5-{[6-(methylsulfonyl)pyridin-3-yl]oxy}phenoxy)propan-1-ol, {(4R,5R)-2-[5-(3-[(1S)-2-methoxy-1-methylethoxy]-5-{[6-(methylsulfonyl)pyridin-3-yl]oxy}phenyl)-1H-pyrrol-2-yl]-4-methyl-4,5-dihydro-1,3-oxazol-5-yl}methanol, {(4R,5S)-2-[5-(3-[(1S)-2-methoxy-1-methylethoxy]-5-{[6-(methylsulfonyl)pyridin-3-yl]oxy}phenyl)-1H-pyrrol-2-yl]-5-methyl-4,5-dihydro-1,3-oxazol-4-yl}methanol, (1S)-1-{(4S)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-4-yl}ethanol, (1R)-1-{(4S)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-4-yl}ethanol, (2S)-2-(3-[5-(5-methyl-1,3,4-oxadiazol-2-yl)-1H-pyrrol-2-yl]-5-{[5-(methylsulfonyl)pyrazin-2-yl]oxy}phenoxy)propan-1-ol, (2S)-2-(3-{5-[(5S)-5-methyl-4,5-dihydro-1,3-oxazol-2-yl]-1H-pyrrol-2-yl}-5-{[5-(methylsulfonyl)pyrazin-2-yl]oxy}phenoxy)propan-1-ol, {(5R)-2-[5-(3-[(1S)-2-methoxy-1-methylethoxy]-5-{[5-(methylsulfonyl)pyrazin-2-yl]oxy}phenyl)-1H-pyrrol-2-yl]-4,5-dihydro-1,3-oxazol-5-yl}methanol, (5S)-2-[5-(3-[(1S)-2-methoxy-1-methylethoxy]-5-{[5-(methylsulfonyl)pyrazin-2-yl]oxy}phenyl)-1H-pyrrol-2-yl]-5-methyl-4,5-dihydro-1,3-oxazol-4-ol, (2S)-2-(3-{5-[(4R)-4-methyl-4,5-dihydro-1,3-oxazol-2-yl]-1H-pyrrol-2-yl}-5-{[5-(methylsulfonyl)pyrazin-2-yl]oxy}phenoxy)propan-1-ol, (2S)-2-(3-{5-[(4R)-4-ethyl-4,5-dihydro-1,3-oxazol-2-yl]-1H-pyrrol-2-yl}-5-{[5-(methylsulfonyl)pyrazin-2-yl]oxy}phenoxy)propan-1-ol, (2S)-2-(3-{5-[(4R,5S)-4,5-dimethyl-4,5-dihydro-1,3-oxazol-2-yl]-1H-pyrrol-2-yl}-5-{[5-(methylsulfonyl)pyrazin-2-yl]oxy}phenoxy)propan-1-ol,
{(4R,5S)-2-[5-(3-{[(2S)-1-methoxypropan-2-yl]oxy}-5-{[5-(methylsulfonyl)pyrazin-2-yl]oxy}phenyl)-1H-pyrrol-2-yl]-5-methyl-4,5-dihydro-1,3-oxazol-4-yl}methanol,
(1S)-1-{(4S)-2-[5-(3-{[(2S)-1-methoxypropan-2-yl]oxy}-5-{[5-(methylsulfonyl)pyrazin-2-yl]oxy}phenyl)-1H-pyrrol-2-yl]-4,5-dihydro-1,3-oxazol-4-yl}ethanol,
(1R)-1-{(4S)-2-[5-(3-{[(2S)-1-methoxypropan-2-yl]oxy}-5-{[5-(methylsulfonyl)pyrazin-2-yl]oxy}phenyl)-1H-pyrrol-2-yl]-4,5-dihydro-1,3-oxazol-4-yl}ethanol,
5-(3-[(1S)-2-Hydroxy-1-methylethoxy]-5-{5-[(5S)-5-methyl-4,5-dihydro-1,3-oxazol-2-yl]-1H-pyrrol-2-yl}phenoxy)-N-methylpyridin-2-sulfonamide,
5-(3-[(1S)-2-hydroxy-1-methylethoxy]-5-{5-[(5S)-5-methyl-4,5-dihydro-1,3-oxazol-2-yl]-1H-pyrrol-2-yl}phenoxy)-N-methylpyridine-2-carboxamide,
5-(3-{5-[(5R)-5-(hydroxymethyl)-4,5-dihydro-1,3-oxazol-2-yl]-1H-pyrrol-2-yl}-5-[(1S)-2-methoxy-1-methylethoxy]phenoxy)-N-methylpyridin-2-carboxamide, or
5-(3-{5-[(5R)-5-(hydroxymethyl)-4,5-dihydro-1,3-oxazol-2-yl]-1H-pyrrol-2-yl}-5-[(1S)-2-methoxy-1-methylethoxy]phenoxy)-N-methylpyridin-2-sulfonamide.

(29) a compound or pharmacologically acceptable salt thereof described in (1) above, wherein the compound represented by the general formula (I) is:
{(5R)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-5-yl}methanol,
(2S)-2-(3-{5-[(4R)-4-methyl-4,5-dihydro-1,3-oxazol-2-yl]-1H-pyrrol-2-yl}-5-{[6-(methylsulfonyl)pyridin-3-yl]oxy}phenoxy)propan-1-ol,
(2S)-2-(3-{5-[(4R)-4-ethyl-4,5-dihydro-1,3-oxazol-2-yl]-1H-pyrrol-2-yl}-5-{[6-(methylsulfonyl)pyridin-3-yl]oxy}phenoxy)propan-1-ol,
{(4R)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-4-yl}methanol,
(2S)-2-(3-{5-[(4R,5S)-4,5-dimethyl-4,5-dihydro-1,3-oxazol-2-yl]-1H-pyrrol-2-yl}-5-{[6-(methylsulfonyl)pyridin-3-yl]oxy}phenoxy)propan-1-ol,
{(4R,5R)-2-[5-(3-[(1S)-2-methoxy-1-methylethoxy]-5-{[6-(methylsulfonyl)pyridin-3-yl]oxy}phenyl)-1H-pyrrol-2-yl]-4-methyl-4,5-dihydro-1,3-oxazol-5-yl}methanol,
{(4R,5S)-2-[5-(3-[(1S)-2-methoxy-1-methylethoxy]-5-{[6-(methylsulfonyl)pyridin-3-yl]oxy}phenyl)-1H-pyrrol-2-yl]-5-methyl-4,5-dihydro-1,3-oxazol-4-yl}methanol,
(1S)-1-{(4S)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-4-yl}ethanol,
(1R)-1-{(4S)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-4-yl}ethanol,
(2S)-2-(3-{5-[(5S)-5-methyl-4,5-dihydro-1,3-oxazol-2-yl]-1H-pyrrol-2-yl}-5-{[5-(methylsulfonyl)pyrazin-2-yl]oxy}phenoxy)propan-1-ol,
{(5R)-2-[5-(3-[(1S)-2-methoxy-1-methylethoxy]-5-{[5-(methylsulfonyl)pyrazin-2-yl]oxy}phenyl)-1H-pyrrol-2-yl]-4,5-dihydro-1,3-oxazol-5-yl}methanol,
(2S)-2-(3-{5-[(4R)-4-methyl-4,5-dihydro-1,3-oxazol-2-yl]-1H-pyrrol-2-yl}-5-{[5-(methylsulfonyl)pyrazin-2-yl]oxy}phenoxy)propan-1-ol,
(2S)-2-(3-{5-[(4R)-4-ethyl-4,5-dihydro-1,3-oxazol-2-yl]-1H-pyrrol-2-yl}-5-{[5-(methylsulfonyl)pyrazin-2-yl]oxy}phenoxy)propan-1-ol,
(2S)-2-(3-{5-[(4R,5S)-4,5-dimethyl-4,5-dihydro-1,3-oxazol-2-yl]-1H-pyrrol-2-yl}-5-{[5-(methylsulfonyl)pyrazin-2-yl]oxy}phenoxy)propan-1-ol,
{(4R,5S)-2-[5-(3-{[(2S)-1-methoxypropan-2-yl]oxy}-5-{[5-(methylsulfonyl)pyrazin-2-yl]oxy}phenyl)-1H-pyrrol-2-yl]-5-methyl-4,5-dihydro-1,3-oxazol-4-yl}methanol,
(1S)-1-{(4S)-2-[5-(3-{[(2S)-1-methoxypropan-2-yl]oxy}-5-{[5-(methylsulfonyl)pyrazin-2-yl]oxy}phenyl)-1H-pyrrol-2-yl]-4,5-dihydro-1,3-oxazol-4-yl}ethanol, or
(1R)-1-{(4S)-2-[5-(3-{[(2S)-1-methoxypropan-2-yl]oxy}-5-{[5-(methylsulfonyl)pyrazin-2-yl]oxy}phenyl)-1H-pyrrol-2-yl]-4,5-dihydro-1,3-oxazol-4-yl}ethanol.

(30) a compound described in (1) above, wherein the compound represented by the general formula (I) is:
{(5R)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-5-yl}methanol,
(2S)-2-(3-{5-[(4R)-4-methyl-4,5-dihydro-1,3-oxazol-2-yl]-1H-pyrrol-2-yl}-5-{[6-(methylsulfonyl)pyridin-3-yl]oxy}phenoxy)propan-1-ol,
(2S)-2-(3-{5-[(4R)-4-ethyl-4,5-dihydro-1,3-oxazol-2-yl]-1H-pyrrol-2-yl}-5-{[6-(methylsulfonyl)pyridin-3-yl]oxy}phenoxy)propan-1-ol,
{(4R)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-4-yl}methanol,
(2S)-2-(3-{5-[(4R,5S)-4,5-dimethyl-4,5-dihydro-1,3-oxazol-2-yl]-1H-pyrrol-2-yl}-5-{[6-(methylsulfonyl)pyridin-3-yl]oxy}phenoxy)propan-1-ol,
{(4R,5R)-2-[5-(3-[(1S)-2-methoxy-1-methylethoxy]-5-{[6-(methylsulfonyl)pyridin-3-yl]oxy}phenyl)-1H-pyrrol-2-yl]-4-methyl-4,5-dihydro-1,3-oxazol-5-yl}methanol,
{(4R,5S)-2-[5-(3-[(1S)-2-methoxy-1-methylethoxy]-5-{[6-(methylsulfonyl)pyridin-3-yl]oxy}phenyl)-1H-pyrrol-2-yl]-5-methyl-4,5-dihydro-1,3-oxazol-4-yl}methanol,
(1S)-1-{(4S)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-4-yl}ethanol,
(1R)-1-{(4S)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-4-yl}ethanol,
(2S)-2-(3-{5-[(5S)-5-methyl-4,5-dihydro-1,3-oxazol-2-yl]-1H-pyrrol-2-yl}-5-{[5-(methylsulfonyl)pyrazin-2-yl]oxy}phenoxy)propan-1-ol,
{(5R)-2-[5-(3-[(1S)-2-methoxy-1-methylethoxy]-5-{[5-(methylsulfonyl)pyrazin-2-yl]oxy}phenyl)-1H-pyrrol-2-yl]-4,5-dihydro-1,3-oxazol-5-yl}methanol,
(2S)-2-(3-{5-[(4R)-4-methyl-4,5-dihydro-1,3-oxazol-2-yl]-1H-pyrrol-2-yl}-5-{[5-(methylsulfonyl)pyrazin-2-yl]oxy}phenoxy)propan-1-ol,
(2S)-2-(3-{5-[(4R)-4-ethyl-4,5-dihydro-1,3-oxazol-2-yl]-1H-pyrrol-2-yl}-5-{[5-(methylsulfonyl)pyrazin-2-yl]oxy}phenoxy)propan-1-ol,
(2S)-2-(3-{5-[(4R,5S)-4,5-dimethyl-4,5-dihydro-1,3-oxazol-2-yl]-1H-pyrrol-2-yl}-5-{[5-(methylsulfonyl)pyrazin-2-yl]oxy}phenoxy)propan-1-ol,
{(4R,5S)-2-[5-(3-{[(2S)-1-methoxypropan-2-yl]oxy}-5-{[5-(methylsulfonyl)pyrazin-2-yl]oxy}phenyl)-1H-pyrrol-2-yl]-5-methyl-4,5-dihydro-1,3-oxazol-4-yl}methanol,
(1S)-1-{(4S)-2-[5-(3-{[(2S)-1-methoxypropan-2-yl]oxy}-5-{[5-(methylsulfonyl)pyrazin-2-yl]oxy}phenyl)-1H-pyrrol-2-yl]-4,5-dihydro-1,3-oxazol-4-yl}ethanol, or
(1R)-1-{(4S)-2-[5-(3-{[(2S)-1-methoxypropan-2-yl]oxy}-5-{[5-(methylsulfonyl)pyrazin-2-yl]oxy}phenyl)-1H-pyrrol-2-yl]-4,5-dihydro-1,3-oxazol-4-yl}ethanol.

(31) a glucokinase activator containing as an active ingredient thereof a compound or pharmacologically acceptable salt thereof described in any one selected from (1) to (30) above;

(32) a pharmaceutical composition containing as an active ingredient thereof a compound or pharmacologically acceptable salt thereof described in any one selected from (1) to (30) above;

(33) the pharmaceutical composition described in (32) above, wherein the pharmaceutical composition has glucokinase activating activity;

(34) the pharmaceutical composition described in (32) above, wherein the pharmaceutical composition is for treating and/or preventing a disease that is treatable and/or preventable by glucokinase activating activity;

(35) the pharmaceutical composition described in (32) above, wherein the pharmaceutical composition is for treating and/or preventing a disease for which the symptoms thereof are treated, improved, diminished and/or prevented by activation of glucokinase and maintenance of glucose homeostasis or regulation of blood glucose level;

(36) the pharmaceutical composition described in (32) above, wherein the pharmaceutical composition is for treating and/or preventing diabetes, impaired glucose tolerance, gestational diabetes, chronic complications of diabetes (including diabetic peripheral neuropathy, diabetic nephropathy, diabetic retinopathy and diabetic macroangiopathy) or metabolic syndrome;

(37) the pharmaceutical composition described in (32) above, wherein the pharmaceutical composition is for treating and/or preventing diabetes or impaired glucose tolerance;

(38) a use of a compound, or pharmacologically acceptable salt thereof, described in any one selected from (1) to (30) above, for producing a pharmaceutical composition;

(39) the use described in (38) above, wherein the pharmaceutical composition is a composition for activating glucokinase;

(40) the use described in (38) above, wherein the pharmaceutical composition is a composition for treating and/or preventing diabetes, impaired glucose tolerance, gestational diabetes, chronic complications of diabetes (including diabetic peripheral neuropathy, diabetic nephropathy, diabetic retinopathy and diabetic macroangiopathy) or metabolic syndrome;

(41) the use described in (38) above, wherein the pharmaceutical composition is a composition for treating and/or preventing diabetes or impaired glucose tolerance;

(42) a glucokinase activation method, comprising administering a pharmacologically effective amount of a compound or pharmacologically acceptable salt thereof described in any one selected from (1) to (30) above to a warm-blooded animal;

(43) a method for treating and/or preventing a disease, comprising administering a pharmacologically effective amount of a compound or pharmacologically acceptable salt thereof described in any one selected from (1) to (30) above to a warm-blooded animal;

(44) the method described in (43) above, wherein the disease is diabetes, impaired glucose tolerance, gestational diabetes, chronic complications of diabetes (including diabetic peripheral neuropathy, diabetic nephropathy, diabetic retinopathy and diabetic macroangiopathy) or metabolic syndrome;

(45) the method described in (43) above, wherein the disease is diabetes or impaired glucose tolerance; and,

(46) the method described in any one selected from (42) to (45) above, wherein the warm-blooded animal is a human.

In the present invention, a "halogen atom" refers to a fluorine atom, a chlorine atom, a bromine atom or an iodine atom. The halogen atom is preferably a fluorine atom or a chlorine atom, and more preferably a chlorine atom.

In the present invention, a "$C_1$-$C_6$ alkyl group" refers to a linear or branched alkyl group having 1 to 6 carbon atom(s). Examples of the $C_1$-$C_6$ alkyl group include a methyl group, an ethyl group, a propyl group, an isopropyl group, a butyl group, an isobutyl group, an s-butyl group, a t-butyl group, a pentyl group, an isopentyl group, a 2-methylbutyl group, a neopentyl group, a 1-ethylpropyl group, a hexyl group, an isohexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group and a 1,2-dimethylbutyl group, and the $C_1$-$C_6$ alkyl group is preferably a linear or branched alkyl group having 1 to 4 carbon atom(s) ($C_1$-$C_4$ alkyl group), more preferably a methyl group or an ethyl group ($C_1$-$C_2$ alkyl group), and even more preferably a methyl group.

In the present invention, a "$C_1$-$C_6$ halogenated alkyl group" refers to a group in which 1 to 5 of the same or different above-mentioned "halogen atom" are bonded to the above-mentioned "$C_1$-$C_6$ alkyl group". Examples of $C_1$-$C_6$ halogenated alkyl groups include a trifluoromethyl group, a trichloromethyl group, a difluoromethyl group, a dichloromethyl group, a dibromomethyl group, a fluoromethyl group, a 2,2,2-trifluoroethyl group, a 2,2,2-trichloroethyl group, a 2-bromoethyl group, a 2-chloroethyl group and a 2-fluoroethyl group, and the $C_1$-$C_6$ halogenated alkyl group is preferably a group in which 1 to 5 of the same or different above-mentioned "halogen atom" are bonded to the above-mentioned "$C_1$-$C_4$ alkyl group" ($C_1$-$C_4$ halogenated alkyl group), more preferably a group in which 1 to 5 of the same or different above-mentioned "halogen atom" are bonded to the above-mentioned "$C_1$-$C_2$ alkyl group" ($C_1$-$C_2$ halogenated alkyl group), and even more preferably a trifluoromethyl group or a fluoromethyl group.

In the present invention, a "$C_2$-$C_6$ alkenyl group" refers to a group among above-mentioned "$C_1$-$C_6$ alkyl group" having one double bond and 2 to 6 carbon atoms. Examples of the $C_2$-$C_6$ alkenyl group include an ethenyl group, a 1-propenyl group, a 2-propenyl group, a 1-methyl-2-propenyl group, a 1-methyl-1-propenyl group, a 2-methyl-1-propenyl group, a 2-methyl-2-propenyl group, a 1-butenyl group, a 2-butenyl group, a 3-butenyl group, a 1-pentenyl group, a 4-pentenyl group, a 1-methyl-4-pentenyl group and a 5-hexenyl group, and the $C_2$-$C_6$ alkenyl group is preferably an alkenyl group having 2 to 4 carbon atoms ($C_2$-$C_4$ alkenyl group), and more preferably a 2-propenyl group.

In the present invention, a "$C_2$-$C_6$ alkynyl group" refers to a group among above-mentioned "$C_1$-$C_6$ alkyl group" having one triple bond and 2 to 6 carbon atoms. Examples of the $C_2$-$C_6$ alkynyl group include an ethynyl group, a 1-propynyl group, a 2-propynyl group, a 1-methyl-2-propynyl group, a 1-butynyl group, a 2-butynyl group, a 1-methyl-2-butynyl group, a 3-butynyl group, a 2-pentynyl group and a 5-hexynyl group, and the $C_2$-$C_6$ alkynyl group is preferably an alkynyl group having 2 to 4 carbon atoms ($C_2$-$C_4$ alkynyl group), and more preferably a 2-propynyl group or a 2-butynyl group.

In the present invention, a "$C_1$-$C_6$ alkyl group substituted with 1 or 2 hydroxy group(s)" refers to a group in which 1 or 2 hydroxy group(s) are bonded to the above-mentioned "$C_1$-$C_6$ alkyl group". Examples of the $C_1$-$C_6$ alkyl group substituted with 1 or 2 hydroxy group(s) include a hydroxymethyl group, a 2-hydroxyethyl group, a 1-hydroxyethyl group, a 3-hydroxypropyl group, a 1,2-dihydroxyethyl group and a 2,3-dihydroxypropyl group, and the $C_1$-$C_6$ alkyl group substituted with 1 or 2 hydroxy group(s) is preferably a group in which 1 or 2 hydroxy group(s) are bonded to the above-mentioned "$C_1$-$C_4$ alkyl group", more preferably a group in which 1 or 2 hydroxy group(s) are bonded to the above-mentioned "$C_1$-$C_2$ alkyl group", and even more preferably a hydroxymethyl group or a hydroxyethyl group.

In the present invention, a "$C_1$-$C_6$ alkoxy group" refers to a group in which the above-mentioned "$C_1$-$C_6$ alkyl group" is bonded to an oxygen atom, and is a linear or branched alkoxy group having 1 to 6 carbon atom(s). Examples of the $C_1$-$C_6$ alkoxy group include a methoxy group, an ethoxy group, a propoxy group, an isopropoxy group, a butoxy group, an isobutoxy group, an s-butoxy group, a t-butoxy group, a pentoxy group, a 2-methylbutoxy group, a 3-ethylpropoxy group, a neopentoxy group, a hexyloxy group and a 2,3-dimethylbutoxy group, and the $C_1$-$C_6$ alkoxy group is preferably a linear or branched alkoxy group having 1 to 4 carbon atom(s) ($C_1$-$C_4$ alkoxy group), more preferably a methoxy group, an ethoxy group, a propoxy group or an isopropoxy group ($C_1$-$C_3$ alkoxy group), even more preferably a methoxy group or an ethoxy group ($C_1$-$C_2$ alkoxy group), and particularly preferably a methoxy group.

In the present invention, a "$C_1$-$C_6$ halogenated alkoxy group" refers to a group in which 1 to 5 of the same or different above-mentioned "halogen atom" are bonded to the above-mentioned "$C_1$-$C_6$ alkoxy group". Examples of the $C_1$-$C_6$ halogenated alkoxy group include a trifluoromethoxy group, a trichloromethoxy group, a difluoromethoxy group, a dichloromethoxy group, a dibromomethoxy group, a fluoromethoxy group, a 2,2,2-trifluoroethoxy group, a 2,2,2-trichloroethoxy group, a 2-chloroethoxy group, a 2-fluoroethoxy group, and a pentafluoroethoxy group, and the $C_1$-$C_6$ halogenated alkoxy group is preferably a group in which 1 to 5 of the same or different above-mentioned "halogen atom" are bonded to the above-mentioned "$C_1$-$C_4$ alkoxy group" ($C_1$-$C_4$ halogenated alkoxy group), more preferably a group in which 1 to 5 of the same or different above-mentioned "halogen atom" are bonded to the above-mentioned "$C_1$-$C_2$ alkoxy group" ($C_1$-$C_2$ halogenated alkoxy group), and even more preferably a trifluoromethoxy group.

In the present invention, a "($C_1$-$C_6$ alkoxy)-($C_1$-$C_6$ alkyl) group" refers to a group in which one above-mentioned "$C_1$-$C_6$ alkoxy group" is bonded to the above-mentioned "$C_1$-$C_6$ alkyl group". Examples of the ($C_1$-$C_6$ alkoxy)-($C_1$-$C_6$ alkyl) group include a methoxymethyl group, an ethoxymethyl group, a propoxymethyl group, an isopropoxymethyl group, a butoxymethyl group, an s-butoxymethyl group, a t-butoxymethyl group, a 2-methoxyethyl group and a 3-isopropoxypropyl group, and the ($C_1$-$C_6$ alkoxy)-($C_1$-$C_6$ alkyl) group is preferably a group in which one above-mentioned "$C_1$-$C_4$ alkoxy group" is bonded to the above-mentioned "$C_1$-$C_4$ alkyl group" (($C_1$-$C_4$ alkoxy)-($C_1$-$C_4$ alkyl) group), more preferably a group in which one above-mentioned "$C_1$-$C_2$ alkoxy group" is bonded to the above-mentioned "$C_1$-$C_2$ alkyl group" (($C_1$-$C_2$ alkoxy)-($C_1$-$C_2$ alkyl) group), and even more preferably a methoxymethyl group.

In the present invention, a "($C_1$-$C_6$ alkoxy)-($C_1$-$C_6$ alkoxy) group" refers to a group in which one above-mentioned "$C_1$-$C_6$ alkoxy group" is bonded to the above-mentioned "$C_1$-$C_6$ alkoxy group". Examples of the ($C_1$-$C_6$ alkoxy)-($C_1$-$C_6$ alkoxy) group include a methoxymethyloxy group, an ethoxymethyloxy group, a propoxymethyloxy group, a butoxymethyloxy group, a 2-methoxyethyloxy group and a 3-isopropoxypropyloxy group, and the ($C_1$-$C_6$ alkoxy)-($C_1$-$C_6$ alkoxy) group is preferably a group in which one above-mentioned "$C_1$-$C_4$ alkoxy group" group is bonded to the above-mentioned "$C_1$-$C_4$ alkoxy group" (($C_1$-$C_4$ alkoxy)-($C_1$-$C_4$ alkoxy) group), more preferably a group in which one above-mentioned "$C_1$-$C_2$ alkoxy group" is bonded to the above-mentioned "$C_1$-$C_2$ alkoxy group" (($C_1$-$C_2$ alkoxy)-($C_1$-$C_7$ alkoxy) group), and even more preferably a methoxymethyloxy group.

In the present invention, a "$C_2$-$C_7$ alkylcarbonyl group" refers to a group in which one above-mentioned "$C_1$-$C_6$ alkyl group" is bonded to a carbonyl group. Examples of the $C_2$-$C_7$ alkylcarbonyl group include an acetyl group, a propionyl group, a butyryl group, an isobutyryl group, a pentanoyl group, a pivaloyl group and a valeryl group, and the $C_2$-$C_7$ alkylcarbonyl group is preferably a group in which one above-mentioned "$C_1$-$C_4$ alkyl group" is bonded to a carbonyl group ($C_2$-$C_5$ alkylcarbonyl group), more preferably an acetyl group or a propionyl group ($C_2$-$C_3$ alkylcarbonyl group), and even more preferably an acetyl group.

In the present invention, a "$C_2$-$C_7$ alkoxycarbonyl group" refers to a group in which one above-mentioned "$C_1$-$C_6$ alkoxy group" is bonded to a carbonyl group. Examples of the $C_2$-$C_7$ alkoxycarbonyl group include a methoxycarbonyl group, an ethoxycarbonyl group, a propoxycarbonyl group, an isopropoxycarbonyl group, a butoxycarbonyl group, an isobutoxycarbonyl group, an s-butoxycarbonyl group and a t-butoxycarbonyl group, and the $C_2$-$C_7$ alkoxycarbonyl group is preferably a group in which one above-mentioned "$C_1$-$C_4$ alkoxy group" is bonded to a carbonyl group ($C_2$-$C_5$ alkoxycarbonyl group), more preferably a methoxycarbonyl group or an ethoxycarbonyl group ($C_2$-$C_3$ alkoxycarbonyl group), and even more preferably a methoxycarbonyl group.

In the present invention, a "$C_2$-$C_7$ alkylcarbonyloxy group" refers to a group in which a carbonyl group to which is bonded one above-mentioned "$C_1$-$C_6$ alkyl group" is bonded to an oxygen atom. Examples of the $C_2$-$C_7$ alkylcarbonyloxy group include an acetoxy group, a propionyloxy group, a butyryloxy group, an isobutyryloxy group, a pentanoyloxy group, a pivaloyloxy group, a valeryloxy group and an isovaleryloxy group, and the $C_2$-$C_7$ alkylcarbonyloxy group is preferably a group in which a carbonyl group to which is bonded one above-mentioned "$C_1$-$C_4$ alkyl group" is bonded to an oxygen atom ($C_2$-$C_5$ alkylcarbonyloxy group), more preferably an acetoxy group or a propionyloxy group ($C_2$-$C_3$ alkylcarbonyloxy group), and even more preferably an acetoxy group.

In the present invention, a "$C_2$-$C_7$ alkoxycarbonyloxy group" refers to a group in which a carbonyl group to which is bonded one above-mentioned "$C_1$-$C_6$ alkoxy group" is bonded to an oxygen atom. Examples of the $C_2$-$C_7$ alkoxycarbonyloxy group include a methoxycarbonyloxy group, an ethoxycarbonyloxy group, a propoxycarbonyloxy group, an isopropoxycarbonyloxy group, a butoxycarbonyloxy group, an s-butoxycarbonyloxy group and a t-butoxycarbonyloxy group, and the $C_2$-$C_7$ alkoxycarbonyloxy group is preferably a group in which a carbonyl group to which is bonded one above-mentioned "$C_1$-$C_4$ alkoxy group" is bonded to an oxygen atom ($C_2$-$C_5$ alkoxycarbonyloxy group), more preferably a methoxycarbonyloxy group or an ethoxycarbonyloxy group ($C_2$-$C_3$ alkoxycarbonyloxy group), and even more preferably a methoxycarbonyloxy group.

In the present invention, a "mono-$C_1$-$C_6$ alkylamino group" refers to a group in which one above-mentioned "$C_1$-$C_6$ alkyl group" is bonded to an amino group. Examples of the mono-$C_1$-$C_6$ alkylamino group include a methylamino group, an ethylamino group, a propylamino group, an isopropylamino group, a butylamino group, an isobutylamino group, an s-butylamino group, a t-butylamino group, a pentylamino group, an isopentylamino group, a 2-methylbutylamino group, a neopentylamino group, a 1-ethylpropylamino group, a hexylamino group and an isohexylamino group, and the mono-$C_1$-$C_6$ alkylamino group is preferably a group in which one above-mentioned "$C_1$-$C_4$ alkyl group" is bonded to an amino group (mono-$C_1$-$C_4$ alkylamino group), more preferably a methylamino group or an ethylamino group (mono-$C_1$-$C_2$ alkylamino group), and even more preferably a methylamino group.

In the present invention, a "mono-$C_1$-$C_6$ halogenated alkylamino group" refers to a group in which one above-mentioned "$C_1$-$C_6$ halogenated alkyl group" is bonded to an amino group. Examples of the mono-$C_1$-$C_6$ halogenated alkylamino group include a trifluoromethylamino group, a trichloromethylamino group, a difluoromethylamino group, a dichloromethylamino group, a dibromomethylamino group, a fluoromethylamino group, a 2,2,2-trifluoroethylamino group, a 2,2,2-trichloroethylamino group, a 2-bromoethylamino group, a 2-chloroethylamino group and a 2-fluoroethylamino group, and the mono-$C_1$-$C_6$ halogenated alkylamino group is preferably a group in which one above-mentioned "$C_1$-$C_4$ halogenated alkyl group" is bonded to an amino group (mono-$C_1$-$C_4$ halogenated alkylamino group), more preferably a group in which one above-mentioned "$C_1$-$C_2$ halogenated alkyl group" is bonded to an amino group (mono-$C_1$-$C_2$ halogenated alkylamino group), and even more preferably a 2-chloroethylamino group.

In the present invention, a "di-($C_1$-$C_6$ alkyl)amino group" refers to a group in which two of the same or different above-mentioned "$C_1$-$C_6$ alkyl group" is bonded to an amino group. Examples of the di-($C_1$-$C_6$ alkyl)amino group include a dimethylamino group, a diethylamino group, a dipropylamino group, a diisopropylamino group, a dibutylamino group, a diisobutylamino group, a dipentylamino group, a diisopentylamino group, a dineopentylamino group, a dihexylamino group, an N-ethyl-N-methylamino group, an N-methyl-N-propyl amino group, an N-isopropyl-N-methylamino group, an N-butyl-N-methylamino group, an N-isobutyl-N-methylamino group, an N-methyl-N-pentylamino group, an N-isopentyl-N-methylamino group, an N-ethyl-N-propylamino group, an N-ethyl-N-isopropylamino group, an N-butyl-N-ethylamino group and an N-ethyl-N-isopentylamino group, and the di-($C_1$-$C_6$ alkyl)amino group is preferably a group in which two of the same or different above-mentioned "$C_1$-$C_4$ alkyl group" is bonded to an amino group (di-($C_1$-$C_4$ alkyl)amino group), more preferably a dimethylamino group, a diethylamino group or an N-ethyl-N-methylamino group (di-($C_1$-$C_2$ alkyl)amino group), and even more preferably a dimethylamino group.

In the present invention, a "di-($C_1$-$C_6$ halogenated alkyl)amino group" refers to a group in which two of the same or different above-mentioned "$C_1$-$C_6$ halogenated alkyl group" is bonded to an amino group. Examples of the "di-($C_1$-$C_6$ halogenated alkyl)amino group include a di-(trifluoromethyl)amino group, a di-(fluoromethyl)amino group, a di-(2,2,2-trichloroethyl)amino group, a di-(2-chloroethyl)amino group and an N-(2-chloroethyl)-N-(2-fluoroethyl)amino group, and the di-($C_1$-$C_6$ halogenated alkyl)amino group is preferably a group in which two of the same or different above-mentioned "$C_1$-$C_4$ halogenated alkyl group" is bonded to an amino group (di-($C_1$-$C_4$ halogenated alkyl)amino group), and more preferably a di-(2-chloroethyl)amino group.

In the present invention, a "$C_1$-$C_6$ alkylthio group" refers to a group in which one above-mentioned "$C_1$-$C_6$ alkyl group" is bonded to a sulfur atom, and is a linear or branched alkylthio group having 1 to 6 carbon atom(s). Examples of the $C_1$-$C_6$ alkylthio group include a methylthio group, an ethylthio group, a propylthio group, an isopropylthio group, a butylthio group, an isobutylthio group, an s-butylthio group, a pentylthio group, a 1-ethylpropylthio group and a hexylthio group, and the $C_1$-$C_6$ alkylthio group is preferably a linear or branched alkylthio group having 1 to 4 carbon atom(s) ($C_1$-$C_4$ alkylthio group), more preferably a methylthio group or an ethylthio group ($C_1$-$C_2$ alkylthio group), and even more preferably a methylthio group.

In the present invention, a "$C_1$-$C_6$ alkylsulfonyl group" refers to a group in which one above-mentioned "$C_1$-$C_6$ alkyl group" is bonded to a sulfonyl group, and is a linear or branched alkylsulfonyl group having 1 to 6 carbon atom(s). Examples of the $C_1$-$C_6$ alkylsulfonyl group include a methylsulfonyl group, an ethylsulfonyl group, a propylsulfonyl group, an isopropylsulfonyl group, a butylsulfonyl group, an isobutylsulfonyl group, an s-butylsulfonyl group and a pentylsulfonyl group, and the $C_1$-$C_6$ alkylsulfonyl group is preferably a linear or branched alkylsulfonyl group having 1 to 4 carbon atom(s) ($C_1$-$C_4$ alkylsulfonyl group), more preferably a methylsulfonyl group or an ethylsulfonyl group ($C_1$-$C_2$ alkylsulfonyl group), and even more preferably a methylsulfonyl group.

In the present invention, a "$C_3$-$C_6$ cycloalkylsulfonyl group" refers to a cyclopropylsulfonyl group, a cyclobutylsulfonyl group, a cyclopentylsulfonyl group or a cyclohexylsulfonyl group. The $C_3$-$C_6$ cycloalkylsulfonyl group is preferably a cyclopropylsulfonyl group.

In the present invention, a "$C_1$-$C_6$ hydroxyalkylsulfonyl group" refers to a group in which one above-mentioned "$C_1$-$C_6$ alkyl group" to which is bonded one hydroxy group is bonded to a sulfonyl group, and is a linear or branched hydroxyalkylsulfonyl group having 1 to 6 carbon atom(s). Examples of the $C_1$-$C_6$ hydroxyalkylsulfonyl group include a hydroxymethylsulfonyl group, a 2-hydroxyethylsulfonyl group, a 1-hydroxyethylsulfonyl group and a 3-hydroxypropylsulfonyl group, and the $C_1$-$C_6$ hydroxyalkylsulfonyl group is preferably a linear or branched hydroxyalkylsulfonyl group having 1 to 4 carbon atom(s) ($C_1$-$C_4$ hydroxyalkylsulfonyl group), more preferably a hydroxymethylsulfonyl group or a hydroxyethylsulfonyl group ($C_1$-$C_2$ hydroxyalkylsulfonyl group), and even more preferably a hydroxymethylsulfonyl group.

In the present invention, a "($C_1$-$C_6$ alkoxy)-($C_1$-$C_6$ alkylsulfonyl) group" refers to a group in which one above-mentioned "$C_1$-$C_6$ alkoxy group" is bonded to the above-mentioned "$C_1$-$C_6$ alkylsulfonyl group". Examples of the ($C_1$-$C_6$ alkoxy)-($C_1$-$C_6$ alkylsulfonyl) group include a methoxymethylsulfonyl group, an ethoxymethylsulfonyl group, a propoxymethylsulfonyl group, an isopropoxymethylsulfonyl group, a butoxymethylsulfonyl group and an s-butoxymethylsulfonyl group, and the ($C_1$-$C_6$ alkoxy)-($C_1$-$C_6$ alkylsulfonyl) group is preferably a group in which one above-mentioned "$C_1$-$C_4$ alkoxy group" is bonded to the above-mentioned "$C_1$-$C_4$ alkylsulfonyl group" (($C_1$-$C_4$ alkoxy)-($C_1$-$C_4$ alkylsulfonyl) group), more preferably a group in which one above-mentioned "$C_1$-$C_2$ alkoxy group" is bonded to the above-mentioned "$C_1$-$C_2$ alkylsulfonyl group" (($C_1$-$C_2$ alkoxy)-($C_1$-$C_2$ alkylsulfonyl) group), and even more preferably a methoxymethylsulfonyl group.

In the present invention, a "group represented by the formula —V—NR$^5$R$^6$ (wherein V represents a carbonyl group or a sulfonyl group, and R$^5$ and R$^6$ may be the same or different and respectively represent a hydrogen atom or a $C_1$-$C_6$ alkyl group, or R$^5$ and R$^6$ together with the nitrogen atom bonded thereto form a 4- to 6-membered saturated heterocycle that may be substituted with 1 or 2 group(s) independently selected from a $C_1$-$C_6$ alkyl group and a hydroxy group, and the 4- to 6-membered saturated heterocycle may further contain one oxygen atom or nitrogen atom)" refers to a "group represented by the formula —C(=O)—NR$^5$R$^6$" or a "group represented by the formula —SO$_2$—NR$^5$R$^6$", the "group represented by the formula —C(=O)—NR$^5$R$^6$" is a carbamoyl group, "mono-C$_1$-C$_6$ alkylaminocarbonyl group (group in which an amino group to which is bonded one above-mentioned "C$_1$-C$_6$ alkyl group" is bonded to a carbonyl group)", "di(C$_1$-C$_6$ alkyl)aminocarbonyl group (group in which an amino group to which are bonded two of the same or different above-mentioned "C$_1$-C$_6$ alkyl group" is bonded to a carbonyl group)" or "group in which a nitrogen atom of a 4- to 6-membered saturated heterocycle, which may be substituted with 1 or 2 group(s) independently selected from a C$_1$-C$_6$ alkyl group and a hydroxy group (4- to 6-membered completely reduced saturated heterocyclic group that contains one nitrogen atom and may further contain one oxygen atom or nitrogen atom), is bonded to a carbonyl group", and the "group represented by the formula —SO$_2$—NR$^5$R$^6$" is a sulfamoyl group, "mono-C$_1$-C$_6$ alkylaminosulfonyl group (group in which an amino group to which is bonded one above-mentioned "C$_1$-C$_6$ alkyl group" is bonded to a sulfonyl group", "di-(C$_1$-C$_6$ alkyl)aminosulfonyl group (group in which an amino group to which are bonded two of the same or different above-mentioned "C$_1$-C$_6$ alkyl group" is bonded to a sulfonyl group", or "group in which a nitrogen atom of a 4- to 6-membered saturated heterocycle, which may be substituted with 1 or 2 group(s) independently selected from a C$_1$-C$_6$ alkyl group and a hydroxy group (4- to 6-membered completely reduced saturated heterocyclic group that contains one nitrogen atom and may further contain one oxygen atom or nitrogen atom), is bonded to a sulfonyl group". Examples of the aforementioned group include a carbamoyl group, a methylaminocarbonyl group, an ethylaminocarbonyl group, a propylaminocarbonyl group, a dimethylaminocarbonyl group, a diethylaminocarbonyl group, a dipropylaminocarbonyl group, an N-ethyl-N-methylaminocarbonyl group, an N-methyl-N-propylaminocarbonyl group, a (1-azetidinyl)carbonyl group, a (3-hydroxy-1-azetidinyl)carbonyl group, a (1-pyrrolidinyl)carbonyl group, a (4-morpholinyl)carbonyl group, a (4-methyl-1-piperazinyl)carbonyl group, a sulfamoyl group, a methylaminosulfonyl group, an ethylaminosulfonyl group, a propylaminosulfonyl group, a dimethylaminosulfonyl group, a diethylaminosulfonyl group, a dipropylaminosulfonyl group, an N-ethyl-N-methylaminosulfonyl group, an N-methyl-N-propylaminosulfonyl group and a (1-azetidinyl)sulfonyl group, and the aforementioned group is preferably a carbamoyl group, a methylaminocarbonyl group, a dimethylaminocarbonyl group, a (1-azetidinyl)carbonyl group, a (1-pyrrolidinyl)carbonyl group, a (4-morpholinyl)carbonyl group, a (4-methyl-1-piperazinyl)carbonyl group, a methylaminosulfonyl group or a (1-azetidinyl)sulfonyl group, more preferably a dimethylaminocarbonyl group, a (1-azetidinyl)carbonyl group, a (1-pyrrolidinyl)carbonyl group or a (4-methyl-1-piperazinyl)carbonyl group, and even more preferably a dimethylaminocarbonyl group or a (1-azetidinyl)carbonyl group.

In the present invention, a "mono-C$_2$-C$_7$ alkylcarbonylamino group" refers to a group in which a carbonyl group to which is bonded one above-mentioned "C$_1$-C$_6$ alkyl group" is bonded to an amino group. Examples of the mono-C$_2$-C$_7$ alkylcarbonylamino group include an acetamido group, an ethylcarbonylamino group, a propylcarbonylamino group, an isopropylcarbonylamino group, a butylcarbonylamino group and an isobutylcarbonylamino group, and the mono-C$_2$-C$_7$ alkylcarbonylamino group is preferably a group in which a carbonyl group to which is bonded one above-mentioned "C$_1$-C$_4$ alkyl group" is bonded to an amino group (mono-C$_2$-C$_5$ alkylcarbonylamino group), more preferably an acetamido group or an ethylcarbonylamino group (mono-C$_2$-C$_3$ alkylcarbonylamino group), and even more preferably an acetamido group.

In the present invention, a "mono-C$_1$-C$_6$ alkylaminocarbonyloxy group" refers to a group in which a carbonyl group, to which is bonded an amino group bonded to one above-mentioned "C$_1$-C$_6$ alkyl group", is bonded to an oxygen atom. Examples of the mono-C$_1$-C$_6$ alkylaminocarbonyloxy group include a methylaminocarbonyloxy group, an ethylaminocarbonyloxy group, a propylaminocarbonyloxy group, an isopropylaminocarbonyloxy group and a butylaminocarbonyloxy group, and the mono-C$_1$-C$_6$ alkylaminocarbonyloxy group is preferably a methylaminocarbonyloxy group or an ethylaminocarbonyloxy group (mono-C$_1$-C$_2$ alkylaminocarbonyloxy group), and more preferably a methylaminocarbonyloxy group.

In the present invention, a "di-(C$_1$-C$_6$ alkyl)aminocarbonyloxy group" refers to a group in which a carbonyl group, to which is bonded an amino group bonded to two of the same or different above-mentioned "C$_1$-C$_6$ alkyl group", is bonded to an oxygen atom. Examples of the di-(C$_1$-C$_6$ alkyl)aminocarbonyloxy group include a dimethylaminocarbonyloxy group, a diethylaminocarbonyloxy group, a dipropylaminocarbonyloxy group, an N-ethyl-N-methylaminocarbonyloxy group and an N-methyl-N-propylaminocarbonyloxy group, and the di-(C$_1$-C$_6$ alkyl)aminocarbonyloxy group is preferably a dimethylaminocarbonyloxy group, a diethylaminocarbonyloxy group or an N-ethyl-N-methylaminocarbonyloxy group (di-(C$_1$-C$_7$ alkyl)aminocarbonyloxy group), and more preferably a dimethylaminocarbonyloxy group.

In the present invention, a "mono-C$_2$-C$_7$ alkoxycarbonylamino group" refers to a group in which a carbonyl group to which is bonded one above-mentioned "C$_1$-C$_6$ alkoxy group" is bonded to an amino group. Examples of the mono-C$_2$-C$_7$ alkoxycarbonylamino group include a methoxycarbonylamino group, an ethoxycarbonylamino group, a propoxycarbonylamino group, an isopropoxycarbonylamino group and a butoxycarbonylamino group, and the mono-C$_2$-C$_7$ alkoxycarbonylamino group is preferably a methoxycarbonylamino group or an ethoxycarbonylamino group (C$_2$-C$_3$ alkoxycarbonylamino group), and more preferably a methoxycarbonylamino group.

In the present invention, a "mono-C$_1$-C$_6$ alkylsulfonylamino group" refers to a group in which a sulfonyl group to which is bonded one above-mentioned "C$_1$-C$_6$ alkyl group" is bonded to an amino group. Examples of the mono-C$_1$-C$_6$ alkylsulfonylamino group include a methylsulfonylamino group, an ethylsulfonylamino group, a propylsulfonylamino group, an isopropylsulfonylamino group, a butylsulfonylamino group, a t-butylsulfonylamino group and a 2-ethylbutylsulfonylamino group, and the mono-C$_1$-C$_6$ alkylsulfonylamino group is preferably a group in which a sulfonyl group to which is bonded one above-mentioned "C$_1$-C$_4$ alkyl group" is bonded to an amino group (mono-C$_1$-C$_4$ alkylsulfonylamino group), more preferably a methylsulfonylamino group or an ethylsulfonylamino group (mono-C$_1$-C$_2$ alkylsulfonylamino group), and even more preferably a methylsulfonylamino group.

In the present invention, a "1,3,4-oxadiazol-2-yl group optionally substituted with a C$_1$-C$_6$ alkyl group at the 5-position" refers to a group in which a C$_1$-C$_6$ alkyl group is substituted at the 5-position of a 1,3,4-oxadiazol-2-yl group. Examples of the aforementioned group include a 5-methyl-1,3,4-oxadiazol-2-yl group and a 5-ethyl-1,3,4-oxadiazol-2-yl group, and the aforementioned group is preferably a 5-methyl-1,3,4-oxadiazol-2-yl group.

In the present invention, a "1,3,4-thiadiazol-2-yl group optionally substituted with a $C_1$-$C_6$ alkyl group at the 5-position" refers to a group in which a $C_1$-$C_6$ alkyl group is substituted at the 5-position of a 1,3,4-thiadiazol-2-yl group. Examples of the aforementioned group include a 5-methyl-1,3,4-thiadiazol-2-yl group and a 5-ethyl-1,3,4-thiadiazol-2-yl group, and the aforementioned group is preferably a 5-methyl-1,3,4-thiadiazol-2-yl group.

In the present invention, a "heterocyclic group" refers to a 4- to 7-membered heterocyclic group that contains 1 to 3 sulfur atom(s), oxygen atom(s) and/or nitrogen atom(s), and may further contain 1 or 2 nitrogen atom(s), and in which the sulfur atom(s) may be bonded to 2 oxygen atoms. Examples of the heterocyclic group include an "aromatic heterocyclic group" such as a furyl group, a thienyl group, a pyrrolyl group, an azepinyl group, a pyrazolyl group, an imidazolyl group, an oxazolyl group, an isoxazolyl group, a thiazolyl group, an isothiazolyl group, a 1,3,4-oxadiazolyl group, a 1,3,4-thiadiazolyl group, a triazolyl group, a tetrazolyl group, a thiadiazolyl group, a pyranyl group, a pyridyl group, a pyridazinyl group, a pyrimidinyl group and a pyrazinyl group, and a "partially or completely reduced saturated heterocyclic group" such as a tetrahydropyranyl group, a tetrahydrothienyl group, a morpholinyl group, a thiomorpholinyl group, a pyrrolidinyl group, a pyrrolinyl group, an imidazolidinyl group, a pyrazolidinyl group, a piperidinyl group, a piperazinyl group, an oxazolinyl group, an oxazolidinyl group, an isoxazolidinyl group, a thiazolinyl group, a thiazolidinyl group, a pyrazolidinyl group, a dioxolanyl group, a dioxanyl group and a 5,6-dihydro-4H-1,3-oxazine group, and the above heterocyclic group may be fused with another cyclic group such as a benzene ring ("fused bicyclic heteroaryl group"), for example, a benzothienyl group, a benzothiazolyl group, a benzooxazolyl group, an isobenzofuranyl group, a 1,3-dihydroisobenzofuranyl group, a quinolyl group, a 1,3-benzodioxolanyl group, a 1,4-benzodioxanyl group, an indolyl group, an isoindolyl group and an indolinyl group. Heterocyclic groups formed by A and $R^1$ together with the carbon atom bonded thereto, that may be substituted with 1 to 3 group(s) independently selected from Substituent Group α, are preferably a 2-pyridyl group, a 5,6-dihydro-4H-1,3-oxazin-2-yl group, a 1,3-thiazol-2-yl group, a 1,3-oxazol-2-yl group, a 1,3,4-oxadiazol-2-yl group, a 1,3,4-thiadiazol-2-yl group, a 4,5-dihydro-1,3-thiazol-2-yl group, a 4,5-dihydro-1,3-oxazol-2-yl group or a 1,3-benzothiazol-2-yl group, more preferably a 1,3-thiazol-2-yl group, a 1,3,4-oxadiazol-2-yl group, a 4,5-dihydro-1,3-thiazol-2-yl group, a 4,5-dihydro-1,3-oxazol-2-yl group, a 1,3,4-thiadiazol-2-yl group or a 5,6-dihydro-4H-1,3-oxazin-2-yl group, and even more preferably a 4,5-dihydro-1,3-oxazol-2-yl group. In $R^2$, the heterocyclic group is preferably a 6-membered heterocyclic group containing 1 or 2 nitrogen atom(s), more preferably a pyridyl group or a pyrazinyl group, and even more preferably a 2-pyridyl group, a 3-pyridyl group or a 2-pyrazinyl group.

In the present invention, a "group represented by formula =$NOR^4$" refers to a group in which one hydroxy group or one above-mentioned "$C_1$-$C_6$ alkoxy group" is bonded to an imino group. The group represented by formula =$NOR^4$ is preferably a group represented by the formula =NOH.

In the present invention, a "heterocyclic group formed by A and $R^1$ together with the carbon atom bonded thereto and which may be substituted with 1 to 3 group(s) independently selected from Substituent Group α" refers to the above-mentioned "heterocyclic group" or the above-mentioned "heterocyclic group" that is substituted by 1 to 3 group(s) independently selected from Substituent Group α. The aforementioned group is preferably a 2-pyridyl group, 5,6-dihydro-4H-1,3-oxazin-2-yl group, 1,3-thiazol-2-yl group, 1,3-oxazol-2-yl group, 1,3,4-oxadiazol-2-yl group, 1,3,4-thiadiazol-2-yl group, 4,5-dihydro-1,3-thiazol-2-yl group, 4,5-dihydro-1,3-oxazol-2-yl group or 1,3-benzothiazol-2-yl group that may be substituted with 1 to 3 group(s) independently selected from Substituent Group γ, more preferably a 1,3-thiazol-2-yl group, a 5-methyl-1,3-thiazol-2-yl group, a 5-methyl-1,3,4-oxadiazol-2-yl group, a 4,5-dihydro-1,3-thiazol-2-yl group, a 4,5-dihydro-1,3-oxazol-2-yl group, a (5S)-5-methyl-4,5-dihydro-1,3-oxazol-2-yl group, a (5R)-5-methyl-4,5-dihydro-1,3-oxazol-2-yl group, a 5-hydroxymethyl-4,5-dihydro-1,3-oxazol-2-yl group, a (5R)-5-hydroxymethyl-4,5-dihydro-1,3-oxazol-2-yl group, a (4R)-4-methyl-4,5-dihydro-1,3-oxazol-2-yl group, a (4R)-4-ethyl-4,5-dihydro-1,3-oxazol-2-yl group, a (4R)-4-hydroxymethyl-4,5-dihydro-1,3-oxazol-2-yl group, a (4S)-4-[(1R)-1-hydroxyethyl]-4,5-dihydro-1,3-oxazol-2-yl group, a (4S)-4-[(1S)-1-hydroxyethyl]-4,5-dihydro-1,3-oxazol-2-yl group, a (4R,5S)-4,5-dimethyl-4,5-dihydro-1,3-oxazol-2-yl group, a (5S)-4-hydroxy-5-methyl-4,5-dihydro-1,3-oxazol-2-yl group, a (4R,5S)-4-hydroxymethyl-5-methyl-4,5-dihydro-1,3-oxazol-2-yl group, a (4R,5R)-5-hydroxymethyl-4-methyl-4,5-dihydro-1,3-oxazol-2-yl group, a 5-carboxyl-1,3-thiazol-2-yl group, a 5-dimethylaminocarbonyl-1,3-thiazol-2-yl group, a 5-methyl-1,3,4-thiadiazol-2-yl group or a 5,6-dihydro-4H-1,3-oxazin-2-yl group, even more preferably a 4,5-dihydro-1,3-oxazol-2-yl group, a (4R)-4-methyl-4,5-dihydro-1,3-oxazol-2-yl group, a (4R)-4-ethyl-4,5-dihydro-1,3-oxazol-2-yl group, a (5S)-5-methyl-4,5-dihydro-1,3-oxazol-2-yl group, a (4R)-4-hydroxymethyl-4,5-dihydro-1,3-oxazol-2-yl group, a (5R)-5-hydroxymethyl-4,5-dihydro-1,3-oxazol-2-yl group, a (4S)-4-[(1R)-1-hydroxyethyl]-4,5-dihydro-1,3-oxazol-2-yl group, a (4S)-4-[(1S)-1-hydroxyethyl]-4,5-dihydro-1,3-oxazol-2-yl group, a (4R,5S)-4,5-dimethyl-4,5-dihydro-1,3-oxazol-2-yl group, a (4R,5S)-4-hydroxymethyl-5-methyl-4,5-dihydro-1,3-oxazol-2-yl group, a (4R,5R)-5-hydroxymethyl-4-methyl-4,5-dihydro-1,3-oxazol-2-yl group, a 1,3-thiazol-2-yl group, a 5-carboxyl-1,3-thiazol-2-yl group, a 5-dimethylaminocarbonyl-1,3-thiazol-2-yl group, a 5-methyl-1,3,4-thiadiazol-2-yl group, a 5-methyl-1,3,4-oxadiazol-2-yl group, a 4,5-dihydro-1,3-thiazol-2-yl group or a 5,6-dihydro-4H-1,3-oxazin-2-yl group, and particularly preferably a 4,5-dihydro-1,3-oxazol-2-yl group, a (4R)-4-methyl-4,5-dihydro-1,3-oxazol-2-yl group, a (4R)-4-ethyl-4,5-dihydro-1,3-oxazol-2-yl group, a (5S)-5-methyl-4,5-dihydro-1,3-oxazol-2-yl group, a (4R)-4-hydroxymethyl-4,5-dihydro-1,3-oxazol-2-yl group, a (5R)-5-hydroxymethyl-4,5-dihydro-1,3-oxazol-2-yl group, a (4S)-4-[(1R)-1-hydroxyethyl]-4,5-dihydro-1,3-oxazol-2-yl group, a (4S)-4-[(1S)-1-hydroxyethyl]-4,5-dihydro-1,3-oxazol-2-yl group, a (4R,5S)-4,5-dimethyl-4,5-dihydro-1,3-oxazol-2-yl group, a (4R,5S)-4-hydroxymethyl-5-methyl-4,5-dihydro-1,3-oxazol-2-yl group or a (4R,5R)-5-hydroxymethyl-4-methyl-4,5-dihydro-1,3-oxazol-2-yl group.

In the present invention, a "phenyl group that may be substituted with 1 to 5 group(s) independently selected from Substituent Group α" refers to a phenyl group or a phenyl group substituted with 1 to 5 group(s) independently selected from Substituent Group β. The aforementioned group is preferably a phenyl group that may be substituted with 1 to 5 group(s) independently selected from Substituent Group δ, more preferably a 4-acetylphenyl group, a 4-(1-hydroxyethyl)phenyl group, a 4-methylsulfonylphenyl group, a 4-(1-azetidinyl)sulfonylphenyl group, a 2-fluoro-4-methoxycarbonylphenyl group, a 4-carbamoyl-2-fluorophenyl group, a 2-fluoro-4-methylaminocarbonylphenyl group, a 4-dimethylaminocarbonyl-2-fluorophenyl group, a 4-(1-azetidinyl)carbonyl-2-fluorophenyl group, a 2-fluoro-4-(1-pyrrolidinyl)carbonylphenyl group, a 2-fluoro-4-(4-morpholinyl)carbonylphenyl group, a 2-fluoro-4-methylaminosulfonylphenyl group, a 4-(1-azetidinyl)sulfonyl-2-fluorophenyl group, a 2-fluoro-4-(5-methyl-1,3,4-oxadiazol-2-yl)phenyl group, a 2-fluoro-4-(5-methyl-1,3,4-thiadiazol-2-yl)phenyl group, a 4-(1-azetidinyl)carbonyl-2-methylphenyl group or a 4-(1-azetidinyl)carbonyl-2-trifluoromethylphenyl group, even more preferably a 4-methylsulfonylphenyl group, a 4-(1-azetidinyl)carbonyl-2-fluorophenyl group or a 2-fluoro-4-(1-pyrrolidinyl)carbonylphenyl group, and particularly preferably a 4-methylsulfonylphenyl group.

In the present invention, a "heterocyclic group that may be substituted with 1 to 3 group(s) independently selected from Substituent Group α" in $R^2$ refers to the above-mentioned "heterocyclic group" or the above-mentioned "heterocyclic group" that is substituted with 1 to 3 group(s) independently selected from Substituent Group α. The aforementioned group is preferably a 2-pyridyl group, 3-pyridyl group or 2-pyrazinyl group that may be substituted with 1 to 3 group(s) independently selected from Substituent Group δ, more preferably a 5-(1-azetidinyl)carbonyl-3-chloro-2-pyridyl group, a 2-methylsulfonyl-5-pyridyl group, a 5-(4-methyl-1-piperazinyl)carbonyl-2-pyrazinyl group, a 2-methylaminocarbonyl-5-pyridyl group, a 2-methylaminosulfonyl-5-pyridyl group or a 5-methylsulfonyl-2-pyrazinyl group, and even more preferably a 2-methylsulfonyl-5-pyridyl group, a 5-methylsulfonyl-2-pyrazinyl group or a 5-(1-azetidinyl)carbonyl-3-chloro-2-pyridyl group.

In the present invention, the general formula (I) is preferably the general formula (Ia).

In the present invention, A is preferably a group represented by the formula =NOH or an oxygen atom, and more preferably an oxygen atom.

In the present invention, $R^1$ is preferably a $C_1$-$C_6$ alkyl group, a $C_1$-$C_6$ alkoxy group or a mono-$C_1$-$C_6$ halogenated alkylamino group, and more preferably a methyl group or a 2-chloroethylamino group.

In the present invention, the heterocyclic group formed by A and $R^1$ together with the carbon atom bonded thereto that may be substituted with 1 to 3 group(s) independently selected from Substituent Group α is preferably a 2-pyridyl group, 5,6-dihydro-4H-1,3-oxazin-2-yl group, 1,3-thiazol-2-yl group, 1,3-oxazol-2-yl group, 1,3,4-oxadiazol-2-yl group, 1,3,4-thiadiazol-2-yl group, 4,5-dihydro-1,3-thiazol-2-yl group, 4,5-dihydro-1,3-oxazol-2-yl group or 1,3-benzothiazol-2-yl group that may be substituted with 1 to 3 group(s) independently selected from Substituent Group γ, more preferably a 1,3-thiazol-2-yl group, a 5-methyl-1,3-thiazol-2-yl group, a 5-methyl-1,3,4-oxadiazol-2-yl group, a 4,5-dihydro-1,3-thiazol-2-yl group, a 4,5-dihydro-1,3-oxazol-2-yl group, a (5S)-5-methyl-4,5-dihydro-1,3-oxazol-2-yl group, a (5R)-5-methyl-4,5-dihydro-1,3-oxazol-2-yl group, a 5-hydroxymethyl-4,5-dihydro-1,3-oxazol-2-yl group, a (5R)-5-hydroxymethyl-4,5-dihydro-1,3-oxazol-2-yl group, a (4R)-4-methyl-4,5-dihydro-1,3-oxazol-2-yl group, a (4R)-4-ethyl-4,5-dihydro-1,3-oxazol-2-yl group, a (4R)-4-hydroxymethyl-4,5-dihydro-1,3-oxazol-2-yl group, a (4S)-4-[(1R)-1-hydroxyethyl]-4,5-dihydro-1,3-oxazol-2-yl group, a (4S)-4-[(1S)-1-hydroxyethyl]-4,5-dihydro-1,3-oxazol-2-yl group, a (4R,5S)-4,5-dimethyl-4,5-dihydro-1,3-oxazol-2-yl group, a (5S)-4-hydroxy-5-methyl-4,5-dihydro-1,3-oxazol-2-yl group, a (4R,5S)-4-hydroxymethyl-5-methyl-4,5-dihydro-1,3-oxazol-2-yl group, a (4R,5R)-5-hydroxymethyl-4-methyl-4,5-dihydro-1,3-oxazol-2-yl group, a 5-carboxyl-1,3-thiazol-2-yl group, a 5-dimethylaminocarbonyl-1,3-thiazol-2-yl group, a 5-methyl-1,3,4-thiadiazol-2-yl group or a 5,6-dihydro-4H-1,3-oxazin-2-yl group, even more preferably a 4,5-dihydro-1,3-oxazol-2-yl group, a (4R)-4-methyl-4,5-dihydro-1,3-oxazol-2-yl group, a (4R)-4-ethyl-4,5-dihydro-1,3-oxazol-2-yl group, a (5S)-5-methyl-4,5-dihydro-1,3-oxazol-2-yl group, a (4R)-4-hydroxymethyl-4,5-dihydro-1,3-oxazol-2-yl group, a (5R)-5-hydroxymethyl-4,5-dihydro-1,3-oxazol-2-yl group, a (4S)-4-[(1R)-1-hydroxyethyl]-4,5-dihydro-1,3-oxazol-2-yl group, a (4S)-4-[(1S)-1-hydroxyethyl]-4,5-dihydro-1,3-oxazol-2-yl group, a (4R,5S)-4,5-dimethyl-4,5-dihydro-1,3-oxazol-2-yl group, a (4R,5S)-4-hydroxymethyl-5-methyl-4,5-dihydro-1,3-oxazol-2-yl group, a 1,3-thiazol-2-yl group, a 5-carboxyl-1,3-thiazol-2-yl group, a 5-dimethylaminocarbonyl-1,3-thiazol-2-yl group, a 5-methyl-1,3,4-thiadiazol-2-yl group, a 5-methyl-1,3,4-oxadiazol-2-yl group, a 4,5-dihydro-1,3-thiazol-2-yl group or a 5,6-dihydro-4H-1,3-oxazin-2-yl group, and particularly preferably a 4,5-dihydro-1,3-oxazol-2-yl group, a (4R)-4-methyl-4,5-dihydro-1,3-oxazol-2-yl group, a (4R)-4-ethyl-4,5-dihydro-1,3-oxazol-2-yl group, a (5S)-5-methyl-4,5-dihydro-1,3-oxazol-2-yl group, a (4R)-4-hydroxymethyl-4,5-dihydro-1,3-oxazol-2-yl group, a (5R)-5-hydroxymethyl-4,5-dihydro-1,3-oxazol-2-yl group, a (4S)-4-[(1R)-1-hydroxyethyl]-4,5-dihydro-1,3-oxazol-2-yl group, a (4S)-4-[(1S)-1-hydroxyethyl]-4,5-dihydro-1,3-oxazol-2-yl group, a (4R,5S)-4,5-dimethyl-4,5-dihydro-1,3-oxazol-2-yl group, a (4R,5S)-4-hydroxymethyl-5-methyl-4,5-dihydro-1,3-oxazol-2-yl group or a (4R,5R)-5-hydroxymethyl-4-methyl-4,5-dihydro-1,3-oxazol-2-yl group.

In the present invention, $R^2$ is preferably a phenyl group that may be substituted with 1 to 5 group(s) independently selected from Substituent Group δ or a 2-pyridyl group, 3-pyridyl group or 2-pyrazinyl group that may be substituted with 1 to 3 group(s) independently selected from Substituent Group δ, more preferably a 4-methylsulfonylphenyl group, a 4-(1-azetidinyl)carbonyl-2-fluorophenyl group, a 2-fluoro-4-(1-pyrrolidinyl)carbonylphenyl group, a 5-(1-azetidinyl)carbonyl-3-chloro-2-pyridyl group, a 2-methylsulfonyl-5-pyridyl group, a 5-(4-methyl-1-piperazinyl)carbonyl-2-pyrazinyl group, a 2-methylaminocarbonyl-5-pyridyl group, a 2-methylaminosulfonyl-5-pyridyl group or a 5-methylsulfonyl-2-pyrazinyl group, and even more preferably a 4-methylsulfonylphenyl group, a 2-methylsulfonyl-5-pyridyl group, a 5-methylsulfonyl-2-pyrazinyl group or a 5-(1-azetidinyl)carbonyl-3-chloro-2-pyridyl group.

In the present invention, $R^3$ is preferably a hydroxy group or a methoxy group.

In the present invention, $R^4$ is preferably a hydrogen atom.

The compound or pharmacologically acceptable salt thereof represented by the general formula (I) of the present invention has all isomers (such as a keto-enol isomer, a diastereomer, an optical isomer, a rotamer, etc.).

The compound or pharmacologically acceptable salt thereof represented by the general formula (I) of the present invention has various isomers because asymmetric carbon atom(s) exist in the molecule. These isomers and mixtures of these isomers of the present invention are all represented by a single formula, specifically, the general formula (I). Accordingly, the present invention includes all of these isomers and mixtures of these isomers in arbitrary ratios.

The aforementioned stereoisomers can be obtained by synthesizing the compound of the present invention using an optically active raw material compound or using an asymmetric synthesis or asymmetric induction technique or by isolating the synthesized compound of the present invention by a common optical resolution or separation method if desired.

The compound or pharmacologically acceptable salt thereof represented by the general formula (Ia) of the present invention is more preferred than a compound or pharmacologically acceptable salt thereof represented by the general formula (Ib) of the present invention.

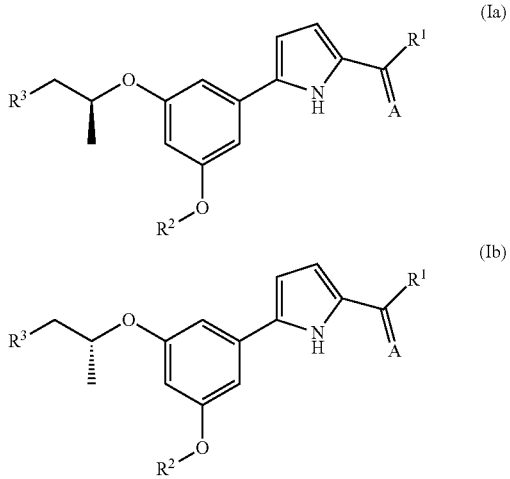

A "pharmacologically acceptable salt thereof" refers to a salt that is free of prominent toxicity and which can be used as a pharmaceutical. The compound represented by the general formula (I) of the present invention can be converted to a salt by reacting with an acid in the case the compound has a basic group such as an amino group, or by reacting with a base in the case of having an acidic group such as a carboxyl group.

Examples of salts based on a basic group include salts of hydrohalic acids such as hydrofluorides, hydrochlorides, hydrobromides or hydroiodides, salts of inorganic acids such as nitrates, perchlorates, sulfates or phosphates; $C_1$-$C_6$ alkylsulfonates such as methanesulfonates, trifluoromethanesulfonates or ethanesulfonates, arylsulfonates such as benzenesulfonates or p-toluenesulfonates; salts of organic acids such as acetates, malates, fumarates, succinates, citrates, ascorbates, tartrates, oxalates or maleates; and, salts of amino acids such as salts of glycine, lysine, arginine, ornithine, glutamatic acid and aspartatic acid.

On the other hand, examples of salts based on acidic groups include metal salts such as alkali metal salts such as sodium salts, potassium salts or lithium salts, alkaline earth metal salts such as calcium salts or magnesium salts, metal salts such as aluminum salts or iron salts; amine salts such as inorganic salts such as ammonium salts, or organic salts such as salts of t-octylamine, dibenzylamine, morpholine, glucosamine, phenylglycine alkyl esters, ethylenediamine, N-methylglucamine, guanidine, diethylamine, triethylamine, dicyclohexylamine, N,N'-dibenzylethylenediamine, chloroprocaine, procaine, diethanolamine, N-benzylphenethylamine, piperazine, tetramethylammonium or tris(hydroxymethyl)aminomethane; and, salts of amino acids such as salts of glycine, lysine, arginine, ornithine, glutamatic acid and aspartatic acid.

The compound or pharmacologically acceptable salt thereof represented by the general formula (I) of the present invention may become a hydrate by incorporating water molecule(s) by being left in the atmosphere or by recrystallizing, and such hydrates are also included in the salts of the present invention.

The compound or pharmacologically acceptable salt thereof represented by the general formula (I) of the present invention may become a solvate by absorbing another type of solvent, and such solvates are also included in the salts of the present invention.

In the present invention, "metabolic syndrome" refers to a disease state that is based on insulin resistance for which there is considerably higher risk for coronary artery disease due to accumulation of multiple coronary vessel risk factors (including lifestyle diseases such as hyperlipemia, diabetes, obesity and hypertension) (Diabetes, Obesity and Metabolism, 9, 2007, 246-258; Journal of the American Medical Association, 285, 2486-2497 (2001); Diabet. Med., 15, 539-553 (1998)).

Effect of the Invention

The compound represented by the general formula (I) of the present invention, or a pharmacologically acceptable salt thereof, has superior GK activating activity, and is useful as a pharmaceutical for the prevention and/or treatment of a disease selected from the group consisting of diabetes, impaired glucose tolerance, gestational diabetes, chronic complications of diabetes (including diabetic peripheral neuropathy, diabetic nephropathy, diabetic retinopathy and diabetic macroangiopathy) and metabolic syndrome in warm-blooded animals (and preferably in mammals, including humans). In addition, the novel compound represented by the general formula (I) provided by the present invention, or a pharmacologically acceptable salt thereof, has superior GK activating activity and is useful as an active ingredient of a pharmaceutical for the prevention and/or treatment of the aforementioned diseases in warm-blooded animals (and preferably in mammals, including humans). Preferred examples of diseases include diabetes and impaired glucose tolerance. The compound represented by the general formula (I) of the present invention, or a pharmacologically acceptable salt thereof, can preferably be used as a pharmaceutical for treatment of the aforementioned diseases.

BEST MODE FOR CARRYING OUT THE INVENTION

The compound represented by the general formula (I) of the present invention can be produced according to the Methods A to L described below.

There are no particular limitations on the solvent used in the reactions of each of the steps of the following Methods A to L provided it dissolves the starting raw material to a certain extent without impairing the reaction, and the solvent is, for example, selected from the solvent group indicated below. The solvent group is composed of hydrocarbons such as pentane, hexane, octane, petroleum ether, ligroin or cyclohexane; amides such as formamide, N,N-dimethylformamide, N,N-dimethylacetamide, N-methyl-2-pyrrolidone, N-methyl-2-pyrrolidinone or hexamethylphosphate triamide; ethers such as diethyl ether, diisopropyl ether, tetrahydrofuran, dioxane, dimethoxyethane or diethylene glycol dimethyl ether; alcohols such as methanol, ethanol, n-propanol, i-propanol, n-butanol, 2-butanol, 2-methyl-1-propanol, t-butanol, isoamyl alcohol, diethylene glycol, glycerin, octanol, cyclohexanol or methyl cellosolve; sulfoxides such as dimethyl sulfoxide; sulfones such as sulfolan; nitriles such as acetonitrile, propionitrile, butyronitrile or isobutyronitrile; esters such as ethyl formate, ethyl acetate, propyl acetate, butyl acetate or diethyl carbonate; ketones such as acetone, methyl ethyl ketone, 4-methyl-2-pentanone, methyl isobutyl ketone, isophorone or cyclohexanone; nitro compounds such as nitroethane or nitrobenzene; halogenated hydrocarbons such as dichloromethane, 1,2-dichloroethane, chlorobenzene, dichlorobenzene, chloroform or carbon tetrachloride; aromatic hydrocarbons such as benzene, toluene or xylene; carboxylic acids such as acetic acid, formic acid, propionic acid, butyric acid or trifluoroacetic acid; amines such as N-methylmorpholine, triethylamine, tripropylamine, tributylamine, diisopropylethylamine, dicyclohexylamine, N-methylpiperidine, pyridine, 2,6-lutidine, 4-pyrrolidinopyridine, picoline, 4-dimethylaminopyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), 1,8-diazabicyclo[5.4.0]undec-7-ene (DBU) or piperidine; water; and, mixed solvents thereof.

Examples of bases used in the reactions of each of the steps of the following Methods A to L include inorganic bases such as alkali metal carbonates such as sodium carbonate, potassium carbonate, lithium carbonate or cesium carbonate; alkali metal hydrogencarbonates such as sodium hydrogencarbonate, potassium hydrogencarbonate or lithium hydrogencarbonate; alkali metal acetates such as sodium acetate, potassium acetate, lithium acetate or cesium acetate; alkali metal hydrides such as lithium hydride, sodium hydride or potassium hydride; alkali metal hydroxides such as sodium hydroxide, potassium hydroxide, barium hydroxide or lithium hydroxide; and, alkali metal fluorides such as sodium fluoride or potassium fluoride; alkali metal alkoxides such as sodium methoxide, sodium ethoxide, sodium t-butoxide, potassium methoxide, potassium ethoxide, potassium t-butoxide or lithium methoxide; alkali metal trialkyl siloxides such as sodium trimethyl siloxide, potassium trimethyl siloxide or lithium trimethyl siloxide; alkali metal mercaptans such as sodium thiomethoxide or sodium thioethoxide; organic bases such as N-methylmorpholine, triethylamine, tripropylamine, tributylamine, N,N-diisopropylethylamine, dicyclohexylamine, N-methylpiperidine, pyridine, 2,6-lutidine, 4-pyrrolidinopyridine, picoline, 4-dimethylaminopyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) or 1,8-diazabicyclo[5.4.0]undec-7-ene (DBU); organometallic bases such as n-butyl lithium, lithium diisopropylamide or lithium bis(trimethylsilyl)amide; and, amino acids such as proline.

Examples of condensation agents used in the reactions of each of the steps of the following Methods A to L include O-(7-azabenzotriazol-1-yl)-N,N,N',N'-tetramethyluronium hexafluorophosphate (HATU), 1-propanephosphonic acid cyclic anhydride (T3P), dicyclohexylcarbodiimide (DCCD), 1-ethyl-3-(dimethylaminopropyl)carbodiimide hydrochloride (WSCI•HCl), 1-ethyl-3-(3-dimethylaminopropyl)carbodiimide hydrochloride (EDCl), 1-ethyl-3-(3-dimethylaminopropyl)carbodiimide (EDAC), 4-(4,6-dimethoxy-1,3,5-triazin-2-yl)-4-methylmorpholinium chloride n hydrate (DMT-MM), isobutyl chloroformate (IBCF), 1,1'-carbonylbis-1H-imidazole (CDI), diethyl cyanophosphonate (DEPC), diphenyl phosphorazidate (DPPA), N-hydroxysuccinimide, N-hydroxy-5-norbornene-2,3-dicarboxylmide and dipyridyl disulfide, and these can be used in the presence of 1-hydroxybenzotriazole (HOBt) or 1-hydroxybenzotriazole monohydrate as necessary.

Examples of demethylation agents used in the reactions of each of the steps of the following Methods A to L include sodium thiomethoxide, sodium thioethoxide, sodium thiophenoxide, iodotrimethylsilane, aluminum chloride, aluminum bromide, boron tribromide, boron triiodide, methylmagnesium iodide and hydrogen bromide.

Examples of palladium catalysts used in the reactions of each of the steps of the following Methods A to L include zero-valent palladium catalysts or divalent palladium catalysts such as tetrakis(triphenylphosphine) palladium (0), palladium-active carbon, palladium (II) acetate, palladium (II) trifluoroacetate, palladium black, palladium (II) bromide, palladium (II) chloride, palladium (II) iodide, palladium (II) cyanide, palladium (II) nitrate, palladium (II) oxide, palladium (II) sulfate, palladium (II) dichlorobis(acetonitrile), palladium (II) dichlorobis(benzonitrile), palladium (II) dichloro (1,5-cyclooctadiene), palladium (II) acetylacetone, palladium (II) sulfide, [1,1'-bis(diphenylphosphino)ferrocene] palladium (II) dichloride, tris(dibenzylideneacetone) dipalladium (0), tetrakis(acetonitrile) palladium (II) tetrafluoroborate and aryl chloride-palladium dimers.

The reaction temperatures in the reactions of each of the steps of the following Methods A to L vary depending on the solvent, starting raw material, reagents and the like, while the reaction times vary depending on the solvent, starting raw material, reagents, reaction temperature and the like.

In the reactions of each of the steps of the following Methods A to L, each desired compound is collected from the reaction mixture according to conventional methods after completion of the reaction. The desired compound is obtained as follows, for example. The reaction mixture is appropriately neutralized and insoluble matter, if present, is removed by filtration. Then, water and an immiscible organic solvent such as ethyl acetate are added, and the organic layer containing the desired compound is separated. The organic layer is washed with water or the like and then dried over anhydrous magnesium sulfate, anhydrous sodium sulfate, anhydrous sodium bicarbonate or the like and filtered. Then, the solvent is evaporated. The resulting desired compound may be isolated and purified if necessary by appropriately combining usual methods, for example, methods suitably used for isolation and purification of organic compounds such as recrystallization and reprecipitation and eluting with an appropriate eluent by application of chromatography. The desired compound insoluble in a solvent may be purified by washing the resulting solid crude product with a solvent. The desired compound in each step may also be used as is for the next reaction without purification.

Method A is a method for producing a compound represented by general formula (Ic) in which $R^3$ is a $C_1$-$C_6$ alkoxy group among compounds represented by general formula (I).

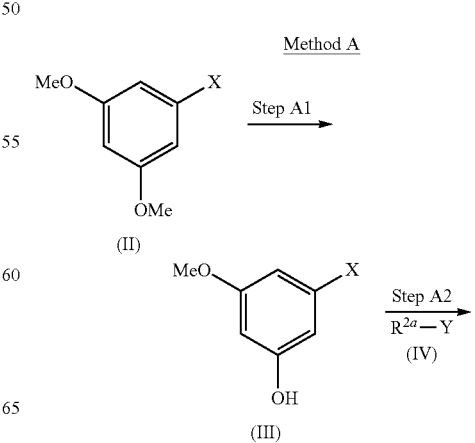

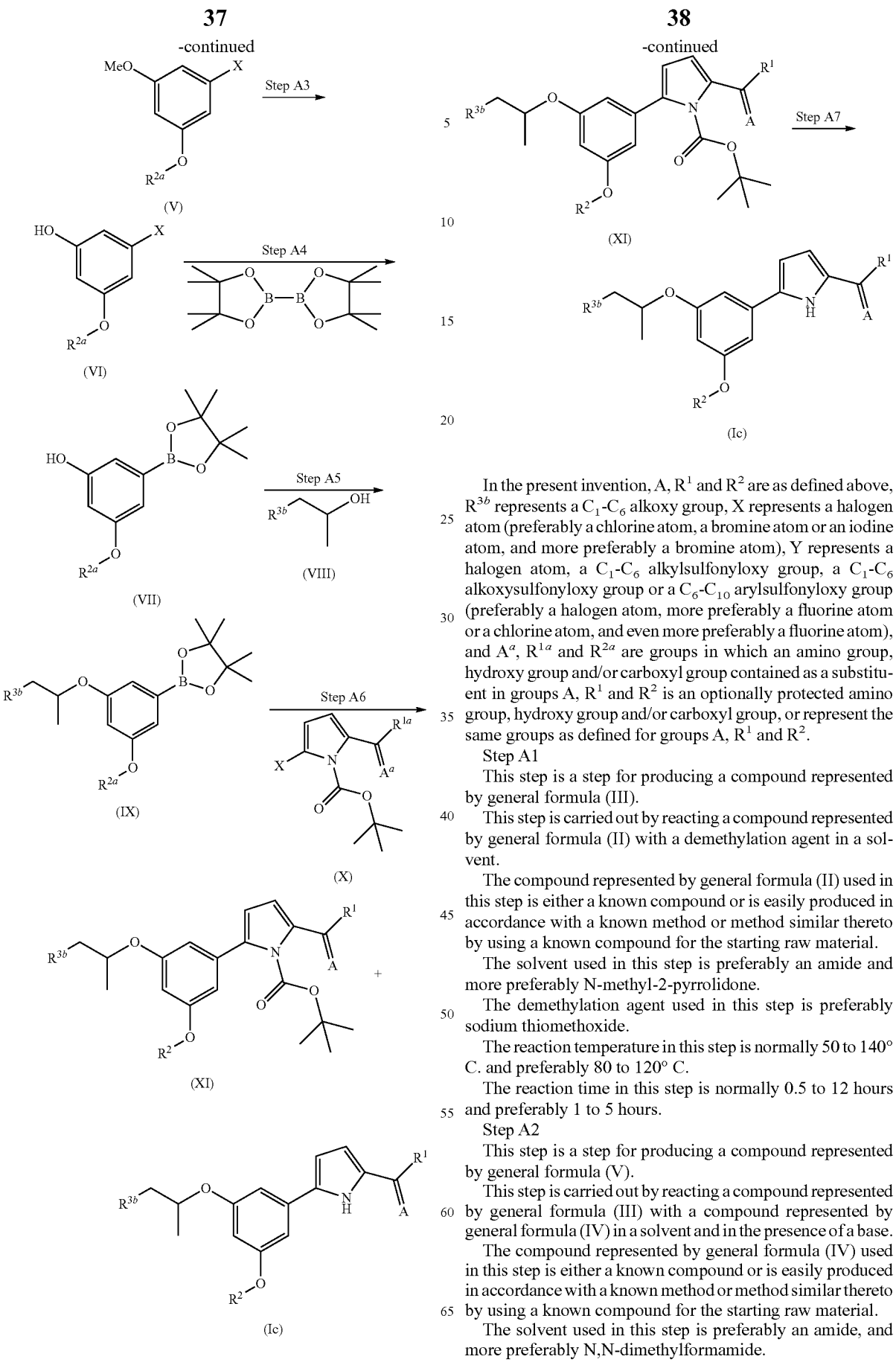

In the present invention, A, $R^1$ and $R^2$ are as defined above, $R^{3b}$ represents a $C_1$-$C_6$ alkoxy group, X represents a halogen atom (preferably a chlorine atom, a bromine atom or an iodine atom, and more preferably a bromine atom), Y represents a halogen atom, a $C_1$-$C_6$ alkylsulfonyloxy group, a $C_1$-$C_6$ alkoxysulfonyloxy group or a $C_6$-$C_{10}$ arylsulfonyloxy group (preferably a halogen atom, more preferably a fluorine atom or a chlorine atom, and even more preferably a fluorine atom), and $A^a$, $R^{1a}$ and $R^{2a}$ are groups in which an amino group, hydroxy group and/or carboxyl group contained as a substituent in groups A, $R^1$ and $R^2$ is an optionally protected amino group, hydroxy group and/or carboxyl group, or represent the same groups as defined for groups A, $R^1$ and $R^2$.

Step A1

This step is a step for producing a compound represented by general formula (III).

This step is carried out by reacting a compound represented by general formula (II) with a demethylation agent in a solvent.

The compound represented by general formula (II) used in this step is either a known compound or is easily produced in accordance with a known method or method similar thereto by using a known compound for the starting raw material.

The solvent used in this step is preferably an amide and more preferably N-methyl-2-pyrrolidone.

The demethylation agent used in this step is preferably sodium thiomethoxide.

The reaction temperature in this step is normally 50 to 140° C. and preferably 80 to 120° C.

The reaction time in this step is normally 0.5 to 12 hours and preferably 1 to 5 hours.

Step A2

This step is a step for producing a compound represented by general formula (V).

This step is carried out by reacting a compound represented by general formula (III) with a compound represented by general formula (IV) in a solvent and in the presence of a base.

The compound represented by general formula (IV) used in this step is either a known compound or is easily produced in accordance with a known method or method similar thereto by using a known compound for the starting raw material.

The solvent used in this step is preferably an amide, and more preferably N,N-dimethylformamide.

The base used in this step is preferably an alkali metal carbonate, and more preferably potassium carbonate.

The reaction temperature in this step is normally 50 to 140° C. and preferably 80 to 120° C.

The reaction time in this step is normally 12 to 72 hours and preferably 24 to 48 hours.

Step A3

This step is a step for producing a compound represented by general formula (VI).

This step is carried out by reacting a compound represented by general formula (V) with a demethylation agent in a solvent.

The solvent used in this step is preferably a halogenated hydrocarbon, and more preferably dichloromethane.

The demethylation agent used in this step is preferably boron tribromide.

The reaction temperature in this step is normally −100 to 40° C. and preferably −78 to 25° C.

The reaction time in this step is normally 1 to 72 hours and preferably 12 to 36 hours.

Step A4

This step is a step for producing a compound represented by general formula (VII).

This step is carried out by reacting a compound represented by general formula (VI) with bis(pinacolato)diboron in a solvent and in the presence of a palladium catalyst and inorganic base.

The solvent used in this step is preferably an amide, and more preferably N,N-dimethylformamide.

The palladium catalyst used in this step is preferably a divalent palladium catalyst, and more preferably [1,1'-bis(diphenylphosphino)ferrocene] palladium (II) dichloride dichloromethane complex.

The inorganic base used in this step is preferably an alkali metal acetate, and more preferably potassium acetate.

The reaction temperature in this step is normally 50 to 130° C. and preferably 70 to 110° C.

The reaction time in this step is normally 1 to 24 hours and preferably 2 to 10 hours.

Step A5

This step is a step for producing a compound represented by general formula (IX).

This step is carried out by reacting a compound represented by general formula (VII) with a compound represented by general formula (VIII) in a solvent and in the presence of triphenylphosphine and diethyl azodicarboxylate.

The compound represented by general formula (VIII) used in this step, and its optical isomers, are either known compounds or are easily produced in accordance with a known method or method similar thereto by using a known compound for the starting raw material.

The solvent used in this step is preferably an ether, and more preferably tetrahydrofuran.

The reaction temperature in this step is normally −20 to 40° C. and preferably 0 to 25° C.

The reaction time in this step is normally 0.5 to 72 hours and preferably 1 to 36 hours.

Step A6

This step is a step for producing a compound represented by general formula (XI) and a compound represented by general formula (Ic).

This step is carried out by reacting a compound represented by general formula (IX) with a compound represented by general formula (X) in a solvent and in the presence of a palladium catalyst and inorganic base, followed by removing a protecting group of an amino group, a hydroxy group and/or a carboxyl group in $A^a$, $R^{1a}$ and $R^{2a}$ as desired.

The solvent used in this step is preferably an ether, an aromatic hydrocarbon, an alcohol, water or a mixed solvent thereof, more preferably dioxane, toluene, ethanol, water or a mixed solvent thereof, and even more preferably a mixed solvent of dioxane and water or a mixed solvent of toluene, ethanol and water.

The palladium catalyst used in this step is preferably a divalent palladium catalyst, and more preferably [1,1'-bis(diphenylphosphino)ferrocene] palladium (II) dichloride dichloromethane complex.

The inorganic base used in this step is preferably an alkaline metal carbonate, and more preferably potassium carbonate.

The reaction temperature in this step is normally 25 to 100° C. and preferably 40 to 70° C.

The reaction time in this step is normally 0.5 to 12 hours and preferably 1 to 5 hours.

Step A7

This step is a step for producing a compound represented by general formula (Ic).

This step is carried out by reacting a compound represented by general formula (XI) with an acid in a solvent.

The solvent used in this step is preferably a halogenated hydrocarbon, and more preferably dichloromethane The acid used in this step is, for example, hydrogen halides such as hydrogen chloride gas or hydrogen bromide gas; mineral acids such as sulfuric acid, hydrobromic acid or hydrochloric acid; organic sulfonic acids such as methanesulfonic acid, p-toluenesulfonic acid, pyridinium p-toluenesulfonate (PPTS), camphorsulfonic acid or trifluoromethanesulfonic acid; carboxylic acids such as acetic acid, formic acid or trifluoroacetic acid; Lewis acids such as aluminum chloride, zinc chloride, zinc iodide, tin tetrachloride, titanium trichloride, boron trifluoride or boron tribromide; methyl sulfate; or an acidic ion exchange resin, preferably a carboxylic acid, and more preferably trifluoroacetic acid.

The reaction temperature in this step is normally −20 to 60° C. and preferably 0 to 40° C.

The reaction time in this step is normally 0.1 to 5 hours and preferably 0.5 to 3 hours.

Method B is a method for producing a compound represented by general formula (Ic) in which $R^3$ is a $C_1$-$C_6$ alkoxy group among compounds represented by general formula (I).

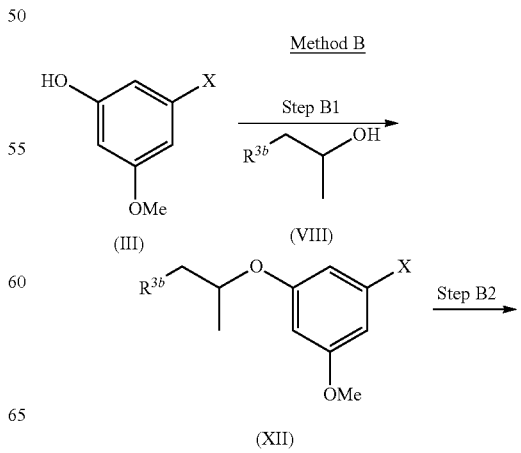

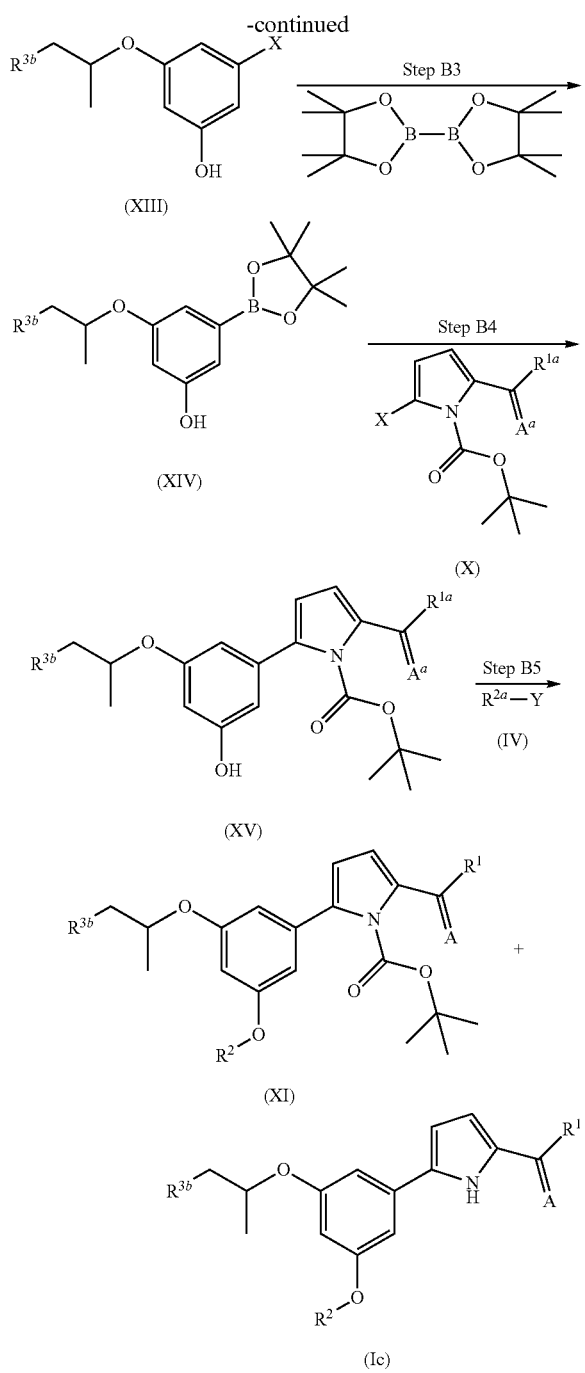

In the present invention, A, $R^1$, $R^2$, $R^{3b}$, $A^a$, $R^{1a}$, $R^{2a}$, X and Y are as defined above.

Step B1

This step is a step for producing a compound represented by general formula (XII).

This step is carried out by reacting a compound represented by general formula (III) obtained in above-mentioned Step A1 of Method A with a compound represented by general formula (VIII) in a solvent and in the presence of triphenylphosphine and diethyl azodicarboxylate.

The solvent used in this step is preferably an aromatic hydrocarbon, and more preferably toluene.

The reaction temperature in this step is normally −20 to 40° C. and preferably 0 to 25° C.

The reaction time in this step is normally 0.1 to 72 hours and preferably 0.5 to 36 hours.

Step B2

This step is a step for producing a compound represented by general formula (XIII).

This step is carried out in the same manner as above-mentioned Step A1 of Method A by reacting a compound represented by general formula (XII) with a demethylation agent.

Step B3

This step is a step for producing a compound represented by general formula (XIV).

This step is carried out in the same manner as above-mentioned Step A4 of Method A by reacting a compound represented by general formula (XIII) with bis(pinacolato)diboron in a solvent and in the presence of a palladium catalyst and inorganic base.

Step B4

This step is a step for producing a compound represented by general formula (XV).

This is carried out in the same manner as above-mentioned Step A6 of Method A by reacting a compound represented by general formula (XIV) with a compound represented by general formula (X) in a solvent and in the presence of a palladium catalyst and inorganic base.

Step B5

This step is a step for producing a compound represented by general formula (XI) and a compound represented by general formula (Ic).

This step is carried out by reacting a compound represented by general formula (XV) with a compound represented by general formula (IV) in a solvent and in the presence of a base, followed by removing a protecting group of an amino group, hydroxy group and/or carboxyl group in $A^a$, $R^{1a}$ and $R^{2a}$ as desired.

The solvent used in this step is preferably a sulfoxide or an amide, and more preferably dimethyl sulfoxide or N,N-dimethylformamide.

The base used in this step is preferably an alkali metal hydride or an alkali metal carbonate, and more preferably sodium hydride or potassium carbonate.

The reaction temperature in this step is normally 50 to 140° C. and preferably 80 to 120° C.

The reaction time in this step is normally 1 to 72 hours and preferably 3 to 36 hours.

Method C is a method for producing a compound represented by general formula (Ic) in which $R^3$ is a $C_1$-$C_6$ alkoxy group among compounds represented by general formula (I).

Method C

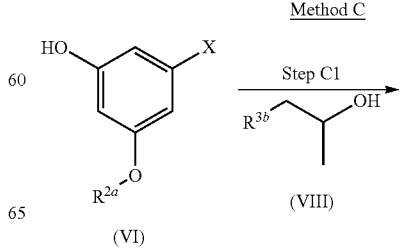

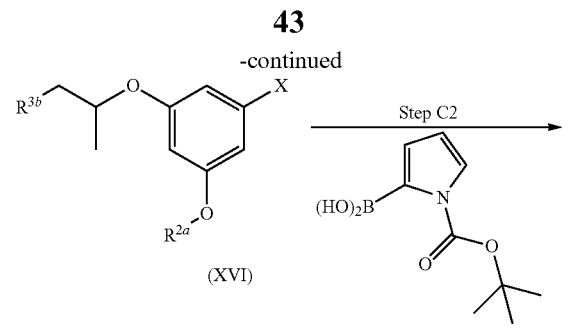
(XVI)

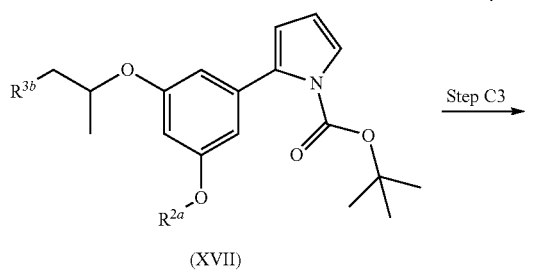
(XVII)

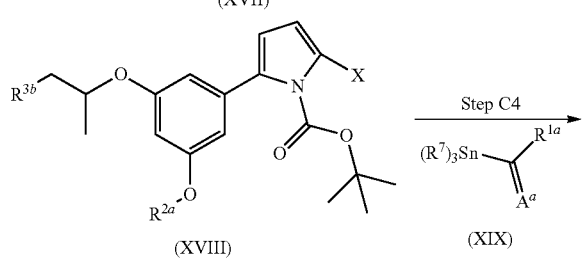
(XVIII)

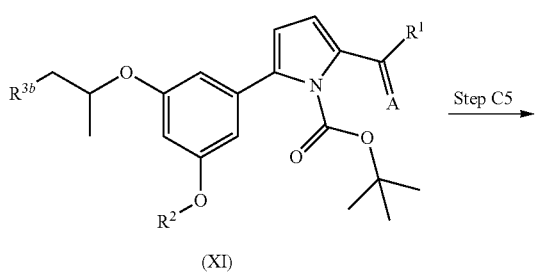
(XI)

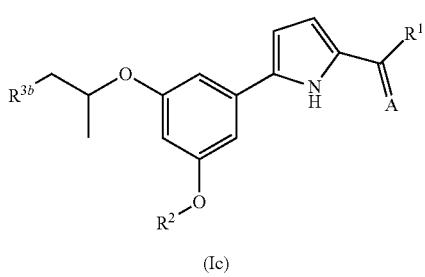
(Ic)

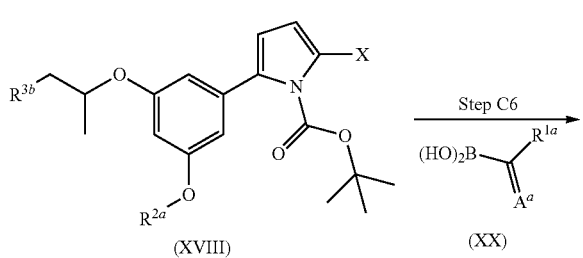
(XVIII)

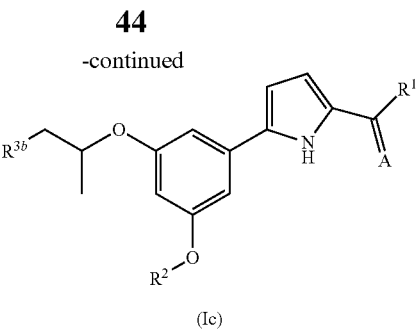
(Ic)

In the present invention, A, $R^1$, $R^2$, $R^{3b}$, $A^a$, $R^{1a}$, $R^{2a}$ and X are as defined above, and $R^7$ represents a $C_1$-$C_6$ alkyl group (and preferably an n-butyl group).

Step C1

This step is a step for producing a compound represented by general formula (XVI).

This step is carried out in the same manner as above-mentioned Step B1 of Method B by reacting a compound represented by general formula (VI) obtained in above-mentioned Step A3 of Method A with a compound represented by general formula (VIII) in a solvent and in the presence of triphenylphosphine and diethyl azodicarboxylate.

Step C2

This step is a step for producing a compound represented by general formula (XVII).

This step is carried out by reacting a compound represented by general formula (XVI) with 1-(t-butoxycarbonyl)pyrrole-2-boronic acid in a solvent and in the presence of a palladium catalyst, triphenylphosphine and an inorganic base.

The solvent used in this step is preferably an ether, water or a mixed solvent thereof, more preferably dimethoxyethane, water or a mixed solvent thereof, and even more preferably a mixed solvent of dimethoxyethane and water.

The palladium catalyst used in this step is preferably a divalent palladium catalyst, and more preferably palladium (II) acetate.

The base used in this step is preferably an alkali metal carbonate, and more preferably potassium carbonate.

The reaction temperature in this step is normally 40 to 100° C. and preferably 60 to 90° C.

The reaction time in this step is normally 1 to 72 hours and preferably 3 to 24 hours.

Step C3

This step is a step for producing a compound represented by general formula (XVIII).

This step is carried out by reacting a compound represented by general formula (XVII) with a halogenating agent in a solvent.

The solvent used in this step is preferably an ether or a mixed solvent of an ether and an alcohol, and more preferably tetrahydrofuran or a mixed solvent of tetrahydrofuran and methanol.

The halogenating agent used in this step is, for example, an inorganic acid such as hydrochloric acid, hydrogen bromide or hydrogen iodide; a halogen molecule such as chlorine, bromine or iodine; or a succinimide such as N-chlorosuccinimide, N-bromosuccinimide or N-iodosuccinimide, preferably a succinimide, and more preferably N-bromosuccinimide.

The reaction temperature in this step is normally −20 to 40° C. and preferably 0 to 25° C.

The reaction time in this step is normally 0.5 to 24 hours and preferably 1 to 12 hours.

45

Step C4

This step is a step for producing a compound represented by general formula (XI).

This step is carried out by reacting a compound represented by general formula (XVIII) with a compound represented by general formula (XIX) in a solvent and in the presence of a palladium catalyst, followed by removing a protecting group of an amino group, hydroxy group and/or carboxyl group in $A^a$, $R^{1a}$ and $R^{2a}$ as desired.

The compound represented by general formula (XIX) used in this step is either a known compound or is easily produced in accordance with a known method or method similar thereto by using a known compound for the starting raw material.

The solvent used in this step is preferably an aromatic hydrocarbon, and more preferably toluene.

The palladium catalyst used in this step is preferably a zero-valent palladium catalyst, and more preferably tetrakis (triphenylphosphine) palladium (0).

The reaction temperature in this step is normally 90 to 130° C. and preferably 100 to 120° C.

The reaction time in this step is normally 1 to 72 hours and preferably 3 to 24 hours.

Step C5

This step is a step for producing a compound represented by general formula (Ic).

This step is carried out in the same manner as above-mentioned step A7 of Method A by reacting a compound represented by general formula (XI) with an acid.

Step C6

This step is a step for producing a compound represented by general formula (Ic).

This step is carried out by reacting a compound represented by general formula (XVIII) with a compound represented by general formula (XX) in a solvent and in the presence of a palladium catalyst and inorganic base, followed by removing a protecting group of an amino group, hydroxy group and/or carboxyl group in $A^a$, $R^{1a}$ and $R^{2a}$ as desired.

The compound represented by general formula (XX) used in this step is either a known compound or is easily produced in accordance with a known method or method similar thereto by using a known compound for the starting raw material.

The solvent used in this step is preferably an ether, water or a mixed solvent thereof, more preferably dimethoxyethane, water or a mixed solvent thereof, and even more preferably a mixed solvent of dimethoxyethane and water.

The palladium catalyst used in this step is preferably a divalent palladium catalyst, and more preferably [1,1'-bis (diphenylphosphino)ferrocene] palladium (II) dichloride dichloromethane complex.

The inorganic base used in this step is preferably an alkali metal carbonate, and more preferably potassium carbonate.

The reaction temperature in this step is normally 60 to 120° C. and preferably 80 to 100° C.

The reaction time in this step is normally 1 to 480 hours and preferably 12 to 240 hours.

Method D is a method for producing a compound represented by general formula (Ie) in which $R^3$ is a hydroxy group among compounds represented by general formula (I).

46

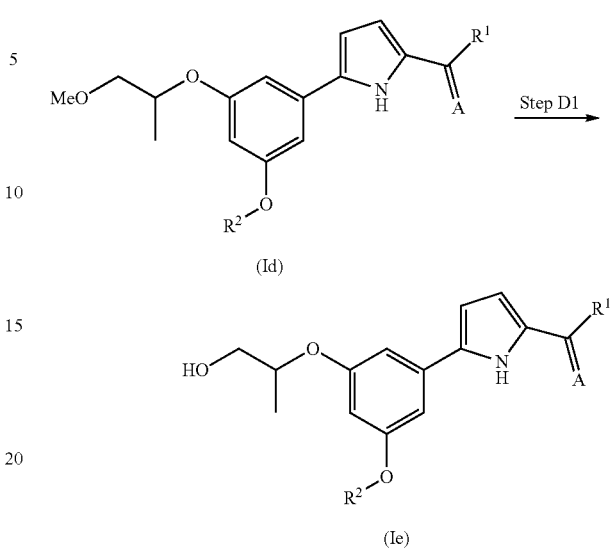

In the present invention, A, $R^1$ and $R^2$ are as defined above.

Step D1

This step is a step for producing a compound represented by general formula (Ie).

This step is carried out by reacting a compound represented by general formula (Id) in which $R^{3b}$ is a methoxy group among compounds represented by general formula (Ic) obtained in above-mentioned Step A6 of Method A, above-mentioned Step A7 of Method A, above-mentioned Step B5 of Method B, above-mentioned Step C5 of Method C and above-mentioned Step C6 of Method C, with a demethylation agent in a solvent.

The solvent used in this step is preferably a halogenated hydrocarbon, and more preferably dichloromethane.

The demethylation agent used in this step is preferably iodotrimethylsilane or boron tribromide, and more preferably boron tribromide.

The reaction temperature in this step is normally −100 to 40° C. and preferably −78 to 25° C.

The reaction time in this step is normally 0.05 to 12 hours and preferably 0.1 to 3 hours.

Method E is a method for producing a compound represented by general formula (X) used in above-mentioned Step A6 of Method A and in above-mentioned Step B4 of Step B.

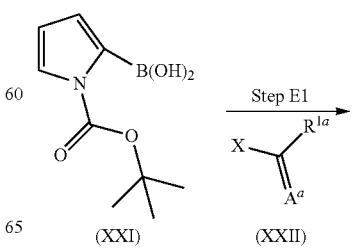

-continued

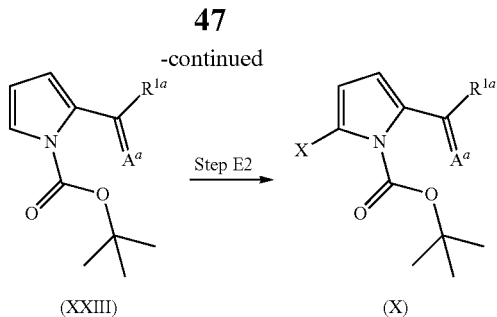

In the present invention, $A^a$, $R^{1a}$ and X are as defined above.

Step E1

This step is a step for producing a compound represented by general formula (XXIII).

This step is carried out in the same manner as above-mentioned Step C2 of Method C by reacting 1-(t-butoxycarbonyl)pyrrole-2-boronic acid (XXI) with a compound represented by general formula (XXII) in a solvent and in the presence of a palladium catalyst, triphenylphosphine and an inorganic base.

The 1-(t-butoxycarbonyl)pyrrole-2-boronic acid (XXI) used in this step is easily produced in accordance with a known method or method similar thereto by using a known compound for the starting raw material.

The compound represented by general formula (XXII) used in this step is either a known compound or is easily produced in accordance with a known method or method similar thereto by using a known compound for the starting raw material.

Step E2

This step is a step for producing a compound represented by general formula (X).

This step is carried out in the same manner as above-mentioned Step C3 of Method C by reacting a compound represented by general formula (XXIII) with a halogenating agent in a solvent.

Method F is a method for producing a compound represented by general formula (X) used in above-mentioned Step A6 of Method A and in Step B4 of Step B.

Method F

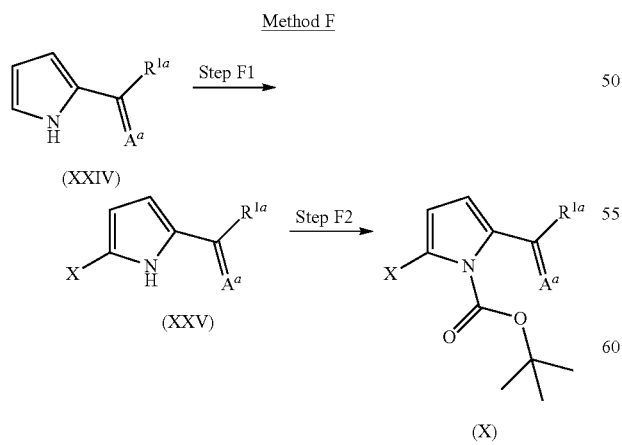

In the present invention, $A^a$, $R^{1a}$ and X are as defined above.

Step F1

This step is a step for producing a compound represented by general formula (XXV).

This step is carried out in the same manner as above-mentioned Step C3 of Method C by reacting a compound represented by general formula (XXIV) with a halogenating agent in a solvent.

The compound represented by general formula (XXIV) used in this step is either a known compound or is easily produced in accordance with a known method or method similar thereto by using a known compound for the starting raw material.

Step F2

This step is a step for producing a compound represented by general formula (X).

This step is carried out by reacting a compound represented by general formula (XXV) with di-t-butyl dicarbonate in a solvent and in the presence of a base.

The solvent used in this step is preferably a halogenated hydrocarbon, and more preferably dichloromethane.

The base used in this step is preferably an organic base, more preferably triethylamine, 4-dimethylaminopyridine or a mixed base thereof, and even more preferably a mixed base of triethylamine and 4-dimethylaminopyridine.

The reaction temperature in this step is normally −20 to 40° C. and preferably 0 to 25° C.

The reaction time in this step is normally 0.1 to 12 hours and preferably 0.5 to 3 hours.

Method G is a method for producing a compound represented by general formula (X) used in above-mentioned Step A6 of Method A and in above-mentioned Step B4 of Method B.

Method G

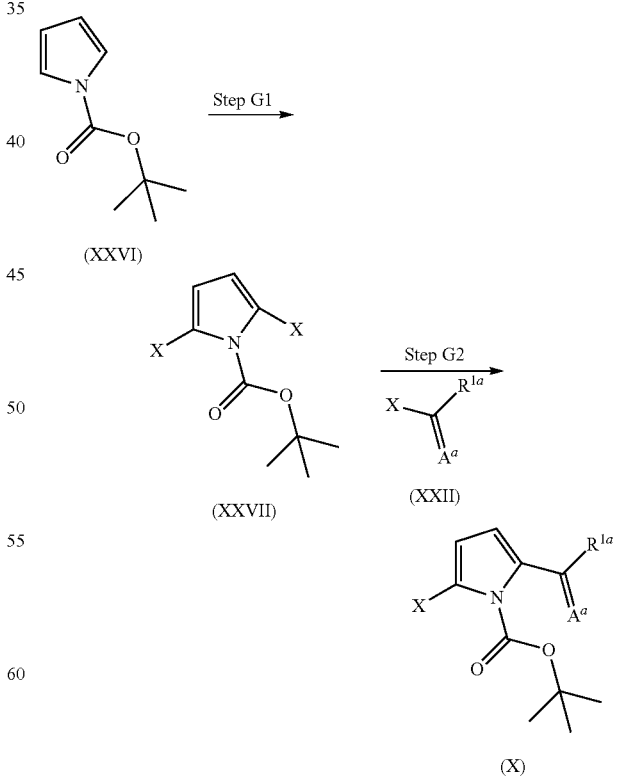

In the present invention, $A^a$, $R^{1a}$ and X are as defined above.

Step G1

This step is a step for producing a compound represented by general formula (XXVII).

This step is carried out in the same manner as abovementioned Step C3 of Method C by reacting t-butyl pyrrole-1-carbonate (XXVI) with a halogenating agent in a solvent.

The t-butyl pyrrole-1-carbonate (XXVI) used in this step is easily produced in accordance with a known method or method similar thereto by using a known compound for the starting raw material.

Step G2

This step is a step for producing a compound represented by general formula (X).

This step is carried out by reacting a compound represented by general formula (XXVII) with a compound represented by general formula (XXII) in a solvent and in the presence of a base.

The solvent used in this step is preferably an ether, and more preferably diethyl ether.

The base used in this step is preferably an organometallic base, and more preferably n-butyl lithium.

The reaction temperature in this step is normally −100 to 40° C. and preferably −78 to 25° C.

The reaction time in this step is normally 0.5 to 24 hours and preferably 1 to 12 hours.

A compound represented by general formula (I) in which A and $R^1$ together with the carbon atom bonded thereto form a heterocyclic group that may be substituted with 1 to 3 group(s) independently selected from Substituent Group α may also be produced in accordance with a method that lastly constructs a heterocyclic ring. For example, Methods H and I indicate methods in the case the heterocyclic group is a 4,5-dihydro-1,3-oxazol-2-yl group or a 1,3,4-oxadiazol-2-yl group. Other heterocyclic groups are also easily produced according to similar methods.

Method H is a method for producing a compound represented by general formula (If), in which the heterocyclic group formed by A and $R^1$ together with the carbon atom bonded thereto that may be substituted with 1 to 3 group(s) independently selected from Substituent Group α is 4,5-dihydro-1,3-oxazol-2-yl group that may be substituted with 1 to 3 group(s) independently selected from Substituent Group α, and $R^3$ is a $C_1$-$C_6$ alkoxy group among compounds represented by general formula (I).

Method H

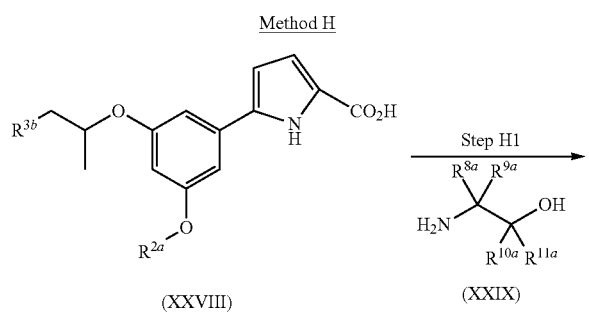

(XXVIII)         (XXIX)

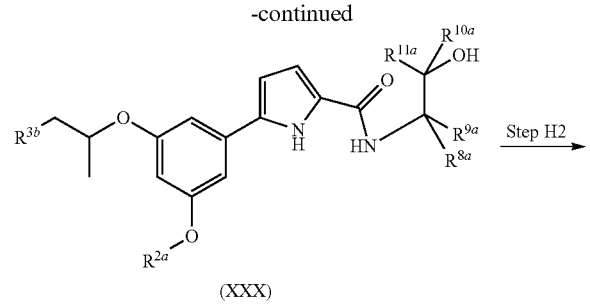

(XXX)

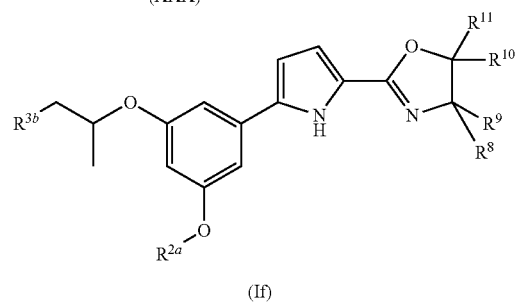

(If)

In the present invention, $R^2$, $R^{3b}$ and $R^{2a}$ are as defined above, $R^8$, $R^9$, $R^{10}$ and $R^{11}$ represent a hydrogen atom or a group belonging to Substituent Group α, and $R^{8a}$, $R^{9a}$, $R^{10a}$ and $R^{11a}$ are groups in which an amino group, hydroxy group and/or carboxyl group contained as a substituent in groups $R^8$, $R^9$, $R^{10}$ and $R^{11}$ is an optionally protected amino group, hydroxy group and/or carboxyl group, or represent the same groups as defined for groups $R^8$, $R^9$, $R^{10}$ and $R^{11}$.

Step H1

This step is a step for producing a compound represented by general formula (XXX).

This step is carried out by reacting a compound represented by general formula (XXVIII) with a compound represented by general formula (XXIX) in a solvent and in the presence of a condensation agent and in the presence or absence of a base.

The compound represented by general formula (XXIX) used in this step is either a known compound or is easily produced in accordance with a known method or method similar thereto by using a known compound for the starting raw material.

The solvent used in this step is preferably an alcohol, a halogenated hydrocarbon or an amide, and more preferably methanol, dichloromethane or N,N-dimethylformamide.

The condensation agent used in this step is preferably DMT-MM, WSCI·HCl or HATU.

The base used in this step is preferably an organic base, and more preferably N-methylmorpholine, 4-dimethylaminopyridine or N,N-diisopropylethylamine.

The reaction temperature in this step is normally −20 to 60° C. and preferably 0 to 30° C.

The reaction time in this step is normally 0.5 to 72 hours and preferably 1 to 24 hours.

Step H2

This step is a step for producing a compound represented by general formula (If).

This step is carried out by reacting a compound represented by general formula (XXX) with a base and methanesulfonic acid anhydride or bis(2-methoxyethyl)aminosulfur trifluoride in a solvent, followed by removing a protecting group of an amino group, hydroxy group and/or carboxyl group in $R^{2a}$, $R^{8a}$, $R^{9a}$, $R^{10a}$ and $R^{11a}$.

The solvent used in this step is preferably an ether, and more preferably tetrahydrofuran or dimethoxyethane.

In the case of using methanesulfonic acid anhydride, the base used in this step is preferably an organic base, and more preferably triethylamine. In the case of using bis(2-methoxyethyl)aminosulfur trifluoride, the base is preferably an alkali metal carbonate, and more preferably potassium carbonate.

The reaction temperature in this step is normally −100 to 85° C., and in the case of using methanesulfonic acid anhydride, is preferably 10 to 60° C. In the case of using bis(2-methoxyethyl)aminosulfur trifluoride, the reaction temperature is preferably −78 to 30° C.

The reaction time in this step is normally 0.5 to 72 hours and preferably 1 to 24 hours.

Method I is a method for producing a compound represented by general formula (Ig), in which the heterocyclic group formed by A and $R^1$ together with the carbon atom bonded thereto that may be substituted with 1 to 3 group(s) independently selected from Substituent Group α is a 1,3,4-oxadiazol-2-yl group that may be substituted with 1 group selected from Substituent Group α, and $R^3$ is a $C_1$-$C_6$ alkoxy group among compounds represented by general formula (I).

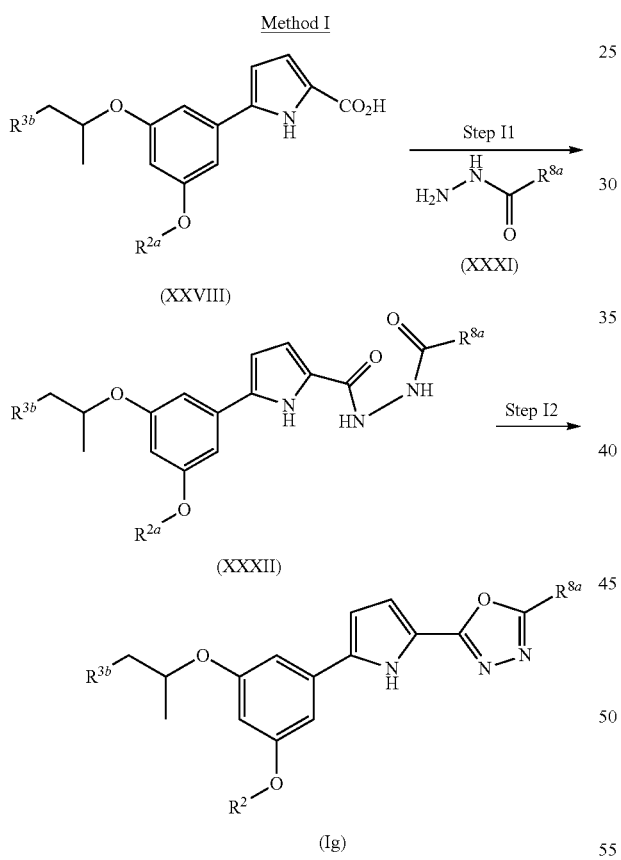

In the present invention, $R^2$, $R^{3b}$, $R^8$, $R^{2a}$ and $R^{8a}$ are as defined above.

Step I1

This step is a step for producing a compound represented by general formula (XXXII).

This step is carried out in the same manner as above-mentioned Step H1 of Method H by reacting a compound represented by general formula (XXVIII) with a compound represented by general formula (XXXI) in a solvent, in the presence of a condensation agent and in the presence or absence of a base.

The compound represented by general formula (XXXI) used in this step is either a known compound or is easily produced in accordance with a known method or method similar thereto by using a known compound for the starting raw material.

Step I2

This step is a step for producing a compound represented by general formula (Ig).

This step is carried out by reacting a compound represented by general formula (XXXII) with p-toluenesulfonyl chloride and base in a solvent, followed by removing a protecting group of an amino group, hydroxy group and/or carboxyl group in $R^{2a}$ and $R^{8a}$ as desired.

The solvent used in this step is preferably a halogenated hydrocarbon, and more preferably dichloromethane.

The base used in this step is preferably an organic base, and more preferably triethylamine.

The reaction temperature in this step is normally −20 to 40° C. and preferably 0 to 30° C.

The reaction time in this step is normally 0.5 to 24 hours and preferably 1 to 12 hours.

Method J is a method for producing a compound represented by general formula (XXVIII) used in above-mentioned Step H1 of Method H, above-mentioned Step I1 of Method I and above-mentioned Step L1 of Method L.

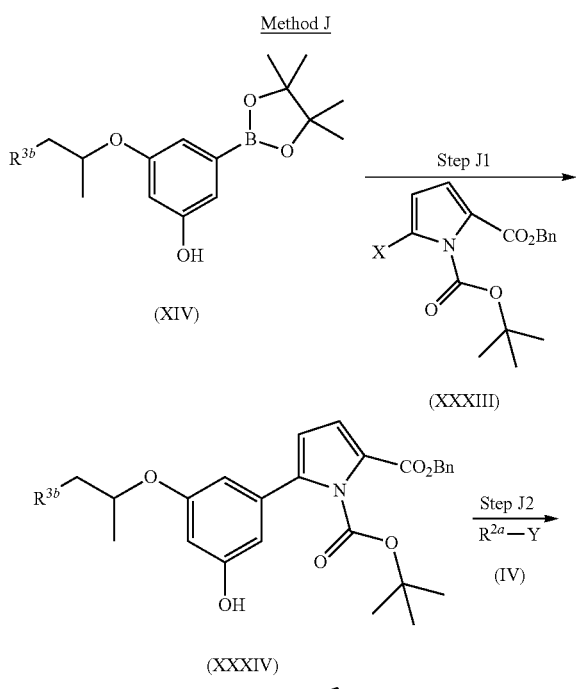

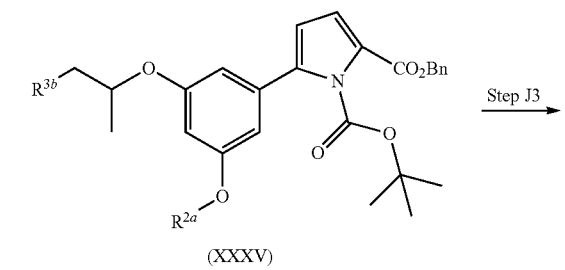

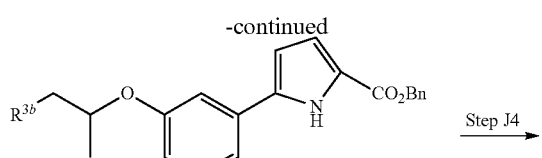

(XXXV)

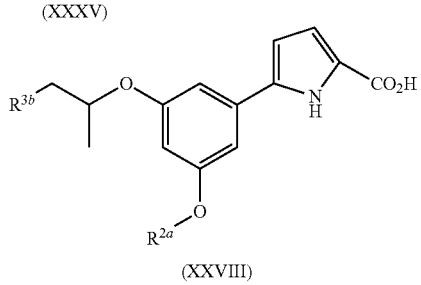

(XXVIII)

In the present invention, $R^{2a}$, $R^{3b}$, X and Y are as defined above.

Step J1

This step is a step for producing a compound represented by general formula (XXXIV).

This step is carried out in the same manner as above-mentioned Step A6 of Method A by reacting a compound represented by general formula (XIV) obtained in above-mentioned Step B3 of Method B with a compound represented by general formula (XXXIII) in a solvent and in the presence of a palladium catalyst and inorganic base.

Step J2

This step is a step for producing a compound represented by general formula (XXXV).

This step is carried out by reacting a compound represented by general formula (XXXIV) with a compound represented by general formula (IV) in a solvent and in the presence of a base.

The solvent used in this step is preferably an amide or a nitrile, and more preferably N,N-dimethylformamide or acetonitrile.

The base used in this step is preferably an alkali metal carbonate, and more preferably potassium carbonate.

The reaction temperature in this step is normally 50 to 140° C. and preferably 60 to 100° C.

The reaction time in this step is normally 1 to 72 hours and preferably 2 to 24 hours.

Step J3

This step is a step for producing a compound represented by general formula (XXXVI).

This step is carried out in the same manner as above-mentioned Step A7 of Method A by reacting a compound represented by general formula (XXXV) with an acid.

Step J4

This step is a step for producing a compound represented by general formula (XXVIII).

This step is carried out by reacting a compound represented by general formula (XXXVI) in a solvent and under hydrogen atmosphere in the presence of a palladium catalyst.

The solvent used in this step is preferably an ether, an alcohol or an ester, and more preferably tetrahydrofuran, methanol, ethanol or ethyl acetate.

The palladium catalyst used in this step is preferably a zero-valent palladium catalyst, and more preferably palladium-active carbon.

The reaction temperature in this step is normally –10 to 40° C. and preferably 0 to 30° C.

The reaction time in this step is normally 0.1 to 72 hours and preferably 0.5 to 24 hours.

Method K is a method for producing a compound represented by general formula (Ih), in which the heterocyclic group formed by A and $R^1$ together with the carbon atom bonded thereto that may be substituted with 1 to 3 group(s) independently selected from Substituent Group α is a 4,5-dihydro-1,3-oxazol-2-yl group that may be substituted with 1 to 3 group(s) independently selected from Substituent Group cc or a 1,3,4-oxadiazol-2-yl group that may be substituted with 1 group selected from Substituent Group α, and $R^3$ is a $C_1$-$C_6$ alkoxy group among compounds represented by general formula (I).

Method K

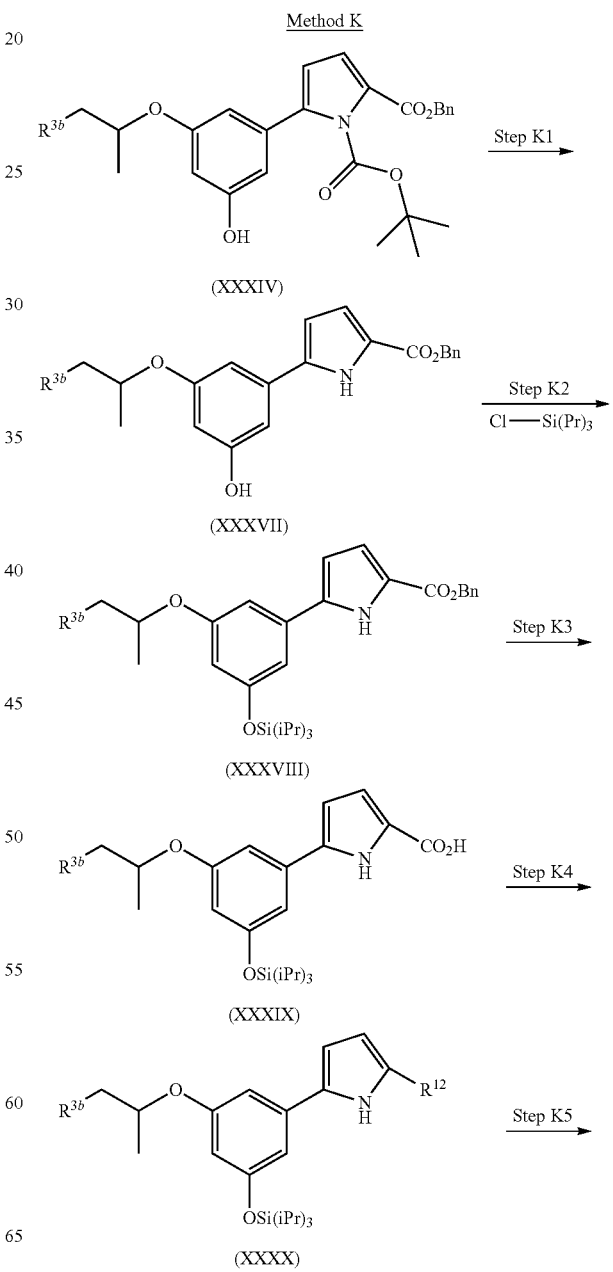

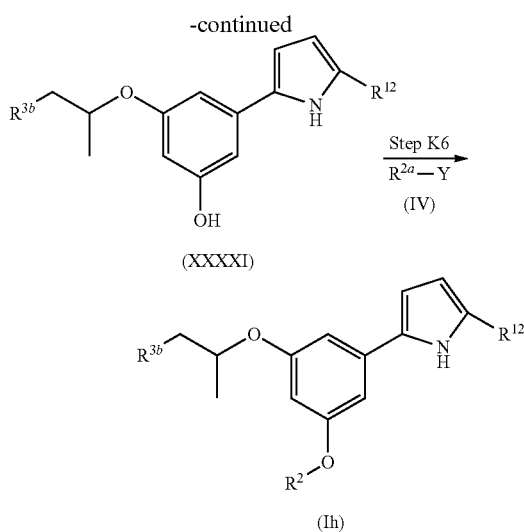

In the present invention, $R^2$, $R^{3b}$, Y and $R^{2a}$ are as defined above, and $R^{12}$ represents a 4,5-dihydro-1,3-oxazol-2-yl group that may be substituted with 1 to 3 group(s) independently selected from Substituent Group α or a 1,3,4-oxadiazol-2-yl group that may be substituted with 1 group selected from Substituent Group α.

Step K1

This step is a step for producing a compound represented by general formula (XXXVII).

This step is carried out in the same manner as abovementioned Step A7 of Method A by reacting a compound represented by general formula (XXXIV) obtained in abovementioned Step J1 of Method J with an acid in a solvent.

Step K2

This step is a step for producing a compound represented by general formula (XXXVIII).

This step is carried out by reacting a compound represented by general formula (XXXVII) with triisopropylsilyl chloride in a solvent and in the presence of a base.

The solvent used in this step is preferably a halogenated hydrocarbon, and more preferably dichloromethane.

The base used in this step is preferably an organic base, and more preferably triethylamine or a mixed base of triethylamine and 4-dimethylaminopyridine.

The reaction temperature in this step is normally –10 to 40° C. and preferably 0 to 30° C.

The reaction time in this step is normally 0.1 to 72 hours and preferably 0.5 to 24 hours.

Step K3

This step is a step for producing a compound represented by general formula (XXXIX).

This step is carried out in the same manner as Step J4 of Method J by reacting a compound represented by general formula (XXXVIII) in a solvent and under hydrogen atmosphere in the presence of a palladium catalyst.

Step K4

This step is a step for producing a compound represented by general formula (XXXX).

This step is carried out in compliance with Method H (Step H1 and Step H2) or Method I (Step I1 and Step I2).

Step K5

This step is a step for producing a compound represented by general formula (XXXXI).

This step is carried out by reacting a compound represented by general formula (XXXX) with tetrabutylammonium fluoride in a solvent.

The solvent used in this step is preferably an ether, and more preferably tetrahydrofuran.

The reaction temperature in this step is normally –10 to 40° C. and preferably 0 to 30° C.

The reaction time in this step is normally 0.1 to 12 hours and preferably 0.5 to 3 hours.

Step K6

This step is a step for producing a compound represented by general formula (Ih).

This step is carried out by reacting a compound represented by general formula (XXXXI) with a compound represented by general formula (IV) in a solvent and in the presence of a base, followed by removing a protecting group of an amino group, hydroxy group and/or carboxyl group in $R^{2a}$ as desired.

The solvent used in this step is preferably an amide or a nitrile, and more preferably N,N-dimethylformamide or acetonitrile.

The base used in this step is preferably an alkali metal carbonate, and more preferably potassium carbonate or cesium carbonate.

The reaction temperature in this step is normally 10 to 140° C. and preferably 20 to 120° C.

The reaction time in this step is normally 1 to 72 hours and preferably 2 to 24 hours.

Method L is a method for producing a compound represented by general formula (If), in which the heterocyclic group formed by A and $R^1$ together with the carbon atom bonded thereto that may be substituted with 1 to 3 group(s) independently selected from Substituent Group α is a 4,5-dihydro-1,3-oxazol-2-yl group that may be substituted with 1 to 3 group(s) independently selected from Substituent Group α, and $R^3$ is a $C_1$-$C_6$ alkoxy group among compounds represented by general formula (I).

Method L

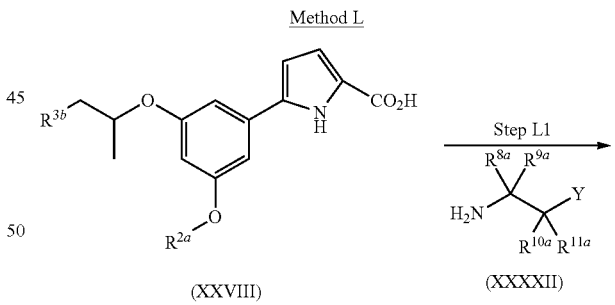

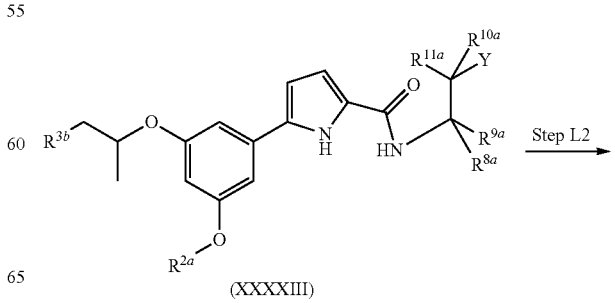

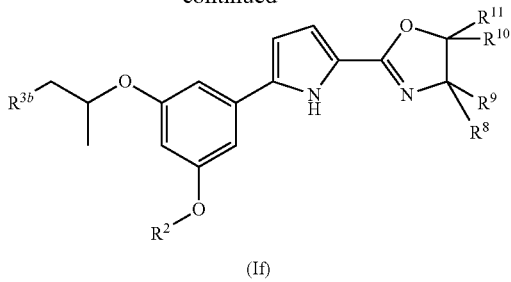

(If)

In the present invention, $R^2$, $R^8$, $R^9$, $R^{10}$, $R^{11}$, $R^{2a}$, $R^{3b}$, $R^{8a}$, $R^{9a}$, $R^{10a}$, $R^{11a}$ and Y are as defined above.

Step L1

This step is a step for producing a compound represented by general formula (XXXXIII).

This step is carried out in the same manner as above-mentioned Step H1 of Method H by reacting a compound represented by general formula (XXVIII) with a compound represented by general formula (XXXXII) in a solvent and in the presence of a condensation agent and base.

The compound represented by general formula (XXXXII) used in this step is either a known compound or is easily produced in accordance with a known method or method similar thereto by using a known compound for the starting raw material.

Step L2

This step is a step for producing a compound represented by general formula (If).

This step is carried out by reacting a compound represented by general formula (XXXXIII) with a base in a solvent, followed by removing a protecting group of an amino group, hydroxy group and/or carboxyl group in $R^{2a}$, $R^{8a}$, $R^{9a}$, $R^{10a}$ and $R^{11a}$ as desired.

The solvent used in this step is preferably an ether, and more preferably tetrahydrofuran.

The base used in this step is preferably an alkali metal hydride, and more preferably sodium hydride.

The reaction temperature in this step is normally −20 to 40° C. and preferably 0 to 25° C.

The reaction time in this step is normally 0.5 to 48 hours and preferably 1 to 24 hours.

In the above descriptions, a protecting group of an "optionally protected amino group", "optionally protected hydroxy group" and "optionally protected carboxyl group" in the definitions of $A^a$, $R^{1a}$, $R^{2a}$, $R^{8a}$, $R^{9a}$, $R^{10a}$ and $R^{11a}$ refers to a protecting group able to be cleaved by a chemical method such as hydrogenolysis, hydrolysis, electrolysis or photolysis that is commonly used in organic synthetic chemistry (refer to, for example, T. W. Greene, et al., *Protective Groups in Organic Synthesis*, 3rd Edition, John Wiley & Sons, Inc. (1999)).

In the above descriptions, there are no particular limitations on the "protecting group" of an "optionally protected hydroxy group" in the definitions of $A^a$, $R^{1a}$, $R^{2a}$, $R^{8a}$, $R^{9a}$, $R^{10a}$ and $R^{11a}$ provided it is a hydroxy group protecting group used in the field of organic synthetic chemistry, and examples include "alkylcarbonyl groups" such as a formyl group, the above-mentioned "$C_2$-$C_7$ alkylcarbonyl group", halogenated alkylcarbonyl groups such as chloroacetyl, dichloroacetyl, trichloroacetyl and trifluoroacetyl, alkoxyalkylcarbonyl groups such as methoxyacetyl, and unsaturated alkylcarbonyl groups such as acryloyl, propioloyl, methacryloyl, crotonoyl, isocrotonoyl and (E)-2-methyl-2-butenoyl; "arylcarbonyl groups" such as an arylcarbonyl groups such as benzoyl, α-naphthoyl and β-naphthoyl, halogenated arylcarbonyl groups such as 2-bromobenzoyl and 4-chlorobenzoyl, $C_1$-$C_6$ alkylated arylcarbonyl groups such as 2,4,6-trimethylbenzoyl and 4-toluoyl, $C_1$-$C_6$ alkoxylated arylcarbonyl groups such as 4-anisoyl, nitroarylcarbonyl groups such as 4-nitrobenzoyl and 2-nitrobenzoyl, $C_2$-$C_7$ alkoxycarbonylated arylcarbonyl groups such as 2-(methoxycarbonyl)benzoyl, and arylated arylcarbonyl groups such as 4-phenylbenzoyl; "alkoxycarbonyl groups" such as the above-mentioned "$C_2$-$C_7$ alkoxycarbonyl group", and $C_2$-$C_7$ alkoxycarbonyl groups substituted with a halogen or tri($C_1$-$C_6$ alkyl)silyl such as 2,2,2-trichloroethoxycarbonyl and 2-trimethylsilylethoxycarbonyl group; "tetrahydropyranyl or tetrahydrothiopyranyl groups" such as tetrahydropyran-2-yl, 3-bromotetrahydropyran-2-yl, 4-methoxytetrahydropyran-4-yl, tetrahydrothiopyran-2-yl and 4-methoxytetrahydrothiopyran-4-yl; "tetrahydrofuranyl or tetrahydrothiofuranyl groups" such as tetrahydrofuran-2-yl and tetrahydrothiofuran-2-yl; "silyl groups" such as tri($C_1$-$C_6$ alkyl)silyl groups such as trimethylsilyl, triethylsilyl, isopropyldimethylsilyl, t-butyldimethylsilyl, methyldiisopropylsilyl, methyl-di-t-butylsilyl and triisopropylsilyl, and ($C_1$-$C_6$ alkyl)diarylsilyl and di-($C_1$-$C_6$ alkyl)arylsilyl groups such as diphenylmethylsilyl, diphenylbutylsilyl, diphenylisopropylsilyl and phenyldiisopropylsilyl; "alkoxymethyl groups" such as a ($C_1$-$C_6$ alkoxy)methyl groups such as methoxymethyl, 1,1-dimethyl-1-methoxymethyl, ethoxymethyl, propoxymethyl, isopropoxymethyl, butoxymethyl and t-butoxymethyl, ($C_1$-$C_6$ alkoxy)-($C_1$-$C_6$ alkoxy)methyl groups such as 2-methoxyethoxymethyl, and ($C_1$-$C_6$ halogenated alkoxy)methyl groups such as 2,2,2-trichloroethoxymethyl and bis(2-chloroethoxy)methyl; "substituted ethyl groups" such as a ($C_1$-$C_6$ alkoxy)ethyl groups such as 1-ethoxyethyl and 1-(isopropoxy)ethyl, and halogenated ethyl groups such as 2,2,2-trichloroethyl; "aralkyl groups" such as a $C_1$-$C_6$ alkyl groups substituted with 1 to 3 aryl group(s) such as benzyl, α-naphthylmethyl, β-naphthylmethyl, diphenylmethyl, triphenylmethyl, β-naphthyldiphenylmethyl and β-anthrylmethyl, and a $C_1$-$C_6$ alkyl groups substituted with 1 to 3 aryl group(s) in which an aryl ring is substituted with a $C_1$-$C_6$ alkyl, $C_1$-$C_6$ alkoxy, nitro, halogen or cyano group such as 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl and 4-cyanobenzyl; "alkenyloxycarbonyl groups" such as a vinyloxycarbonyl and allyloxycarbonyl; and, "aralkyloxycarbonyl groups" in which an aryl ring is optionally substituted with 1 or 2 $C_1$-$C_6$ alkoxy or nitro group(s) such as a benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl, and preferably alkylcarbonyl groups, silyl groups or aralkyl groups.

In the above descriptions, there are no particular limitations on the "protecting group" of an "optionally protected carboxyl group" in the definitions of $A^a$, $R^{1a}$, $R^{2a}$, $R^{8a}$, $R^{9a}$, $R^{10a}$ and $R^{11a}$ provided it is a carboxyl group protecting group used in the field of organic synthetic chemistry, and examples include the above-mentioned "$C_1$-$C_6$ alkyl group"; the above-mentioned "$C_2$-$C_6$ alkenyl group"; the above-mentioned "$C_2$-$C_6$ alkynyl group"; the above-mentioned "$C_1$-$C_6$ halogenated alkyl group"; $C_1$-$C_6$ hydroxyalkyl groups such as hydroxymethyl and 2-hydroxyethyl; ($C_2$-$C_7$ alkylcarbonyl)-($C_1$-$C_6$ alkyl) groups such as acetylmethyl; the above-mentioned "aralkyl groups", and the above-mentioned "silyl groups", and preferably $C_1$-$C_6$ alkyl groups or aralkyl groups.

In the above descriptions, there are no particular limitations on the "protecting group" of an "optionally protected amino group" in the definitions of $A^a$, $R^{1a}$, $R^{2a}$, $R^{8a}$, $R^{9a}$, $R^{10a}$ and $R^{11a}$ provided it is an amino group protecting group used in the field of organic synthetic chemistry, and examples include groups similar to the "alkylcarbonyl groups", "arylcarbonyl groups", "alkoxycarbonyl groups", "silyl groups", "aralkyl groups", "alkenyloxycarbonyl groups" and "aralkyloxycarbonyl groups" in the previously listed "hydroxy group protecting groups", and "substituted methylene groups that form a Schiff's base" such as N,N-dimethylaminomethylene, benzylidene, 4-methoxybenzylidene, 4-nitrobenzylidene, salicylidene, 5-chlorosalicylidene, diphenylmethylene and (5-chloro-2-hydroxyphenyl)phenylmethylene, preferably alkylcarbonyl groups, arylcarbonyl groups or alkoxycarbonyl groups, and more preferably alkoxycarbonyl groups.

The steps requiring protection/deprotection are performed according to known methods (for example, the methods described in Theodora W. Greene, Peter G. M. Wuts, "Protective Groups in Organic Synthesis," 1999, A Wiley-Interscience Publication, etc.).

The compound or pharmacologically acceptable salt thereof of the present invention can be administered in various forms. Examples of the route of administration include oral administration using tablets, capsules, granules, emulsions, pills, powders, syrups (solutions), and the like and parenteral administration using injections (intravenous, intramuscular, subcutaneous, or intraperitoneal administration), drip infusions, suppositories (rectal administration), and the like. These various formulations can be prepared as drug products according to usual methods using aids usually used in the field of drug formulation such as excipients, binders, disintegrants, lubricants, flavoring agents, dissolving aids, suspending agents, and coating agents in addition to an active ingredient.

In the use as a tablet, examples of carriers that can be used include excipients such as lactose, sucrose, sodium chloride, glucose, urea, starch, calcium carbonate, kaolin, crystalline cellulose, and silicic acid; binders such as water, ethanol, propanol, simple syrup, glucose solution, starch solution, gelatin solution, carboxymethylcellulose, shellac, methylcellulose, potassium phosphate, and polyvinylpyrrolidone; disintegrants such as dry starch, sodium alginate, agar powder, laminaran powder, sodium hydrogencarbonate, calcium carbonate, polyoxyethylene sorbitan fatty acid esters, sodium lauryl sulfate, stearic monoglyceride, starch, and lactose; disintegration inhibitors such as sucrose, stearin, cocoa butter, and hydrogenated oil; absorption enhancers such as quaternary ammonium salts and sodium lauryl sulfate; humectants such as glycerine and starch; adsorbents such as starch, lactose, kaolin, bentonite, and colloidal silicic acid; lubricants such as purified talc, stearate, fluoboric acid powder, and polyethylene glycol, and so forth. Furthermore, tablets coated in usual ways such as, for example, sugar-coated tablets, gelatin-coated tablets, enteric-coated tablets, film-coated tablets, double-layer tablets, and multilayered tablets can be prepared as required.

In the use as a pill, examples of carriers that can be used include excipients such as glucose, lactose, cocoa butter, starch, hydrogenated vegetable oil, kaolin, and talc; binders such as powdered gum arabic, powdered tragacanth, gelatin, and ethanol; disintegrants such as laminaran, and agar, and so forth.

In the use as a suppository, a wide range of carriers known in this field can be used, and examples thereof include polyethylene glycol, cocoa butter, higher alcohols, higher alcohol esters, gelatin, semisynthetic glycerides, and so forth.

In the use as an injection, the formulations can be prepared as solutions, emulsions, or suspensions. Preferably, these solutions, emulsions, and suspensions are sterilized and are isotonic with blood. Solvents for producing these solutions, emulsions, and suspensions are not particularly limited so long as they can be used as diluents for medical use, and examples thereof include water, ethanol, propylene glycol, ethoxylated isostearyl alcohol, polyoxylated isostearyl alcohol, polyoxy ethylene sorbitan fatty acid esters, and so forth. In this case, a sufficient amount of sodium chloride, glucose, or glycerine may be added to the formulation to prepare an isotonic solution, and usual dissolving aids, buffers, soothing agents, and the like may also be added.

Furthermore, coloring agents, preservatives, perfumes, flavoring agents, sweeteners, and the like can be added to the above-mentioned formulation, if necessary. Furthermore, other drugs can also be added.

The amount of active ingredient compound contained in the above-mentioned formulations is not particularly limited, but is usually 0.5 to 70% by weight of the total composition, preferably 1 to 30% by weight.

The dose varies depending on symptoms, age, and the like of the patient (a warm-blooded animal, in particular, a human). In the case of oral administration, the recommended adult daily dosage is from 0.1 mg as the lower limit (preferably 1 mg, more preferably 10 mg) to 2000 mg as the upper limit (preferably 100 mg), which is divided into 1 to 6 doses depending on the symptoms.

EXAMPLES

Although the following provides a more detailed explanation of the present invention through examples and test examples thereof, the scope of the present invention is not limited thereby.

Elution in column chromatography indicated in the examples was carried out under observation by thin layer chromatography (TLC). During TLC observations, Silica Gel 60F$_{254}$ manufactured by Merck was used for the TLC plate, the solvent used for the elution solvent in column chromatography was used for the developing solvent, and a UV detector was used for the detection method. Silica Gel SK-85 (230 to 400 mesh) manufactured by Merck or Silica Gel FL100B manufactured by Fuji Silysia Chemical was used for the column silica gel. An automated chromatography system (Purif-α2) and a disposable column (Purif-pack) manufactured by Moritex were also suitably used in addition to ordinary column chromatography. A Silica Gel 60F$_{254}$ plate having a thickness of 0.5 mm and measuring 20×20 cm manufactured by Merck was used for purification by preparative TLC. Furthermore, the abbreviations used in the examples have the meanings indicated below:

mg: milligrams, g: grams, mL: milliliters, MHz: megahertz, HATU: O-(7-azabenzotriazol-1-yl)-N,N,N',N'-tetramethyluronium hexafluorophosphate, WSCI•HCl: 1-ethyl-3-(dimethylaminopropyl)carbodiimide hydrochloride, HOBT•H$_2$O: 1-hydroxybenzotriazole monohydrate.

In the following examples, nuclear magnetic resonance (referred to as $^1$H-NMR) spectra were obtained using tetramethylsilane for the standard substance, and chemical shift values are indicated with δ values (ppm). In the splitting patterns, a singlet is indicated with an "s", a doublet with a "d", a triplet with a "t", a quartet with a "q", a broad pattern with "br", and a multiplet with an "m".

Mass spectrometry referred to as (MS) was carried out with the Fast Atom Bombardment (FAB) method, Electron Ionization (E1) method or Electron Spray Ionization (ESI) method.

Example 1

2-(5-{3-[(1S)-2-Methoxy-1-methylethoxy]-5-[4-(methylsulfonyl)phenoxy]phenyl}-1H-pyrrol-2-yl)-1,3-thiazole

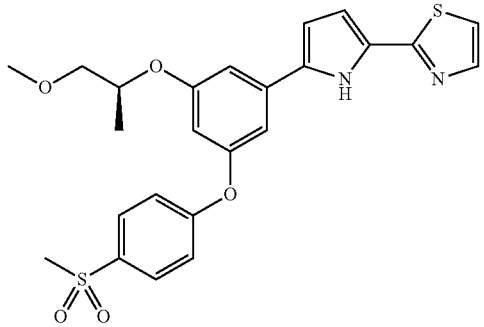

(1a) 3-Bromo-5-methoxyphenol

Commercially available 1-bromo-3,5-dimethoxybenzene (18.74 g, 86.3 mmol) was dissolved in 1-methyl-2-pyrrolidone (100 mL), and sodium thiomethoxide (6.74 g, 96.2 mmol) was added, followed by stirring at 100° C. for 3 hours under nitrogen atmosphere. The reaction solution was cooled to room temperature, 1N hydrochloric acid (200 mL) was added, and extraction was carried out with diethyl ether (500 mL). The organic layer was washed with saturated brine, and subsequently dried over sodium sulfate. The solvent was distilled off under reduced pressure, and the resulting residue was purified using silica gel column chromatography (elution solvent: ethyl acetate/hexane=20%-25%) to afford the desired compound (15.03 g, yield 86%) as a white solid.

$^1$H-NMR (CDCl$_3$, 400 MHz): δ 3.77 (3H, s), 4.82 (1H, s), 6.33 (1H, t, J=2.4 Hz), 6.61 (1H, t, J=2.0 Hz), 6.66 (1H, t, J=2.0 Hz).

(1b) 1-Bromo-3-methoxy-5-[4-(methylsulfonyl)phenoxy]benzene

3-Bromo-5-methoxyphenol (13.10 g, 64.5 mmol) synthesized in Example (1a) and commercially available 4-fluorophenylmethylsulfone (10.45 g, 60.0 mmol) were dissolved in N,N-dimethylformamide (100 mL), and potassium carbonate (25.00 g, 181 mmol) was added, followed by stirring at 100° C. for 36 hours under nitrogen atmosphere. The reaction solution was cooled to room temperature, with potassium carbonate being removed by Celite filtration, and subsequently 0.1N hydrochloric acid (500 mL) was added and extraction was carried out twice with diethyl ether (400 mL) and ethyl acetate (100 mL). The organic layer was washed with saturated brine, and subsequently dried over sodium sulfate. The solvent was distilled off under reduced pressure, and the resulting solid was washed with diethyl ether to afford the desired compound (18.30 g, yield 79%) as a pale brown solid.

$^1$H-NMR (CDCl$_3$, 400 MHz): δ 3.07 (3H, s), 3.80 (3H, s), 6.56 (1H, t, J=2.4 Hz), 6.81 (1H, t, J=2.0 Hz), 6.92 (1H, t, J=2.0 Hz), 7.12 (2H, d, J=9.0 Hz), 7.92 (2H, d, J=9.0 Hz).

(1c) 3-Bromo-5-[4-(methylsulfonyl)phenoxy]phenol

1-Bromo-3-methoxy-5-[4-(methylsulfonyl)phenoxy]benzene (18.29 g, 51.2 mmol) synthesized in Example (1b) was dissolved in dichloromethane (400 mL) and cooled to −78° C., and boron tribromide (1.0M dichloromethane solution, 100 mL, 100 mmol) was added using a dropping funnel over 30 minutes under nitrogen atmosphere. The mixture was stirred at −78° C. for 2 hours, followed by raising the temperature naturally, and stirring at room temperature overnight. A saturated aqueous sodium hydrogencarbonate solution was added under cooling with an ice bath to neutralize the reaction solution, and extraction was carried out twice with dichloromethane (500 mL) and methanol (50 mL). The organic layer was washed with saturated brine, and subsequently dried over sodium sulfate. The solvent was distilled off under reduced pressure to afford the desired compound (16.89 g, yield 96%) as a pale yellow solid.

$^1$H-NMR (DMSO-D$_6$, 400 MHz): δ 3.19 (3H, s), 6.49 (1H, t, J=2.1 Hz), 6.77 (1H, t, J=2.0 Hz), 6.84 (1H, t, J=2.0 Hz), 7.23 (2H, d, J=8.6 Hz), 7.94 (2H, d, 9.0 Hz), 10.27 (1H, s).

(1d) 3-[4-(Methylsulfonyl)phenoxy]-5-(4,4,5,5-tetramethyl-1,3,2-dioxaborolan-2-yl)phenol 3-Bromo-5-[4-(methylsulfonyl)phenoxy]phenol (10.10 g, 29.4 mmol) synthesized in Example (1c) was dissolved in N,N-dimethylformamide (100 mL), and bis(pinacolato)diboron (11.09 g, 43.7 mmol), [1,1'-bis(diphenylphosphino)ferrocene]palladium (II) dichloride dichloromethane complex (722 mg, 0.884 mmol) and potassium acetate (14.92 g, 152 mmol) were added, followed by stirring at 90° C. for 5 hours under nitrogen atmosphere. After the reaction solution was cooled to room temperature, it was diluted with ethyl acetate (400 mL), and the insolubles were removed by Celite filtration. Water (400 mL) was added to the filtrate to separate it, and the organic layer was washed with saturated brine, followed by drying over sodium sulfate. The solvent was distilled off under reduced pressure, and the resulting residue was purified using silica gel column chromatography (elution solvent: ethyl acetate/hexane=30%-50%) to afford the desired compound (11.88 g, yield ~100%) as a white solid.

$^1$H-NMR (CDCl$_3$, 400 MHz): δ 1.33 (12H, s), 3.06 (3H, s), 5.16 (1H, s), 6.69 (1H, t, J=2.4 Hz), 7.06-7.12 (4H, m), 7.87 (2H, t, J=9.0 Hz).

(1e) 2-{3-[(1S)-2-Methoxy-1-methylethoxy]-5-[4-(methylsulfonyl)phenoxy]phenyl}-4,4,5,5-tetramethyl-1,3,2-dioxaborolane 3-[4-(Methylsulfonyl)phenoxy]-5-(4,4,5,5-tetramethyl-1,3,2-dioxaborolan-2-yl)phenol (13.20 g, 33.8 mmol) synthesized in Example (1d) was dissolved in tetrahydrofuran (300 mL), and (R)-(−)-1-methoxy-2-propanol (3.70 mL, 37.8 mmol) and triphenylphosphine (9.78 g, 37.3 mmol) were added, and subsequently cooled to 0° C. Diethyl azodicarboxylate (40% toluene solution, 16.2 mL, 37.2 mmol) was added dropwise over 10 minutes under nitrogen atmosphere and stirring was carried out at 0° C. for 30 minutes, followed by raising the temperature naturally and stirring at room temperature overnight. Water (300 mL) and ethyl acetate (300 mL) were added, and the solution was separated. The organic layer was washed with saturated brine, and subsequently dried over sodium sulfate. The solvent was distilled off under reduced pressure, and the resulting residue was purified using silica gel column chromatography (elution solvent: ethyl acetate/hexane=20%-40%) to afford the desired compound (11.94 g, yield 76%) as a colorless oil.

$^1$H-NMR (CDCl$_3$, 400 MHz): δ 1.31 (3H, d, J=6.7 Hz), 1.33 (12H, s), 3.05 (3H, s), 3.40 (3H, s), 3.48 (1H, dd, J=4.3, 10.2 Hz), 3.57 (1H, dd, J=5.9, 10.2 Hz), 4.58-4.62 (1H, m), 6.76 (1H, t, J=2.4 Hz), 7.05-7.09 (3H, m), 7.24 (1H, d, J=2.4 Hz), 7.87 (2H, d, J=9.0 Hz).

(1f) t-Butyl 2-(1,3-thiazol-2-yl)-1H-pyrrole-1-carboxylate

Commercially available 1-(t-butoxycarbonyl)pyrrole-2-boronic acid (10.06 g, 47.7 mmol) was dissolved in a mixed solvent of 1,2-dimethoxyethane (150 mL) and water (25 mL), and 2-bromothiazole (4.40 mL, 48.8 mmol), palladium (II) acetate (535 mg, 2.38 mmol), triphenylphosphine (2.50 g, 9.53 mmol) and potassium carbonate (19.50 g, 141 mmol) were added, followed by stirring at 90° C. for 16 hours under nitrogen atmosphere. The reaction solution was cooled to room temperature, water (300 mL) and ethyl acetate (400 mL) were added, and the solution was separated. The organic layer was washed with saturated brine, and subsequently dried over sodium sulfate. The solvent was distilled off under reduced pressure, and the resulting residue was purified using silica gel column chromatography (elution solvent: ethyl acetate/hexane=0%-20%) to afford the desired compound (6.71 g, yield 56%) as a pale yellow oil.

$^1$H-NMR (CDCl$_3$, 400 MHz): δ 1.42 (9H, s), 6.26 (1H, t, J=3.4 Hz), 6.58 (1H, dd, J=1.6, 3.5 Hz), 7.37 (1H, d, J=3.1 Hz), 7.41 (1H, dd, J=1.6, 3.1 Hz), 7.85 (1H, d, J=3.1 Hz).

(1g) t-Butyl 2-bromo-5-(1,3-thiazol-2-yl)-1H-pyrrole-1-carboxylate t-Butyl 2-(1,3-thiazol-2-yl)-1H-pyrrole-1-carboxylate (6.70 g, 26.8 mmol) synthesized in Example (1f) was dissolved in tetrahydrofuran (100 mL) and cooled to 0° C. With stirring under nitrogen atmosphere, N-bromosuccinimide (4.79 g, 26.9 mmol) was divided into 5 parts to be added every 10 minutes, followed by further stirring at 0° C. for 2 hours. A saturated aqueous sodium hydrogencarbonate solution (200 mL) was added, and extraction was carried out with ethyl acetate (300 mL). The organic layer was washed with saturated brine, and subsequently dried over sodium sulfate. The solvent was distilled off under reduced pressure, and the resulting residue was purified using silica gel column chromatography (elution solvent: ethyl acetate/hexane=0%-16%) to afford the desired compound (7.55 g, yield 86%) as a white solid.

$^1$H-NMR (CDCl$_3$, 400 MHz): δ 1.47 (9H, s), 6.30 (1H, d, J=3.9 Hz), 6.52 (1H, d, J=3.9 Hz), 7.29 (1H, d, J=3.1 Hz), 7.79 (1H, d, J=3.1 Hz).

(1h) t-Butyl 2-{3-[(1S)-2-methoxy-1-methylethoxy]-5-[4-(methylsulfonyl)phenoxy]phenyl}-5-(1,3-thiazol-2-yl)-1H-pyrrole-1-carboxylate 2-{3-[(1S)-2-Methoxy-1-methylethoxy]-5-[4-(methylsulfonyl)phenoxy]phenyl}-4,4,5,5-tetramethyl-1,3,2-dioxaborolane (6.44 g, 13.9 mmol) synthesized in Example (1e) and t-butyl 2-bromo-5-(1,3-thiazol-2-yl)-1H-pyrrole-1-carboxylate (5.21 g, 15.8 mmol) synthesized in Example (1g) were dissolved in a mixed solvent of 1,4-dioxane (200 mL) and water (50 mL), and [1,1'-bis(diphenylphosphino)ferrocene]palladium (II) dichloride dichloromethane complex (564 mg, 0.691 mmol) and potassium carbonate (9.67 g, 70.0 mmol) were added, followed by stirring at 50° C. for 3 hours under nitrogen atmosphere. After the reaction solution was cooled to room temperature, water (200 mL) was added, and extraction was carried out with ethyl acetate (400 mL). The organic layer was washed with saturated brine, and subsequently dried over sodium sulfate. The solvent was distilled off under reduced pressure, and the resulting residue was purified using silica gel column chromatography (elution solvent: ethyl acetate/hexane=30%-50%) to afford the desired compound (7.12 g, yield 88%) as a pale yellow oil.

$^1$H-NMR (CDCl$_3$, 500 MHz): δ 1.31 (9H, s), 1.32 (3H, d, J=6.4 Hz), 3.05 (3H, s), 3.40 (3H, s), 3.49 (1H, dd, J=3.9, 10.3 Hz), 3.58 (1H, dd, J=5.9, 10.3 Hz), 4.53-4.57 (1H, m), 6.27 (1H, d, J=3.9 Hz), 6.58 (1H, d, J=3.9 Hz), 6.65 (1H, s), 6.72 (1H, s), 6.89 (1H, s), 7.15 (2H, d, J=8.8 Hz), 7.31 (1H, d, J=3.4 Hz), 7.81 (1H, d, J=3.4 Hz), 7.89 (2H, d, J=8.8 Hz).

(1i) 2-(5-{3-[(1S)-2-Methoxy-1-methylethoxy]-5-[4-(methylsulfonyl)phenoxy]phenyl}-1H-pyrrol-2-yl)-1,3-thiazole t-Butyl 2-{3-[(1S)-2-methoxy-1-methylethoxy]-5-[4-(methylsulfonyl)phenoxy]phenyl}-5-(1,3-thiazol-2-yl)-1H-pyrrole-1-carboxylate (7.16 g, 12.2 mmol) synthesized in Example (1h) was dissolved in dichloromethane (15 mL), and cooled to 0° C. Trifluoroacetic acid (30 mL) was added dropwise with stirring under nitrogen atmosphere. Stirring was carried out at room temperature for 30 minutes, followed by further stirring at 40° C. for 30 minutes. The solvent was distilled off under reduced pressure followed by dilution with ethyl acetate (300 mL), a saturated aqueous sodium hydrogencarbonate solution (200 mL) was added, and the solution was separated. The organic layer was washed with saturated brine, and subsequently dried over sodium sulfate. The solvent was distilled off under reduced pressure, and the resulting residue was purified using silica gel column chromatography (elution solvent: ethyl acetate/hexane=30%-50%) to afford the desired compound (5.21 g, yield 88%) as a pale yellow solid.

$^1$H-NMR (CDCl$_3$, 400 MHz): δ 1.33 (3H, d, J=6.3 Hz), 3.07 (3H, s), 3.42 (3H, s), 3.51 (1H, dd, J=3.9, 10.2 Hz), 3.59 (1H, dd, J=5.9, 10.2 Hz), 4.55-4.60 (1H, m), 6.53-6.56 (2H, m), 6.73 (1H, dd, J=2.4, 3.5 Hz), 6.85 (1H, t, J=2.0 Hz), 7.02 (1H, t, J=2.0 Hz), 7.14 (2H, d, J=8.6 Hz), 7.17 (1H, d, J=3.5 Hz), 7.67 (1H, d, J=3.5 Hz), 7.91 (2H, d, J=8.6 Hz), 9.60 (1H, brs).

MS (ESI) m/z: 485.12291 (M+H)$^+$.

Example 2

(2S)-2-{3-[4-(Methylsulfonyl)phenoxy]-5-[5-(1,3-thiazol-2-yl)-1H-pyrrol-2-yl]phenoxy}propan-1-ol

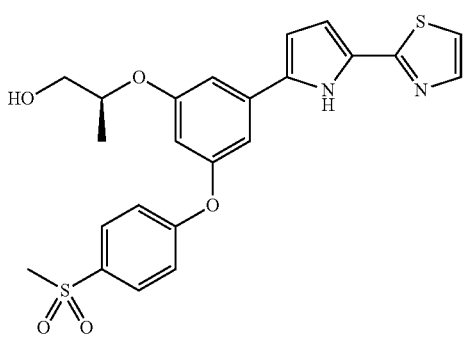

Under nitrogen atmosphere, 2-(5-{3-[(1S)-2-methoxy-1-methylethoxy]-5-[4-(methylsulfonyl)phenoxy]phenyl}-1H-pyrrol-2-yl)-1,3-thiazole (88.8 mg, 0.183 mmol) synthesized in Example (1i) was dissolved in dichloromethane (5 mL), and a boron tribromide/dichloromethane solution (1.0M, 220 μL, 0.22 mmol) was added at −78° C. Subsequently, the temperature was brought back to room temperature, followed by stirring for 30 minutes. A saturated aqueous sodium hydrogencarbonate solution was added to the reaction solution, and extraction was carried out with ethyl acetate. The organic layer was washed with saturated brine, and subsequently dried over sodium sulfate. The solvent was distilled off under reduced pressure, and the resulting residue was purified using silica gel column chromatography (elution solvent: ethyl acetate/hexane=0%-50%) to afford the desired compound (52.2 mg, yield 61%) as a pale yellow solid.

$^1$H-NMR (CDCl$_3$, 400 MHz): δ 1.31 (3H, d, J=6.3 Hz), 3.07 (3H, s), 3.76-3.79 (2H, m), 4.56 (1H, dd, J=10.6, 6.3 Hz), 6.52-6.55 (2H, m), 6.74 (1H, dd, J=3.7, 2.5 Hz), 6.87 (1H, t, J=1.8 Hz), 7.01 (1H, t, J=1.8 Hz), 7.14 (2H, d, J=9.0 Hz), 7.68 (1H, d, J=3.5 Hz), 7.91 (2H, dt, J=9.5, 2.3 Hz), 9.73 (1H, s).

MS (FAB) m/z: 471 (M+H)$^+$.

Example 3

2-(5-{3-[(1S)-2-Methoxy-1-methylethoxy]-5-[4-(methylsulfonyl)phenoxy]phenyl}-1H-pyrrol-2-yl)-5-methyl-1,3-thiazole

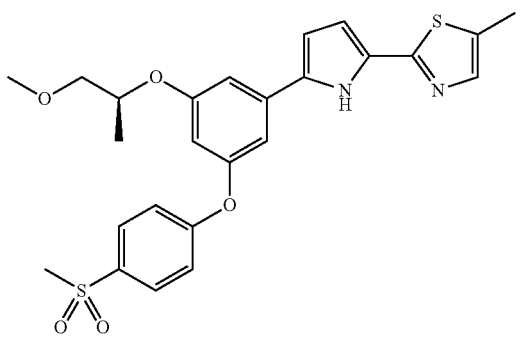

(3a) 2-[1-(Triisopropylsilyl)-1H-pyrrol-2-yl]-1,3-thiazole 2-(1H-Pyrrol-2-yl)-1,3-thiazole (1.42 g, 9.45 mmol) known in the literature {Eur. J. Org. Chem. (European Journal of Organic Chemistry) vol. 2000, no. 13, 2449-2458 (2000)} was dissolved in N,N-dimethylformamide (100 mL), and cooled to 0° C. Sodium hydride (60% oil, 570 mg, 14.3 mmol) and triisopropylsilyl chloride (4.0 mL, 18.7 mmol) were added, and stirring was carried out at room temperature for 30 minutes under nitrogen atmosphere. Water (100 mL) and diethyl ether (100 mL) were added, and the solution was separated. The organic layer was washed with saturated brine, and subsequently dried over anhydrous magnesium sulfate. The solvent was distilled off under reduced pressure, and the resulting residue was purified using silica gel column chromatography (elution solvent: hexane) to afford the desired compound (2.33 g, yield 80%) as a pale yellow oil.

$^1$H-NMR (CDCl$_3$, 400 MHz): δ 1.09 (18H, d, J=7.4 Hz), 1.74 (3H, m), 6.30 (1H, t, J=3.1 Hz), 6.78 (1H, dd, J=1.5, 3.1 Hz), 7.04 (1H, m), 7.13 (1H, d, J=3.1 Hz), 7.64 (1H, d, J=3.1 Hz).

(3b) 5-Methyl-2-[1-(triisopropylsilyl)-1H-pyrrol-2-yl]-1,3-thiazole

2-[1-(Triisopropylsilyl)-1H-pyrrol-2-yl]-1,3-thiazole (317 mg, 1.03 mmol) synthesized in Example (3a) was dissolved in tetrahydrofuran (10 mL), and cooled to −78° C. n-Butyl lithium (2.64M hexane solution, 0.51 mL, 1.35 mmol) was added dropwise, followed by stirring for 40 minutes, and subsequently iodomethane (0.13 mL, 2.09 mmol) was added and stirring was carried out for 3 hours with the temperature being gradually raised from −78° C. to room temperature. Water (10 mL) was added, and extraction was carried out with diethyl ether (20 mL). The organic layer was washed with saturated brine, and subsequently dried over anhydrous magnesium sulfate. The solvent was distilled off under reduced pressure, and the resulting residue was purified using silica gel column chromatography (elution solvent: hexane) to afford the desired compound (215 mg, yield 65%) as a colorless oil.

$^1$H-NMR (CDCl$_3$, 400 MHz): δ 1.09 (18H, d, J=7.8 Hz), 1.73 (3H, m), 2.44 (3H, s), 6.28 (1H, m), 6.68 (1H, m), 7.04 (1H, m), 7.01 (1H, m), 7.27 (1H, brs).

(3c) 5-Methyl-2-(1H-pyrrol-2-yl)-1,3-thiazole

5-Methyl-2-[1-(triisopropylsilyl)-1H-pyrrol-2-yl]-1,3-thiazole (215 mg, 0.67 mmol) synthesized in Example (3b) was dissolved in tetrahydrofuran (8 mL), and tetrabutylammonium fluoride (1M tetrahydrofuran solution, 0.87 mL, 0.87 mmol) was added, followed by stirring at room temperature for 30 minutes under nitrogen atmosphere. Water (10 mL) was added, and extraction was carried out with diethyl ether (20 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=5%-30%) to afford the desired compound (100 mg, yield 91%) as a white solid.

$^1$H-NMR (CDCl$_3$, 400 MHz): δ 2.46 (3H, s), 6.25 (1H, m), 6.61 (1H, m), 6.87 (1H, m), 7.30 (1H, brs), 9.68 (1H, brs).

(3d) 2-(5-Bromo-1H-pyrrol-2-yl)-5-methyl-1,3-thiazole

5-Methyl-2-(1H-pyrrol-2-yl)-1,3-thiazole (100 mg, 0.61 mmol) synthesized in Example (3c) was dissolved in tetrahydrofuran (7 mL), and cooled to 0° C. N-Bromosuccinimide (108 mg, 0.61 mmol) was added, and stirring was carried out at room temperature for 18 hours under nitrogen atmosphere. Water (10 mL) was added, and the solution was separated with diethyl ether (20 mL). The organic layer was washed with saturated brine, and subsequently dried over anhydrous magnesium sulfate. The solvent was distilled off under reduced pressure, and the resulting residue was used as it is in the next reaction.

(3e) t-Butyl 2-bromo-5-(5-methyl-1,3-thiazol-2-yl)-1H-pyrrole-1-carboxylate

A crude purified product of 2-(5-bromo-1H-pyrrol-2-yl)-5-methyl-1,3-thiazole synthesized in Example (3d) was dissolved in dichloromethane (8 mL), and di-t-butyl dicarbonate (165 mg, 1.35 mmol), triethylamine (0.18 mL, 1.29 mmol) and 4-dimethylaminopyridine (8.0 mg, 0.065 mmol) were added, followed by stirring at room temperature for 1.5 hours under nitrogen atmosphere. Water (10 mL) was added, and extraction was carried out with dichloromethane (10 mL). The organic layer was washed with saturated brine, and subsequently dried over anhydrous magnesium sulfate. The solvent was distilled off under reduced pressure, and the result-

(3f) 2-(5-{3-[(1S)-2-Methoxy-1-methylethoxy]-5-[4-(methylsulfonyl)phenoxy]phenyl}-1H-pyrrol-2-yl)-5-methyl-1,3-thiazole 2-{3-[(1S)-2-Methoxy-1-methylethoxy]-5-[4-(methylsulfonyl)phenoxy]phenyl}-4,4,5,5-tetramethyl-1,3,2-dioxaborolane (220 mg, 0.492 mmol) synthesized in Example (1e) and t-butyl 2-bromo-5-(5-methyl-1,3-thiazol-2-yl)-1H-pyrrole-1-carboxylate (598 mg, 1.49 mmol) synthesized in Example (3e) were dissolved in 1,4-dioxane (10 mL) and [1,1'-bis(diphenylphosphino)ferrocene]palladium (II) dichloride dichloromethane complex (20.0 mg, 0.024 mmol) and an aqueous sodium carbonate solution (3M, 0.33 mL, 0.990 mmol) were added, followed by stirring at 50° C. for 20 hours under nitrogen atmosphere. After the reaction solution was cooled to room temperature, water (10 mL) was added, and extraction was carried out with ethyl acetate (20 mL). The organic layer was washed with saturated brine, subsequently dried over anhydrous magnesium sulfate, and the solvent was distilled off under reduced pressure.

The resulting residue was dissolved in dichloromethane (10 mL), and cooled to 0° C. Trifluoroacetic acid (10 mL) was added dropwise with stirring under nitrogen atmosphere. After stirring at room temperature for 30 minutes, the solvent was distilled off under reduced pressure followed by dilution with ethyl acetate (30 mL), a saturated aqueous sodium hydrogencarbonate solution (20 mL) was added, and the solution was separated. The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=10%-40%) to afford the desired compound (49.6 mg, yield 20%) as a pale yellow solid.

$^1$H-NMR (CDCl$_3$, 400 MHz): δ 1.32 (3H, d, J=6.3 Hz), 2.46 (3H, brs), 3.07 (3H, s), 3.41 (3H, s), 3.50 (1H, dd, J=3.9, 10.2 Hz), 3.61 (1H, dd, J=5.9, 10.2 Hz), 4.56 (1H, m), 6.50-6.54 (2H, m), 6.63 (1H, dd, J=2.4, 3.9 Hz), 6.85 (1H, t, J=2.0 Hz), 7.02 (1H, t, J=2.0 Hz), 7.13 (1H, d, J=8.6 Hz), 7.29 (1H, t, J=2.0 Hz), 7.90 (2H, d, J=8.6 Hz), 9.89 (1H, brs).

MS (ESI) m/z: 521.11551 (M+Na)$^+$.

Example 4

2-(5-{3-[(1S)-2-Methoxy-1-methylethoxy]-5-[4-(methylsulfonyl)phenoxy]phenyl}-1H-pyrrol-2-yl)-1,3-benzothiazole

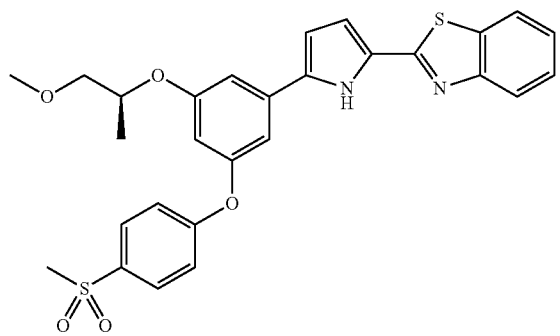

(4a) t-Butyl 2-(1,3-benzothiazol-2-yl)-1H-pyrrole-1-carboxylate

Commercially available 1-(t-butoxycarbonyl)pyrrole-2-boronic acid (417 mg, 1.98 mmol) was dissolved in 1,2-dimethoxyethane (20 mL), and 2-chloro-1,3-benzothiazole (0.25 mL, 2.02 mmol), palladium (II) acetate (23.0 mg, 0.102 mmol), triphenylphosphine (105 mg, 0.400 mmol) and an aqueous potassium carbonate solution (3M, 1.3 mL, 0.433 mmol) were added, followed by stirring at 100° C. for 22 hours under nitrogen atmosphere. The reaction solution was cooled to room temperature, water (20 mL) and ethyl acetate (20 mL) were added, and the solution was separated. The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=0%-20%) to afford the desired compound (490 mg, yield 82%) as a pale yellow oil.

$^1$H-NMR (CDCl$_3$, 400 MHz): δ 1.38 (9H, s), 6.30 (1H, t, J=3.1 Hz), 6.72 (1H, dd, J=2.0, 3.1 Hz), 7.39 (1H, ddd, J=1.2, 7.0, 8.0 Hz), 7.46 (1H, dd, J=2.0, 3.1 Hz), 7.49 (1H, ddd, J=1.2, 7.0, 8.0 Hz), 7.89 (1H, brd, J=8.0 Hz), 8.05 (1H, dt, J=1.2, 8.0 Hz).

(4b) t-Butyl 2-bromo-5-(1,3-benzothiazol-2-yl)-1H-pyrrole-1-carboxylate t-Butyl 2-(1,3-benzothiazol-2-yl)-1H-pyrrole-1-carboxylate (490 mg, 1.63 mmol) synthesized in Example (4a) was dissolved in tetrahydrofuran (20 mL), and cooled to 0° C. N-Bromosuccinimide (290 mg, 1.63 mmol) was added, and stirring was carried out at room temperature for 14 hours under nitrogen atmosphere. Water (20 mL) was added, and extraction was carried out with diethyl ether (20 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=0%-16%) to afford the desired compound (548 mg, yield 89%) as a pale yellow solid.

$^1$H-NMR (CDCl$_3$, 400 MHz): δ 1.52 (9H, s), 6.34 (1H, d, J=3.9 Hz), 6.69 (1H, d, J=3.9 Hz), 7.37 (1H, dt, J=1.2, 8.0 Hz), 7.46 (1H, dt, J=1.2, 8.0 Hz), 7.86 (1H, brd, J=8.0 Hz), 7.93 (1H, brd, J=8.0 Hz).

(4c) 2-(5-{3-[(1S)-2-Methoxy-1-methylethoxy]-5-[4-(methylsulfonyl)phenoxy]phenyl}-1H-pyrrol-2-yl)-1,3-benzothiazole 2-{3-[(1S)-2-Methoxy-1-methylethoxy]-5-[4-(methylsulfonyl)phenoxy]phenyl}-4,4,5,5-tetramethyl-1,3,2-dioxaborolane (305 mg, 0.682 mmol) synthesized in Example (1e) and t-butyl 2-bromo-5-(1,3-benzothiazol-2-yl)-1H-pyrrole-1-carboxylate (260 mg, 0.686 mmol) synthesized in Example (4b) were dissolved in 1,2-dimethoxyethane (20 mL), and [1,1'-bis(diphenylphosphino)ferrocene]palladium (II) dichloride dichloromethane complex (28 mg, 0.034 mmol) and an aqueous potassium carbonate solution (3M, 0.44 mL, 1.32 mmol) were added, followed by stirring at 50° C. for 17 hours under nitrogen atmosphere. After the reaction solution was cooled to room temperature, water (20 mL) was added, and extraction was carried out with ethyl acetate (20 mL). The organic layer was washed with saturated brine, subsequently dried over anhydrous magnesium sulfate, and the solvent was distilled off under reduced pressure.

The resulting residue was dissolved in dichloromethane (10 mL), and cooled to 0° C. Trifluoroacetic acid (10 mL) was added dropwise with stirring under nitrogen atmosphere. After stirring at room temperature for 30 minutes, the solvent was distilled off under reduced pressure followed by dilution with ethyl acetate (30 mL), a saturated aqueous sodium hydrogencarbonate solution (20 mL) was added, and the solution was separated. The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=10%-40%) to afford the desired compound (174 mg, yield 48%) as a yellow solid.

$^1$H-NMR (CDCl$_3$, 400 MHz): δ 1.34 (3H, d, J=6.3 Hz), 3.07 (3H, s), 3.42 (3H, s), 3.51 (1H, dd, J=3.9, 10.2 Hz), 3.61 (1H, dd, J=6.3, 10.2 Hz), 4.58 (1H, m), 6.57 (1H, t, J=2.0 Hz), 6.60 (1H, dd, J=2.7, 3.9 Hz), 6.88 (1H, dd, J=2.4, 3.9 Hz), 6.92 (1H, t, J=2.0 Hz), 7.08 (1H, t, J=2.0 Hz), 7.13 (2H, d, J=8.6 Hz), 7.32 (1H, dt, J=1.2, 7.4 Hz), 7.44 (1H, brt, J=7.4 Hz), 7.83 (1H, brd, J=7.4 Hz), 7.91 (2H, d, J=8.6 Hz), 10.10 (1H, brs).

MS (ESI) m/z: 535.13653 (M+H)$^+$.

Example 5

2-(5-{3-[(1S)-2-Methoxy-1-methylethoxy]-5-[4-(methylsulfonyl)phenoxy]phenyl}-1H-pyrrol-2-yl)-1,3-thiazole-5-carboxylic acid

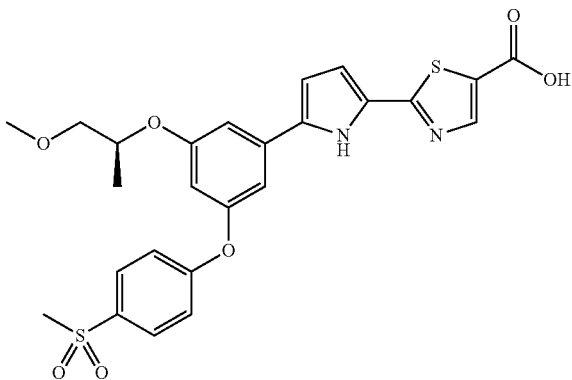

(5a) Ethyl 2-[1-(t-butoxycarbonyl)-1H-pyrrol-2-yl]-1,3-thiazole-5-carboxylate

Commercially available 1-(t-butoxycarbonyl)pyrrole-2-boronic acid (850 mg, 4.3 mmol) was dissolved in 1,2-dimethoxyethane (30 mL), and commercially available ethyl 2-bromo-1,3-thiazole-5-carboxylate (0.50 mL, 3.35 mmol), palladium (II) acetate (38.0 mg, 0.169 mmol), triphenylphosphine (176 mg, 0.671 mmol) and an aqueous potassium carbonate solution (3M, 2.20 mL, 6.60 mmol) were added, followed by stirring at 100° C. for 14 hours under nitrogen atmosphere. The reaction solution was cooled to room temperature, water (30 mL) and ethyl acetate (40 mL) were added, and the solution was separated. The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=0%-30%) to afford the desired compound (800 mg, yield 74%) as a yellow solid.

$^1$H-NMR (CDCl$_3$, 400 MHz): δ 1.39 (3H, t, J=7.0 Hz), 1.50 (9H, s), 4.38 (2H, q, J=7.0 Hz), 6.28 (1H, dd, J=3.1, 3.5 Hz), 6.79 (1H, dd, J=2.0, 3.5 Hz), 7.43 (1H, dd, J=2.0, 3.1 Hz), 8.39 (1H, s).

(5b) Ethyl 2-[5-bromo-1-(t-butoxycarbonyl)-1H-pyrrol-2-yl]-1,3-thiazole-5-carboxylate Ethyl 2-[1-(t-butoxycarbonyl)-1H-pyrrol-2-yl]-1,3-thiazole-5-carboxylate (800 mg, 2.48 mmol) synthesized in Example (5a) was dissolved in tetrahydrofuran (30 mL), and cooled to 0° C. N-Bromosuccinimide (442 mg, 2.48 mmol) was added with stirring under nitrogen atmosphere, and subsequently stirring was carried out at room temperature for 19 hours. A saturated aqueous sodium hydrogencarbonate solution (30 mL) was added, and extraction was carried out with ethyl acetate (30 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=0%-30%) to afford the desired compound (598 mg, yield 60%) as a pale yellow solid.

$^1$H-NMR (CDCl$_3$, 400 MHz): δ 1.39 (3H, t, J=7.0 Hz), 1.50 (9H, s), 4.38 (2H, q, J=7.0 Hz), 6.32 (1H, d, J=3.8 Hz), 6.64 (1H, d, J=3.8 Hz), 8.31 (1H, s).

(5c) Ethyl 2-(5-{3-[(1S)-2-methoxy-1-methylethoxy]-5-[4-(methylsulfonyl)phenoxy]phenyl}-1H-pyrrol-2-yl)-1,3-thiazole-5-carboxylate 2-{3-[(1S)-2-Methoxy-1-methylethoxy]-5-[4-(methylsulfonyl)phenoxy]phenyl}-4,4,5,5-tetramethyl-1,3,2-dioxaborolane (666 mg, 1.49 mmol) synthesized in Example (1e) and ethyl 2-[5-bromo-1-(t-butoxycarbonyl)-1H-pyrrol-2-yl]-1,3-thiazole-5-carboxylate (598 mg, 1.49 mmol) synthesized in Example (5b) were dissolved in a mixed solvent of toluene (14 mL) and ethanol (6 mL), and [1,1'-bis(diphenylphosphino)ferrocene]palladium (II) dichloride dichloromethane complex (61.0 mg, 0.075 mmol) and an aqueous sodium carbonate solution (2M, 1.50 mL, 3.00 mmol) were added, followed by stirring at 100° C. for 19 hours under nitrogen atmosphere. After the reaction solution was cooled to room temperature, water (10 mL) was added, and extraction was carried out with ethyl acetate (20 mL). The organic layer was washed with saturated brine, subsequently dried over anhydrous magnesium sulfate, and the solvent was distilled off under reduced pressure.

The resulting residue was dissolved in dichloromethane (10 mL), and cooled to 0° C. Trifluoroacetic acid (10 mL) was added dropwise with stirring under nitrogen atmosphere. After stirring at room temperature for 30 minutes, the solvent was distilled off under reduced pressure followed by dilution with ethyl acetate (30 mL), a saturated aqueous sodium hydrogencarbonate solution (20 mL) was added, and the solution was separated. The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=30%-50%) to afford the desired compound (505 mg, yield 61%) as a pale yellow solid.

$^1$H-NMR (CDCl$_3$, 400 MHz): δ 1.34 (3H, d, J=6.3 Hz), 1.39 (3H, t, J=7.0 Hz), 3.07 (3H, s), 3.42 (3H, s), 3.51 (1H, dd, J=4.3, 10.2 Hz), 3.61 (1H, dd, J=6.3, 10.2 Hz), 4.37 (2H, q,

J=7.0 Hz), 4.59 (1H, m), 6.56 (1H, dd, J=2.7, 3.9 Hz), 6.58 (1H, t, J=2.0 Hz), 6.83 (1H, dd, J=2.7, 3.9 Hz), 6.87 (1H, t, J=2.0 Hz), 7.03 (1H, t, J=2.0 Hz), 7.14 (2H, d, J=9.0 Hz), 7.91 (2H, d, J=9.0 Hz), 8.25 (1H, s), 9.64 (1H, brs).

MS (ESI) m/z: 557.14052 (M+H)$^+$.

(5d) 2-(5-{3-[(1S)-2-Methoxy-1-methylethoxy]-5-[4-(methylsulfonyl)phenoxy]phenyl}-1H-pyrrol-2-yl)-1,3-thiazole-5-carboxylic acid Ethyl 2-(5-{3-[(1S)-2-methoxy-1-methylethoxy]-5-[4-(methylsulfonyl)phenoxy]phenyl}-1H-pyrrol-2-yl)-1,3-thiazole-5-carboxylate (53.5 mg, 0.096 mmol) synthesized in Example (5c) was dissolved in ethanol (4 mL). An aqueous sodium hydroxide solution (5M, 2 mL) was added, and stirring was carried out at 70° C. for 30 minutes. After cooling to room temperature, hydrochloric acid (2M, 5 mL) and ethyl acetate (10 mL) were added, and the solution was separated. The organic layer was washed with saturated brine, and subsequently dried over anhydrous magnesium sulfate. The solvent was distilled off under reduced pressure, to afford the desired compound (52.5 mg, yield ~100%) as a pale yellow solid.

$^1$H-NMR (DMSO, 400 MHz): δ 1.25 (3H, d, J=6.3 Hz), 3.19 (3H, s), 3.30 (3H, s), 3.44-3.52 (2H, m), 4.78 (1H, m), 6.56 (1H, brt, J=2.0 Hz), 6.73 (1H, brd, J=10.2 Hz), 7.21 (2H, d, J=8.6 Hz), 7.27 (1H, brt, J=2.0 Hz), 7.41 (1H, brt, J=2.0 Hz), 7.93 (2H, d, J=8.6 Hz), 12.0 (1H, brs).

MS (ESI) m/z: 529.11053 (M+H)$^+$.

Example 6

N-Ethyl-2-(5-{3-[(1S)-2-methoxy-1-methylethoxy]-5-[4-(methylsulfonyl)phenoxy]phenyl}-1H-pyrrol-2-yl)-1,3-thiazole-5-carboxamide

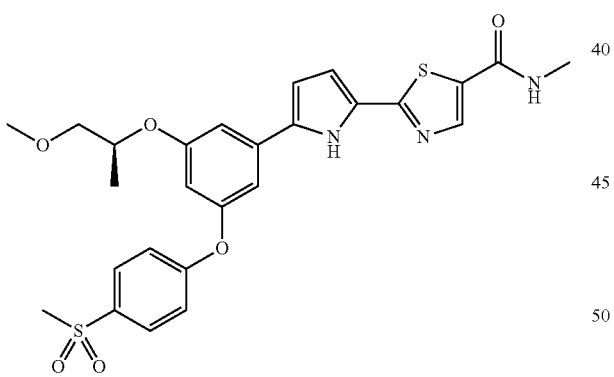

2-(5-{3-[(1S)-2-Methoxy-1-methylethoxy]-5-[4-(methylsulfonyl)phenoxy]phenyl}-1H-pyrrol-2-yl)-1,3-thiazole-5-carboxylic acid (62.8 mg, 0.119 mmol) synthesized in Example (5d) was dissolved in N,N-dimethylformamide (5 mL), and ethylamine hydrochloride (23.3 mg, 0.286 mmol), HATU (63.8 mg, 0.168 mmol) and N,N-diisopropylethylamine (80 µL, 0.46 mmol) were added, followed by stirring at room temperature for 20 hours under nitrogen atmosphere. Water (20 mL) was added to the reaction solution, and extraction was carried out with ethyl acetate (20 mL). The organic layer was washed with saturated brine, and subsequently dried over sodium sulfate. The solvent was distilled off under reduced pressure, and the resulting residue was purified using silica gel column chromatography (elution solvent: ethyl acetate/hexane=50%-80%) to afford the desired compound (57.7 mg, yield 87%) as a yellow solid.

$^1$H-NMR (CDCl$_3$, 400 MHz): δ 1.27 (3H, t, J=7.4 Hz), 1.34 (3H, d, J=6.3 Hz), 3.08 (3H, s), 3.43 (3H, s), 3.47-3.53 (3H, m), 3.60 (1H, dd, J=6.3, 10.2 Hz), 4.56-4.60 (1H, m), 5.88 (1H, brs), 6.55-6.59 (2H, m), 6.80 (1H, dd, J=2.3, 3.9 Hz), 6.86 (1H, t, J=1.6 Hz), 7.02 (1H, t, J=1.8 Hz), 7.14 (2H, d, J=6.6 Hz), 7.92 (2H, d, J=6.6 Hz), 7.98 (1H, s), 9.56 (1H, brs).

MS (ESI) m/z: 556.15812 (M+H)$^+$.

Example 7

2-(5-{3-[(1S)-2-Methoxy-1-methylethoxy]-5-[4-(methylsulfonyl)phenoxy]phenyl}-1H-pyrrol-2-yl)-N,N-dimethyl-1,3-thiazole-5-carboxamide

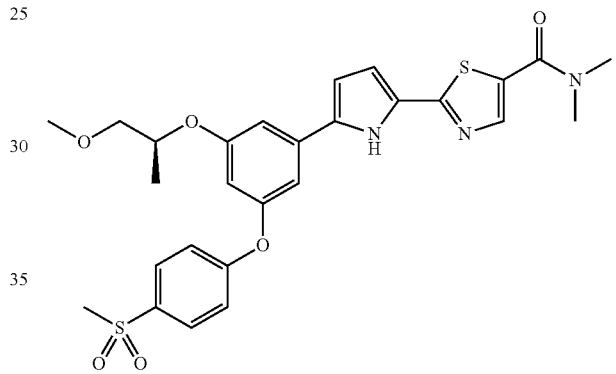

2-(5-{3-[(1S)-2-Methoxy-1-methylethoxy]-5-[4-(methylsulfonyl)phenoxy]phenyl}-1H-pyrrol-2-yl)-1,3-thiazole-5-carboxylic acid (62.8 mg, 0.119 mmol) synthesized in Example (5d) was dissolved in N,N-dimethylformamide (5 mL), and dimethylamine hydrochloride (27.0 mg, 0.331 mmol), HATU (68.2 mg, 0.179 mmol) and N,N-diisopropylethylamine (80 µL, 0.46 mmol) were added, followed by stirring at room temperature for 20 hours under nitrogen atmosphere. Water (20 mL) was added to the reaction solution, and extraction was carried out with ethyl acetate (20 mL). The organic layer was washed with saturated brine, and subsequently dried over sodium sulfate. The solvent was distilled off under reduced pressure, and the resulting residue was purified using silica gel column chromatography (elution solvent: ethyl acetate/hexane=60%-90%) to afford the desired compound (59.8 mg, yield 90%) as a yellow solid.

$^1$H-NMR (CDCl$_3$, 400 MHz): δ 1.34 (3H, d, J=6.3 Hz), 3.07 (3H, s), 3.32 (6H, brs), 3.42 (3H, s), 3.51 (1H, dd, J=4.3, 10.2 Hz), 3.59 (1H, dd, J=6.3, 10.2 Hz), 4.55-4.60 (1H, m), 6.55-6.58 (2H, m), 6.79 (1H, dd, J=2.4, 3.9 Hz), 6.86 (1H, t, J=1.8 Hz), 7.02 (1H, t, J=1.8 Hz), 7.14 (2H, d, J=9.0 Hz), 7.89 (1H, s), 7.91 (2H, d, J=9.0 Hz), 9.52 (1H, brs).

MS (ESI) m/z: 556.15717 (M+H)$^+$.

Example 8

[2-(5-{3-[(1S)-2-Methoxy-1-methylethoxy]-5-[4-(methylsulfonyl)phenoxy]phenyl}-1H-pyrrol-2-yl)-1,3-thiazol-5-yl]methanol

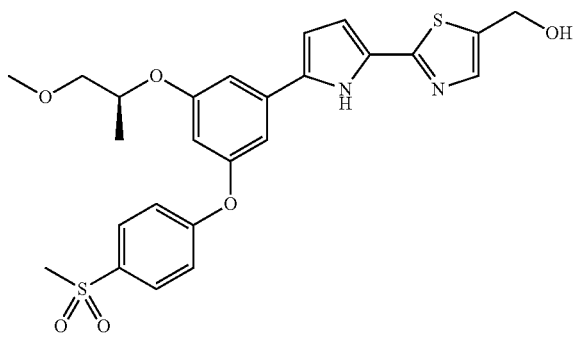

Lithium aluminum hydride (22 mg, 0.580 mmol) was suspended in tetrahydrofuran (2 mL). Ethyl 2-(5-{3-[(1S)-2-methoxy-1-methylethoxy]-5-[4-(methylsulfonyl)phenoxy]phenyl}-1H-pyrrol-2-yl)-1,3-thiazole-5-carboxylate (106 mg, 0.190 mmol) synthesized in Example (5c) was dissolved in tetrahydrofuran (2 mL), followed by dropwise addition at 0° C. under nitrogen atmosphere. After stirring at 0° C. for 30 minutes, water (22 μL) and an aqueous sodium hydroxide solution (5M, 88 μL) were added dropwise sequentially and slowly. After filtration through Celite, the solvent was distilled off under reduced pressure, and the resulting residue was purified using silica gel column chromatography (elution solvent: ethyl acetate/hexane=50%-100%) to afford the desired compound (48 mg, yield 49%) as a pale yellow solid.

$^1$H-NMR (CDCl$_3$, 400 MHz): δ 1.30 (3H, d, J=6.3 Hz), 3.06 (3H, s), 3.41 (3H, s), 3.50 (1H, dd, J=3.9, 10.5 Hz), 3.58 (1H, dd, J=6.3, 10.5 Hz), 4.48 (1H, m), 4.82 (2H, brs), 6.51-6.54 (2H, m), 6.70 (1H, dd, J=2.4, 3.9 Hz), 6.86 (1H, brt, J=2.0 Hz), 7.00 (1H, brt, J=2.0 Hz), 7.12 (2H, d, J=9.0 Hz), 7.47 (1H, brs), 7.89 (2H, d, J=9.0 Hz), 10.20 (1H, brs).

MS (ESI) m/z: 515.12920 (M+H)$^+$.

Example 9

1-[2-(5-{3-[(1S)-2-Methoxy-1-methylethoxy]-5-[4-(methylsulfonyl)phenoxy]phenyl}-1H-pyrrol-2-yl)-1,3-thiazol-4-yl]ethane-1,2-diol

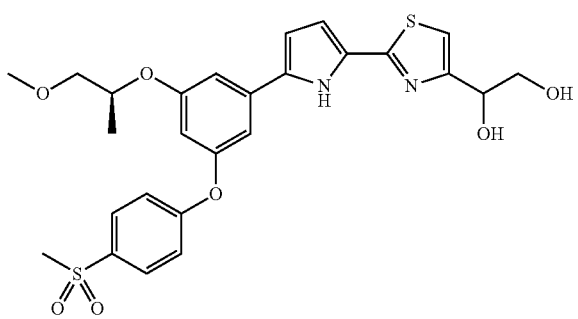

(9a) Ethyl (2-bromo-1,3-thiazol-4-yl)(oxo)acetate

Commercially available ethyl (2-formamido-1,3-thiazol-4-yl)(oxo)acetate (5.09 g, 22.3 mmol) was dissolved in a mixed solvent of ethanol (50 mL) and 1,4-dioxane, and 30% sulfuric acid (12 mL) was added, followed by stirring at 60° C. for 1 hour. The reaction solution was cooled to room temperature, water (20 mL) and ethyl acetate (20 mL) were added, and the solution was separated. The solvent was distilled off under reduced pressure, and 30% sulfuric acid (40 mL) and potassium bromide (9.3 g, 78.2 mmol) were added, followed by cooling to 0° C. Sodium nitrite (20.0 g, 290 mmol) was dissolved in water (40 mL), followed by dropwise addition over 1 hour, and stirring was further carried out at 0° C. for 1 hour. The solution was separated with ethyl acetate (200 mL), the organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=0%-20%) to afford the desired compound (3.07 g, yield 52%) as a yellow oil.

$^1$H-NMR (CDCl$_3$, 400 MHz): δ 1.43 (3H, t, J=7.0 Hz), 4.45 (2H, q, J=7.0 Hz) 8.55 (1H, s).

(9b) 1-(2-Bromo-1,3-thiazol-4-yl)ethane-1,2-diol

Ethyl (2-bromo-1,3-thiazol-4-yl)(oxo)acetate (3.07 g, 11.6 mmol) synthesized in Example (9a) was dissolved in methanol (100 mL), and cooled to 0° C. Sodium borohydride (1.32 g, 34.9 mmol) was added in small portions, and stirring was carried out at 0° C. for 1.5 hours, followed by stirring at room temperature for further 2 hours. Dilute hydrochloric acid (1M, 100 mL) was added, and the solution was separated with ethyl acetate (200 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=20%-80%) to afford the desired compound (1.10 g, yield 42%) as a yellow oil.

$^1$H-NMR (CDCl$_3$, 400 MHz): δ 3.87 (1H, dd, J=5.9, 11.3 Hz), 3.97 (1H, dd, J=3.5, 11.3 Hz), 4.89 (1H, dd, J=3.5, 5.3 Hz) 7.27 (1H, s).

(9c) t-Butyl 2-[4-(1,2-dihydroxyethyl)-1,3-thiazol-2-yl]-1H-pyrrole-1-carboxylate 1-(2-Bromo-1,3-thiazol-4-yl)ethane-1,2-diol (1.10 g, 4.91 mmol) synthesized in Example (9b) and commercially available 1-(t-butoxycarbonyl)pyrrole-2-boronic acid (1.55 g, 7.35 mmol) were dissolved in 1,2-dimethoxyethane (40 mL), and palladium (II) acetate (55.0 mg, 0.245 mmol), triphenylphosphine (260 mg, 0.991 mmol) and an aqueous potassium carbonate solution (3M, 4.9 mL, 14.7 mmol) were added, followed by stirring at 100° C. for 14 hours under nitrogen atmosphere. The reaction solution was cooled to room temperature, water (30 mL) and ethyl acetate (40 mL) were added, and the solution was separated. The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=50%-100%) to afford the desired compound (868 mg, yield 59%) as a brown oil.

¹H-NMR (CDCl₃, 400 MHz): δ 1.46 (9H, s), 3.95 (2H, m), 4.89 (1H, m), 6.25 (1H, t, J=3.5 Hz), 6.60 (1H, dd, J=2.0, 3.5 Hz), 7.31 (1H, brs), 7.40 (1H, dd, J=2.0, 3.5 Hz).

(9d) t-Butyl 2-bromo-5-[4-(1,2-dihydroxyethyl)-1,3-thiazol-2-yl]-1H-pyrrole-1-carboxylate t-Butyl 2-[4-(1,2-dihydroxyethyl)-1,3-thiazol-2-yl]-1H-pyrrole-1-carboxylate (868 mg, 2.80 mmol) synthesized in Example (9c) was dissolved in tetrahydrofuran (30 mL), and cooled to 0° C. N-Bromosuccinimide (498 mg, 2.80 mmol) was added, and stirring was carried out at room temperature for 14 hours under nitrogen atmosphere. Water (20 mL) was added, and extraction was carried out with diethyl ether (20 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=0%-30%) to afford the desired compound (527 mg, yield 48%) as a pale yellow oil.
¹H-NMR (CDCl₃, 400 MHz): δ 1.53 (9H, s), 3.92 (2H, m), 4.87 (1H, m), 6.31 (1H, d, J=3.5 Hz), 6.54 (1H, d, J=3.5 Hz), 7.23 (1H, brs).

(9e) 1-[2-(5-{3-[(1S)-2-Methoxy-1-methylethoxy]-5-[4-(methylsulfonyl)phenoxy]phenyl}-1H-pyrrol-2-yl)-1,3-thiazol-4-yl]ethane-1,2-diol 2-{3-[(1S)-2-Methoxy-1-methylethoxy]-5-[4-(methylsulfonyl)phenoxy]phenyl}-4,4,5,5-tetramethyl-1,3,2-dioxaborolane (600 mg, 1.35 mmol) synthesized in Example (1e) and t-butyl 2-bromo-5-[4-(1,2-dihydroxyethyl)-1,3-thiazol-2-yl]-1H-pyrrole-1-carboxylate (525 mg, 1.35 mmol) synthesized in Example (9d) were dissolved in a mixed solvent of toluene (30 mL) and ethanol (10 mL), and[1,1'-bis(diphenylphosphino)ferrocene]palladium (II) dichloride dichloromethane complex (55 mg, 0.067 mmol) and an aqueous potassium carbonate solution (3M, 0.90 mL, 2.70 mmol) were added, followed by stirring at 100° C. for 16 hours under nitrogen atmosphere. After the reaction solution was cooled to room temperature, water (20 mL) was added, and extraction was carried out with ethyl acetate (40 mL). The organic layer was washed with saturated brine, subsequently dried over anhydrous magnesium sulfate, and the solvent was distilled off under reduced pressure.
The resulting residue was dissolved in dichloromethane (10 mL), and cooled to 0° C. Trifluoroacetic acid (10 mL) was added dropwise with stirring under nitrogen atmosphere. After stirring at room temperature for 30 minutes, the solvent was distilled off under reduced pressure followed by dilution with ethyl acetate (30 mL), a saturated aqueous sodium hydrogencarbonate solution (20 mL) was added, and the solution was separated. The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=50%-100%) to afford the desired compound (331 mg, yield 45%) as a pale yellow solid.
¹H-NMR (CDCl₃, 400 MHz): δ 1.32 (3H, d, J=6.3 Hz), 3.05 (3H, s), 3.40 (3H, s), 3.50 (1H, dd, J=3.9, 10.2 Hz), 3.59 (1H, dd, J=6.3, 10.2 Hz), 3.85-3.98 (2H, m), 4.58 (1H, m), 4.90 (1H, brs), 6.48-6.54 (2H, m), 6.67 (1H, brs), 6.89 (1H, brs), 7.07 (1H, brs), 7.12 (2H, d, J=8.6 Hz), 7.88 (2H, d, J=8.6 Hz), 10.39 (1H, brs).
MS (ESI) m/z: 545.14151 (M+H)⁺.

Example 10

2-(5-{3-[(1S)-2-Methoxy-1-methylethoxy]-5-[4-(methylsulfonyl)phenoxy]phenyl}-1H-pyrrol-2-yl)-5-methylpyrazine

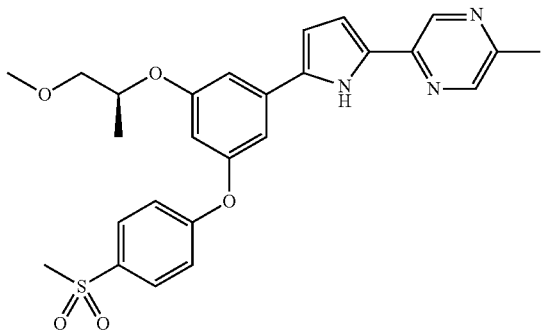

(10a) t-Butyl 2-(5-methylpyrazin-2-yl)-1H-pyrrole-1-carboxylate

Commercially available 2-bromo-5-methylpyrazine (260 mg, 1.50 mmol) and commercially available 1-(t-butoxycarbonyl)pyrrole-2-boronic acid (380 mg, 1.80 mmol) were dissolved in 1,2-dimethoxyethane (20 mL), and palladium (II) acetate (17.0 mg, 0.076 mmol), triphenylphosphine (79.0 mg, 0.301 mmol) and an aqueous potassium carbonate solution (1.5M, 2.0 mL, 3.00 mmol) were added, followed by stirring at 100° C. for 19 hours under nitrogen atmosphere. The reaction solution was cooled to room temperature, water (20 mL) and ethyl acetate (20 mL) were added, and the solution was separated. The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=5%-30%) to afford the desired compound (373 mg, yield 96%) as a yellow oil.
¹H-NMR (CDCl₃, 400 MHz): δ 1.41 (9H, s), 2.59 (3H, s), 6.28 (1H, m), 6.48 (1H, m), 7.41 (1H, m), 8.45 (1H, brs), 8.56 (1H, brs).

(10b) t-Butyl 2-bromo-5-(5-methylpyrazin-2-yl)-1H-pyrrole-1-carboxylate t-Butyl 2-(5-methylpyrazin-2-yl)-1H-pyrrole-1-carboxylate (373 mg, 1.44 mmol) synthesized in Example (10a) was dissolved in tetrahydrofuran (20 mL), and cooled to 0° C. N-Bromosuccinimide (256 mg, 1.44 mmol) was added, and stirring was carried out at room temperature for 14 hours under nitrogen atmosphere. Water (20 mL) was added, and extraction was carried out with diethyl ether (20 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=0%-30%) to afford the desired compound (425 mg, yield 87%) as a pale yellow oil.
¹H-NMR (CDCl₃, 400 MHz): δ 1.50 (9H, s), 2.57 (3H, s), 6.33 (1H, d, J=3.5 Hz), 6.54 (1H, d, J=3.5 Hz), 8.35 (1H, brs), 8.62 (1H, brd, J=1.6 Hz).

(10c) 2-(5-{3-[(1S)-2-Methoxy-1-methylethoxy]-5-[4-(methylsulfonyl)phenoxy]phenyl}-1H-pyrrol-2-yl)-5-methylpyrazine 2-{3-[(1S)-2-Methoxy-1-methylethoxy]-5-[4-(methylsulfonyl)phenoxy]phenyl}-4,4,5,5-tetramethyl-1,3,2-dioxaborolane (250 mg, 0.559 mmol) synthesized in Example (1e) and t-butyl 2-bromo-5-(5-methylpyrazin-2-yl)-1H-pyrrole-1-carboxylate (200 mg, 0.591 mmol) synthesized in Example (10b) were dissolved in a mixed solvent of toluene (20 mL) and ethanol (8 mL), and [1,1'-bis(diphenylphosphino)ferrocene]palladium (II) dichloride dichloromethane complex (23 mg, 0.028 mmol) and an aqueous potassium carbonate solution (3M, 0.40 mL, 1.20 mmol) were added, followed by stirring at 100° C. for 7 hours under nitrogen atmosphere. After the reaction solution was cooled to room temperature, water (20 mL) was added, and extraction was carried out with ethyl acetate (20 mL). The organic layer was washed with saturated brine, subsequently dried over anhydrous magnesium sulfate, and the solvent was distilled off under reduced pressure.

The resulting residue was dissolved in dichloromethane (10 mL), and cooled to 0° C. Trifluoroacetic acid (10 mL) was added dropwise with stirring under nitrogen atmosphere. After stirring at room temperature for 30 minutes, the solvent was distilled off under reduced pressure followed by dilution with ethyl acetate (30 mL), a saturated aqueous sodium hydrogencarbonate solution (20 mL) was added, and the solution was separated. The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=10%-60%) to afford the desired compound (124 mg, yield 45%) as a yellow solid.

$^1$H-NMR (CDCl$_3$, 400 MHz): δ 1.34 (3H, d, J=6.3 Hz), 2.55 (3H, s), 3.07 (3H, s), 3.42 (3H, s), 3.52 (1H, dd, J=3.9, 10.2 Hz), 3.61 (1H, dd, J=5.9, 10.2 Hz), 4.58 (1H, m), 6.55 (1H, t, J=2.0 Hz), 6.59 (1H, dd, J=2.8, 3.9 Hz), 6.81 (1H, dd, J=2.4, 3.9 Hz), 6.88 (1H, t, J=2.0 Hz), 7.04 (1H, t, J=2.0 Hz), 7.14 (2H, d, J=9.0 Hz), 7.91 (2H, d, J=9.0 Hz), 8.28 (1H, brs), 8.76 (1H, d, J=1.6 Hz), 9.62 (1H, brs).

MS (ESI) m/z: 494.17511 (M+H)$^+$.

Example 11

6-(5-{3-[(1S)-2-Methoxy-1-methylethoxy]-5-[4-(methylsulfonyl)phenoxy]phenyl}-1H-pyrrol-2-yl)nicotinic acid

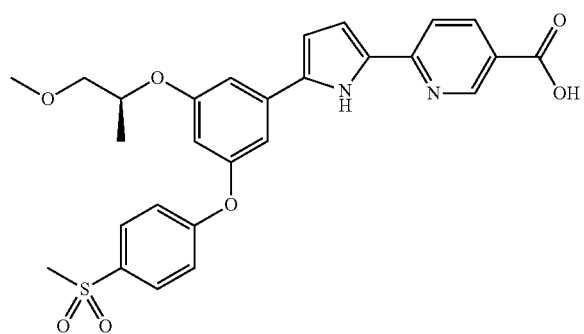

(11a) Methyl 6-[1-(t-butoxycarbonyl)-1H-pyrrol-2-yl]nicotinate

Commercially available methyl 6-bromonicotinate (650 mg, 3.01 mmol) and commercially available 1-(t-butoxycarbonyl)pyrrole-2-boronic acid (960 mg, 4.34 mmol) were dissolved in 1,2-dimethoxyethane (30 mL), and palladium (II) acetate (34.0 mg, 0.151 mmol), triphenylphosphine (158 mg, 0.602 mol) and an aqueous potassium carbonate solution (2M, 4.5 mL, 9.00 mmol) were added, followed by stirring at 100° C. for 15 hours under nitrogen atmosphere. The reaction solution was cooled to room temperature, water (20 mL) and ethyl acetate (30 mL) were added, and the solution was separated. The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=0%-20%) to afford the desired compound (835 mg, yield 92%) as a yellow solid.

$^1$H-NMR (CDCl$_3$, 400 MHz): δ 1.39 (9H, s), 3.95 (3H, s), 6.26 (1H, t, J=3.5 Hz), 6.53 (1H, m), 7.39 (1H, m), 7.47 (1H, dd, J=0.8, 8.2 Hz), 8.27 (1H, dd, J=2.4, 8.2 Hz), 9.19 (1H, dd, J=0.8, 2.4 Hz).

(11b) Methyl 6-[5-bromo-1-(t-butoxycarbonyl)-1H-pyrrol-2-yl]nicotinate

Methyl 6-[1-(t-butoxycarbonyl)-1H-pyrrol-2-yl]nicotinate (835 mg, 2.76 mmol) synthesized in Example (11a) was dissolved in tetrahydrofuran (30 mL), and cooled to 0° C. N-Bromosuccinimide (492 mg, 2.76 mmol) was added, and stirring was carried out at room temperature for 19 hours under nitrogen atmosphere. Water (30 mL) was added, and extraction was carried out with diethyl ether (30 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=0%-30%) to afford the desired compound (712 mg, yield 68%) as a pale yellow oil.

$^1$H-NMR (CDCl$_3$, 400 MHz): δ 1.54 (9H, s), 3.94 (3H, s), 6.30 (1H, d, J=3.5 Hz), 6.62 (1H, d, J=3.5 Hz), 7.51 (1H, brd, J=8.6 Hz), 8.23 (1H, dd, J=2.0, 8.6 Hz), 9.07 (1H, m).

(11c) Ethyl 6-(5-{3-[(1S)-2-methoxy-1-methylethoxy]-5-[4-(methylsulfonyl)phenoxy]phenyl}-1H-pyrrol-2-yl)nicotinate 2-{3-[(1S)-2-Methoxy-1-methylethoxy]-5-[4-(methylsulfonyl)phenoxy]phenyl}-4,4,5,5-tetramethyl-1,3,2-dioxaborolane (398 mg, 0.890 mmol) synthesized in Example (1e) and methyl 6-[5-bromo-1-(t-butoxycarbonyl)-1H-pyrrol-2-yl]nicotinate (403 mg, 0.493 mmol) synthesized in Example (11b) were dissolved in a mixed solvent of toluene (20 mL) and ethanol (8 mL), and [1,1'-bis(diphenylphosphino)ferrocene]palladium (II) dichloride dichloromethane complex (40 mg, 0.049 mmol) and an aqueous potassium carbonate solution (3M, 0.60 mL, 1.80 mmol) were added, followed by stirring at 100° C. for 20 hours under nitrogen atmosphere. After the reaction solution was cooled to room temperature, water (20 mL) was added, and extraction was carried out with ethyl acetate (20 mL). The organic layer was washed with saturated brine, subsequently dried over anhydrous magnesium sulfate, and the solvent was distilled off under reduced pressure.

The resulting residue was dissolved in dichloromethane (10 mL), and cooled to 0° C. Trifluoroacetic acid (10 mL) was added dropwise with stirring under nitrogen atmosphere. After stirring at room temperature for 30 minutes, the solvent was distilled off under reduced pressure followed by dilution with ethyl acetate (30 mL), a saturated aqueous sodium hydrogencarbonate solution (20 mL) was added, and the solution was separated. The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=10%-60%) to afford the desired compound (173 mg, yield 35%) as a yellow solid.

¹H-NMR (CDCl₃, 400 MHz): δ 1.34 (3H, d, J=6.3 Hz), 1.42 (3H, t, J=7.0 Hz), 3.07 (3H, s), 3.42 (3H, s), 3.52 (1H, dd, J=3.9, 10.2 Hz), 3.61 (1H, dd, J=6.3, 10.2 Hz), 4.41 (2H, q, J=7.0 Hz), 4.58 (1H, m), 6.55 (1H, t, J=2.0 Hz), 6.60 (1H, dd, J=2.0, 3.9 Hz), 6.85 (1H, dd, J=2.0, 3.9 Hz), 7.06 (1H, t, J=2.0 Hz), 7.14 (2H, d, J=9.0 Hz), 7.57 (1H, dd, J=0.8, 8.6 Hz), 7.90 (2H, d, J=9.0 Hz), 8.21 (1H, dd, J=2.0, 8.6 Hz), 9.06 (1H, dd, J=0.8, 2.0 Hz), 9.94 (1H, brs), m).

MS (ESI) m/z: 551.18403 (M+H)⁺.

(11d) 6-(5-{3-[(1S)-2-Methoxy-1-methylethoxy]-5-[4-(methylsulfonyl)phenoxy]phenyl}-1H-pyrrol-2-yl)nicotinic acid Ethyl 6-(5-{3-[(1S)-2-methoxy-1-methylethoxy]-5-[4-(methylsulfonyl)phenoxy]phenyl}-1H-pyrrol-2-yl)nicotinate (42.0 mg, 0.076 mmol) synthesized in Example (11c) was dissolved in ethanol (4 mL). An aqueous sodium hydroxide solution (5M, 2 mL) was added, and stirring was carried out at 70° C. for 2 hours. After cooling to room temperature, hydrochloric acid (2M, 5 mL) and ethyl acetate (10 mL) were added, and the solution was separated. The organic layer was washed with saturated brine, and subsequently dried over anhydrous magnesium sulfate. The solvent was distilled off under reduced pressure, to afford the desired compound (39.6 mg, yield 99%) as a pale yellow solid.

¹H-NMR (DMSO, 400 MHz): δ 1.26 (3H, d, J=6.3 Hz), 3.20 (3H, s), 3.31 (3H, s), 3.45-3.55 (2H, m), 4.83 (1H, m), 6.58 (1H, brs), 6.80 (1H, brs), 7.01 (1H, brs), 7.22 (2H, d, J=9.0 Hz), 7.31 (1H, brs), 7.45 (1H, brs), 7.88 (1H, d, J=8.6 Hz), 7.93 (2H, d, J=9.0 Hz), 8.18 (1H, d, J=8.6 Hz), 9.00 (1H, s), 11.92 (1H, brs).

MS (ESI) m/z: 523.15247 (M+H)⁺.

Example 12

[6-(5-{3-[(1S)-2-Methoxy-1-methylethoxy]-5-[4-(methylsulfonyl)phenoxy]phenyl}-1H-pyrrol-2-yl)pyridin-3-yl]methanol

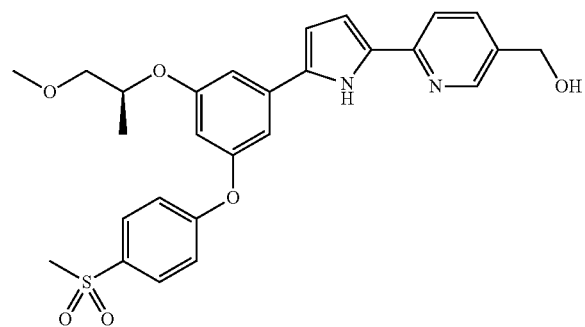

Lithium aluminum hydride (12 mg, 0.316 mmol) was suspended in tetrahydrofuran (2 mL). Ethyl 6-(5-{3-[(1S)-2-methoxy-1-methylethoxy]-5-[4-(methylsulfonyl)phenoxy]phenyl}-1H-pyrrol-2-yl)nicotinate (56.0 mg, 0.102 mmol) synthesized in Example (11c) was dissolved in tetrahydrofuran (2 mL), followed by dropwise addition at 0° C. under nitrogen atmosphere. After stirring at 0° C. for 30 minutes, water (12 μL) and an aqueous sodium hydroxide solution (5M, 48 μL) were added dropwise slowly and sequentially. After filtration through Celite, the solvent was distilled off under reduced pressure, and the resulting residue was purified using silica gel column chromatography (elution solvent: ethyl acetate/hexane=50%-100%) to afford the desired compound (33 mg, yield 64%) as a pale yellow solid.

¹H-NMR (CDCl₃, 400 MHz): δ 1.34 (3H, d, J=6.3 Hz), 3.06 (3H, s), 3.42 (3H, s), 3.51 (1H, dd, J=3.9, 10.2 Hz), 3.60 (1H, dd, J=5.9, 10.2 Hz), 4.57 (1H, m), 4.69 (2H, brs), 6.52 (1H, brt, J=2.0 Hz), 6.57 (1H, m), 6.74 (1H, m), 6.90 (1H, brt, J=2.0 Hz), 7.06 (1H, brt, J=2.0 Hz), 7.13 (2H, d, J=8.6 Hz), 7.55 (1H, brd, J=8.2 Hz), 7.69 (1H, brd, J=8.2 Hz), 7.89 (2H, d, J=8.6 Hz), 8.41 (1H, brs), 10.00 (1H, brs).

MS (ESI) m/z: 509.17476 (M+H)⁺.

Example 13

2-(5-{3-[(1S)-2-Methoxy-1-methylethoxy]-5-[4-(methylsulfonyl)phenoxy]phenyl}-1H-pyrrol-2-yl)-1,3-oxazole

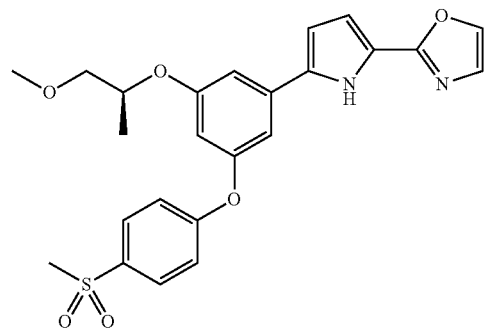

(13a) 1-Bromo-3-[(1S)-2-methoxy-1-methylethoxy]-5-[4-(methylsulfonyl)phenoxy]benzene 3-Bromo-5-[4-(methylsulfonyl)phenoxy]phenol (4.86 g, 14.2 mmol) synthesized in Example (1c) was dissolved in toluene (100 mL), and (R)-(−)-1-methoxy-2-propanol (1.77 mL, 18.1 mmol) and triphenylphosphine (4.10 g, 15.6 mmol) were added, followed by cooling to 0° C. Under nitrogen atmosphere, diethyl azodicarboxylate (40% toluene solution, 7.75 mL, 17.1 mmol) was added dropwise over 10 minutes and stirring was carried out at 0° C. for 30 minutes, followed by raising the temperature naturally and stirring at room temperature overnight. Water (100 mL) and ethyl acetate (100 mL) were added, and the solution was separated. The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=20%-40%) to afford the desired compound (5.06 g, yield 86%) as a pale yellow oil.

¹H-NMR (CDCl₃, 400 MHz): δ 1.28 (3H, d, J=6.3 Hz), 3.05 (3H, s), 3.37 (3H, s), 3.46 (1H, dd, J=3.9, 10.2 Hz), 3.54 (1H, dd, J=6.3, 10.2 Hz), 4.49 (1H, m), 6.56 (1H, d, J=2.0 Hz), 6.77 (1H, d, J=2.0 Hz), 6.93 (1H, d, J=2.0 Hz), 7.10 (2H, d, J=9.0 Hz), 7.89 (2H, d, J=9.0 Hz).

(13b) t-Butyl 2-{3-[(1S)-2-methoxy-1-methylethoxy]-5-[4-(methylsulfonyl)phenoxy]phenyl}-1H-pyrrole-1-carboxylate 1-Bromo-3-[(1S)-2-methoxy-1-methylethoxy]-5-[4-(methylsulfonyl)phenoxy]benzene (2.38 g, 5.73 mmol) synthesized in Example (13a) and 1-(t-butoxycarbonyl)pyrrole-2-boronic acid (1.45 g, 6.87 mmol) were dissolved in a mixed solvent of 1,2-dimethoxyethane (50 mL) and water (6 mL), and palladium (II) acetate (40 mg, 0.178 mmol), triphenylphosphine (180 mg, 0.686 mmol) and potassium carbonate (2.38 g, 17.2 mmol) was added, followed by stirring at 90° C. for 18 hours under nitrogen atmosphere. The reaction solution was cooled to room temperature, water (30 mL) and ethyl acetate (50 mL) were added, and the solution was separated. The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=20%-40%) to afford the desired compound (2.71 g, yield 94%) as a brown oil.

¹H-NMR (CDCl₃, 400 MHz): δ 1.32 (3H, d, J=6.3 Hz), 1.44 (9H, s), 3.05 (3H, s), 3.41 (3H, s), 3.49 (1H, dd, J=4.3, 10.2 Hz), 3.58 (1H, dd, J=6.3, 10.2 Hz), 4.53 (1H, m), 6.19-6.23 (2H, m), 6.61 (1H, t, J=2.4 Hz), 6.63 (1H, dd, J=1.6, 2.0 Hz), 6.79 (1H, dd, J=1.6, 2.4 Hz), 7.15 (2H, d, J=9.0 Hz), 7.31 (1H, dd, J=2.0, 3.2 Hz), 7.88 (2H, d, J=9.0 Hz).

(13c) t-Butyl 2-bromo-5-{3-[(1S)-2-methoxy-1-methylethoxy]-5-[4-(methylsulfonyl)phenoxy]phenyl}-1H-pyrrole-1-carboxylate t-Butyl 2-{3-[(1S)-2-methoxy-1-methylethoxy]-5-[4-(methylsulfonyl)phenoxy]phenyl}-1H-pyrrole-1-carboxylate (2.70 g, 5.38 mmol) synthesized in Example (13b) was dissolved in tetrahydrofuran (50 mL), and cooled to 0° C. After addition of N-bromosuccinimide (960 mg, 5.38 mmol) with stirring under nitrogen atmosphere, stirring was carried out at room temperature for 4 hours. Water (50 mL) was added, and extraction was carried out with ethyl acetate (50 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=20%-40%) to afford the desired compound (2.93 g, yield 94%) as a brown oil.

¹H-NMR (CDCl₃, 400 MHz): δ 1.31 (3H, d, J=6.3 Hz), 1.42 (9H, s), 3.05 (3H, s), 3.39 (3H, s), 3.48 (1H, dd, J=4.3, 10.2 Hz), 3.57 (1H, dd, J=6.3, 10.2 Hz), 4.53 (1H, m), 6.21 (1H, d, J=3.5 Hz), 6.30 (1H, d, J=3.5 Hz), 6.57 (1H, t, J=2.4 Hz), 6.61 (1H, d, J=2.4 Hz), 6.75 (1H, d, J=2.4 Hz), 7.12 (2H, d, J=9.0 Hz), 7.89 (2H, d, J=9.0 Hz).

(13d) 2-(5-{3-[(1S)-2-Methoxy-1-methylethoxy]-5-[4-(methylsulfonyl)phenoxy]phenyl}-1H-pyrrol-2-yl)-1,3-oxazole t-Butyl 2-bromo-5-{3-[(1S)-2-methoxy-1-methylethoxy]-5-[4-(methylsulfonyl)phenoxy]phenyl}-1H-pyrrole-1-carboxylate (102.9 mg, 0.177 mmol) synthesized in Example (13c) was dissolved in toluene (5 mL), and 2-(tri-n-butylstannyl)oxazole (133.7 mg, 0.373 mmol) and tetrakis(triphenylphosphine) palladium (20.5 mg, 0.0177 mmol) was added, followed by heating to reflux for 18 hours under nitrogen atmosphere. The reaction solution was cooled to room temperature, water (20 mL) was added thereto, and extraction was carried out with ethyl acetate (20 mL). The organic layer was washed with saturated brine, and subsequently dried over sodium sulfate. The solvent was distilled off under reduced pressure, and the resulting residue was purified using silica gel column chromatography (elution solvent: ethyl acetate/hexane=35%-55%) to afford t-butyl 2-{3-[(1S)-2-methoxy-1-methylethoxy]-5-[4-(methylsulfonyl)phenoxy]phenyl}-5-(1,3-oxazol-2-yl)-1H-pyrrole-1-carboxylate.

This was dissolved in dichloromethane (1 mL), and trifluoroacetic acid (2 mL) was added thereto, followed by stirring at room temperature for 2 hours, and subsequently the solvent was distilled off under reduced pressure. The residue was diluted with ethyl acetate (20 mL), washed with a saturated aqueous sodium hydrogencarbonate solution, followed by further washing with saturated brine and drying over sodium sulfate. The solvent was distilled off under reduced pressure, and the resulting residue was purified using silica gel column chromatography (elution solvent: ethyl acetate/hexane=65%) to afford the desired compound (15.6 mg, yield 19%) as a pale yellow solid.

¹H-NMR (CDCl₃, 400 MHz): δ ppm 1.34 (3H, d, J=6.3 Hz), 3.07 (3H, s), 3.42 (3H, s), 3.51 (1H, dd, J=4.3, 10.2 Hz), 3.60 (1H, dd, J=6.3, 10.2 Hz), 4.56-4.60 (1H, m), 6.55-6.57 (2H, m), 6.84-6.86 (2H, m), 7.02 (1H, t, J=1.7 Hz), 7.13 (1H, s), 7.15 (2H, d, J=8.6 Hz), 7.61 (1H, s), 7.91 (2H, d, J=9.0 Hz), 9.52 (1H, brs).

MS (ESI) m/z: 469.14163 (M+H)⁺.

Example 14

3-(5-{3-[(1S)-2-Methoxy-1-methylethoxy]-5-[4-(methylsulfonyl)phenoxy]phenyl}-1H-pyrrol-2-yl)-1H-pyrazole

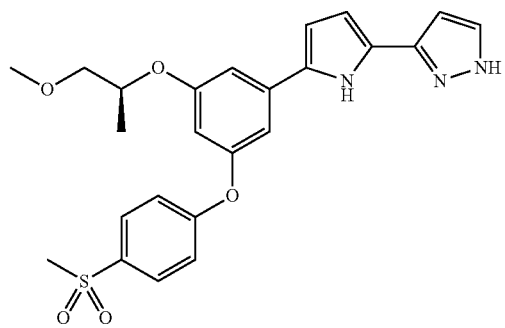

t-Butyl 2-bromo-5-{3-[(1S)-2-methoxy-1-methylethoxy]-5-[4-(methylsulfonyl)phenoxy]phenyl}-1H-pyrrole-1-carboxylate (375 mg, 0.446 mmol) synthesized in Example (13c) and commercially available 1H-pyrazol-3-ylboronic acid (120 mg, 1.00 mmol) were dissolved in a mixed solvent of 1,2-dimethoxyethane (20 mL) and water (5 mL), [1,1'-bis(diphenylphosphino)ferrocene]palladium (II) dichloride dichloromethane complex (28 mg, 0.034 mmol) and an aqueous potassium carbonate solution (3M, 0.65 mL, 1.95 mmol) were added, and stirring was carried out at 100° C. for 7 days under nitrogen atmosphere. After the reaction solution was cooled to room temperature, water (10 mL) was added, and extraction was carried out with ethyl acetate (20 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=20%-80%) to afford the desired compound (106 mg, yield 35%) as a pale yellow solid.

$^1$H-NMR (CDCl$_3$, 400 MHz): δ 1.33 (3H, d, J=6.3 Hz), 3.07 (3H, s), 3.42 (3H, s), 3.51 (1H, dd, J=3.9, 10.2 Hz), 3.60 (1H, dd, J=6.3, 10.2 Hz), 4.57 (1H, m), 6.549-6.55 (4H, m), 6.83 (1H, brs), 7.00 (1H, brs), 7.14 (2H, d, J=9.0 Hz), 7.57 (1H, d, J=2.4 Hz), 7.90 (2H, d, J=9.0 Hz), 9.30 (1H, brs).

MS (ESI) m/z: 468.15954 (M+H)$^+$.

Example 15

1-(5-{3-[(1S)-2-Methoxy-1-methylethoxy]-5-[4-(methylsulfonyl)phenoxy]phenyl}-1H-pyrrol-2-yl)ethanone

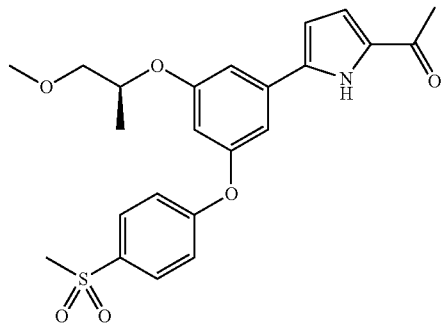

(15a) 1-(5-Bromo-1H-pyrrol-2-yl)ethanone

2-Acetylpyrrole (2.00 g, 18.3 mmol) was dissolved in a mixed solvent of tetrahydrofuran (100 mL) and methanol (50 mL), and N-bromosuccinimide (3.26 g, 18.3 mmol) was added with stirring at room temperature under nitrogen atmosphere. After stirring for 1 hour, the solvent was distilled off under reduced pressure. A saturated aqueous sodium hydrogencarbonate solution (200 mL) was added, and extraction was carried out with ethyl acetate (300 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=10%-20%) to afford the desired compound (770 mg, yield 22%) as a white solid.

$^1$H-NMR (CDCl$_3$, 400 MHz): 2.40 (3H, s), 6.24 (1H, dd, J=2.4, 4.0 Hz), 6.80 (1H, dd, J=2.9, 4.0 Hz), 9.37 (1H, brs).

(15b) t-Butyl 2-acetyl-5-bromo-1H-pyrrole-1-carboxylate 1-(5-Bromo-1H-pyrrol-2-yl) ethanone (770 mg, 4.1 mmol) synthesized in Example (15a) was dissolved in dichloromethane (30 mL), and triethylamine (0.57 mL, 4.1 mmol) and 4-dimethylaminopyridine (500 mg, 4.1 mmol) were added. Di-t-butyl dicarbonate (930 mg, 4.3 mmol) was dissolved in dichloromethane (10 mL), and the solution was added, followed by stirring at room temperature for 3 hours under nitrogen atmosphere. The reaction solution was diluted with dichloromethane (200 mL), washed with 1N hydrochloric acid, a saturated aqueous sodium hydrogencarbonate solution and saturated brine, and subsequently dried over anhydrous magnesium sulfate. The solvent was distilled off under reduced pressure, and the resulting residue was purified using silica gel column chromatography (elution solvent: ethyl acetate/hexane=0%-20%) to afford the desired product (538 mg, yield 46%) as a white solid.

$^1$H-NMR (CDCl$_3$, 400 MHz): δ 1.64 (9H, s), 2.40 (3H, s), 6.24 (1H, d, J=3.9 Hz), 6.82 (1H, d, J=3.9 Hz).

(15c) 1-(5-{3-[(1S)-2-Methoxy-1-methylethoxy]-5-[4-(methylsulfonyl)phenoxy]phenyl}-1H-pyrrol-2-yl)ethanone 2-{3-[(1S)-2-Methoxy-1-methylethoxy]-5-[4-(methylsulfonyl)phenoxy]phenyl}-4,4,5,5-tetramethyl-1,3,2-dioxaborolane (146 mg, 0.33 mmol) synthesized in Example (1e) and t-butyl 2-acetyl-5-bromo-1H-pyrrole-1-carboxylate (141 mg, 0.49 mmol) synthesized in Example (15b) were dissolved in a mixed solvent of toluene (3 mL) and ethanol (1.3 mL), [1,1'-bis(diphenylphosphino)ferrocene]palladium (II) dichloride dichloromethane complex (13 mg, 0.016 mmol) and an aqueous potassium carbonate solution (2M, 0.41 mL, 0.83 mmol) were added, and stirring was carried out at 100° C. for 1.5 hours under nitrogen atmosphere. After the reaction solution was cooled to room temperature, water (20 mL) was added, and extraction was carried out with ethyl acetate (60 mL). The organic layer was washed with saturated brine, subsequently dried over anhydrous magnesium sulfate, and the solvent was distilled off under reduced pressure.

The resulting residue was dissolved in dichloromethane (2 mL), and trifluoroacetic acid (1 mL, 13.0 mmol) was added, followed by stirring at room temperature for 1 hour under nitrogen atmosphere. The solvent was distilled off under reduced pressure, a saturated aqueous sodium hydrogencarbonate solution (30 mL) was added, and extraction was carried out with ethyl acetate (70 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=10%-50%) to afford the desired compound (95 mg, yield 66%) as a pale yellow solid.

$^1$H-NMR (CDCl$_3$, 400 MHz): δ 1.34 (3H, d, J=6.3 Hz,), 2.44 (3H, s), 3.07 (3H, s), 3.41 (3H, s), 3.51 (1H, dd, J=4.0, 10.2 Hz), 3.59 (1H, dd, J=6.2, 10.2 Hz), 4.56-4.59 (1H, m), 6.53 (1H, dd, J=2.9, 3.5 Hz), 6.62 (1H, t, J=2.0 Hz), 6.86 (1H, t, J=1.6 Hz), 6.93 (1H, dd, J=2.5, 3.9 Hz), 7.02 (1H, s), 7.14 (2H, d, J=8.9 Hz), 7.91 (2H, d, J=8.8 Hz), 9.64 (1H, brs).

MS (ESI) m/z: 444.14808 (M+H)$^+$.

Example 16

(1E)-1-(5-{3-[(1S)-2-Methoxy-1-methylethoxy]-5-[4-(methylsulfonyl)phenoxy]phenyl}-1H-pyrrol-2-yl)ethanone oxime

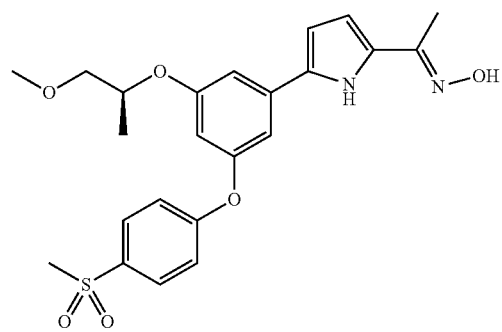

1-(5-{3-[(1S)-2-Methoxy-1-methylethoxy]-5-[4-(methylsulfonyl)phenoxy]phenyl}-1H-pyrrol-2-yl)ethanone (117 mg, 0.26 mmol) synthesized in Example (15c) was dissolved in methanol (6 mL), and hydroxylamine hydrochloride (37 mg, 0.53 mmol) and sodium acetate (26 mg, 0.32 mmol) were added, followed by heating to reflux for 6 hours under nitrogen atmosphere. The reaction solution was diluted with dichloromethane (60 mL), washed with water and saturated brine, and subsequently dried over anhydrous magnesium sulfate. The solvent was distilled off under reduced pressure, and the resulting residue was purified using silica gel column chromatography (elution solvent: ethyl acetate/hexane=30%-50%) to afford the desired product (50 mg, yield 41%) as a white solid.

$^1$H-NMR (CDCl$_3$, 400 MHz): δ 1.32 (3H, d, J=6.2 Hz), 2.19 (3H, s), 3.06 (3H, s), 3.41 (3H, s), 3.50 (1H, dd, J=4.1, 10.2 Hz), 3.58 (1H, dd, J=6.1, 10.2 Hz), 4.52-4.57 (1H, m), 6.47 (2H, d, J=2.7 Hz), 6.53 (1H, t, J=2.0 Hz), 6.79 (1H, t, J=1.5 Hz), 6.89 (1H, brs), 6.95 (1H, t, J=1.8 Hz), 7.13 (2H, d, J=8.8 Hz), 7.90 (2H, d, J=8.8 Hz), 9.03 (1H, brs)

MS (ESI) m/z: 459.15898 (M+H)$^+$.

Example 17

Ethyl 5-{3-[(1S)-2-methoxy-1-methylethoxy]-5-[4-(methylsulfonyl)phenoxy]phenyl}-1H-pyrrole-2-carboxylate

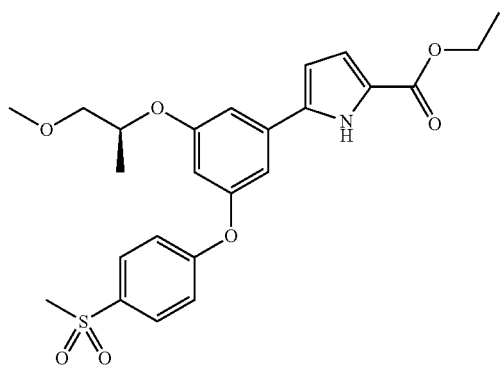

(17a) Ethyl 5-bromo-1H-pyrrole-2-carboxylate

Commercially available ethyl 1H-pyrrole-2-carboxylate (5.10 g, 30.7 mmol) was dissolved in a mixed solvent of tetrahydrofuran (120 mL) and methanol (60 mL), and cooled to 0° C. N-Bromosuccinimide (6.52 g, 30.7 mmol) was added, and stirring was carried out at room temperature for 18 hours under nitrogen atmosphere. Water (150 mL) and ethyl acetate (200 mL) were added, and the solution was separated. The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=5%-30%) to afford the desired compound (3.20 g, yield 40%) as a white solid.

$^1$H-NMR (CDCl$_3$, 400 MHz): δ 1.36 (3H, t, J=7.1 Hz), 4.32 (2H, q, J=7.1 Hz), 6.21 (1H, dd, J=2.7, 3.9 Hz), 6.82 (1H, dd, J=2.7, 3.9 Hz), 9.21 (1H, brs).

(17b) 1-t-Butyl 2-ethyl 5-bromo-1H-pyrrole-1,2-dicarboxylate

Ethyl 5-bromo-1H-pyrrole-2-carboxylate (3.20 g, 14.7 mmol) synthesized in Example (17a) was dissolved in dichloromethane (100 mL), di-t-butyl dicarbonate (3.85 g, 17.6 mmol), triethylamine (2.70 mL, 19.4 mmol) and 4-dimethylaminopyridine (180 mg, 1.47 mmol) were added, and stirring was carried out at room temperature for 1 hour under nitrogen atmosphere. Water (100 mL) was added, and extraction was carried out with dichloromethane (100 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=0%-20%) to afford the desired compound as a colorless oil (4.37 g, yield 94%).

$^1$H-NMR (CDCl$_3$, 400 MHz): δ 1.34 (3H, t, J=7.0 Hz), 1.63 (9H, s), 4.30 (2H, q, J=7.0 Hz), 6.23 (1H, d, J=3.9 Hz), 6.83 (1H, d, J=3.9 Hz).

(17c) 1-t-Butyl 2-ethyl 5-{3-[(1S)-2-methoxy-1-methylethoxy]-5-[4-(methylsulfonyl)phenoxy]phenyl}-1H-pyrrole-1,2-dicarboxylate 2-{3-[(1S)-2-Methoxy-1-methylethoxy]-5-[4-(methylsulfonyl)phenoxy]phenyl}-4,4,5,5-tetramethyl-1,3,2-dioxaborolane (8.73 g, 18.9 mmol) synthesized in Example (1e) and 1-t-butyl 2-ethyl 5-bromo-1H-pyrrole-1,2-dicarboxylate (8.37 g, 26.3 mmol) synthesized in Example (17b) were dissolved in a mixed solvent of toluene (180 mL) and ethanol (77 mL), [1,1'-bis(diphenylphosphino)ferrocene]palladium (II) dichloride dichloromethane complex (770 mg, 0.94 mmol) and an aqueous potassium carbonate solution (2M, 23.7 mL, 47.2 mmol) were added, and stirring was carried out at 100° C. for 1 hour under nitrogen atmosphere. After the reaction solution was cooled to room temperature, water (200 mL) was added, and extraction was carried out with ethyl acetate (400 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=10%-50%) to afford the desired compound (9.44 g, yield 84%) as a pale yellow oil.

$^1$H-NMR (CDCl$_3$, 400 MHz): δ 1.31 (3H, d, J=6.3 Hz), 1.35 (3H, t, J=7.0 Hz), 1.46 (9H, s), 3.05 (3H, s), 3.39 (3H, s), 3.48 (1H, dd, J=4.3, 10.2 Hz), 3.57 (1H, dd, J=5.9, 10.2 Hz), 4.32 (2H, q, J=7.0 Hz), 4.53 (1H, m), 6.22 (1H, d, J=3.9 Hz), 6.65 (1H, m), 6.73 (1H, m), 6.88 (1H, m), 6.89 (1H, d, J=3.9 Hz), 7.12 (1H, d, J=9.0 Hz), 7.89 (2H, d, J=9.0 Hz).

(17d) Ethyl 5-{3-[(1S)-2-methoxy-1-methylethoxy]-5-[4-(methylsulfonyl)phenoxy]phenyl}-1H-pyrrole-2-carboxylate 1-t-Butyl 2-ethyl 5-{3-[(1S)-2-methoxy-1-methylethoxy]-5-[4-(methylsulfonyl)phenoxy]phenyl}-1H-pyrrole-1,2-dicarboxylate (9.44 g, 16.5 mmol) synthesized in Example (17c) was dissolved in dichloromethane (90 mL), and cooled to 0° C. Trifluoroacetic acid (45 mL) was added dropwise with stirring under nitrogen atmosphere, and stirring was carried out at room temperature for 1 hour. The solvent was distilled off under reduced pressure, followed by dilution with ethyl acetate (300 mL), a saturated aqueous sodium hydrogencarbonate solution (200 mL) was added, and the solution was separated. The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=10%-50%) to afford the desired compound (6.34 g, yield 81%) as a pale yellow solid.

$^1$H-NMR (CDCl$_3$, 400 MHz): δ 1.33 (3H, d, J=6.3 Hz), 1.37 (2H, t, J=7.0 Hz), 3.07 (3H, s), 3.41 (3H, s), 3.51 (1H, dd, J=3.9, 10.2 Hz), 3.60 (1H, dd, J=6.3, 10.2 Hz), 4.34 (2H, q, J=7.0 Hz), 4.58 (1H, m), 6.51 (1H, dd, J=2.5, 4.0 Hz), 6.58 (1H, m), 6.86 (1H, m), 6.93 (1H, dd, J=2.5, 4.0 Hz), 7.01 (1H, m), 7.13 (2H, d, J=8.8 Hz), 7.91 (2H, d, J=8.8 Hz), 9.41 (1H, brs).

MS (ESI) m/z: 474.16048 (M+H)$^+$.

Example 18

N-(2-Chloroethyl)-5-{3-[(1S)-2-methoxy-1-methylethoxy]-5-[4-(methylsulfonyl)phenoxy]phenyl}-1H-pyrrole-2-carboxamide

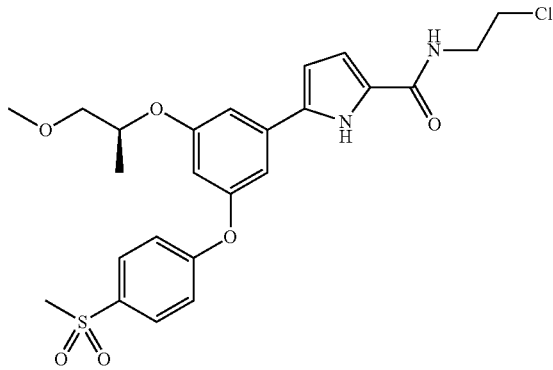

(18a) 5-{3-[(1S)-2-Methoxy-1-methylethoxy]-5-[4-(methylsulfonyl)phenoxy]phenyl}-1H-pyrrole-2-carboxylic acid Ethyl 5-{3-[(1S)-2-methoxy-1-methylethoxy]-5-[4-(methylsulfonyl)phenoxy]phenyl}-1H-pyrrole-2-carboxylate (4.36 g, 9.2 mmol) synthesized in Example (17d) was dissolved in ethanol (100 mL), and a 4N aqueous sodium hydroxide solution (23 mL, 92 mmol) was added, followed by heating to reflux for 1 hour under nitrogen atmosphere. To the reaction solution, 2N hydrochloric acid (45 mL) was added to neutralize it, and the solvent was distilled off under reduced pressure. 1N hydrochloric acid was used to make the solution acidic, and extraction was carried out with ethyl acetate (300 mL). The organic layer was washed with saturated brine, and subsequently dried over anhydrous magnesium sulfate. The solvent was distilled off under reduced pressure, to afford the desired product (4.06 g, yield 99%) as a white solid.

$^1$H-NMR (CDCl$_3$, 400 MHz): δ 1.34 (3H, d, J=6.3 Hz,), 3.07 (3H, s), 3.46 (3H, s), 3.55 (1H, dd, J=4.2, 10.4 Hz), 3.66 (1H, dd, J=6.3, 10.5 Hz), 4.70-4.75 (1H, m), 6.53 (1H, dd, J=2.6, 3.9 Hz), 6.59 (1H, t, J=2.0 Hz), 6.91 (1H, t, J=1.6 Hz,), 7.04 (1H, dd, J=2.3, 3.9 Hz), 7.25 (1H, m), 7.14 (2H, d, J=8.9 Hz), 7.91 (2H, d, J=8.8 Hz), 10.13 (1H, brs).

(18b) N-(2-Chloroethyl)-5-{3-[(1S)-2-methoxy-1-methylethoxy]-5-[4-(methylsulfonyl)phenoxy]phenyl}-1H-pyrrole-2-carboxamide 5-{3-[(1S)-2-Methoxy-1-methylethoxy]-5-[4-(methylsulfonyl)phenoxy]phenyl}-1H-pyrrole-2-carboxylic acid (150 mg, 0.34 mmol) synthesized in Example (18a), 2-chloroethylamine hydrochloride (78 mg, 0.68 mmol) and 4-dimethylaminopyridine (41 mg, 0.34 mmol) were dissolved in dichloromethane (15 mL), WSCI•HCl (71 mg, 0.37 mmol) was added at room temperature, and stirring was carried out for 2 hours under nitrogen atmosphere. The reaction solution was diluted with dichloromethane (150 mL), washed with 1N hydrochloric acid, a saturated aqueous sodium hydrogencarbonate solution and saturated brine, and subsequently dried over anhydrous magnesium sulfate. The solvent was distilled off under reduced pressure, and the resulting residue was purified using silica gel column chromatography (elution solvent: ethyl acetate/hexane=30%-60%) to afford the desired product (105 mg, yield 62%) as a white solid.

$^1$H-NMR (CDCl$_3$, 500 MHz): δ 1.33 (3H, d, J=6.3 Hz), 3.07 (3H, s), 3.42 (3H, s), 3.51 (1H, dd, J=4.0, 10.3 Hz), 3.59 (1H, dd, J=6.1, 10.4 Hz), 3.70 (2H, t, J=5.4 Hz), 3.77 (2H, t, J=5.4 Hz), 4.55-4.59 (1H, m), 6.26-6.29 (1H, brm), 6.50 (1H, dd, J=2.9, 3.9 Hz), 6.58 (1H, t, J=2.2 Hz), 6.63 (1H, dd, J=2.5, 3.8 Hz), 6.83 (1H, t, J=1.7 Hz), 6.99 (1H, t, J=2.0 Hz), 7.14 (2H, d, J=8.8 Hz), 7.91 (2H, d, J=8.8 Hz), 9.52 (1H, brs).

MS (ESI) m/z: 507.13566 (M+H)$^+$.

Example 19

N-(2-Chloroethyl)-5-{3-[(1S)-2-hydroxy-1-methylethoxy]-5-[4-(methylsulfonyl)phenoxy]phenyl}-1H-pyrrole-2-carboxamide

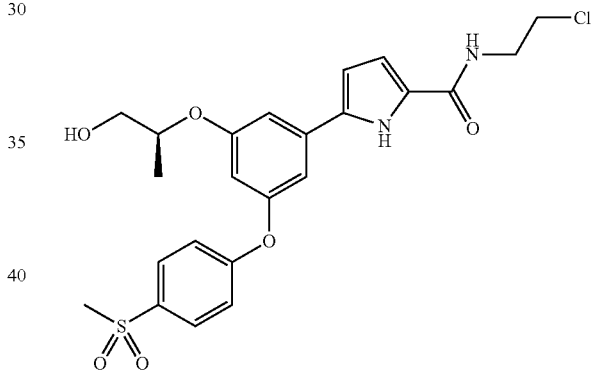

N-(2-Chloroethyl)-5-{3-[(1S)-2-methoxy-1-methylethoxy]-5-[4-(methylsulfonyl)phenoxy]phenyl}-1H-pyrrole-2-carboxamide (88 mg, 0.17 mmol) synthesized in Example (18b) was dissolved in dichloromethane (5 mL), and cooled to −78° C., and a 1.0 mol/L boron tribromide dichloromethane solution (0.19 mL, 0.19 mmol) was added under nitrogen atmosphere. The temperature was raised naturally, the solution was stirred at room temperature for 30 minutes, subsequently a saturated aqueous sodium hydrogencarbonate solution was added to neutralize the reaction solution, and extraction was carried out with dichloromethane (60 mL). The organic layer was washed with saturated brine, and subsequently dried over sodium sulfate. The solvent was distilled off under reduced pressure, and the resulting residue was purified using silica gel column chromatography (elution solvent: ethyl acetate/hexane=50%-80%) to afford the desired product (55 mg, yield 64%) as a white solid.

$^1$H-NMR (CDCl$_3$, 500 MHz): δ 1.31 (3H, d, J=6.3 Hz), 2.1 (1H, brm), 3.08 (3H, s), 3.70 (2H, t, J=5.2 Hz), 3.76-3.80 (4H, m), 4.52-4.56 (1H, m), 6.27-6.30 (1H, brm), 6.50 (1H, dd, J=2.9, 3.8 Hz), 6.57 (1H, t, J=2.1 Hz), 6.64 (1H, dd, J=2.3, 3.9 Hz), 6.85 (1H, t, J=1.7 Hz), 6.98 (1H, t, J=1.8 Hz), 7.14 (2H, d, J=8.8 Hz), 7.91 (2H, d, J=8.8 Hz), 9.56 (1H, brs)

MS (FAB) m/z: 493 (M+H)$^+$.

Example 20

2-(5-{3-[(1S)-2-Methoxy-1-methylethoxy]-5-[4-(methylsulfonyl)phenoxy]phenyl}-1H-pyrrol-2-yl)-4,5-dihydro-1,3-oxazole

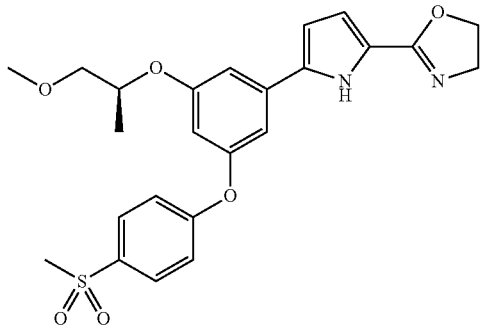

N-(2-Chloroethyl)-5-{3-[(1S)-2-methoxy-1-methylethoxy]-5-[4-(methylsulfonyl)phenoxy]phenyl}-1H-pyrrole-2-carboxamide (177 mg, 0.349 mmol) synthesized in Example (18b) was dissolved in tetrahydrofuran (5 mL), and cooled to 0° C. Sodium hydride (40 mg, 0.917 mmol) was added, and the temperature was raised to room temperature, followed by stirring for 19 hours. After the reaction solution was cooled to 0° C., water (5 mL) was added, and extraction was carried out with ethyl acetate (10 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=50%-100%) to afford the desired compound (118 mg, yield 72%) as a white solid.

$^1$H-NMR (CDCl$_3$, 400 MHz): δ 1.33 (3H, d, J=6.3 Hz), 3.07 (3H, s), 3.41 (3H, s), 3.50 (1H, dd, J=3.9, 10.2 Hz), 3.59 (1H, dd, J=6.3, 10.2 Hz), 3.98 (2H, t, J=9.4 Hz), 4.40 (2H, t, J=9.4 Hz), 4.56 (1H, m), 6.50 (1H, d, J=3.9 Hz), 6.56 (1H, brt, J=2.0 Hz), 6.75 (1H, d, J=3.9 Hz), 6.83 (1H, brt, J=2.0 Hz), 7.00 (1H, brt, J=2.0 Hz), 7.13 (2H, d, J=9.0 Hz), 7.90 (2H, d, J=9.0 Hz).

MS (ESI) m/z: 471.16050 (M+H)$^+$.

Example 21

(2S)-2-{3-[5-(4,5-Dihydro-1,3-oxazol-2-yl)-1H-pyrrol-2-yl]-5-[4-(methylsulfonyl)phenoxy]phenoxyl}propan-1-ol

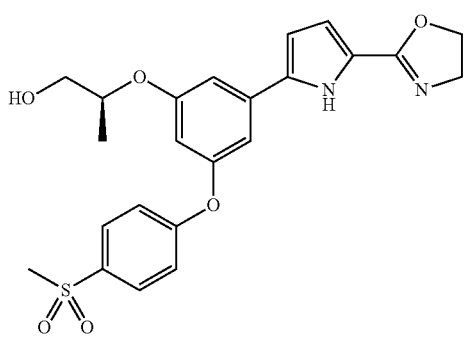

2-(5-{3-[(1S)-2-Methoxy-1-methylethoxy]-5-[4-(methylsulfonyl)phenoxy]phenyl}-1H-pyrrol-2-yl)-4,5-dihydro-1,3-oxazole (3.17 g, 6.74 mmol) synthesized in Example 20 was dissolved in dichloromethane (100 mL), and cooled to −78° C., and a 1.0 mol/l boron tribromide dichloromethane solution (7.07 mL, 7.07 mmol) was added under nitrogen atmosphere. The temperature was raised naturally, followed by stirring at room temperature for 30 minutes, subsequently a saturated aqueous sodium hydrogencarbonate solution was added to neutralize the reaction solution, and extraction was carried out with dichloromethane (200 mL). The organic layer was washed with saturated brine, and subsequently dried over sodium sulfate. The solvent was distilled off under reduced pressure, and the resulting residue was washed with ethyl acetate (100 mL) and ethanol (50 mL) to afford the desired product (1.96 g, yield 64%) as a white solid.

$^1$H-NMR (CDCl$_3$, 500 MHz): δ 1.29 (3H, d, J=6.3 Hz), 3.06 (3H, s), 3.79 (2H, d, J=5.9 Hz), 4.00 (2H, t, J=9.3 Hz), 4.42 (2H, t, J=9.4 Hz), 4.58-4.63 (1H, m), 6.40 (1H, t, J=2.2 Hz), 6.47 (1H, d, J=3.9 Hz), 6.75 (1H, d, J=3.8 Hz), 6.79 (1H, t, J=1.7 Hz), 6.94 (1H, t, J=1.8 Hz), 7.09 (2H, d, J=8.8 Hz), 7.88 (2H, d, J=8.8 Hz).

MS (ESI) m/z: 457.14357 (M+H)$^+$.

Example 22

2-(5-{3-[(1S)-2-Methoxy-1-methylethoxy]-5-[4-(methylsulfonyl)phenoxy]phenyl}-1H-pyrrol-2-yl)-5-methyl-1,3,4-thiadiazole

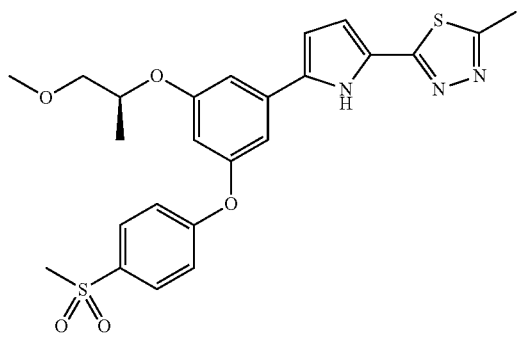

(22a) N'-Acetyl-5-{3-[(1S)-2-methoxy-1-methylethoxy]-5-[4-(methylsulfonyl)phenoxy]phenyl}-1H-pyrrole-2-carbohydrazide 5-{3-[(1S)-2-Methoxy-1-methylethoxy]-5-[4-(methylsulfonyl)phenoxy]phenyl}-1H-pyrrole-2-carboxylic acid (114.5 mg, 0.257 mmol) synthesized in Example (18a) was dissolved in N,N-dimethylformamide (4 mL), acetohydrazide (39.4 mg, 0.531 mmol), HATU (150.1 mg, 0.395 mol) and N,N-diisopropylethylamine (70 μL, 0.40 mmol) were added, and stirring was carried out at room temperature for 20 hours under nitrogen atmosphere. Water (20 mL) was added to the reaction solution, and extraction was carried out with ethyl acetate (20 mL). The organic layer was washed with saturated brine, and subsequently dried over sodium sulfate. The solvent was distilled off under reduced pressure, and the resulting residue was purified using silica gel column chromatography (elution solvent: ethyl acetate/hexane=10%-100%) to afford the desired compound (73.0 mg, yield 57%) as a white solid.

$^1$H-NMR (CDCl$_3$, 400 MHz): δ 1.29 (3H, d, J=6.3 Hz), 1.99 (3H, s), 3.06 (3H, s), 3.40 (3H, s), 3.49 (1H, dd, J=3.9, 10.2 Hz), 3.57 (1H, dd, J=6.3, 10.2 Hz), 4.58-4.63 (1H, m), 6.46 (1H, dd, J=2.7, 3.9 Hz), 6.53 (1H, s), 6.78 (1H, dd, J=2.4, 3.9 Hz), 6.86 (1H, s), 7.10 (2H, d, J=9.0 Hz), 7.13 (1H, s), 7.88 (2H, d, J=8.6 Hz), 8.63 (1H, brs), 9.08 (1H, brs), 10.20 (1H, brs).
MS (ESI) m/z: 524.14725 (M+Na)+.

(22b) 2-(5-{3-[(1S)-2-Methoxy-1-methylethoxy]-5-[4-(methylsulfonyl)phenoxy]phenyl}-1H-pyrrol-2-yl)-5-methyl-1,3,4-thiadiazole N'-Acetyl-5-{3-[(1S)-2-methoxy-1-methylethoxy]-5-[4-(methylsulfonyl)phenoxy]phenyl}-1H-pyrrole-2-carbohydrazide (58.1 mg, 0.116 mmol) synthesized in Example (22a) was dissolved in toluene (4 mL), 2,4-bis-(4-methoxyphenyl)-1,3-dithia-2,4-diphosphetane 2,4-disulfide (63.5 mg, 0.157 mmol) and pyridine (20 µL, 0.25 mmol) were added, and stirring was carried out at 90° C. for 5 hours under nitrogen atmosphere. The reaction solution was cooled to room temperature, water (20 mL) was added to the reaction solution, and extraction was carried out with ethyl acetate (20 mL). The organic layer was washed with saturated brine, and subsequently dried over sodium sulfate. The solvent was distilled off under reduced pressure, and the resulting residue was purified using silica gel column chromatography (elution solvent: ethyl acetate/hexane=40%-80%) to afford the desired compound (50.6 mg, yield 87%) as a pale yellow solid.
¹H-NMR (CDCl₃, 500 MHz): δ 1.34 (3H, d, J=6.4 Hz), 2.77 (3H, s), 3.07 (3H, s), 3.42 (3H, s), 3.51 (1H, dd, J=4.4, 10.3 Hz), 3.60 (1H, dd, J=6.4, 10.3 Hz), 4.57-4.61 (1H, m), 6.55 (1H, t, J=3.4 Hz), 6.58 (1H, t, J=1.9 Hz), 6.67 (1H, dd, J=2.4, 3.9 Hz), 6.87 (1H, t, J=1.7 Hz), 7.03 (1H, s), 7.14 (2H, d, J=8.8 Hz), 7.91 (2H, d, J=8.8 Hz), 9.74 (1H, brs).
MS (ESI) m/z: 500.12981 (M+H)+.

Example 23

2-(5-{3-[(1S)-2-Methoxy-1-methylethoxy]-5-[4-(methylsulfonyl)phenoxy]phenyl}-1H-pyrrol-2-yl)-5-methyl-1,3,4-oxadiazole

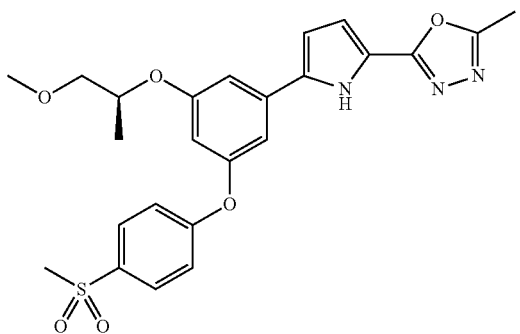

N'-Acetyl-5-{3-[(1S)-2-methoxy-1-methylethoxy]-5-[4-(methylsulfonyl)phenoxy]phenyl}-1H-pyrrole-2-carbohydrazide (86.5 mg, 0.172 mmol) synthesized in Example (22a) was dissolved in acetonitrile (5 mL), (methoxycarbonysulfamoyl)triethylammonium hydroxide (60.7 mg, 0.258 mmol) and triethylamine (36 µL, 0.26 mmol) were added, and stirring was carried out at 80° C. for 3 hours under nitrogen atmosphere. The reaction solution was cooled to room temperature, water (20 mL) was added to the reaction solution, and extraction was carried out with ethyl acetate (30 mL). The organic layer was washed with saturated brine, and subsequently dried over sodium sulfate. The solvent was distilled off under reduced pressure, and the resulting residue was purified using silica gel column chromatography (elution solvent: ethyl acetate/hexane=50%-75%) to afford the desired compound (49.1 mg, yield 59%) as a white solid.
¹H-NMR (CDCl₃, 400 MHz): δ 1.34 (3H, d, J=6.3 Hz), 2.58 (3H, s), 3.08 (3H, s), 3.42 (3H, s), 3.51 (1H, dd, J=3.9, 10.2 Hz), 3.60 (1H, dd, J=6.3, 10.2 Hz), 4.55-4.61 (1H, m), 6.57-6.60 (2H, m), 6.85-6.87 (2H, m), 7.02 (1H, s), 7.14 (2H, d, J=8.6 Hz), 7.91 (2H, d, J=8.6 Hz), 9.65 (1H, brs).
MS (ESI) m/z: 484.15505 (M+H)+.

Example 24

5-Methoxy-2-(5-{3-[(1S)-2-methoxy-1-methylethoxy]-5-[4-(methylsulfonyl)phenoxy]phenyl}-1H-pyrrol-2-yl)-1,3-oxazole

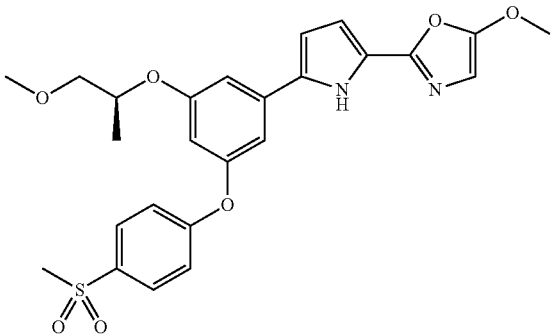

(24a) Methyl N-[(5-{3-[(1S)-2-methoxy-1-methylethoxy]-5-[4-(methylsulfonyl)phenoxy]phenyl}-1H-pyrrol-2-yl)carbonyl]glycinate 5-{3-[(1S)-2-Methoxy-1-methylethoxy]-5-[4-(methylsulfonyl)phenoxy]phenyl}-1H-pyrrole-2-carboxylic acid (275 mg, 0.617 mmol) synthesized in Example (18a) was dissolved in dichloromethane (10 mL), and glycine methyl ester hydrochloride (120 mg, 0.956 mmol), WSCI•HCl (180 mg, 0.939 mmol) and 4-dimethylaminopyridine (150 mg, 1.23 mmol) were added, followed by stirring at room temperature for 2 hours under nitrogen atmosphere. 1N hydrochloric acid (10 mL) was added, and the solution was separated with dichloromethane (15 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=20%-60%) to afford the desired product (270 mg, yield 85%) as a white solid.
¹H-NMR (CDCl₃, 400 MHz): δ 1.31 (3H, d, J=6.3 Hz), 3.07 (3H, s), 3.41 (3H, s), 3.50 (1H, dd, J=3.9, 10.2 Hz), 3.59 (1H, dd, J=6.3, 10.2 Hz), 3.78 (3H, s), 4.56 (1H, m), 6.48 (1H, brt, J=3.9 Hz), 6.54-6.58 (2H, m), 6.69 (1H, dd, J=2.4, 3.9 Hz), 6.89 (1H, t, J=2.0 Hz), 7.02 (1H, t, J=2.0 Hz), 7.12 (2H, d, J=8.6 Hz), 7.89 (2H, d, J=8.9 Hz), 10.11 (1H, brs).

(24b) 5-Methoxy-2-(5-{3-[(1S)-2-methoxy-1-methylethoxy]-5-[4-(methylsulfonyl)phenoxy]phenyl}-1H-pyrrol-2-yl)-1,3-oxazole Methyl N-[(5-{3-[(1S)-2-methoxy-1-methylethoxy]-5-[4-(methylsulfonyl)phenoxy]phenyl}-1H-pyrrol-2-yl)carbonyl]glycinate (270 mg, 0.523 mmol) synthesized in Example (24a) was dissolved in acetonitrile (10 mL), and triphenylphosphine (410 mg, 1.56 mmol), triethylamine (0.22 mL, 1.58 mmol) and carbon tetrachloride (0.33 mL, 3.42 mmol) were added, followed by stirring at room temperature for 15 hours under nitrogen atmosphere. Water (10 mL) was added, and the solution was separated with ethyl acetate (15 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=10%-40%) to afford the desired product (162 mg, yield 62%) as an orange solid.

$^1$H-NMR (CDCl$_3$, 400 MHz): δ 1.32 (3H, d, J=6.3 Hz), 3.07 (3H, s), 3.41 (3H, s), 3.50 (1H, dd, J=3.9, 10.2 Hz), 3.59 (1H, dd, J=6.3, 10.2 Hz), 3.92 (3H, s), 4.55 (1H, m), 6.08 (1H, s), 6.51-6.55 (2H, m), 6.70 (1H, dd, J=2.4, 3.9 Hz), 6.83 (1H, t, J=2.0 Hz), 6.99 (1H, t, J=2.0 Hz), 7.12 (2H, d, J=9.0 Hz), 7.90 (2H, d, J=9.0 Hz), 9.77 (1H, brs).

MS (ESI) m/z: 499.15601 (M+H)$^+$.

Example 25

2-(5-{3-[(1S)-2-Methoxy-1-methylethoxy]-5-[4-(methylsulfonyl)phenoxy]phenyl}-1H-pyrrol-2-yl)-4,5-dihydro-1,3-thiazole

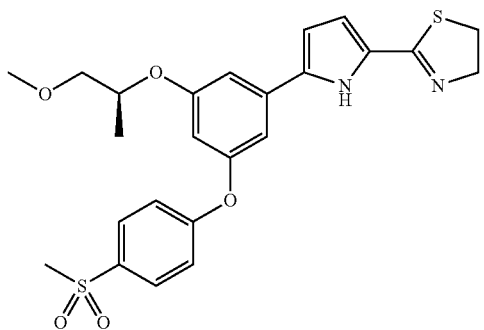

(25a) 2-(Tritylthio)ethaneamine

Hydrochloric acid 2-aminoethanethiol (5.16 g, 45.4 mmol) was dissolved in dichloromethane (80 mL), and trifluoroacetic acid (7.0 mL, 90.8 mmol) and triphenylmethyl chloride (13.29 g, 47.7 mmol) were added, followed by stirring at room temperature for 1 hour. A 1N aqueous sodium hydroxide solution (150 mL) was added, and extraction was carried out with dichloromethane (500 mL). The organic layer was washed with saturated brine, and subsequently dried over anhydrous magnesium sulfate. The solvent was distilled off under reduced pressure, methanol (100 mL) was added to the resulting residue, and the deposited by-product was removed by filtration. 1N hydrochloric acid (300 mL) was added to make the solution acidic, and the deposit was filtered off. After the by-product was washed with dichloromethane (50 mL) to remove it, the solution was made alkaline with a 1N aqueous sodium hydroxide solution, and extraction was carried out with dichloromethane (600 mL). The organic layer was washed with saturated brine, and subsequently dried over anhydrous magnesium sulfate. The solvent was distilled off under reduced pressure, to afford the desired product (8.77 g, yield 60%) as a white solid.

$^1$H-NMR (CDCl$_3$, 400 MHz): δ 2.33 (2H, t, J=6.6 Hz), 2.59 (2H, t, J=6.6 Hz), 7.19-7.23 (3H, m), 7.26-7.30 (6H, m), 7.41-7.44 (6H, m).

(25b) 5-{3-[(1S)-2-Methoxy-1-methylethoxy]-5-[4-(methylsulfonyl)phenoxy]phenyl}-N-[2-(tritylthio)ethyl]-1H-pyrrole-2-carboxamide To 5-{3-[(1S)-2-methoxy-1-methylethoxy]-5-[4-(methylsulfonyl)phenoxy]phenyl}-1H-pyrrole-2-carboxylic acid (940 mg, 2.1 mmol) synthesized in Example (18a), 2-(tritylthio)ethaneamine (1.01 g, 3.17 mmol) synthesized in Example (25a) and 4-dimethylaminopyridine (13 mg, 0.1 mmol) were added, followed by dissolution in dichloromethane (50 mL), and subsequently WSCI•HCl (445 mg, 2.3 mmol) was added at room temperature, and stirring was carried out for 1 hour under nitrogen atmosphere. The reaction solution was diluted with dichloromethane (150 mL), washed with 1N hydrochloric acid, a saturated aqueous sodium hydrogencarbonate solution and saturated brine, and subsequently dried over anhydrous magnesium sulfate. The solvent was distilled off under reduced pressure, and the resulting residue was purified using silica gel column chromatography (elution solvent: ethyl acetate/hexane=10%-55%) to afford the desired product (1.08 g, yield 69%) as a white solid.

$^1$H-NMR (CDCl$_3$, 400 MHz): δ 1.33 (3H, d, J=6.3 Hz), 2.50 (2H, t, J=6.5 Hz), 3.07 (3H, s), 3.27 (2H, dt, J=5.9, 6.2 Hz), 3.42 (3H, s), 3.51 (1H, dd, J=4.0, 10.4 Hz), 3.59 (1H, dd, J=5.9, 10.4 Hz), 4.55-4.59 (1H, m), 5.99 (1H, brm), 6.48 (1H, dd, J=2.8, 3.9 Hz), 6.53 (1H, dd, J=2.5, 3.9 Hz), 6.57 (1H, t, J=2.3 Hz), 6.81 (1H, t, J=2.2 Hz), 6.98 (1H, t, J=2.1 Hz), 7.14 (2H, d, J=8.9 Hz), 7.19-7.30 (9H, m), 7.42 (6H, dd, J=1.6, 7.3 Hz), 7.91 (2H, d, J=8.9 Hz), 9.41 (1H, brs).

(25c) 2-(5-{3-[(1S)-2-Methoxy-1-methylethoxy]-5-[4-(methylsulfonyl)phenoxy]phenyl}-1H-pyrrol-2-yl)-4,5-dihydro-1,3-thiazole Triphenylphosphine oxide (2.41 g, 8.7 mmol) was dissolved in dichloromethane (20 mL), and trifluoromethanesulfonic anhydride (0.73 mL, 4.3 mmol) was added dropwise slowly at 0° C. After stirring for 10 minutes, a dichloromethane (15 mL) solution of 5-{3-[(1S)-2-methoxy-1-methylethoxy]-5-[4-(methylsulfonyl)phenoxy]phenyl}-N[2-(tritylthio)ethyl]-1H-pyrrole-2-carboxamide synthesized in Example (25b) was added. After reaction solution was stirred at room temperature for 30 minutes, the solvent was distilled off under reduced pressure, a saturated aqueous sodium hydrogencarbonate solution was added, and extraction was carried out with ethyl acetate (200 mL). The organic layer was washed with saturated brine, and dried over anhydrous magnesium sulfate. The solvent was distilled off under reduced pressure, and the resulting residue was purified using silica gel column chromatography (elution solvent: ethyl acetate/hexane=50%-80%) to afford the desired product (636 mg, yield 90%) as a white solid.

$^1$H-NMR (CDCl$_3$, 500 MHz): δ 1.33 (3H, d, J=6.3 Hz), 3.07 (3H, s), 3.39 (2H, t, J=8.4 Hz), 3.41 (3H, s), 3.50 (1H, dd, J=3.9, 10.3 Hz), 3.59 (1H, dd, J=5.9, 10.3 Hz), 4.33 (2H, t, J=8.7 Hz), 4.55-4.59 (1H, m), 6.50 (1H, d, J=3.9 Hz), 6.56 (1H, t, J=2.5 Hz), 6.64 (1H, d, J=3.9 Hz), 6.83 (1H, t, J=2.0 Hz), 7.00 (1H, t, J=2.4 Hz), 7.13 (2H, d, J=8.8 Hz), 7.90 (2H, d, J=8.8 Hz).

MS (ESI) m/z: 487.13595 (M+H)$^+$.

Example 26

(2S)-2-{3-[5-(4,5-Dihydro-1,3-thiazol-2-yl)-1H-pyrrol-2-yl]-5-[4-(methylsulfonyl)phenoxy]phenoxy}propan-1-ol

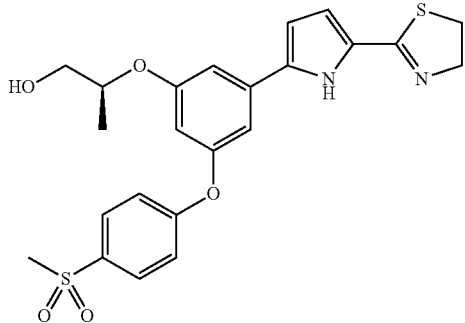

2-(5-{3-[(1S)-2-Methoxy-1-methylethoxy]-5-[4-(methylsulfonyl)phenoxy]phenyl}-1H-pyrrol-2-yl)-4,5-dihydro-1,3-thiazole (88 mg, 0.18 mmol) synthesized in Example (25c) was dissolved in dichloromethane (5 mL), and cooled to −78° C., a 1.0 mol/L boron tribromide dichloromethane solution (0.22 mL, 0.22 mmol) was added under nitrogen atmosphere. After the temperature was raised naturally and the solution was stirred at room temperature for 1 hour, subsequently a saturated aqueous sodium hydrogencarbonate solution was added to neutralize the reaction solution, followed by extraction with dichloromethane (60 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=40%-100%) to afford the desired product (46 mg, yield 54%) as a pale yellow solid.

$^1$H-NMR (CDCl$_3$, 500 MHz): δ 1.29 (3H, d, J=6.4 Hz), 3.27 (3H, s), 3.40 (2H, t, J=8.1 Hz), 3.76-3.78 (2H, m), 4.33 (2H, t, J=8.2 Hz), 4.55-4.59 (1H, m), 6.47 (1H, d, J=2.4 Hz), 6.49 (1H, d, J=3.7 Hz), 6.65 (1H, d, J=3.7 Hz), 6.82 (1H, s), 6.96 (1H, s), 7.11 (2H, d, J=8.7 Hz), 7.90 (2H, d, J=8.7 Hz).

MS (ESI) m/z: 473.12049 (M+H)$^+$.

Example 27

Methyl 2-(5-{3-[(1S)-2-methoxy-1-methylethoxy]-5-[4-(methylsulfonyl)phenoxy]phenyl}-1H-pyrrol-2-yl)-4,5-dihydro-1,3-oxazole-5-carboxylate

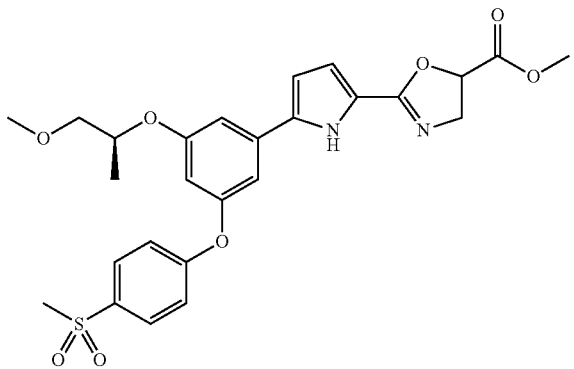

(27a) Methyl 2-hydroxy-3-{[(5-{3-[(1S)-2-methoxy-1-methylethoxy]-5-[4-(methylsulfonyl)phenoxy]phenyl}-1H-pyrrol-2-yl)carbonyl]amino}propanoate 5-{3-[(1S)-2-Methoxy-1-methylethoxy]-5-[4-(methylsulfonyl)phenoxy]phenyl}-1H-pyrrole-2-carboxylic acid (420 mg, 0.943 mmol) synthesized in Example (18a) was dissolved in dichloromethane (10 mL), and DL-isoserine methyl ester hydrochloride (300 mg, 1.93 mmol), WSCI•HCl (270 mg, 1.41 mmol) and 4-dimethylaminopyridine (230 mg, 1.88 mmol) were added, followed by stirring at room temperature for 1.5 hours under nitrogen atmosphere. 1N hydrochloric acid (10 mL) was added, and the solution was separated with dichloromethane (15 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=50%-80%) to afford the desired product (400 mg, yield 78%) as a white solid.

$^1$H-NMR (CDCl$_3$, 400 MHz): δ 1.32 (3H, d, J=6.3 Hz), 3.07 (3H, s), 3.41 (3H, s), 3.50 (1H, dd, J=3.9, 10.2 Hz), 3.60 (1H, dd, J=6.3, 10.2 Hz), 3.72-3.85 (2H, m), 3.80 (3H, s), 4.38 (1H, brt, J=4.7 Hz), 4.58 (1H, m), 6.43 (1H, brs), 6.47 (1H, m), 6.56 (1H, t, J=2.0 Hz), 6.63 (1H, dd, J=2.4, 3.9 Hz), 6.86 (1H, t, J=2.0 Hz), 7.01 (1H, t, J=2.0 Hz), 7.12 (2H, d, J=9.0 Hz), 7.90 (2H, d, J=9.0 Hz), 9.85 (1H, brs).

(27b) Methyl 2-(5-{3-[(1S)-2-methoxy-1-methylethoxy]-5-[4-(methylsulfonyl)phenoxy]phenyl}-1H-pyrrol-2-yl)-4,5-dihydro-1,3-oxazole-5-carboxylate Methyl 2-hydroxy-3-{[(5-{3-[(1S)-2-methoxy-1-methylethoxy]-5-[4-(methylsulfonyl)phenoxy]phenyl}-1H-pyrrol-2-yl)carbonyl]amino}propanoate (686 mg, 1.26 mmol) synthesized in Example (27a) was dissolved in tetrahydrofuran (15 mL), and methanesulfonic anhydride (330 mg, 1.89 mmol) and triethylamine (0.53 mL, 3.80 mmol) were added, followed by stirring at room temperature for 19 hours under nitrogen atmosphere. A saturated aqueous sodium hydrogencarbonate solution (10 mL) was added, and the solution was separated with ethyl acetate (20 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=30%-70%) to afford the desired product (586 mg, yield 88%) as a white solid.

$^1$H-NMR (CDCl$_3$, 400 MHz): δ 1.33 (3H, d, J=6.3 Hz), 3.07 (3H, s), 3.41 (3H, s), 3.50 (1H, dd, J=3.9, 10.2 Hz), 3.60 (1H, dd, J=6.3, 10.2 Hz), 4.10 (1H, dd, J=7.0, 14.5 Hz), 4.30 (1H, dd, J=10.6, 14.5 Hz), 4.56 (1H, m), 5.07 (1H, dd, J=7.0, 10.6 Hz), 6.52 (1H, d, J=3.9 Hz), 6.57 (1H, t, J=2.0 Hz), 6.83 (1H, t, J=2.0 Hz), 6.86 (1H, d, J=3.9 Hz), 7.00 (1H, t, J=2.0 Hz), 7.14 (2H, d, J=9.0 Hz), 7.90 (2H, d, J=9.0 Hz), 9.66 (1H, brs).

MS (ESI) m/z: 529.16412 (M+H)$^+$.

Example 28

2-(5-{3-[(1S)-2-Methoxy-1-methylethoxy]-5-[4-(methylsulfonyl)phenoxy]phenyl}-1H-pyrrol-2-yl)-N,N-dimethyl-4,5-dihydro-1,3-oxazole-5-carboxamide

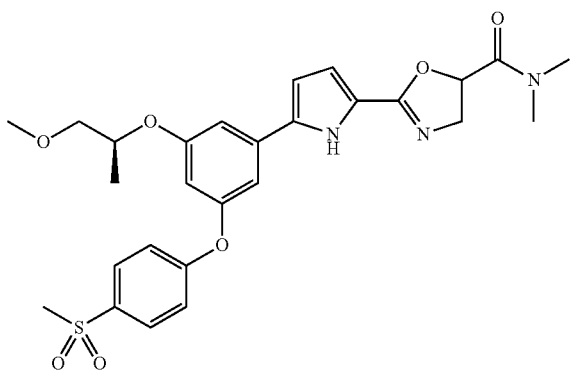

(28a) 2-(5-{3-[(1S)-2-Methoxy-1-methylethoxy]-5-[4-(methylsulfonyl)phenoxy]phenyl}-1H-pyrrol-2-yl)-4,5-dihydro-1,3-oxazole-5-carboxylic acid Methyl 2-(5-{3-[(1S)-2-methoxy-1-methylethoxy]-5-[4-(methylsulfonyl)phenoxy]phenyl}-1H-pyrrol-2-yl)-4,5-dihydro-1,3-oxazole-5-carboxylate (60.5 mg, 0.114 mmol) synthesized in Example (27b) was dissolved in ethanol (4 mL). An aqueous sodium hydroxide solution (5M, 2 mL) was added, and stirring was carried out at 70° C. for 2.5 hours. After cooling to room temperature, hydrochloric acid (2M, 5 mL) and ethyl acetate (10 mL) were added, and the solution was separated. The organic layer was washed with saturated brine, and subsequently dried over anhydrous magnesium sulfate. The solvent was distilled off under reduced pressure to afford the desired compound (69.3 mg, yield ~100%) as a pale yellow solid.

$^1$H-NMR (CDCl$_3$, 500 MHz): δ 1.34 (3H, d, J=6.3 Hz), 3.07 (3H, s), 3.42 (3H, s), 3.55-3.63 (2H, m), 4.28-4.44 (2H, m), 4.78 (1H, m), 5.49 (1H, brs), 6.60-6.68 (2H, m), 7.10 (1H, brs), 7.14 (2H, d, J=8.3 Hz), 7.26 (1H, m), 7.39 (1H, brd, J=8.3 Hz), 7.89 (2H, d, J=8.3 Hz), 13.10 (1H, brs).

MS (ESI) m/z: 515.14638 (M+H)$^+$.

(28b) 2-(5-{3-[(1S)-2-Methoxy-1-methylethoxy]-5-[4-(methylsulfonyl)phenoxy]phenyl}-1H-pyrrol-2-yl)-N,N-dimethyl-4,5-dihydro-1,3-oxazole-5-carboxamide 2-(5-{3-[(1S)-2-Methoxy-1-methylethoxy]-5-[4-(methylsulfonyl)phenoxy]phenyl}-1H-pyrrol-2-yl)-4,5-dihydro-1,3-oxazole-5-carboxylic acid (154 mg, 0.299 mmol) synthesized in Example (28a) was dissolved in dichloromethane (10 mL), and dimethylamine hydrochloride (75.0 mg, 0.920 mmol), WSCI•HCl (115 mg, 0.600 mmol) and 4-dimethylaminopyridine (110 mg, 0.900 mmol) were added, followed by stirring at room temperature for 2 days under nitrogen atmosphere. Water (10 mL) was added, and the solution was separated with dichloromethane (15 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=70%-100%) to afford the desired product (107 mg, yield 66%) as a white solid.

$^1$H-NMR (CDCl$_3$, 400 MHz): δ 1.33 (3H, d, J=6.3 Hz), 3.02 (3H, s), 3.07 (3H, s), 3.15 (3H, s), 3.42 (3H, s), 3.50 (1H, dd, J=3.9, 10.2 Hz), 3.60 (1H, dd, J=5.9, 10.2 Hz), 4.19 (1H, ddd, J=1.2, 10.2, 14.1 Hz), 4.33 (1H, brdd, J=7.8, 14.1 Hz), 4.57 (1H, m), 5.27 (1H, dd, J=7.8, 10.2 Hz), 6.50 (1H, d, J=3.9 Hz), 6.56 (1H, d, J=2.0 Hz), 6.78 (1H, d, J=3.9 Hz), 6.83 (1H, t, J=2.0 Hz), 7.01 (1H, d, J=2.0 Hz), 7.13 (2H, d, J=8.6 Hz), 7.90 (2H, d, J=8.9 Hz), 9.80 (1H, brs).

MS (ESI) m/z: 542.19865 (M+H)$^+$.

Example 29

[2-(5-{3-[(1S)-2-Methoxy-1-methylethoxy]-5-[4-(methylsulfonyl)phenoxy]phenyl}-1H-pyrrol-2-yl)-4,5-dihydro-1,3-oxazol-5-yl]methanol

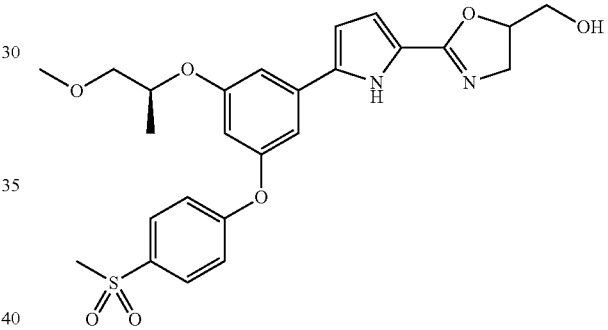

Lithium aluminum hydride (17.0 mg, 0.448 mmol) was suspended in tetrahydrofuran (2 mL). Methyl 2-(5-{3-[(1S)-2-methoxy-1-methylethoxy]-5-[4-(methylsulfonyl)phenoxy]phenyl}-1H-pyrrol-2-yl)-4,5-dihydro-1,3-oxazole-5-carboxylate (77.0 mg, 0.146 mmol) synthesized in Example (27b) was dissolved in tetrahydrofuran (2 mL), followed by dropwise addition at 0° C. under nitrogen atmosphere. After stirring at 0° C. for 30 minutes, water (17 μL) and an aqueous sodium hydroxide solution (5M, 68 μL) were added dropwise slowly and sequentially. After filtration through Celite, the solvent was distilled off under reduced pressure, and the resulting residue was purified using silica gel column chromatography (elution solvent: ethyl acetate/hexane=50%-100%) to afford the desired compound (54.1 mg, yield 74%) as a white solid.

$^1$H-NMR (CDCl$_3$, 500 MHz): δ 1.29-1.33 (3H, m), 3.06 (3H, s), 3.41 (3H, s), 3.49 (1H, m), 3.58 (1H, m), 3.63-3.76 (2H, m), 3.83 (1H, m), 3.97 (1H, m), 4.59 (1H, m), 4.76 (1H, m), 6.46 (1H, m), 6.54 (1H, brs), 6.72 (1H, m), 6.69 (1H, brs), 7.05 (1H, m), 7.13 (2H, d, J=8.8 Hz), 7.89 (2H, d, J=8.8 Hz).

MS (ESI) m/z: 501.17097 (M+H)$^+$.

Example 30

5-(Fluoromethyl)-2-(5-{3-[(1S)-2-methoxy-1-methylethoxy]-5-[4-(methylsulfonyl)phenoxy]phenyl}-1H-pyrrol-2-yl)-4,5-dihydro-1,3-oxazole

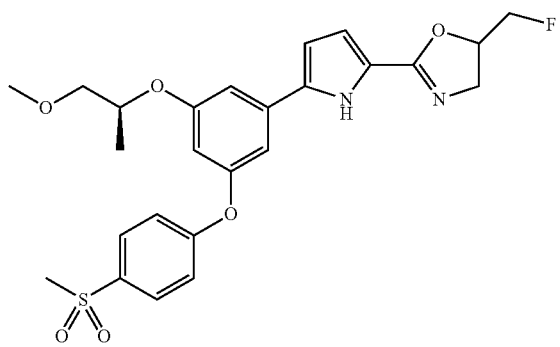

[2-(5-{3-[(1S)-2-Methoxy-1-methylethoxy]-5-[4-(methylsulfonyl)phenoxy]phenyl}-1H-pyrrol-2-yl)-4,5-dihydro-1,3-oxazol-5-yl]methanol (100 mg, 0.20 mmol) synthesized in Example 29 was dissolved in dichloromethane (5 mL), and bis(2-methoxyethyl)aminosulfur trifluoride (81 μL, 0.44 mmol) was added at 0° C. After stirring at room temperature for 6 hours, a saturated aqueous sodium hydrogencarbonate solution was added, and extraction was carried out with dichloromethane (60 mL). The organic layer was washed with saturated brine, and subsequently dried over sodium sulfate. The solvent was distilled off under reduced pressure, and the resulting residue was purified using silica gel column chromatography (elution solvent: ethyl acetate/hexane=80%-100%) to afford the desired product (61 mg, yield 61%) as a white solid.

$^1$H-NMR (CDCl$_3$, 500 MHz): δ 1.33 (3H, d, J=6.3 Hz), 3.07 (3H, s), 3.42 (3H, s), 3.51 (1H, dd, J=4.1, 10.3 Hz), 3.59 (1H, dd, J=6.3, 10.3 Hz), 3.82 (1H, dd, J=7.4, 14.5 Hz), 4.10 (1H, ddd, J=1.4, 10.1, 14.6 Hz), 4.49 (1H, ddd, J=5.5, 10.5, 37.9 Hz), 4.54-4.58 (1H, m), 4.62 (1H, ddd, J=3.0, 10.6, 33.3 Hz), 4.85-4.96 (1H, m), 6.51 (1H, d, J=3.9 Hz), 6.57 (1H, t, J=2.1 Hz), 6.80 (1H, d, J=3.6 Hz), 6.81 (1H, t, J=1.9 Hz), 6.98 (1H, t, J=1.8 Hz), 7.13 (2H, d, J=8.9 Hz), 7.91 (2H, d, J=8.9 Hz)

MS (ESI) m/z: 503.16398 (M+H)$^+$.

Example 31

(5S)-2-(5-{3-[(1S)-2-Methoxy-1-methylethoxy]-5-[4-(methylsulfonyl)phenoxy]phenyl}-1H-pyrrol-2-yl)-5-methyl-4,5-dihydro-1,3-oxazole

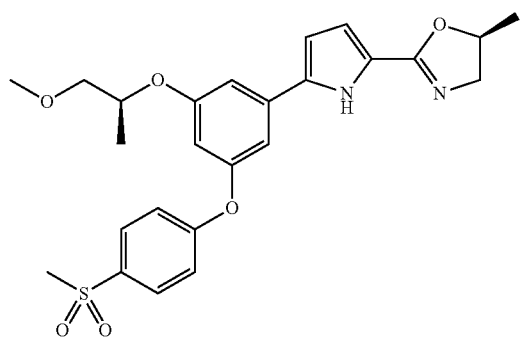

(31a) N-[(2R)-2-Hydroxypropyl]-5-{3-[(1S)-2-methoxy-1-methylethoxy]-5-[4-(methylsulfonyl)phenoxy]phenyl}-1H-pyrrole-2-carboxamide 5-{3-[(1S)-2-Methoxy-1-methylethoxy]-5-[4-(methylsulfonyl)phenoxy]phenyl}-1H-pyrrole-2-carboxylic acid (204 mg, 0.458 mmol) synthesized in Example (18a) was dissolved in dichloromethane (10 mL), and (R)-(−)-1-amino-2-propanol (72.0 μmL, 0.914 mmol), WSCI•HCl (130 mg, 0.678 mmol) and 4-dimethylaminopyridine (115 mg, 0.941 mmol) were added, followed by stirring at room temperature for 18 hours under nitrogen atmosphere. 1N hydrochloric acid (10 mL) was added, and the solution was separated with dichloromethane (15 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=60%-100%) to afford the desired product (191 mg, yield 83%) as a white solid.

$^1$H-NMR (CDCl$_3$, 400 MHz): δ 1.21 (3H, d, J=6.3 Hz), 1.31 (3H, d, J=6.3 Hz), 3.07 (3H, s), 3.24 (3H, s), 3.41 (3H, s), 3.51 (1H, dd, J=3.9, 10.2 Hz), 3.57 (1H, m), 3.59 (1H, dd, J=6.3, 10.2 Hz), 3.98 (1H, m), 4.56 (1H, m), 6.47 (1H, dd, J=2.7, 3.9 Hz), 6.50 (1H, brs), 6.55 (1H, t, J=2.0 Hz), 6.64 (1H, dd, J=2.4, 3.9 Hz), 6.87 (1H, t, J=2.0 Hz), 7.00 (1H, t, J=2.0 Hz), 7.12 (2H, d, J=9.0 Hz), 7.89 (2H, d, J=9.0 Hz), 10.09 (1H, brs).

(31b) (5S)-2-(5-{3-[(1S)-2-Methoxy-1-methylethoxy]-5-[4-(methylsulfonyl)phenoxy]phenyl}-1H-pyrrol-2-yl)-5-methyl-4,5-dihydro-1,3-oxazole N-[(2R)-2-Hydroxypropyl]-5-{3-[(1S)-2-methoxy-1-methylethoxy]-5-[4-(methylsulfonyl)phenoxy]phenyl}-1H-pyrrole-2-carboxamide (191 mg, 0.380 mmol) synthesized in Example (31a) was dissolved in tetrahydrofuran (10 mL), and anhydrous methanesulfonic acid (100 mg, 0.574 mmol) and triethylamine (0.16 mL, 1.15 mmol) were added, followed by stirring at room temperature for 18 hours under nitrogen atmosphere. A saturated aqueous sodium hydrogencarbonate solution (10 mL) was added, and the solution was separated with ethyl acetate (20 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=30%-70%) to afford the desired product (136 mg, yield 74%) as a white solid.

$^1$H-NMR (CDCl$_3$, 400 MHz): δ 1.33 (3H, d, J=6.3 Hz), 1.42 (3H, d, J=6.3 Hz), 3.07 (3H, s), 3.41 (3H, s), 3.50 (1H, dd, J=4.3, 10.2 Hz), 3.52 (1H, dd, J=7.4, 14.1 Hz), 3.59 (1H, dd, J=6.3, 10.2 Hz), 4.06 (1H, dd, J=9.4, 14.1 Hz), 4.57 (1H, m), 4.82 (1H, m), 6.50 (1H, d, J=3.9 Hz), 6.55 (1H, t, J=2.0 Hz), 6.75 (1H, d, J=3.9 Hz), 6.83 (1H, t, J=2.0 Hz), 7.00 (1H, t, J=2.0 Hz), 7.13 (2H, d, J=9.0 Hz), 7.90 (2H, d, J=9.0 Hz).

MS (ESI) m/z: 485.17394 (M+H)$^+$.

Example 32

(2S)-2-(3-{5-[(5S)-5-Methyl-4,5-dihydro-1,3-oxazol-2-yl]-1H-pyrrol-2-yl}-5-[4-(methylsulfonyl)phenoxy]phenoxy)propan-1-ol

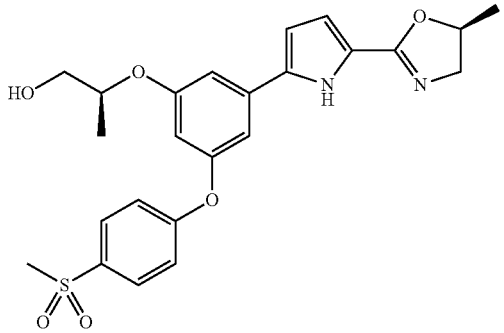

(5S)-2-(5-{3-[(1S)-2-Methoxy-1-methylethoxy]-5-[4-(methylsulfonyl)phenoxy]phenyl}-1H-pyrrol-2-yl)-5-methyl-4,5-dihydro-1,3-oxazole (280 mg, 0.58 mmol) synthesized in Example (31b) was dissolved in dichloromethane (10 mL) and cooled to −78° C., and a 1.0 mol/l boron tribromide dichloromethane solution (0.61 mL, 0.61 mmol) was added under nitrogen atmosphere. After the temperature was raised naturally and the solution was stirred at room temperature for 30 minutes, a saturated aqueous sodium hydrogencarbonate solution was added to neutralize the reaction solution, followed by extraction with dichloromethane (60 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate) to afford the desired product (222 mg, yield 82%) as a white solid.

$^1$H-NMR (CDCl$_3$, 500 MHz): δ 1.28 (3H, d, J=6.3 Hz), 1.43 (3H, d, J=6.3 Hz), 3.07 (3H, s), 3.55 (1H, dd, J=7.3, 13.9 Hz), 3.79 (2H, d, J=5.4 Hz), 4.09 (1H, dd, J=9.2, 14.0 Hz), 4.60-4.64 (1H, m), 4.81-4.87 (1H, m), 6.36 (1H, t, J=2.3 Hz), 6.46 (1H, d, J=3.9 Hz), 6.75 (1H, d, J=3.9 Hz), 6.91 (1H, t, J=1.9 Hz), 7.08 (2H, d, J=8.9 Hz), 7.88 (2H, d, J=8.9 Hz).

MS (ESI) m/z: 471.15892 (M+H)$^+$.

Example 33

(5R)-2-(5-{3-[(1S)-2-Methoxy-1-methylethoxy]-5-[4-(methylsulfonyl)phenoxy]phenyl}-1H-pyrrol-2-yl)-5-methyl-4,5-dihydro-1,3-oxazole

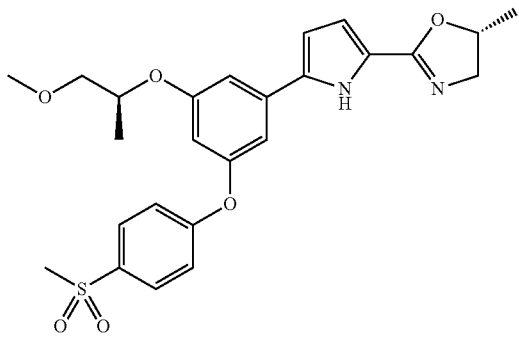

(33a) N-[(2S)-2-Hydroxypropyl]-5-{3-[(1S)-2-methoxy-1-methylethoxy]-5-[4-(methylsulfonyl)phenoxy]phenyl}-1H-pyrrole-2-carboxamide 5-{3-[(1S)-2-Methoxy-1-methylethoxy]-5-[4-(methylsulfonyl)phenoxy]phenyl}-1H-pyrrole-2-carboxylic acid (305 mg, 0.685 mmol) synthesized in Example (18a) was dissolved in dichloromethane (10 mL), and (S)-(+)-1-amino-2-propanol (110 μmL, 1.40 mmol), WSCI•HCl (200 mg, 1.04 mmol) and 4-dimethylaminopyridine (170 mg, 1.39 mmol) were added, followed by stirring at room temperature for 16 hours under nitrogen atmosphere. 1N hydrochloric acid (10 mL) was added, and the solution was separated with dichloromethane (15 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=60%-100%) to afford the desired product (285 mg, yield 83%) as a white solid.

$^1$H-NMR (CDCl$_3$, 400 MHz): δ 1.24 (3H, d, J=6.3 Hz), 1.33 (3H, d, J=6.3 Hz), 3.07 (3H, s), 3.28 (3H, s), 3.42 (3H, s), 3.51 (1H, dd, J=3.9, 10.2 Hz), 3.56-3.65 (2H, m), 4.01 (1H, m), 4.58 (1H, m), 6.35 (1H, brt, J=5.5 Hz), 6.49 (1H, dd, J=2.7, 3.9 Hz), 6.57 (1H, t, J=2.0 Hz), 6.62 (1H, dd, J=2.4, 3.9 Hz), 6.84 (1H, t, J=2.0 Hz), 7.00 (1H, t, J=2.0 Hz), 7.13 (2H, d, J=8.6 Hz), 7.90 (2H, d, J=8.6 Hz), 9.66 (1H, brs).

(33b) (5R)-2-(5-{3-[(1S)-2-Methoxy-1-methylethoxy]-5-[4-(methylsulfonyl)phenoxy]phenyl}-1H-pyrrol-2-yl)-5-methyl-4,5-dihydro-1,3-oxazole N-[(2S)-2-Hydroxypropyl]-5-{3-[(1S)-2-methoxy-1-methylethoxy]-5-[4-(methylsulfonyl)phenoxy]phenyl}-1H-pyrrole-2-carboxamide (285 mg, 0.567 mmol) synthesized in Example (33a) was dissolved in tetrahydrofuran (10 mL), and anhydrous methanesulfonic acid (130 mg, 0.746 mmol) and triethylamine (0.24 mL, 1.72 mmol) were added, followed by stirring at room temperature for 21 hours under nitrogen atmosphere. A saturated aqueous sodium hydrogencarbonate solution (10 mL) was added, and the solution was separated with ethyl acetate (20 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=30%-70%) to afford the desired product (155 mg, yield 56%) as a white solid.

$^1$H-NMR (CDCl$_3$, 400 MHz): δ 1.31 (3H, d, J=6.3 Hz), 1.41 (3H, d, J=6.3 Hz), 3.06 (3H, s), 3.40 (3H, s), 3.50 (1H, dd, J=3.9, 10.2 Hz), 3.51 (1H, dd, J=8.2, 14.1 Hz), 3.58 (1H, dd, J=5.9, 10.2 Hz), 4.04 (1H, dd, J=9.4, 14.1 Hz), 4.56 (1H, m), 4.80 (1H, m), 6.50 (1H, d, J=3.9 Hz), 6.55 (1H, t, J=2.0 Hz), 6.74 (1H, d, J=3.9 Hz), 6.84 (1H, t, J=2.0 Hz), 7.00 (1H, t, J=2.0 Hz), 7.12 (2H, d, J=9.0 Hz), 7.89 (2H, d, J=9.0 Hz).

MS (ESI) m/z: 485.17398 (M+H)$^+$.

Example 34

(5R)-2-(5-{3-[(1S)-2-Methoxy-1-methylethoxy]-5-[4-(methylsulfonyl)phenoxy]phenyl}-1H-pyrrol-2-yl)-5-(trifluoromethyl)-4,5-dihydro-1,3-oxazole

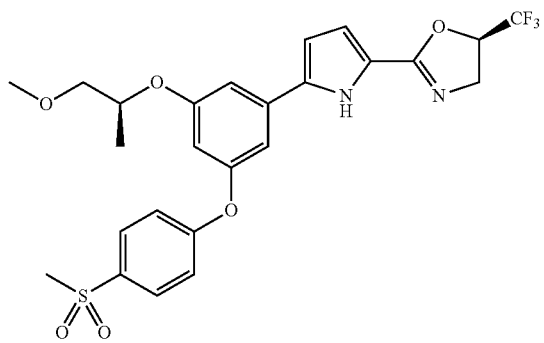

(34a) 5-{3-[(1S)-2-Methoxy-1-methylethoxy]-5-[4-(methylsulfonyl)phenoxy]phenyl}-N-[(2S)-3,3,3-trifluoro-2-hydroxypropyl]-1H-pyrrole-2-carboxamide 5-{3-[(1S)-2-Methoxy-1-methylethoxy]-5-[4-(methylsulfonyl)phenoxy]phenyl}-1H-pyrrole-2-carboxylic acid (408 mg, 0.94 mmol) synthesized in Example (18a), (2S)-3-amino-1,1,1-trifluoro-2-propanol (177 mg, 1.37 mmol) and 4-dimethylaminopyridine (224 mg, 1.87 mmol) were dissolved in dichloromethane (20 mL), and WSCI•HCl (193 mg, 1.01 mmol) was added at room temperature, followed by stirring for 2 hours under nitrogen atmosphere. The reaction solution was diluted with dichloromethane (200 mL), washed with 1N hydrochloric acid, a saturated aqueous sodium hydrogencarbonate solution and saturated brine, and subsequently dried over anhydrous magnesium sulfate. The solvent was distilled off under reduced pressure, and the resulting residue was purified using silica gel column chromatography (elution solvent: ethyl acetate/hexane=50%-70%) to afford the desired product (339 mg, yield 67%) as a white amorphous substance.

$^1$H-NMR (CDCl$_3$, 500 MHz): δ 1.31 (3H, d, J=6.3 Hz), 3.08 (3H, s), 3.42 (3H, s), 3.52 (1H, dd, J=3.9, 10.3 Hz), 3.60 (1H, dd, J=6.2, 10.2 Hz), 3.58-3.65 (1H, m), 3.85 (1H, ddd, J=2.7, 6.6, 14.9 Hz), 4.08-4.15 (1H, brm), 4.53-4.60 (1H, m), 4.74 (1H, d, J=5.5 Hz), 6.37 (1H, t, J=6.1 Hz), 6.50 (1H, dd, J=3.0, 4.0 Hz), 6.58 (1H, t, J=2.2 Hz), 6.67 (1H, dd, J=2.7, 4.0 Hz), 6.84 (1H, t, J=1.7 Hz), 6.99 (1H, t, J=2.0 Hz), 7.13 (2H, d, J=8.9 Hz), 7.91 (2H, d, J=8.9 Hz), 9.82 (1H, brs).

(34b) (5R)-2-(5-{3-[(1S)-2-Methoxy-1-methylethoxy]-5-[4-(methylsulfonyl)phenoxy]phenyl}-1H-pyrrol-2-yl)-5-(trifluoromethyl)-4,5-dihydro-1,3-oxazole 5-{3-[(1S)-2-Methoxy-1-methylethoxy]-5-[4-(methylsulfonyl)phenoxy]phenyl}-N-[(2S)-3,3,3-trifluoro-2-hydroxypropyl]-1H-pyrrole-2-carboxamide (339 mg, 0.61 mmol) synthesized in Example (34a) was dissolved in tetrahydrofuran (10 mL), and triethylamine (0.51 mL, 3.66 mmol) and anhydrous methanesulfonic acid (296 mg, 1.71 mmol) were added at 0° C., followed by heating at 120° C. for 30 hours. To the reaction solution, a saturated aqueous sodium hydrogencarbonate solution was added, and extraction was carried out with ethyl acetate (60 mL). After washing with saturated brine, drying was carried out over anhydrous magnesium sulfate. The solvent was distilled off under reduced pressure, and the resulting residue was purified using silica gel column chromatography (elution solvent: ethyl acetate/hexane=30%-50%) to afford the desired product (328 mg, yield 84%) as a white solid.

$^1$H-NMR (CDCl$_3$, 500 MHz): δ 1.33 (3H, d, J=6.3 Hz), 3.08 (3H, s), 3.42 (3H, s), 3.51 (1H, dd, J=3.9, 10.4 Hz), 3.59 (1H, dd, J=6.3, 10.1 Hz), 4.15 (1H, dd, J=6.5, 15.4 Hz), 4.22 (1H, dd, 10.0, 15.4 Hz), 4.55-4.59 (1H, m), 4.88-4.92 (1H, m), 6.52 (1H, dd, J=2.4, 4.0 Hz), 6.58 (1H, t, J=2.2 Hz), 6.82 (1H, t, J=1.8 Hz), 6.84 (1H, dd, J=2.3, 3.9 Hz), 6.98 (1H, t, J=2.0 Hz), 7.13 (2H, d, J=8.8 Hz), 7.91 (2H, d, J=8.8 Hz), 9.25 (1H, brs).

MS (ESI) m/z: 539.14603 (M+H)$^+$.

Example 35

[(5R)-2-(5-{3-[(1S)-2-Methoxy-1-methylethoxy]-5-[4-(methylsulfonyl)phenoxy]phenyl}-1H-pyrrol-2-yl)-4,5-dihydro-1,3-oxazol-5-yl]methanol

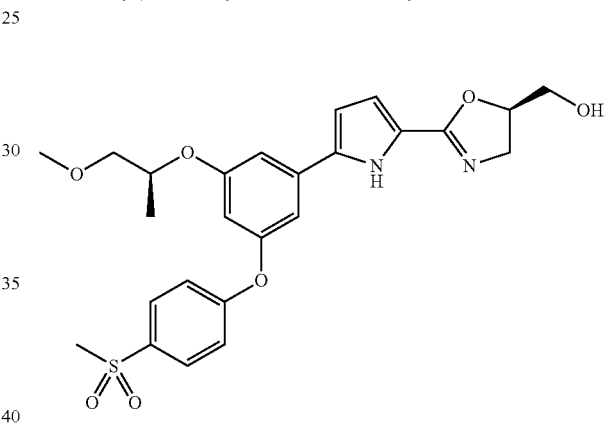

(35a) N-[(2S)-2,3-Dihydroxypropyl]-5-{3-[(1S)-2-methoxy-1-methylethoxy]-5-[4-(methylsulfonyl)phenoxy]phenyl}-1H-pyrrole-2-carboxamide 5-{3-[(1S)-2-Methoxy-1-methylethoxy]-5-[4-(methylsulfonyl)phenoxy]phenyl}-1H-pyrrole-2-carboxylic acid (338 mg, 0.759 mmol) synthesized in Example (18a) was dissolved in dichloromethane (10 mL), and (S)-(−)-3-amino-1,2-propanediol (105 mg, 1.15 mmol), WSCI•HCl (220 mg, 1.15 mmol) and 4-dimethylaminopyridine (185 mg, 1.51 mmol) were added, followed by stirring at room temperature for 3 days under nitrogen atmosphere. 1N hydrochloric acid (10 mL) was added, and the solution was separated with dichloromethane (15 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=70%-100%) to afford the desired product (265 mg, yield 68%) as a white solid.

$^1$H-NMR (CDCl$_3$, 400 MHz): δ 1.33 (3H, d, J=6.3 Hz), 3.07 (3H, s), 3.42 (3H, s), 3.51 (1H, dd, J=3.9, 10.2 Hz), 3.553-3.64 (4H, m), 3.85 (1H, m), 4.57 (1H, m), 6.38 (1H, m), 6.50 (1H, dd, J=2.7, 3.9 Hz), 6.58 (1H, t, J=2.0 Hz), 6.64 (1H, dd, J=2.4, 3.9 Hz), 6.84 (1H, t, J=2.0 Hz), 7.00 (1H, t, J=2.0 Hz), 7.13 (2H, d, J=9.0 Hz), 7.91 (2H, d, J=9.0 Hz), 9.59 (1H, brs).

(35b) N-{(2S)-2-Hydroxy-3-[(triisopropylsilyl)oxy] propyl}-5-{3-[(1S)-2-methoxy-1-methylethoxy]-5-[4-(methylsulfonyl)phenoxy]phenyl}-1H-pyrrole-2-carboxamide N-[(2S)-2,3-Dihydroxypropyl]-5-{3-[(1S)-2-methoxy-1-methylethoxy]-5-[4-(methylsulfonyl)phenoxy]phenyl}-1H-pyrrole-2-carboxamide (265 mg, 0.514 mmol) synthesized in Example (35a) was dissolved in dichloromethane (10 mL), and triisopropylsilyl chloride (0.12 mL, 0.691 mmol), triethylamine (0.21 mL, 1.51 mmol) and 4-dimethylaminopyridine (6.0 mg, 0.049 mmol) were added, followed by stirring at room temperature for 24 hours under nitrogen atmosphere. Water (10 mL) was added, and the solution was separated with dichloromethane (20 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=20%-50%) to afford the desired product (177 mg, yield 51%) as a white solid.
$^1$H-NMR (CDCl$_3$, 400 MHz): δ 1.04-1.13 (21H, m), 1.32 (3H, d, J=6.3 Hz), 3.07 (3H, s), 3.21 (1H, d, J=4.3 Hz), 3.38 (1H, m), 3.42 (3H, s), 3.51 (1H, dd, J=3.9, 10.2 Hz), 3.60 (1H, dd, J=6.3, 10.2 Hz), 3.67 (1H, dd, J=6.3, 9.8 Hz), 3.73 (1H, m), 3.76 (1H, dd, J=5.0, 9.8 Hz), 3.86 (1H, m), 4.58 (1H, m), 6.43 (1H, brt, J=5.9 Hz), 6.48 (1H, dd, J=2.8, 3.9 Hz), 6.56 (1H, t, J=2.0 Hz), 6.61 (1H, dd, J=2.4, 3.9 Hz), 6.85 (1H, t, J=2.0 Hz), 7.00 (1H, t, J=2.0 Hz), 7.13 (2H, d, J=8.6 Hz), 7.90 (2H, d, J=8.6 Hz), 9.80 (1H, brs).

(35c) (5S)-2-(5-{3-[(1S)-2-Methoxy-1-methylethoxy]-5-[4-(methylsulfonyl)phenoxy]phenyl}-1H-pyrrol-2-yl)-5-{[(triisopropylsilyl)oxy]methyl}-4,5-dihydro-1,3-oxazole N-{(2S)-2-Hydroxy-3-[(triisopropylsilyl)oxy]propyl}-5-{3-[(1S)-2-methoxy-1-methylethoxy]-5-[4-(methylsulfonyl)phenoxy]phenyl}-1H-pyrrole-2-carboxamide (177 mg, 0.262 mmol) synthesized in Example (35b) was dissolved in tetrahydrofuran (10 mL), and anhydrous methanesulfonic acid (70.0 mg, 0.402 mmol) and triethylamine (0.22 mL, 1.58 mmol) were added, followed by stirring at 70° C. for 3 days under nitrogen atmosphere. A saturated aqueous sodium hydrogencarbonate solution (10 mL) was added, and the solution was separated with ethyl acetate (20 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=30%-60%) to afford the desired product (180 mg, yield ~100%) as a yellow oil.
$^1$H-NMR (CDCl$_3$, 400 MHz): δ 1.02-1.10 (21H, m), 1.33 (3H, d, J=6.3 Hz), 3.07 (3H, s), 3.41 (3H, s), 3.50 (1H, dd, J=4.3, 10.2 Hz), 3.59 (1H, dd, J=6.3, 10.2 Hz), 3.82-3.90 (3H, m), 4.00 (1H, dd, J=9.8, 14.1 Hz), 4.58 (1H, m), 4.75 (1H, m), 6.49 (1H, d, J=3.9 Hz), 6.55 (1H, t, J=2.0 Hz), 6.73 (1H, d, J=3.9 Hz), 6.83 (1H, t, J=2.0 Hz), 7.00 (1H, t, J=2.0 Hz), 7.13 (2H, d, J=9.0 Hz), 7.90 (2H, d, J=9.0 Hz), 9.59 (1H, brs).

(35d) [(5R)-2-(5-{3-[(1S)-2-Methoxy-1-methylethoxy]-5-[4-(methylsulfonyl)phenoxy]phenyl}-1H-pyrrol-2-yl)-4,5-dihydro-1,3-oxazol-5-yl]methanol (5S)-2-(5-{3-[(1S)-2-Methoxy-1-methylethoxy]-5-[4-(methylsulfonyl)phenoxy]phenyl}-1H-pyrrol-2-yl)-5-{[(triisopropylsilyl)oxy]methyl}-4,5-dihydro-1,3-oxazole (180 mg, 0.262 mmol) synthesized in Example (35c) was dissolved in tetrahydrofuran (10 mL), and tetrabutylammonium fluoride (1M tetrahydrofuran solution, 0.53 mL, 0.53 mmol) was added, followed by stirring at room temperature for 30 minutes under nitrogen atmosphere. Water (10 mL) was added, and extraction was carried out with ethyl acetate (20 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=60%-100%) to afford the desired compound (103 mg, yield 79%) as a white solid.
$^1$H-NMR (CDCl$_3$, 400 MHz): δ 1.27 (3H, d, J=6.3 Hz), 3.07 (3H, s), 3.42 (3H, s), 3.49 (1H, dd, J=3.9, 10.2 Hz), 3.58 (1H, dd, J=6.3, 10.2 Hz), 3.67 (1H, dd, J=5.1, 12.5 Hz), 3.74 (1H, dd, J=7.4, 14.5 Hz), 3.84 (1H, dd, J=3.1, 12.5 Hz), 4.00 (1H, dd, J=9.8, 14.5 Hz), 4.54 (1H, m), 4.78 (1H, m), 6.46 (1H, d, J=3.9 Hz), 6.55 (1H, t, J=2.0 Hz), 6.71 (1H, d, J=3.9 Hz), 6.85 (1H, t, J=2.0 Hz), 6.98 (1H, t, J=2.0 Hz), 7.14 (2H, d, J=8.6 Hz), 7.90 (2H, d, J=9.0 Hz), 9.59 (1H, brs).
MS (ESI) m/z: 501.16898 (M+H)$^+$.

Example 36

2-(5-{3-[(1S)-2-Methoxy-1-methylethoxy]-5-[4-(methylsulfonyl)phenoxy]phenyl}-1H-pyrrol-2-yl)-5,5-dimethyl-4,5-dihydro-1,3-oxazole

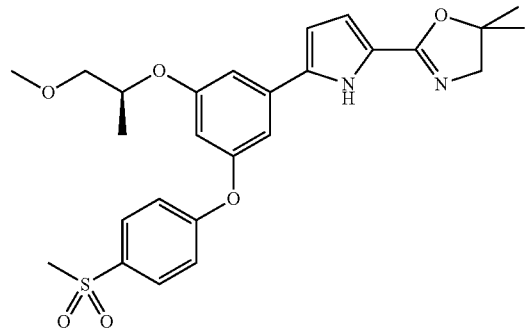

(36a) N-(2-Hydroxy-2-methylpropyl)-5-{3-[(1S)-2-methoxy-1-methylethoxy]-5-[4-(methylsulfonyl)phenoxy]phenyl}-1H-pyrrole-2-carboxamide 5-{3-[(1S)-2-Methoxy-1-methylethoxy]-5-[4-(methylsulfonyl)phenoxy]phenyl}-1H-pyrrole-2-carboxylic acid (300 mg, 0.673 mmol) synthesized in Example (18a) was dissolved in dichloromethane (10 mL), and 1-amino-2-methyl-2-propanol (150 mg, 1.68 mmol), WSCI•HCl (185 mg, 0.965 mmol) and 4-dimethylaminopyridine (165 mg, 1.35 mmol) were added, followed by stirring at room temperature for 17 hours under nitrogen atmosphere. 1N hydrochloric acid (10 mL) was added, and the solution was separated with dichloromethane (15 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=60%-100%) to afford the desired product (307 mg, yield 88%) as a white solid.

$^1$H-NMR (CDCl$_3$, 400 MHz): δ 1.26 (6H, s), 1.32 (3H, d, J=6.3 Hz), 3.07 (3H, s), 3.41 (3H, s), 3.41 (2H, m), 3.51 (1H, dd, J=3.9, 10.2 Hz), 3.59 (1H, dd, J=6.3, 10.2 Hz), 4.58 (1H, m), 4.46 (1H, brs), 6.48 (1H, dd, J=2.7, 3.9 Hz), 6.56 (1H, t, J=2.0 Hz), 6.65 (1H, dd, J=2.4, 3.9 Hz), 6.86 (1H, t, J=2.0 Hz), 7.00 (1H, t, J=2.0 Hz), 7.12 (2H, d, J=9.0 Hz), 7.90 (2H, d, J=9.0 Hz), 9.86 (1H, brs).

(36b) 2-(5-{3-[(1S)-2-Methoxy-1-methylethoxy]-5-[4-(methylsulfonyl)phenoxy]phenyl}-1H-pyrrol-2-yl)-5,5-dimethyl-4,5-dihydro-1,3-oxazole N-(2-Hydroxy-2-methylpropyl)-5-{3-[(1S)-2-methoxy-1-methylethoxy]-5-[4-(methylsulfonyl)phenoxy]phenyl}-1H-pyrrole-2-carboxamide (307 mg, 0.594 mmol) synthesized in Example (36a) was dissolved in tetrahydrofuran (10 mL), and anhydrous methanesulfonic acid (160 mg, 0.918 mmol) and triethylamine (0.25 mL, 1.79 mmol) were added, followed by stirring at room temperature for 4 days under nitrogen atmosphere. A saturated aqueous sodium hydrogencarbonate solution (10 mL) was added, and the solution was separated with ethyl acetate (20 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=30%-70%) to afford the desired product (187 mg, yield 63%) as a white solid.

$^1$H-NMR (CDCl$_3$, 400 MHz): δ 1.33 (3H, d, J=6.3 Hz), 1.47 (6H, s), 3.07 (3H, s), 3.41 (3H, s), 3.50 (1H, dd, J=3.9, 10.2 Hz), 3.59 (1H, dd, J=6.3, 10.2 Hz), 3.69 (1H, s), 4.57 (1H, m), 6.50 (1H, d, J=3.9 Hz), 6.55 (1H, t, J=2.0 Hz), 6.74 (1H, d, J=3.9 Hz), 6.83 (1H, t, J=2.0 Hz), 7.00 (1H, t, J=2.0 Hz), 7.13 (2H, d, J=9.0 Hz), 7.90 (2H, d, J=9.0 Hz).

MS (ESI) m/z: 499.18990 (M+H)$^+$.

Example 37

2-(5-{3-[(1S)-2-Methoxy-1-methylethoxy]-5-[4-(methylsulfonyl)phenoxy]phenyl}-1H-pyrrol-2-yl)-5,6-dihydro-4H-1,3-oxazine

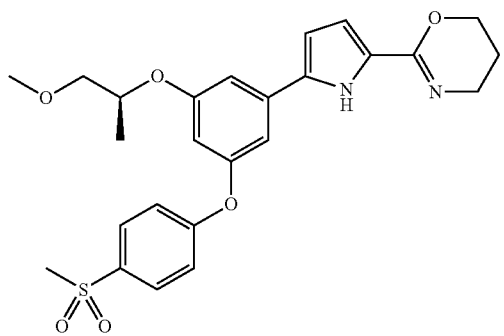

(37a) N-(3-Hydroxypropyl)-5-{3-[(1S)-2-methoxy-1-methylethoxy]-5-[4-(methylsulfonyl)phenoxy]phenyl}-1H-pyrrole-2-carboxamide 5-{3-[(1S)-2-Methoxy-1-methylethoxy]-5-[4-(methylsulfonyl)phenoxy]phenyl}-1H-pyrrole-2-carboxylic acid (250 mg, 0.561 mmol) synthesized in Example (18a) was dissolved in dichloromethane (10 mL), and 3-amino-1-propanol (90.04, 1.18 mmol), WSCI·HCl (165 mg, 0.861 mmol) and 4-dimethylaminopyridine (140 mg, 1.15 mmol) were added, followed by stirring at room temperature for 16 hours under nitrogen atmosphere. 1N hydrochloric acid (10 mL) was added, and the solution was separated with dichloromethane (15 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=60%-100%) to afford the desired product (216 mg, yield 77%) as a white solid.

$^1$H-NMR (CDCl$_3$, 400 MHz): δ 1.33 (3H, d, J=6.3 Hz), 1.78 (2H, m), 3.07 (3H, s), 3.42 (3H, s), 3.51 (1H, dd, J=3.9, 10.2 Hz), 3.56-3.62 (3H, m), 3.71 (2H, m), 4.58 (1H, m), 6.32 (1H, brs), 6.49 (1H, dd, J=2.7, 3.9 Hz), 6.56-6.60 (2H, m), 6.84 (1H, t, J=2.0 Hz), 6.99 (1H, t, J=2.0 Hz), 7.13 (2H, d, J=9.0 Hz), 7.91 (2H, d, J=9.0 Hz), 9.63 (1H, brs).

(37b) 2-(5-{3-[(1S)-2-Methoxy-1-methylethoxy]-5-[4-(methylsulfonyl)phenoxy]phenyl}-1H-pyrrol-2-yl)-5,6-dihydro-4H-1,3-oxazine N-(3-Hydroxypropyl)-5-{3-[(1S)-2-methoxy-1-methylethoxy]-5-[4-(methylsulfonyl)phenoxy]phenyl}-1H-pyrrole-2-carboxamide (216 mg, 0.430 mmol) synthesized in Example (37a) was dissolved in tetrahydrofuran (10 mL), and anhydrous methanesulfonic acid (115 mg, 0.660 mmol) and triethylamine (0.18 mL, 1.29 mmol) were added, followed by stirring at room temperature for 4 days, further at 80° C. for 17 hours, under nitrogen atmosphere. A saturated aqueous sodium hydrogencarbonate solution (10 mL) was added, and the solution was separated with ethyl acetate (20 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=50%-90%) to afford the desired product (150 mg, yield 72%) as a pale brownish solid.

$^1$H-NMR (CDCl$_3$, 400 MHz): δ 1.32 (3H, d, J=6.3 Hz), 1.98 (2H, m), 3.06 (3H, s), 3.41 (3H, s), 3.48-3.54 (3H, m), 3.59 (1H, dd, J=6.3, 10.2 Hz), 4.32 (2H, brt, J=5.5 Hz), 4.56 (1H, m), 6.46 (1H, d, J=3.9 Hz), 6.53 (1H, t, J=2.0 Hz), 6.62 (1H, d, J=3.9 Hz), 6.82 (1H, t, J=2.0 Hz), 6.99 (1H, t, J=2.0 Hz), 7.12 (2H, d, J=9.0 Hz), 7.89 (2H, d, J=9.0 Hz).

MS (ESI) m/z: 485.17572 (M+H)$^+$.

Example 38

Methyl 4-{3-[(1S)-2-methoxy-1-methylethoxy]-5-[5-(1,3-thiazol-2-yl)-1H-pyrrol-2-yl]phenoxy}benzoate

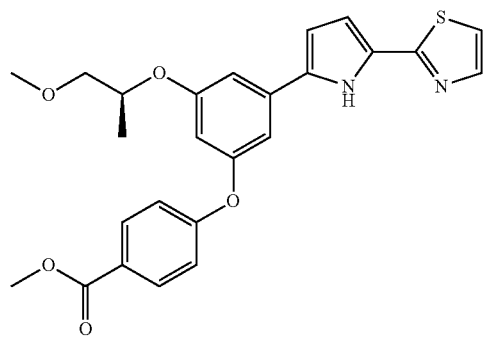

(38a) 1-Bromo-3-methoxy-5-[(1S)-2-methoxy-1-methylethoxy]benzene

3-Bromo-5-methoxyphenol (7.60 g, 37.4 mmol) synthesized in Example (1a) was dissolved in toluene (100 mL), and R-(−)-1-methoxy-2-propanol (4.40 mL, 44.9 mmol) and triphenylphosphine (13.8 g, 52.6 mmol) were added, followed by dropwise addition of diethyl azodicarboxylate (2.2 mol/l toluene solution, 24 mL, 52.8 mmol) at 0° C. and stirring at room temperature for 1.5 hours under nitrogen atmosphere. The solvent was distilled off under reduced pressure, diethyl ether (100 mL) was added, and the deposit was filtered to be removed. The mother liquor was distilled off under reduced pressure, and the resulting residue was purified using silica gel column chromatography (elution solvent: ethyl acetate/hexane=10%-20%) to afford the desired compound (9.22 g, yield 89%) as a colorless liquid.

$^1$H-NMR (CDCl$_3$, 400 MHz): δ 1.30 (3H, d, J=6.3 Hz), 3.40 (3H, s), 3.47 (1H, dd, J=10.6, 4.3 Hz), 3.55 (1H, dd, J=10.4, 6.1 Hz), 3.76 (3H, s), 4.46-4.52 (1H, m), 6.42 (1H, t, J=2.2 Hz), 6.65 (1H, dd, J=2.3, 1.6 Hz), 6.69 (1H, t, J=2.0 Hz).

MS (EI) m/z: 274 (M)$^+$.

(38b) 3-Bromo-5-[(1S)-2-methoxy-1-methylethoxy]phenol

1-Bromo-3-methoxy-5-[(1S)-2-methoxy-1-methylethoxy]benzene (9.21 g, 33.5 mmol) synthesized in Example (38a) was dissolved in 1-methyl-2-pyrrolidone (100 mL), and sodium thiomethoxide (2.75 g, 37.3 mmol) was added, followed by stirring at 130° C. for 3 for hours under nitrogen atmosphere. The reaction solution was cooled to room temperature, 2N hydrochloric acid (500 mL) was added, and extraction was carried out with diethyl ether (300 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=20%-25%) to afford the desired compound (8.30 g, yield 95%) as a colorless liquid.

$^1$H-NMR (CDCl$_3$, 400 MHz): δ 1.29 (3H, d, J=6.3 Hz), 3.41 (3H, s), 3.46 (1H, dd, J=10.2, 4.3 Hz), 3.55 (1H, dd, J=10.6, 5.9 Hz), 4.45-4.51 (1H, m), 4.96 (1H, br s), 6.36 (1H, t, J=2.0 Hz), 6.59 (1H, t, J=2.0 Hz), 6.68 (1H, t, J=2.0 Hz).

MS (EI) m/z: 260 (M)$^+$.

(38c) 3-[(1S)-2-Methoxy-1-methylethoxy]-5-(4,4,5,5-tetramethyl-1,3,2-dioxaborolan-2-yl)phenol 3-Bromo-5-[(1S)-2-methoxy-1-methylethoxy]phenol (8.30 g, 31.8 mmol) synthesized in Example (38b) was dissolved in N,N-dimethylformamide (100 mL), and bis(pinacolato)diboron (10.50 g, 41.3 mmol), [1,1'-bis(diphenylphosphino)ferrocene]palladium (II) dichloride dichloromethane complex (810 mg, 0.992 mmol) and potassium acetate (15.50 g, 158 mmol) were added, followed by stirring at 90° C. for 3 hours under nitrogen atmosphere. After the reaction solution was cooled to room temperature, water (500 mL) was added, and extraction was carried out with diethyl ether (300 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=20%-30%) to afford the desired compound (8.75 g, yield 89%) as a brownish oil.

$^1$H-NMR (CDCl$_3$, 400 MHz): δ 1.26 (3H, d, J=4.1 Hz), 1.33 (12H, s), 3.41 (1H, s), 3.47 (1H, dd, J=10.2, 4.7 Hz), 3.57 (1H, dd, J=10.6, 5.9 Hz), 4.52-4.58 (1H, m), 4.80 (1H, brs), 6.55 (1H, t, J=2.4 Hz), 6.83 (1H, d, J=2.4 Hz), 6.95 (1H, d, J=2.4 Hz).

MS (FAB) m/z: 309 (M+H)$^+$.

(38d) t-Butyl 2-{3-hydroxy-5-[(1S)-2-methoxy-1-methylethoxy]phenyl}-5-(1,3-thiazol-2-yl)-1H-pyrrole-1-carboxylate 3-[(1S)-2-Methoxy-1-methylethoxy]-5-(4,4,5,5-tetramethyl-1,3,2-dioxaborolan-2-yl)phenol (3.30 g, 10.7 mmol) synthesized in Example (38c) and t-butyl 2-bromo-5-(1,3-thiazol-2-yl)-1H-pyrrole-1-carboxylate (4.10 g, 12.5 mmol) synthesized in Example (1g) were dissolved in a mixed solvent of 1,4-dioxane (100 mL) and water (25 mL), and [1,1'-bis(diphenylphosphino)ferrocene]palladium (II) dichloride dichloromethane complex (400 mg, 0.490 mmol) and potassium carbonate (7.20 g, 52.1 mmol) were added, followed by stirring at 50° C. for 4 hours under nitrogen atmosphere. After the reaction solution was cooled to room temperature, water (200 mL) was added, and extraction was carried out with ethyl acetate (400 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=25%-40%) to afford the desired compound (3.72 g, yield 81%) as a pale yellow oil.

$^1$H-NMR (CDCl$_3$, 400 MHz): δ 1.24-1.29 (12H, m), 3.40 (3H, s), 3.47 (1H, dd, J=4.4, 10.3 Hz), 3.57 (1H, dd, J=5.9, 10.3 Hz), 4.48-4.54 (1H, m), 5.74 (1H, brs), 6.19 (1H, brs), 6.39-6.44 (2H, brs), 6.55 (1H, brs), 6.60 (1H, d, J=3.9 Hz), 7.31 (1H, d, J=3.0 Hz), 7.81 (1H, d, J=3.4 Hz).

(38e) t-Butyl 2-{3-[4-(methoxycarbonyl)phenoxy]-5-[(1S)-2-methoxy-1-methylethoxy]phenyl}-5-(1,3-thiazol-2-yl)-1H-pyrrole-1-carboxylate t-Butyl 2-{3-hydroxy-5-[(1S)-2-methoxy-1-methylethoxy]phenyl}-5-(1,3-thiazol-2-yl)-1H-pyrrole-1-carboxylate (117 mg, 0.272 mmol) synthesized in Example (38d) was dissolved in dichloromethane (20 mL), and 4-methoxycarbonylphenyl boronic acid (100 mg, 0.556 mmol), copper (II) acetate (80 mg, 0.440 mmol), triethylamine (0.20 mL, 1.435 mmol) and molecular sieves 4A (100 mg) were added, followed by stirring at room temperature for 3 days under nitrogen atmosphere. The deposit of this reaction solution was Celite filtered. This mother liquor was distilled off under reduced pressure, and the resulting residue was purified using silica gel column chromatography (elution solvent: ethyl acetate/hexane=15%-25%) to afford the desired compound (70 mg, yield 46%) as a yellow oil.

$^1$H-NMR (CDCl$_3$, 400 MHz): δ 1.31 (12H, m), 3.40 (3H, s), 3.48 (1H, dd, J=10.2, 4.3 Hz), 3.57 (1H, dd, J=10.2, 5.9 Hz), 3.90 (3H, s), 4.48-4.58 (1H, m), 6.25 (1H, d, J=3.5 Hz), 6.58 (1H, d, J=3.5 Hz), 6.63 (1H, t, J=2.4 Hz), 6.70 (1H, dd, J=2.4, 1.2 Hz), 6.84 (1H, dd, J=2.4, 1.6 Hz), 7.04 (2H, d, J=9.0 Hz), 7.33 (1H, d, J=3.1 Hz), 7.80 (1H, d, J=3.5 Hz), 8.00 (2H, d, J=9.0 Hz).

(38f) Methyl 4-{3-[(1S)-2-methoxy-1-methylethoxy]-5-[5-(1,3-thiazol-2-yl)-1H-pyrrol-2-yl]phenoxy}benzoate t-Butyl 2-{3-[4-(methoxycarbonyl)phenoxy]-5-[(1S)-2-methoxy-1-methylethoxy]phenyl}-5-(1,3-thiazol-2-yl)-1H-pyrrole-1-carboxylate (70 mg, 0.124 mmol) synthesized in Example (38e) was dissolved in dichloromethane (1.0 mL).

Trifluoroacetic acid (2.0 mL) was added dropwise with stirring under nitrogen atmosphere, and stirring was carried out at room temperature for 2 hours. The solvent was distilled off under reduced pressure, followed by dilution with ethyl acetate (30 mL), a saturated aqueous sodium hydrogencarbonate solution (20 mL) was added, and the solution was separated. The organic layer was washed with saturated brine, and subsequently dried over sodium sulfate. The solvent was distilled off under reduced pressure, and the resulting residue was purified using silica gel column chromatography (elution solvent: ethyl acetate/hexane=30%-50%) to afford the desired compound (65 mg, yield ~100%) as a pale yellow liquid.

$^1$H-NMR (CDCl$_3$, 400 MHz): δ 1.33 (3H, d, J=6.3 Hz), 3.42 (3H, s), 3.52 (1H, dd, J=3.9, 10.2 Hz), 3.60 (1H, dd, J=5.9, 10.2 Hz), 3.91 (3H, s), 4.60-4.70 (1H, m), 6.56-6.59 (2H, m), 6.86 (1H, brs), 6.93 (1H, brs), 7.05 (2H, d, J=9.0 Hz), 7.15 (1H, brs), 7.70 (1H, brs), 8.02 (2H, d, J=9.0 Hz).

MS (ESI) m/z: 465.19025 (M+H)$^+$.

Example 39

1-(4-{3-[(1S)-2-Methoxy-1-methylethoxy]-5-[5-(1,3-thiazol-2-yl)-1H-pyrrol-2-yl]phenoxy}phenyl)ethanone

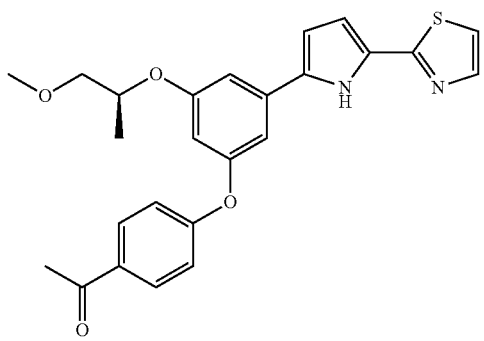

(39a) t-Butyl 2-{3-(4-acetylphenoxy)-5-[(1S)-2-methoxy-1-methylethoxy]phenyl}-5-(1,3-thiazol-2-yl)-1H-pyrrole-1-carboxylate t-Butyl 2-{3-hydroxy-5-[(1S)-2-methoxy-1-methylethoxy]phenyl}-5-(1,3-thiazol-2-yl)-1H-pyrrole-1-carboxylate (92 mg, 0.214 mmol) synthesized in Example (38d) was dissolved in dichloromethane (10 mL), and 4-acetylphenylboronic acid (70 mg, 0.427 mmol), copper (II) acetate (60 mg, 0.330 mmol), triethylamine (0.15 mL, 1.08 mmol) and molecular sieves 4A (90 mg) were added, followed by stirring at room temperature for 1 day under nitrogen atmosphere. The deposit of this reaction solution was Celite filtered. This mother liquor was distilled off under reduced pressure, and the resulting residue was purified using silica gel column chromatography (elution solvent: ethyl acetate/hexane=15%-25%) to afford the desired compound (73 mg, yield 62%) as a yellow oil.

$^1$H-NMR (CDCl$_3$, 400 MHz): δ 1.32 (12H, m), 2.57 (3H, s), 3.40 (3H, s), 3.48 (1H, dd, J=10.2, 4.3 Hz), 3.57 (1H, dd, J=10.2, 5.9 Hz), 4.53-4.54 (1H, m), 6.26 (1H, d, J=3.9 Hz), 6.59 (1H, d, J=3.5 Hz), 6.63 (1H, t, J=2.3 Hz), 6.71 (1H, t, J=1.8 Hz), 6.85 (1H, dd, J=2.2, 1.4 Hz), 7.06 (2H, dt, J=9.4, 2.4 Hz), 7.30 (1H, d, J=3.1 Hz), 7.80 (1H, d, J=3.1 Hz), 7.94 (2H, dt, J=9.4, 2.4 Hz).

(39b) 1-(4-{3-[(1S)-2-Methoxy-1-methylethoxy]-5-[5-(1,3-thiazol-2-yl)-1H-pyrrol-2-yl]phenoxy}phenyl)ethanone t-Butyl 2-{3-(4-acetylphenoxy)-5-[(1S)-2-methoxy-1-methylethoxy]phenyl}-5-(1,3-thiazol-2-yl)-1H-pyrrole-1-carboxylate (73 mg, 0.133 mmol) synthesized in Example (39a) was dissolved in dichloromethane (1.0 mL). Trifluoroacetic acid (2.0 mL) was added dropwise with stirring under nitrogen atmosphere, and stirring was carried out at room temperature for 2.5 hours. The solvent was distilled off under reduced pressure, and the resulting residue was purified using silica gel column chromatography (elution solvent: ethyl acetate/hexane=30%-40%) to afford the desired compound (56 mg, yield 94%) as a pale yellow liquid.

$^1$H-NMR (CDCl$_3$, 400 MHz): δ 1.34 (3H, d, J=6.3 Hz), 2.59 (3H, s), 3.42 (3H, s), 3.52 (1H, dd, J=10.3, 3.9 Hz), 3.59 (1H, dd, J=10.3, 5.9 Hz), 4.61-4.68 (1H, m), 6.54-6.59 (2H, m), 6.82 (1H, d, J=2.9 Hz), 6.91 (1H, s), 7.06-7.11 (3H, br m), 7.18-7.20 (1H, br m), 7.68-7.70 (1H, br m), 7.96 (2H, d, J=8.8 Hz), 10.51 (1H, br s).

MS (ESI) m/z: 449.15388 (M+H)$^+$.

Example 40

1-(4-{3-[(1S)-2-Methoxy-1-methylethoxy]-5-[5-(1,3-thiazol-2-yl)-1H-pyrrol-2-yl]phenoxy}phenyl)ethanol

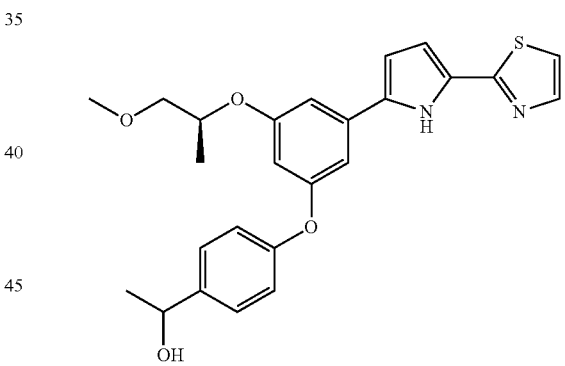

1-(4-{3-[(1S)-2-Methoxy-1-methylethoxy]-5-[5-(1,3-thiazol-2-yl)-1H-pyrrol-2-yl]phenoxy}phenyl)ethanone (30 mg, 0.067 mmol) synthesized in Example (39b) was dissolved in a mixed solvent of tetrahydrofuran (3.0 mL) and methanol (1.0 mL), and sodium borohydride (10 mg, 0.264 mmol) was added, followed by stirring at room temperature for 3 hours under nitrogen atmosphere. To this reaction solution, a saturated aqueous ammonium chloride solution (10 mL) was added, and extraction was carried out with ethyl acetate (10 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=40%-60%) to afford the desired compound (27.5 mg, yield 91%) as a white solid.

$^1$H-NMR (CDCl$_3$, 400 MHz): δ 1.33 (3H, d, J=6.3 Hz), 1.53 (3H, d, J=6.3 Hz), 3.42 (3H, s), 3.49 (1H, dd, J=9.4, 5.1

Hz), 3.59 (1H, dd, J=10.2, 5.9 Hz), 4.52-4.59 (1H, m), 4.92 (1H, q, J=6.3 Hz), 6.47-6.52 (2H, m), 6.72 (1H, t, J=2.7 Hz), 6.92 (1H, s), 7.04 (2H, d, J=8.2 Hz), 7.16 (1H, d, J=3.1 Hz), 7.37 (2H, d, J=9.0 Hz), 7.67 (1H, d, J=3.1 Hz), 9.72 (1H, br s).
MS (ESI) m/z: 451.16915 (M+H)⁺.

Example 41

2-(5-{3-[4-(Azetidin-1-ylcarbonyl)-2-fluorophenoxy]-5-[(1S)-2-methoxy-1-methylethoxy]phenyl}-1H-pyrrol-2-yl)-1,3-thiazole

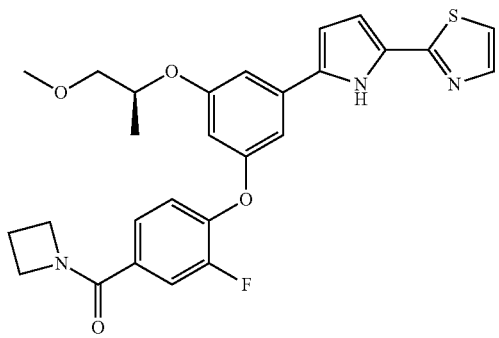

(41a) 1-(3,4-Difluorobenzoyl)azetidine

Commercially available 3,4-difluorobenzoic acid (3.00 g, 19.0 mmol) was dissolved in dichloromethane (50 mL), and N,N-dimethylformamide (0.10 mL) was added, followed by dropwise addition of oxalyl chloride (1.98 mL, 22.8 mmol) and stirring at room temperature overnight under nitrogen atmosphere. The solvent was distilled off under reduced pressure, and the resulting residue was dissolved in dichloromethane (100 mL), and azetidine hydrochloride (2.27 g, 24.2 mmol) and triethylamine (6.60 mL, 47.4 mmol) were added, followed by stirring at room temperature for 4.5 hours under nitrogen atmosphere. 0.5N hydrochloric acid (100 mL) was added, and extraction was carried out with dichloromethane (100 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=40%-50%) to afford the desired compound (600 mg, yield 16%) as a colorless liquid.
¹H-NMR (CDCl₃, 400 MHz): δ 2.37 (2H, m), 4.23 (2H, t, J=7.4 Hz), 4.32 (2H, t, J=7.4 Hz), 7.20 (1H, m), 7.40 (1H, m), 7.50 (1H, m).

(41b) 2-(5-{3-[4-(Azetidin-1-ylcarbonyl)-2-fluorophenoxy]-5-[(1S)-2-methoxy-1-methylethoxy]phenyl}-1H-pyrrol-2-yl)-1,3-thiazole t-Butyl 2-{3-hydroxy-5-[(1S)-2-methoxy-1-methylethoxy]phenyl}-5-(1,3-thiazol-2-yl)-1H-pyrrole-1-carboxylate (70 mg, 0.163 mmol) synthesized in Example (38d) and 1-(3,4-difluorobenzoyl)azetidine (68 mg, 0.345 mmol) synthesized in Example (41a) were dissolved in dimethyl sulfoxide (3.0 mL), and sodium hydride (60%, 25 mg, 0.63 mmol) was added, followed by stirring at 100° C. for 5 hours under nitrogen atmosphere. The reaction solution was cooled to room temperature, 2N hydrochloric acid (30 mL) was added, and extraction was carried out with diethyl ether (30 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=60%-80%) to afford the desired compound (54 mg, yield 65%) as a yellow solid.
¹H-NMR (CDCl₃, 400 MHz): δ 1.32 (3H, d, J=6.3 Hz), 2.38 (2H, m), 3.41 (3H, s), 3.50 (1H, dd, J=3.9, 10.2 Hz), 3.58 (1H, dd, J=6.3, 10.2 Hz), 4.20-4.26 (2H, brs), 4.33-4.40 (2H, brs), 4.57 (1H, m), 6.49-6.52 (2H, m), 6.71 (1H, dd, J=2.4, 3.9 Hz), 6.82 (1H, dd, J=1.6, 2.4 Hz), 6.94 (1H, dd, J=1.6, 2.4 Hz), 7.07 (1H, t, J=8.2 Hz), 7.16 (1H, d, J=3.5 Hz), 7.40 (1H, ddd, J=1.2, 2.4, 8.6 Hz), 7.52 (1H, dd, J=2.0, 11.0 Hz), 7.68 (1H, d, J=3.2 Hz), 9.62 (1H, brs).
MS (ESI) m/z: 508.17094 (M+H)⁺.

Example 42

1-(3-Fluoro-4-{3-[(1S)-2-methoxy-1-methylethoxy]-5-[5-(1,3-thiazol-2-yl)-1H-pyrrol-2-yl]phenoxy}benzoyl)azetidin-3-ol

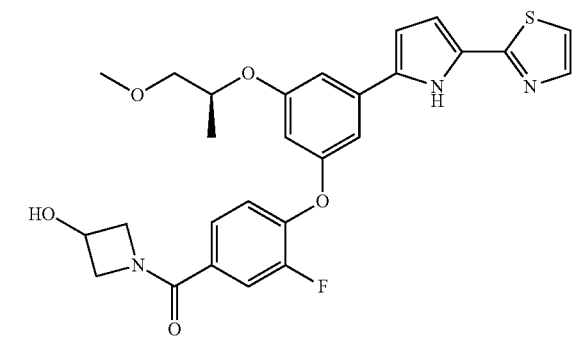

(42a) 1-(3,4-difluorobenzoyl)-3-(tetrahydro-2H-pyran-2-yloxy)azetidine

Commercially available 3,4-difluorobenzoic acid (1.00 g, 6.33 mmol) was dissolved in methanol (10 mL), and 3-hydroxyazetidine hydrochloride (830 mg, 7.58 mmol), 4-(4,6-dimethoxy-1,3,5-triazin-2-yl)-4-methylmorpholinium chloride n hydrate (2.10 g, 7.59 mmol) and N-methylmorpholine (0.85 mL, 2.83 mmol) were added, followed by stirring at room temperature for 2.5 hours under nitrogen atmosphere. The insolubles were removed by Celite filtration, and the solvent was distilled off under reduced pressure. The resulting residue was purified using silica gel column chromatography (elution solvent: ethyl acetate/hexane=50%-70%).
The resulting compound was dissolved in dichloromethane (20 mL), and 3,4-dihydro-2H-pyrane (1.00 mL, 11.1 mmol) and pyridinium p-toluenesulfonate (250 mg, 0.99 mmol) were added, followed by stirring at room temperature overnight under nitrogen atmosphere. To the reaction solution, triethylamine (0.5 mL) was added, the solvent was distilled off under reduced pressure, and the resulting residue was purified using silica gel column chromatography (elution solvent: ethyl acetate/hexane=35%-50%) to afford the desired compound (2.24 g, yield ~100%) as a colorless liquid.
¹H-NMR (CDCl₃, 400 MHz): δ 1.48-1.65 (4H, br m), 1.68-1.89 (2H, br m), 3.46-3.55 (2H, br m), 3.83-3.88 (2H, br m), 4.02-4.47 (2H, br m), 4.55-4.66 (2H, br m), 7.18-7.21 (1H, m), 7.38-7.42 (1H, m), 7.47-7.52 (1H, m).

(42b) 2-(5-{3-(2-Fluoro-4-{[3-(tetrahydro-2H-pyran-2-yloxy)azetidin-1-yl]carbonyl}phenoxy)-5-[(1S)-2-methoxy-1-methylethoxy]phenyl}-1H-pyrrol-2-yl)-1,3-thiazole t-Butyl 2-{3-hydroxy-5-[(1S)-2-methoxy-1-methylethoxy]phenyl}-5-(1,3-thiazol-2-yl)-1H-pyrrole-1-carboxylate (150 mg, 0.348 mmol) synthesized in Example (38d) and 1-(3,4-difluorobenzoyl)-3-(tetrahydro-2H-pyran-2-yloxy)azetidine (220 mg, 0.740 mmol) synthesized in Example (42a) were dissolved in dimethyl sulfoxide (5.0 mL), and sodium hydride (60%, 70 mg, 1.75 mmol) was added, followed by stirring at 100° C. for 1.5 hours under nitrogen atmosphere. The reaction solution was cooled to room temperature, saturated brine (30 mL) was added, and extraction was carried out with ethyl acetate (30 mL). Subsequently, drying was carried out over anhydrous magnesium sulfate. The solvent was distilled off under reduced pressure, and the resulting residue was purified using silica gel column chromatography (elution solvent: ethyl acetate/hexane=65%-85%) to afford the desired compound (158 mg, yield 75%) as a white solid.

$^1$H-NMR (CDCl$_3$, 400 MHz): δ 1.33 (3H, d, J=6.3 Hz), 1.48-1.90 (6H, m), 3.41 (3H, s), 3.46-3.55 (2H, m), 3.50 (1H, dd, J=10.2, 4.3 Hz), 3.59 (1H, dd, J=10.4, 6.1 Hz), 3.80-3.89 (2H, m), 4.40-4.64 (4H, m), 6.51-6.52 (2H, m), 6.72 (1H, dd, J=3.5, 2.7 Hz), 6.82 (1H, br s), 6.94 (1H, br s), 7.06 (1H, t, J=8.4 Hz), 7.17 (1H, d, J=3.5 Hz), 7.34-7.44 (1H, m), 7.52 (1H, dd, J=10.0, 5.0 Hz), 7.68 (1H, d, J=3.1 Hz), 9.52 (1H, br s).

MS (ESI) m/z: 608.22267 (M+H)$^+$.

(42c) 1-(3-Fluoro-4-{3-[(1S)-2-methoxy-1-methylethoxy]-5-[5-(1,3-thiazol-2-yl)-1H-pyrrol-2-yl]phenoxy}benzoyl)azetidin-3-ol 2-(5-{3-(2-Fluoro-4-{[3-(tetrahydro-2H-pyran-2-yloxy)azetidin-1-yl]carbonyl}phenoxy)-5-[(1S)-2-methoxy-1-methylethoxy]phenyl}-1H-pyrrol-2-yl)-1,3-thiazole (110 mg, 0.181 mmol) synthesized in Example (42b) was dissolved in methanol (10 mL), and 10-camphorsulfonic acid (20 mg, 0.086 mmol) was added, followed by stirring at room temperature overnight under nitrogen atmosphere. To the reaction solution, triethylamine (0.1 mL) was added, and the solvent was distilled off under reduced pressure. The resulting residue was purified using silica gel column chromatography (elution solvent: ethyl acetate/hexane=90%-100%) to afford the desired compound (62 mg, yield 65%) as a yellow solid.

$^1$H-NMR (CDCl$_3$, 400 MHz): δ 1.33 (3H, d, J=6.3 Hz), 2.28 (1H, br s), 3.41 (3H, s), 3.50 (1H, dd, J=10.4, 4.1 Hz), 3.59 (1H, dd, J=10.2, 5.9 Hz), 4.08 (1H, br s), 4.23 (1H, br s), 4.45-4.58 (2H, m), 4.52-4.60 (1H, m), 4.71-4.80 (2H, m), 6.50-6.53 (2H, m), 6.73 (1H, dd, J=3.5, 2.7 Hz), 6.83 (1H, t, J=1.8 Hz), 6.95-6.97 (1H, m), 7.06 (1H, t, J=8.2 Hz), 7.17 (1H, d, J=3.1 Hz), 7.37-7.40 (1H, m), 7.50-7.53 (1H, m), 7.68 (1H, d, J=3.1 Hz), 9.61 (1H, br s).

MS (ESI) m/z: 524.16841 (M+H)$^+$.

Example 43

Methyl 3-fluoro-4-{3-[(1S)-2-methoxy-1-methylethoxy]-5-[5-(1,3-thiazol-2-yl)-1H-pyrrol-2-yl]phenoxy}benzoate

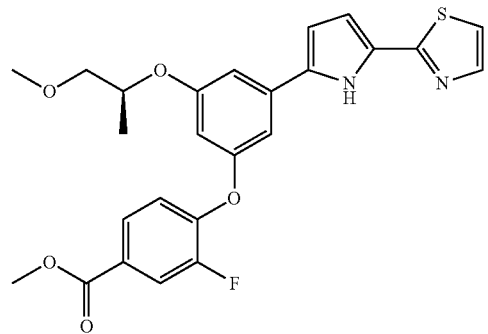

t-Butyl 2-{3-hydroxy-5-[(1S)-2-methoxy-1-methylethoxy]phenyl}-5-(1,3-thiazol-2-yl)-1H-pyrrole-1-carboxylate (485 mg, 1.127 mmol) synthesized in Example (38d) and commercially available methyl 3,4-difluorobenzoate (540 mg, 3.137 mmol) were dissolved in dimethyl sulfoxide (10 mL), and sodium hydride (60%, 180 mg, 4.50 mmol) was added, followed by stirring at 100° C. for 2.5 hours under nitrogen atmosphere. The reaction solution was cooled to room temperature, water (50 mL) was added, and extraction was carried out with diethyl ether (50 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=10%-30%) to afford the desired compound (97 mg, yield 18%) as a white solid.

$^1$H-NMR (CDCl$_3$, 400 MHz): δ 1.31 (3H, d, J=6.3 Hz), 3.39 (3H, s), 3.48 (1H, dd, J=10.2, 3.9 Hz), 3.57 (1H, dd, J=10.2, 5.9 Hz), 3.91 (3H, s), 4.51-4.59 (1H, m), 6.49-6.52 (2H, m), 6.71 (1H, dd, J=3.9, 2.3 Hz), 6.82-6.85 (1H, br m), 6.98 (1H, br s), 7.05 (1H, t, J=8.2 Hz), 7.15 (1H, d, J=3.1 Hz), 7.66 (1H, d, J=3.1 Hz), 7.78 (1H, d, J=9.8 Hz), 7.85 (1H, dd, J=11.1, 2.2 Hz), 9.78-9.87 (1H, m).

MS (ESI) m/z: 483.13782 (M+H)$^+$.

Example 44

3-Fluoro-4-{3-[(1S)-2-methoxy-1-methylethoxy]-5-[5-(1,3-thiazol-2-yl)-1H-pyrrol-2-yl]phenoxy}benzamide

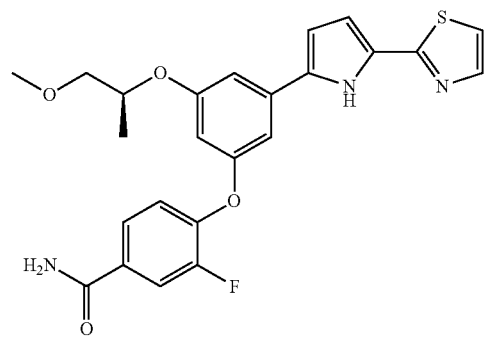

(44a) 3-Fluoro-4-{3-[(1S)-2-methoxy-1-methylethoxy]-5-[5-(1,3-thiazol-2-yl)-1H-pyrrol-2-yl]phenoxy}benzoic acid Methyl 3-fluoro-4-{3-[(1S)-2-methoxy-1-methylethoxy]-5-[5-(1,3-thiazol-2-yl)-1H-pyrrol-2-yl]phenoxy}benzoate (611 mg, 1.42 mmol) synthesized in Example 43 was dissolved in methanol (18 mL), and water (3 mL) and lithium hydroxide monohydrate (298 mg, 7.10 mmol) were added, followed by stirring at 60° C. for 4 hours under nitrogen atmosphere. To the reaction solution, water (50 mL) was added, and extraction was carried out twice with ethyl acetate (40 mL), followed by drying over sodium sulfate. The solvent was distilled off under reduced pressure, and the resulting residue was purified using silica gel column chromatography (elution solvent: ethyl acetate/hexane=30%-75%) to afford the desired compound (519 mg, yield 88%) as a white solid.

$^1$H-NMR (CDCl$_3$, 400 MHz): δ 1.38 (3H, d, J=6.3 Hz), 3.45 (3H, s), 3.55 (1H, dd, J=10.2, 4.3 Hz), 3.64 (1H, dd, J=10.2, 5.9 Hz), 4.60-4.67 (1H, m), 6.63 (1H, dd, J=3.9, 2.7 Hz), 6.74 (1H, t, J=2.2 Hz), 6.84 (1H, dd, J=3.9, 2.3 Hz), 6.99 (1H, t, J=8.2 Hz), 7.16-7.14 (2H, m), 7.41 (1H, t, J=1.8 Hz), 7.55 (1H, dt, J=8.6, 1.0 Hz), 7.61 (1H, d, J=3.1 Hz), 7.72 (1H, dd, J=10.6, 2.0 Hz), 11.85 (1H, s).

(44b) 3-Fluoro-4-{3-[(1S)-2-methoxy-1-methylethoxy]-5-[5-(1,3-thiazol-2-yl)-1H-pyrrol-2-yl]phenoxy}benzamide 3-Fluoro-4-{3-[(1S)-2-methoxy-1-methylethoxy]-5-[5-(1,3-thiazol-2-yl)-1H-pyrrol-2-yl]phenoxyl}benzoic acid (40.0 mg, 0.163 mmol) synthesized in Example (44a) was dissolved in dichloromethane (5 mL), and 28% aqueous ammonia solution (0.50 mL), WSCI•HCl (19.6 mg, 0.102 mmol) and HOBt•H$_2$O (13.1 mg, 0.086 mmol) were added, followed by stirring at room temperature for 7 hours under nitrogen atmosphere. To the reaction solution, water (10 mL) was added, and extraction was carried out with ethyl acetate (20 mL). The organic layer was washed with saturated brine, and subsequently dried over sodium sulfate. The solvent was distilled off under reduced pressure, and the resulting residue was purified using silica gel column chromatography (elution solvent: ethyl acetate/hexane=0%-75%) to afford the desired compound (11.3 mg, yield 28%) as a white solid.

$^1$H-NMR (CDCl$_3$, 400 MHz): δ 1.33 (3H, d, J=6.3 Hz), 3.42 (3H, s), 3.51 (1H, dd, J=10.3, 5.4 Hz), 3.59 (1H, dd, J=10.3, 5.9 Hz), 4.54-4.61 (1H, m), 6.51-6.54 (2H, m), 6.73 (1H, dd, J=3.4, 2.4 Hz), 6.84 (1H, s), 6.97 (1H, s), 7.09 (1H, t, J=8.1 Hz), 7.18 (1H, d, J=2.9 Hz), 7.53 (1H, d, J=8.8 Hz), 7.67-7.73 (2H, m), 9.60 (1H, br s).

MS (ESI) m/z: 468.13800 (M+H)$^+$.

Example 45

3-Fluoro-4-{3-[(1S)-2-methoxy-1-methylethoxy]-5-[5-(1,3-thiazol-2-yl)-1H-pyrrol-2-yl]phenoxy}-N-methylbenzamide

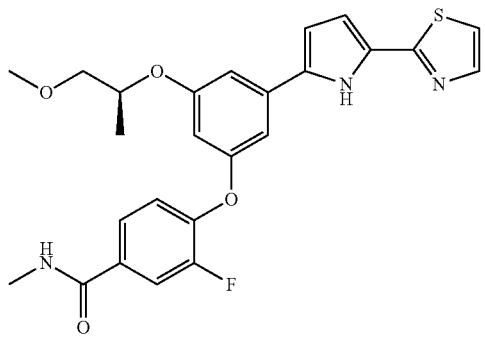

3-Fluoro-4-{3-[(1S)-2-methoxy-1-methylethoxy]-5-[5-(1,3-thiazol-2-yl)-1H-pyrrol-2-yl]phenoxy}benzoic acid (40.0 mg, 0.163 mmol) synthesized in Example (44a) was dissolved in tetrahydrofuran (5 mL), and methylamine hydrochloride (17.3 mg, 0.256 mmol), HATU (64.5 mg, 0.170 mmol) and N,N-diisopropylethylamine (89 μL, 0.51 mmol) were added, followed by stirring at room temperature for 4 hours under nitrogen atmosphere. To the reaction solution, saturated brine (15 mL) was added, and extraction was carried out twice with ethyl acetate (15 mL), followed by drying over sodium sulfate. The solvent was distilled off under reduced pressure, and the resulting residue was purified using silica gel column chromatography (elution solvent: ethyl acetate/hexane=0%-55%) to afford the desired compound (41 mg, yield ~100%) as a pale yellow solid.

$^1$H-NMR (CDCl$_3$, 400 MHz): δ 1.32 (3H, d, J=6.3 Hz), 3.03 (3H, d, J=4.7 Hz), 3.41 (3H, s), 3.50 (1H, dd, J=10.2, 3.9 Hz), 3.58 (1H, dd, J=10.2, 6.3 Hz), 4.52-4.60 (1H, m), 6.49-6.53 (2H, m), 6.72 (1H, dd, J=3.9, 2.3 Hz), 6.79 (1H, t, J=2.0 Hz), 6.94 (1H, t, J=2.0 Hz), 7.08 (1H, t, J=8.0 Hz), 7.17 (1H, d, J=3.5 Hz), 7.47 (1H, d, J=8.6 Hz), 7.65 (1H, dd, J=10.9, 2.0 Hz), 7.68 (1H, d, J=3.9 Hz), 9.48 (1H, br s).

MS (ESI) m/z: 482.15436 (M+H)$^+$.

Example 46

3-Fluoro-4-{3-[(1S)-2-methoxy-1-methylethoxy]-5-[5-(1,3-thiazol-2-yl)-1H-pyrrol-2-yl]phenoxy}-N,N-dimethylbenzamide

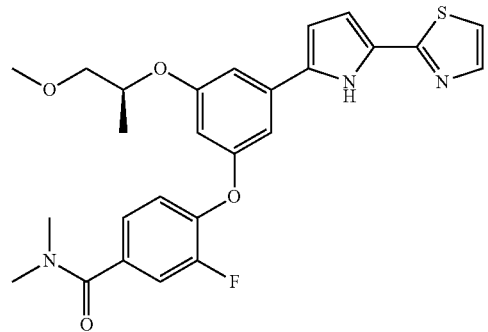

3-Fluoro-4-{3-[(1S)-2-methoxy-1-methylethoxy]-5-[5-(1,3-thiazol-2-yl)-1H-pyrrol-2-yl]phenoxy}benzoic acid (40.0 mg, 0.163 mmol) synthesized in Example (44a) was dissolved in tetrahydrofuran (5 mL), and dimethylamine hydrochloride (20.1 mg, 0.246 mmol), HATU (64.5 mg, 0.170 mmol) and N,N-diisopropylethylamine (89 μL, 0.51 mmol) were added, followed by stirring at room temperature for 4 hours under nitrogen atmosphere. To the reaction solution, saturated brine (15 mL) was added, and extraction was carried out twice with ethyl acetate (15 mL), followed by drying over sodium sulfate. The solvent was distilled off under reduced pressure, and the resulting residue was purified using silica gel column chromatography (elution solvent: ethyl acetate/hexane=0%-75%) to afford the desired compound (45 mg, yield 99%) as a pale yellow solid.

$^1$H-NMR (CDCl$_3$, 400 MHz): δ 1.32 (3H, d, J=6.3 Hz), 3.02-3.14 (6H, br m), 3.41 (3H, s), 3.50 (1H, dd, J=10.2, 3.9 Hz), 3.58 (1H, dd, J=10.2, 5.9 Hz), 4.52-4.61 (1H, m), 6.49-6.54 (2H, m), 6.73 (1H, dd, J=3.7, 1.9 Hz), 6.85 (1H, t, J=1.6 Hz), 6.95 (1H, t, J=1.6 Hz), 7.08 (1H, t, J=8.0 Hz), 7.16-7.20 (2H, m), 7.29 (1H, dd, J=10.8, 1.8 Hz), 7.68 (1H, d, J=3.1 Hz), 9.65 (1H, br s).

MS (ESI) m/z: 496.17025 (M+H)$^+$.

Example 47

2-(5-{3-[2-Fluoro-4-(pyrrolidin-1-ylcarbonyl)phenoxy]-5-[(1S)-2-methoxy-1-methylethoxy]phenyl}-1H-pyrrol-2-yl)-1,3-thiazole

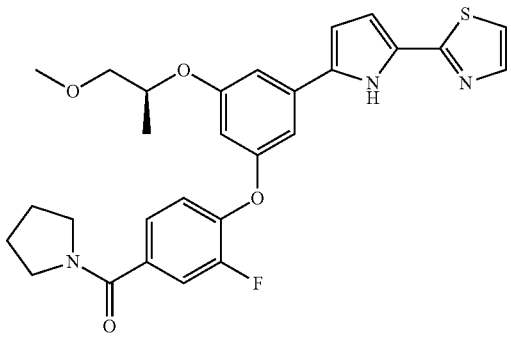

3-Fluoro-4-{3-[(1S)-2-methoxy-1-methylethoxy]-5-[5-(1,3-thiazol-2-yl)-1H-pyrrol-2-yl]phenoxy}benzoic acid (40.0 mg, 0.085 mmol) synthesized in Example (44a) was dissolved in tetrahydrofuran (5 mL), and pyrrolidine (21 µL, 0.26 mmol), HATU (64.9 mg, 0.171 mmol) and N,N-diisopropylethylamine (89 µL, 0.51 mmol) were added, followed by stirring at room temperature for 20 hours under nitrogen atmosphere. To the reaction solution, saturated brine (15 mL) was added, and extraction was carried out twice with ethyl acetate (15 mL), followed by drying over sodium sulfate. The solvent was distilled off under reduced pressure, and the resulting residue was purified using silica gel column chromatography (elution solvent: ethyl acetate/hexane=0%-75%) to afford the desired compound (32 mg, yield 72%) as a white solid.

$^1$H-NMR (CDCl$_3$, 400 MHz): δ 1.29 (3H, d, J=6.3 Hz), 1.84-1.98 (4H, m), 3.38 (3H, s), 3.41-3.49 (3H, m), 3.55 (1H, dd, J=10.2, 5.9 Hz), 3.61 (2H, t, J=6.8 Hz), 4.48-4.56 (1H, m), 6.46-6.49 (2H, m), 6.68 (1H, dd, J=3.9, 2.7 Hz), 6.78 (1H, t, J=1.8 Hz), 6.89 (1H, t, J=2.0 Hz), 7.04 (1H, t, J=8.2 Hz), 7.13 (1H, d, J=3.1 Hz), 7.25-7.29 (1H, m), 7.38 (1H, dd, J=10.9, 2.0 Hz), 7.64 (1H, d, J=3.5 Hz), 9.51 (1H, br s).

MS (ESI) m/z: 522.18695 (M+H)$^+$.

Example 48

4-(3-Fluoro-4-{3-[(1S)-2-methoxy-1-methylethoxy]-5-[5-(1,3-thiazol-2-yl)-1H-pyrrol-2-yl]phenoxy}benzoyl)morpholine

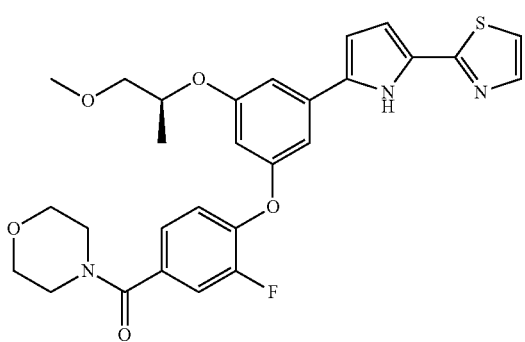

3-Fluoro-4-{3-[(1S)-2-methoxy-1-methylethoxy]-5-[5-(1,3-thiazol-2-yl)-1H-pyrrol-2-yl]phenoxy}benzoic acid (49.0 mg, 0.105 mmol) synthesized in Example (44a) was dissolved in tetrahydrofuran (5 mL), and morpholine (22 pt, 0.26 mmol), HATU (64.5 mg, 0.170 mmol) and N,N-diisopropylethylamine (89 µL, 0.51 mmol) were added, followed by stirring at room temperature for 4 hours under nitrogen atmosphere. To the reaction solution, saturated brine (15 mL) was added, and extraction was carried out twice with ethyl acetate (15 mL), followed by drying over sodium sulfate. The solvent was distilled off under reduced pressure, and the resulting residue was purified using silica gel column chromatography (elution solvent: ethyl acetate/hexane=0%-75%) to afford the desired compound (39 mg, yield 70%) as a pale yellow solid.

$^1$H-NMR (CDCl$_3$, 400 MHz): δ 1.33 (3H, d, J=6.3 Hz), 3.42 (3H, s), 3.51 (1H, dd, J=10.2, 4.3 Hz), 3.59 (1H, dd, J=10.2, 5.9 Hz), 3.72 (8H, br s), 4.52-4.61 (1H, m), 6.49-6.54 (2H, m), 6.72 (1H, dd, J=3.7, 2.5 Hz), 6.82 (1H, t, J=1.8 Hz), 6.93 (1H, t, J=1.8 Hz), 7.09 (1H, t, J=8.2 Hz), 7.16-7.19 (2H, m), 7.30 (1H, dd, J=10.6, 2.0 Hz), 7.69 (1H, d, J=3.1 Hz), 9.45 (1H, br s).

MS (ESI) m/z: 538.18048 (M+H)$^+$.

Example 49

2-(3-Fluoro-4-{3-[(1S)-2-methoxy-1-methylethoxy]-5-[5-(1,3-thiazol-2-yl)-1H-pyrrol-2-yl]phenoxy}phenyl)-5-methyl-1,3,4-thiadiazole

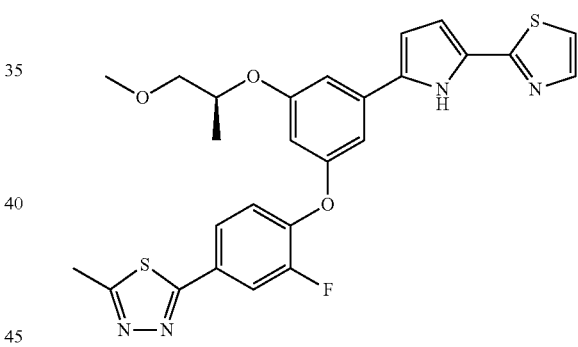

(49a) N'-Acetyl-3-fluoro-4-{3-[(1S)-2-methoxy-1-methylethoxy]-5-[5-(1,3-thiazol-2-yl)-1H-pyrrol-2-yl]phenoxy}benzohydrazide 3-Fluoro-4-{3-[(1S)-2-methoxy-1-methylethoxy]-5-[5-(1,3-thiazol-2-yl)-1H-pyrrol-2-yl]phenoxy}benzoic acid (84 mg, 0.179 mmol) synthesized in Example (44a) was dissolved in dichloromethane (5.0 mL), and acetohydrazide (40 mg, 0.540 mmol), HATU (200 mg, 0.526 mmol) and N,N-diisopropylethylamine (0.15 mL, 0.861 mmol) were added, followed by stirring at room temperature overnight under nitrogen atmosphere. The solvent was distilled off under reduced pressure, and the resulting residue was purified using silica gel column chromatography (elution solvent: ethyl acetate) to afford the desired compound (110 mg, yield ~100%) as a white solid.

$^1$H-NMR (CDCl$_3$, 400 MHz): δ 1.44 (3/2H, d, J=6.3 Hz), 1.49 (3/2H, d, J=6.3 Hz), 2.05 (3H, s), 3.46 (3H, s), 3.55 (1H, dd, J=10.8, 4.1 Hz), 3.65 (1H, dd, J=10.0, 6.1 Hz), 4.58-4.69 (1H, m), 6.69 (1H, d, J=2.3 Hz), 6.73 (1H, s), 6.77 (1H, d,

J=2.7 Hz), 7.12 (1H, br s), 7.16 (1H, br s), 7.29 (1H, br s), 7.34 (1H, br s), 7.37 (1H, br s), 7.45 (1H, d, J=8.2 Hz), 7.62 (1H, br s), 11.51 (1H, br s), 11.79 (1H, br s), 12.56 (1H, br s).

MS (ESI) m/z: 547.14358 (M+Na)+.

(49b) 2-(3-Fluoro-4-{3-[(1S)-2-methoxy-1-methylethoxy]-5-[5-(1,3-thiazol-2-yl)-1H-pyrrol-2-yl]phenoxy}phenyl)-5-methyl-1,3,4-thiadiazole N'-Acetyl-3-fluoro-4-{3-[(1S)-2-methoxy-1-methylethoxy]-5-[5-(1,3-thiazol-2-yl)-1H-pyrrol-2-yl]phenoxy}benzohydrazide (40 mg, 0.076 mmol) synthesized in Example (49a) was dissolved in a mixed solvent of toluene (4.0 mL) and acetonitrile (2.0 mL), and 2,4-bis-(4-methoxyphenyl)-1,3-dithia-2,4-diphosphetane 2,4-disulfide (45 mg, 0.111 mmol) and pyridine (0.03 mL, 0.372 mmol) were added, followed by stirring at 100° C. for 4 hours under nitrogen atmosphere. The reaction solution was cooled to room temperature, the solvent was distilled off under reduced pressure, and the resulting residue was purified using silica gel column chromatography (elution solvent: ethyl acetate/hexane=60%-80%) to afford the desired compound (28 mg, yield 70%) as a yellow solid.

$^1$H-NMR (CDCl$_3$, 400 MHz): δ 1.34 (3H, d, J=6.3 Hz), 2.83 (3H, s), 3.42 (3H, s), 3.51 (1H, dd, J=10.3, 4.4 Hz), 3.60 (1H, dd, J=10.3, 5.9 Hz), 4.57-4.63 (1H, m), 6.54-6.54 (2H, m), 6.77 (1H, s), 6.87 (1H, s), 7.00 (1H, s), 7.14-7.17 (2H, m), 7.64 (1H, dd, J=8.3, 1.0 Hz), 7.68 (1H, d, J=3.4 Hz), 7.84 (1H, dd, J=11.2, 2.0 Hz), 10.01 (1H, br s).

MS (ESI) m/z: 523.12785 (M+H)+.

Example 50

2-(3-Fluoro-4-{3-[(1S)-2-methoxy-1-methylethoxy]-5-[5-(1,3-thiazol-2-yl)-1H-pyrrol-2-yl]phenoxy}phenyl)-5-methyl-1,3,4-oxadiazole

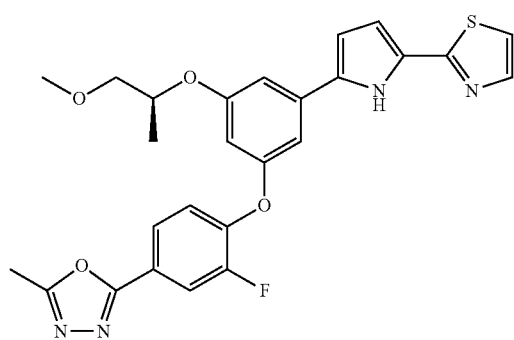

N'-Acetyl-3-fluoro-4-{3-[(1S)-2-methoxy-1-methylethoxy]-5-[5-(1,3-thiazol-2-yl)-1H-pyrrol-2-yl]phenoxy}benzohydrazide (45 mg, 0.086 mmol) synthesized in Example (49a) was dissolved in acetonitrile (3.0 mL), and (methoxycarbonylsulfamoyl)triethylammonium hydroxide (50 mg, 0.210 mmol) and triethylamine (0.05 mL, 0.359 mmol) were added, followed by stirring at 100° C. for 1 day under nitrogen atmosphere. The solvent was distilled off under reduced pressure, and the resulting residue was purified using silica gel column chromatography (elution solvent: ethyl acetate/hexane=80%-100%) to afford the desired compound (26 mg, yield 60%) as a colorless liquid.

$^1$H-NMR (CDCl$_3$, 400 MHz): δ 1.34 (3H, d, J=6.3 Hz), 2.63 (3H, s), 3.42 (3H, s), 3.50 (1H, dd, J=10.2, 4.3 Hz), 3.60 (1H, dd, J=10.2, 5.9 Hz), 4.54-4.62 (1H, m), 6.50-6.55 (2H, m), 6.72 (1H, dd, J=3.5, 2.0 Hz), 6.86 (1H, s), 6.99 (1H, s), 7.12-7.19 (2H, m), 7.67 (1H, d, J=3.1 Hz), 7.78 (1H, d, J=9.0 Hz), 7.87 (1H, dd, J=10.8, 1.4 Hz), 9.94 (1H, br s).

MS (ESI) m/z: 507.14909 (M+H)+.

Example 51

4-{3-[(1S)-2-Methoxy-1-methylethoxy]-5-[5-(1,3-thiazol-2-yl)-1H-pyrrol-2-yl]phenoxy}-3-methylbenzaldehyde

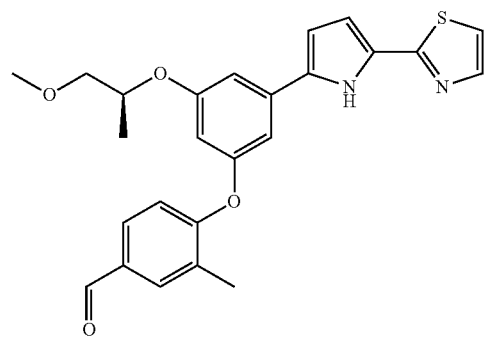

t-Butyl 2-{3-hydroxy-5-[(1S)-2-methoxy-1-methylethoxy]phenyl}-5-(1,3-thiazol-2-yl)-1H-pyrrole-1-carboxylate (150 mg, 0.348 mmol) synthesized in Example (38d) and commercially available 4-fluoro-3-methylbenzaldehyde (0.14 mL, 1.148 mmol) were dissolved in dimethyl sulfoxide (5.0 mL), and sodium hydride (60%, 40 mg, 1.00 mmol) was added, followed by stirring at 100° C. for 4 hours under nitrogen atmosphere. The reaction solution was cooled to room temperature, a saturated aqueous ammonium chloride solution (30 mL) was added, and extraction was carried out with diethyl ether (30 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=25%-30%) to afford the desired compound (84 mg, yield 54%) as a yellow solid.

$^1$H-NMR (CDCl$_3$, 400 MHz): δ 1.33 (3H, d, J=6.3 Hz), 2.39 (3H, s), 3.42 (3H, s), 3.50 (1H, dd, J=10.2, 3.9 Hz), 3.60 (1H, dd, J=10.4, 6.1 Hz), 4.55-4.64 (1H, m), 6.50 (1H, t, J=2.2 Hz), 6.53 (1H, dd, J=3.7, 2.9 Hz), 6.74 (1H, t, J=2.5 Hz), 6.83 (1H, t, J=2.0 Hz), 6.96 (1H, d, J=8.2 Hz), 7.00-7.02 (1H, m), 7.17 (1H, d, J=3.1 Hz), 7.65 (1H, d, J=2.3 Hz), 7.68 (1H, d, J=3.1 Hz), 7.81 (1H, d, J=1.2 Hz), 9.90 (1H, br s), 9.92 (1H, s).

MS (ESI) m/z: 449.15343 (M+H)+.

Example 52

(4-{3-[(1S)-2-Methoxy-1-methylethoxy]-5-[5-(1,3-thiazol-2-yl)-1H-pyrrol-2-yl]phenoxy}-3-methylphenyl)methanol

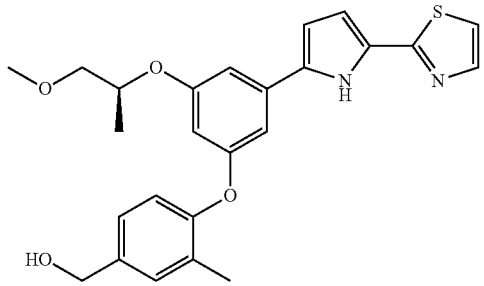

4-{3-[(1S)-2-Methoxy-1-methylethoxy]-5-[5-(1,3-thiazol-2-yl)-1H-pyrrol-2-yl]phenoxy}-3-methylbenzaldehyde (32 mg, 0.071 mmol) synthesized in Example 51 was dissolved in methanol (3.0 mL), and sodium borohydride (5 mg, 0.132 mmol) was added, followed by stirring at 0° C. for 4 hours under nitrogen atmosphere. The reaction solution was brought to room temperature, a saturated aqueous ammonium chloride solution (10 mL) was added, and extraction was carried out with ethyl acetate (10 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=50%-75%) to afford the desired compound (26 mg, yield 81%) as a white solid.

$^1$H-NMR (CDCl$_3$, 400 MHz): δ 1.32 (3H, d, J=6.3 Hz), 2.26 (3H, s), 3.41 (3H, s), 3.49 (1H, dd, J=10.2, 4.3 Hz), 3.58 (1H, dd, J=10.2, 5.9 Hz), 4.51-4.60 (1H, m), 4.67 (2H, br s), 6.40 (1H, t, J=2.2 Hz), 6.49 (1H, dd, J=3.5, 2.7 Hz), 6.70-6.72 (2H, m), 6.86 (1H, dd, J=3.5, 1.6 Hz), 6.96 (1H, dd, J=8.2 Hz), 7.15 (1H, d, J=3.5 Hz), 7.19 (1H, dd, J=8.2, 2.0 Hz), 7.28 (1H, d, J=2.3 Hz), 7.66 (1H, d, J=3.5 Hz), 9.72 (1H, br s).

MS (ESI) m/z: 451.16757 (M+H)$^+$.

Example 53

2-(5-{3-[4-(Azetidin-1-ylcarbonyl)-2-methylphenoxy]-5-[(1S)-2-methoxy-1-methylethoxy]phenyl}-1H-pyrrol-2-yl)-1,3-thiazole

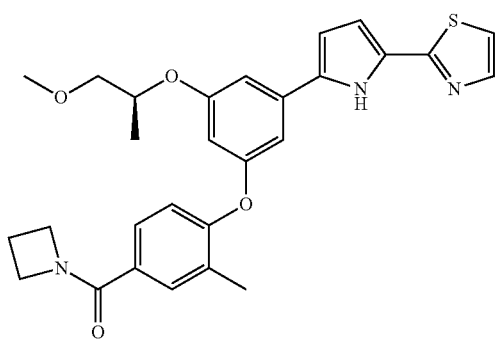

(53a) 4-{3-[(1S)-2-Methoxy-1-methylethoxy]-5-[5-(1,3-thiazol-2-yl)-1H-pyrrol-2-yl]phenoxy}-3-methylbenzoic acid 4-{3-[(1S)-2-Methoxy-1-methylethoxy]-5-[5-(1,3-thiazol-2-yl)-1H-pyrrol-2-yl]phenoxy}-3-methylbenzaldehyde (50 mg, 0.11 mmol) synthesized in Example 51 was dissolved in a mixed solvent of t-butanol (5.0 mL) and water (2.0 mL), and 2-methyl-2-butene (0.15 mL, 1.42 mmol) and sodium dihydrogen phosphate dihydrate (80 mg, 0.51 mmol) were added, followed by slow addition of sodium chlorite (25 mg, 0.28 mmol) at 0° C. and stirring at 0° C. for 2 hours under nitrogen atmosphere. An aqueous sodium hydrogen sulfite solution (5 mL) was added at 0° C., and stirring was carried out at room temperature for 10 minutes. An aqueous sodium hydrogen sulfite solution (15 mL) was added, and extraction was carried out with ethyl acetate (30 mL). The organic layer was washed with saturated brine, and subsequently dried over anhydrous magnesium sulfate. The solvent was distilled off under reduced pressure to afford the desired compound (58 mg, yield ~100%) as a yellow solid.

$^1$H-NMR (CDCl$_3$, 400 MHz): δ 1.34 (3H, d, J=6.3 Hz), 2.33 (3H, s), 3.41 (3H, s), 3.52 (1H, dd, J=10.6, 4.3 Hz), 3.60 (1H, dd, J=10.2, 5.9 Hz), 4.62-4.71 (1H, m), 6.54-6.57 (2H, m), 6.85-6.87 (2H, m), 7.08-7.16 (2H, m), 7.15 (1H, d, J=3.5 Hz), 7.64 (1H, s), 7.64 (1H, d, J=3.5 Hz), 7.87 (1H, s).

(53b) 2-(5-{3-[4-(Azetidin-1-ylcarbonyl)-2-methylphenoxy]-5-[(1S)-2-methoxy-1-methylethoxy]phenyl}-1H-pyrrol-2-yl)-1,3-thiazole 4-{3-[(1S)-2-Methoxy-1-methylethoxy]-5-[5-(1,3-thiazol-2-yl)-1H-pyrrol-2-yl]phenoxy}-3-methylbenzoic acid (58 mg, 0.125 mmol) synthesized in Example (53a) and azetidine hydrochloride (29 mg, 0.310 mmol) were dissolved in dichloromethane (10.0 mL), and HATU (95 mg, 0.250 mmol) and N,N-diisopropylethylamine (0.15 mL, 0.861 mmol) were added, followed by stirring at room temperature overnight under nitrogen atmosphere. The solvent was distilled off under reduced pressure, and the resulting residue was purified using silica gel column chromatography (elution solvent: ethyl acetate/hexane=75%-90%) to afford the desired compound (58 mg, yield 92%) as a yellow solid.

$^1$H-NMR (CDCl$_3$, 400 MHz): δ 1.32 (3H, d, J=6.3 Hz), 2.30 (3H, s), 2.31-2.39 (2H, m), 3.41 (3H, s), 3.49 (1H, dd, J=10.4, 4.1 Hz), 3.59 (1H, dd, J=10.2, 5.9 Hz), 4.22-4.25 (2H, br m), 4.33-4.36 (2H, br m), 4.52-4.60 (1H, m), 6.43 (1H, t, J=2.3 Hz), 6.50 (1H, dd, J=3.7, 2.9 Hz), 6.72 (1H, dd, J=3.9, 2.3 Hz), 6.76 (1H, t, J=1.8 Hz), 6.90 (1H, s), 6.92-6.93 (1H, m), 7.16 (1H, d, J=3.1 Hz), 7.42 (1H, dd, J=8.2, 2.0 Hz), 7.59 (1H, d, J=1.6 Hz), 7.67 (1H, d, J=3.1 Hz), 9.73 (1H, br s).

MS (ESI) m/z: 504.19979 (M+H)$^+$.

Example 54

2-(5-{3-[4-(Azetidin-1-ylcarbonyl)-2-(trifluoromethyl)phenoxy]-5-[(1S)-2-methoxy-1-methylethoxy]phenyl}-1H-pyrrol-2-yl)-1,3-thiazole

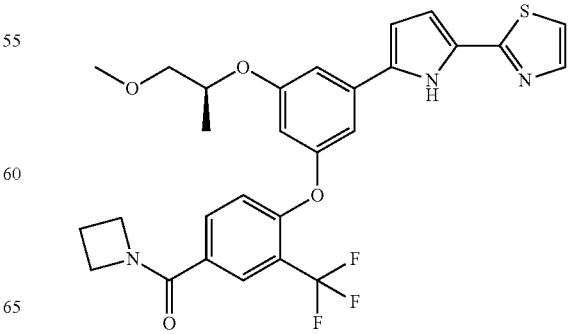

(54a)
1-[4-Fluoro-3-(trifluoromethyl)benzoyl]azetidine

Commercially available 4-fluoro-3-(trifluoromethyl)benzoic acid (230 mg, 1.10 mmol) was dissolved in dichloromethane (50 mL), and azetidine hydrochloride (120 mg, 1.28 mmol), HATU (550 mg, 1.45 mmol) and N,N-diisopropylethylamine (0.50 mL, 2.87 mmol) were added, followed by stirring at room temperature for 4 hours under nitrogen atmosphere. 0.5N hydrochloric acid (100 mL) was added, and extraction was carried out with dichloromethane (100 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=60%-80%) to afford the desired compound (211 mg, yield 78%) as a colorless liquid.

$^1$H-NMR (CDCl$_3$, 400 MHz): δ 2.35-2.43 (2H, m), 4.25 (2H, t, J=7.6 Hz), 4.33 (2H, t, J=7.4 Hz), 7.83-7.87 (1H, m), 7.93 (1H, dd, J=6.6, 2.0 Hz).

(54b) 2-(5-{3-[4-(Azetidin-1-ylcarbonyl)-2-(trifluoromethyl)phenoxy]-5-[(1S)-2-methoxy-1-methylethoxy]phenyl}-1H-pyrrol-2-yl)-1,3-thiazole t-Butyl 2-{3-hydroxy-5-[(1S)-2-methoxy-1-methylethoxy]phenyl}-5-(1,3-thiazol-2-yl)-1H-pyrrole-1-carboxylate (119 mg, 0.276 mmol) synthesized in Example (38d) and 1-[4-fluoro-3-(trifluoromethyl)benzoyl]azetidine (145 mg, 0.587 mmol) synthesized in Example (54a) were dissolved in dimethyl sulfoxide (8.0 mL), and sodium hydride (60%, 39 mg, 0.97 mmol) was added, followed by stirring at 100° C. for 2 hours under nitrogen atmosphere. The reaction solution was cooled to room temperature, a saturated aqueous ammonium chloride solution (30 mL) was added, and extraction was carried out with ethyl acetate (30 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=45%-60%) to afford the desired compound (105 mg, yield 68%) as a yellow solid.

$^1$H-NMR (CDCl$_3$, 400 MHz): δ 1.33 (3H, d, J=6.3 Hz), 2.34-2.42 (2H, m), 3.42 (3H, s), 3.50 (1H, dd, J=10.2, 4.3 Hz), 3.60 (1H, dd, J=10.2, 5.9 Hz), 4.25 (2H, t, J=6.8 Hz), 4.36 (2H, t, J=6.6 Hz), 4.56-4.60 (1H, m), 6.54-6.55 (2H, m), 6.73 (1H, dd, J=3.7, 2.5 Hz), 6.87 (1H, t, J=1.6 Hz), 6.99 (1H, d, J=8.6 Hz), 7.03 (1H, t, J=1.8 Hz), 7.17 (1H, d, J=3.1 Hz), 7.68 (1H, d, J=3.1 Hz), 7.74 (1H, dd, J=8.6, 2.3 Hz), 8.00 (1H, d, J=2.0 Hz), 9.73 (1H, br s).

MS (ESI) m/z: 558.16727 (M+H)$^+$.

Example 55

2-(5-{3-[4-(Azetidin-1-yl sulfonyl)phenoxy]-5-[(1S)-2-methoxy-1-methylethoxy]phenyl}-1H-pyrrol-2-yl)-1,3-thiazole

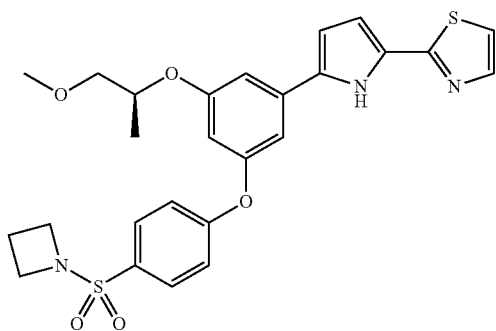

(55a) 1-[(4-Fluorophenyl)sulfonyl]azetidine

Commercially available 4-fluorophenylsulfonylchloride (225 mg, 1.15 mmol) was suspended in water (8 mL), and azetidine hydrochloride (90.0 mg, 0.96 mmol) and potassium carbonate (293 mg, 2.12 mmol) were added, followed by stirring at room temperature for 16 hours. To the reaction solution, water (15 mL) was added, followed by extraction twice with diethyl ether (15 mL), and washing was carried out with saturated brine (15 mL), followed by drying over sodium sulfate. The solvent was distilled off under reduced pressure, followed by vacuum drying, to afford the desired compound (170 mg, yield 82%) as a white solid.

$^1$H-NMR (CDCl$_3$, 400 MHz): δ 2.10-2.17 (2H, m), 3.82 (4H, t, J=7.8 Hz), 7.28-7.30 (2H, m), 7.88-7.92 (2H, m).

(55b) 2-(5-{3-[4-(Azetidin-1-ylsulfonyl)phenoxy]-5-[(1S)-2-methoxy-1-methylethoxy]phenyl}-1H-pyrrol-2-yl)-1,3-thiazole t-Butyl 2-{3-hydroxy-5-[(1S)-2-methoxy-1-methylethoxy]phenyl}-5-(1,3-thiazol-2-yl)-1H-pyrrole-1-carboxylate (60.0 mg, 0.139 mmol) synthesized in Example (38d) and 1-[(4-fluorophenyl)sulfonyl]azetidine (60.0 mg, 0.279 mmol) synthesized in Example (55a) were dissolved in N-methylpyrrolidone (5.0 mL), and sodium hydride (60%, 24 mg, 0.60 mmol) was added, followed by stirring at 100° C. for 6 hours under nitrogen atmosphere. The reaction solution was cooled to room temperature, water (20 mL) was added, and extraction was carried out with ethyl acetate (30 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=0%-35%) to afford the desired compound (42 mg, yield 57%) as a white solid.

$^1$H-NMR (CDCl$_3$, 400 MHz): δ 1.37 (3H, d, J=6.8 Hz), 2.12-2.18 (2H, m), 3.45 (3H, s), 3.54 (1H, dd, J=10.3, 4.4 Hz), 3.64 (1H, dd, J=10.0, 6.1 Hz), 3.83 (4H, t, J=7.6 Hz), 4.59-4.65 (1H, m), 6.57 (1H, t, J=3.4 Hz), 6.60 (1H, t, J=2.0 Hz), 6.76 (1H, t, J=3.7 Hz), 6.92 (1H, s), 7.07 (1H, s), 7.18 (2H, d, J=8.3 Hz), 7.21 (1H, d, J=2.9 Hz), 7.71 (1H, d, J=2.9 Hz), 7.84 (2H, d, J=8.8 Hz), 9.76 (1H, br s).

MS (ESI) m/z: 526.14773 (M+H)$^+$.

Example 56

2-(5-{3-[4-(Azetidin-1-ylsulfonyl)-2-fluorophenoxy]-5-[(1S)-2-methoxy-1-methylethoxy]phenyl}-1H-pyrrol-2-yl)-1,3-thiazole

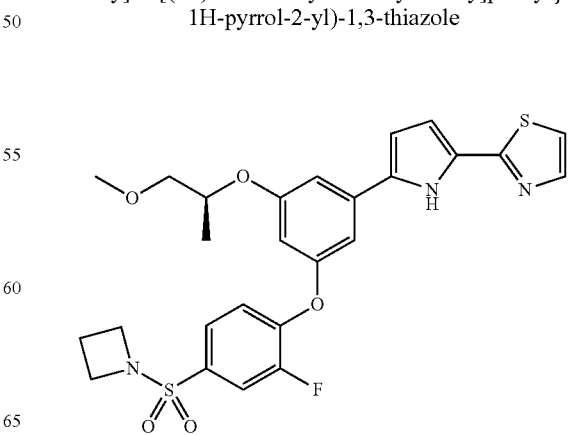

(56a) 1-[(3,4-Difluorophenyl)sulfonyl]azetidine

Commercially available 3,4-difluorophenylsulfonylchloride (117 μL, 0.87 mmol) was dissolved in dichloromethane (5 mL), and azetidine hydrochloride (68 mg, 0.73 mmol) and triethylamine (203 μL, 1.45 mmol) were added, followed by stirring at room temperature for 2 hours. To the reaction solution, water (15 mL) was added, and extraction was carried out twice with dichloromethane (15 mL). Washing was carried out with saturated brine (15 mL), followed by drying over sodium sulfate. The solvent was distilled off under reduced pressure, and the resulting residue was purified using silica gel column chromatography (elution solvent: ethyl acetate/hexane=10%-50%) to afford the desired compound (132 mg, yield 78%) as a colorless oil.

$^1$H-NMR (CDCl$_3$, 400 MHz): δ 2.10-2.18 (2H, m), 3.82 (4H, t, J=7.6 Hz), 7.35-7.41 (1H, m), 7.66-7.62 (1H, m), 7.72-7.68 (1H, m).

(56b) 2-(5-{3-[4-(Azetidin-1-ylsulfonyl)-2-fluorophenoxy]-5-[(1S)-2-methoxy-1-methylethoxy]phenyl}-1H-pyrrol-2-yl)-1,3-thiazole t-Butyl 2-{3-hydroxy-5-[(1S)-2-methoxy-1-methylethoxy]phenyl}-5-(1,3-thiazol-2-yl)-1H-pyrrole-1-carboxylate (65.0 mg, 0.151 mmol) synthesized in Example (38d) and 1-[(3,4-difluorophenyl)sulfonyl]azetidine (42.3 mg, 0.181 mmol) synthesized in Example (56a) were dissolved in N-methylpyrrolidone (5.0 mL), and sodium hydride (55%, 20 mg, 0.45 mmol) was added, followed by stirring at 100° C. for 4 hours under nitrogen atmosphere. The reaction solution was cooled to room temperature, a saturated aqueous ammonium chloride solution (20 mL) was added, and extraction was carried out with ethyl acetate (30 mL). The organic layer was washed with saturated brine, and subsequently dried over anhydrous magnesium sulfate. The solvent was distilled off under reduced pressure, and the resulting residue was purified twice using silica gel column chromatography (elution solvent: ethyl acetate/hexane=0%-35%) to afford the desired compound (35.6 mg, yield 43%) as a white solid.

$^1$H-NMR (CDCl$_3$, 400 MHz): δ 1.34 (3H, d, J=6.3 Hz), 2.11-2.20 (2H, m), 3.42 (3H, s), 3.51 (1H, dd, J=10.4, 4.1 Hz), 3.60 (1H, dd, J=10.4, 6.1 Hz), 3.84 (4H, t, J=7.6 Hz), 4.55-4.63 (1H, m), 6.53-6.56 (2H, m), 6.73 (1H, dd, J=3.9, 2.3 Hz), 6.89 (1H, t, J=2.0 Hz), 7.03 (1H, t, J=1.8 Hz), 7.14 (1H, t, J=8.0 Hz), 7.18 (1H, d, J=3.5 Hz), 7.57 (1H, d, J=8.6 Hz), 7.67-7.71 (2H, m), 9.79 (1H, br s).

MS (ESI) m/z: 544.13720 (M+H)$^+$.

Example 57

3-Fluoro-4-{3-[(1S)-2-methoxy-1-methylethoxy]-5-[5-(1,3-thiazol-2-yl)-1H-pyrrol-2-yl]phenoxy}-N,N-dimethylbenzenesulfonamide

(57a) 3,4-Difluoro-N,N-dimethylbenzenesulfonamide

Commercially available 3,4-difluorophenylsulfonylchloride (117 μL, 0.87 mmol) was dissolved in dichloromethane (5 mL), and dimethylamine hydrochloride (59 mg, 0.73 mmol) and triethylamine (203 μL, 1.45 mmol) were added, followed by stirring at room temperature for 2 hours. To the reaction solution, water (15 mL) was added, followed by extraction twice with dichloromethane (15 mL), and washing was carried out with saturated brine (15 mL), followed by drying over sodium sulfate. The solvent was distilled off under reduced pressure, followed by vacuum drying, to afford the desired compound (41.0 mg, yield 26%) as a colorless oil.

$^1$H-NMR (CDCl$_3$, 400 MHz): δ 2.74 (6H, s), 7.32-7.38 (1H, m), 7.59-7.55 (1H, m), 7.61-7.66 (1H, m).

(57b) 3-Fluoro-4-{3-[(1S)-2-methoxy-1-methylethoxy]-5-[5-(1,3-thiazol-2-yl)-1H-pyrrol-2-yl]phenoxy}-N,N-dimethylbenzenesulfonamide t-Butyl 2-{3-hydroxy-5-[(1S)-2-methoxy-1-methylethoxy]phenyl}-5-(1,3-thiazol-2-yl)-1H-pyrrole-1-carboxylate (65.0 mg, 0.151 mmol) synthesized in Example (38d) and 3,4-difluoro-N,N-dimethylbenzenesulfonamide (40.1 mg, 0.181 mmol) synthesized in Example (57a) were dissolved in N-methylpyrrolidone (5.0 mL), and sodium hydride (55%, 20 mg, 0.45 mmol) was added, followed by stirring at 100° C. for 4 hours under nitrogen atmosphere. The reaction solution was cooled to room temperature, a saturated aqueous ammonium chloride solution (20 mL) was added, and extraction was carried out with ethyl acetate (30 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=0%-35%) to afford the desired compound (31.0 mg, yield 39%) as a white solid.

$^1$H-NMR (CDCl$_3$, 400 MHz): δ 1.34 (3H, d, J=6.3 Hz), 2.76 (6H, s), 3.42 (3H, s), 3.51 (1H, dd, J=10.4, 4.1 Hz), 3.60 (1H, dd, J=10.4, 6.1 Hz), 4.55-4.62 (1H, m), 6.53-6.55 (2H, m), 6.73 (1H, dd, J=3.7, 2.5 Hz), 6.87 (1H, t, J=1.8 Hz), 7.02 (1H, t, J=1.8 Hz), 7.12 (1H, t, J=8.0 Hz), 7.18 (1H, d, J=3.5 Hz), 7.52-7.49 (1H, m), 7.63 (1H, dd, J=9.8, 2.0 Hz), 7.68 (1H, d, J=3.1 Hz), 9.79 (1H, s).

MS (ESI) m/z: 532.13886 (M+H)$^+$.

Example 58

3-Fluoro-4-{3-[(1S)-2-methoxy-1-methylethoxy]-5-[5-(1,3-thiazol-2-yl)-1H-pyrrol-2-yl]phenoxy}-N-methylbenzenesulfonamide

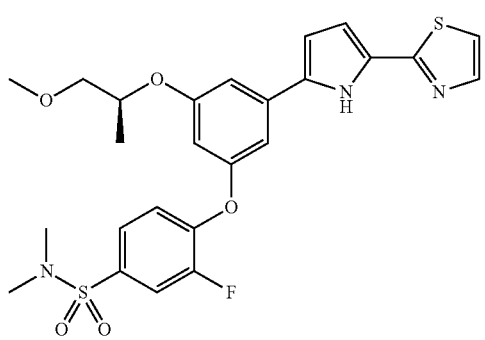

(58a) 3,4-Difluoro-N-methylbenzenesulfonamide

Commercially available 3,4-difluorophenylsulfonylchloride (117 μL, 0.87 mmol) was dissolved in dichloromethane (5 mL), and methylamine hydrochloride (49 mg, 0.73 mmol) and triethylamine (203 μL, 1.45 mmol) were added, followed by stirring at room temperature for 2 hours. To the reaction solution, water (15 mL) was added, extraction was carried out twice with dichloromethane (15 mL), and washing was carried out with saturated brine (15 mL), followed by drying over sodium sulfate. The solvent was distilled off under reduced pressure, followed by vacuum drying, to afford the desired compound (44.7 mg, yield 30%) as a colorless oil.

$^1$H-NMR (CDCl$_3$, 400 MHz): δ 2.70 (3H, d, J=5.5 Hz), 4.43 (1H, br s), 7.36-7.30 (1H, m), 7.64-7.68 (1H, m), 7.69-7.74 (1H, m).

(58b) 3-Fluoro-4-{3-[(1S)-2-methoxy-1-methylethoxy]-5-[5-(1,3-thiazol-2-yl)-1H-pyrrol-2-yl]phenoxy}-N-methylbenzenesulfonamide t-Butyl 2-{3-hydroxy-5-[(1S)-2-methoxy-1-methylethoxy]phenyl}-5-(1,3-thiazol-2-yl)-1H-pyrrole-1-carboxylate (60.0 mg, 0.139 mmol) synthesized in Example (38d) and 3,4-difluoro-N-methylbenzenesulfonamide (47.4 mg, 0.229 mmol) synthesized in Example (58a) were dissolved in N,N-dimethylformamide (5.0 mL), and potassium carbonate (77.0 mg, 0.557 mmol) was added, followed by stirring at 100° C. for 19 hours under nitrogen atmosphere. The reaction solution was cooled to room temperature, water (20 mL) was added, and extraction was carried out with ethyl acetate (30 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=0%-25%) to afford the desired compound (21.1 mg, yield 30%) as a white solid.

$^1$H-NMR (CDCl$_3$, 400 MHz): δ 1.33 (4H, d, J=5.9 Hz), 2.69 (3H, d, J=5.4 Hz), 3.42 (3H, s), 3.51 (1H, dd, J=10.3, 4.4 Hz), 3.60 (1H, dd, J=10.3, 5.9 Hz), 4.55-4.61 (1H, m), 5.22 (1H, s), 6.55 (2H, dt, J=8.3, 2.7 Hz), 6.74 (1H, t, J=2.9 Hz), 6.89 (1H, s), 7.01 (1H, t, J=1.7 Hz), 7.12 (1H, t, J=8.1 Hz), 7.16-7.18 (1H, m), 7.56-7.61 (2H, m), 7.69 (1H, d, J=9.8 Hz), 9.96 (1H, br s).

MS (ESI) m/z: 518.12006 (M+H)$^+$.

Example 59

5-(Azetidin-1-ylcarbonyl)-2-{3-[(1S)-2-methoxy-1-methylethoxy]-5-[5-(1,3-thiazol-2-yl)-1H-pyrrol-2-yl]phenoxyl}pyridine

(59a) 5-(Azetidin-1-ylcarbonyl)-2-chloropyridine

Commercially available 6-chloronicotinic acid (160 mg, 1.01 mmol) was dissolved in dichloromethane (5 mL), and azetidine hydrochloride (130 mg, 1.39 mmol), HATU (420 mg, 1.10 mmol) and N,N-diisopropylethylamine (0.50 mL, 2.87 mmol) were added, followed by stirring at room temperature overnight under nitrogen atmosphere. The solvent was distilled off under reduced pressure, and the resulting residue was purified using silica gel column chromatography (elution solvent: ethyl acetate/hexane=40%-50%) to afford the desired compound (210 mg, yield ~100%) as a colorless liquid.

$^1$H-NMR (CDCl$_3$, 400 MHz): δ 2.40 (2H, m), 4.25 (2H, t, J=7.6 Hz), 4.35 (2H, t, J=7.6 Hz), 7.40 (1H, dd, J=0.8, 8.6 Hz), 7.97 (1H, dd, J=2.4, 8.2 Hz), 8.62 (1H, dd, J=0.8, 2.4 Hz).

(59b) 5-(Azetidin-1-ylcarbonyl)-2-{3-[(1S)-2-methoxy-1-methylethoxy]-5-[5-(1,3-thiazol-2-yl)-1H-pyrrol-2-yl]phenoxy}pyridine t-Butyl 2-{3-hydroxy-5-[(1S)-2-methoxy-1-methylethoxy]phenyl}-5-(1,3-thiazol-2-yl)-1H-pyrrole-1-carboxylate (84 mg, 0.195 mmol) synthesized in Example (38d) and 5-(azetidin-1-ylcarbonyl)-2-chloropyridine (110 mg, 0.559 mmol) synthesized in Example (59a) were dissolved in dimethyl sulfoxide (3.0 mL), and sodium hydride (60%, 30 mg, 0.75 mmol) was added, followed by stirring at 100° C. for 2 hours under nitrogen atmosphere. The reaction solution was cooled to room temperature, 2N hydrochloric acid (30 mL) was added, and extraction was carried out with ethyl acetate (30 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=75%-90%) to afford the desired compound (56 mg, yield 59%) as a yellow solid.

$^1$H-NMR (CDCl$_3$, 400 MHz): δ 1.34 (3H, d, J=6.3 Hz), 2.38 (2H, m), 3.42 (3H, s), 3.50 (1H, dd, J=4.3, 10.2 Hz), 3.60 (1H, dd, J=5.9, 10.2 Hz), 4.24 (2H, t, J=7.4 Hz), 4.36 (2H, t, J=6.6 Hz), 4.57 (1H, m), 6.54 (1H, dd, J=2.7, 3.9 Hz), 6.64 (1H, t, J=2.3 Hz), 6.73 (1H, dd, J=2.4, 3.9 Hz), 6.97 (2H, m), 7.07 (1H, t, J=1.8 Hz), 7.16 (1H, d, J=3.5 Hz), 7.67 (1H, d, J=3.1 Hz), 8.07 (1H, dd, J=2.7, 8.6 Hz), 8.45 (1H, d, J=2.4 Hz), 9.85 (1H, brs).

MS (ESI) m/z: 491.17450 (M+H)$^+$.

Example 60

5-(Azetidin-1-ylcarbonyl)-3-chloro-2-{3-[(1S)-2-methoxy-1-methylethoxy]-5-[5-(1,3-thiazol-2-yl)-1H-pyrrol-2-yl]phenoxyl}pyridine

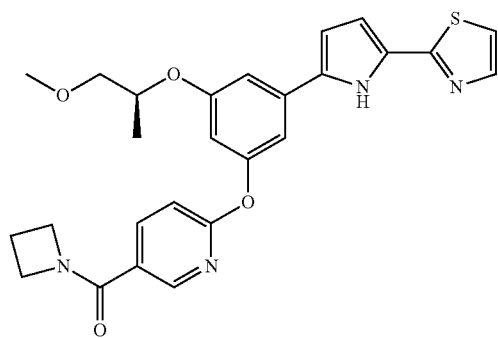

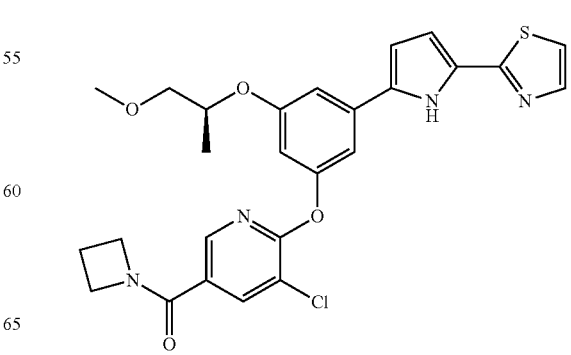

(60a) 5-(Azetidin-1-ylcarbonyl)-2,3-dichloropyridine

Commercially available 5,6-dichloronicotinic acid (200 mg, 1.04 mmol) was dissolved in dichloromethane (5.0 mL), and azetidine hydrochloride (125 mg, 1.34 mmol), HATU (440 mg, 1.16 mmol) and N,N-diisopropylethylamine (0.45 mL, 2.58 mmol) were added, followed by stirring at room temperature for 5 hours under nitrogen atmosphere. 0.5N hydrochloric acid (30 mL) was added, and extraction was carried out with dichloromethane (30 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=60%-80%) to afford the desired compound (162 mg, yield 67%) as a colorless liquid.

$^1$H-NMR (CDCl$_3$, 400 MHz): δ 2.38-2.46 (2H, m), 4.25 (2H, t, J=7.6 Hz), 4.37 (2H, t, J=7.6 Hz), 8.10 (1H, d, J=2.3 Hz), 8.51 (1H, d, J=2.3 Hz).

(60b) 5-(Azetidin-1-ylcarbonyl)-3-chloro-2-{3-[(1S)-2-methoxy-1-methylethoxy]-5-[5-(1,3-thiazol-2-yl)-1H-pyrrol-2-yl]phenoxyl}pyridine t-Butyl 2-{3-hydroxy-5-[(1S)-2-methoxy-1-methylethoxy]phenyl}-5-(1,3-thiazol-2-yl)-1H-pyrrole-1-carboxylate (70 mg, 0.163 mmol) synthesized in Example (38d) and 5-(azetidin-1-ylcarbonyl)-2,3-dichloropyridine (75 mg, 0.325 mmol) synthesized in Example (60a) were dissolved in dimethyl sulfoxide (5.0 mL), and sodium hydride (60%, 30 mg, 0.75 mmol) was added, and stirring was carried out at 100° C. for 3.5 hours under nitrogen atmosphere. The reaction solution was cooled to room temperature, a saturated aqueous ammonium chloride solution (30 mL) was added, and extraction was carried out with ethyl acetate (30 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=85%-100%) to afford the desired compound (58 mg, yield 68%) as a yellow solid.

$^1$H-NMR (CDCl$_3$, 400 MHz): δ 1.35 (3H, d, J=5.9 Hz), 2.34-2.42 (2H, m), 3.42 (3H, s), 3.51 (1H, dd, J=10.6, 4.7 Hz), 3.61 (1H, dd, J=10.4, 5.7 Hz), 4.21-4.27 (2H, m), 4.34-4.37 (2H, m), 4.56-4.59 (1H, m), 6.54 (1H, t, J=2.9 Hz), 6.66 (1H, t, J=1.8 Hz), 6.72 (1H, t, J=2.9 Hz), 6.96 (1H, s), 7.05 (1H, s), 7.16 (1H, dd, J=3.3, 0.6 Hz), 7.68 (1H, dd, J=3.3, 0.6 Hz), 8.16 (1H, dd, J=2.0, 0.8 Hz), 8.26 (1H, dd, J=1.8, 1.0 Hz), 9.57 (1H, br s).

MS (ESI) m/z: 525.13929 (M+H)$^+$.

Example 61

5-(Azetidin-1-ylcarbonyl)-2-{3-[(1S)-2-methoxy-1-methylethoxy]-5-[5-(1,3-thiazol-2-yl)-1H-pyrrol-2-yl]phenoxy}-3-methylpyridine

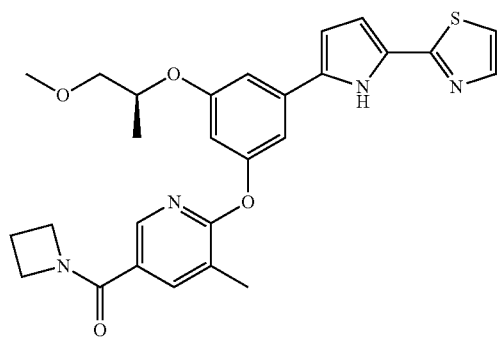

(61a) 5-(Azetidin-1-ylcarbonyl)-2-chloro-3-methylpyridine

Commercially available 6-chloro-5-methylnicotinic acid (200 mg, 1.29 mmol) was dissolved in dichloromethane (7.0 mL), and azetidine hydrochloride (160 mg, 1.71 mmol), HATU (1000 mg, 2.63 mmol) and N,N-diisopropylethylamine (0.69 mL, 3.96 mmol) were added, followed by stirring at room temperature overnight under nitrogen atmosphere. 0.5N hydrochloric acid (30 mL) was added, and extraction was carried out with dichloromethane (30 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=60%-75%) to afford the desired compound (160 mg, yield 64%) as a colorless liquid.

$^1$H-NMR (CDCl$_3$, 400 MHz): δ 2.32 (3H, s), 2.36-2.42 (2H, m), 4.24 (2H, t, J=7.6 Hz), 4.35 (2H, t, J=7.6 Hz), 7.95 (1H, dd, J=9.3, 1.0 Hz), 8.26 (1H, d, J=1.0 Hz).

(61b) 5-(Azetidin-1-ylcarbonyl)-2-{3-[(1S)-2-methoxy-1-methylethoxy]-5-[5-(1,3-thiazol-2-yl)-1H-pyrrol-2-yl]phenoxy}-3-methylpyridine t-Butyl 2-{3-hydroxy-5-[(1S)-2-methoxy-1-methylethoxy]phenyl}-5-(1,3-thiazol-2-yl)-1H-pyrrole-1-carboxylate (59 mg, 0.137 mmol) synthesized in Example (38d) and 5-(azetidin-1-ylcarbonyl)-2-chloro-3-methylpyridine (45 mg, 0.232 mmol) synthesized in Example (61a) were dissolved in dimethyl sulfoxide (3.0 mL), and sodium hydride (60%, 25 mg, 0.63 mmol) was added, followed by stirring at 80° C. for 4.5 hours under nitrogen atmosphere. The reaction solution was cooled to room temperature, a saturated aqueous ammonium chloride solution (30 mL) was added, and extraction was carried out with ethyl acetate (30 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=60%-80%) to afford the desired compound (50 mg, yield 72%) as a yellow solid.

$^1$H-NMR (CDCl$_3$, 400 MHz): δ 1.35 (3H, d, J=6.3 Hz), 2.32-2.38 (2H, m), 2.40 (3H, s), 3.42 (3H, s), 3.51 (1H, dd, J=10.2, 4.3 Hz), 3.60 (1H, dd, J=10.2, 5.9 Hz), 4.23 (2H, t, J=7.2 Hz), 4.34 (2H, t, J=6.6 Hz), 4.56-4.58 (1H, m), 6.53 (1H, dd, J=3.9, 2.7 Hz), 6.63 (1H, t, J=2.0 Hz), 6.72 (1H, dd, J=3.9, 2.3 Hz), 6.92 (1H, t, J=1.8 Hz), 7.00 (1H, dd, J=3.9, 1.6 Hz), 7.16 (1H, d, J=3.1 Hz), 7.67 (1H, d, J=3.1 Hz), 7.94 (1H, dd, J=2.3, 0.8 Hz), 8.22 (1H, d, J=2.3 Hz), 9.46 (1H, br s).

MS (ESI) m/z: 505.19091 (M+H)$^+$.

Example 62

Methyl 5-{3-[(1S)-2-methoxy-1-methylethoxy]-5-[5-(1,3-thiazol-2-yl)-1H-pyrrol-2-yl]phenoxyl}pyrazine-2-carboxylate

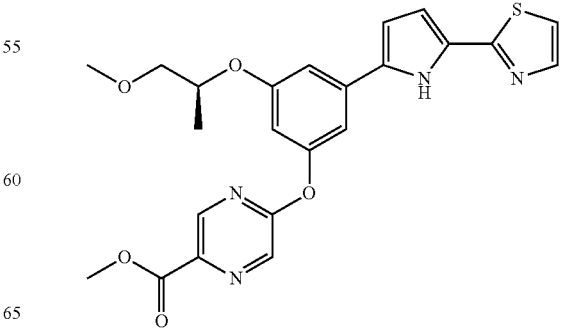

(62a) Methyl 5-hydroxypyrazine-2-carboxylate

Commercially available 5-hydroxypyrazine-2-carboxylic acid (1.00 g, 7.14 mmol) was dissolved in methanol (5 mL), and a 4N hydrochloric acid/dioxane solution (25 mL) was added, followed by stirring at 60° C. for 1.5 hours and heating to reflux at 80° C. for 2.5 hours. The reaction solution was brought back to room temperature, the solvent was distilled off under reduced pressure, and ethyl acetate (20 mL) was added to the resulting residue to allow it to be suspended. The resulting precipitate was filtered off, and washed with ethyl acetate, followed by vacuum drying, to afford the desired compound (673 mg, yield 61%) as an orange-brown solid.

$^1$H-NMR (CD$_3$OD, 400 MHz): δ 3.31 (1H, s), 3.85 (3H, s), 8.00 (1H, d, J=1.2 Hz), 8.13 (1H, d, J=1.2 Hz).

(62b) Methyl 5-Chloropyrazine-2-carboxylate

Methyl 5-hydroxypyrazine-2-carboxylate (673 mg, 4.37 mmol) synthesized in Example (62a) was dissolved in phosphorous oxytrichloride (6.1 mL), and a few drops of N,N-dimethylformamide were added, followed by heating to reflux for 2 hours under nitrogen atmosphere. The reaction solution was poured into ice water, and extraction was carried out three times with chloroform (30 mL). The organic layer was washed with saturated aqueous sodium hydrogencarbonate solution and saturated brine (100 mL each), and subsequently dried over sodium sulfate. The solvent was distilled off under reduced pressure to afford the desired compound (611 mg, yield 81%) as a gray solid.

$^1$H-NMR (CDCl$_3$, 400 MHz): δ 4.05 (3H, s), 8.71 (1H, d, J=1.6 Hz), 9.10 (1H, d, J=1.2 Hz).

(62c) Methyl 5-{3-[(1S)-2-methoxy-1-methylethoxy]-5-[5-(1,3-thiazol-2-yl)-1H-pyrrol-2-yl]phenoxyl}pyrazine-2-carboxylate t-Butyl 2-{3-hydroxy-5-[(1S)-2-methoxy-1-methylethoxy]phenyl}-5-(1,3-thiazol-2-yl)-1H-pyrrole-1-carboxylate (200 mg, 0.464 mmol) synthesized in Example (38d) and methyl 5-chloropyrazine-2-carboxylate (120 mg, 0.695 mmol) synthesized in Example (62b) were dissolved in N,N-dimethylformamide (10 mL), and potassium carbonate (257 mg, 1.86 mmol) was added, followed by stirring at 80° C. for 7 hours under nitrogen atmosphere. The reaction solution was cooled to room temperature, water (40 mL) was added, and extraction was carried out with ethyl acetate (40 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=0%-50%). The resulting yellow solid was dissolved in dichloromethane (2 mL), and trifluoroacetic acid (4 mL) was added, followed by stirring at room temperature for 1.5 hours. To the reaction solution, a saturated aqueous sodium hydrogencarbonate solution (40 mL) was added, and extraction was carried out twice with ethyl acetate (40 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=0%-50%) to afford the desired compound (164 mg, yield 93%) as a yellow solid.

$^1$H-NMR (CDCl$_3$, 400 MHz): δ 1.35 (3H, d, J=6.3 Hz), 3.42 (3H, s), 3.52 (1H, dd, J=10.2, 4.3 Hz), 3.60 (1H, dd, J=10.2, 5.9 Hz), 4.02 (3H, s), 4.56-4.63 (1H, m), 6.55 (1H, dd, J=3.9, 2.7 Hz), 6.67 (1H, t, J=2.2 Hz), 6.75 (1H, dd, J=3.9, 2.3 Hz), 6.98 (1H, t, J=1.8 Hz), 7.10 (1H, t, J=1.8 Hz), 7.18 (1H, d, J=3.5 Hz), 7.68 (1H, d, J=3.1 Hz), 8.51 (1H, d, J=1.2 Hz), 8.87 (1H, d, J=1.2 Hz), 9.74 (1H, br s).

MS (ESI) m/z: 467 (M+H)$^+$.

Example 63

2-(Azetidin-1-ylcarbonyl)-5-{3-[(1S)-2-methoxy-1-methylethoxy]-5-[5-(1,3-thiazol-2-yl)-1H-pyrrol-2-yl]phenoxyl}pyrazine

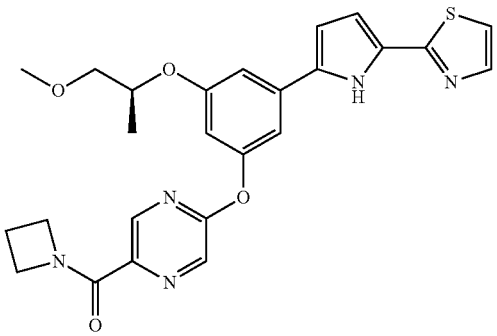

(63a) 5-{3-[(1S)-2-Methoxy-1-methylethoxy]-5-[5-(1,3-thiazol-2-yl)-1H-pyrrol-2-yl]phenoxyl}pyrazine-2-carboxylic acid Methyl 5-{3-[(1S)-2-methoxy-1-methylethoxy]-5-[5-(1,3-thiazol-2-yl)-1H-pyrrol-2-yl]phenoxyl}pyrazine-2-carboxylate (423 mg, 0.907 mmol) synthesized in Example (62c) was dissolved in methanol (10 mL), and water (2 mL) and lithium hydroxide monohydrate (76.2 mg, 1.82 mmol) were added, followed by stirring at 50° C. for 1 hour under nitrogen atmosphere. To the reaction solution, water (30 mL) was added, and extraction was carried out twice with ethyl acetate (30 mL), followed by drying over sodium sulfate. The solvent was distilled off under reduced pressure, and the resulting residue was purified using silica gel column chromatography (elution solvent: dichloromethane/methanol=0%-10%) to afford the desired compound (269 mg, yield 66%) as a pale yellow solid.

$^1$H-NMR (CDCl$_3$, 400 MHz): δ 1.38 (3H, d, J=6.3 Hz), 3.44 (3H, s), 3.54 (1H, dd, J=10.2, 4.3 Hz), 3.63 (1H, dd, J=10.2, 5.9 Hz), 4.60-4.65 (1H, m), 6.62 (1H, dd, J=3.9, 2.3 Hz), 6.71 (1H, t, J=2.2 Hz), 6.82 (1H, dd, J=3.9, 2.3 Hz), 7.16-7.18 (2H, m), 7.37 (1H, s), 7.67 (1H, d, J=3.5 Hz), 8.54 (1H, d, J=1.2 Hz), 8.81 (1H, s), 11.30 (1H, br s).

(63b) 2-(Azetidin-1-ylcarbonyl)-5-{3-[(1S)-2-methoxy-1-methylethoxy]-5-[5-(1,3-thiazol-2-yl)-1H-pyrrol-2-yl]phenoxy}pyrazine 5-{3-[(1S)-2-Methoxy-1-methylethoxy]-5-[5-(1,3-thiazol-2-yl)-1H-pyrrol-2-yl]phenoxy}pyrazine-2-carboxylic acid (28.0 mg, 0.062 mmol) synthesized in Example (63a) was dissolved in tetrahydrofuran (3 mL), and azetidine hydrochloride (17.4 mg, 0.186 mmol), HATU (35.3 mg, 0.093 mmol) and N,N-diisopropylethylamine (65 μL, 0.37 mmol) were added, followed by stirring at room temperature for 28 hours under nitrogen atmosphere. To the reaction solution, water (15 mL) was added, and extraction was carried out with ethyl acetate (15 mL), followed by drying over sodium sulfate. The solvent was distilled off under reduced pressure, and the resulting residue was purified using preparative TLC (developing solvent: methanol/dichloromethane=15%) to afford the desired compound (29.1 mg, yield 96%) as a white solid.

$^1$H-NMR (CDCl$_3$, 400 MHz): δ 1.35 (3H, d, J=5.9 Hz), 2.35-2.41 (2H, m), 3.42 (3H, s), 3.51 (1H, dd, J=10.3, 3.9 Hz), 3.60 (1H, dd, J=10.3, 5.9 Hz), 4.26 (2H, t, J=7.8 Hz), 4.54-4.60 (1H, m), 4.69 (2H, t, J=7.8 Hz), 6.54 (1H, t, J=3.2 Hz), 6.65 (1H, s), 6.73 (1H, t, J=2.9 Hz), 6.95 (1H, s), 7.06 (1H, t, J=1.7 Hz), 7.17 (1H, d, J=2.9 Hz), 7.67 (1H, d, J=3.4 Hz), 8.31 (1H, s), 8.88 (1H, s), 9.69 (1H, br s).

MS (ESI) m/z: 492.16821 (M+H)$^+$.

Example 64

2-{3-[(1S)-2-Methoxy-1-methylethoxy]-5-[5-(1,3-thiazol-2-yl)-1H-pyrrol-2-yl]phenoxy}-5-[(4-methylpiperazin-1-yl)carbonyl]pyrazine

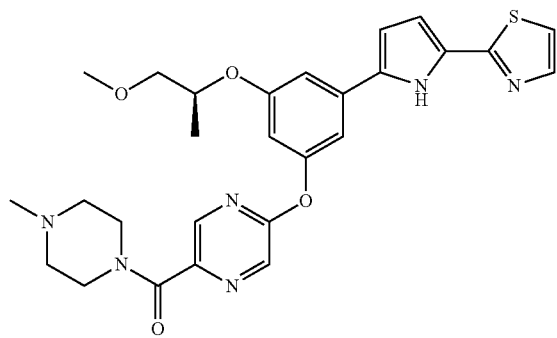

5-{3-[(1S)-2-Methoxy-1-methylethoxy]-5-[5-(1,3-thiazol-2-yl)-1H-pyrrol-2-yl]phenoxyl}pyrazine-2-carboxylic acid (40.4 mg, 0.089 mmol) synthesized in Example (63a) was dissolved in tetrahydrofuran (5 mL), and 1-methylpiperazine (30 μL, 0.27 mmol), HATU (67.9 mg, 0.18 mmol) and N,N-diisopropylethylamine (93 μL, 0.54 mmol) were added, followed by stirring at room temperature for 12 hours under nitrogen atmosphere. To the reaction solution, water (15 mL) was added, and extraction was carried out with ethyl acetate (15 mL), followed by drying over sodium sulfate. The solvent was distilled off under reduced pressure, and the resulting residue was purified using silica gel column chromatography (elution solvent: methanol/dichloromethane=0%-5%) to afford the desired compound (47 mg, yield 98%) as a pale yellow solid.

$^1$H-NMR (CDCl$_3$, 400 MHz): δ 1.35 (3H, d, J=6.3 Hz), 2.37 (3H, s), 2.50 (2H, br s), 2.56 (2H, br s), 3.42 (3H, s), 3.52 (1H, dd, J=10.2, 4.3 Hz), 3.61 (1H, dd, J=10.4, 6.1 Hz), 3.75 (2H, br s), 3.85 (2H, br s), 4.54-4.62 (1H, m), 6.54 (1H, t, J=3.3 Hz), 6.65 (1H, t, J=2.0 Hz), 6.73 (1H, dd, J=3.9, 2.3 Hz), 6.95 (1H, t, J=1.8 Hz), 7.06 (1H, t, J=1.8 Hz), 7.17 (1H, d, J=3.1 Hz), 7.68 (1H, d, J=3.1 Hz), 8.35 (1H, d, J=1.2 Hz), 8.56 (1H, d, J=1.2 Hz), 9.59 (1H, br s).

MS (ESI) m/z: 535.21022 (M+H)$^+$.

Example 65

5-{3-[(1S)-2-Methoxy-1-methylethoxy]-5-[5-(1,3-thiazol-2-yl)-1H-pyrrol-2-yl]phenoxy}-2-(methylsulfonyl)pyridine

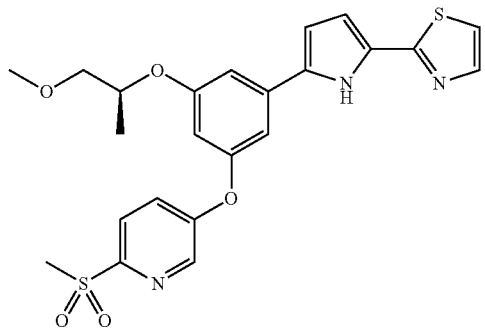

(65a) 5-Bromo-2-(methylthio)pyridine

Commercially available 2,5-dibromo pyridine (6.01 g, 25.4 mmol) was dissolved in N,N-dimethylformamide (50 mL), and sodium thiomethoxide (2.20 g, 31.4 mmol) was added, followed by stirring at 0° C. for 3.5 hours under nitrogen atmosphere. The reaction solution was brought back to room temperature, water (250 mL) was added, and extraction was carried out with diethyl ether (250 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=3%-5%) to afford the desired compound (4.90 g, yield 94%) as a white solid.

$^1$H-NMR (CDCl$_3$, 400 MHz): δ 2.54 (3H, s), 7.08 (1H, d, J=8.2 Hz), 7.58 (1H, dd, J=8.6, 2.3 Hz), 8.49 (1H, d, J=2.0 Hz).

(65b) 5-Fluoro-2-(methylsulfonyl)pyridine

5-Bromo-2-(methylthio)pyridine (4.90 g, 24.0 mmol) synthesized in Example (65a) was dissolved in tetrahydrofuran (100 mL), and n-butyl lithium (1.57 mol/L hexane solution, 17.0 mL, 26.7 mmol) was added dropwise at −78° C., followed by stirring at −78° C. for 1 hour under nitrogen atmosphere. N-fluorobenzenesulfonimide (11.0 g, 34.9 mmol) was dissolved in tetrahydrofuran (25 mL), followed by dropwise addition to the reaction solution at −78° C., and stirring was carried out at −78° C. for 2 hours under nitrogen atmosphere. The reaction solution was brought back to room temperature, and stirring was carried out for 1.5 hours. A saturated aqueous ammonium chloride solution (200 mL) was added, and extraction was carried out with diethyl ether (300 mL). The organic layer was washed with saturated brine, and subsequently dried over anhydrous magnesium sulfate. The solvent was distilled off under slightly reduced pressure.

The resulting residue was dissolved in methylene chloride (150 mL), and m-chloroperbenzoic acid (65%, 16.5 g, 62.1 mmol) was slowly added at 0° C., followed by stirring at 0° C. for 1.5 hours under nitrogen atmosphere. After removal of white solid material by Celite filtration, a saturated aqueous sodium hydrogencarbonate solution (100 mL) was added, and extraction was carried out with methylene chloride (400 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=3%-5%) to afford the desired compound (1.95 g, yield 46%) as a yellowish white solid.

$^1$H-NMR (CDCl$_3$, 400 MHz): δ 3.24 (3H, s), 7.67 (1H, ddd, J=9.9, 6.9, 1.9 Hz), 8.16 (1H, dd, J=8.6, 4.3 Hz), 8.59 (1H, d, J=2.7 Hz).

(65c) 5-{3-[(1S)-2-Methoxy-1-methylethoxy]-5-[5-(1,3-thiazol-2-yl)-1H-pyrrol-2-yl]phenoxy}-2-(methylsulfonyl)pyridine t-Butyl 2-{3-hydroxy-5-[(1S)-2-methoxy-1-methylethoxy]phenyl}-5-(1,3-thiazol-2-yl)-1H-pyrrole-1-carboxylate (70.0 mg, 0.16 mmol) synthesized in Example (38d) and 5-fluoro-2-(methylsulfonyl)pyridine (35.0 mg, 0.20 mmol) synthesized in Example (65b) were dissolved in N,N-dimethylformamide (5 mL), and stirring was carried out at 90° C. for 3 days under nitrogen atmosphere. To the reaction solution, water (15 mL) was added, followed by extraction with ethyl acetate (30 mL), and washing was carried out with saturated brine (30 ml), followed by drying over sodium sulfate. The solvent was distilled off under reduced pressure, and the resulting residue was purified using silica gel column chromatography (elution solvent: ethyl acetate/hexane=0%-40%) to afford the desired compound (28 mg, yield 35%) as a pale yellow solid.

$^1$H-NMR (CDCl$_3$, 400 MHz): δ 1.33 (3H, d, J=6.3 Hz), 3.24 (3H, s), 3.42 (3H, s), 3.51 (1H, dd, J=10.4, 4.1 Hz), 3.59 (1H, dd, J=10.2, 6.3 Hz), 4.58 (1H, dd, J=10.4, 6.1 Hz), 6.54-6.56 (2H, m), 6.73 (1H, dd, J=3.7, 2.5 Hz), 6.86 (1H, t, J=1.8 Hz), 7.04 (1H, t, J=2.0 Hz), 7.18 (1H, d, J=3.5 Hz), 7.43 (1H, dd, J=8.6, 2.7 Hz), 7.68 (1H, d, J=3.1 Hz), 8.05 (1H, d, J=9.0 Hz), 8.49 (1H, d, J=2.7 Hz), 9.62 (1H, br s).

MS (ESI) m/z: 486.11507 (M+H)$^+$.

Example 66

2-(5-{3-[4-(Azetidin-1-ylcarbonyl)-2-fluorophenoxy]-5-[(1S)-2-methoxy-1-methylethoxy]phenyl}-1H-pyrrol-2-yl)-5-methyl-1,3,4-oxadiazole

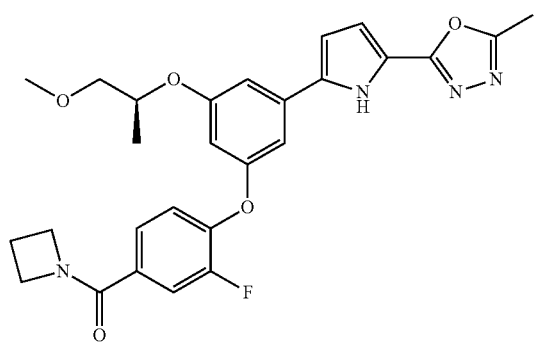

(66a) t-Butyl 2,5-dibromo-1H-pyrrole-1-carboxylate

Commercially available t-butyl 1-pyrrolecarboxylate (46.68 g, 279 mmol) was dissolved in tetrahydrofuran (500 mL), and cooled to −78° C. To this, was added N-bromosuccinimide (100.48 g, 565 mmol) in small portions over 1 hour. The temperature of the reaction solution was raised naturally, and stirring was carried out at room temperature for 18 hours. The reaction solution was cooled to 0° C. followed by addition of sodium sulphite (36.43 g) and stirring for 30 minutes, and subsequently hexane (200 mL) was added to give a precipitate, which was removed by Celite filtration. The solvent of the filtrate was distilled off under reduced pressure, and the resulting residue was purified using silica gel column chromatography (elution solvent: ethyl acetate/hexane=1%-5%) to afford the desired compound (52.69 g, yield 58%) as a colorless oil.

$^1$H-NMR (CDCl$_3$, 500 MHz): δ 1.65 (9H, s), 6.25 (2H, s).
MS (EI) m/z: 323 (M$^+$).

(66b) 2-Benzyl 1-t-butyl 5-bromo-1H-pyrrole-1,2-dicarboxylate t-Butyl 2,5-dibromo-1H-pyrrole-1-carboxylate (10.98 g, 33.8 mmol) synthesized in Example (66a) was dissolved in diethyl ether (135 mL), and cooled to −78° C. n-Butyl lithium (2.77M hexane solution, 12.8 mL, 35.5 mmol) was added dropwise slowly, and stirring was carried out for 1 hour. To the reaction solution, benzyl chloroformate (6.25 mL, 44.0 mmol) was added dropwise slowly, and stirring was carried out for 30 minutes. With the temperature of the reaction solution being gradually raised to room temperature, stirring was carried out for 1 hour. To the reaction solution, were added a saturated aqueous ammonium chloride solution (200 mL) and diethyl ether (300 mL), and the solution was separated. The organic layer was washed with saturated brine, and subsequently dried over sodium sulfate. The solvent was distilled off under reduced pressure, and the resulting residue was purified using silica gel column chromatography (elution solvent: ethyl acetate/hexane=5%-45%) to afford the desired compound (8.80 g, yield 68%) as a reddish brown oil.

$^1$H-NMR (CDCl$_3$, 400 MHz): δ 1.56 (9H, s), 5.26 (2H, s), 6.21 (1H, d, J=3.9 Hz), 6.85 (1H, d, J=3.9 Hz), 7.28-7.39 (5H, m).
MS (FAB) m/z: 380 (M+H)$^+$.

(66c) 2-Benzyl 1-t-butyl 5-{3-hydroxy-5-[(1S)-2-methoxy-1-methylethoxy]phenyl}-1H-pyrrole-1,2-dicarboxylate 2-Benzyl 1-t-butyl 5-bromo-1H-pyrrole-1,2-dicarboxylate (8.75 g, 23.0 mmol) synthesized in Example (66b) and 3-[(1S)-2-methoxy-1-methylethoxy]-5-(4,4,5,5-tetramethyl-1,3,2-dioxaborolan-2-yl)phenol (7.11 g, 23.1 mmol) synthesized in Example (38c) were dissolved in a mixed solvent of 1,4-dioxane (92 mL) and water (23 mL), and [1,1'-bis(diphenylphosphino)ferrocene]palladium (II) dichloride dichloromethane complex (570 mg, 0.698 mmol) and potassium carbonate (7.95 g, 57.5 mmol) were added, followed by stirring at 55° C. for 3 hours under nitrogen atmosphere. After the reaction solution was cooled to room temperature, water (200 mL) was added, and extraction was carried out with ethyl acetate (200 mL). The organic layer was washed with saturated brine, and subsequently dried over anhydrous sodium sulfate. The solvent was distilled off under reduced pressure, and the resulting residue was purified using silica gel column chromatography (elution solvent: ethyl acetate/hexane=15%-35%) to afford the desired compound (8.32 g, yield 75%) as a brown oil.

$^1$H-NMR (CDCl$_3$, 500 MHz): δ 1.29 (3H, d, J=6.3 Hz), 1.41 (9H, s), 3.40 (3H, s), 3.47 (1H, dd, J=10.3, 4.4 Hz), 3.57

(1H, dd, J=10.3, 5.9 Hz), 4.48-4.54 (1H, m), 5.20 (1H, s), 5.30 (2H, s), 6.17 (1H, d, J=3.4 Hz), 6.44 (1H, s), 6.48 (1H, s), 6.57 (1H, s), 6.94 (1H, d, J=3.4 Hz), 7.42-7.31 (5H, m).

MS (FAB) m/z: 481 (M+).

(66d) Benzyl-5-{3-(2-Fluoro-4-formylphenoxy)-5-[(1S)-2-methoxy-1-methylethoxy]phenyl}-1H-pyrrole-2-carboxylate 2-Benzyl 1-t-butyl 5-{3-hydroxy-5-[(1S)-2-methoxy-1-methylethoxy]phenyl}-1H-pyrrole-1,2-dicarboxylate (8.30 g, 17.2 mmol) synthesized in Example (66c) was dissolved in N,N-dimethylformamide (86 mL), and 3,4-difluorobenzaldehyde (2.85 mL, 25.9 mmol) and potassium carbonate (11.96 g, 86.5 mmol) were added, followed by stirring at 90° C. for 24 hours under nitrogen atmosphere. The reaction solution was cooled to room temperature, water (100 mL) was added, and extraction was carried out with diethyl ether (300 mL). The organic layer was washed with saturated brine, and subsequently dried over anhydrous magnesium sulfate.

The solvent was distilled off under reduced pressure to give a residue, which was dissolved in dichloromethane (20 mL), and trifluoroacetic acid (10 mL) was added, followed by stirring at room temperature for 1 hour. The solvent was distilled off under reduced pressure to give a residue, which was dissolved in ethyl acetate (200 mL), and washed with saturated aqueous sodium hydrogencarbonate solution (200 mL). After washing further with saturated brine, drying was carried out over anhydrous magnesium sulfate. The solvent was distilled off under reduced pressure to give a residue, which was purified using silica gel column chromatography (elution solvent: ethyl acetate/hexane=15%-35%) to afford the desired compound (6.34 g, yield 73%) as a white solid.

$^1$H-NMR (CDCl$_3$, 400 MHz): δ 1.32 (3H, d, J=6.3 Hz), 3.40 (3H, s), 3.50 (1H, dd, J=10.2, 3.9 Hz), 3.58 (1H, dd, J=10.4, 6.1 Hz), 4.53-4.60 (1H, m), 5.32 (2H, s), 6.50 (1H, t, J=3.3 Hz), 6.59 (1H, s), 6.83 (1H, s), 6.96-6.98 (2H, m), 7.12 (1H, t, J=8.0 Hz), 7.32-7.44 (5H, m), 7.62 (1H, d, J=8.2 Hz), 7.72 (1H, dd, J=10.4, 1.8 Hz), 9.29 (1H, s), 9.92 (1H, d, J=2.0 Hz).

MS (FAB) m/z: 503 (M+).

(66e) 4-(3-{5-[(Benzyloxy)carbonyl]-1H-pyrrol-2-yl}-5-[(1S)-2-methoxy-1-methylethoxy]phenoxy)-3-fluorobenzoic acid Benzyl 5-{3-(2-Fluoro-4-formylphenoxy)-5-[(1S)-2-methoxy-1-methylethoxy]phenyl}-1H-pyrrole-2-carboxylate (6.33 g, 12.6 mmol) synthesized in Example (66d) was suspended in a mixed solvent of t-butanol (120 mL) and water (40 mL), and sodium dihydrogen phosphate dihydrate (8.86 g, 56.8 mmol) and 2-methyl-2-butene (12.05 mL, 113 mmol) were added. Under ice cooling, sodium chlorite (80%, 2.93 g, 25.9 mmol) was added slowly, and stirring was carried out at room temperature for 2 hours. Saturated brine (200 mL) was added, followed by extraction with dichloromethane (200 mL), and drying was carried out over anhydrous magnesium sulfate to afford the desired compound (7.17 g, yield ~100%) as a pale yellow oil.

$^1$H-NMR (CDCl$_3$, 400 MHz): δ 1.36 (3H, d, J=6.3 Hz), 3.43 (3H, s), 3.53 (1H, dd, J=10.2, 3.9 Hz), 3.62 (1H, dd, J=10.2, 5.9 Hz), 4.58-4.65 (1H, m), 5.34 (2H, s), 6.55 (1H, dd, J=3.9, 2.7 Hz), 6.69 (1H, t, J=2.0 Hz), 7.02-7.06 (3H, m), 7.11 (1H, s), 7.34-7.44 (5H, m), 7.66 (1H, d, J=8.6 Hz), 7.77 (1H, dd, J=10.9, 2.0 Hz), 10.68 (1H, br s).

MS (FAB) m/z: 519 (M+).

(66f) Benzyl 5-{3-[4-(Azetidin-1-ylcarbonyl)-2-fluorophenoxy]-5-[(1S)-2-methoxy-1-methylethoxy]phenyl}-1H-pyrrole-2-carboxylate benzyl 4-(3-{5-[(Benzyloxy)carbonyl]-1H-pyrrol-2-yl}-5-[(1S)-2-methoxy-1-methylethoxy]phenoxy)-3-fluorobenzoic acid (7.14 g, 13.7 mmol) synthesized in Example (66e) was dissolved in dichloromethane (120 mL). Under ice cooling, azetidine hydrochloride (1.772 g, 18.9 mmol), WSCI•HCl (3.62 g, 18.9 mmol), triethylamine (2.65 mL, 19.1 mmol) and 4-dimethylaminopyridine (464 mg, 3.80 mmol) were added, and stirring was carried out at room temperature for 6 hours under nitrogen atmosphere. To the reaction solution, 0.5N hydrochloric acid (300 mL) was added, and extraction was carried out with dichloromethane (300 mL). The organic layer was washed with saturated brine, and subsequently dried over anhydrous sodium sulfate. The solvent was distilled off under reduced pressure, and the resulting residue was purified using silica gel column chromatography (elution solvent: ethyl acetate/hexane=60%-85%) to afford the desired compound (4.12 g, yield 59%) as a white solid.

$^1$H-NMR (CDCl$_3$, 400 MHz): δ 1.31 (3H, d, J=6.3 Hz), 2.34-2.41 (2H, m), 3.40 (3H, s), 3.49 (1H, dd, J=10.4, 4.1 Hz), 3.57 (1H, dd, J=10.4, 6.1 Hz), 4.21-4.27 (2H, br m), 4.33-4.39 (2H, br m), 4.51-4.57 (1H, m), 5.33 (2H, s), 6.48 (1H, dd, J=3.9, 2.7 Hz), 6.53 (1H, t, J=2.2 Hz), 6.78 (1H, t, J=1.8 Hz), 6.89 (1H, t, J=1.8 Hz), 6.97 (1H, dd, J=3.9, 2.3 Hz), 7.06 (1H, t, J=8.0 Hz), 7.34-7.44 (6H, m), 7.52 (1H, dd, J=10.9, 2.0 Hz), 9.19 (1H, br s).

MS (FAB) m/z: 558 (M+).

(66g) 5-{3-[4-(Azetidin-1-ylcarbonyl)-2-fluorophenoxy]-5-[(1S)-2-methoxy-1-methylethoxy]phenyl}-1H-pyrrole-2-carboxylic acid Benzyl 5-{3-[4-(azetidin-1-ylcarbonyl)-2-fluorophenoxy]-5-[(1S)-2-methoxy-1-methylethoxy]phenyl}-1H-pyrrole-2-carboxylate (4.25 g, 7.61 mmol) synthesized in Example (66f) was dissolved in ethanol (150 mL), and a 10% palladium carbon catalyst (804 mg) was added, followed by stirring for 2 hours under hydrogen atmosphere. The palladium carbon catalyst was removed by Celite filtration, and the solvent was distilled off under reduced pressure to afford the desired compound (3.45 g, yield 97%) as a white solid.

$^1$H-NMR (CDCl$_3$, 400 MHz): δ 1.31 (3H, d, J=6.3 Hz), 2.32-2.40 (2H, m), 3.44 (3H, s), 3.52 (1H, dd, J=10.0, 4.1 Hz), 3.64 (1H, dd, J=10.0, 6.3 Hz), 4.20-4.26 (2H, br m), 4.31-4.38 (2H, br m), 4.66-4.72 (1H, m), 6.48-6.50 (2H, m), 6.86 (1H, s), 7.00 (1H, s), 7.05 (1H, t, J=7.6 Hz), 7.16 (1H, s), 7.38 (1H, d, J=7.8 Hz), 7.50 (1H, d, J=11.3 Hz), 10.17 (1H, br s).

MS (ESI) m/z: 469.17889 (M+H)+.

(66h) N'-Acetyl-5-{3-[4-(azetidin-1-ylcarbonyl)-2-fluorophenoxy]-5-[(1S)-2-methoxy-1-methylethoxy]phenyl}-1H-pyrrole-2-carbohydrazide 5-{3-[4-(Azetidin-1-ylcarbonyl)-2-fluorophenoxy]-5-[(1S)-2-methoxy-1-methylethoxy]phenyl}-1H-pyrrole-2-carboxylic acid (126 mg, 0.27 mmol) synthesized in Example (66g) and acetohydrazide (40 mg, 0.54 mmol) were dissolved in dichloromethane (5 mL), and HATU (153 mg, 0.40 mmol) and N,N-diisopropylethylamine (70 μL, 0.40 mmol) were added at room temperature, followed by stirring under nitrogen atmosphere for 1 hour. The reaction solution was diluted with dichloromethane (60 mL), washed with 1N hydrochloric acid, a saturated aqueous sodium hydrogencarbonate solution and saturated brine, and subsequently dried over anhydrous magnesium sulfate. The solvent was distilled off under reduced pressure, and the resulting residue was purified using silica gel column chromatography (elution solvent: methanol/dichloromethane=5%) to afford the desired product (87 mg, yield 62%) as a white solid.

$^1$H-NMR (CDCl$_3$, 400 MHz): δ 1.26 (3H, d, J=6.3 Hz), 1.91 (3H, s), 2.30-3.38 (2H, m), 3.37 (3H, s), 3.46 (1H, dd, J=3.8, 10.1 Hz) 3.58 (1H, dd, J=6.2, 10.1 Hz), 4.18-4.24 (2H, brm), 4.30-4.36 (2H, brm), 4.55-4.59 (1H, m), 6.43 (1H, dd, J=2.7, 4.0 Hz), 6.46 (1H, t, J=2.1 Hz), 6.81 (1H, dd, J=2.4, 4.1 Hz), 6.87 (1H, s), 7.01 (1H, t, J=8.2 Hz), 7.07 (1H, s), 7.35 (1H, d, J=8.6 Hz), 7.46 (1H, dd, J=2.0, 10.9 Hz), 9.10 (1H, brs), 9.36 (1H, brs), 10.62 (1H, brs).

(66i) 2-(5-{3-[4-(Azetidin-1-ylcarbonyl)-2-fluorophenoxy]-5-[(1S)-2-methoxy-1-methylethoxy]phenyl}-1H-pyrrol-2-yl)-5-methyl-1,3,4-oxadiazole N'-Acetyl-5-{3-[4-(azetidin-1-ylcarbonyl)-2-fluorophenoxy]-5-[(1S)-2-methoxy-1-methylethoxy]phenyl}-1H-pyrrole-2-carbohydrazide (86 mg, 0.16 mmol) synthesized in Example (66h) was dissolved in dichloromethane (5 mL), and triethylamine (0.1 mL, 0.72 mmol) and p-toluenesulfonic acid chloride (69 mg, 0.36 mmol) were added, followed by stirring at room temperature overnight. The reaction solution was diluted with dichloromethane (60 mL), washed with 1N hydrochloric acid, a saturated aqueous sodium hydrogencarbonate solution and saturated brine, and subsequently dried over anhydrous magnesium sulfate. The solvent was distilled off under reduced pressure, and the resulting residue was purified using silica gel column chromatography (elution solvent: ethyl acetate/hexane=50%-100%) to afford the desired product (57 mg, yield 69%) as a white solid.

$^1$H-NMR (CDCl$_3$, 400 MHz): δ 1.33 (3H, d, J=6.3 Hz), 2.34-3.42 (2H, m), 2.58 (3H, s), 3.41 (3H, s), 3.50 (1H, dd, J=3.9, 10.4 Hz) 3.59 (1H, dd, J=6.1, 10.3 Hz), 4.22-4.27 (2H, brm), 4.35-4.40 (2H, brm), 4.54-4.59 (1H, m), 6.54 (1H, t, J=2.2 Hz), 6.55 (1H, dd, J=2.2, 2.7 Hz), 6.80 (1H, t, J=1.7 Hz), 6.85 (1H, dd, J=1.9, 2.4 Hz), 6.93 (1H, dd, J=1.2, 1.6 Hz), 7.08 (1H, t, J=8.2 Hz), 7.41 (1H, d, J=8.5 Hz), 7.52 (1H, dd, J=2.0, 11.1 Hz), 9.49 (1H, brs).

MS (ESI) m/z: 507.20129 (M+H)$^+$.

Example 67

(2S)-2-{3-[4-(Azetidin-1-ylcarbonyl)-2-fluorophenoxy]-5-[5-(5-methyl-1,3,4-oxadiazol-2-yl)-1H-pyrrol-2-yl]phenoxy}propan-1-ol

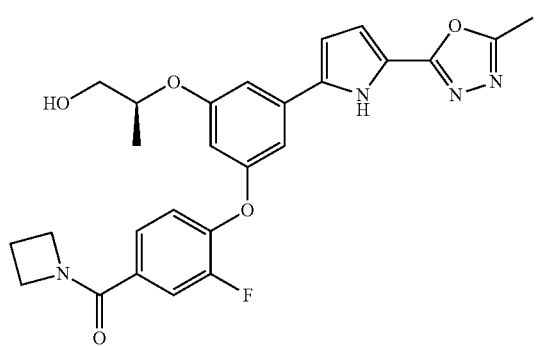

2-(5-{3-[4-(Azetidin-1-ylcarbonyl)-2-fluorophenoxy]-5-[(1S)-2-methoxy-1-methylethoxy]phenyl}-1H-pyrrol-2-yl)-5-methyl-1,3,4-oxadiazole (379.2 mg, 0.748 mmol) synthesized in Example (66i) was dissolved in dichloromethane (15 mL), and a boron tribromide/dichloromethane solution (1M, 750 μL, 0.75 mmol) was added at −78° C. under nitrogen atmosphere, followed by stirring at 0° C. for 3 hours. To the reaction solution, a saturated aqueous sodium hydrogencarbonate solution was added, and extraction was carried out with ethyl acetate. The organic layer was washed with saturated brine, and subsequently dried over sodium sulfate. The solvent was distilled off under reduced pressure, and the resulting residue was purified using silica gel column chromatography (elution solvent: methanol/dichloromethane=2%-8%) to afford the desired compound (76.9 mg, yield 21%) as a pale yellow solid.

$^1$H-NMR (CDCl$_3$, 400 MHz): δ 1.29 (3H, d, J=6.3 Hz), 2.34-2.42 (2H, m), 2.58 (3H, s), 2.80 (1H, t, J=6.1 Hz), 3.76-3.79 (2H, m), 4.22-4.26 (2H, br m), 4.35-4.39 (2H, br m), 4.52-4.59 (1H, m), 6.45 (1H, t, J=2.2 Hz), 6.53 (1H, dd, J=3.9, 2.7 Hz), 6.79 (1H, t, J=1.8 Hz), 6.84 (1H, dd, J=3.9, 2.3 Hz), 6.91 (1H, t, J=1.8 Hz), 7.05 (1H, t, J=8.2 Hz), 7.38-7.41 (1H, m), 7.51 (1H, dd, J=10.9, 2.0 Hz), 9.92 (1H, br s).

MS (ESI) m/z: 493.18999 (M+H)$^+$.

Example 68

2-(5-{3-[4-(Azetidin-1-ylcarbonyl)-2-fluorophenoxy]-5-[(1S)-2-methoxy-1-methylethoxy]phenyl}-1H-pyrrol-2-yl)-4,5-dihydro-1,3-oxazole

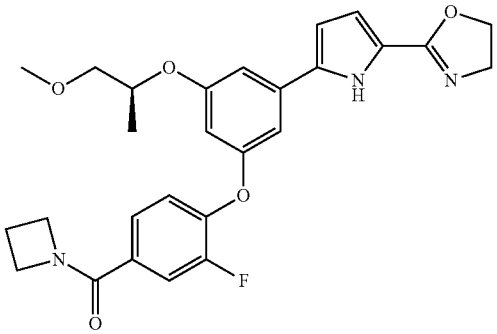

(68a) 5-{3-[4-(Azetidin-1-ylcarbonyl)-2-fluorophenoxy]-5-[(1S)-2-methoxy-1-methylethoxy]phenyl}-N-(2-chloroethyl)-1H-pyrrole-2-carboxamide 5-{3-[4-(Azetidin-1-ylcarbonyl)-2-fluorophenoxy]-5-[(1S)-2-methoxy-1-methylethoxy]phenyl}-1H-pyrrole-2-carboxylic acid (66 mg, 0.15 mmol) synthesized in Example (66g), 2-chloroethylamine hydrochloride (34 mg, 0.30 mmol) and 4-dimethylaminopyridine (18 mg, 0.15 mmol) were dissolved in dichloromethane (10 mL), and WSCI•HCl (31 mg, 0.16 mmol) was added at room temperature, followed by stirring for 1 hour under nitrogen atmosphere. The reaction solution was diluted with dichloromethane (60 mL), washed with 1N hydrochloric acid, a saturated aqueous sodium hydrogencarbonate solution and saturated brine, and subsequently dried over anhydrous magnesium sulfate. The solvent was distilled off under reduced pressure, and the resulting residue was purified using silica gel column chromatography (elution solvent: ethyl acetate/hexane=30%-60%) to afford the desired product (56 mg, yield 79%) as a white solid.

$^1$H-NMR (CDCl$_3$, 400 MHz): δ 1.32 (3H, d, J=6.3 Hz), 2.35-3.49 (2H, m), 3.41 (3H, s), 3.50 (1H, dd, J=4.1, 10.7 Hz) 3.58 (1H, dd, J=6.1, 10.3 Hz), 3.71 (2H, t, J=5.4 Hz), 3.77 (2H, t, J=5.6 Hz), 4.22-4.27 (2H, brm), 4.35-4.40 (2H, brm), 4.53-4.57 (1H, m), 6.24-6.28 (1H, m), 6.47 (1H, t, J=3.0 Hz), 6.52 (1H, t, J=2.1 Hz), 6.62 (1H, dd, J=2.5, 4.1 Hz), 6.78 (1H, t, J=1.6 Hz), 6.90 (1H, t, J=1.6 Hz), 7.06 (1H, t, J=8.0 Hz), 7.40 (1H, d, J=8.5 Hz), 7.52 (1H, dd, J=2.0, 11.0 Hz), 9.43 (1H, brs).

(68b) 2-(5-{3-[4-(Azetidin-1-ylcarbonyl)-2-fluorophenoxy]-5-[(1S)-2-methoxy-1-methylethoxy]phenyl}-1H-pyrrol-2-yl)-4,5-dihydro-1,3-oxazole 5-{3-[4-(Azetidin-1-ylcarbonyl)-2-fluorophenoxy]-5-[(1S)-2-methoxy-1-methylethoxy]phenyl}-N-(2-chloroethyl)-1H-pyrrole-2-carboxamide (85 mg, 0.16 mmol) synthesized in Example (68a) was dissolved in tetrahydrofuran (3 mL), and sodium hydride (37 mg, 0.82 mmol) was added at 0° C., followed by stirring at room temperature for 20 hours. To the reaction solution, a saturated aqueous sodium hydrogencarbonate solution was added, and extraction was carried out with ethyl acetate (50 mL). After washing with saturated brine, drying was carried out over anhydrous magnesium sulfate. The solvent was distilled off under reduced pressure, and the resulting residue was purified using silica gel column chromatography (elution solvent: ethyl acetate 100%-methanol/chloroform=2%) to afford the desired product (33 mg, yield 41%) as a pale yellow solid.

$^1$H-NMR (CDCl$_3$, 400 MHz): δ 1.32 (3H, d, J=6.3 Hz), 2.34-3.41 (2H, m), 3.41 (3H, s), 3.49 (1H, dd, J=3.9, 10.5 Hz) 3.58 (1H, dd, J=5.9, 10.2 Hz), 4.00 (2H, t, J=9.3 Hz), 4.22-4.26 (2H, brm), 4.35-4.39 (2H, brm), 4.40 (2H, t, J=9.3 Hz), 4.53-4.57 (1H, m), 6.48 (1H, d, J=3.8 Hz), 6.51 (1H, t, J=2.0 Hz), 6.75 (1H, d, J=3.8 Hz), 6.78 (1H, t, J=1.6 Hz), 6.91 (1H, s), 7.06 (1H, t, J=8.1 Hz), 7.40 (1H, d, J=8.5 Hz), 7.52 (1H, dd, J=2.0, 11.0 Hz).

MS (ESI) m/z: 494.20834 (M+H)$^+$.

Example 69

(5S)-2-(5-{3-[4-(Azetidin-1-ylcarbonyl)-2-fluorophenoxy]-5-[(1S)-2-methoxy-1-methylethoxy]phenyl}-1H-pyrrol-2-yl)-5-methyl-4,5-dihydro-1,3-oxazole

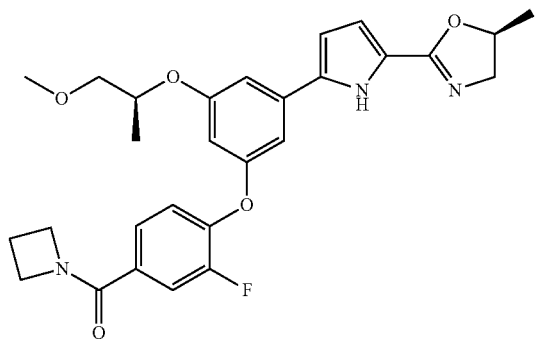

(69a) 5-{3-[4-(Azetidin-1-ylcarbonyl)-2-fluorophenoxy]-5-[(1S)-2-methoxy-1-methylethoxy]phenyl}-N-[(2R)-2-hydroxypropyl]-1H-pyrrole-2-carboxamide 5-{3-[4-(Azetidin-1-ylcarbonyl)-2-fluorophenoxy]-5-[(1S)-2-methoxy-1-methylethoxy]phenyl}-1H-pyrrole-2-carboxylic acid (580 mg, 1.24 mmol) synthesized in Example (66g) was dissolved in dichloromethane (15 mL), and (R)-(−)-1-amino-2-propanol (196 μL, 2.48 mmol), WSCI•HCl (366 mg, 1.91 mmol) and 4-dimethylaminopyridine (228 mg, 1.87 mmol) were added, followed by stirring at room temperature for 18 hours under nitrogen atmosphere. To the reaction solution, 0.25N hydrochloric acid (100 mL) was added, and extraction was carried out with ethyl acetate (100 mL). The organic layer was washed with saturated brine, and subsequently dried over sodium sulfate. The solvent was distilled off under reduced pressure, and the resulting residue was purified using silica gel column chromatography (elution solvent: methanol/dichloromethane=3%-9%) to afford the desired compound (486 mg, yield 75%) as a white solid.

$^1$H-NMR (CDCl$_3$, 400 MHz): δ 1.22 (3H, d, J=6.3 Hz), 1.30 (3H, d, J=6.3 Hz), 2.33-2.41 (2H, m), 2.77 (1H, d, J=3.9 Hz), 3.22-3.29 (1H, m), 3.41 (3H, s), 3.50 (1H, dd, J=10.2, 3.9 Hz), 3.55-3.62 (2H, m), 3.94-4.01 (1H, br m), 4.20-4.26 (2H, br m), 4.33-4.39 (2H, br m), 4.51-4.59 (1H, m), 6.43-6.46 (2H, m), 6.51 (1H, t, J=2.2 Hz), 6.62 (1H, dd, J=3.9, 2.3 Hz), 6.80 (1H, t, J=1.8 Hz), 6.91 (1H, t, J=1.8 Hz), 7.04 (1H, t, J=8.2 Hz), 7.37 (1H, d, J=8.6 Hz), 7.50 (1H, dd, J=11.3, 2.0 Hz), 9.80 (1H, br s).

MS (FAB) m/z: 526 (M+H)$^+$.

(69b) (5S)-2-(5-{3-[4-(Azetidin-1-ylcarbonyl)-2-fluorophenoxy]-5-[(1S)-2-methoxy-1-methylethoxy]phenyl}-1H-pyrrol-2-yl)-5-methyl-4,5-dihydro-1,3-oxazole 5-{3-[4-(Azetidin-1-ylcarbonyl)-2-fluorophenoxy]-5-[(1S)-2-methoxy-1-methylethoxy]phenyl}-N-[(2R)-2-hydroxypropyl]-1H-pyrrole-2-carboxamide (464 mg, 0.883 mmol) synthesized in Example (69a) was dissolved in tetrahydrofuran (17 mL), and anhydrous methanesulfonic acid (558 mg, 3.20 mmol) and triethylamine (860 μL, 6.20 mmol) were added, followed by stirring at room temperature for 3 days under nitrogen atmosphere. To the reaction solution, saturated aqueous sodium hydrogencarbonate solution was added, and extraction was carried out with ethyl acetate. The organic layer was washed with saturated brine, and subsequently dried over sodium sulfate. The solvent was distilled off under reduced pressure, and the resulting residue was purified using silica gel column chromatography (elution solvent: methanol/dichloromethane=3%-9%) to afford the desired compound (228 mg, yield 51%) as a white solid.

$^1$H-NMR (CDCl$_3$, 400 MHz): δ 1.31 (3H, d, J=6.3 Hz), 1.43 (3H, d, J=6.3 Hz), 2.34-2.41 (2H, m), 3.41 (3H, s), 3.50 (1H, dd, J=10.2, 3.9 Hz), 3.52-3.59 (2H, m), 4.08 (1H, dd, J=13.9, 9.2 Hz), 4.22-4.26 (2H, br m), 4.35-4.38 (2H, br m), 4.53-4.60 (1H, m), 4.80-4.89 (1H, m), 6.48 (1H, d, J=3.9 Hz), 6.51 (1H, t, J=2.2 Hz), 6.77 (1H, d, J=3.9 Hz), 6.79 (1H, t, J=1.8 Hz), 6.93 (1H, s), 7.05 (1H, t, J=8.2 Hz), 7.37-7.40 (1H, m), 7.51 (1H, dd, J=10.9, 2.0 Hz).

MS (ESI) m/z: 508.22382 (M+H)$^+$.

Example 70

(2S)-2-(3-[4-(Azetidin-1-ylcarbonyl)-2-fluorophenoxy]-5-{5-[(5S)-5-methyl-4,5-dihydro-1,3-oxazol-2-yl]-1H-pyrrol-2-yl}phenoxy)propan-1-ol

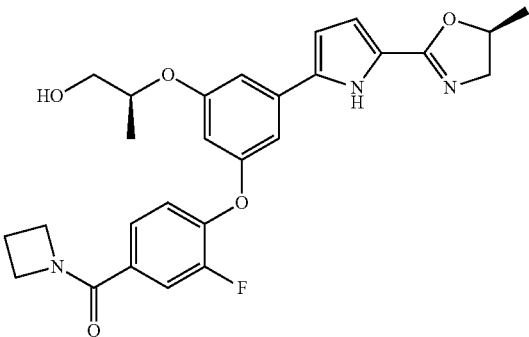

(5S)-2-(5-{3-[4-(Azetidin-1-ylcarbonyl)-2-fluorophenoxy]-5-[(1S)-2-methoxy-1-methylethoxy]phenyl}-1H-pyrrol-2-yl)-5-methyl-4,5-dihydro-1,3-oxazole (337.8 mg, 0.666 mmol) synthesized in Example (69b) was dissolved in dichloromethane (10 mL), and a boron tribromide/dichloromethane solution (1M, 1 mL, 1 mmol) was added at −78° C. under nitrogen atmosphere, followed by stirring at room temperature for 1 hour. To the reaction solution, a saturated aqueous sodium hydrogencarbonate solution was added, and extraction was carried out with ethyl acetate. The organic layer was washed with saturated brine, and subsequently dried over sodium sulfate. The solvent was distilled off under reduced pressure, and the resulting residue was purified using silica gel column chromatography (elution solvent: methanol/dichloromethane=2%-8%) to afford the desired compound (93.7 mg, yield 29%) as a pale yellow solid.

$^1$H-NMR (CDCl$_3$, 400 MHz): δ 1.26 (3H, d, J=6.3 Hz), 1.43 (3H, d, J=6.3 Hz), 2.33-2.41 (2H, m), 3.55 (1H, dd, J=13.7, 7.4 Hz), 3.73-3.81 (2H, m), 4.08 (1H, dd, J=13.7, 9.4 Hz), 4.22-4.26 (2H, br m), 4.33-4.37 (2H, br m), 4.56-4.64 (1H, m), 4.81-4.90 (1H, m), 6.30 (1H, t, J=2.2 Hz), 6.44 (1H, d, J=3.9 Hz), 6.74-6.76 (2H, m), 6.86 (1H, s), 7.00 (1H, t, J=8.2 Hz), 7.34-7.37 (1H, m), 7.49 (1H, dd, J=10.9, 2.0 Hz).

MS (ESI) m/z: 494.20864 (M+H)$^+$.

Example 71

5-(Azetidin-1-ylcarbonyl)-3-chloro-2-{3-[(1S)-2-methoxy-1-methylethoxy]-5-[5-(5-methyl-1,3,4-oxadiazol-2-yl)-1H-pyrrol-2-yl]phenoxyl}pyridine

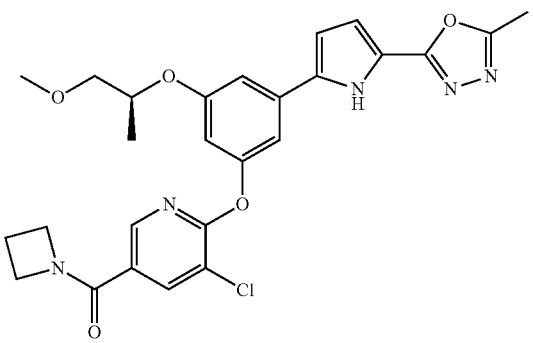

(71a) 5-(3-{[5-(Azetidin-1-ylcarbonyl)-3-chloropyridin-2-yl]oxy}-5-[(1S)-2-methoxy-1-methylethoxy]phenyl)-1H-pyrrole-2-carboxylic acid 2-Benzyl 1-t-butyl 5-{3-hydroxy-5-[(1S)-2-methoxy-1-methylethoxy]phenyl}-1H-pyrrole-1,2-dicarboxylate (5.21 g, 10.82 mmol) synthesized in Example (66c) and 5-(azetidin-1-ylcarbonyl)-2,3-dichloropyridine (2.55 g, 11.04 mmol) synthesized in Example (60a) were dissolved in acetonitrile (100 mL), and potassium carbonate (4.30 g, 31.11 mmol) was added, followed by stirring for 1 day with heating to reflux under nitrogen atmosphere. The reaction solution was cooled to room temperature, water (200 mL) was added, and extraction was carried out with ethyl acetate (200 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=75%-90%).

The resulting compound was dissolved in trifluoroacetic acid (15 mL), and stirring was carried out at room temperature for 1.5 hours under nitrogen atmosphere. The solvent was distilled off under reduced pressure, and the resulting residue was purified using silica gel column chromatography (elution solvent: ethyl acetate/hexane=75%-90%).

The resulting compound was dissolved in tetrahydrofuran (20 mL), and palladium carbon (800 mg) was added, followed by stirring at room temperature for 4 hours under hydrogen atmosphere. After Celite filtration, the solvent was distilled off. To the resulting residue, a saturated aqueous sodium hydrogencarbonate solution (30 mL) was added, and extraction was carried out with diethyl ether. To the resulting aqueous layer, 2N hydrochloric acid (50 mL) was added, and extraction was carried out with ethyl acetate. The resulting organic layer was washed with saturated brine, and subsequently dried over anhydrous magnesium sulfate. The solvent was distilled off under reduced pressure to afford the desired compound (3.52 g, yield 67%) as a white solid.

$^1$H-NMR (CDCl$_3$, 400 MHz): δ 1.35 (3H, d, J=6.3 Hz), 2.35-2.42 (2H, m), 3.45 (3H, s), 3.54 (1H, dd, J=10.0, 4.1 Hz), 3.65 (1H, dd, J=10.4, 6.1 Hz), 4.24 (2H, t, J=7.6 Hz), 4.35 (2H, t, J=6.3 Hz), 4.65-4.71 (1H, m), 6.53 (1H, dd, J=3.5, 2.7 Hz), 6.70 (1H, t, J=2.2 Hz), 7.01-7.02 (2H, br m), 7.21 (1H, s), 8.16 (1H, d, J=2.3 Hz), 8.27 (1H, d, J=2.0 Hz), 9.97 (1H, br s).

(71b) 5-(Azetidin-1-ylcarbonyl)-3-chloro-2-{3-[(1S)-2-methoxy-1-methylethoxy]-5-[5-(5-methyl-1,3,4-oxadiazol-2-yl)-1H-pyrrol-2-yl]phenoxyl}pyridine 5-(3-{[5-(Azetidin-1-ylcarbonyl)-3-chloropyridin-2-yl]oxy}-5-[(1S)-2-methoxy-1-methylethoxy]phenyl)-1H-pyrrole-2-carboxylic acid (600 mg, 1.23 mmol) synthesized in Example (71a) was dissolved in dichloromethane (15 mL), and acetohydrazide (200 mg, 2.70 mmol), WSCI•HCl (510 mg, 2.66 mmol) and 4-dimethylaminopyridine (300 mg, 2.46 mmol) were added, followed by stirring at room temperature for 1 day under nitrogen atmosphere. A saturated aqueous ammonium chloride solution (100 mL) was added, and extraction was carried out with dichloromethane (100 mL). The organic layer was washed with saturated brine, subsequently dried over anhydrous magnesium sulfate, and the solvent was distilled off under reduced pressure.

This residue was dissolved in dichloromethane (15 mL), and p-toluenesulfonyl chloride (500 mg, 2.62 mmol) and triethylamine (1.0 mL, 7.17 mmol) were added, followed by stirring at room temperature for 5 hours under nitrogen atmosphere. To the reaction solution, a saturated aqueous ammonium chloride solution (30 mL) was added, and extraction was carried out with dichloromethane (30 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate) to afford the desired compound (520 mg, yield 81%) as a white solid.

$^{1}$H-NMR (CDCl$_{3}$, 400 MHz): δ 1.35 (3H, d, J=6.3 Hz), 2.35-2.43 (1H, m), 2.59 (3H, s), 3.42 (3H, s), 3.52 (1H, dd, J=10.2, 4.3 Hz), 3.61 (1H, dd, J=10.2, 5.9 Hz), 4.24 (2H, t, J=7.4 Hz), 4.37 (2H, t, J=7.6 Hz), 4.56-4.62 (1H, m), 6.58 (1H, dd, J=3.9, 2.7 Hz), 6.70 (1H, t, J=2.2 Hz), 6.85 (1H, dd, J=3.9, 2.3 Hz), 6.96 (1H, t, J=1.6 Hz), 7.05 (1H, t, J=2.0 Hz), 8.17 (1H, d, J=2.0 Hz), 8.27 (1H, d, J=2.0 Hz), 9.57 (1H, br s).
MS (ESI) m/z: 524.17210 (M+H)$^{+}$.

Example 72

(2S)-2-(3-{[5-(Azetidin-1-ylcarbonyl)-3-chloropyridin-2-yl]oxy}-5-[5-(5-methyl-1,3,4-oxadiazol-2-yl)-1H-pyrrol-2-yl]phenoxy)propan-1-ol

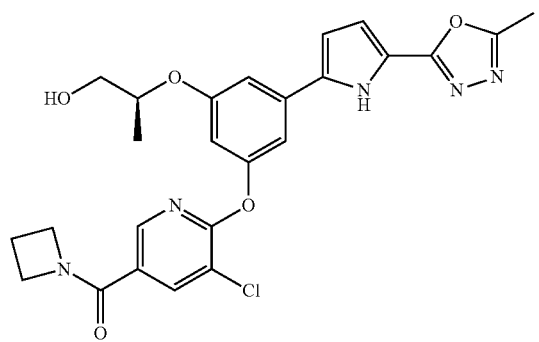

5-(Azetidin-1-ylcarbonyl)-3-chloro-2-{3-[(1S)-2-methoxy-1-methylethoxy]-5-[5-(5-methyl-1,3,4-oxadiazol-2-yl)-1H-pyrrol-2-yl]phenoxyl}pyridine (370 mg, 0.706 mmol) synthesized in Example (71b) was dissolved in dichloromethane (10 mL), and boron tribromide (1.0 mol/L dichloromethane solution, 1.10 mL, 1.10 mmol) was added dropwise at −78° C., followed by stirring at room temperature for 1 hour under nitrogen atmosphere. To this reaction solution, a saturated aqueous ammonium chloride solution (20 mL) was added, and extraction was carried out with dichloromethane (20 mL). The organic layer was washed with saturated brine, and subsequently dried over anhydrous magnesium sulfate. The solvent was distilled off under reduced pressure, and the resulting residue was purified using silica gel column chromatography (elution solvent: methanol/dichloromethane=1%-3%) to afford the desired compound (205 mg, yield 57%) as a white solid.

$^{1}$H-NMR (CDCl$_{3}$, 400 MHz): δ 1.30 (3H, d, J=6.3 Hz), 1.78 (1H, d, J=7.8 Hz), 2.34-2.42 (2H, m), 2.57 (3H, s), 2.71-2.87 (1H, m), 3.73-3.80 (2H, m), 4.23 (2H, t, J=7.6 Hz), 4.35 (2H, t, J=7.4 Hz), 4.52-4.58 (1H, m), 6.56 (1H, t, J=2.9 Hz), 6.64 (1H, d, J=1.6 Hz), 6.84 (1H, dd, J=3.9, 2.3 Hz), 6.96 (1H, t, J=1.8 Hz), 7.01 (1H, t, J=1.8 Hz), 8.16 (1H, d, J=2.0 Hz), 8.26 (1H, d, J=2.3 Hz), 9.92 (1H, s).
MS (ESI) m/z: 510.15468 (M+H)$^{+}$.

Example 73

5-(Azetidin-1-ylcarbonyl)-3-chloro-2-{3-[5-(4,5-dihydro-1,3-oxazol-2-yl)-1H-pyrrol-2-yl]-5-[(1S)-2-methoxy-1-methylethoxy]phenoxy}pyridine

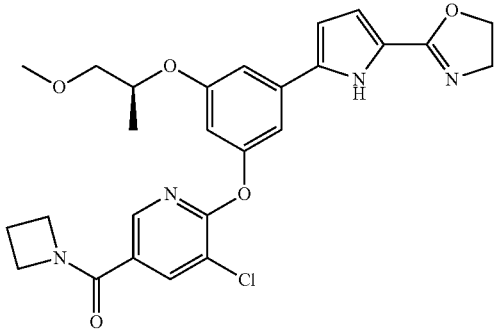

(73a) 5-(3-{[5-(Azetidin-1-ylcarbonyl)-3-chloropyridin-2-yl]oxy}-5-[(1S)-2-methoxy-1-methylethoxy]phenyl)-N-(2-chloroethyl)-1H-pyrrole-2-carboxamide 5-(3-{[5-(Azetidin-1-ylcarbonyl)-3-chloropyridin-2-yl]oxy}-5-[(1S)-2-methoxy-1-methylethoxy]phenyl)-1H-pyrrole-2-carboxylic acid (800 mg, 1.65 mmol) synthesized in Example (71a) was dissolved in dichloromethane (10.0 mL), and 2-chloroethylamine hydrochloride (300 mg, 2.59 mmol), WSCI•HCl (630 mg, 3.29 mmol) and 4-dimethylaminopyridine (400 mg, 3.27 mmol) were added, followed by stirring at room temperature under nitrogen atmosphere for 2.5 days. To the reaction solution, a saturated aqueous ammonium chloride solution (30 mL) was added, and extraction was carried out with dichloromethane (30 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate) to afford the desired compound (210 mg, yield 23%) as a white solid.

$^{1}$H-NMR (CDCl$_{3}$, 400 MHz): δ 1.34 (3H, d, J=6.3 Hz), 2.35-2.42 (2H, m), 3.42 (3H, s), 3.51 (1H, dd, J=10.6, 4.7 Hz), 3.60 (1H, dd, J=10.2, 5.9 Hz), 3.68-3.73 (2H, m), 3.75-3.80 (2H, m), 4.24 (2H, t, J=7.8 Hz), 4.36 (2H, t, J=7.0 Hz), 4.55-4.60 (1H, m), 6.27 (1H, t, J=5.7 Hz), 6.50 (1H, dd, J=3.9, 2.7 Hz), 6.63 (1H, dd, J=3.7, 2.5 Hz), 6.68 (1H, t, J=2.2 Hz), 6.95 (1H, t, J=1.8 Hz), 7.03 (1H, t, J=1.8 Hz), 8.16 (1H, d, J=2.3 Hz), 8.26 (1H, d, J=2.0 Hz), 9.55 (1H, br s).

(73b) 5-(Azetidin-1-ylcarbonyl)-3-chloro-2-{3-[5-(4,5-dihydro-1,3-oxazol-2-yl)-1H-pyrrol-2-yl]-5-[(1S)-2-methoxy-1-methylethoxy]phenoxyl}pyridine 5-(3-{[5-(Azetidin-1-ylcarbonyl)-3-chloropyridin-2-yl]oxy}-5-[(1S)-2-methoxy-1-methylethoxy]phenyl)-N-(2-chloroethyl)-1H-pyrrole-2-carboxamide (210 mg, 0.384 mmol) synthesized in Example (73a) was dissolved in tetrahydrofuran (10.0 mL), and sodium hydride (60%, 80 mg, 2.00 mmol) was added, followed by stirring at room temperature for 7.5 hours under nitrogen atmosphere. To the reaction solution, a saturated aqueous ammonium chloride solution (30 mL) was added, and extraction was carried out with dichloromethane (30 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate) to afford the desired compound (120 mg, yield 62%) as a white solid.

$^1$H-NMR (CDCl$_3$, 500 MHz): δ 1.34 (3H, d, J=6.3 Hz), 2.35-2.42 (2H, m), 3.41 (3H, s), 3.50 (1H, dd, J=10.3, 4.4 Hz), 3.60 (1H, dd, J=10.3, 5.9 Hz), 4.00 (2H, t, J=9.3 Hz), 4.24 (2H, t, J=6.8 Hz), 4.36 (2H, t, J=6.3 Hz), 4.40 (2H, t, J=9.3 Hz), 4.55-4.61 (1H, m), 6.50 (1H, d, J=3.9 Hz), 6.66 (1H, t, J=2.0 Hz), 6.75 (1H, d, J=3.9 Hz), 6.94 (1H, s), 7.04 (1H, t, J=5.1 Hz), 8.15 (1H, d, J=2.0 Hz), 8.26 (1H, d, J=2.0 Hz).

MS (ESI) m/z: 511.17658 (M+H)$^+$.

Example 74

5-(Azetidin-1-ylcarbonyl)-3-chloro-2-(3-[(1S)-2-methoxy-1-methylethoxy]-5-5-[(5S)-5-methyl-4,5-dihydro-1,3-oxazol-2-yl]-1H-pyrrol-2-yl phenoxy)pyridine

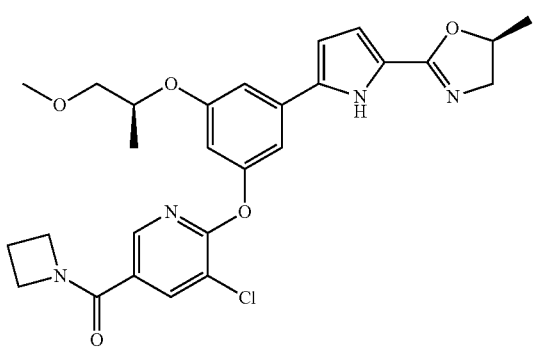

5-(3-{[5-(Azetidin-1-ylcarbonyl)-3-chloropyridin-2-yl]oxy}-5-[(1S)-2-methoxy-1-methylethoxy]phenyl)-1H-pyrrole-2-carboxylic acid (800 mg, 1.65 mmol) synthesized in Example (71a) was dissolved in dichloromethane (15 mL), and (R)-(−)-1-amino-2-propanol (0.35 mL, 4.45 mmol), WSCI·HCl (630 mg, 3.29 mmol) and 4-dimethylaminopyridine (800 mg, 6.55 mmol) were added, followed by stirring at room temperature for 8 hours under nitrogen atmosphere. To the reaction solution, a saturated aqueous ammonium chloride solution (30 mL) was added, and extraction was carried out with dichloromethane (30 mL). The organic layer was washed with saturated brine, and subsequently dried over anhydrous magnesium sulfate. The solvent was distilled off under reduced pressure, and the resulting residue was purified using silica gel column chromatography (elution solvent: methanol/dichloromethane=3%-8%) to afford a yellow solid.

This was dissolved in tetrahydrofuran (15 mL), and anhydrous methanesulfonic acid (500 mg, 2.87 mmol) and triethylamine (0.80 mL, 5.74 mmol) were added, followed by stirring at room temperature overnight under nitrogen atmosphere. To the reaction solution, a saturated aqueous ammonium chloride solution (30 mL) was added, and extraction was carried out with dichloromethane (30 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate) to afford the desired compound (520 mg, yield 60%) as a yellow solid.

$^1$H-NMR (CDCl$_3$, 400 MHz): δ 1.34 (3H, d, J=6.3 Hz), 1.43 (3H, d, J=6.3 Hz), 2.35-2.42 (2H, m), 3.41 (3H, s), 3.45-3.64 (3H, m), 4.08-4.12 (1H, m), 4.23 (2H, t, J=7.0 Hz), 4.36 (2H, t, J=8.4 Hz), 4.54-4.62 (1H, m), 4.84-4.87 (1H, m), 6.51 (1H, d, J=3.5 Hz), 6.66 (1H, t, J=2.2 Hz), 6.75-6.78 (1H, m), 6.94 (1H, s), 7.02-7.09 (1H, m), 8.16 (1H, d, J=2.0 Hz), 8.26 (1H, d, J=2.0 Hz).

MS (ESI) m/z: 525.19126 (M+H)$^+$.

Example 75

(2S)-2-(3-{[5-(Azetidin-1-ylcarbonyl)-3-chloropyridin-2-yl]oxy}-5-{5-[(5S)-5-methyl-4,5-dihydro-1,3-oxazol-2-yl]-1H-pyrrol-2-yl}phenoxy)propan-1-ol

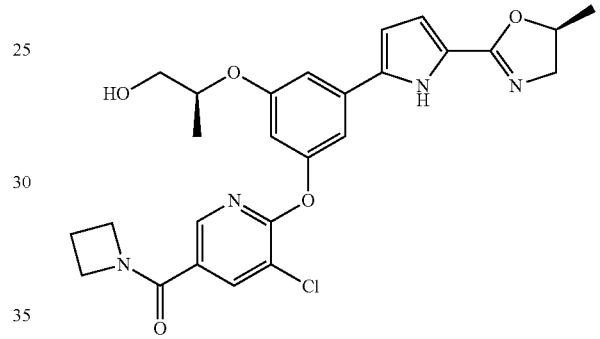

5-(azetidin-1-ylcarbonyl)-3-chloro-2-(3-[(1S)-2-methoxy-1-methylethoxy]-5-{5-[(5S)-5-methyl-4,5-dihydro-1,3-oxazol-2-yl]-1H-pyrrol-2-yl}phenoxy)pyridine (320 mg, 0.610 mmol) synthesized in Example 74 was dissolved in dichloromethane (10 mL), and boron tribromide (1.0 mol/L dichloromethane solution, 0.92 mL, 0.92 mmol) was added dropwise at −78° C., followed by stirring at room temperature for 1 hour under nitrogen atmosphere. To this reaction solution, a saturated aqueous ammonium chloride solution (20 mL) was added, and extraction was carried out with dichloromethane (20 mL). The organic layer was washed with saturated brine, and subsequently dried over anhydrous magnesium sulfate. The solvent was distilled off under reduced pressure, and the resulting residue was purified using silica gel column chromatography (elution solvent: methanol/dichloromethane=1%-3%) to afford the desired compound (165 mg, yield 53%) as a yellow solid.

$^1$H-NMR (CDCl$_3$, 400 MHz): δ 1.28 (3H, d, J=6.3 Hz), 1.40 (3H, d, J=5.9 Hz), 2.34-2.42 (2H, m), 3.52 (1H, dd, J=13.7, 7.4 Hz), 3.76 (2H, d, J=5.5 Hz), 4.06 (1H, dd, J=13.9, 9.2 Hz), 4.23 (2H, t, J=7.8 Hz), 4.34 (2H, t, J=7.4 Hz), 4.51-4.60 (1H, m), 4.76-4.86 (1H, m), 6.44 (1H, d, J=3.1 Hz), 6.53 (1H, s), 6.72 (1H, d, J=3.5 Hz), 6.87-6.92 (2H, m), 8.15 (1H, d, J=2.0 Hz), 8.23 (1H, d, J=1.2 Hz), 10.05 (1H, br s).

MS (ESI) m/z: 511.17339 (M+H)$^+$.

Example 76

5-(3-[(1S)-2-Methoxy-1-methylethoxy]-5-{5-[(5S)-5-methyl-4,5-dihydro-1,3-oxazol-2-yl]-1H-pyrrol-2-yl}phenoxy)-2-(methylsulfonyl)pyridine

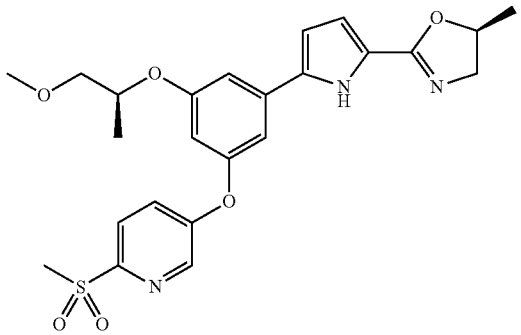

(76a) Benzyl 5-(3-[(1S)-2-Methoxy-1-methylethoxy]-5-{[6-(methylsulfonyl)pyridin-3-yl]oxy}phenyl)-1H-pyrrole-2-carboxylate 2-Benzyl 1-t-butyl 5-{3-hydroxy-5-[(1S)-2-methoxy-1-methylethoxy]phenyl}-1H-pyrrole-1,2-dicarboxylate (5.05 g, 10.49 mmol) synthesized in Example (66c) and 5-fluoro-2-(methylsulfonyl)pyridine (2.05 g, 11.70 mmol) synthesized in Example (65b) were dissolved in N,N-dimethylformamide (30 mL), and potassium carbonate (4.50 g, 32.56 mmol) was added, followed by stirring at 80° C. for 3 hours under nitrogen atmosphere. The reaction solution was cooled to room temperature, water (150 mL) was added, and extraction was carried out with diethyl ether (150 mL). The organic layer was washed with saturated brine, subsequently dried over anhydrous magnesium sulfate, and the solvent was distilled off under reduced pressure.

The resulting compound was dissolved in trifluoroacetic acid (10 mL), and stirring was carried out at room temperature for 1 hour under nitrogen atmosphere. The solvent was distilled off under reduced pressure, and the resulting residue was purified using silica gel column chromatography (elution solvent: ethyl acetate/hexane=35%-50%) to afford the desired compound (5.08 g, yield 90%) as a white oil.

$^1$H-NMR (CDCl$_3$, 400 MHz): δ 1.33 (3H, d, J=6.3 Hz), 3.23 (3H, s), 3.41 (3H, s), 3.51 (1H, dd, J=10.3, 3.9 Hz), 3.58 (1H, dd, J=10.3, 6.3 Hz), 4.54-4.61 (1H, m), 5.33 (2H, s), 6.51 (1H, t, J=3.2 Hz), 6.59 (1H, s), 6.86 (1H, s), 6.99 (1H, t, J=2.9 Hz), 7.02 (1H, s), 7.32-7.45 (7H, m), 8.04 (1H, d, J=8.8 Hz), 8.48 (1H, s), 9.36 (1H, br s).

(76b) 5-(3-[(1S)-2-Methoxy-1-methylethoxy]-5-{[6-(methylsulfonyl)pyridin-3-yl]oxy}phenyl)-1H-pyrrole-2-carboxylic acid Benzyl 5-(3-[(1S)-2-methoxy-1-methylethoxy]-5-{[6-(methylsulfonyl)pyridin-3-yl]oxy}phenyl)-1H-pyrrole-2-carboxylate (5.08 g, 9.47 mmol) synthesized in Example (76a) was dissolved in ethyl acetate (30 mL), and a 10% palladium carbon catalyst (1.10 g) was added, followed by stirring at room temperature for 3 hours under hydrogen atmosphere. After Celite filtration, the solvent was distilled off under reduced pressure to afford the desired compound as a white solid (4.30 g, yield ~100%).

$^1$H-NMR (CDCl$_3$, 400 MHz): δ 1.34 (3H, d, J=5.9 Hz), 3.23 (3H, s), 3.47 (3H, s), 3.57 (1H, dd, J=9.8, 3.9 Hz), 3.67 (1H, dd, J=10.0, 6.6 Hz), 4.72-4.80 (1H, m), 6.52 (1H, s), 6.59 (1H, s), 6.92 (1H, s), 7.03 (1H, s), 7.32 (1H, s), 7.45 (1H, dd, J=8.5, 1.7 Hz), 8.05 (1H, d, J=8.8 Hz), 8.49 (1H, d, J=2.4 Hz), 10.31 (1H, br s).

(76c) 5-(3-[(1S)-2-Methoxy-1-methylethoxy]-5-{5-[(5S)-5-methyl-4,5-dihydro-1,3-oxazol-2-yl]-1H-pyrrol-2-yl}phenoxy)-2-(methylsulfonyl)pyridine 5-(3-[(1S)-2-Methoxy-1-methylethoxy]-5-{[6-(methylsulfonyl)pyridin-3-yl]oxy}phenyl)-1H-pyrrole-2-carboxylic acid (1000 mg, 2.24 mmol) synthesized in Example (76b) was dissolved in methanol (20 mL), and (R)-(−)-1-amino-2-propanol (0.40 mL, 5.08 mmol) and 4-(4,6-dimethoxy-1,3,5-triazin-2-yl)-4-methylmorpholinium chloride n hydrate (1000 mg, 3.61 mmol) were added, followed by stirring at room temperature overnight under nitrogen atmosphere. The solvent was distilled off under reduced pressure, and the resulting residue was purified using silica gel column chromatography (elution solvent: methanol/methylene chloride=1%-3%) to afford a yellow solid.

This was dissolved in tetrahydrofuran (20 mL), and anhydrous methanesulfonic acid (600 mg, 3.44 mmol) and triethylamine (0.70 mL, 5.02 mmol) were added, followed by stirring at room temperature overnight under nitrogen atmosphere. To the reaction solution, a saturated aqueous ammonium chloride solution (50 mL) was added, and extraction was carried out with methylene chloride (50 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=1%-3%) to afford the desired compound (450 mg, yield 41%) as a white solid.

$^1$H-NMR (CDCl$_3$, 400 MHz): δ 1.33 (3H, d, J=6.3 Hz), 1.43 (3H, d, J=6.3 Hz), 3.23 (3H, s), 3.42 (3H, s), 3.49-3.61 (4H, m), 4.09 (1H, dd, J=13.9, 8.8 Hz), 4.53-4.63 (1H, m), 4.79-4.88 (1H, m), 6.51 (1H, d, J=3.9 Hz), 6.57 (1H, d, J=1.6 Hz), 6.76 (1H, d, J=3.9 Hz), 6.83 (1H, s), 7.02 (1H, s), 7.44 (1H, dd, J=8.6, 2.3 Hz), 8.05 (1H, d, J=8.6 Hz), 8.49 (1H, s).
MS (ESI) m/z: 486.17067 (M+H)$^+$.

Example 77

(2S)-2-(3-{5-[(5S)-5-Methyl-4,5-dihydro-1,3-oxazol-2-yl]-1H-pyrrol-2-yl}-5-{[6-(methylsulfonyl)pyridin-3-yl]oxy}phenoxy)propan-1-ol

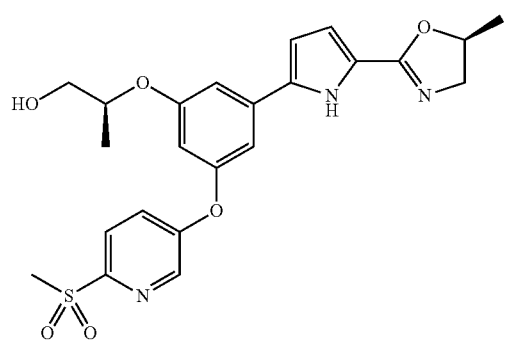

5-(3-[(1S)-2-Methoxy-1-methylethoxy]-5-{5-[(5S)-5-methyl-4,5-dihydro-1,3-oxazol-2-yl]-1H-pyrrol-2-yl}phenoxy)-2-(methylsulfonyl)pyridine (310 mg, 0.638 mmol) synthesized in Example (76c) was dissolved in methylene chloride (7.0 mL), and boron tribromide (1.0 mol/L dichloromethane solution, 1.00 mL, 1.0 mmol) was added dropwise at −78° C., followed by stirring at room temperature for 1 hour under nitrogen atmosphere. To this reaction solution, a saturated aqueous ammonium chloride solution (20 mL) was added, and extraction was carried out with methylene chloride (20 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=1%-3%) to afford the desired compound (245 mg, yield 81%) as a white solid.

$^1$H-NMR (CDCl$_3$, 400 MHz): δ 1.29 (3H, d, J=6.3 Hz), 1.43 (3H, d, J=6.3 Hz), 3.23 (3H, s), 3.55 (1H, dd, J=13.9, 7.2 Hz), 3.79 (2H, d, J=5.1 Hz), 4.09 (1H, dd, J=14.1, 9.4 Hz), 4.56-4.63 (1H, m), 4.81-4.88 (1H, m), 6.38 (1H, br s), 6.48 (1H, t, J=3.3 Hz), 6.75 (1H, d, J=3.5 Hz), 6.80 (1H, br s), 6.96 (1H, br s), 7.39 (1H, br s), 8.03 (1H, d, J=8.2 Hz), 8.45 (1H, s).

MS (ESI) m/z: 472.15208 (M+H)$^+$.

Example 78

5-{3-[5-(4,5-Dihydro-1,3-oxazol-2-yl)-1H-pyrrol-2-yl]-5-[(1S)-2-methoxy-1-methylethoxy]phenoxy}-2-(methylsulfonyl)pyridine

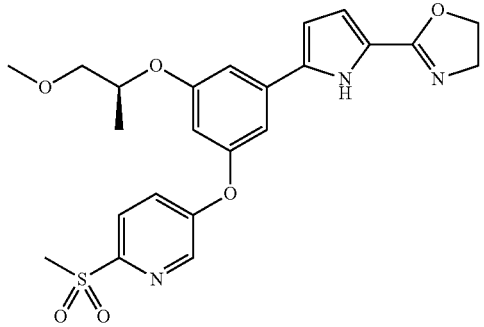

(78a) 3-Bromo-5-methoxyphenol

Commercially available 1-bromo-3,5-dimethoxybenzene (18.74 g, 86.3 mmol) was dissolved in 1-methyl-2-pyrrolidone (100 mL), and sodium thiomethoxide (6.74 g, 96.2 mmol) was added, followed by stirring at 100° C. for 3 hours under nitrogen atmosphere. The reaction solution was cooled to room temperature, 1N hydrochloric acid (200 mL) was added, and extraction was carried out with diethyl ether (500 mL). The organic layer was washed with saturated brine, and subsequently dried over sodium sulfate. The solvent was distilled off under reduced pressure, and the resulting residue was purified using silica gel column chromatography (elution solvent: ethyl acetate/hexane=20%-25%) to afford the desired compound (15.03 g, yield 86%) as a white solid.

$^1$H-NMR (CDCl$_3$, 400 MHz): δ 3.77 (3H, s), 4.82 (1H, s), 6.33 (1H, t, J=2.4 Hz), 6.61 (1H, t, J=2.0 Hz), 6.66 (1H, t, J=2.0 Hz).

(78b) 1-Bromo-3-methoxy-5-[(1S)-2-methoxy-1-methylethoxy]benzene

3-Bromo-5-methoxyphenol (7.60 g, 37.4 mmol) synthesized in Example (78a) was dissolved in toluene (100 mL), and R-(−)-1-methoxy-2-propanol (4.40 mL, 44.9 mmol) and triphenylphosphine (13.8 g, 52.6 mmol) were added, followed by dropwise addition of diethyl azodicarboxylate (2.2 mol/l toluene solution, 24 mL, 52.8 mmol) at 0° C. and stirring at room temperature for 1.5 hours under nitrogen atmosphere. The solvent was distilled off under reduced pressure, diethyl ether (100 mL) was added, and the deposit was filtered to be removed. The mother liquor was distilled off under reduced pressure, and the resulting residue was purified using silica gel column chromatography (elution solvent: ethyl acetate/hexane=10%-20%) to afford the desired compound (9.22 g, yield 89%) as a colorless liquid.

$^1$H-NMR (CDCl$_3$, 400 MHz): δ 1.30 (3H, d, J=6.3 Hz), 3.40 (3H, s), 3.47 (1H, dd, J=10.6, 4.3 Hz), 3.55 (1H, dd, J=10.4, 6.1 Hz), 3.76 (3H, s), 4.46-4.52 (1H, m), 6.42 (1H, t, J=2.2 Hz), 6.65 (1H, dd, J=2.3, 1.6 Hz), 6.69 (1H, t, J=2.0 Hz).

MS (EI) m/z: 274 (M)$^+$.

(78c) 3-Bromo-5-[(1S)-2-methoxy-1-methylethoxy]phenol

1-Bromo-3-methoxy-5-[(1S)-2-methoxy-1-methylethoxy]benzene (9.21 g, 33.5 mmol) synthesized in Example (78b) was dissolved in 1-methyl-2-pyrrolidone (100 mL), and sodium thiomethoxide (2.75 g, 37.3 mmol) was added, followed by stirring at 130° C. for 3 hours under nitrogen atmosphere. The reaction solution was cooled to room temperature, 2N hydrochloric acid (500 mL) was added, and extraction was carried out with diethyl ether (300 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=20%-25%) to afford the desired compound (8.30 g, yield 95%) as a colorless liquid.

$^1$H-NMR (CDCl$_3$, 400 MHz): δ 1.29 (3H, d, J=6.3 Hz), 3.41 (3H, s), 3.46 (1H, dd, J=10.2, 4.3 Hz), 3.55 (1H, dd, J=10.6, 5.9 Hz), 4.45-4.51 (1H, m), 4.96 (1H, br s), 6.36 (1H, t, J=2.0 Hz), 6.59 (1H, t, J=2.0 Hz), 6.68 (1H, t, J=2.0 Hz).

MS (EI) m/z: 260 (M)$^+$.

(78d) 3-[(1S)-2-Methoxy-1-methylethoxy]-5-(4,4,5,5-tetramethyl-1,3,2-dioxaborolan-2-yl)phenol 3-Bromo-5-[(1S)-2-methoxy-1-methylethoxy]phenol (8.30 g, 31.8 mmol) synthesized in Example (78c) was dissolved in N,N-dimethylformamide (100 mL), and bis(pinacolato)diboron (10.50 g, 41.3 mmol), [1,1'-bis(diphenylphosphino)ferrocene]palladium (II) dichloride dichloromethane complex (810 mg, 0.992 mmol) and potassium acetate (15.50 g, 158 mmol) were added, followed by stirring at 90° C. for 3 hours under nitrogen atmosphere. After the reaction solution was cooled to room temperature, water (500 mL) was added, and extraction was carried out with diethyl ether (300 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=20%-30%) to afford the desired compound (8.75 g, yield 89%) as a brown oil.

$^1$H-NMR (CDCl$_3$, 400 MHz): δ 1.26 (3H, d, J=4.1 Hz), 1.33 (12H, s), 3.41 (1H, s), 3.47 (1H, dd, J=10.2, 4.7 Hz), 3.57 (1H, dd, J=10.6, 5.9 Hz), 4.52-4.58 (1H, m), 4.80 (1H, brs), 6.55 (1H, t, J=2.4 Hz), 6.83 (1H, d, J=2.4 Hz), 6.95 (1H, d, J=2.4 Hz).

MS (FAB) m/z: 309 (M+H)$^+$.

(78e) t-Butyl 2,5-dibromo-1H-pyrrole-1-carboxylate

Commercially available t-butyl 1-pyrrolecarboxylate (46.68 g, 279 mmol) was dissolved in tetrahydrofuran (500 mL), and cooled to −78° C. To this, N-bromosuccinimide (100.48 g, 565 mmol) was added in small portions over 1 hour. The temperature of the reaction solution was raised naturally, and stirring was carried out at room temperature for 18 hours. The reaction solution was cooled to 0° C., sodium sulphite (36.43 g) was added, followed by stirring for 30 minutes, and subsequently hexane (200 mL) was added to give a precipitate, which was removed by Celite filtration. The solvent of the filtrate was distilled off under reduced pressure, and the resulting residue was purified using silica gel column chromatography (elution solvent: ethyl acetate/hexane=1%-5%) to afford the desired compound (52.69 g, yield 58%) as a colorless oil.

$^1$H-NMR (CDCl$_3$, 500 MHz): δ 1.65 (9H, s), 6.25 (2H, s).
MS (EI) m/z: 323 (M$^+$).

(78f) 2-Benzyl 1-t-butyl 5-bromo-1H-pyrrole-1,2-dicarboxylate t-Butyl 2,5-dibromo-1H-pyrrole-1-carboxylate (10.98 g, 33.8 mmol) synthesized in Example (78e) was dissolved in diethyl ether (135 mL), and cooled to −78° C. n-Butyl lithium (2.77 mol/L hexane solution, 12.8 mL, 35.5 mmol) was added dropwise slowly, and stirring was carried out for 1 hour. To the reaction solution, benzyl chloroformate (6.25 mL, 44.0 mmol) was added dropwise slowly, and stirring was carried out for 30 minutes. With the temperature of the reaction solution being raised gradually to room temperature, stirring was carried out for 1 hour. To the reaction solution, were added a saturated aqueous ammonium chloride solution (200 mL) and diethyl ether (300 mL), and the solution was separated. The organic layer was washed with saturated brine, and subsequently dried over sodium sulfate. The solvent was distilled off under reduced pressure, and the resulting residue was purified using silica gel column chromatography (elution solvent: ethyl acetate/hexane=5%-45%) to afford the desired compound (8.80 g, yield 68%) as a reddish brown oil.

$^1$H-NMR (CDCl$_3$, 400 MHz): δ 1.56 (9H, s), 5.26 (2H, s), 6.21 (1H, d, J=3.9 Hz), 6.85 (1H, d, J=3.9 Hz), 7.28-7.39 (5H, m).
MS (FAB) m/z: 380 (M+H)$^+$.

(78g) 2-Benzyl 1-t-butyl 5-{3-hydroxy-5-[(1S)-2-methoxy-1-methylethoxy]phenyl}-1H-pyrrole-1,2-dicarboxylate 2-Benzyl 1-t-butyl 5-bromo-1H-pyrrole-1,2-dicarboxylate (8.75 g, 23.0 mmol) synthesized in Example (78f) and 3-[(1S)-2-methoxy-1-methylethoxy]-5-(4,4,5,5-tetramethyl-1,3,2-dioxaborolan-2-yl)phenol (7.11 g, 23.1 mmol) synthesized in Example (78d) were dissolved in a mixed solvent of 1,4-dioxane (92 mL) and water (23 mL), and [1,1'-bis(diphenylphosphino)ferrocene]palladium (II) dichloride dichloromethane complex (570 mg, 0.698 mmol) and potassium carbonate (7.95 g, 57.5 mmol) were added, followed by stirring at 55° C. for 3 hours under nitrogen atmosphere. After the reaction solution was cooled to room temperature, water (200 mL) was added, and extraction was carried out with ethyl acetate (200 mL). The organic layer was washed with saturated brine, and subsequently dried over anhydrous sodium sulfate. The solvent was distilled off under reduced pressure, and the resulting residue was purified using silica gel column chromatography (elution solvent: ethyl acetate/hexane=15%-35%) to afford the desired compound (8.32 g, yield 75%) as a brown oil.

$^1$H-NMR (CDCl$_3$, 500 MHz): δ 1.29 (3H, d, J=6.3 Hz), 1.41 (9H, s), 3.40 (3H, s), 3.47 (1H, dd, J=10.3, 4.4 Hz), 3.57 (1H, dd, J=10.3, 5.9 Hz), 4.48-4.54 (1H, m), 5.20 (1H, s), 5.30 (2H, s), 6.17 (1H, d, J=3.4 Hz), 6.44 (1H, s), 6.48 (1H, s), 6.57 (1H, s), 6.94 (1H, d, J=3.4 Hz), 7.42-7.31 (5H, m).
MS (FAB) m/z: 481 (M$^+$).

(78h) 5-Bromo-2-(methylthio)pyridine

Commercially available 2,5-dibromo pyridine (6.01 g, 25.4 mmol) was dissolved in N,N-dimethylformamide (50 mL), and sodium thiomethoxide (2.20 g, 31.4 mmol) was added, followed by stirring at 0° C. for 3.5 hours under nitrogen atmosphere. The reaction solution was brought back to room temperature, water (250 mL) was added, and extraction was carried out with diethyl ether (250 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=3%-5%) to afford the desired compound (4.90 g, yield 94%) as a white solid.

$^1$H-NMR (CDCl$_3$, 400 MHz): δ 2.54 (3H, s), 7.08 (1H, d, J=8.2 Hz), 7.58 (1H, dd, J=8.6, 2.3 Hz), 8.49 (1H, d, J=2.0 Hz).

(78i) 5-Fluoro-2-(methylsulfonyl)pyridine

5-Bromo-2-(methylthio)pyridine (4.90 g, 24.0 mmol) synthesized in Example (78h) was dissolved in tetrahydrofuran (100 mL), and n-butyl lithium (1.57 mol/L hexane solution, 17.0 mL, 26.7 mmol) was added dropwise at −78° C., followed by stirring at −78° C. for 1 hour under nitrogen atmosphere. N-Fluorobenzenesulfonimide (11.0 g, 34.9 mmol) was dissolved in tetrahydrofuran (25 mL), followed by dropwise addition to the reaction solution at −78° C., and stirring was carried out at −78° C. for 2 hours under nitrogen atmosphere. The reaction solution was brought back to room temperature, and stirring was carried out for 1.5 hours. A saturated aqueous ammonium chloride solution (200 mL) was added, and extraction was carried out with diethyl ether (300 mL). The organic layer was washed with saturated brine, and subsequently dried over anhydrous magnesium sulfate. The solvent was distilled off under slightly reduced pressure.

The resulting residue was dissolved in methylene chloride (150 mL), and m-chloroperbenzoic acid (65%, 16.5 g, 62.1 mmol) was added slowly at 0° C., followed by stirring at 0° C. for 1.5 hours under nitrogen atmosphere. After the white solid material was removed by Celite filtration, a saturated aqueous sodium hydrogencarbonate solution (100 mL) was added, and extraction was carried out with methylene chloride (400 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=3%-5%) to afford the desired compound (1.95 g, yield 46%) as a yellowish white solid.

$^1$H-NMR (CDCl$_3$, 400 MHz): δ 3.24 (3H, s), 7.67 (1H, ddd, J=9.9, 6.9, 1.9 Hz), 8.16 (1H, dd, J=8.6, 4.3 Hz), 8.59 (1H, d, J=2.7 Hz).

(78j) Benzyl 5-(3-[(1S)-2-methoxy-1-methylethoxy]-5-{[6-(methylsulfonyl)pyridin-3-yl]oxy}phenyl)-1H-pyrrole-2-carboxylate 2-Benzyl 1-t-butyl 5-{3-hydroxy-5-[(1S)-2-methoxy-1-methylethoxy]phenyl}-1H-pyrrole-1,2-dicarboxylate (5.05 g, 10.49 mmol) synthesized in Example (78g) and 5-fluoro-2-(methylsulfonyl)pyridine (2.05 g, 11.70 mmol) synthesized in Example (78i) were dissolved in N,N-dimethylformamide (30 mL), and potassium carbonate (4.50 g, 32.56 mmol) was added, followed by stirring at 80° C. for 3 hours under nitrogen atmosphere. The reaction solution was cooled to room temperature, water (150 mL) was added, and extraction was carried out with diethyl ether (150 mL). The organic layer was washed with saturated brine, subsequently dried over anhydrous magnesium sulfate, and the solvent was distilled off under reduced pressure.

The resulting compound was dissolved in trifluoroacetic acid (10 mL), and stirring was carried out at room temperature for 1 hour under nitrogen atmosphere. The solvent was distilled off under reduced pressure, and the resulting residue was purified using silica gel column chromatography (elution solvent: ethyl acetate/hexane=35%-50%) to afford the desired compound (5.08 g, yield 90%) as a white oil.

$^1$H-NMR (CDCl$_3$, 400 MHz): δ 1.33 (3H, d, J=6.3 Hz), 3.23 (3H, s), 3.41 (3H, s), 3.51 (1H, dd, J=10.3, 3.9 Hz), 3.58 (1H, dd, J=10.3, 6.3 Hz), 4.54-4.61 (1H, m), 5.33 (2H, s), 6.51 (1H, t, J=3.2 Hz), 6.59 (1H, s), 6.86 (1H, s), 6.99 (1H, t, J=2.9 Hz), 7.02 (1H, s), 7.32-7.45 (7H, m), 8.04 (1H, d, J=8.8 Hz), 8.48 (1H, s), 9.36 (1H, br s).

(78k) 5-(3-[(1S)-2-Methoxy-1-methylethoxy]-5-{[6-(methylsulfonyl)pyridin-3-yl]oxy}phenyl)-1H-pyrrole-2-carboxylic acid Benzyl 5-(3-[(1S)-2-methoxy-1-methylethoxy]-5-{[6-(methylsulfonyl)pyridin-3-yl]oxy}phenyl)-1H-pyrrole-2-carboxylate (5.08 g, 9.47 mmol) synthesized in Example (78j) was dissolved in ethyl acetate (30 mL), and a 10% palladium carbon catalyst (1.10 g) was added, followed by stirring at room temperature for 3 hours under hydrogen atmosphere. After Celite filtration, the solvent was distilled off under reduced pressure to afford the desired compound (4.30 g, yield ~100%) as a white solid.

$^1$H-NMR (CDCl$_3$, 400 MHz): δ 1.34 (3H, d, J=5.9 Hz), 3.23 (3H, s), 3.47 (3H, s), 3.57 (1H, dd, J=9.8, 3.9 Hz), 3.67 (1H, dd, J=10.0, 6.6 Hz), 4.72-4.80 (1H, m), 6.52 (1H, s), 6.59 (1H, s), 6.92 (1H, s), 7.03 (1H, s), 7.32 (1H, s), 7.45 (1H, dd, J=8.5, 1.7 Hz), 8.05 (1H, d, J=8.8 Hz), 8.49 (1H, d, J=2.4 Hz), 10.31 (1H, br s).

(78l) 5-{3-[5-(4,5-Dihydro-1,3-oxazol-2-yl)-1H-pyrrol-2-yl]-5-[(1S)-2-methoxy-1-methylethoxy]phenoxy}-2-(methylsulfonyl)pyridine 5-(3-[(1S)-2-Methoxy-1-methylethoxy]-5-{[6-(methylsulfonyl)pyridin-3-yl]oxy}phenyl)-1H-pyrrole-2-carboxylic acid (1.00 g, 2.24 mmol) synthesized in Example (78k) was dissolved in methanol (20 mL), and ethanolamine (0.30 mL, 4.97 mmol) and 4-(4,6-dimethoxy-1,3,5-triazin-2-yl)-4-methylmorpholinium chloride n hydrate (1.00 g, 3.61 mmol) were added, followed by stirring at room temperature for 1 day under nitrogen atmosphere. The solvent was distilled off under reduced pressure, and the resulting residue was purified using silica gel column chromatography (elution solvent: methanol/methylene chloride=1%-3%) to afford a compound as a white solid.

This was dissolved in tetrahydrofuran (20 mL), and anhydrous methanesulfonic acid (700 mg, 4.02 mmol) and triethylamine (0.85 mL, 6.10 mmol) were added, followed by stirring at 50° C. for 5 hours under nitrogen atmosphere. To the reaction solution, a saturated aqueous ammonium chloride solution (30 mL) was added, and extraction was carried out with methylene chloride (30 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=1%-3%) to afford the desired compound (410 mg, yield 39%) as a white solid.

$^1$H-NMR (CDCl$_3$, 400 MHz): δ 1.33 (3H, d, J=6.3 Hz), 3.23 (3H, s), 3.42 (3H, s), 3.51 (1H, dd, J=10.2, 3.9 Hz), 3.59 (1H, dd, J=10.6, 6.3 Hz), 4.00 (2H, t, J=9.2 Hz), 4.43 (2H, t, J=9.4 Hz), 4.55-4.61 (1H, m), 6.51 (1H, d, J=3.5 Hz), 6.57 (1H, t, J=2.2 Hz), 6.77 (1H, d, J=3.9 Hz), 6.84 (1H, t, J=1.8 Hz), 7.03 (1H, t, J=1.6 Hz), 7.44 (1H, dd, J=8.6, 2.7 Hz), 8.05 (1H, d, J=8.6 Hz), 8.49 (1H, d, J=2.7 Hz).

MS (ESI) m/z: 472.15408 (M+H)$^+$.

Example 79

(2S)-2-(3-[5-(4,5-Dihydro-1,3-oxazol-2-yl)-1H-pyrrol-2-yl]-5-{[6-(methylsulfonyl)pyridin-3-yl]oxy}phenoxy)propan-1-ol

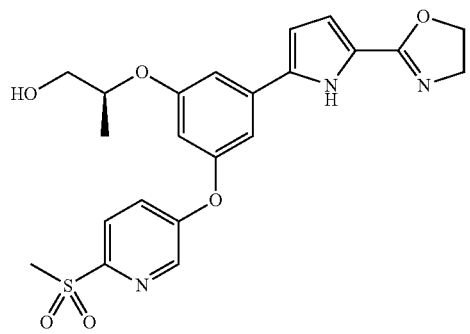

5-{3-[5-(4,5-Dihydro-1,3-oxazol-2-yl)-1H-pyrrol-2-yl]-5-[(1S)-2-methoxy-1-methylethoxy]phenoxy}-2-(methylsulfonyl)pyridine (230 mg, 0.49 mmol) synthesized in Example (78l) was dissolved in methylene chloride (10 mL), and boron tribromide (1.0 mol/L methylene chloride solution, 0.75 mL, 0.75 mmol) was added dropwise at −78° C., followed by stirring at room temperature for 1.5 hours under nitrogen atmosphere. To this reaction solution, a saturated aqueous ammonium chloride solution (20 mL) was added, and extraction was carried out with methylene chloride (20 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=2%-4%) to afford the desired compound (170 mg, yield 76%) as a white solid.

$^1$H-NMR (CDCl$_3$, 400 MHz): δ 1.30 (3H, d, J=6.3 Hz), 3.23 (3H, s), 3.79 (2H, d, J=5.9 Hz), 4.01 (2H, t, J=9.4 Hz), 4.43 (2H, t, J=9.4 Hz), 4.55-4.61 (1H, m), 6.44 (1H, t, J=2.2

Hz), 6.49 (1H, d, J=3.9 Hz), 6.76 (1H, d, J=3.5 Hz), 6.81 (1H, t, J=2.0 Hz), 6.96 (1H, s), 7.40 (1H, dd, J=8.6, 2.3 Hz), 8.04 (1H, d, J=8.6 Hz), 8.46 (1H, d, J=2.3 Hz).

MS (ESI) m/z: 458.13852 (M+H)⁺.

Example 80

5-{3-[(1S)-2-Methoxy-1-methylethoxy]-5-[5-(5-methyl-1,3,4-oxadiazol-2-yl)-1H-pyrrol-2-yl]phenoxy}-2-(methylsulfonyl)pyridine

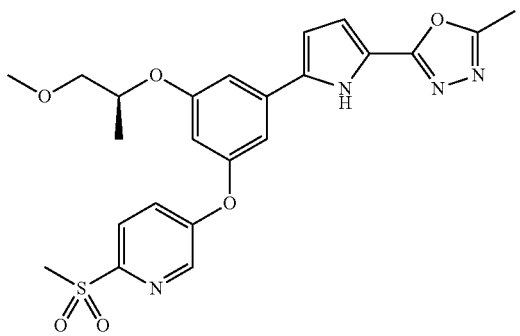

5-(3-[(1S)-2-Methoxy-1-methylethoxy]-5-{[6-(methylsulfonyl)pyridin-3-yl]oxy}phenyl)-1H-pyrrole-2-carboxylic acid (600 mg, 1.34 mmol) synthesized in Example (78k) was dissolved in methylene chloride (20 mL), and acetohydrazide (220 mg, 2.97 mmol), WSCI•HCl (580 mg, 3.03 mmol) and 4-dimethylaminopyridine (150 mg, 1.23 mmol) were added, followed by stirring at room temperature overnight under nitrogen atmosphere. A saturated aqueous ammonium chloride solution (100 mL) was added, and extraction was carried out with methylene chloride (100 mL). The organic layer was washed with saturated brine, subsequently dried over anhydrous magnesium sulfate, and the solvent was distilled off under reduced pressure.

This residue was dissolved in methylene chloride (20 mL), and p-toluenesulfonyl chloride (510 mg, 2.68 mmol) and triethylamine (0.75 mL, 5.38 mmol) were added, followed by stirring at room temperature for 4 hours under nitrogen atmosphere. To the reaction solution, a saturated aqueous ammonium chloride solution (50 mL) was added, and extraction was carried out with methylene chloride (50 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=60-80%) to afford the desired compound (450 mg, yield 69%) as a white solid.

¹H-NMR (CDCl₃, 400 MHz): δ 1.35 (3H, d, J=6.3 Hz), 2.59 (3H, s), 3.24 (3H, s), 3.42 (3H, s), 3.52 (1H, dd, J=10.6, 3.5 Hz), 3.61 (1H, dd, J=11.3, 5.5 Hz), 4.51-4.72 (1H, m), 6.59-6.61 (2H, br m), 6.87-6.90 (2H, br m), 7.06 (1H, br s), 7.46 (1H, d, J=8.6 Hz), 8.06 (1H, d, J=8.6 Hz), 8.50 (1H, d, J=1.6 Hz), 9.66 (1H, br s).

MS (ESI) m/z: 485.14739 (M+H)⁺.

Example 81

(2S)-2-(3-[5-(5-Methyl-1,3,4-oxadiazol-2-yl)-1H-pyrrol-2-yl]-5-{[6-(methylsulfonyl)pyridin-3-yl]oxy}phenoxy)propan-1-ol

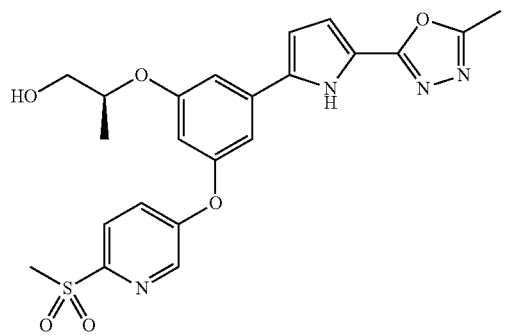

5-{3-[(1S)-2-Methoxy-1-methylethoxy]-5-[5-(5-methyl-1,3,4-oxadiazol-2-yl)-1H-pyrrol-2-yl]phenoxy}-2-(methylsulfonyl)pyridine (320 mg, 0.660 mmol) synthesized in Example 80 was dissolved in methylene chloride (10 mL), and boron tribromide (1.0 mol/L methylene chloride solution, 1.00 mL, 1.00 mmol) was added dropwise at −78° C., and stirring was carried out at room temperature for 1 hour under nitrogen atmosphere. To this reaction solution, a saturated aqueous ammonium chloride solution (20 mL) was added, and extraction was carried out with methylene chloride (20 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=1%-3%) to afford the desired compound (190 mg, yield 61%) as a yellow solid.

¹H-NMR (CDCl₃, 400 MHz): δ 1.29 (3H, d, J=6.3 Hz), 2.34 (1H, br s), 2.55 (3H, s), 3.21 (3H, s), 3.76 (2H, br s), 4.49-4.58 (1H, m), 6.52 (1H, s), 6.55 (1H, dd, J=3.9, 2.7 Hz), 6.81-6.84 (2H, m), 7.00 (1H, t, J=2.0 Hz), 7.42 (1H, dd, J=8.6, 2.7 Hz), 8.03 (1H, d, J=8.6 Hz), 8.45 (1H, d, J=2.7 Hz), 9.76 (1H, br s).

MS (ESI) m/z: 471.13599 (M+H)⁺.

Example 82

{(5R)-2-[5-(3-[(1S)-2-Methoxy-1-methylethoxy]-5-{[6-(methylsulfonyl)pyridin-3-yl]oxy}phenyl)-1H-pyrrol-2-yl]-4,5-dihydro-1,3-oxazol-5-yl}methanol

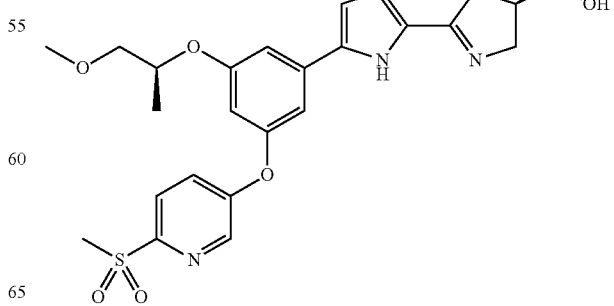

(82a) 5-(3-{[(2S)-1-Methoxypropan-2-yl]oxy}-5-{5-[(5R)-5-{[(tripropan-2-ylsilyl)oxy]methyl}-4,5-dihydro-1,3-oxazol-2-yl]-1H-pyrrol-2-yl}phenoxy)-2-(methylsulfonyl)pyridine 5-(3-[(1S)-2-Methoxy-1-methylethoxy]-5-{[6-(methylsulfonyl)pyridin-3-yl]oxy}phenyl)-1H-pyrrole-2-carboxylic acid (1.70 g, 3.81 mmol) synthesized in Example (78k) was dissolved in methanol (30 mL), and (S)-(−)-3-amino-1,2-propanediol (0.80 g, 8.78 mmol) and 4-(4,6-dimethoxy-1,3,5-triazin-2-yl)-4-methylmorpholinium chloride n hydrate (1.70 g, 6.14 mmol) were added, followed by stirring at room temperature for 3 days under nitrogen atmosphere. The solvent was distilled off under reduced pressure, and the resulting residue was purified using silica gel column chromatography (elution solvent: methanol/methylene chloride=7%-10%) to afford a yellow solid.

This was dissolved in methylene chloride (40 mL), and triisopropylchlorosilane (1.32 mL, 6.17 mmol), 4-dimethylaminopyridine (0.75 g, 6.14 mmol) and triethylamine (2.87 mL, 20.59 mmol) were added, followed by stirring at room temperature for 1 day under nitrogen atmosphere. To the reaction solution, a saturated aqueous ammonium chloride solution (50 mL) was added, and extraction was carried out with methylene chloride (50 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=1%) to afford a yellow solid.

This was dissolved in tetrahydrofuran (30 mL), and anhydrous methanesulfonic acid (1.05 g, 6.03 mmol) and triethylamine (1.70 mL, 12.20 mmol) were added, followed by stirring at 50° C. for 4.5 hours under nitrogen atmosphere. To the reaction solution, a saturated aqueous ammonium chloride solution (50 mL) was added, and extraction was carried out with methylene chloride (50 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=50%-70%) to afford the desired compound (1.18 g, yield 47%) as a pale yellow solid.

$^1$H-NMR (CDCl$_3$, 500 MHz): δ 0.99-1.16 (21H, m), 1.32 (3H, d, J=6.3 Hz), 3.23 (3H, s), 3.40 (3H, s), 3.50 (1H, dd, J=10.3, 3.9 Hz), 3.58 (1H, dd, J=10.3, 5.9 Hz), 3.81-3.90 (2H, m), 3.92-4.01 (2H, m), 4.51-4.62 (1H, br s), 4.70-4.78 (1H, br s), 6.49 (1H, d, J=3.9 Hz), 6.56 (1H, s), 6.72 (1H, t, J=2.0 Hz), 6.83 (1H, s), 7.01 (1H, s), 7.43 (1H, dd, J=7.6, 1.7 Hz), 8.04 (1H, d, J=8.3 Hz), 8.48 (1H, d, J=2.4 Hz).

(82b) {(5R)-2-[5-(3-[(1S)-2-Methoxy-1-methylethoxy]-5-{[6-(methylsulfonyl)pyridin-3-yl]oxy}phenyl)-1H-pyrrol-2-yl]-4,5-dihydro-1,3-oxazol-5-yl}methanol 5-(3-{[(2S)-1-Methoxypropan-2-yl]oxy}-5-{5-[(5R)-5-{[(tripropan-2-ylsilyl)oxy]methyl}-4,5-dihydro-1,3-oxazol-2-yl]-1H-pyrrol-2-yl}phenoxy)-2-(methylsulfonyl)pyridine (1.18 g, 1.79 mmol) synthesized in Example (82a) was dissolved in tetrahydrofuran (10 mL), and tetrabutylammonium fluoride (1.0 mol/L tetrahydrofuran solution, 2.00 mL, 2.00 mmol) was added at room temperature, followed by stirring at room temperature for 30 minutes under nitrogen atmosphere. To this reaction solution, a saturated aqueous ammonium chloride solution (20 mL) was added, and extraction was carried out with methylene chloride (20 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=2%-3%) to afford the desired compound (680 mg, yield 76%) as a white solid.

$^1$H-NMR (CDCl$_3$, 400 MHz): δ 1.27 (3H, d, J=6.3 Hz), 3.21 (3H, s), 3.40 (3H, s), 3.48 (1H, dd, J=10.2, 3.9 Hz), 3.56 (1H, dd, J=10.2, 6.3 Hz), 3.68 (1H, dd, J=12.1, 5.1 Hz), 3.75 (1H, dd, J=14.5, 7.4 Hz), 3.85 (1H, d, J=9.4 Hz), 4.00 (1H, dd, J=14.1, 9.8 Hz), 4.53 (1H, br s), 4.78 (1H, br s), 6.46 (1H, d, J=3.9 Hz), 6.55 (1H, t, J=2.2 Hz), 6.72 (1H, d, J=3.9 Hz), 6.81 (1H, d, J=2.0 Hz), 6.97 (1H, s), 7.42 (1H, dd, J=8.6, 2.7 Hz), 8.03 (1H, d, J=8.6 Hz), 8.46 (1H, d, J=2.7 Hz).

MS (ESI) m/z: 502.16243 (M+H)$^+$.

Example 83

(2S)-2-(3-{5-[(5R)-5-(Hydroxymethyl)-4,5-dihydro-1,3-oxazol-2-yl]-1H-pyrrol-2-yl}-5-{[6-(methylsulfonyl)pyridin-3-yl]oxy}phenoxy)propan-1-ol

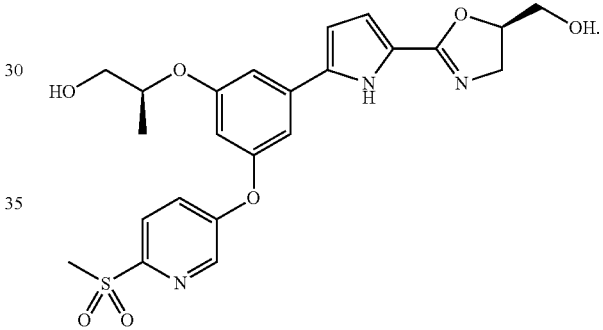

{(5R)-2-[5-(3-[(1S)-2-Methoxy-1-methylethoxy]-5-{[6-(methylsulfonyl)pyridin-3-yl]oxy}phenyl)-1H-pyrrol-2-yl]-4,5-dihydro-1,3-oxazol-5-yl}methanol (520 mg, 1.04 mmol) synthesized in Example (82b) was dissolved in methylene chloride (10 mL), and boron tribromide (1.0 mol/L methylene chloride solution, 2.00 mL, 2.00 mmol) was added dropwise at −78° C., followed by stirring at room temperature for 4 hours under nitrogen atmosphere. To this reaction solution, a 1N aqueous sodium hydroxide solution (20 mL) was added, and extraction was carried out with methylene chloride (20 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=3%-5%) to afford the desired compound (148 mg, yield 29%) as a white solid.

$^1$H-NMR (CDCl$_3$, 400 MHz): δ 1.30 (3H, d, J=5.9 Hz), 3.23 (3H, s), 3.70-3.82 (3H, m), 3.90-3.99 (2H, m), 4.07 (1H, t, J=11.5 Hz), 4.62 (1H, br s), 4.95 (1H, br s), 6.47 (2H, d, J=3.9 Hz), 6.86 (2H, d, J=3.9 Hz), 7.15 (1H, s), 7.40 (1H, dd, J=8.8, 2.4 Hz), 8.03 (1H, d, J=8.8 Hz), 8.45 (1H, d, J=2.4 Hz), 11.26 (1H, br s).

MS (ESI) m/z: 488.14896 (M+H)$^+$.

Example 84

(2S)-2-(3-{5-[(4R)-4-Methyl-4,5-dihydro-1,3-oxazol-2-yl]-1H-pyrrol-2-yl}-5-{[6-(methylsulfonyl)pyridin-3-yl]oxy}phenoxy)propan-1-ol

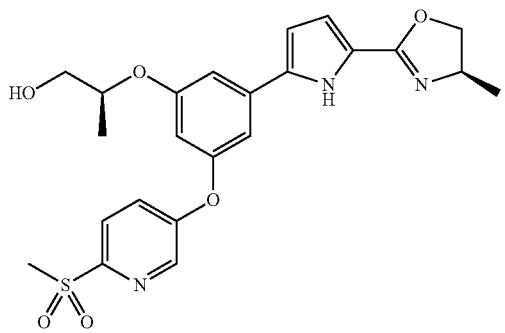

(84a) N-[(1R)-2-Hydroxy-1-methylethyl]-5-(3-[(1S)-2-methoxy-1-methylethoxy]-5-{[6-(methylsulfonyl)pyridin-3-yl]oxy}phenyl)-1H-pyrrole-2-carboxamide 5-(3-[(1S)-2-Methoxy-1-methylethoxy]-5-{[6-(methylsulfonyl)pyridin-3-yl]oxy}phenyl)-1H-pyrrole-2-carboxylic acid (2.00 g, 4.48 mmol) synthesized in Example (78k), D-alaninol (0.52 mL, 6.72 mmol), HOBT•H$_2$O (0.73 g, 5.38 mmol) and N-methylmorpholine (0.99 mL, 8.96 mmol) were dissolved in methylene chloride (40 mL), and WSCI•HCl (0.94 g, 4.93 mmol) was added at room temperature, followed by stirring for 30 hours under nitrogen atmosphere. The reaction solution was diluted with methylene chloride (100 mL), washed with 1N hydrochloric acid, a saturated aqueous sodium hydrogencarbonate solution and saturated brine, and subsequently dried over anhydrous magnesium sulfate. The solvent was distilled off under reduced pressure, and the resulting residue was purified using silica gel column chromatography (elution solvent: ethyl acetate/hexane=50%-90%) to afford the desired compound (1.94 g, 86%) as a white solid.

$^1$H-NMR (CDCl$_3$, 500 MHz): δ 1.27 (3H, d, J=6.8 Hz), 1.33 (3H, d, J=6.3 Hz), 3.23 (3H, s), 3.41 (3H, s), 3.51 (1H, dd, J=3.9, 10.3 Hz), 3.57-3.64 (2H, m), 3.76 (1H, dd, J=3.5, 11.0 Hz), 4.21-4.27 (1H, brm), 4.55-4.60 (1H, m), 6.06 (1H, d, J=7.3 Hz), 6.48 (1H, dd, J=2.7, 4.0 Hz), 6.57 (1H, t, J=2.1 Hz), 6.60 (1H, dd, J=2.0, 2.3 Hz), 6.84 (1H, t, J=1.7 Hz), 7.01 (1H, t, J=1.7 Hz), 7.44 (1H, dd, J=2.7, 8.7 Hz), 8.04 (1H, d, J=8.7 Hz), 8.47 (1H, d, J=2.7 Hz), 9.71 (1H, brs).

(84b) 5-(3-[(1S)-2-Methoxy-1-methylethoxy]-5-{5-[(4R)-4-methyl-4,5-dihydro-1,3-oxazol-2-yl]-1H-pyrrol-2-yl}phenoxy)-2-(methylsulfonyl)pyridine N-[(1R)-2-Hydroxy-1-methylethyl]-5-(3-[(1S)-2-methoxy-1-methylethoxy]-5-{[6-(methylsulfonyl)pyridin-3-yl]oxy}phenyl)-1H-pyrrole-2-carboxamide (1.94 g, 3.85 mmol) synthesized in Example (84a) was dissolved in tetrahydrofuran (35 mL), and anhydrous methanesulfonic acid (1.38 g, 7.70 mmol) and triethylamine (2.15 mL, 15.41 mmol) were added, followed by stirring at 50° C. for 1.5 hours under nitrogen atmosphere. A saturated aqueous sodium hydrogencarbonate solution (30 mL) was added, and the solution was separated with ethyl acetate (50 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=30%-75%) to afford the desired compound (1.59 g, yield 85%) as a white solid.

$^1$H-NMR (CDCl$_3$, 400 MHz): δ 1.33 (6H, d, J=6.3 Hz), 3.23 (3H, s), 3.41 (3H, s), 3.50 (1H, dd, J=3.9, 10.2 Hz), 3.59 (1H, dd, J=6.1, 10.4 Hz), 3.93 (1H, t, J=7.8 Hz), 4.30-4.36 (1H, m), 4.50 (1H, dd, J=8.2, 9.2 Hz), 4.56-4.60 (1H, m), 6.51 (1H, d, J=3.9 Hz), 6.57 (1H, t, J=2.2 Hz), 6.75 (1H, d, J=3.8 Hz), 6.84 (1H, t, J=1.8 Hz), 7.04 (1H, t, J=1.8 Hz), 7.44 (1H, dd, J=2.8, 8.7 Hz), 8.05 (1H, d, J=8.8 Hz), 8.45 (1H, d, J=2.7 Hz).

(84c) (2S)-2-(3-{5-[(4R)-4-Methyl-4,5-dihydro-1,3-oxazol-2-yl]-1H-pyrrol-2-yl}-5-{[6-(methylsulfonyl)pyridin-3-yl]oxy}phenoxy)propan-1-ol 5-(3-[(1S)-2-Methoxy-1-methylethoxy]-5-{5-[(4R)-4-methyl-4,5-dihydro-1,3-oxazol-2-yl]-1H-pyrrol-2-yl}phenoxy)-2-(methylsulfonyl)pyridine (1.20 g, 2.47 mmol) synthesized in Example (84b) was dissolved in methylene chloride (25 mL), followed by cooling to −78° C., and boron tribromide (1.0 mol/L methylene chloride solution, 2.72 mL, 2.72 mmol) was added under nitrogen atmosphere. After the temperature was raised naturally and stirring was carried out at room temperature for 30 minutes, a saturated aqueous sodium hydrogencarbonate solution was added to neutralize the reaction solution, followed by extraction with methylene chloride (80 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=70%-100%) to afford the desired compound (895 mg, 77%) as a white solid.

$^1$H-NMR (CDCl$_3$, 400 MHz): δ 1.29 (3H, d, J=6.2 Hz), 1.34 (1H, d, J=6.6 Hz), 3.23 (3H, s), 3.79-3.81 (2H, m), 3.95 (1H, t, J=7.9 Hz), 4.32-4.38 (1H, m), 4.52 (1H, dd, J=8.1, 9.3 Hz), 4.61-4.65 (1H, m), 6.35 (1H, t, J=2.2 Hz), 6.47 (1H, d, J=3.9 Hz), 6.75 (1H, d, J=3.8 Hz), 6.80 (1H, dd, J=1.4, 2.4 Hz), 6.97 (1H, t, J=1.8 Hz), 7.37 (1H, dd, J=2.7, 8.8 Hz), 8.02 (1H, d, J=8.8 Hz), 8.43 (1H, d, J=2.7 Hz).

MS (ESI) m/z: 472.15382 (M+H)$^+$.

Example 85

(2S)-2-(3-{5-[(4R)-4-Ethyl-4,5-dihydro-1,3-oxazol-2-yl]-1H-pyrrol-2-yl}-5-{[6-(methylsulfonyl)pyridin-3-yl]oxy}phenoxy)propan-1-ol

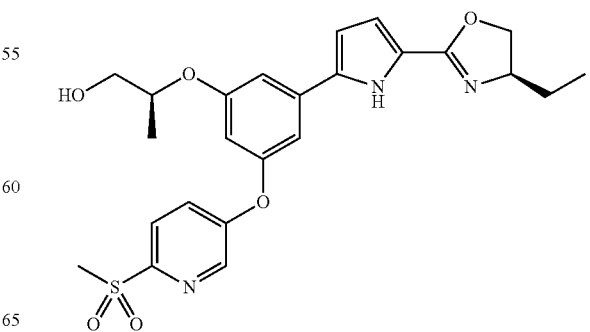

(85a) N-[(1R)-1-(Hydroxymethyl)propyl]-5-(3-[(1S)-2-methoxy-1-methylethoxy]-5-{[6-(methylsulfonyl)pyridin-3-yl]oxy}phenyl)-1H-pyrrole-2-carboxamide 5-(3-[(1S)-2-Methoxy-1-methylethoxy]-5-{[6-(methylsulfonyl)pyridin-3-yl]oxy}phenyl)-1H-pyrrole-2-carboxylic acid (1.20 g, 2.69 mmol) synthesized in Example (78k), (R)-(−)-2-amino-1-butanol (0.38 mL, 4.03 mmol), HOBT•H$_2$O (0.44 g, 3.23 mmol) and N-methylmorpholine (0.59 mL, 5.38 mmol) were dissolved in methylene chloride (30 mL), and WSCI•HCl (0.62 g, 3.23 mmol) was added at room temperature, followed by stirring for 6 hours under nitrogen atmosphere. The reaction solution was diluted with methylene chloride (50 mL), washed with 1N hydrochloric acid, a saturated aqueous sodium hydrogencarbonate solution and saturated brine, and subsequently dried over anhydrous magnesium sulfate. The solvent was distilled off under reduced pressure, and the resulting residue was purified using silica gel column chromatography (elution solvent: ethyl acetate/hexane=50%-90%) to afford the desired compound (1.18 g, 85%) as a white solid.
$^1$H-NMR (CDCl$_3$, 400 MHz): δ 1.01 (3H, t, J=7.4 Hz), 1.33 (3H, d, J=6.3 Hz), 1.67-1.74 (2H, m), 3.23 (3H, s), 3.42 (3H, s), 3.51 (1H, dd, J=3.9, 10.4 Hz), 3.59 (1H, dd, J=6.2, 10.4 Hz), 3.69 (1H, dd, J=5.7, 10.9 Hz), 3.79 (1H, dd, 3.4, 11.0 Hz), 4.01-4.06 (1H, brm), 4.56-4.60 (1H, m), 6.02 (1H, d, J=8.3 Hz), 6.49 (1H, dd, J=2.9, 3.9 Hz), 6.58 (1H, t, J=2.3 Hz), 6.61 (1H, dd, J=2.5, 4.1 Hz), 6.84 (1H, t, J=1.8 Hz), 7.02 (1H, t, J=1.8 Hz), 7.45 (1H, dd, J=2.8, 8.7 Hz), 8.05 (1H, d, J=8.7 Hz), 8.45 (1H, dd, J=0.8, 2.8 Hz), 9.60 (1H, brs).

(85b) 5-(3-{5-[(4R)-4-Ethyl-4,5-dihydro-1,3-oxazol-2-yl]-1H-pyrrol-2-yl}-5-[(1S)-2-methoxy-1-methylethoxy]phenoxy)-2-(methylsulfonyl)pyridine N-[(1R)-1-(Hydroxymethyl)propyl]-5-(3-[(1S)-2-methoxy-1-methylethoxy]-5-{[6-(methylsulfonyl)pyridin-3-yl]oxy}phenyl)-1H-pyrrole-2-carboxamide (1.18 g, 2.28 mmol) synthesized in Example (85a) was dissolved in tetrahydrofuran (20 mL), and anhydrous methanesulfonic acid (0.82 g, 4.56 mmol) and triethylamine (1.27 mL, 9.12 mmol) were added, followed by stirring at 50° C. for 1.5 hours under nitrogen atmosphere. A saturated aqueous sodium hydrogencarbonate solution (30 mL) was added, and the solution was separated with ethyl acetate (50 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=40%-70%) to afford the desired compound (1.06 g, yield 93%) as a white solid.
$^1$H-NMR (CDCl$_3$, 400 MHz): δ 0.99 (3H, t, J=7.4 Hz), 1.34 (3H, d, J=6.4 Hz), 1.56-1.65 (1H, m), 1.66-1.74 (1H, m), 3.23 (3H, s), 3.41 (3H, s), 3.50 (1H, dd, J=4.0, 10.2 Hz), 3.60 (1H, dd, J=6.1, 10.3 Hz), 4.02 (1H, t, J=7.8 Hz), 4.16-4.20 (1H, m), 4.46 (1H, t, J=8.7 Hz), 4.56-4.60 (1H, m), 6.51 (1H, d, J=3.9 Hz), 6.56 (1H, t, J=2.2 Hz), 6.74 (1H, d, J=3.8 Hz), 6.85 (1H, t, J=1.7 Hz), 7.05 (1H, t, J=1.7 Hz), 7.44 (1H, dd, J=2.7, 8.7 Hz), 8.05 (1H, dd, J=0.8, 8.5 Hz), 8.45 (1H, dd, J=0.8, 2.7 Hz).

(85c) (2S)-2-(3-{5-[(4R)-4-Ethyl-4,5-dihydro-1,3-oxazol-2-yl]-1H-pyrrol-2-yl}-5-{[6-(methylsulfonyl)pyridin-3-yl]oxy}phenoxy)propan-1-ol 5-(3-{5-[(4R)-4-Ethyl-4,5-dihydro-1,3-oxazol-2-yl]-1H-pyrrol-2-yl}-5-[(1S)-2-methoxy-1-methylethoxy]phenoxy)-2-(methylsulfonyl)pyridine (1.06 g, 2.12 mmol) synthesized in Example (85b) was dissolved in methylene chloride (20 mL), followed by cooling to −78° C., and boron tribromide (1.0 mol/L methylene chloride solution, 2.33 mL, 2.33 mmol) was added under nitrogen atmosphere. After the temperature was raised naturally and stirring was carried out at room temperature for 30 minutes, a saturated aqueous sodium hydrogencarbonate solution was added to neutralize the reaction solution, followed by extraction with methylene chloride (80 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=70%-100%) to afford the desired compound (738 mg, 71%) as a white solid.
$^1$H-NMR (CDCl$_3$, 400 MHz): δ 1.02 (3H, t, J=7.4 Hz), 1.28 (3H, d, J=6.2 Hz), 1.58-1.66 (1H, m), 1.67-1.74 (1H, m), 3.22 (3H, s), 3.80-3.82 (2H, m), 4.03 (1H, t, J=8.0 Hz), 4.16-4.23 (1H, m), 4.49 (1H, t, J=8.7 Hz), 4.62-4.68 (1H, m), 6.29 (1H, d, J=2.2 Hz), 6.45 (1H, t, J=3.7 Hz), 6.74 (1H, d, J=3.9 Hz), 6.79 (1H, t, J=1.8 Hz), 6.95 (1H, t, J=1.7 Hz), 7.35 (1H, dd, J=2.7, 8.7 Hz), 8.01 (1H, d, 8.7 Hz), 8.42 (1H, d, J=2.7 Hz).
MS (ESI) m/z: 486.16955 (M+H)$^+$.

Example 86

{(4R)-2-[5-(3-[(1S)-2-Methoxy-1-methylethoxy]-5-{[6-(methylsulfonyl)pyridin-3-yl]oxy}phenyl)-1H-pyrrol-2-yl]-4,5-dihydro-1,3-oxazol-4-yl}methanol

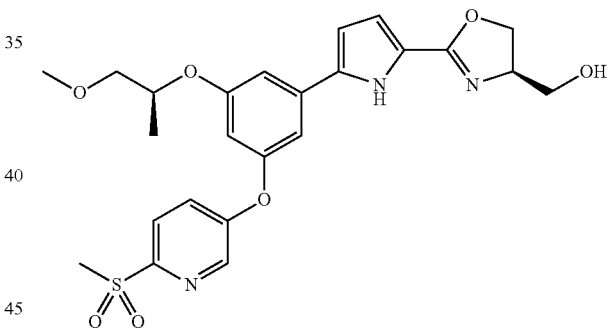

(86a) Methyl N-{[5-(3-[(1S)-2-methoxy-1-methylethoxy]-5-{[6-(methylsulfonyl)pyridin-3-yl]oxy}phenyl)-1H-pyrrol-2-yl]carbonyl}-L-serinate 5-(3-[(1S)-2-Methoxy-1-methylethoxy]-5-{[6-(methylsulfonyl)pyridin-3-yl]oxy}phenyl)-1H-pyrrole-2-carboxylic acid (1.60 g, 3.58 mmol) synthesized in Example (78k), L-serine methyl ester hydrochloride (0.61 g, 3.94 mmol), HOBT•H$_2$O (0.53 g, 3.94 mmol) and N-methylmorpholine (0.79 mL, 7.17 mmol) were dissolved in a mixed solvent of methylene chloride (30 mL) and N,N-dimethylformamide (7 mL), and WSCI•HCl (0.82 g, 4.30 mmol) was added at room temperature, followed by stirring for 15 hours under nitrogen atmosphere. The reaction solution was diluted with methylene chloride (100 mL), washed with 1N hydrochloric acid, a saturated aqueous sodium hydrogencarbonate solution and saturated brine, and subsequently dried over anhydrous magnesium sulfate. The solvent was distilled off under reduced pressure, and the resulting residue was purified using silica gel column chromatography (elution solvent: ethyl acetate/hexane=50%-80%) to afford the desired compound (1.91 g, 97%) as a white solid.

¹H-NMR (CDCl₃, 500 MHz): δ 1.33 (3H, d, J=6.4 Hz), 3.22 (3H, s), 3.41 (3H, s), 3.50 (1H, dd, J=3.8, 10.3 Hz), 3.58 (1H, dd, J=6.3, 10.3 Hz), 3.78 (3H, s), 3.98 (1H, dd, J=3.4, 11.3 Hz), 4.04 (1H, dd, J=3.9, 11.3 Hz), 4.56-4.59 (1H, brm), 4.80-4.83 (1H, m), 6.48 (1H, dd, J=2.7, 3.8 Hz), 6.56 (1H, t, J=2.0 Hz), 6.74 (1H, dd, J=2.0, 2.4 Hz), 6.88 (1H, t, J=1.7 Hz), 6.97 (1H, d, J=7.5 Hz), 7.04 (1H, t, J=1.9 Hz), 7.43 (1H, dd, J=2.8, 8.8 Hz), 8.03 (1H, d, J=8.8 Hz), 8.46 (1H, d, J=2.8 Hz), 10.5 (1H, brs).

(86b) Methyl (4S)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazole-4-carboxylate Methyl N-{[5-(3-[(1S)-2-methoxy-1-methylethoxy]-5-{[6-(methylsulfonyl)pyridin-3-yl]oxy}phenyl)-1H-pyrrol-2-yl]carbonyl}-L-serinate (1.91 g, 3.57 mmol) synthesized in Example (86a) was dissolved in methylene chloride (40 mL), and bis(2-methoxyethyl)aminosulfur trifluoride (0.85 mL, 4.64 mmol) was added dropwise at −78° C. After stirring for 30 minutes under nitrogen atmosphere, potassium carbonate (0.74 g, 5.35 mmol) was added, and stirring was carried out at 0° C. for 10 minutes, followed by further stirring at room temperature for 3 hours. A saturated aqueous sodium hydrogencarbonate solution (30 mL) was added, followed by extraction with methylene chloride (100 mL), and the organic layer was washed with saturated brine and dried over anhydrous magnesium sulfate. The solvent was distilled off under reduced pressure, and the resulting residue was purified using silica gel column chromatography (elution solvent: ethyl acetate/hexane=30%-70%) to afford the desired compound (1.76 g, 93%) as a white powder.

¹H-NMR (CDCl₃, 500 MHz): δ 1.34 (3H, d, J=6.2 Hz), 3.23 (3H, s), 3.42 (3H, s), 3.51 (1H, dd, J=4.1, 10.3 Hz), 3.59 (1H, dd, J=6.3, 10.3 Hz), 3.82 (1H, s), 4.56-4.60 (2H, m), 4.67 (1H, t, J=8.2 Hz), 4.90 (1H, dd, J=5.2, 7.8 Hz), 6.50 (1H, d, J=3.8 Hz), 6.59 (1H, t, J=2.2 Hz), 6.81 (1H, d, J=3.9 Hz), 6.84 (1H, t, J=1.7 Hz), 7.03 (1H, s), 7.45 (1H, dd, J=2.7, 8.6 Hz), 8.06 (1H, d, J=8.7 Hz), 8.48 (1H, d, J=2.7 Hz).

(86c) {(4R)-2-[5-(3-[(1S)-2-Methoxy-1-methylethoxy]-5-{[6-(methylsulfonyl)pyridin-3-yl]oxy}phenyl)-1H-pyrrol-2-yl]-4,5-dihydro-1,3-oxazol-4-yl}methanol Methyl (4S)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazole-4-carboxylate (1.76 g, 3.32 mmol) synthesized in Example (86b) was dissolved in tetrahydrofuran (30 mL), and lithium aluminum hydride (0.25 g, 6.65 mmol) was added at 0° C. After stirring for 30 minutes under nitrogen atmosphere, water (0.25 mL), a 5N aqueous sodium hydroxide solution (0.25 mL) and water (0.75 mL) were added in this order, and stirring was carried out for 10 minutes. Ethyl acetate (100 mL) was added followed by stirring for 5 minutes, and subsequently drying was carried out over anhydrous magnesium sulfate. The solvent was distilled off under reduced pressure, and the resulting residue was purified using silica gel column chromatography (elution solvent: methanol/methylene chloride=0%-5%) to afford the desired compound (1.15 g, 69%) as a white powder.

¹H-NMR (CDCl₃, 400 MHz): δ 1.34 (3H, d, J=6.3 Hz), 3.23 (3H, s), 3.41 (3H, s), 3.51 (1H, dd, J=4.1, 10.4 Hz), 3.58-3.62 (2H, m), 3.97 (1H, d, J=12.2 Hz), 4.10-4.15 (2H, m), 4.31-4.39 (2H, m), 4.56-4.60 (1H, m), 6.37 (1H, d, J=3.8 Hz), 6.47 (1H, d, J=3, 9 Hz), 6.57 (1H, t, J=2.2 Hz), 6.87 (1H, dd, J=1.2, 1.4 Hz), 7.05 (1H, t, J=1.8 Hz), 7.46 (1H, dd, J=2.8, 8.8 Hz), 8.05 (1H, dd, J=0.7, 8.8 Hz), 8.50 (1H, dd, J=0.7, 2.8 Hz).

MS (ESI) m/z: 502.16431 (M+H)⁺.

Example 87

(2S)-2-(3-{5-[(4R)-4-(Hydroxymethyl)-4,5-dihydro-1,3-oxazol-2-yl]-1H-pyrrol-2-yl}-5-{[6-(methylsulfonyl)pyridin-3-yl]oxy}phenoxy)propan-1-ol

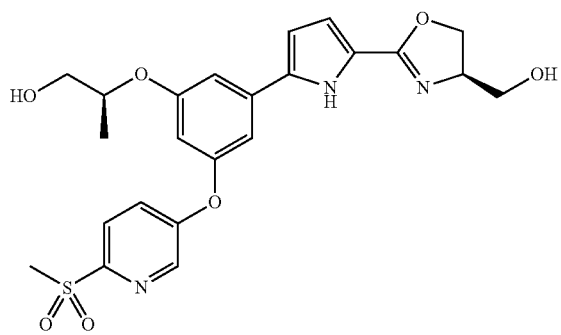

{(4R)-2-[5-(3-[(1S)-2-Methoxy-1-methylethoxy]-5-{[6-(methylsulfonyl)pyridin-3-yl]oxy}phenyl)-1H-pyrrol-2-yl]-4,5-dihydro-1,3-oxazol-4-yl}methanol (200 mg, 0.40 mmol) synthesized in Example (86c) was dissolved in methylene chloride (5 mL), followed by cooling to −78° C., and boron tribromide (1.0 mol/L methylene chloride solution, 0.80 mL, 0.80 mmol) was added under nitrogen atmosphere. After the temperature was raised naturally and stirring was carried out at room temperature for 30 minutes, a saturated aqueous sodium hydrogencarbonate solution was added to neutralize the reaction solution, followed by extraction with methylene chloride (80 mL). The organic layer was washed with 1N aqueous sodium hydroxide solution and saturated brine, and subsequently dried over anhydrous magnesium sulfate. The solvent was distilled off under reduced pressure, and the resulting residue was purified using silica gel column chromatography (elution solvent: methanol/methylene chloride=0%-4%) to afford the desired compound (143 mg, 74%) as a white solid.

¹H-NMR (CDCl₃, 400 MHz): δ 1.31 (3H, d, J=6.3 Hz), 3.23 (3H, s), 3.65 (1H, dd, J=3.5, 12.1 Hz), 3.74-3.80 (2H, m), 3.95 (1H, dd, J=2.7, 12.2 Hz), 4.20 (1H, t, J=6.8 Hz), 4.34-4.41 (1H, m), 4.41 (1H, t, J=9.8 Hz), 4.57-4.61 (1H, m), 6.37 (1H, d, J=3.9 Hz), 6.48 (1H, t, J=2.2 Hz), 6.53 (1H, d, J=3.9 Hz), 6.85 (1H, t, J=1.8 Hz), 7.01 (1H, t, J=1.8 Hz), 7.42 (1H, dd, J=2.7, 8.8 Hz), 8.04 (1H, d, J=8.8 Hz), 8.47 (1H, d, J=2.7 Hz)

MS (ESI) m/z: 488.14910 (M+H)⁺.

Example 88

(2S)-2-(3-{5-[(4R,5S)-4,5-Dimethyl-4,5-dihydro-1,3-oxazol-2-yl]-1H-pyrrol-2-yl}-5-{[6-(methylsulfonyl)pyridin-3-yl]oxy}phenoxy)propan-1-ol

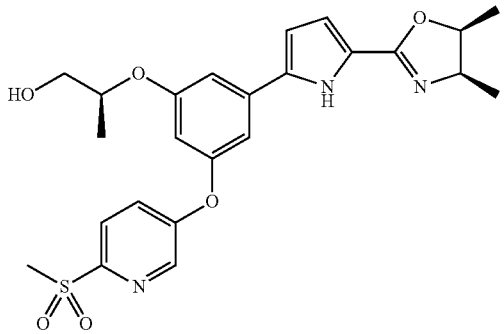

(88a) (2R,3R)-3-aminobutan-2-ol (2R,3R)-3-(Dibenzylamino) butan-2-ol ([α]$^{23}_D$-82°, c: 1.60, chloroform solution) (2.70 g, 10.0 mmol) synthesized according to a method known to the public (J. Org. Chem., 2006, 71, 6420.) was dissolved in methanol (20 mL), and palladium hydroxide carbon (0.85 g) was added, followed by stirring at 60 psi and at room temperature for 4 hours under hydrogen atmosphere. After Celite filtration, the solvent was distilled off under reduced pressure to afford the desired compound (0.73 g, yield 82%) as a colorless liquid.

$^1$H-NMR (CDCl$_3$, 400 MHz): δ 1.10 (3H, d, J=6.6 Hz), 1.17 (3H, d, J=6.3 Hz), 2.60-2.67 (1H, m), 3.31-3.37 (1H, m).

(88b) N-[(1R,2R)-2-Hydroxy-1-methylpropyl]-5-(3-[(1S)-2-methoxy-1-methylethoxy]-5-{[6-(methylsulfonyl)pyridin-3-yl]oxy}phenyl)-1H-pyrrole-2-carboxamide 5-(3-[(1S)-2-Methoxy-1-methylethoxy]-5-{[6-(methylsulfonyl)pyridin-3-yl]oxy}phenyl)-1H-pyrrole-2-carboxylic acid (2.00 g, 4.48 mmol) synthesized in Example (78k) and (2R,3R)-3-aminobutan-2-ol (0.94 g, 8.96 mmol) synthesized in Example (88a) were dissolved in methanol (30 mL), and 4-(4,6-dimethoxy-1,3,5-triazin-2-yl)-4-methylmorpholinium chloride n hydrate (2.84 g, 8.96 mmol) was added at room temperature, followed by stirring for 3 days under nitrogen atmosphere. The solvent was distilled off under reduced pressure, water (30 mL) was added, and the solution was separated with ethyl acetate (70 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=50%-90%) to afford the desired compound (1.33 g, 57%) as a white solid.

$^1$H-NMR (CDCl$_3$, 400 MHz): δ 1.23 (3H, t, J=6.3 Hz), 1.27 (3H, d, J=6.6 Hz), 1.33 (3H, d, J=6.3 Hz), 3.23 (3H, s), 3.41 (3H, s), 3.52 (1H, dd, J=3.9, 10.3 Hz), 3.59 (1H, dd, J=6.2, 10.3 Hz), 3.82-3.86 (1H, m), 4.05-4.09 (1H, m), 4.58-4.62 (1H, m), 6.17 (1H, d, J=8.7 Hz), 6.49 (1H, dd, J=2.9, 3.9 Hz), 6.57 (1H, t, J=2.2 Hz), 6.63 (1H, dd, J=2.3, 3.9 Hz), 6.86 (1H, t, J=1.8 Hz), 7.05 (1H, t, J=1.8 Hz), 7.44 (1H, dd, J=2.8, 8.7 Hz), 8.04 (1H, d, J=8.7 Hz), 8.48 (1H, d, J=2.8 Hz), 9.83 (1H, brs).

(88c) 5-(3-{5-[(4R,5S)-4,5-Dimethyl-4,5-dihydro-1,3-oxazol-2-yl]-1H-pyrrol-2-yl}-5-[(1S)-2-methoxy-1-methylethoxy]phenoxy)-2-(methylsulfonyl)pyridine N-[(1R,2R)-2-Hydroxy-1-methylpropyl]-5-(3-[(1S)-2-methoxy-1-methylethoxy]-5-{[6-(methylsulfonyl)pyridin-3-yl]oxy}phenyl)-1H-pyrrole-2-carboxamide (1.33 g, 2.57 mmol) synthesized in Example (88b) was dissolved in tetrahydrofuran (25 mL), and anhydrous methanesulfonic acid (0.92 g, 5.14 mmol) and triethylamine (1.43 mL, 10.28 mmol) were added, followed by stirring at 50° C. for 5 hours under nitrogen atmosphere. A saturated aqueous sodium hydrogencarbonate solution (40 mL) was added, and the solution was separated with ethyl acetate (80 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=40%-70%) to afford the desired compound (0.95 g, yield 74%) as a white solid.

$^1$H-NMR (CDCl$_3$, 500 MHz): δ 1.20 (3H, t, J=6.9 Hz), 1.33 (3H, d, J=6.3 Hz), 1.33 (3H, d, J=6.6 Hz), 3.23 (3H, s), 3.41 (3H, s), 3.50 (1H, dd, J=4.0, 10.4 Hz), 3.58 (1H, dd, J=6.1, 10.4 Hz), 4.24-4.29 (1H, m), 4.55-4.58 (1H, m), 4.79-4.84 (1H, m), 6.50 (1H, d, J=3.8 Hz), 6.56 (1H, t, J=2.2 Hz), 6.74 (1H, d, J=3.8 Hz), 6.83 (1H, t, J=1.8 Hz), 7.01 (1H, t, J=1.8 Hz), 7.43 (1H, dd, J=2.8, 8.6 Hz), 8.05 (1H, d, J=8.6 Hz), 8.48 (1H, d, J=2.8 Hz).

(88d) (2S)-2-(3-{5-[(4R,5S)-4,5-Dimethyl-4,5-dihydro-1,3-oxazol-2-yl]-1H-pyrrol-2-yl}-5-{[6-(methylsulfonyl)pyridin-3-yl]oxy}phenoxy)propan-1-ol 5-(3-{5-[(4R,5S)-4,5-Dimethyl-4,5-dihydro-1,3-oxazol-2-yl]-1H-pyrrol-2-yl}-5-[(1S)-2-methoxy-1-methylethoxy]phenoxy)-2-(methylsulfonyl)pyridine (0.95 g, 1.96 mmol) synthesized in Example (88c) was dissolved in methylene chloride (20 mL) and cooled to −78° C., and boron tribromide (1.0 mol/L methylene chloride solution, 2.15 mL, 2.15 mmol) was added under nitrogen atmosphere. After the temperature was raised naturally and the solution was stirred at room temperature for 30 minutes, a saturated aqueous sodium hydrogencarbonate solution was added to neutralize the reaction solution, followed by extraction with methylene chloride (80 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=70%-100%) to afford the desired compound (617 mg, 67%) as a white solid.

$^1$H-NMR (CDCl$_3$, 400 MHz): δ 1.23 (3H, t, J=7.0 Hz), 1.27 (3H, d, J=6.2 Hz), 1.34 (3H, d, J=6.6 Hz), 3.23 (3H, s), 3.81-3.83 (2H, m), 4.27-4.35 (1H, m), 4.65-4.70 (1H, m), 4.81-4.89 (1H, m), 6.24 (1H, t, J=2.2 Hz), 6.44 (1H, d, J=3.8 Hz), 6.73 (1H, d, J=3.8 Hz), 6.76 (1H, dd, J=1.2, 2.2 Hz), 6.92 (1H, t, J=1.7 Hz), 7.32 (1H, dd, J=2.8, 8.8 Hz), 8.00 (1H, d, J=8.8 Hz), 8.41 (1H, d, J=2.8 Hz).

MS (ESI) m/z: 486.17002 (M+H)$^+$.

Example 89

{(4R,5R)-2-[5-(3-[(1S)-2-Methoxy-1-methyl-ethoxy]-5-{[6-(methylsulfonyl)pyridin-3-yl]oxy}phenyl)-1H-pyrrol-2-yl]-4-methyl-4,5-dihydro-1,3-oxazol-5-yl}methanol

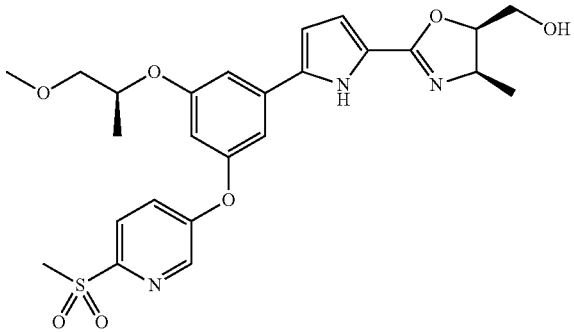

(89a) (2R,3R)-3-[(Diphenylmethyl)amino]-1-[(tripropan-2-ylsilyl)oxy]butan-2-ol Molecular sieves 4A (10 g) were added into dehydrated methylene chloride (200 mL). Into this system, were added titanium tetraisopropoxide (8.8 mL, 30 mmol) and L-(+)-tartaric acid diethyl (6.2 mL, 36 mmol) at −20° C., and stirring was carried out at the same temperature for 15 minutes. (2E)-2-Buten-1-ol (25 mL, 295 mmol), which was dissolved in dehydrated methylene chloride (50 mL), was added dropwise at −20° C., and stirring was carried out at the same temperature for 15 minutes. Subsequently, into the system, t-butyl hydroperoxide (methylene chloride was added to conduct a solution-separating operation, followed by further addition of molecular sieves 4A (5 g) and stirring for 20 minutes) (5-6 mol/L decane solution, 100 mL, 0.5-0.6 mmol) was added at −20° C., and stirring was carried out at −20° C. for 8.5 hours under nitrogen atmosphere, and the solution was left still overnight at −30° C.

Into this system, were added n-tributylphosphine (75 mL, 300 mmol), titanium tetraisopropoxide (135 mL, 460 mmol) and 1,1-diphenylmethanamine (75 mL, 440 mmol) at room temperature, and stirring was carried out at the same temperature for 1 week. To the reaction solution, water (30 mL) was added, and the deposit was filtered off. To the mother liquor, water (400 mL) was added, and extraction was carried out with methylene chloride (1 L). The solvent was distilled off under reduced pressure, and the resulting residue was purified using silica gel column chromatography (elution solvent: ethyl acetate/hexane=15%-40%) to afford a dark brown liquid.

This liquid was dissolved in methylene chloride (300 mL), and triethylamine (85 mL, 610 mmol) and triisopropylsilyl chloride (50 mL, 234 mmol) were added at room temperature, followed by stirring at room temperature for 1.5 days. A saturated aqueous ammonium chloride solution (500 mL) was added, and extraction was carried out with methylene chloride (500 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=0%-5%) to afford the desired compound (80.5 g, yield 64%) as a white solid.

$^1$H-NMR (CDCl$_3$, 400 MHz): δ 0.96-1.07 (21H, m), 1.10 (3H, d, J=6.3 Hz), 2.72-2.81 (1H, m), 3.28 (1H, br s), 3.56-3.63 (1H, m), 3.72 (1H, dd, J=10.2, 5.9 Hz), 3.80 (1H, dd, J=10.2, 3.9 Hz), 4.98 (1H, s), 7.15-7.20 (2H, m), 7.23-7.29 (4H, m), 7.34-7.40 (4H, m).

(89b) Benzyl{(2R,3R)-3-hydroxy-4-[(tripropan-2-ylsilyl)oxy]butan-2-yl}carbamate (2R,3R)-3-[(Diphenylmethyl)amino]-1-[(triisopropan-2-ylsilyl)oxy]butan-2-ol (10.3 g, 24.1 mmol) synthesized in Example (89a) was dissolved in ethanol (40 mL), and palladium carbon (3.20 g) was added, followed by stirring at room temperature for 6 hours under hydrogen atmosphere. After Celite filtration, the solvent was distilled off under reduced pressure to afford a compound as a colorless liquid.

This was dissolved in water (40 mL) heated to 50° C., and sodium hydrogencarbonate (4.50 g, 53.6 mmol) and benzyl chloroformate (3.50 mL, 24.5 mmol) were added at room temperature, followed by d stirring at room temperature for 5 hours. Methylene chloride (100 mL) was added, and extraction was carried out. The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=10%-15%) to afford the desired compound (7.00 g, yield 73%) as a colorless liquid.

$^1$H-NMR (CDCl$_3$, 400 MHz): δ 1.04-1.09 (21H, m), 1.18 (3H, d, J=6.8 Hz), 2.67 (1H, br s), 3.65-3.73 (2H, m), 3.77 (1H, dd, J=10.0, 3.7 Hz), 3.86 (1H, br s), 5.10 (2H, s), 5.27 (1H, br s), 7.30-7.38 (5H, m).

(89c) (5R,6S)-5,10-Dimethyl-3-oxo-1-phenyl-9,9-di(propan-2-yl)-2,8-dioxa-4-aza-9-silaundecan-6-yl 4-nitrobenzoate Benzyl {(2R,3R)-3-hydroxy-4-[(tripropan-2-ylsilyl)oxy]butan-2-yl}carbamate (7.00 g, 17.7 mmol) synthesized in Example (89b) was dissolved in toluene (80 mL), and 4-nitro benzoic acid (6.10 g, 36.5 mmol) and triphenylphosphine (11.85 g, 45.2 mmol) were added, followed by cooling to 0° C. Under nitrogen atmosphere, diethyl azodicarboxylate (40% toluene solution, 20.3 mL, 44.7 mmol) was added dropwise over 10 minutes, and stirring was carried out at room temperature for 4 hours. The solvent was distilled off under reduced pressure, and the resulting residue was purified using silica gel column chromatography (elution solvent: ethyl acetate/hexane=10%-15%) to afford the desired compound (7.90 g, yield 82%) as a yellow liquid.

$^1$H-NMR (CDCl$_3$, 400 MHz): δ 0.96-1.09 (21H, m), 1.29 (3H, d, J=7.0 Hz), 3.90-4.01 (1H, m), 4.25-4.32 (1H, m), 4.95-5.10 (3H, m), 5.13-5.20 (1H, m), 7.24-7.39 (5H, m), 8.14-8.21 (2H, m), 8.23-8.30 (2H, m).

(89d) Benzyl {(2R,3S)-3-hydroxy-4-[(tripropan-2-ylsilyl)oxy]butan-2-yl}carbamate (5R,6S)-5,10-Dimethyl-3-oxo-1-phenyl-9,9-di(propan-2-yl)-2,8-dioxa-4-aza-9-silaundecan-6-yl 4-nitrobenzoate (7.90 g, 14.5 mmol) synthesized in Example (89c) was dissolved in methylene chloride (150 mL), and diisobutylaluminum hydride (1.0 mol/L hexane solution, 30.0 mL, 30.0 mmol) was added, followed by stirring at −40° C. for 8 hours under nitrogen atmosphere. The reaction solution was brought back to 0° C., and methanol (5.0 mL) was added, followed by addition of a 5N aqueous sodium hydroxide solution (150 mL), and extraction was carried out with methylene chloride (200 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=10%-15%) to afford the desired compound (3.70 g, yield 65%) as a colorless liquid.

$^1$H-NMR (CDCl$_3$, 400 MHz): δ 1.01-1.13 (21H, m), 1.26 (3H, d, J=6.6 Hz), 2.72 (1H, br s), 3.55-3.67 (2H, m), 3.73 (2H, br s), 5.10 (2H, s), 5.13 (1H, br s), 7.31-7.36 (5H, m).

(89e) (2S,3R)-3-amino-1-[(tripropan-2-ylsilyl)oxy]butan-2-ol

Benzyl {(2R,3S)-3-hydroxy-4-[(tripropan-2-ylsilyl)oxy]butan-2-yl}carbamate (3.70 g, 9.35 mmol) synthesized in Example (89d) was dissolved in ethanol (30 mL), and palladium carbon (1.00 g) was added, followed by stirring at room temperature for 8 hours under hydrogen atmosphere. After Celite filtration, the solvent was distilled off under reduced pressure to afford the desired compound (2.65 g, yield ~100%) as a pale yellow liquid.

$^1$H-NMR (CDCl$_3$, 400 MHz): δ 1.04-1.14 (24H, m), 2.95-3.02 (1H, m), 3.30-3.35 (1H, m), 3.66 (1H, dd, J=9.8, 6.3 Hz), 3.76 (1H, dd, J=9.8, 4.3 Hz).

(89f) N-{(1R,2S)-2-Hydroxy-1-methyl-3-[(triisopropylsilyl)oxy]propyl}-5-(3-[(1S)-2-methoxy-1-methylethoxy]-5-{[6-(methylsulfonyl)pyridin-3-yl]oxy}phenyl)-1H-pyrrole-2-carboxamide 5-(3-[(1S)-2-Methoxy-1-methylethoxy]-5-{[6-(methylsulfonyl)pyridin-3-yl]oxy}phenyl)-1H-pyrrole-2-carboxylic acid (1.20 g, 2.69 mmol) synthesized in Example (78k), (2S,3R)-3-amino-1-[(tripropan-2-ylsilyl)oxy]butan-2-ol (1.08 g, 4.11 mmol) synthesized in Example (89e), HOBT·H$_2$O (0.44 g, 3.23 mmol) and N-methylmorpholine (0.59 mL, 5.38 mmol) were dissolved in N,N-dimethylformamide (20 mL), and WSCI·HCl (0.62 g, 3.23 mmol) was added at room temperature, followed by stirring for 18 hours under nitrogen atmosphere. To the reaction solution, saturated brine (30 mL) was added, and extraction was carried out with ethyl acetate (60 mL). After washing with 1N hydrochloric acid, a saturated aqueous sodium hydrogencarbonate solution and saturated brine, drying was carried out over anhydrous magnesium sulfate. The solvent was distilled off under reduced pressure, and the resulting residue was purified using silica gel column chromatography (elution solvent: ethyl acetate/hexane=20%-50%) to afford the desired compound (1.69 g, 91%) as a white powder.

$^1$H-NMR (CDCl$_3$, 400 MHz): δ 1.03-1.13 (21H, m), 1.34 (3H, d, J=6.3 Hz), 1.35 (3H, d, J=6.8 Hz), 3.23 (3H, s), 3.42 (3H, s), 3.51 (1H, dd, J=4.0, 10.3 Hz), 3.54-3.61 (2H, m), 3.73-3.78 (2H, m), 4.14-4.18 (1H, m), 4.56-4.60 (1H, m), 6.31 (1H, brm), 6.49 (1H, dd, J=2.9, 3.9 Hz), 6.57-6.60 (2H, m), 6.84 (1H, dd, J=1.5, 2.3 Hz), 7.02 (1H, t, J=1.8 Hz), 7.45 (1H, dd, J=2.8, 8.8 Hz), 8.09 (1H, d, J=8.7 Hz), 8.49 (1H, d, J=2.7 Hz), 9.52 (1H, brs).

(89g) 5-(3-[(1S)-2-Methoxy-1-methylethoxy]-5-{5-[(4R,5R)-4-methyl-5-{[(triisopropylsilyl)oxy]methyl}-4,5-dihydro-1,3-oxazol-2-yl]-1H-pyrrol-2-yl}phenoxy)-2-(methylsulfonyl)pyridine N-[(1R,2S)-2-Hydroxy-1-methyl-3-[(triisopropylsilyl)oxy]propyl]-5-(3-[(1S)-2-methoxy-1-methylethoxy]-5-{[6-(methylsulfonyl)pyridin-3-yl]oxy}phenyl)-1H-pyrrole-2-carboxamide (1.69 g, 2.45 mmol) synthesized in Example (89O was dissolved in tetrahydrofuran (25 mL), and anhydrous methanesulfonic acid (0.88 g, 4.90 mmol) and triethylamine (1.37 mL, 9.80 mmol) were added, followed by stirring at 50° C. for 5 hours under nitrogen atmosphere. A saturated aqueous sodium hydrogencarbonate solution (40 mL) was added, and the solution was separated with ethyl acetate (60 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=10%-50%) to afford the desired compound (1.23 g, yield 75%) as a white solid.

$^1$H-NMR (CDCl$_3$, 400 MHz): δ 1.04-1.14 (21H, m), 1.34 (6H, d, J=6.3 Hz), 3.23 (3H, s), 3.42 (3H, s), 3.50 (1H, dd, J=4.0, 10.3 Hz), 3.59 (1H, dd, J=6.1, 10.3 Hz), 3.94 (2H, d, J=5.3 Hz), 4.37-4.41 (1H, m), 4.56-4.60 (1H, m), 4.65-4.69 (1H, m), 6.49 (1H, d, J=3.9 Hz), 6.56 (1H, t, J=2.1 Hz), 6.74 (1H, d, J=3.8 Hz), 6.85 (1H, s), 7.04 (1H, s), 7.44 (1H, dd, J=2.8, 8.6 Hz), 8.05 (1H, d, J=8.6 Hz), 8.48 (1H, d, J=2.8 Hz).

(89h) {(4R,5R)-2-[5-(3-[(1S)-2-Methoxy-1-methylethoxy]-5-{[6-(methylsulfonyl)pyridin-3-yl]oxy}phenyl)-1H-pyrrol-2-yl]-4-methyl-4,5-dihydro-1,3-oxazol-5-yl}methanol 5-(3-[(1S)-2-Methoxy-1-methylethoxy]-5-{5-[(4R,5R)-4-methyl-5-{[(triisopropylsilyl)oxy]methyl}-4,5-dihydro-1,3-oxazol-2-yl]-1H-pyrrol-2-yl}phenoxy)-2-(methylsulfonyl)pyridine (1.23 g, 1.83 mmol) synthesized in Example (89g) was dissolved in tetrahydrofuran (20 mL), and tetrabutylammonium fluoride (1.0 mol/L tetrahydrofuran solution, 2.11 mL, 2.11 mmol) is added at room temperature, followed by stirring at room temperature for 1 hour under nitrogen atmosphere. Water (20 mL) was added, and extraction was carried out with ethyl acetate (50 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=90%-100%) to afford the desired compound (715 mg, yield 76%) as a white solid.

$^1$H-NMR (CDCl$_3$, 400 MHz): δ 1.26 (3H, d, J=7.1 Hz), 1.31 (3H, d, J=6.3 Hz), 3.23 (3H, s), 3.42 (3H, s), 3.50 (1H, dd, J=3.9, 10.3 Hz), 3.59 (1H, dd, J=6.3, 10.3 Hz), 3.85 (2H, d, J=5.4 Hz), 4.36-4.42 (1H, m), 4.53-4.48 (1H, m), 4.70-4.76 (1H, m), 6.50 (1H, d, J=3.8 Hz), 6.57 (1H, t, J=2.1 Hz), 6.77 (1H, d, J=3.8 Hz), 6.84 (1H, t, 1.8 Hz), 7.00 (1H, t, 1.8 Hz), 7.43 (1H, dd, J=2.8, 8.8 Hz), 8.04 (1H, d, J=8.8 Hz), 8.48 (1H, d, J=2.8 Hz).

MS (ESI) m/z: 516.17829 (M+H)$^+$.

Example 90

(2S)-2-(3-{5-[(4R,5R)-5-(Hydroxymethyl)-4-methyl-4,5-dihydro-1,3-oxazol-2-yl]-1H-pyrrol-2-yl}-5-{[6-(methylsulfonyl)pyridin-3-yl]oxy}phenoxy)propan-1-ol

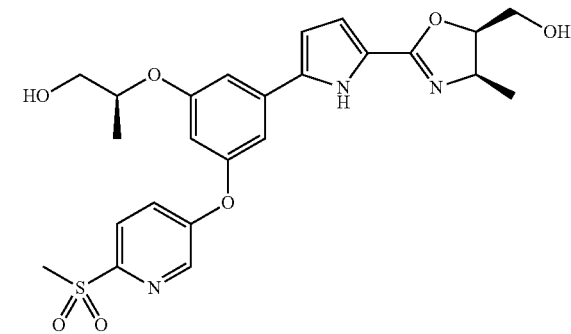

{(4R,5R)-2-[5-(3-[(1S)-2-Methoxy-1-methylethoxy]-5-{[6-(methylsulfonyl)pyridin-3-yl]oxy}phenyl)-1H-pyrrol-2-yl]-4-methyl-4,5-dihydro-1,3-oxazol-2-yl}methanol (200 mg, 0.39 mmol) synthesized in Example (89h) was dissolved in methylene chloride (5 mL), and boron tribromide (1.0 mol/L methylene chloride solution, 0.78 mL, 0.78 mmol) was added at −78° C. under nitrogen atmosphere, and subsequently the temperature was brought back to room temperature and stirring was carried out for 45 minutes. To the reaction solution, a saturated aqueous sodium hydrogencarbonate solution was added, and extraction was carried out with methylene chloride. The organic layer was washed with saturated brine, and subsequently dried over sodium sulfate. The solvent was distilled off under reduced pressure, and the resulting residue was purified using silica gel column chromatography (elution solvent: methanol/methylene chloride=0%-4%) to afford the desired compound (87 mg, yield 45%) as a white solid.

$^1$H-NMR (CDCl$_3$, 400 MHz): δ 1.29 (6H, t, J=5.9 Hz), 3.23 (3H, s), 3.79 (2H, d, J=4.9 Hz), 3.85 (2H, d, J=6.3 Hz), 4.41 (1H, dt, J=16.3, 7.1 Hz), 4.59 (1H, dd, J=11.5, 5.6 Hz), 4.73-4.77 (1H, m), 6.38 (1H, s), 6.46 (1H, d, J=3.4 Hz), 6.77 (1H, d, J=3.9 Hz), 6.81 (1H, s), 6.98 (1H, s), 7.35 (1H, d, J=8.8 Hz), 8.01 (1H, d, J=8.8 Hz), 8.44 (1H, s).

MS (ESI) m/z: 502.16510 (M+H)$^+$.

Example 91

{(4R,5S)-2-[5-(3-[(1S)-2-Methoxy-1-methylethoxy]-5-{[6-(methylsulfonyl)pyridin-3-yl]oxy}phenyl)-1H-pyrrol-2-yl]-5-methyl-4,5-dihydro-1,3-oxazol-4-yl}methanol

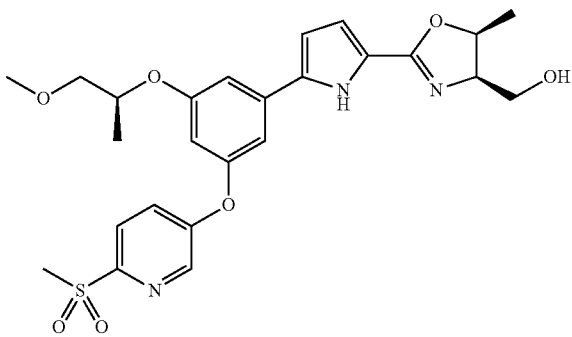

(91a) N-[(1R,2R)-2-Hydroxy-1-(hydroxymethyl)propyl]-5-(3-[(1S)-2-methoxy-1-methylethoxy]-5-{[6-(methylsulfonyl)pyridin-3-yl]oxy}phenyl)-1H-pyrrole-2-carboxamide 5-(3-[(1S)-2-Methoxy-1-methylethoxy]-5-{[6-(methylsulfonyl)pyridin-3-yl]oxy}phenyl)-1H-pyrrole-2-carboxylic acid (1.20 g, 2.69 mmol) synthesized in Example (78k) and commercially available L-threoninol (0.57 g, 5.38 mmol) were dissolved in methanol (25 mL), and 4-(4,6-dimethoxy-1,3,5-triazin-2-yl)-4-methylmorpholinium chloride n hydrate (1.70 g, 5.38 mmol) was added at room temperature, followed by stirring for 3.5 hours under nitrogen atmosphere. The solvent was distilled off under reduced pressure, and the resulting residue was diluted with ethyl acetate (100 mL). After washing with 1N hydrochloric acid, a saturated aqueous sodium hydrogencarbonate solution and saturated brine, drying was carried out over anhydrous magnesium sulfate, the solvent was distilled off under reduced pressure, and the resulting residue was purified using silica gel column chromatography (elution solvent: methanol/methylene chloride=0%-6%) to afford the desired compound (883 mg, 62%) as a white solid.

$^1$H-NMR (CDCl$_3$, 400 MHz): δ 1.23 (3H, d, J=6.4 Hz), 1.30 (3H, d, J=6.3 Hz), 3.23 (3H, s), 3.42 (3H, s), 3.51 (1H, dd, J=3.9, 10.2 Hz), 3.58 (1H, dd, J=6.4, 10.4 Hz), 3.87 (2H, d, J=4.0 Hz), 3.97-4.03 (1H, brm), 4.22-4.26 (1H, m), 4.55-4.58 (1H, m), 6.49 (1H, dd, J=2.8, 3.9 Hz), 6.57 (1H, t, J=2.2 Hz), 6.68-6.71 (2H, m), 6.86 (1H, t, J=1.7 Hz), 7.02 (1H, t, J=1.8 Hz), 7.44 (1H, dd, J=2.7, 8.7 Hz), 8.04 (1H, d, J=8.8 Hz), 8.47 (1H, d, J=2.7 Hz), 10.05 (1H, brs).

(91b) N-[(1R,2R)-2-Hydroxy-1-{[(triisopropylsilyl)oxy]methyl}propyl]-5-(3-[(1S)-2-methoxy-1-methylethoxy]-5-{[6-(methylsulfonyl)pyridin-3-yl]oxy}phenyl)-1H-pyrrole-2-carboxamide N-[(1R,2R)-2-Hydroxy-1-(hydroxymethyl)propyl]-5-(3-[(1S)-2-methoxy-1-methylethoxy]-5-{[6-(methylsulfonyl)pyridin-3-yl]oxy}phenyl)-1H-pyrrole-2-carboxamide (883 mg, 1.65 mmol) synthesized in Example (91a), triethylamine (1.15 mL, 8.27 mmol) and 4-dimethylaminopyridine (404 mg, 3.31 mmol) were dissolved in methylene chloride (20 mL), and triisopropylsilyl chloride (0.60 mL, 2.81 mmol) was added at room temperature, followed by stirring for 20 hours under nitrogen atmosphere. The solvent was distilled off under reduced pressure, and the resulting residue was purified using silica gel column chromatography (elution solvent: ethyl acetate/hexane=30%-60%) to afford the desired compound (1.03 g, 90%) as a white solid.

$^1$H-NMR (CDCl$_3$, 400 MHz): δ 1.05-1.08 (18H, m), 1.09-1.16 (3H, m), 1.23 (3H, d, J=6.4 Hz), 1.34 (3H, d, J=6.3 Hz), 3.24 (3H, s), 3.42 (3H, s), 3.52 (1H, dd, J=4.0, 10.2 Hz), 3.60 (1H, dd, J=6.2, 10.4 Hz), 3.99-4.04 (1H, m), 4.03-4.06 (2H, m), 4.30-4.35 (1H, m), 4.56-4.61 (1H, m), 6.51 (1H, t, J=3.4 Hz), 6.59 (1H, t, J=2.2 Hz), 6.62-6.66 (2H, m), 6.85 (1H, t, J=1.8 Hz), 7.03 (1H, t, J=1.7 Hz), 7.46 (1H, dd, J=2.7, 8.8 Hz), 8.06 (1H, d, J=8.8 Hz), 8.49 (1H, d, J=2.7 Hz), 9.49 (1H, brs).

(91c) 5-(3-[(1S)-2-Methoxy-1-methylethoxy]-5-{5-[(4R,5S)-5-methyl-4-{[(triisopropylsilyl)oxy]methyl}-4,5-dihydro-1,3-oxazol-2-yl]-1H-pyrrol-2-yl}phenoxy)-2-(methylsulfonyl)pyridine N-[(1R,2R)-2-Hydroxy-1-{[(triisopropylsilyl)oxy]methyl}propyl]-5-(3-[(1S)-2-methoxy-1-methylethoxy]-5-{[6-(methylsulfonyl)pyridin-3-yl]oxy}phenyl)-1H-pyrrole-2-carboxamide (1.03 g, 1.49 mmol) synthesized in Example (91b) was dissolved in tetrahydrofuran (20 mL), and anhydrous methanesulfonic acid (0.54 g, 2.99 mmol) and triethylamine (0.83 mL, 5.97 mmol) were added, followed by stirring at 50° C. for 4.5 hours under nitrogen atmosphere. A saturated aqueous sodium hydrogencarbonate solution (30 mL) was added, and the solution was separated with ethyl acetate (50 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=20%-50%) to afford the desired compound (901 mg, yield 90%) as a white solid.

$^1$H-NMR (CDCl$_3$, 500 MHz): δ 1.03-1.13 (21H, m), 1.33 (3H, d, J=6.3 Hz), 1.52 (3H, d, J=6.6 Hz), 3.23 (3H, s), 3.41

(3H, s), 3.50 (1H, dd, J=3.9, 10.4 Hz), 3.58 (1H, dd, J=6.2, 10.5 Hz), 3.81 (1H, t, J=9.5 Hz), 3.95 (1H, dd, J=3.9, 10.4 Hz), 4.21-4.25 (2H, m), 4.56-4.59 (1H, m), 4.89-4.93 (1H, m), 6.50 (1H, d, J=3.9 Hz), 6.56 (1H, t, J=2.2 Hz), 6.76 (1H, d, J=3.9 Hz), 6.84 (1H, s), 7.02 (1H, s), 7.44 (1H, dd, J=2.7, 8.8 Hz), 8.05 (1H, d, J=8.8 Hz), 8.48 (1H, d, J=2.7 Hz).

(91d) {(4R,5S)-2-[5-(3-[(1S)-2-Methoxy-1-methylethoxy]-5-{[6-(methylsulfonyl)pyridin-3-yl]oxy}phenyl)-1H-pyrrol-2-yl]-5-methyl-4,5-dihydro-1,3-oxazol-4-yl}methanol 5-(3-[(1S)-2-Methoxy-1-methylethoxy]-5-{5-[(4R,5S)-5-methyl-4-{[(triisopropylsilyl)oxy]methyl}-4,5-dihydro-1,3-oxazol-2-yl]-1H-pyrrol-2-yl}phenoxy)-2-(methylsulfonyl)pyridine (901 mg, 1.34 mmol) synthesized in Example (91c) was dissolved in tetrahydrofuran (15 mL), and tetrabutylammonium fluoride (1 mol/L tetrahydrofuran solution, 1.54 mL, 1.54 mmol) was added at 0° C., followed by stirring at room temperature for 1 hour under nitrogen atmosphere. Water (20 mL) was added, and extraction was carried out with ethyl acetate (40 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=80%-100%) to afford the desired compound (578 mg, yield 84%) as a white solid.

$^1$H-NMR (CDCl$_3$, 400 MHz): δ 1.33 (3H, d, J=6.3 Hz), 1.39 (3H, d, J=6.8 Hz), 3.23 (3H, s), 3.41 (3H, s), 3.50 (1H, dd, J=4.1, 10.4 Hz), 3.59 (1H, dd, J=6.1, 10.4 Hz), 3.77 (1H, dd, J=6.2, 11.2 Hz), 3.84 (1H, dd, J=3.7, 11.8 Hz), 4.22-4.27 (1H, m), 4.54-4.61 (1H, m), 4.83-4.90 (1H, m), 6.45 (1H, d, J=3.8 Hz), 6.55 (1H, t, J=2.2 Hz), 6.68 (1H, d, J=3.9 Hz), 6.90 (1H, t, 1.8 Hz), 7.07 (1H, t, 1.8 Hz), 7.43 (1H, dd, J=2.8, 8.7 Hz), 8.04 (1H, d, J=8.7 Hz), 8.49 (1H, d, J=2.8 Hz).

MS (ESI) m/z: 516.17933 (M+H)$^+$.

Example 92

(2S)-2-(3-{5-[(4R,5S)-4-(Hydroxymethyl)-5-methyl-4,5-dihydro-1,3-oxazol-2-yl]-1H-pyrrol-2-yl}-5-{[6-(methylsulfonyl)pyridin-3-yl]oxy}phenoxy)propan-1-ol

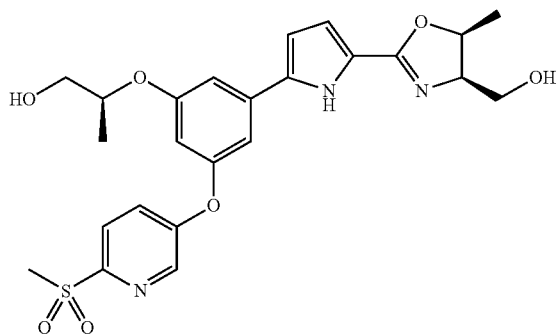

{(4R,5S)-2-[5-(3-[(1S)-2-Methoxy-1-methylethoxy]-5-{[6-(methylsulfonyl)pyridin-3-yl]oxy}phenyl)-1H-pyrrol-2-yl]-5-methyl-4,5-dihydro-1,3-oxazol-4-yl}methanol (178 mg, 0.35 mmol) synthesized in Example (91d) was dissolved in methylene chloride (5 mL), and boron tribromide (1.0 mol/L methylene chloride solution, 0.70 mL, 0.70 mmol) was added at −78° C., and subsequently the temperature was brought back to room temperature and stirring was carried out for 45 minutes. To the reaction solution, a saturated aqueous sodium hydrogencarbonate solution was added, and extraction was carried out with methylene chloride. The organic layer was washed with saturated brine, and subsequently dried over sodium sulfate. The solvent was distilled off under reduced pressure, and the resulting residue was purified using silica gel column chromatography (elution solvent: methanol/methylene chloride=0%-4%) to afford the desired compound (142 mg, yield 82%) as a white solid.

$^1$H-NMR (CDCl$_3$, 400 MHz): δ 1.30 (3H, d, J=6.3 Hz), 1.43 (3H, d, J=6.6 Hz), 3.23 (3H, s), 3.76-3.87 (4H, m), 4.22-4.27 (1H, m), 4.53-4.60 (1H, m), 4.92-4.84 (1H, m), 6.45 (1H, d, J=3.9 Hz), 6.48 (1H, s), 6.69 (1H, d, J=3.9 Hz), 6.87 (1H, t, J=1.8 Hz), 7.02 (1H, s), 7.41 (1H, dd, J=8.6, 2.7 Hz), 8.03 (1H, d, J=8.6 Hz), 8.47 (1H, d, J=2.7 Hz).

MS (ESI) m/z: 502.16583 (M+H)$^+$.

Example 93

(1S)-1-{(4S)-2-[5-(3-[(1S)-2-Methoxy-1-methylethoxy]-5-{[6-(methylsulfonyl)pyridin-3-yl]oxy}phenyl)-1H-pyrrol-2-yl]-4,5-dihydro-1,3-oxazol-4-yl}ethanol

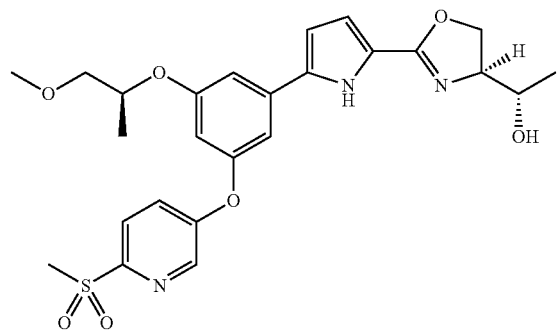

(93a) N-[(1S,2S)-2-Hydroxy-1-(hydroxymethyl)propyl]-5-(3-[(1S)-2-methoxy-1-methylethoxy]-5-{[6-(methylsulfonyl)pyridin-3-yl]oxy}phenyl)-1H-pyrrole-2-carboxamide 5-(3-[(1S)-2-Methoxy-1-methylethoxy]-5-{[6-(methylsulfonyl)pyridin-3-yl]oxy}phenyl)-1H-pyrrole-2-carboxylic acid (1.20 g, 2.69 mmol) synthesized in Example (78k), commercially available D-threoninol (0.34 g, 3.23 mmol), HOBT•H$_2$O (0.40 g, 3.23 mmol) and N-methylmorpholine (0.59 mL, 5.38 mmol) were dissolved in N,N-dimethylformamide (20 mL), and WSCI•HCl (0.62 g, 3.23 mmol) was added at room temperature, followed by stirring for 20 hours under nitrogen atmosphere. To the reaction solution, saturated brine (30 mL) was added, and extraction was carried out with ethyl acetate (60 mL). After washing with 1N hydrochloric acid, a saturated aqueous sodium hydrogencarbonate solution and saturated brine, drying was carried out over anhydrous magnesium sulfate. The solvent was distilled off under reduced pressure, and the resulting residue was purified using silica gel column chromatography (elution solvent: methanol/methylene chloride=0%-7%) to afford the desired compound (1.24 g, 86%) as a white solid.

¹H-NMR (CDCl₃, 400 MHz): δ 1.25 (3H, d, J=6.3 Hz), 1.33 (3H, d, J=6.3 Hz), 3.23 (3H, s), 3.42 (3H, s), 3.51 (1H, dd, J=3.9, 10.3 Hz), 3.59 (1H, dd, J=6.3, 10.4 Hz), 3.90-3.91 (2H, m), 3.98-4.03 (1H, brm), 4.23-4.29 (1H, m), 4.56-4.60 (1H, m), 6.50 (1H, t, J=3.2 Hz), 6.58 (1H, t, J=2.2 Hz), 6.66 (1H, brm), 6.69-6.70 (1H, m), 6.85 (1H, t, J=1.7 Hz), 7.03 (1H, t, J=1.7 Hz), 7.44 (1H, dd, J=2.7, 8.7 Hz), 8.04 (1H, d, J=8.7 Hz), 8.48 (1H, d, J=2.7 Hz), 9.77 (1H, brs).

(93b) (1S)-1-{(4S)-2-[5-(3-[(1S)-2-Methoxy-1-methylethoxy]-5-{[6-(methylsulfonyl)pyridin-3-yl]oxy}phenyl)-1H-pyrrol-2-yl]-4,5-dihydro-1,3-oxazol-4-yl}ethanol N-[(1S,2S)-2-Hydroxy-1-(hydroxymethyl)propyl]-5-(3-[(1S)-2-methoxy-1-methylethoxy]-5-{[6-(methylsulfonyl)pyridin-3-yl]oxy}phenyl)-1H-pyrrole-2-carboxamide (1.24 g, 2.32 mmol) synthesized in Example (93a) was dissolved in tetrahydrofuran (20 mL), and anhydrous methanesulfonic acid (0.63 g, 3.49 mmol) and triethylamine (0.97 mL, 6.97 mmol) were added at 0° C., followed by stirring for 1 hour under nitrogen atmosphere. The temperature was raised naturally, and stirring was carried out at room temperature for 2 hours, followed by stirring at 50° C. for 2 hours. A saturated aqueous sodium hydrogencarbonate solution (30 mL) was added, and the solution was separated with ethyl acetate (50 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=60%-100%) to afford the desired compound (800 mg, yield 67%) as a white solid.

¹H-NMR (CDCl₃, 500 MHz): δ 1.24 (3H, d, J=6.3 Hz), 1.33 (3H, d, J=6.3 Hz), 3.23 (3H, s), 3.40 (3H, s), 3.50 (1H, dd, J=4.0, 10.3 Hz), 3.58 (1H, dd, J=6.3, 10.3 Hz), 3.71 (1H, t, J=6.2 Hz), 4.08-4.14 (2H, m), 4.41-4.44 (1H, m), 4.54-4.59 (1H, m), 6.50 (1H, d, J=3.9 Hz), 6.56 (1H, t, J=2.1 Hz), 6.74 (1H, d, J=3.9 Hz), 6.86 (1H, t, 2.0 Hz), 7.05 (1H, t, 1.9 Hz), 7.42 (1H, dd, J=2.7, 8.8 Hz), 8.03 (1H, d, J=8.8 Hz), 8.47 (1H, d, J=2.8 Hz).

MS (ESI) m/z: 516.17981 (M+H)⁺.

Example 94

(2S)-2-[3-(5-{(4S)-4-[(1S)-1-Hydroxyethyl]-4,5-dihydro-1,3-oxazol-2-yl}-1H-pyrrol-2-yl)-5-{[6-(methylsulfonyl)pyridin-3-yl]oxy}phenoxy]propan-1-ol

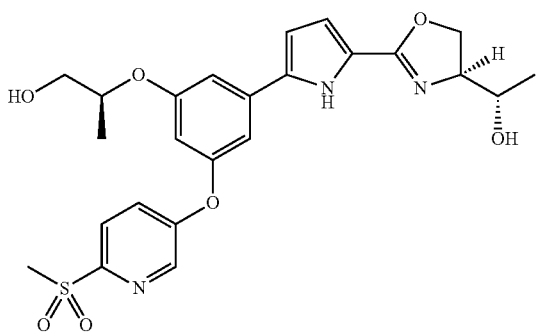

(1S)-1-{(4S)-2-[5-(3-[(1S)-2-Methoxy-1-methylethoxy]-5-{[6-(methylsulfonyl)pyridin-3-yl]oxy}phenyl)-1H-pyrrol-2-yl]-4,5-dihydro-1,3-oxazol-4-yl}ethanol (187 mg, 0.36 mmol) synthesized in Example (93b) was dissolved in methylene chloride (5 mL) and subsequently cooled to −78° C., and boron tribromide (1.0 mol/L methylene chloride solution, 0.73 mL, 0.73 mmol) was added under nitrogen atmosphere. The temperature was raised naturally, followed by stirring at room temperature for 30 minutes, and subsequently a saturated aqueous sodium hydrogencarbonate solution was added to neutralize the reaction solution, followed by extraction with methylene chloride (70 mL). The organic layer was washed with a 1N aqueous sodium hydroxide solution and saturated brine, and subsequently dried over anhydrous magnesium sulfate. The solvent was distilled off under reduced pressure, and the resulting residue was purified using silica gel column chromatography (elution solvent: methanol/methylene chloride-0%-4%) to afford the desired compound (134 mg, 74%) as a white solid.

¹H-NMR (CDCl₃, 500 MHz): δ 1.28 (6H, d, J=6.6 Hz), 3.22 (3H, s), 3.72-3.81 (3H, m), 4.13-4.19 (2H, m), 4.42-4.45 (1H, m), 4.59-4.65 (1H, m), 6.41 (1H, t, J=2.2 Hz), 6.45 (1H, d, J=3.9 Hz), 6.72 (1H, d, J=3.9 Hz), 6.83 (1H, s), 6.99 (1H, s), 7.37 (1H, dd, J=2.7, 8.8 Hz), 8.02 (1H, d, J=8.8 Hz), 8.44 (1H, d, J=2.7 Hz).

MS (ESI) m/z: 502.16521 (M+H)⁺.

Example 95

(1R)-1-{(4S)-2-[5-(3-[(1S)-2-Methoxy-1-methylethoxy]-5-{[6-(methylsulfonyl)pyridin-3-yl]oxy}phenyl)-1H-pyrrol-2-yl]-4,5-dihydro-1,3-oxazol-4-yl}ethanol

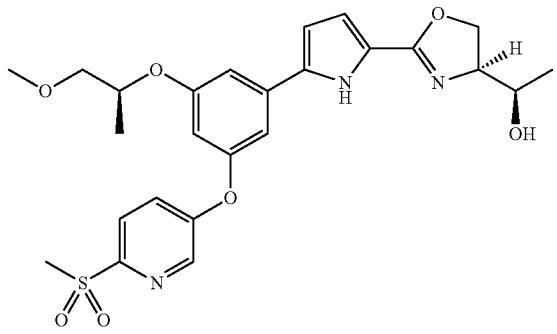

(95a) N-[(1S,2R)-2-Hydroxy-1-(hydroxymethyl)propyl]-5-(3-[(1S)-2-methoxy-1-methylethoxy]-5-{[6-(methylsulfonyl)pyridin-3-yl]oxy}phenyl)-1H-pyrrole-2-carboxamide 5-(3-[(1S)-2-Methoxy-1-methylethoxy]-5-{[6-(methylsulfonyl)pyridin-3-yl]oxy}phenyl)-1H-pyrrole-2-carboxylic acid (1.47 g, 3.29 mmol) synthesized in Example (78k), commercially available D-allo-threoninol (0.52 g, 4.94 mmol), HOBT·H₂O (0.49 g, 3.62 mmol) and N-methylmorpholine (0.72 mL, 6.58 mmol) were dissolved in N,N-dimethylformamide (10 mL), and WSCI·HCl (0.76 g, 3.95 mmol) was added at room temperature, followed by stirring for 5.5 hours under nitrogen atmosphere. To the reaction solution, saturated brine (40 mL) was added, and extraction was carried out with ethyl acetate (70 mL). After washed with saturated brine, drying was carried out over anhydrous magnesium sulfate. The solvent was distilled off under reduced pressure, and the resulting residue was purified using silica gel column chromatography (elution solvent: methanol/methylene chloride=0%-6%) to afford the desired compound (1.42 g, 81%) as a white solid.

¹H-NMR (CDCl₃, 500 MHz): δ 1.31 (3H, d, J=6.2 Hz), 1.32 (3H, d, J=6.6 Hz), 2.84-2.86 (1H, m), 2.89 (1H, d, J=6.2 Hz), 3.23 (3H, s), 3.42 (3H, s), 3.51 (1H, dd, J=3.9, 10.3 Hz), 3.59 (1H, dd, J=6.3, 10.3 Hz), 3.80-3.84 (1H, brm), 3.92-3.96 (1H, m), 4.07-4.11 (2H, brm), 4.54-4.59 (1H, m), 6.49 (1H, dd, J=2.9, 3.9 Hz), 6.57 (1H, t, J=2.2 Hz), 6.67 (1H, dd, J=2.3, 3.9 Hz), 6.80 (1H, d, J=8.0 Hz), 6.86 (1H, t, J=1.8 Hz), 7.01 (1H, t, J=1.8 Hz), 7.43 (1H, dd, J=2.8, 8.7 Hz), 8.03 (1H, d, J=8.7 Hz), 8.47 (1H, d, J=2.8 Hz), 9.94 (1H, brs).

(95b) (1R)-1-{(4S)-2-[5-(3-[(1S)-2-Methoxy-1-methylethoxy]-5-{[6-(methylsulfonyl)pyridin-3-yl]oxy}phenyl)-1H-pyrrol-2-yl]-4,5-dihydro-1,3-oxazol-4-yl}ethanol N-[(1S,2R)-2-Hydroxy-1-(hydroxymethyl)propyl]-5-(3-[(1S)-2-methoxy-1-methylethoxy]-5-{[6-(methylsulfonyl)pyridin-3-yl]oxy}phenyl)-1H-pyrrole-2-carboxamide (1.42 g, 2.66 mmol) synthesized in Example (95a) was dissolved in tetrahydrofuran (25 mL), and anhydrous methanesulfonic acid (0.72 g, 3.99 mmol) and triethylamine (1.11 mL, 7.98 mmol) were added at 0° C., followed by stirring for 1 hour under nitrogen atmosphere. The temperature was raised naturally, and stirring was carried out at room temperature for 1 hour, followed by stirring at 50° C. for 2 hours. A saturated aqueous sodium hydrogencarbonate solution (30 mL) was added, and the solution was separated with ethyl acetate (50 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=50%-100%) to afford the desired compound (758 mg, yield 55%) as a white solid.

¹H-NMR (CDCl₃, 400 MHz): δ 1.15 (3H, d, J=6.3 Hz), 1.35 (3H, d, J=6.3 Hz), 3.23 (3H, s), 3.41 (3H, s), 3.51 (1H, dd, J=4.0, 10.4 Hz), 3.59 (1H, dd, J=6.2, 10.4 Hz), 4.20-4.27 (4H, m), 4.56-4.62 (1H, m), 6.36 (1H, d, J=3.8 Hz), 6.41 (1H, d, J=3.8 Hz), 6.57 (1H, t, J=2.1 Hz), 6.90 (1H, t, 1.8 Hz), 7.07 (1H, t, 1.8 Hz), 7.45 (1H, dd, J=2.8, 8.7 Hz), 8.05 (1H, d, J=8.7 Hz), 8.50 (1H, d, J=2.8 Hz).

MS (ESI) m/z: 516.17893 (M+H)⁺.

Example 96

(2S)-2-[3-(5-{(4S)-4-[(1R)-1-Hydroxyethyl]-4,5-dihydro-1,3-oxazol-2-yl}-1H-pyrrol-2-yl)-5-{[6-(methylsulfonyl)pyridin-3-yl]oxy}phenoxy]propan-1-ol

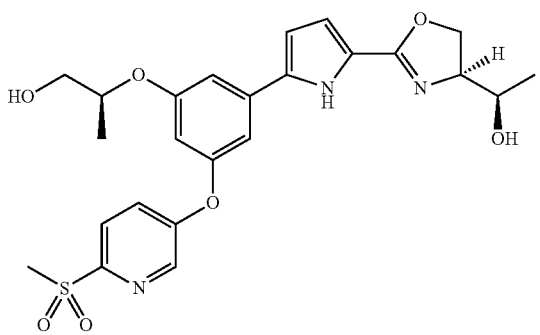

(1R)-1-{(4S)-2-[5-(3-[(1S)-2-Methoxy-1-methylethoxy]-5-{[6-(methylsulfonyl)pyridin-3-yl]oxy}phenyl)-1H-pyrrol-2-yl]-4,5-dihydro-1,3-oxazol-4-yl}ethanol (178 mg, 0.35 mmol) synthesized in Example (95b) was dissolved in methylene chloride (5 mL) and subsequently cooled to −78° C., and boron tribromide (1.0 mol/L methylene chloride solution, 0.69 mL, 0.69 mmol) was added under nitrogen atmosphere. The temperature was raised naturally, followed by stirring at room temperature for 30 minutes, and subsequently a saturated aqueous sodium hydrogencarbonate solution was added to neutralize the reaction solution, followed by extraction with methylene chloride (70 mL). The organic layer was washed with a 1N aqueous sodium hydroxide solution and saturated brine, and subsequently dried over anhydrous magnesium sulfate. The solvent was distilled off under reduced pressure, and the resulting residue was purified using silica gel column chromatography (elution solvent: methanol/methylene chloride=0%-4%) to afford the desired compound (132 mg, 76%) as a white solid.

¹H-NMR (CDCl₃, 400 MHz): δ 1.19 (3H, d, 6.3 Hz), 1.31 (3H, d, J=6.3 Hz), 3.23 (3H, s), 3.73-3.81 (2H, m), 4.17-4.25 (2H, m), 4.32 (1H, s), 4.34 (1H, d, J=1.5 Hz), 4.57-4.61 (1H, m), 6.39 (1H, d, J=3.9 Hz), 6.49 (1H, d, J=2.1 Hz), 6.54 (1H, d, J=3.9 Hz), 6.87 (1H, t, J=1.8 Hz), 7.02 (1H, t, J=1.8 Hz), 7.42 (1H, dd, J=2.8, 8.6 Hz), 8.04 (1H, d, J=8.6 Hz), 8.47 (1H, d, J=2.8 Hz).

MS (ESI) m/z: 502.16427 (M+H)⁺.

Example 97

2-{3-[(1S)-2-Methoxy-1-methylethoxy]-5-[5-(5-methyl-1,3,4-oxadiazol-2-yl)-1H-pyrrol-2-yl]phenoxy}-5-(methylsulfonyl)pyrazine

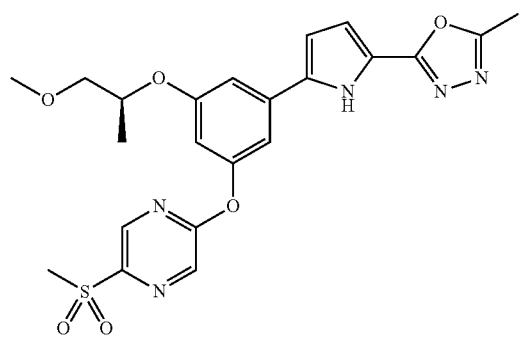

(97a) 5-(Methylsulfanyl)pyrazine-2-amine

2-Aminopyrazine (50.8 g, 0.53 mol) was dissolved in methylene chloride (1.0 L), and N-bromosuccinimide (97.9 g, 0.55 mol) was added at 0° C. over 30 minutes, followed by stirring at 0° C. for 2.5 hours under nitrogen atmosphere. The reaction solution was brought back to room temperature, and the deposit was filtered off. The deposit which was filtered off was washed with ethyl acetate. The mother liquor was collected, and the solvent was distilled off under reduced pressure. This operation was repeated twice to give a mother liquor, of which the solvent was distilled off under reduced pressure to afford a compound as a yellow solid.

This was dissolved in N,N-dimethylformamide (300 mL), and sodium thiomethoxide (75.0 g, 1.07 mol) was added, followed by stirring at 100° C. for 3 hours under nitrogen atmosphere. The reaction solution was brought back to room temperature, and water (1.5 L) was added, followed by extraction with ethyl acetate (1.0 L). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=20%-30%) to afford the desired compound (42.5 g, yield 56%) as an orange solid.

$^1$H-NMR (CDCl$_3$, 400 MHz): δ 2.52 (3H, s), 4.41 (2H, br s), 7.92 (1H, d, J=1.6 Hz), 7.98 (1H, d, J=1.6 Hz).

(97b) 2-Chloro-5-(methylsulfanyl)pyrazine

Sodium nitrite (50.9 g, 0.74 Mop was dissolved in water (150 mL), followed by dropwise addition into a 5N aqueous hydrochloric acid solution (1.0 L) at 0° C. over 1 hour. Subsequently, 5-(methylsulfanyl)pyrazine-2-amine (40.4 g, 0.28 mol) synthesized in Example (97a) was added at 0° C. over 40 minutes, and stirring was carried out at 0° C. for 1 hour. The reaction solution was brought back to room temperature, and water (500 mL) was added, followed by extraction with ethyl acetate (1.0 L). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=10%-20%) to afford the desired compound (11.9 g, yield 26%) as a white solid.

$^1$H-NMR (CDCl$_3$, 400 MHz): δ 2.57 (3H, s), 8.24 (1H, d, J=1.2 Hz), 8.39 (1H, d, J=1.2 Hz).

(97c) 2-Chloro-5-(methylsulfonyl)pyrazine

2-Chloro-5-(methylsulfanyl)pyrazine (10.82 g, 67.4 mmol) synthesized in Example (97b) was dissolved in methylene chloride (200 mL), and m-chloroperbenzoic acid (approximately 65%, 37.4 g, approximately 140 mmol) was added slowly at 0° C., followed by stirring at 0° C. for 1.5 hours under nitrogen atmosphere. A saturated aqueous sodium hydrogencarbonate solution (300 mL) was added, and extraction was carried out with methylene chloride (400 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=30%-50%) to afford the desired compound (10.1 g, yield 78%) as a white solid.

$^1$H-NMR (CDCl$_3$, 400 MHz): δ 3.27 (3H, s), 8.70 (1H, d, J=1.2 Hz), 9.09 (1H, d, J=1.2 Hz).

(97d) Benzyl 5-(3-[(1S)-2-Methoxy-1-methylethoxy]-5-{[5-(methylsulfonyl)pyrazin-2-yl]oxy}phenyl)-1H-pyrrole-2-carboxylate 2-Benzyl 1-t-butyl 5-{3-hydroxy-5-[(1S)-2-methoxy-1-methylethoxy]phenyl}-1H-pyrrole-1,2-dicarboxylate (3.40 g, 7.06 mmol) synthesized in Example (78g) and 2-chloro-5-(methylsulfonyl)pyrazine (1.92 g, 7.06 mmol) synthesized in Example (97c) were dissolved in acetonitrile (35 mL), and potassium carbonate (2.93 g, 21.2 mmol) was added, followed by heating to reflux for 11 hours under nitrogen atmosphere. The reaction solution was cooled to room temperature, and water (100 mL) was added, followed by extraction twice with ethyl acetate (50 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=0%-50%).

The resulting brown solid (3.85 g) was dissolved in methylene chloride (5 mL), and trifluoroacetic acid (5 mL) was added, followed by stirring at room temperature for 1 hour. To the reaction solution, a saturated aqueous sodium hydrogencarbonate solution (50 mL) was added, and extraction was carried out twice with ethyl acetate (50 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=0%-60%) to afford the desired compound (3.58 g, yield 88%) as a white solid.

$^1$H-NMR (CDCl$_3$, 400 MHz): δ 1.35 (3H, d, J=6.3 Hz), 3.24 (3H, s), 3.42 (3H, s), 3.52 (1H, dd, J=10.3, 3.9 Hz), 3.60 (1H, dd, J=10.3, 5.9 Hz), 4.57-4.61 (1H, m), 5.34 (2H, s), 6.53 (1H, dd, J=3.9, 2.9 Hz), 6.70 (1H, t, J=2.2 Hz), 6.93 (1H, t, J=1.5 Hz), 6.99 (1H, dd, J=3.9, 2.4 Hz), 7.06 (1H, t, J=1.7 Hz), 7.34-7.45 (5H, m), 8.50 (1H, d, J=1.5 Hz), 8.81 (1H, d, J=1.5 Hz), 9.18 (1H, s).

(97e) 5-(3-[(1S)-2-Methoxy-1-methylethoxy]-5-{[5-(methylsulfonyl)pyrazin-2-yl]oxy}phenyl)-1H-pyrrole-2-carboxylic acid Benzyl 5-(3-[(1S)-2-methoxy-1-methylethoxy]-5-{[5-(methylsulfonyl)pyrazin-2-yl]oxy}phenyl)-1H-pyrrole-2-carboxylate (3.58 g, 6.66 mmol) synthesized in Example (97d) was dissolved in methanol (100 mL), and a 10% palladium carbon catalyst (2.00 g) was added, followed by stirring at room temperature for 3 hours under hydrogen atmosphere. The palladium carbon catalyst was removed by Celite filtration, followed by washing with tetrahydrofuran. The solvent was distilled off under reduced pressure to afford the desired compound (2.56 g, 86%) as a white solid.

$^1$H-NMR (CDCl$_3$, 400 MHz): δ 1.34 (3H, d, J=6.3 Hz), 3.22 (3H, s), 3.45 (3H, s), 3.55 (1H, dd, J=10.2, 3.9 Hz), 3.66 (1H, dd, J=9.4, 5.9 Hz), 4.72 (1H, s), 6.49 (1H, s), 6.66 (1H, s), 6.99 (2H, s), 7.29 (1H, s), 8.47 (1H, s), 8.79 (1H, s), 10.23 (1H, br s).

(97f) 2-{3-[(1S)-2-Methoxy-1-methylethoxy]-5-[5-(5-methyl-1,3,4-oxadiazol-2-yl)-1H-pyrrol-2-yl]phenoxy}-5-(methylsulfonyl)pyrazine 5-(3-[(1S)-2-Methoxy-1-methylethoxy]-5-{[5-(methylsulfonyl)pyrazin-2-yl]oxy}phenyl)-1H-pyrrole-2-carboxylic acid (700 mg, 1.56 mmol) synthesized in Example (97e) and 4-dimethylaminopyridine (172 mg, 1.41 mmol) were dissolved in methylene chloride (15 mL), and WSCI•HCl (689 mg, 3.60 mmol) and acetohydrazide (255 mg, 3.44 mmol) were added at room temperature, followed by stirring for 14 hours under nitrogen atmosphere. The reaction solution was diluted with methylene chloride (50 mL), and washed with a saturated aqueous sodium hydrogencarbonate solution and saturated brine, followed by drying over anhydrous magnesium sulfate, and subsequently the solvent was distilled off under reduced pressure.

The resulting yellow solid (788 mg) was dissolved in methylene chloride (10 mL), and p-toluenesulfonyl chloride (597 mg, 3.13 mmol) and triethylamine (0.87 mL, 6.26 mmol) were added, followed by stirring at room temperature for 6 hours under nitrogen atmosphere. To the reaction solution, a saturated aqueous sodium hydrogencarbonate solution (30 mL) was added, and extraction was carried out twice with methylene chloride (30 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=0%-5%) to afford the desired compound (456 mg, yield 60%) as a pale yellow solid.

$^1$H-NMR (CDCl$_3$, 400 MHz): δ 1.36 (3H, d, J=6.3 Hz), 2.59 (3H, s), 3.24 (3H, s), 3.42 (3H, s), 3.53 (1H, dd, J=10.4, 4.1 Hz), 3.61 (1H, dd, J=10.2, 5.9 Hz), 4.56-4.63 (1H, m), 6.59 (1H, t, J=3.1 Hz), 6.69 (1H, t, J=2.0 Hz), 6.86 (1H, dd, J=3.7, 2.5 Hz), 6.95 (1H, t, J=1.6 Hz), 7.08 (1H, t, J=1.8 Hz), 8.51 (1H, d, J=1.2 Hz), 8.81 (1H, d, J=1.2 Hz), 9.43 (1H, s).

MS (ESI) m/z: 486.14274 (M+H)$^+$.

Example 98

(2S)-2-(3-[5-(5-Methyl-1,3,4-oxadiazol-2-yl)-1H-pyrrol-2-yl]-5-{[5-(methylsulfonyl)pyrazin-2-yl]oxy}phenoxy)propan-1-ol

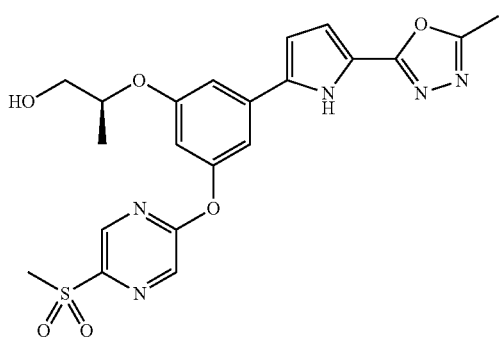

2-{3-[(1S)-2-Methoxy-1-methylethoxy]-5-[5-(5-methyl-1,3,4-oxadiazol-2-yl)-1H-pyrrol-2-yl]phenoxy}-5-(methylsulfonyl)pyrazine (382 mg, 0.79 mmol) synthesized in Example (97f) was dissolved in methylene chloride (10 mL), and boron tribromide (1.0 mol/L methylene chloride solution, 1.58 mL, 1.58 mmol) was added at −78° C. under nitrogen atmosphere. Subsequently the temperature was brought back to room temperature, followed by stirring for 1.5 hours under nitrogen atmosphere. To the reaction solution, a saturated aqueous sodium hydrogencarbonate solution was added, and extraction was carried out with ethyl acetate. The organic layer was washed with saturated brine, and subsequently dried over sodium sulfate. The solvent was distilled off under reduced pressure, and the resulting residue was purified using silica gel column chromatography (elution solvent: methanol/methylene chloride=0%-5%) to afford the desired compound (219 mg, yield 59%) as a white solid.

$^1$H-NMR (CDCl$_3$, 400 MHz): δ 1.32 (3H, d, J=6.3 Hz), 2.59 (3H, s), 2.70 (1H, br s), 3.25 (3H, s), 3.79-3.82 (2H, m), 4.54-4.61 (1H, m), 6.57 (1H, t, J=3.1 Hz), 6.63 (1H, t, J=2.0 Hz), 6.86 (1H, dd, J=3.7, 2.5 Hz), 6.96 (1H, t, J=1.8 Hz), 7.07 (1H, t, J=1.8 Hz), 8.50 (1H, d, J=1.6 Hz), 8.80 (1H, d, J=1.2 Hz), 9.84 (1H, br s).

MS (ESI) m/z: 472.12965 (M+H)$^+$.

Example 99

2-(3-[(1S)-2-Methoxy-1-methylethoxy]-5-{5-[(5S)-5-methyl-4,5-dihydro-1,3-oxazol-2-yl]-1H-pyrrol-2-yl}phenoxy)-5-(methylsulfonyl)pyrazine

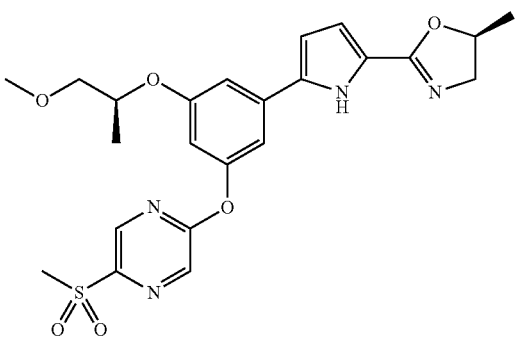

5-(3-[(1S)-2-Methoxy-1-methylethoxy]-5-{[5-(methylsulfonyl)pyrazin-2-yl]oxy}phenyl)-1H-pyrrole-2-carboxylic acid (700 mg, 1.56 mmol) synthesized in Example (97e) and 4-dimethylaminopyridine (96 mg, 0.78 mmol) were dissolved in methylene chloride (20 mL), and WSCI•HCl (480 mg, 2.50 mmol) and (R)-1-amino-2-propanol (283 μL, 3.60 mmol) were added at room temperature, followed by stirring for 14 hours under nitrogen atmosphere. The reaction solution was diluted with methylene chloride (60 mL), washed with saturated aqueous sodium hydrogencarbonate solution and saturated brine, and subsequently dried over anhydrous magnesium sulfate. The solvent was distilled off under reduced pressure, and the resulting residue was purified using silica gel column chromatography (elution solvent: methanol/methylene chloride=0%-8%).

The resulting white solid (546 mg) was dissolved in tetrahydrofuran (15 mL), and anhydrous methanesulfonic acid (377 mg, 2.16 mmol) and triethylamine (0.45 mL, 3.25 mmol) were added, followed by stirring at 50° C. for 4 hours under nitrogen atmosphere. To the reaction solution, a saturated aqueous sodium hydrogencarbonate solution (30 mL) was added, and extraction was carried out twice with ethyl acetate (30 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=0%-5%) to afford the desired compound (509 mg, yield 67%) as a pale yellow solid.

$^1$H-NMR (CDCl$_3$, 400 MHz): δ 1.34 (3H, d, J=6.3 Hz), 1.42 (3H, d, J=6.3 Hz), 3.24 (3H, s), 3.42 (3H, s), 3.49-3.62 (3H, m), 4.07 (1H, dd, J=13.5, 8.8 Hz), 4.53-4.61 (1H, m), 4.79-4.87 (1H, m), 6.51 (1H, d, J=3.9 Hz), 6.65 (1H, t, J=2.0 Hz), 6.75 (1H, d, J=3.9 Hz), 6.91 (1H, t, J=1.6 Hz), 7.06 (1H, t, J=1.8 Hz), 8.49 (1H, s), 8.81 (1H, s).

MS (ESI) m/z: 487.16506 (M+H)$^+$.

Example 100

(2S)-2-(3-{5-[(5S)-5-Methyl-4,5-dihydro-1,3-oxazol-2-yl]-1H-pyrrol-2-yl}-5-{[5-(methylsulfonyl)pyrazin-2-yl]oxy}phenoxy)propan-1-ol

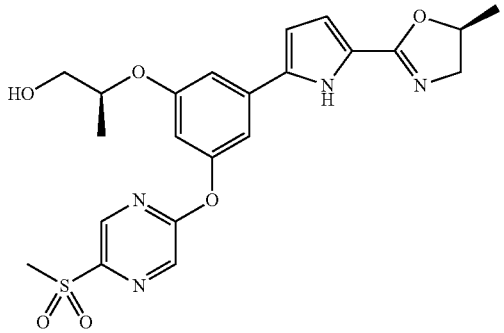

2-(3-[(1S)-2-Methoxy-1-methylethoxy]-5-{5-[(5S)-5-methyl-4,5-dihydro-1,3-oxazol-2-yl]-1H-pyrrol-2-yl}phenoxy)-5-(methylsulfonyl)pyrazine (426 mg, 0.88 mmol) synthesized in Example 99 was dissolved in methylene chloride (10 mL), and boron tribromide (1.0 mol/L methylene chloride solution, 1.76 mL, 1.76 mmol) was added at −78° C. under nitrogen atmosphere. Subsequently, the temperature was brought back to room temperature, followed by stirring for 1.5 hours. To the reaction solution, a saturated aqueous sodium hydrogencarbonate solution was added, and extraction was carried out with methylene chloride. The organic layer was washed with saturated brine, and subsequently dried over sodium sulfate. The solvent was distilled off under reduced pressure, and the resulting residue was purified using silica gel column chromatography (elution solvent: methanol/methylene chloride=0%-5%) to afford the desired compound (243 mg, yield 59%) as a white solid.

$^1$H-NMR (CDCl$_3$, 400 MHz): δ 1.31 (3H, d, J=6.3 Hz), 1.44 (3H, d, J=6.3 Hz), 3.25 (3H, s), 3.56 (1H, dd, J=13.9, 7.2 Hz), 3.80 (2H, d, J=5.5 Hz), 4.10 (1H, dd, J=14.1, 9.4 Hz), 4.61 (1H, q, J=5.6 Hz), 4.86 (1H, dt, J=11.6, 4.5 Hz), 6.47 (1H, d, J=3.5 Hz), 6.50 (1H, s), 6.75 (1H, d, J=3.5 Hz), 6.89 (1H, s), 6.99 (1H, s), 8.47 (1H, d, J=1.2 Hz), 8.80 (1H, d, J=1.2 Hz).

MS (ESI) m/z: 473.14774 (M+H)$^+$.

Example 101

{(5R)-2-[5-(3-[(1S)-2-Methoxy-1-methylethoxy]-5-{[5-(methylsulfonyl)pyrazin-2-yl]oxy}phenyl)-1H-pyrrol-2-yl]-4,5-dihydro-1,3-oxazol-5-yl}methanol

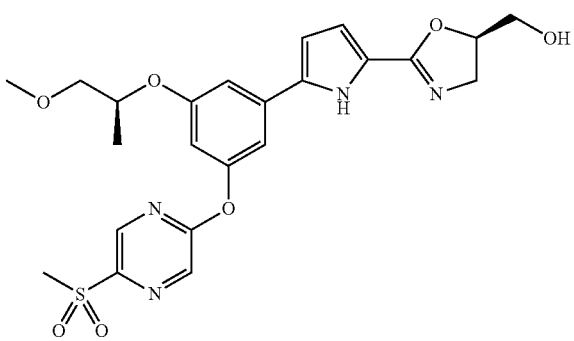

(101a) N-[(2S)-2,3-dihydroxypropyl]-5-(3-[(1S)-2-methoxy-1-methylethoxy]-5-{[5-(methylsulfonyl)pyrazin-2-yl]oxy}phenyl)-1H-pyrrole-2-carboxamide 5-(3-[(1S)-2-Methoxy-1-methylethoxy]-5-{[5-(methylsulfonyl)pyrazin-2-yl]oxy}phenyl)-1H-pyrrole-2-carboxylic acid (1.07 g, 2.39 mmol) synthesized in Example (97e) was dissolved in methylene chloride (20 mL), and WSCI•HCl (732 mg, 3.82 mmol), (S)-(−)-3-amino-1,2-propanediol (500 mg, 5.49 mmol) and 4-dimethylaminopyridine (146 mg, 1.19 mmol) were added at room temperature, followed by stirring for 25 hours under nitrogen atmosphere. The reaction solution was diluted with ethyl acetate (50 mL), washed with a saturated aqueous sodium hydrogencarbonate solution and saturated brine, and subsequently dried over anhydrous magnesium sulfate. The solvent was distilled off under reduced pressure, and the resulting residue was purified using silica gel column chromatography (elution solvent: methanol/methylene chloride=0%-5%) to afford the desired product (666 mg, 54%) as a white solid.

$^1$H-NMR (CDCl$_3$, 400 MHz): δ 1.35 (4H, d, J=6.1 Hz), 3.24 (4H, s), 3.42 (3H, s), 3.53 (1H, dd, J=10.3, 3.9 Hz), 3.59-3.63 (5H, m), 3.84-3.87 (1H, m), 4.58 (1H, dt, J=11.7, 5.2 Hz), 6.41 (1H, s), 6.50 (1H, t, J=3.2 Hz), 6.64 (1H, dd, J=3.7, 2.7 Hz), 6.68 (1H, d, J=2.0 Hz), 6.95 (1H, s), 7.08 (1H, s), 8.50 (1H, s), 8.81 (1H, s), 9.79 (1H, s).

(101b) N-{(2S)-2-Hydroxy-3-[(triisopropylsilyl)oxy]propyl}-5-(3-[(1S)-2-methoxy-1-methylethoxy]-5-{[5-(methylsulfonyl)pyrazin-2-yl]oxy}phenyl)-1H-pyrrole-2-carboxamide N-[(2S)-2,3-Dihydroxypropyl]-5-(3-[(1S)-2-methoxy-1-methylethoxy]-5-{[5-(methylsulfonyl)pyrazin-2-yl]oxy}phenyl)-1H-pyrrole-2-carboxamide (666 mg, 1.28 mmol) synthesized in Example (101a) was dissolved in methylene chloride (20 mL), and triethylamine (0.89 mL, 6.40 mmol), triisopropylsilyl chloride (410 μL, 1.92 mmol) and 4-dimethylaminopyridine (234 mg, 1.92 mmol) were added, followed by stirring for 14 hours under nitrogen atmosphere. The reaction solution was diluted with methylene chloride (50 mL), washed with water and saturated brine, and subsequently dried over anhydrous magnesium sulfate. The solvent was distilled off under reduced pressure, and the resulting residue was purified using silica gel column chromatography (elution solvent: ethyl acetate/hexane=10%-60%) to afford the desired product (558 mg, 64%) as a white solid.

$^1$H-NMR (CDCl$_3$, 400 MHz): δ1.06-1.15 (21H, m), 1.35 (3H, d, J=6.3 Hz), 3.13 (1H, d, J=3.9 Hz), 3.24 (3H, s), 3.42 (3H, s), 3.52 (1H, dd, J=10.3, 3.9 Hz), 3.60 (1H, dd, J=10.3, 6.8 Hz), 3.68 (1H, dd, J=10.0, 6.1 Hz), 3.73 (1H, td, J=7.0, 3.1 Hz), 3.77 (1H, dd, J=10.0, 4.6 Hz), 3.87 (1H, s), 4.58 (1H, dd, J=10.3, 6.3 Hz), 6.33 (1H, t, J=5.6 Hz), 6.50 (1H, t, J=3.2 Hz), 6.60 (1H, t, J=3.2 Hz), 6.67 (1H, s), 6.92 (1H, s), 7.06 (1H, s), 8.50 (1H, d, J=1.0 Hz), 8.81 (1H, d, J=1.0 Hz), 9.44 (1H, s).

(101c) 2-(3-[(1S)-2-Methoxy-1-methylethoxy]-5-{5-[(5R)-5-{[(triisopropylsilyl)oxy]methyl}-4,5-dihydro-1,3-oxazol-2-yl]-1H-pyrrol-2-yl}phenoxy)-5-(methylsulfonyl)pyrazine N-{(2S)-2-hydroxy-3-[(triisopropylsilyl)oxy]propyl}-5-(3-[(1S)-2-methoxy-1-methylethoxy]-5-{[5-(methylsulfonyl)pyrazin-2-yl]oxy}phenyl)-1H-pyrrole-2-carboxamide (558 mg, 0.82 mmol) synthesized in Example (101b) was dissolved in tetrahydrofuran (20 mL), and anhydrous methanesulfonic acid (287 mg, 1.65 mmol) and triethylamine (0.34 mL, 2.47 mmol) were added, followed by stirring at 50° C. for 6 hours under nitrogen atmosphere. To the reaction solution, water (40 mL) was added, and extraction was carried out twice with methylene chloride (40 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=0%-5%) to afford the desired compound (496 mg, yield 94%) as a white solid.

$^1$H-NMR (CDCl$_3$, 400 MHz): δ 1.00-1.13 (21H, m), 1.34 (3H, d, J=6.3 Hz), 3.24 (3H, s), 3.42 (3H, s), 3.51 (1H, dd, J=10.6, 3.9 Hz), 3.60 (1H, dd, J=10.4, 6.1 Hz), 3.83-4.04 (4H, m), 4.57 (1H, td, J=6.3, 4.3 Hz), 4.72-4.79 (1H, m), 6.50 (1H, d, J=3.9 Hz), 6.65 (1H, t, J=2.0 Hz), 6.73 (1H, d, J=3.9 Hz), 6.90 (1H, t, J=1.8 Hz), 7.05 (1H, t, J=1.8 Hz), 8.49 (1H, d, J=1.2 Hz), 8.81 (1H, d, J=1.2 Hz).

(101d) {(5R)-2-[5-(3-[(1S)-2-Methoxy-1-methylethoxy]-5-{[5-(methylsulfonyl)pyrazin-2-yl]oxy}phenyl)-1H-pyrrol-2-yl]-4,5-dihydro-1,3-oxazol-5-yl}methanol 2-(3-[(1S)-2-Methoxy-1-methylethoxy]-5-{5-[(5R)-5-{[(triisopropylsilyl)oxy]methyl}-4,5-dihydro-1,3-oxazol-2-yl]-1H-pyrrol-2-yl}phenoxy)-5-(methylsulfonyl)pyrazine (496 mg, 0.82 mmol) synthesized in Example (101c) was dissolved in tetrahydrofuran (20 mL), and tetrabutylammonium fluoride (1.0 mol/L tetrahydrofuran solution, 0.82 mL, 0.82 mmol) was added, followed by stirring for 2 hours under nitrogen atmosphere. To the reaction solution, water (40 mL) was added, and extraction was carried out twice with ethyl acetate (40 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=0%-5%) to afford the desired compound (133 mg, yield 35%) as a white solid.

$^1$H-NMR (CDCl$_3$, 400 MHz): δ 1.32 (3H, d, J=6.3 Hz), 3.24 (3H, s), 3.42 (3H, s), 3.51 (1H, dd, J=10.4, 4.1 Hz), 3.60 (1H, dd, J=10.2, 5.9 Hz), 3.71 (1H, dd, J=12.5, 5.5 Hz), 3.79 (1H, dd, J=14.3, 7.6 Hz), 3.88 (1H, dd, J=12.5, 3.1 Hz), 4.04 (1H, dd, J=14.3, 10.0 Hz), 4.57 (1H, dd, J=10.0, 5.7 Hz), 4.85-4.78 (1H, m), 6.50 (1H, d, J=3.9 Hz), 6.66 (1H, t, J=2.2 Hz), 6.77 (1H, d, J=3.9 Hz), 6.93 (1H, s), 7.06 (1H, s), 8.49 (1H, d, J=1.2 Hz), 8.81 (1H, d, J=1.6 Hz).

MS (ESI) m/z: 503.15918 (M+H)$^+$.

Example 102

(2S)-2-(3-{5-[(5R)-5-(Hydroxymethyl)-4,5-dihydro-1,3-oxazol-2-yl]-1H-pyrrol-2-yl}-5-{[5-(methylsulfonyl)pyrazin-2-yl]oxy}phenoxy)propan-1-ol

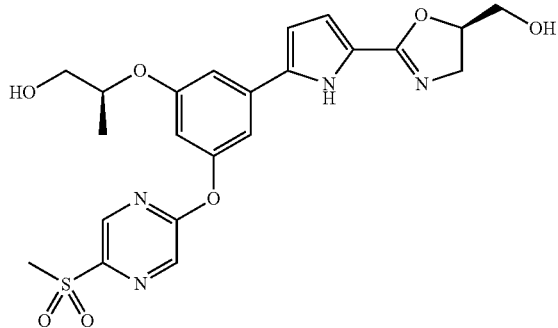

{(5R)-2-[5-(3-[(1S)-2-Methoxy-1-methylethoxy]-5-{[5-(methylsulfonyl)pyrazin-2-yl]oxy}phenyl)-1H-pyrrol-2-yl]-4,5-dihydro-1,3-oxazol-5-yl}methanol (105 mg, 0.21 mmol) synthesized in Example (101d) was dissolved in methylene chloride (10 mL), and boron tribromide (1.0 mol/L methylene chloride solution, 315 μL, 0.315 mmol) was added at –78° C. under nitrogen atmosphere, and subsequently the temperature was brought back to room temperature, followed by stirring for 1 hour. To the reaction solution, a saturated aqueous sodium hydrogencarbonate solution was added, and extraction was carried out with methylene chloride. The organic layer was washed with saturated brine, and subsequently dried over sodium sulfate. The solvent was distilled off under reduced pressure, and the resulting residue was purified using silica gel column chromatography (elution solvent: methanol/methylene chloride=0%-7.5%) to afford the desired compound (67 mg, yield 66%) as a white solid.

$^1$H-NMR (CDCl$_3$, 400 MHz): δ 1.29 (3H, d, J=6.3 Hz), 3.24 (3H, s), 3.70-3.91 (5H, m), 4.03 (1H, dd, J=14.1, 9.8 Hz), 4.55 (1H, dd, J=10.6, 5.9 Hz), 4.85-4.78 (1H, m), 6.47 (1H, d, J=3.9 Hz), 6.58 (1H, t, J=2.0 Hz), 6.75 (1H, d, J=3.5 Hz), 6.92 (1H, t, J=1.8 Hz), 7.01 (1H, t, J=1.6 Hz), 8.48 (1H, d, J=1.2 Hz), 8.80 (1H, d, J=1.2 Hz).

MS (ESI) m/z: 489.14448 (M+H)$^+$.

Example 103

(5S)-2-[5-(3-[(1S)-2-Methoxy-1-methylethoxy]-5-{[5-(methylsulfonyl)pyrazin-2-yl]oxy}phenyl)-1H-pyrrol-2-yl]-5-methyl-4,5-dihydro-1,3-oxazol-4-ol

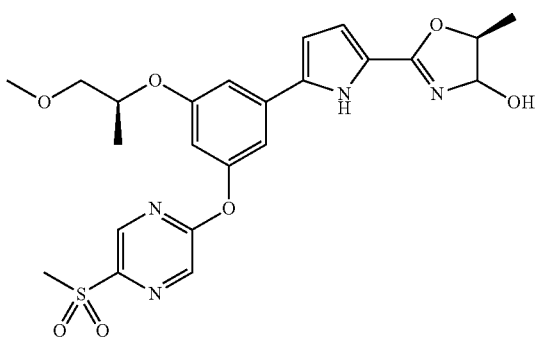

(103a) Benzyl L-threoninate

L-threonine 21.2 g (178 mmol) was dissolved in toluene (100 mL), and benzyl alcohol (100 mL, 966 mmol) and p-toluenesulfonic acid monohydrate (35.0 g, 194 mmol) were added, followed by heating to reflux for 17 hours under nitrogen atmosphere. After cooling to room temperature, water (200 mL) was added, followed by washing three times with ethyl acetate (100 mL). To the aqueous layer, a saturated aqueous sodium hydrogencarbonate solution was added, and extraction was carried out three times with ethyl acetate (100 mL). After the organic layer was washed with saturated brine, drying was carried out over anhydrous magnesium sulfate, and the resulting residue was purified using silica gel column chromatography (elution solvent: methanol/methylene chloride=0%-15%) to afford the desired product (10.6 g, yield 28%) as a white solid.

$^1$H-NMR (CDCl$_3$, 400 MHz): δ 1.22 (3H, d, J=6.3 Hz), 3.30 (1H, d, J=6.3 Hz), 3.49 (1H, brs), 5.19 (2H, s), 7.34-7.39 (5H, m).

(103b) Benzyl N-{[5-(3-[(1S)-2-methoxy-1-methoxyethoxy]-5-{[5-(methylsulfonyl)pyrazin-2-yl]oxy}phenyl)-1H-pyrrol-2-yl]carbonyl}-L-threoninate 5-{3-[(1S)-2-Methoxy-1-methylethoxy]-5-{[5-[5-(methylsulfonyl)pyrazin-2-yl]oxy)phenyl}-1H-pyrrole-2-carboxylic acid (9.49 g, 21.2 mmol) synthesized in Example (97e) was dissolved in N,N-dimethylformamide (200 mL), and benzyl L-threoninate (4.44 g, 21.2 mmol) synthesized in Example (103a), WSCI•HCl (4.88 g, 25.5 mmol), HOBT•H₂O (3.15 g, 23.3 mmol) and N-methylmorpholine (4.66 mL, 42.4 mmol) were added, followed by stirring at room temperature for 1.5 hours under nitrogen atmosphere. Water (200 mL) was added, and extraction was carried out twice with ethyl acetate (200 ml). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=70%-100%) to afford the desired product (13.5 g, yield ~100%) as a pale yellow oil.

¹H-NMR (CDCl₃, 400 MHz): δ 1.27 (3H, d, J=6.3 Hz), 1.35 (3H, d, J=6.3 Hz), 3.24 (3H, s), 3.42 (3H, s), 3.52 (1H, dd, J=4.3, 10.2 Hz), 3.61 (1H, dd, J=5.9, 10.2 Hz), 4.44 (1H, m), 4.59 (1H, m), 4.81 (1H, dd, J=2.7, 8.6 Hz), 5.21 (1H, d, J=12.5 Hz), 5.25 (1H, d, J=12.5 Hz), 6.52 (1H, t, J=3.9 Hz), 6.67 (1H, t, J=2.0 Hz), 6.71 (1H, brd, J=8.6 Hz), 6.75 (1H, dd, J=2.4, 3.9 Hz), 6.94 (1H, t, J=1.9 Hz), 7.08 (1H, t, J=1.9 Hz), 7.33-7.38 (5H, m), 8.49 (2H, m), 8.81 (2H, m), 9.63 (1H, brs).

(103c) Benzyl (4S,5S)-2-[5-(3-[(1S)-2-methoxy-1-methoxyethoxy]-5-{[5-(methylsulfonyl)pyrazin-2-yl]oxy}phenyl)-1H-pyrrol-2-yl]-5-methyl-4,5-dihydro-1,3-oxazole-4-carboxylate Benzyl N-{[5-(3-[(1S)-2-methoxy-1-methoxyethoxy]-5-{[5-(methylsulfonyl)pyrazin-2-yl]oxy}phenyl)-1H-pyrrol-2-yl]carbonyl}-L-threoninate (13.5 g, 21.2 mmol) synthesized in Example (103b) was dissolved in methylene chloride (150 mL), and cooled to −78° C. Bis(2-methoxyethyl)amino sulfur trifluoride (5.47 mL, 29.7 mmol) was added dropwise, and stirring was carried out at −78° C. for 40 minutes. Potassium carbonate (5.86 g, 42.4 mmol) was added, and stirring was carried out for 1.5 hours with the temperature being raised gradually to room temperature. A saturated aqueous sodium hydrogencarbonate solution (100 mL) was added at 0° C., and extraction was carried out twice with methylene chloride (100 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=40%-70%) to afford the desired product (9.68 g, yield 74%) as a white solid.

¹H-NMR (CDCl₃, 400 MHz): δ 1.29 (3H, d, J=6.3 Hz), 1.35 (3H, d, J=6.3 Hz), 3.23 (3H, s), 3.41 (3H, s), 3.51 (1H, dd, J=3.9, 10.2 Hz), 3.60 (1H, dd, J=5.9, 10.2 Hz), 4.58 (1H, m), 4.94 (1H, d, J=9.8 Hz), 5.02 (1H, m), 5.19 (1H, d, J=12.1 Hz), 5.24 (1H, d, J=12.1 Hz), 6.51 (1H, t, J=3.9 Hz), 6.66 (1H, t, J=2.4 Hz), 6.78 (1H, t, J=3.9 Hz), 6.94 (1H, t, J=2.0 Hz), 7.08 (1H, t, J=2.4 Hz), 7.35-7.39 (5H, m), 8.48 (2H, d, J=1.2 Hz), 8.81 (2H, d, J=1.2 Hz).

(103d) (5S)-2-[5-(3-[(1S)-2-Methoxy-1-methylethoxy]-5-{[5-(methylsulfonyl)pyrazin-2-yl]oxy}phenyl)-1H-pyrrol-2-yl]-5-methyl-4,5-dihydro-1,3-oxazol-4-ol Benzyl (4S,5S)-2-[5-(3-[(1S)-2-methoxy-1-methoxyethoxy]-5-{[5-(methylsulfonyl)pyrazin-2-yl]oxy}phenyl)-1H-pyrrol-2-yl]-5-methyl-4,5-dihydro-1,3-oxazole-4-carboxylate (1.53 g, 2.47 mmol) synthesized in Example (103c) was dissolved in tetrahydrofuran (50 mL), and a 10% palladium carbon catalyst (600 mg) was added, followed by stirring at room temperature for 2.5 hours under hydrogen atmosphere. The palladium carbon catalyst was removed by Celite filtration, followed by washing with ethyl acetate. The solvent was distilled off under reduced pressure.

The resulting residue was dissolved in acetonitrile (60 mL), and a solution of cerium (IV) diammonium nitrate (2.03 g, 3.70 mmol) in water (30 mL) was added dropwise at 0° C. After stirring at room temperature for 17 hours under nitrogen atmosphere, a saturated aqueous sodium hydrogencarbonate solution (30 mL) was added, and extraction was carried out twice with ethyl acetate (50 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=70%-100%) to afford the desired product (645 mg, yield 52%) as a white solid.

¹H-NMR (CDCl₃, 400 MHz): δ 1.34 (3H, d, J=6.3 Hz), 1.37 (6/3H, d, J=6.7 Hz), 1.47 (3/3H, d, J=6.7 Hz), 3.23 (3H, s), 3.41 (3H, s), 3.50 (1H, dd, J=4.3, 10.2 Hz), 3.60 (1H, dd, J=5.9, 10.2 Hz), 4.50-4.66 (2H, m), 5.39 (2/3H, d, J=3.1 Hz), 5.66 (1/3H, d, J=6.7 Hz), 6.50 (1H, brd, J=3.9 Hz), 6.65 (1H, t, J=2.4 Hz), 6.82 (1H, brd, J=3.9 Hz), 6.94 (1H, t, J=2.0 Hz), 7.08 (1H, t, J=2.0 Hz), 8.48 (2H, d, J=1.2 Hz), 8.80 (2H, d, J=1.2 Hz).

MS (ESI) m/z: 503.16004 (M+H)⁺.

Example 104

(5S)-2-[5-(3-[(1S)-2-Hydroxy-1-methylethoxy]-5-{[5-(methylsulfonyl)pyrazin-2-yl]oxy}phenyl)-1H-pyrrol-2-yl]-5-methyl-4,5-dihydro-1,3-oxazol-4-ol

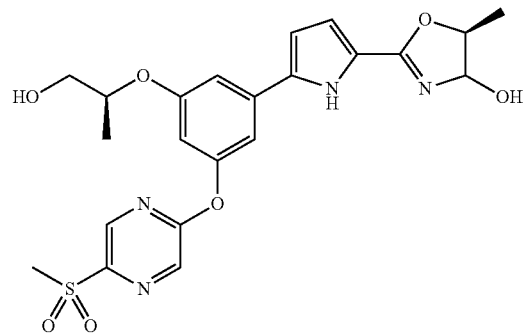

(5S)-2-[5-(3-[(1S)-2-Methoxy-1-methylethoxy]-5-{[5-(methylsulfonyl)pyrazin-2-yl]oxy}phenyl)-1H-pyrrol-2-yl]-5-methyl-4,5-dihydro-1,3-oxazol-4-ol (410 mg, 0.816 mmol) synthesized in Example (103d) was dissolved in methylene chloride (20 mL), and cooled to −78° C. Boron tribromide (1.0 mol/L methylene chloride solution, 2.04 mL, 2.04 mmol) was added, and stirring was carried out for 2 hours with the temperature being raised gradually to room temperature. A saturated aqueous sodium hydrogencarbonate solution (20 mL) was added, and extraction was carried out twice with methylene chloride (20 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=2%-10%) to afford the desired product (362 mg, yield 91%) as a white solid.

$^1$H-NMR (CDCl$_3$, 400 MHz): δ 1.30 (3H, d, J=6.3 Hz), 1.38 (6/3H, d, J=6.7 Hz), 1.49 (3/3H, d, J=6.7 Hz), 3.23 (3H, s), 3.76 (2H, brd, J=5.5 Hz), 4.51-4.57 (2H, m), 5.39 (2/3H, d, J=3.5 Hz), 5.66 (1/3H, d, J=6.7 Hz), 6.49 (1H, d, J=3.9 Hz), 6.61 (1H, t, J=2.4 Hz), 6.81 (1H, d, J=3.9 Hz), 6.94 (1H, t, J=2.0 Hz), 7.06 (1H, t, J=2.0 Hz), 8.47 (2H, d, J=1.2 Hz), 8.78 (2H, d, J=1.2 Hz).

MS (ESI) m/z: 489.14439 (M+H)$^+$.

Example 105

(5S)-2-[5-(3-[(1S)-2-Hydroxy-1-methylethoxy]-5-{[5-(methylsulfonyl)pyrazin-2-yl]oxy}phenyl)-1H-pyrrol-2-yl]-5-methyl-4,5-dihydro-1,3-oxazol-4(5H)-one

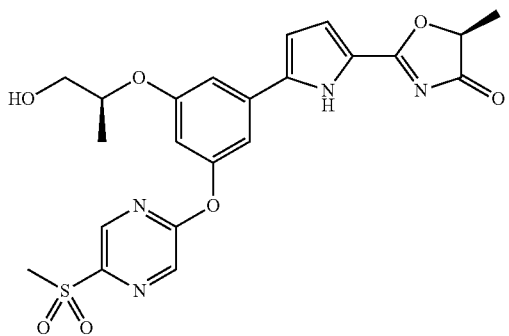

(105a) (5S)-2-[5-(3-[(1S)-2-Methoxy-1-methylethoxy]-5-{[5-(methylsulfonyl)pyrazin-2-yl]oxy}phenyl)-1H-pyrrol-2-yl]-5-methyl-4,5-dihydro-1,3-oxazol-4(5H)-one (5S)-2-[5-(3-[(1S)-2-Methoxy-1-methylethoxy]-5-{[5-(methylsulfonyl)pyrazin-2-yl]oxy}phenyl)-1H-pyrrol-2-yl]-5-methyl-4,5-dihydro-1,3-oxazol-4-ol (80.0 mg, 0.159 mmol) synthesized in Example (103d) was dissolved in methylene chloride (10 mL), and pyridinium dichromate (240 mg, 0.638 mmol) and molecular sieves 4A (200 mg) were added, followed by stirring at room temperature for 2 hours under nitrogen atmosphere. After Celite filtration, the solvent was distilled off under reduced pressure, and the resulting residue was purified using silica gel column chromatography (elution solvent: ethyl acetate/hexane=50%-70%) to afford the desired product (44.1 mg, yield 55%) as a white solid.

$^1$H-NMR (CDCl$_3$, 400 MHz): δ 1.36 (3H, d, J=6.3 Hz), 1.62 (3H, d, J=7.0 Hz), 3.25 (3H, s), 3.42 (3H, s), 3.52 (1H, dd, J=3.9, 10.2 Hz), 3.62 (1H, dd, J=5.9, 10.2 Hz), 4.62 (1H, m), 4.81 (1H, q, J=7.0 Hz), 6.68 (1H, d, J=3.9 Hz), 6.76 (1H, t, J=2.4 Hz), 7.03 (1H, t, J=2.0 Hz), 7.17 (1H, t, J=2.0 Hz), 7.26 (1H, d, J=3.9 Hz), 8.52 (2H, d, J=1.2 Hz), 8.82 (2H, d, J=1.2 Hz).

(105b) (5S)-2-[5-(3-[(1S)-2-Hydroxy-1-methylethoxy]-5-{[5-(methylsulfonyl)pyrazin-2-yl]oxy}phenyl)-1H-pyrrol-2-yl]-5-methyl-4,5-dihydro-1,3-oxazol-4(5H)-one (5S)-2-[5-(3-[(1S)-2-Methoxy-1-methylethoxy]-5-{[5-(methylsulfonyl)pyrazin-2-yl]oxy}phenyl)-1H-pyrrol-2-yl]-5-methyl-4,5-dihydro-1,3-oxazol-4(5H)-one (100 mg, 0.200 mmol) synthesized in Example (105a) was dissolved in methylene chloride (10 mL), and cooled to −78° C. Boron tribromide (1.0 mol/L methylene chloride solution, 0.260 mL, 0.260 mmol) was added, and stirring was carried out for 2 hours with the temperature being raised gradually to room temperature. A saturated aqueous sodium hydrogencarbonate solution (10 mL) was added, and extraction was carried out twice with methylene chloride (10 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=0%-10%) to afford the desired product (98.0 mg, yield ~100%) as a white solid.

$^1$H-NMR (CDCl$_3$, 400 MHz): δ 1.32 (3H, d, J=6.3 Hz), 1.63 (3H, dd, J=2.7, 7.0 Hz), 3.26 (3H, s), 3.80-3.84 (2H, m), 4.62 (1H, m), 4.84 (1H, q, J=7.0 Hz), 6.66 (1H, d, J=3.9 Hz), 6.69 (1H, m), 7.03 (1H, m), 7.20 (1H, m), 7.26 (1H, brd, J=3.9 Hz), 8.51 (2H, d, J=1.2 Hz), 8.81 (2H, d, J=1.2 Hz).

MS (ESI) m/z: 487.12874 (M+H)$^+$.

Example 106

(2S)-2-(3-{5-[(5S)-5-Ethyl-4,5-dihydro-1,3-oxazol-2-yl]-1H-pyrrol-2-yl}-5-{[5-(methylsulfonyl)pyrazin-2-yl]oxy}phenoxy)propan-1-ol

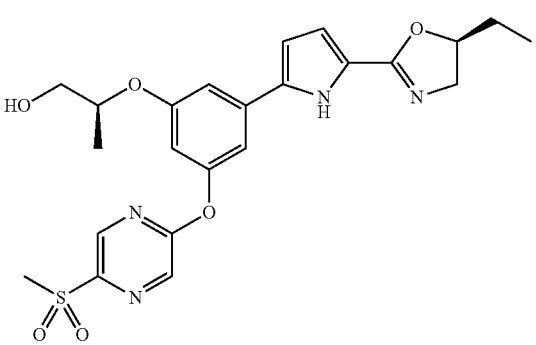

(106a) Benzyl 5-{3-hydroxy-5-[(1S)-2-methoxy-1-methylethoxy]phenyl}-1H-pyrrole-2-carboxylate 3-[(1S)-2-Methoxy-1-methylethoxy]-5-(4,4,5,5-tetramethyl-1,3,2-dioxaborolan-2-yl)phenol (26.79 g, 86.9 mmol) synthesized in Example (78d) and 2-benzyl 1-t-butyl 5-bromo-1H-pyrrole-1,2-dicarboxylate (32.32 g, 85.0 mmol) synthesized in Example (78f) were dissolved in 1,4-dioxane (360 mL)+water (90 mL), and [1,1'-bis(diphenylphosphino)ferrocene]palladium (II) dichloride dichloromethane complex (2.34 g, 2.87 mmol) and potassium carbonate (30.40 g, 220 mmol) were added, followed by stirring at 60° C. for 3 hours under nitrogen atmosphere. After the reaction solution was cooled to room temperature, water (1000 mL) was added, and extraction was carried out with ethyl acetate (700 mL). The organic layer was washed with saturated brine, subsequently dried over anhydrous sodium sulfate, and the solvent was distilled off under reduced pressure.

The resulting residue was dissolved in methylene chloride (100 mL), and trifluoroacetic acid (120 mL) was added, followed by stirring at room temperature for 1 hour. After the reaction solution was concentrated under reduced pressure, it was diluted with ethyl acetate (500 mL), washed with saturated aqueous sodium hydrogencarbonate solution and saturated brine, subsequently dried over anhydrous sodium sulfate, and the solvent was distilled off under reduced pressure. The resulting residue was purified using silica gel column chromatography (elution solvent: ethyl acetate/hexane=30%-50%) to afford the desired compound (17.40 g, yield 54%) as a brown oil.

$^1$H-NMR (CDCl$_3$, 400 Hz): δ 1.31 (3H, d, J=6.3 Hz), 3.42 (3H, s), 3.49 (1H, dd, J=9.8, 4.3 Hz), 3.59 (1H, dd, J=10.2, 6.3 Hz), 4.52-4.59 (1H, m), 5.35 (2H, s), 6.42 (1H, t, J=2.0 Hz), 6.47 (1H, dd, J=3.9, 2.7 Hz), 6.72 (1H, s), 6.77 (1H, br s), 6.80 (1H, s), 6.98 (1H, dd, J=3.9, 2.7 Hz), 7.45-7.33 (5H, m), 9.94 (1H, br s).

MS (FAB) m/z: 382 (M+H)$^+$.

(106b) Benzyl 5-{3-[(1S)-2-methoxy-1-methylethoxy]-5-[(triisopropylsilyl)oxy]phenyl}-1H-pyrrole-2-carboxylate Benzyl 5-{3-hydroxy-5-[(1S)-2-methoxy-1-methylethoxy]phenyl}-1H-pyrrole-2-carboxylate (27.35 g, 71.7 mmol) synthesized in Example (106a) was dissolved in methylene chloride (350 mL), and triisopropylsilyl chloride (18.4 mL, 86.0 mmol), triethylamine (30.0 mL, 215 mmol) and 4-dimethylaminopyridine (10.53 g, 86.2 mmol) were added, followed by stirring at room temperature for 4 hours under nitrogen atmosphere. Water (400 mL) was added to separate the solution, and the organic layer was washed with saturated brine, followed by drying over anhydrous magnesium sulfate. The solvent was distilled off under reduced pressure, and the resulting residue was purified using silica gel column chromatography (elution solvent: ethyl acetate/hexane=3%-20%) to afford the desired product (34.41 g, yield 89%) as a pale yellow oil.

$^1$H-NMR (CDCl$_3$, 400 Hz): δ 1.11 (18H, d, J=7.0 Hz), 1.22-1.30 (3H, m), 1.32 (3H, d, J=6.3 Hz), 3.41 (3H, s), 3.49 (1H, dd, J=10.2, 4.3 Hz), 3.58 (1H, dd, J=10.2, 5.9 Hz), 4.49-4.56 (1H, m), 5.33 (2H, s), 6.43 (1H, t, J=2.3 Hz), 6.47 (1H, dd, J=3.9, 2.7 Hz), 6.66 (1H, t, J=2.0 Hz), 6.71 (1H, t, J=1.8 Hz), 6.98 (1H, dd, J=3.9, 2.7 Hz), 7.32-7.45 (5H, m), 9.19 (1H, br s).

MS (FAB) m/z: 538 (M+H)$^+$.

(106c) 5-{3-[(1S)-2-Methoxy-1-methylethoxy]-5-[(triisopropylsilyl)oxy]phenyl}-1H-pyrrole-2-carboxylic acid Benzyl 5-{3-[(1S)-2-methoxy-1-methylethoxy]-5-[(triisopropylsilyl)oxy]phenyl}-1H-pyrrole-2-carboxylate (34.40 g, 64.0 mmol) synthesized in Example (106b) was dissolved in ethanol (320 mL), and a 10% palladium carbon catalyst (3.54 g) was added, followed by stirring for 2 hours under hydrogen atmosphere. The palladium carbon catalyst was removed by Celite filtration, and the solvent was distilled off under reduced pressure to afford the desired compound (27.31 g, yield 95%) as a white solid.

$^1$H-NMR (CDCl$_3$, 400 Hz): δ 1.11 (18H, d, J=7.4 Hz), 1.22-1.30 (3H, m), 1.33 (3H, d, J=6.3 Hz), 3.46 (1H, s), 3.51 (1H, dd, J=10.2, 4.7 Hz), 3.66 (1H, dd, J=10.2, 5.9 Hz), 4.61-4.69 (1H, m), 6.43 (1H, t, J=2.0 Hz), 6.51 (1H, dd, J=3.7, 2.2 Hz), 6.74 (1H, t, J=1.6 Hz), 6.98 (1H, t, J=1.6 Hz), 7.05 (1H, dd, J=3.9, 2.3 Hz), 10.02 (1H, br s).

MS (FAB) m/z: 448 (M+H)$^+$.

(106d) N-[(2R)-2-Hydroxybutyl]-5-(3-{[(2S)-1-methoxypropan-2-yl]oxy}-5-[(tripropan-2-ylsilyl)oxy]phenyl)-1H-pyrrole-2-carboxamide 5-{3-[(1S)-2-Methoxy-1-methylethoxy]-5-[(triisopropylsilyl)oxy]phenyl}-1H-pyrrole-2-carboxylic acid (1.03 g, 2.30 mmol) synthesized in Example (106c) was dissolved in methylene chloride (20 mL), and (2R)-1-aminobutan-2-ol (0.40 g, 4.49 mmol) synthesized according to a method known to the public (Angew. Chem. Int. Ed. 2007, 46, 2245.), WSC•HCl (1.15 g, 6.00 mmol) and 4-dimethylaminopyridine (280 mg, 2.29 mmol) were added, followed by stirring at room temperature overnight under nitrogen atmosphere. To the reaction solution, a saturated aqueous ammonium chloride solution (30 mL) was added, and extraction was carried out with methylene chloride (30 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=60%-80%) to afford the desired compound (1.01 g, yield 85%) as a white solid.

$^1$H-NMR (CDCl$_3$, 400 MHz): δ 0.99 (3H, t, J=7.4 Hz), 1.11 (18H, d, J=7.0 Hz), 1.23-1.30 (3H, m), 1.31 (3H, d, J=6.3 Hz), 1.49-1.60 (2H, m), 3.27-3.35 (1H, m), 3.42 (3H, s), 3.49 (1H, dd, J=10.2, 4.3 Hz), 3.59 (1H, dd, J=10.2, 5.9 Hz), 3.62-3.69 (1H, m), 3.70-3.76 (1H, m), 4.49-4.56 (1H, m), 6.33 (1H, t, J=5.7 Hz), 6.41 (1H, t, J=2.2 Hz), 6.45 (1H, dd, J=3.5, 3.1 Hz), 6.61 (1H, dd, J=3.7, 2.5 Hz), 6.67 (1H, t, J=1.8 Hz), 6.73 (1H, t, J=1.8 Hz), 9.58 (1H, s).

(106e) (5S)-5-Ethyl-2-[5-(3-{[(2S)-1-methoxypropan-2-yl]oxy}-5-[(tripropan-2-ylsilyl)oxy]phenyl)-1H-pyrrol-2-yl]-4,5-dihydro-1,3-oxazole N-[(2R)-2-Hydroxybutyl]-5-(3-{[(2S)-1-methoxypropan-2-yl]oxy}-5-[(tripropan-2-ylsilyl)oxy]phenyl)-1H-pyrrole-2-carboxamide (1.01 g, 1.95 mmol) synthesized in Example (106d) was dissolved in tetrahydrofuran (40 mL), and anhydrous methanesulfonic acid (600 mg, 3.44 mmol) and triethylamine (1.60 mL, 11.48 mmol) were added, followed by stirring at 50° C. for 8 hours under nitrogen atmosphere. To the reaction solution, a saturated aqueous ammonium chloride solution (50 mL) was added, and extraction was carried out with methylene chloride (80 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=50%-70%) to afford the desired compound (980 mg, yield 100%) as a yellow solid.

$^1$H-NMR (CDCl$_3$, 400 MHz): δ 1.01 (3H, t, J=7.4 Hz), 1.09-1.14 (18H, m), 1.24-1.30 (3H, m), 1.32 (3H, d, J=6.3 Hz), 1.71-1.82 (2H, m), 3.42 (3H, s), 3.49 (1H, dd, J=10.2, 4.3 Hz), 3.57-3.63 (2H, m), 4.04 (2H, dd, J=14.1, 9.4 Hz), 4.51-4.56 (1H, m), 4.62-4.68 (1H, m), 6.39 (1H, t, J=2.2 Hz), 6.46 (1H, d, J=3.9 Hz), 6.71 (1H, s), 6.75 (1H, s), 6.76 (1H, s).

(106f) 2-(3-{5-[(5S)-5-Ethyl-4,5-dihydro-1,3-oxazol-2-yl]-1H-pyrrol-2-yl}-5-{[(2S)-1-methoxypropan-2-yl]oxy}phenoxy)-5-(methylsulfonyl)pyrazine (5S)-5-Ethyl-2-[5-(3-{[(2S)-1-methoxypropan-2-yl]oxy}-5-[(tripropan-2-ylsilyl)oxy]phenyl)-1H-pyrrol-2-yl]-4,5-dihydro-1,3-oxazole (980 mg, 1.95 mmol) synthesized in Example (106e) was dissolved in tetrahydrofuran (20 mL), and tetrabutylammonium fluoride (1.0 mol/L tetrahydrofuran solution, 4.00 mL, 4.00 mmol) was added at room temperature, followed by stirring at room temperature for 1.5 hours under nitrogen atmosphere. To this reaction solution, a saturated aqueous ammonium chloride solution (30 mL) was added, and extraction was carried out with methylene chloride (40 mL). The organic layer was washed with saturated brine, and subsequently dried over anhydrous magnesium sulfate. The solvent was distilled off under reduced pressure to afford a yellow solid.

This was dissolved in acetonitrile (20 mL), and 2-chloro-5-(methylsulfonyl)pyrazine (420 mg, 2.18 mmol) synthesized in Example (97c) and cesium carbonate (1.42 g, 4.36 mmol) were added at room temperature, followed by stirring at room temperature for 2 hours under nitrogen atmosphere. To this reaction solution, water (30 mL) was added, and extraction was carried out with methylene chloride (40 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate=100%) to afford the desired compound (860 mg, yield 88%) as a yellow solid.

$^1$H-NMR (CDCl$_3$, 400 MHz): δ 1.08 (3H, t, J=7.4 Hz), 1.38 (3H, d, J=6.3 Hz), 1.81-1.94 (2H, m), 3.24 (3H, s), 3.42 (3H, s), 3.56 (1H, dd, J=10.6, 3.9 Hz), 3.62 (1H, dd, J=10.6, 5.9 Hz), 3.74 (1H, dd, J=12.7, 7.6 Hz), 4.17 (1H, dd, J=12.1, 9.8 Hz), 4.74 (1H, br s), 4.99 (1H, br s), 6.61 (1H, d, J=4.3 Hz), 6.74 (1H, s), 7.06 (1H, s), 7.20 (1H, s), 7.40 (1H, s), 8.50 (1H, d, J=1.2 Hz), 8.82 (1H, d, J=1.2 Hz).

(106g) (2S)-2-(3-{5-[(5S)-5-Ethyl-4,5-dihydro-1,3-oxazol-2-yl]-1H-pyrrol-2-yl}-5-{[5-(methylsulfonyl)pyrazin-2-yl]oxy}phenoxy)propan-1-ol 2-(3-{5-[(5S)-5-Ethyl-4,5-dihydro-1,3-oxazol-2-yl]-1H-pyrrol-2-yl}-5-{[(2S)-1-methoxypropan-2-yl]oxy}phenoxy)-5-(methylsulfonyl)pyrazine (860 mg, 1.72 mmol) synthesized in Example (1060 was dissolved in methylene chloride (20 mL), and boron tribromide (1.0 mol/L methylene chloride solution, 2.50 mL, 2.50 mmol) was added dropwise at –78° C., followed by stirring at room temperature for 2 hours under nitrogen atmosphere. To this reaction solution, a saturated aqueous sodium hydrogencarbonate solution (20 mL) was added, and extraction was carried out with methylene chloride (20 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=2%-4%) to afford the desired compound (764 mg, yield 91%) as a yellow solid.

$^1$H-NMR (CDCl$_3$, 400 MHz): δ 1.02 (3H, t, J=7.4 Hz), 1.33 (3H, d, J=6.3 Hz), 1.67-1.85 (2H, m), 3.23 (3H, s), 3.63 (1H, dd, J=13.7, 7.8 Hz), 3.73-3.83 (2H, m), 4.07 (1H, dd, J=13.7, 9.4 Hz), 4.60 (1H, br s), 4.72 (1H, br s), 6.51 (1H, d, J=3.9 Hz), 6.60 (1H, s), 6.81 (1H, d, J=3.5 Hz), 6.96 (1H, s), 7.12 (1H, s), 8.48 (1H, d, J=1.2 Hz), 8.80 (1H, d, J=1.2 Hz).

MS (ESI) m/z: 487.16397 (M+H)$^+$.

Example 107

(2S)-2-(3-{5-[(4R)-4-Methyl-4,5-dihydro-1,3-oxazol-2-yl]-1H-pyrrol-2-yl}-5-{[5-(methylsulfonyl)pyrazin-2-yl]oxy}phenoxy)propan-1-ol

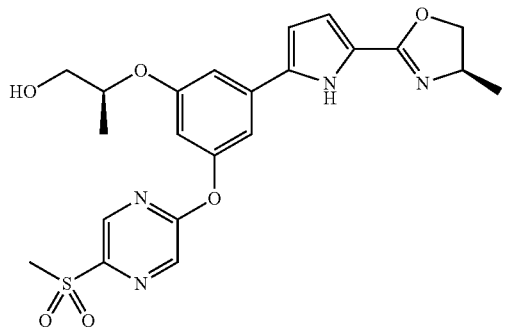

(107a) N-[(2R)-1-Hydroxypropan-2-yl]-5-(3-{[(2S)-1-methoxypropan-2-yl]oxy}-5-[(tripropan-2-ylsilyl)oxy]phenyl)-1H-pyrrole-2-carboxamide 5-{3-[(1S)-2-Methoxy-1-methylethoxy]-5-[(triisopropylsilyl)oxy]phenyl}-1H-pyrrole-2-carboxylic acid (2.25 g, 5.03 mmol) synthesized in Example (106c) was dissolved in methanol (50 mL), and D-alaninol (0.70 mL, 8.97 mmol) and 4-(4,6-dimethoxy-1,3,5-triazin-2-yl)-4-methylmorpholinium chloride n hydrate (3.05 g, 11.02 mmol) were added, followed by stirring at room temperature for 1 day under nitrogen atmosphere. After the solvent was distilled off under reduced pressure, a saturated aqueous ammonium chloride solution (50 mL) was added, and extraction was carried out with ethyl acetate (80 mL). The organic layer was washed with saturated brine, and subsequently dried over anhydrous magnesium sulfate. The resulting residue was purified using silica gel column chromatography (elution solvent: ethyl acetate/hexane=80%-100%) to afford the desired compound (1.95 g, yield 75%) as a white solid.

$^1$H-NMR (CDCl$_3$, 400 MHz): δ 1.11 (18H, d, J=7.4 Hz), 1.23-1.28 (3H, m), 1.28 (3H, d, J=7.0 Hz), 1.32 (3H, d, J=5.9 Hz), 3.42 (3H, s), 3.49 (1H, dd, J=10.2, 4.3 Hz), 3.59 (1H, dd, J=10.2, 5.9 Hz), 3.64 (1H, dd, J=11.1, 6.1 Hz), 3.77 (1H, dd, J=10.9, 3.5 Hz), 4.24 (1H, br s), 4.53 (1H, br s), 6.05 (1H, s), 6.41 (1H, t, J=2.0 Hz), 6.45 (1H, t, J=3.3 Hz), 6.60 (1H, dd, J=3.7, 2.5 Hz), 6.67 (1H, t, J=1.8 Hz), 6.74 (1H, t, J=1.8 Hz), 9.60 (1H, s).

(107b) (4R)-2-[5-(3-{[(2S)-1-Methoxypropan-2-yl]oxy}-5-[(tripropan-2-ylsilyl)oxy]phenyl)-1H-pyrrol-2-yl]-4-methyl-4,5-dihydro-1,3-oxazole N-[(2R)-1-Hydroxypropan-2-yl]-5-(3-{[(2S)-1-methoxypropan-2-yl]oxy}-5-[(tripropan-2-ylsilyl)oxy]phenyl)-1H-pyrrole-2-carboxamide (1.95 g, 3.76 mmol) synthesized in Example (107a) was dissolved in tetrahydrofuran (30 mL), and anhydrous methanesulfonic acid (1.25 g, 7.18 mmol) and triethylamine (2.80 mL, 20.09 mmol) were added, followed by stirring at 50° C. for 1 day under nitrogen atmosphere. To the reaction solution, a saturated aqueous ammonium chloride solution (80 mL) was added, and extraction was carried out with methylene chloride (120 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=50%-80%) to afford the desired compound (1.18 g, yield 64%) as a yellow solid.

$^1$H-NMR (CDCl$_3$, 400 MHz): δ 1.12 (18H, d, J=7.4 Hz), 1.23-1.31 (3H, m), 1.31-1.35 (6H, m), 3.42 (3H, s), 3.49 (1H, dd, J=10.2, 4.7 Hz), 3.59 (1H, dd, J=10.2, 5.9 Hz), 3.93 (1H, t, J=7.8 Hz), 4.33 (1H, br s), 4.49 (1H, dd, J=9.0, 8.2 Hz), 4.54 (1H, br s), 6.40 (1H, t, J=2.2 Hz), 6.46 (1H, d, J=3.5 Hz), 6.72 (1H, t, J=1.8 Hz), 6.74 (1H, d, J=3.9 Hz), 6.77 (1H, t, J=1.8 Hz).

(107c) 3-{[(2S)-1-Methoxypropan-2-yl]oxy}-5-{5-[(4R)-4-methyl-4,5-dihydro-1,3-oxazol-2-yl]-1H-pyrrol-2-yl}phenol (4R)-2-[5-(3-{[(2S)-1-Methoxypropan-2-yl]oxy}-5-[(tripropan-2-ylsilyl)oxy]phenyl)-1H-pyrrol-2-yl]-4-methyl-4,5-dihydro-1,3-oxazole (1.18 g, 2.42 mmol) synthesized in Example (107b) was dissolved in tetrahydrofuran (10 mL), and tetrabutylammonium fluoride (1.0 mol/L tetrahydrofuran solution, 3.00 mL, 3.00 mmol) was added at room temperature, followed by stirring at room temperature for 30 minutes under nitrogen atmosphere. To this reaction solution, a saturated aqueous ammonium chloride solution (30 mL) was added, and extraction was carried out with methylene chloride (40 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=1%-3%) to afford the desired compound (720 mg, yield 90%) as a yellow solid.

$^1$H-NMR (CDCl$_3$, 400 MHz): δ 1.32 (3H, d, J=6.3 Hz), 1.49 (3H, d, J=6.3 Hz), 3.42 (3H, s), 3.48 (1H, dd, J=10.2, 4.7 Hz), 3.59 (1H, dd, J=10.2, 5.9 Hz), 4.02 (1H, t, J=7.6 Hz), 4.47-4.61 (3H, m), 6.38 (1H, t, J=2.2 Hz), 6.48 (1H, d, J=3.9 Hz), 6.73 (1H, t, J=1.8 Hz), 6.76 (1H, d, J=3.9 Hz), 7.09 (1H, s), 11.09 (1H, s).

(107d) 2-Bromo-5-(methylsulfonyl)pyrazine 2,5-Dibromopyrazine (270 mg, 1.14 mmol) was dissolved in tetrahydrofuran (10 mL), and sodium thiomethoxide (320 mg, 4.57 mmol) was added at room temperature, followed by stirring at room temperature for 2.5 hours under nitrogen atmosphere. To this reaction solution, water (10 mL) was added, and extraction was carried out with diethyl ether (10 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=5%-10%) to afford a yellow solid.

This was dissolved in methylene chloride (10 mL), and m-chloroperbenzoic acid (approximately 65%, 580 mg, approximately 2.2 mmol) was added at room temperature, followed by stirring at room temperature for 1 hour under nitrogen atmosphere. To this reaction solution, a saturated aqueous sodium hydrogencarbonate solution (10 mL) was added, and extraction was carried out with methylene chloride (10 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=15%-25%) to afford the desired compound (190 mg, yield 70%) as a white solid.

$^1$H-NMR (CDCl$_3$, 400 MHz): δ 3.26 (3H, s), 8.80 (1H, d, J=1.2 Hz), 9.06 (1H, d, J=1.2 Hz).

(107e) 2-(3-{[(2S)-1-Methoxypropan-2-yl]oxy}-5-{5-[(4R)-4-methyl-4,5-dihydro-1,3-oxazol-2-yl]-1H-pyrrol-2-yl}phenoxy)-5-(methylsulfonyl)pyrazine 3-{[(2S)-1-Methoxypropan-2-yl]oxy}-5-{5-[(4R)-4-methyl-4,5-dihydro-1,3-oxazol-2-yl]-1H-pyrrol-2-yl}phenol (340 mg, 1.03 mmol) synthesized in Example (107c) was dissolved in acetonitrile (10 mL), and 2-bromo-5-(methylsulfonyl)pyrazine (300 mg, 1.27 mmol) synthesized in Example (107d) and cesium carbonate (850 mg, 2.61 mmol) were added at room temperature, followed by stirring at room temperature for 4.5 hours under nitrogen atmosphere. To this reaction solution, water (20 mL) was added, and extraction was carried out with methylene chloride (30 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate=100%) to afford the desired compound (456 mg, yield 91%) as a white solid.

$^1$H-NMR (CDCl$_3$, 400 MHz): δ 1.33 (3H, d, J=4.3 Hz), 1.35 (3H, d, J=3.9 Hz), 3.24 (3H, s), 3.42 (3H, s), 3.51 (1H, dd, J=10.2, 3.9 Hz), 3.60 (1H, dd, J=10.4, 6.1 Hz), 3.93 (1H, t, J=7.8 Hz), 4.33 (1H, br s), 4.51 (1H, t, J=8.6 Hz), 4.58 (1H, br s), 6.52 (1H, d, J=3.9 Hz), 6.66 (1H, t, J=2.2 Hz), 6.76 (1H, d, J=3.9 Hz), 6.92 (1H, t, J=1.8 Hz), 7.07 (1H, d, J=1.6 Hz), 8.49 (1H, d, J=1.2 Hz), 8.81 (1H, d, J=1.6 Hz).

(107f) (2S)-2-(3-{5-[(4R)-4-Methyl-4,5-dihydro-1,3-oxazol-2-yl]-1H-pyrrol-2-yl}-5-{[5-(methylsulfonyl)pyrazin-2-yl]oxy}phenoxy)propan-1-ol 2-(3-{[(2S)-1-Methoxypropan-2-yl]oxy}-5-{5-[(4R)-4-methyl-4,5-dihydro-1,3-oxazol-2-yl]-1H-pyrrol-2-yl}phenoxy)-5-(methylsulfonyl)pyrazine (456 mg, 0.94 mmol) synthesized in Example (107e) was dissolved in methylene chloride (5.0 mL), and boron tribromide (1.0 mol/L methylene chloride solution, 1.50 mL, 1.50 mmol) was added dropwise at −78° C., followed by stirring at room temperature for 3 hours under nitrogen atmosphere. To this reaction solution, a saturated aqueous sodium hydrogencarbonate solution (10 mL) was added, and extraction was carried out with methylene chloride (20 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=4%-6%) to afford the desired compound (330 mg, yield 74%) as a white solid.

$^1$H-NMR (CDCl$_3$, 400 MHz): δ 1.33 (3H, d, J=6.3 Hz), 1.40 (3H, d, J=6.6 Hz), 3.22 (3H, s), 3.71 (1H, dd, J=11.7, 4.3 Hz), 3.81 (1H, dd, J=11.7, 6.6 Hz), 4.05-4.14 (1H, m), 4.38-4.45 (1H, m), 4.59-4.67 (2H, m), 6.53 (1H, d, J=3.9 Hz), 6.62 (1H, t, J=2.2 Hz), 6.87 (1H, d, J=3.9 Hz), 6.98 (1H, s), 7.27 (1H, s), 8.47 (1H, d, J=1.2 Hz), 8.79 (1H, d, J=1.2 Hz).

MS (ESI) m/z: 473.14930 (M+H)$^+$.

Example 108

(2S)-2-(3-{5-[(4R)-4-Ethyl-4,5-dihydro-1,3-oxazol-2-yl]-1H-pyrrol-2-yl}-5-{[5-(methylsulfonyl)pyrazin-2-yl]oxy}phenoxy)propan-1-ol

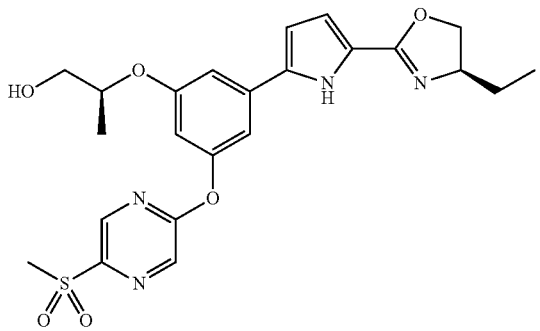

(108a) (4R)-4-Ethyl-2-[5-(3-{[(2S)-1-methoxypropan-2-yl]oxy}-5-[(tripropan-2-ylsilyl)oxy]phenyl)-1H-pyrrol-2-yl]-4,5-dihydro-1,3-oxazole 5-{3-[(1S)-2-Methoxy-1-methylethoxy]-5-[(triisopropylsilyl)oxy]phenyl}-1H-pyrrole-2-carboxylic acid (1.40 g, 3.13 mmol) synthesized in Example (106c) was dissolved in methanol (20 mL), and (R)-(−)-2-amino-1-butanol (0.65 g, 7.29 mmol) and 4-(4,6-dimethoxy-1,3,5-triazin-2-yl)-4-methylmorpholinium chloride n hydrate (1.75 g, 6.32 mmol) was added, followed by stirring at room temperature for 2 days under nitrogen atmosphere. After the solvent was distilled off under reduced pressure, a saturated aqueous ammonium chloride solution (50 mL) was added, and extraction was carried out with methylene chloride (100 mL). The organic layer was washed with saturated aqueous sodium hydrogencarbonate solution and saturated brine, and subsequently dried over anhydrous magnesium sulfate. The resulting residue was purified using silica gel column chromatography (elution solvent: ethyl acetate/hexane=50%-80%) to afford a compound as a white foam.

This was dissolved in tetrahydrofuran (20 mL), and anhydrous methanesulfonic acid (0.80 g, 4.59 mmol) and triethylamine (1.20 mL, 8.61 mmol) were added, followed by stirring at 50° C. overnight under nitrogen atmosphere. To the reaction solution, a saturated aqueous ammonium chloride solution (60 mL) was added, and extraction was carried out with methylene chloride (100 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=70%-90%) to afford the desired compound (965 mg, yield 62%) as a white solid.

$^1$H-NMR (CDCl$_3$, 400 MHz): δ 1.00 (3H, t, J=7.6 Hz), 1.07-1.14 (18H, m), 1.23-1.31 (3H, m), 1.32 (3H, d, J=6.3 Hz), 1.56-1.65 (1H, m), 1.68-1.77 (1H, m), 3.41 (3H, s), 3.48 (1H, dd, J=10.0, 4.6 Hz), 3.59 (1H, dd, J=10.0, 5.6 Hz), 4.01 (1H, t, J=7.8 Hz), 4.15-4.21 (1H, m), 4.44 (1H, t, J=8.8 Hz), 4.49-4.54 (1H, m), 6.39 (1H, t, J=2.0 Hz), 6.46 (1H, d, J=3.9 Hz), 6.71 (1H, t, J=1.7 Hz), 6.74 (1H, d, J=3.4 Hz), 6.76 (1H, t, J=1.7 Hz).

(108b) 3-{5-[(4R)-4-Ethyl-4,5-dihydro-1,3-oxazol-2-yl]-1H-pyrrol-2-yl}-5-{[(2S)-1-methoxypropan-2-yl]oxy}phenol (4R)-4-Ethyl-2-[5-(3-{[(2S)-1-methoxypropan-2-yl]oxy}-5-[(tripropan-2-ylsilyl)oxy]phenyl)-1H-pyrrol-2-yl]-4,5-dihydro-1,3-oxazole (965 mg, 1.93 mmol) synthesized in Example (108a) was dissolved in tetrahydrofuran (10 mL), and tetrabutylammonium fluoride (1.0 mol/L tetrahydrofuran solution, 2.50 mL, 2.50 mmol) was added at room temperature, followed by stirring at room temperature for 1 hour under nitrogen atmosphere. To this reaction solution, a saturated aqueous ammonium chloride solution (30 mL) was added, and extraction was carried out with methylene chloride (40 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=2%-4%) to afford the desired compound (550 mg, yield 83%) as a white solid.

$^1$H-NMR (CDCl$_3$, 400 MHz): δ 1.10 (3H, t, J=7.4 Hz), 1.32 (3H, d, J=6.3 Hz), 1.73 (1H, td, J=14.1, 7.0 Hz), 1.85 (1H, td, J=14.0, 7.0 Hz), 3.41 (3H, s), 3.48 (1H, dd, J=10.2, 4.7 Hz), 3.59 (1H, dd, J=10.2, 5.9 Hz), 4.09-4.15 (1H, m), 4.32-4.40 (1H, m), 4.48-4.57 (2H, m), 6.36 (1H, t, J=2.2 Hz), 6.47 (1H, d, J=3.5 Hz), 6.72 (1H, t, J=1.8 Hz), 6.76 (1H, d, J=3.9 Hz), 7.10 (1H, t, J=1.8 Hz), 11.12 (1H, br s).

(108c) 2-(3-{5-[(4R)-4-Ethyl-4,5-dihydro-1,3-oxazol-2-yl]-1H-pyrrol-2-yl}-5-{[(2S)-1-methoxypropan-2-yl]oxy}phenoxy)-5-(methylsulfonyl)pyrazine 3-{5-[(4R)-4-Ethyl-4,5-dihydro-1,3-oxazol-2-yl]-1H-pyrrol-2-yl}-5-{[(2S)-1-methoxypropan-2-yl]oxy}phenol (272 mg, 0.79 mmol) synthesized in Example (108b) was dissolved in acetonitrile (5.0 mL), and 2-chloro-5-(methylsulfonyl)pyrazine (220 mg, 1.14 mmol) synthesized in Example (97c) and cesium carbonate (640 mg, 1.96 mmol) were added at room temperature, followed by stirring at room temperature for 3.5 hours under nitrogen atmosphere. To this reaction solution, water (20 mL) was added, and extraction was carried out with methylene chloride (30 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=2%-3%) to afford the desired compound (417 mg, yield ~100%) as a pale yellow solid.

$^1$H-NMR (CDCl$_3$, 400 MHz): δ 0.96 (3H, t, J=7.4 Hz), 1.34 (3H, d, J=6.3 Hz), 1.53-1.60 (1H, m), 1.65-1.72 (1H, m), 3.23 (3H, s), 3.41 (3H, s), 3.50 (1H, dd, J=10.2, 4.3 Hz), 3.59 (1H, dd, J=10.6, 5.9 Hz), 4.01 (1H, t, J=7.8 Hz), 4.11-4.19 (1H, m), 4.41-4.46 (1H, m), 4.57 (1H, br s), 6.50 (1H, d, J=3.9 Hz), 6.64 (1H, t, J=2.2 Hz), 6.73 (1H, d, J=3.5 Hz), 6.94 (1H, d, J=1.6 Hz), 7.09 (1H, d, J=1.6 Hz), 8.47 (1H, d, J=0.8 Hz), 8.80 (1H, d, J=0.8 Hz).

(108d) (2S)-2-(3-{5-[(4R)-4-Ethyl-4,5-dihydro-1,3-oxazol-2-yl]-1H-pyrrol-2-yl}-5-{[5-(methylsulfonyl)pyrazin-2-yl]oxy}phenoxy)propan-1-ol 2-(3-{5-[(4R)-4-Ethyl-4,5-dihydro-1,3-oxazol-2-yl]-1H-pyrrol-2-yl}-5-{[(2S)-1-methoxypropan-2-yl]oxy}phenoxy)-5-(methylsulfonyl)pyrazine (417 mg, 0.83 mmol) synthesized in Example (108c) was dissolved in methylene chloride (10 mL), and boron tribromide (1.0 mol/L methylene chloride solution, 1.00 mL, 1.00 mmol) was added dropwise at −78° C., followed by stirring at room temperature for 1 hour under nitrogen atmosphere. To this reaction solution, a 1N aqueous sodium hydroxide solution (20 mL) was added, and extraction was carried out with methylene chloride (20 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=3%-4%) to afford the desired compound (325 mg, yield 80%) as a white solid.

$^1$H-NMR (CDCl$_3$, 400 MHz): δ 1.01 (3H, t, J=7.4 Hz), 1.30 (3H, d, J=6.3 Hz), 1.57-1.64 (1H, m), 1.68-1.75 (1H, m), 3.23 (3H, s), 3.78-3.80 (2H, m), 4.02 (1H, t, J=8.0 Hz), 4.16-4.22 (1H, m), 4.47 (1H, t, J=8.8 Hz), 4.57-4.63 (1H, m), 6.45 (1H, d, J=3.5 Hz), 6.49 (1H, s), 6.73 (1H, d, J=3.9 Hz), 6.90 (1H, s), 7.01 (1H, s), 8.44 (1H, s), 8.79 (1H, s).

MS (ESI) m/z: 487.16468 (M+H)$^+$.

Example 109

(2S)-2-(3-{5-[(4R,5S)-4,5-Dimethyl-4,5-dihydro-1,3-oxazol-2-yl]-1H-pyrrol-2-yl}-5-{[5-(methylsulfonyl)pyrazin-2-yl]oxy}phenoxy)propan-1-ol

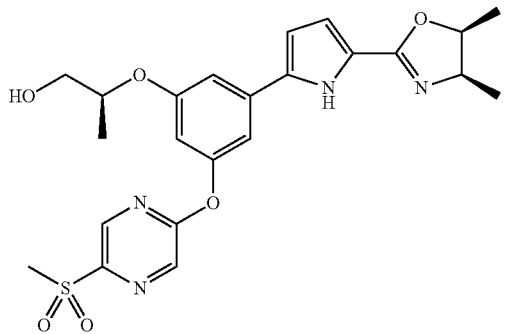

(109a) N-[(2R,3R)-3-Hydroxybutan-2-yl]-5-(3-{[(2S)-1-methoxypropan-2-yl]oxy}-5-[(tripropan-2-ylsilyl)oxy]phenyl)-1H-pyrrole-2-carboxamide 5-{3-[(1S)-2-Methoxy-1-methylethoxy]-5-[(triisopropylsilyl)oxy]phenyl}-1H-pyrrole-2-carboxylic acid (0.89 g, 1.99 mmol) synthesized in Example (106c) was dissolved in methanol (20 mL), and (2R,3R)-3-aminobutan-2-ol (0.41 g, 4.60 mmol) synthesized in Example (88a) and 4-(4,6-dimethoxy-1,3,5-triazin-2-yl)-4-methylmorpholinium chloride n hydrate (1.20 g, 4.34 mmol) were added, followed by stirring at room temperature for 3 days under nitrogen atmosphere. After the solvent was distilled off under reduced pressure, a saturated aqueous ammonium chloride solution (50 mL) was added, and extraction was carried out with methylene chloride (80 mL). The organic layer was washed with saturated brine, and subsequently dried over anhydrous magnesium sulfate. The resulting residue was purified using silica gel column chromatography (elution solvent: ethyl acetate/hexane=60%-80%) to afford the desired compound (722 mg, yield 70%) as a white foam.

$^1$H-NMR (CDCl$_3$, 400 MHz): δ 1.11 (18H, d, J=7.0 Hz), 1.22-1.29 (3H, m), 1.24 (3H, d, J=6.3 Hz), 1.28 (3H, d, J=7.0 Hz), 1.32 (3H, d, J=6.3 Hz), 2.34 (1H, br s), 3.42 (3H, s), 3.49 (1H, dd, J=10.2, 4.3 Hz), 3.59 (1H, dd, J=10.2, 5.5 Hz), 3.84 (1H, br s), 4.03-4.13 (1H, m), 4.49-4.56 (1H, m), 6.06 (1H, d, J=8.6 Hz), 6.41 (1H, t, J=2.2 Hz), 6.45 (1H, dd, J=3.7, 2.9 Hz), 6.61 (1H, dd, J=3.9, 2.3 Hz), 6.67 (1H, t, J=1.8 Hz), 6.73 (1H, t, J=2.0 Hz), 9.49 (1H, br s).

(109b) (4R,5S)-2-[5-(3-{[(2S)-1-Methoxypropan-2-yl]oxy}-5-[(tripropan-2-ylsilyl)oxy]phenyl)-1H-pyrrol-2-yl]-4,5-dimethyl-4,5-dihydro-1,3-oxazole N-[(2R,3R)-3-Hydroxybutan-2-yl]-5-(3-{[(2S)-1-methoxypropan-2-yl]oxy}-5-[(tripropan-2-ylsilyl)oxy]phenyl)-1H-pyrrole-2-carboxamide (722 mg, 1.39 mmol) synthesized in Example (109a) was dissolved in tetrahydrofuran (30 mL), and anhydrous methanesulfonic acid (430 mg, 2.47 mmol) and triethylamine (1.20 mL, 8.61 mmol) were added, and stirring was carried out at 50° C. overnight under nitrogen atmosphere. The reaction solution was brought back to room temperature, and a saturated aqueous ammonium chloride solution (50 mL) was added, followed by extraction with methylene chloride (50 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=40%-70%) to afford the desired compound (700 mg, yield 100%) as a yellow liquid.

$^1$H-NMR (CDCl$_3$, 400 MHz): δ 1.11 (18H, d, J=7.0 Hz), 1.21 (3H, d, J=7.0 Hz), 1.23-1.30 (3H, m), 1.31 (3H, d, J=6.3 Hz), 1.33 (3H, d, J=6.6 Hz), 3.42 (3H, s), 3.48 (1H, dd, J=10.2, 4.3 Hz), 3.58 (1H, dd, J=10.2, 5.9 Hz), 4.24-4.32 (1H, m), 4.48-4.56 (1H, m), 4.78-4.85 (1H, m), 6.39 (1H, t, J=2.2 Hz), 6.46 (1H, d, J=3.5 Hz), 6.70 (1H, s), 6.73-6.75 (2H, m).

(109c) 3-{5-[(4R,5S)-4,5-Dimethyl-4,5-dihydro-1,3-oxazol-2-yl]-1H-pyrrol-2-yl}-5-{[(2S)-1-methoxypropan-2-yl]oxy}phenol (4R,5S)-2-[5-(3-{[(2S)-1-Methoxypropan-2-yl]oxy}-5-[(tripropan-2-ylsilyl)oxy]phenyl)-1H-pyrrol-2-yl]-4,5-dimethyl-4,5-dihydro-1,3-oxazole (700 mg, 1.39 mmol) synthesized in Example (109b) was dissolved in tetrahydrofuran (10 mL), and tetrabutylammonium fluoride (1.0 mol/L tetrahydrofuran solution, 2.00 mL, 2.00 mmol) was added at room temperature, followed by stirring at room temperature for 30 minutes under nitrogen atmosphere. To this reaction solution, a saturated aqueous ammonium chloride solution (30 mL) was added, and extraction was carried out with methylene chloride (30 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=2%-3%) to afford the desired compound (420 mg, yield 88%) as a yellow liquid.

$^1$H-NMR (CDCl$_3$, 400 MHz): δ 1.33 (3H, d, J=6.3 Hz), 1.35-1.40 (6H, m), 3.41 (3H, s), 3.48 (1H, dd, J=10.0, 4.5 Hz), 3.59 (1H, dd, J=10.2, 5.5 Hz), 4.40-4.48 (1H, m), 4.48-4.56 (1H, m), 4.86-4.94 (1H, m), 6.38 (1H, t, J=2.0 Hz), 6.47 (1H, d, J=3.9 Hz), 6.72 (1H, s), 6.75 (1H, d, J=3.9 Hz), 7.09 (1H, s).

(109d) 2-(3-{5-[(4R,5S)-4,5-Dimethyl-4,5-dihydro-1,3-oxazol-2-yl]-1H-pyrrol-2-yl}-5-{[(2S)-1-methoxypropan-2-yl]oxy}phenoxy)-5-(methylsulfonyl)pyrazine 3-{5-[(4R,5S)-4,5-Dimethyl-4,5-dihydro-1,3-oxazol-2-yl]-1H-pyrrol-2-yl}-5-{[(2S)-1-methoxypropan-2-yl]oxy}phenol (420 mg, 1.22 mmol) synthesized in Example (109c) was dissolved in acetonitrile (20 mL), and 2-chloro-5-(methylsulfonyl)pyrazine (345 mg, 1.46 mmol) synthesized in Example (97c) and cesium carbonate (1.02 g, 3.13 mmol) were added at room temperature, followed by stirring at room temperature overnight under nitrogen atmosphere. To this reaction solution, water (30 mL) was added, and extraction was carried out with methylene chloride (40 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=2%-3%) to afford the desired compound (513 mg, yield 84%) as a white solid.

$^1$H-NMR (CDCl$_3$, 400 MHz): δ 1.19-1.28 (6H, m), 1.35 (3H, d, J=6.6 Hz), 3.24 (3H, s), 3.42 (3H, s), 3.51 (1H, dd, J=10.2, 4.3 Hz), 3.61 (1H, dd, J=10.4, 5.7 Hz), 4.25-4.35 (1H, m), 4.57-4.63 (1H, m), 4.81-4.91 (1H, m), 6.52 (1H, d, J=3.9 Hz), 6.76 (1H, s), 6.96 (1H, s), 7.12 (1H, s), 8.49 (1H, d, J=1.2 Hz), 8.81 (1H, d, J=1.6 Hz).

(109e) ((2S)-2-(3-{5-[(4R,5S)-4,5-Dimethyl-4,5-dihydro-1,3-oxazol-2-yl]-1H-pyrrol-2-yl}-5-{[5-(methylsulfonyl)pyrazin-2-yl]oxy}phenoxy)propan-1-ol 2-(3-{5-[(4R,5S)-4,5-Dimethyl-4,5-dihydro-1,3-oxazol-2-yl]-1H-pyrrol-2-yl}-5-{[(2S)-1-methoxypropan-2-yl]oxy}phenoxy)-5-(methylsulfonyl)pyrazine (513 mg, 1.02 mmol) synthesized in Example (109d) was dissolved in methylene chloride (10 mL), and boron tribromide (1.0 mol/L methylene chloride solution, 1.50 mL, 1.50 mmol) was added dropwise at –78° C., followed by stirring at room temperature for 2 hours under nitrogen atmosphere. To this reaction solution, a saturated aqueous sodium hydrogencarbonate solution (20 mL) was added, and extraction was carried out with methylene chloride (20 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=4%-5%) to afford the desired compound (390 mg, yield 79%) as a pale yellow solid.

$^1$H-NMR (CDCl$_3$, 400 MHz): δ 1.22 (3H, d, J=7.0 Hz), 1.32 (3H, d, J=6.3 Hz), 1.34 (3H, d, J=6.6 Hz), 3.23 (3H, s), 3.76-3.79 (2H, m), 4.25-4.33 (1H, m), 4.54-4.60 (1H, m), 4.81-4.88 (1H, m), 6.49 (1H, d, J=3.9 Hz), 6.59 (1H, s), 6.75 (1H, d, J=3.9 Hz), 6.95 (1H, s), 7.09 (1H, s), 8.47 (1H, s), 8.80 (1H, d, J=1.2 Hz).

MS (ESI) m/z: 487.16580 (M+H)$^+$.

Example 110

{(4R,5S)-2-[5-(3-{[(2S)-1-Methoxypropan-2-yl]oxy}-5-{[5-(methylsulfonyl)pyrazin-2-yl]oxy}phenyl)-1H-pyrrol-2-yl]-5-methyl-4,5-dihydro-1,3-oxazol-4-yl}methanol

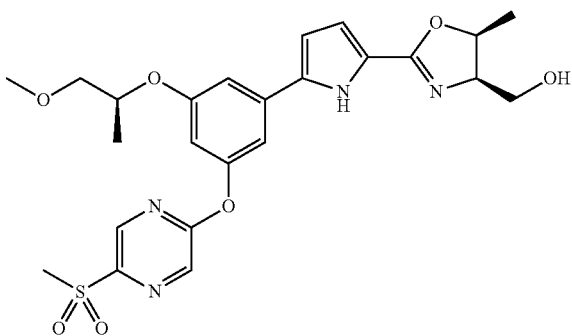

(110a) N-[(2R,3R)-1,3-Dihydroxybutan-2-yl]-5-(3-{[(2S)-1-methoxypropan-2-yl]oxy}-5-[(tripropan-2-ylsilyl)oxy]phenyl)-1H-pyrrole-2-carboxamide 5-{3-[(1S)-2-Methoxy-1-methylethoxy]-5-[(triisopropylsilyl)oxy]phenyl}-1H-pyrrole-2-carboxylic acid (2.05 g, 4.58 mmol) synthesized in Example (106c) was dissolved in methanol (20 mL), and commercially available L-threoninol (1.50 g, 14.27 mmol) and 4-(4,6-dimethoxy-1,3,5-triazin-2-yl)-4-methylmorpholinium chloride n hydrate (2.85 g, 10.30 mmol) were added, followed by stirring at room temperature for 3 days under nitrogen atmosphere. After the solvent was distilled off under reduced pressure, a saturated aqueous ammonium chloride solution (50 mL) was added, and extraction was carried out with methylene chloride (80 mL). The organic layer was washed with saturated brine, and subsequently dried over anhydrous magnesium sulfate. The resulting residue was purified using silica gel column chromatography (elution solvent: methanol/methylene chloride=3%-7%) to afford the desired compound (2.10 g, yield 86%) as a white foam.

$^1$H-NMR (CDCl$_3$, 400 MHz): δ 1.11 (18H, d, J=7.4 Hz), 1.21-1.33 (6H, m), 1.22 (3H, d, J=6.3 Hz), 3.44 (3H, s), 3.49 (1H, dd, J=10.2, 3.9 Hz), 3.57 (1H, dd, J=10.2, 6.3 Hz), 3.83 (2H, br s), 3.96 (1H, br s), 4.26 (1H, ddd, J=12.5, 6.3, 2.0 Hz), 4.45-4.53 (1H, m), 6.41 (1H, t, J=2.2 Hz), 6.44 (1H, dd, J=3.5, 2.7 Hz), 6.68-6.72 (3H, m), 6.72-6.77 (1H, m), 10.36 (1H, s).

(110b) N-{(2R,3R)-3-Hydroxy-1-[(tripropan-2-ylsilyl)oxy]butan-2-yl}-5-(3-{[(2S)-1-methoxypropan-2-yl]oxy}-5-[(tripropan-2-ylsilyl)oxy]phenyl)-1H-pyrrole-2-carboxamide N-[(2R,3R)-1,3-Dihydroxybutan-2-yl]-5-(3-{[(2S)-1-methoxypropan-2-yl]oxy}-5-[(tripropan-2-ylsilyl)oxy]phenyl)-1H-pyrrole-2-carboxamide (2.10 g, 3.93 mmol) synthesized in Example (110a) was dissolved in methylene chloride (50 mL), and triisopropylchlorosilane (1.50 mL, 7.01 mmol), 4-dimethylaminopyridine (1.50 g, 12.27 mmol) and triethylamine (5.00 mL, 35.87 mmol) were added, followed by stirring at room temperature for 1 day under nitrogen atmosphere. To the reaction solution, a saturated aqueous ammonium chloride solution (50 mL) was added, and extraction was carried out with methylene chloride (50 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=25-40%) to afford the desired compound (2.52 g, yield 93%) as a white solid.

$^1$H-NMR (CDCl$_3$, 500 MHz): δ 1.07 (18H, d, J=6.8 Hz), 1.12 (18H, d, J=7.3 Hz), 1.21-1.31 (9H, m), 1.32 (3H, d, J=6.3 Hz), 3.42 (3H, s), 3.49 (1H, dd, J=10.3, 4.4 Hz), 3.55 (1H, br s), 3.59 (1H, dd, J=10.3, 5.9 Hz), 4.00-4.04 (1H, m), 4.04-4.06 (2H, m), 4.29-4.34 (1H, m), 4.49-4.55 (1H, m), 6.41 (1H, t, J=2.2 Hz), 6.46 (1H, dd, J=3.9, 2.9 Hz), 6.60 (1H, s), 6.61 (1H, dd, J=3.4, 2.4 Hz), 6.67 (1H, t, J=2.0 Hz), 6.72 (1H, t, J=2.0 Hz), 9.34 (1H, s).

(110c) (4R,5S)-2-[5-(3-{[(2S)-1-Methoxypropan-2-yl]oxy}-5-[(tripropan-2-ylsilyl)oxy]phenyl)-1H-pyrrol-2-yl]-5-methyl-4{-[(tripropan-2-ylsilyl)oxy]methyl}-4,5-dihydro-1,3-oxazole N-{(2R,3R)-3-Hydroxy-1-[(tripropan-2-ylsilyl)oxy]butan-2-yl}-5-(3-{[(2S)-1-methoxypropan-2-yl]oxy}-5-[(tripropan-2-ylsilyl)oxy]phenyl)-1H-pyrrole-2-carboxamide (2.52 g, 3.65 mmol) synthesized in Example (110b) was dissolved in tetrahydrofuran (20 mL), and anhydrous methanesulfonic acid (1.05 g, 6.03 mmol) and triethylamine (2.00 mL, 14.35 mmol) were added, followed by stirring at 50° C. for 1 day under nitrogen atmosphere. To the reaction solution, a saturated aqueous ammonium chloride solution (50 mL) was added, and extraction was carried out with methylene chloride (50 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=10%-30%) to afford the desired compound (2.30 g, yield 94%) as a pale yellow liquid.

$^1$H-NMR (CDCl$_3$, 400 MHz): δ 1.06 (18H, d, J=5.1 Hz), 1.11 (18H, d, J=7.4 Hz), 1.22-1.30 (6H, m), 1.31 (3H, d, J=6.3 Hz), 1.52 (3H, d, J=6.3 Hz), 3.42 (3H, s), 3.48 (1H, dd, J=10.2, 4.7 Hz), 3.59 (1H, dd, J=10.4, 5.7 Hz), 3.82 (1H, dd, J=10.2, 9.0 Hz), 3.98 (1H, dd, J=10.2, 3.9 Hz), 4.24 (1H, td, J=8.7, 3.9 Hz), 4.48-4.55 (1H, m), 4.86-4.96 (1H, m), 6.39 (1H, t, J=2.2 Hz), 6.45 (1H, d, J=3.9 Hz), 6.67 (1H, s), 6.71 (1H, s), 6.75 (1H, d, J=3.9 Hz).

(110d) {(4R,5S)-2-[5-(3-{[(2S)-1-Methoxypropan-2-yl]oxy}-5-{[5-(methylsulfonyl)pyrazin-2-yl]oxy}phenyl)-1H-pyrrol-2-yl]-5-methyl-4,5-dihydro-1,3-oxazol-4-yl}methanol (4R,5S)-2-[5-(3-{[(2S)-1-Methoxypropan-2-yl]oxy}-5-[(tripropan-2-ylsilyl)oxy]phenyl)-1H-pyrrol-2-yl]-5-methyl-4-{[(tripropan-2-ylsilyl)oxy]methyl}-4,5-dihydro-1,3-oxazole (2.30 g, 3.42 mmol) synthesized in Example (110c) was dissolved in tetrahydrofuran (20 mL), and tetrabutylammonium fluoride (1.0 mol/L tetrahydrofuran solution, 8.00 mL, 8.00 mmol) was added at room temperature, followed by stirring at room temperature for 30 minutes under nitrogen atmosphere. To this reaction solution, a saturated aqueous ammonium chloride solution (60 mL) was added, and extraction was carried out with methylene chloride (80 mL). The organic layer was washed with saturated brine, and subsequently dried over anhydrous magnesium sulfate. The solvent was distilled off under reduced pressure, and the resulting residue was purified using silica gel column chromatography (elution solvent: methanol/ethyl acetate=5%-10%) to afford a white solid (2.10 g).

1.20 g of the resulting compound was dissolved in acetonitrile (15 mL), and 2-chloro-5-(methylsulfonyl)pyrazine (410 mg, 2.13 mmol) synthesized in Example (97c) and potassium carbonate (0.85 g, 6.15 mmol) were added at 0° C., followed by stirring under nitrogen atmosphere at 0° C. for 5 hours, and further at room temperature for 3 hours. To this reaction solution, water (30 mL) was added, and extraction was carried out with methylene chloride (40 mL). The organic layer was washed with saturated brine, and subsequently dried over anhydrous magnesium sulfate. The solvent was distilled off under reduced pressure, and the resulting residue was purified using silica gel column chromatography (elution solvent: methanol/ethyl acetate=4%-6%) to afford the desired compound (964 mg, yield 95%) as a white solid.

$^1$H-NMR (CDCl$_3$, 400 MHz): δ 1.35 (3H, d, J=6.3 Hz), 1.40 (3H, d, J=6.3 Hz), 3.23 (3H, s), 3.41 (3H, s), 3.50 (1H, dd, J=10.2, 4.3 Hz), 3.60 (1H, dd, J=10.2, 5.9 Hz), 3.77 (1H, dd, J=11.5, 6.1 Hz), 3.85 (1H, dd, J=11.7, 3.5 Hz), 4.22-4.28 (1H, m), 4.54-4.60 (1H, m), 4.82-4.88 (1H, m), 6.45 (1H, d, J=3.5 Hz), 6.65 (1H, t, J=2.2 Hz), 6.67 (1H, d, J=2.3 Hz), 6.94 (1H, t, J=1.8 Hz), 7.10 (1H, t, J=1.8 Hz), 8.48 (1H, d, J=1.2 Hz), 8.80 (1H, d, J=1.2 Hz).

MS (ESI) m/z: 517.17452 (M+H)$^+$.

Example 111

(2S)-2-(3-{5-[(4R,5S)-4-(Hydroxymethyl)-5-methyl-4,5-dihydro-1,3-oxazol-2-yl)]-1H-pyrrol-2-yl}-5-{[5-(methylsulfonyl)pyrazin-2-yl]oxy}phenoxy)propan-1-ol

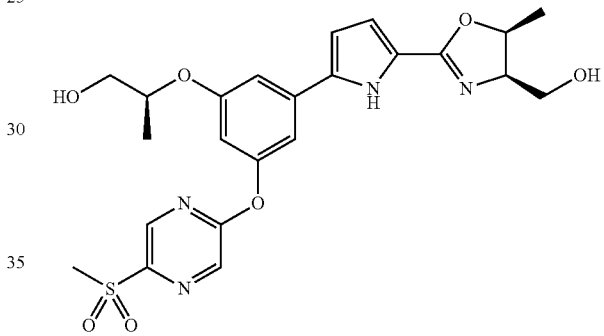

{(4R,5S)-2-[5-(3-{[(2S)-1-Methoxypropan-2-yl]oxy}-5-{[5-(methylsulfonyl)pyrazin-2-yl]oxy}phenyl)-1H-pyrrol-2-yl]-5-methyl-4,5-dihydro-1,3-oxazol-4-yl}methanol (209 mg, 0.40 mmol) synthesized in Example (110d) was dissolved in methylene chloride (5.0 mL), and boron tribromide (1.0 mol/L methylene chloride solution, 0.80 mL, 0.80 mmol) was added dropwise at −78° C., followed by stirring at room temperature for 40 minutes under nitrogen atmosphere. To this reaction solution, a 1N aqueous sodium hydroxide solution (10 mL) was added, and extraction was carried out with methylene chloride (20 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=4%-6%) to afford the desired compound (169 mg, yield 83%) as a white solid.

$^1$H-NMR (CDCl$_3$, 400 MHz): δ 1.31 (3H, d, J=6.3 Hz), 1.41 (3H, d, J=6.6 Hz), 3.23 (3H, s), 3.76 (2H, d, J=4.7 Hz), 3.70-3.80 (1H, m), 3.85 (1H, dd, J=11.7, 3.9 Hz), 4.21-4.25 (1H, m), 4.49-4.60 (1H, m), 4.82-4.89 (1H, m), 6.43 (1H, d, J=2.7 Hz), 6.59 (1H, s), 6.67 (1H, d, J=2.7 Hz), 6.95 (1H, s), 7.07 (1H, s), 8.47 (1H, s), 8.78 (1H, s).

MS (ESI) m/z: 503.15957 (M+H)$^+$.

Example 112

(1S)-1-{(4S)-2-[5-(3-{[(2S)-1-Methoxypropan-2-yl]oxy}-5-{[5-(methylsulfonyl)pyrazin-2-yl]oxy}phenyl)-1H-pyrrol-2-yl]-4,5-dihydro-1,3-oxazol-4-yl}ethanol

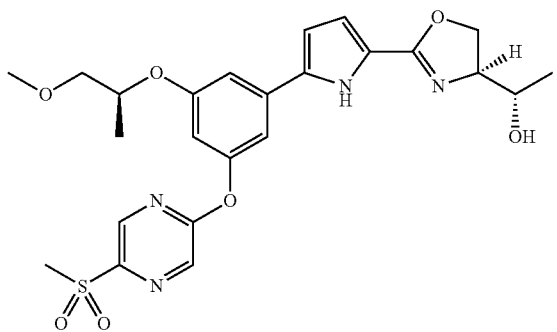

(112a) N-[(2S,3S)-1,3-Dihydroxybutan-2-yl]-5-(3-{[(2S)-1-methoxypropan-2-yl]oxy}-5-[(tripropan-2-ylsilyl)oxy]phenyl)-1H-pyrrole-2-carboxamide 5-{3-[(1S)-2-Methoxy-1-methylethoxy]-5-[(triisopropylsilyl)oxy]phenyl}-1H-pyrrole-2-carboxylic acid (1.75 g, 3.91 mmol) synthesized in Example (106c) was dissolved in methanol (30 mL), and D-threoninol (1.00 g, 9.51 mmol) and 4-(4,6-dimethoxy-1,3,5-triazin-2-yl)-4-methylmorpholinium chloride n hydrate (2.85 g, 10.30 mmol) were added, followed by stirring at room temperature for 5 days under nitrogen atmosphere. After the solvent was distilled off under reduced pressure, a saturated aqueous ammonium chloride solution (50 mL) was added, and extraction was carried out with methylene chloride (80 mL). The organic layer was washed with saturated brine, and subsequently dried over anhydrous magnesium sulfate. The resulting residue was purified using silica gel column chromatography (elution solvent: methanol/methylene chloride=3%-7%) to afford the desired compound (1.76 g, yield 84%) as a white solid.

$^1$H-NMR (CDCl$_3$, 400 MHz): δ 1.08 (18H, d, J=7.4 Hz), 1.18-1.25 (6H, m), 1.27 (3H, d, J=6.3 Hz), 2.83 (2H, br s), 3.38 (3H, s), 3.45 (1H, dd, J=10.2, 4.3 Hz), 3.55 (1H, dd, J=10.2, 5.9 Hz), 3.87 (2H, s), 3.94-4.01 (2H, m), 4.22 (1H, br s), 4.46-4.52 (1H, m), 6.37 (1H, br s), 6.40-6.43 (1H, m), 6.59-6.66 (3H, m), 6.70 (1H, s), 9.78 (1H, br s).

(112b) (1S)-1-{(4S)-2-[5-(3-{[(2S)-1-Methoxypropan-2-yl]oxy}-5-[(tripropan-2-ylsilyl)oxy]phenyl)-1H-pyrrol-2-yl]-4,5-dihydro-1,3-oxazol-4-yl}ethanol N-[(2S,3S)-1,3-Dihydroxybutan-2-yl]-5-(3-{[(2S)-1-methoxypropan-2-yl]oxy}-5-[(tripropan-2-ylsilyl)oxy]phenyl)-1H-pyrrole-2-carboxamide (1.76 g, 3.29 mmol) synthesized in Example (112a) was dissolved in tetrahydrofuran (20 mL), and anhydrous methanesulfonic acid (0.54 g, 3.10 mmol) and triethylamine (1.00 mL, 7.17 mmol) were added at −40° C., followed by stirring at the same temperature for 4 hours under nitrogen atmosphere, and then at 50° C. overnight. To the reaction solution, a saturated aqueous ammonium chloride solution (50 mL) was added, and extraction was carried out with methylene chloride (50 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=2%-5%) to afford the desired compound (880 mg, yield 52%) as a white foam.

$^1$H-NMR (CDCl$_3$, 400 MHz): δ 1.12 (18H, d, J=7.0 Hz), 1.22-1.30 (6H, m), 1.32 (3H, d, J=6.3 Hz), 3.42 (3H, s), 3.48 (1H, dd, J=10.2, 4.3 Hz), 3.59 (1H, dd, J=10.2, 5.9 Hz), 3.69-3.75 (1H, m), 4.10-4.20 (2H, m), 4.45 (1H, br s), 4.53 (1H, br s), 6.40 (1H, t, J=1.6 Hz), 6.47 (1H, d, J=3.9 Hz), 6.70 (1H, s), 6.75 (1H, s), 6.77 (1H, d, J=3.9 Hz).

(112c) 3-(5-{(4S)-4-[(1S)-1-Hydroxyethyl]-4,5-dihydro-1,3-oxazol-2-yl}-1H-pyrrol-2-yl)-5-{[(2S)-1-methoxypropan-2-yl]oxy}phenol (1S)-1-{(4S)-2-[5-(3-{[(2S)-1-Methoxypropan-2-yl]oxy}-5-[(tripropan-2-ylsilyl)oxy]phenyl)-1H-pyrrol-2-yl]-4,5-dihydro-1,3-oxazol-4-yl}ethanol (1.48 g, 2.88 mmol) synthesized in Example (112b) was dissolved in tetrahydrofuran (20 mL), and tetrabutylammonium fluoride (1.0 mol/L tetrahydrofuran solution, 3.50 mL, 3.50 mmol) was added at room temperature, followed by stirring at room temperature for 1.5 hours under nitrogen atmosphere. To this reaction solution, a saturated aqueous ammonium chloride solution (50 mL) was added, and extraction was carried out with methylene chloride (50 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=3%-6%) to afford the desired compound (880 mg, yield 85%) as a white solid.

$^1$H-NMR (CDCl$_3$, 400 MHz): δ 1.32 (3H, d, J=6.3 Hz), 1.37 (3H, d, J=6.3 Hz), 3.42 (3H, s), 3.46 (1H, dd, J=10.2, 4.7 Hz), 3.61 (1H, dd, J=10.0, 5.7 Hz), 3.85-3.92 (1H, m), 4.25-4.36 (2H, m), 4.49-4.56 (2H, m), 6.48 (1H, d, J=3.9 Hz), 6.54 (1H, t, J=2.0 Hz), 6.73 (1H, t, J=1.8 Hz), 6.79 (1H, d, J=3.5 Hz), 7.06 (1H, s).

(112d) (1S)-1-{(4S)-2-[5-(3-{[(2S)-1-Methoxypropan-2-yl]oxy}-5-{[5-(methylsulfonyl)pyrazin-2-yl]oxy}phenyl)-1H-pyrrol-2-yl]-4,5-dihydro-1,3-oxazol-4-yl}ethanol 3-(5-{(4S)-4-[(1S)-1-Hydroxyethyl]-4,5-dihydro-1,3-oxazol-2-yl}-1H-pyrrol-2-yl)-5-{[(2S)-1-methoxypropan-2-yl]oxy}phenol (880 mg, 2.44 mmol) synthesized in Example (112c) was dissolved in acetonitrile (20 mL), and 2-chloro-5-(methylsulfonyl)pyrazine (630 mg, 3.27 mmol) synthesized in Example (97c) and potassium carbonate (1.20 g, 8.68 mmol) were added, followed by stirring at room temperature for 4 hours under nitrogen atmosphere. Water (50 mL) was added, and extraction was carried out with methylene chloride (50 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=1%-3%) to afford the desired compound (1.00 g, yield 79%) as a white solid.

$^1$H-NMR (CDCl$_3$, 400 MHz): δ 1.28 (3H, d, J=6.3 Hz), 1.35 (3H, d, J=6.3 Hz), 3.23 (3H, s), 3.41 (3H, s), 3.51 (1H, dd, J=10.2, 4.3 Hz), 3.60 (1H, dd, J=10.2, 6.3 Hz), 3.73 (1H, br s), 4.11-4.22 (2H, m), 4.46 (1H, br s), 4.60 (1H, br s), 6.52 (1H, d, J=3.9 Hz), 6.67 (1H, t, J=2.0 Hz), 6.78 (1H, d, J=3.9 Hz), 6.96 (1H, s), 7.12 (1H, s), 8.49 (1H, s), 8.81 (1H, s).

MS (ESI) m/z: 517.17608 (M+H)$^+$.

Example 113

(2S)-2-[3-(5-{(4S)-4-[(1S)-1-Hydroxyethyl]-4,5-dihydro-1,3-oxazol-2-yl}-1H-pyrrol-2-yl)-5-{[5-(methylsulfonyl)pyrazin-2-yl]oxy}phenoxy]propan-1-ol

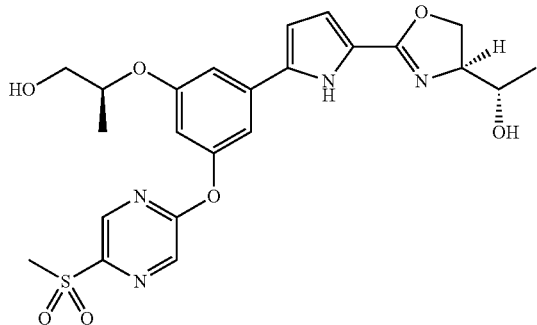

(1S)-1-{(4S)-2-[5-(3-{[(2S)-1-Methoxypropan-2-yl]oxy}-5-{[5-(methylsulfonyl)pyrazin-2-yl]oxy}phenyl)-1H-pyrrol-2-yl]-4,5-dihydro-1,3-oxazol-4-yl}ethanol (204 mg, 0.395 mmol) synthesized in Example (112d) was dissolved in methylene chloride (5.0 mL), and boron tribromide (1.0 mol/L methylene chloride solution, 0.80 mL, 0.80 mmol) was added dropwise at −78° C., followed by stirring at room temperature for 1.5 hours under nitrogen atmosphere. To this reaction solution, a 1N aqueous sodium hydroxide solution (10 mL) was added, and extraction was carried out with methylene chloride (20 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=3%-5%) to afford the desired compound (159 mg, yield 80%) as a white solid.

$^1$H-NMR (CDCl$_3$, 400 MHz): δ 1.28 (3H, d, J=6.3 Hz), 1.32 (3H, d, J=6.3 Hz), 3.24 (3H, s), 3.73-3.78 (3H, m), 4.12-4.23 (2H, m), 4.46 (1H, br s), 4.52-4.59 (1H, m), 6.50 (1H, d, J=3.9 Hz), 6.62 (1H, t, J=2.0 Hz), 6.76 (1H, d, J=3.9 Hz), 6.94 (1H, t, J=1.8 Hz), 7.08 (1H, s), 8.49 (1H, d, J=1.2 Hz), 8.80 (1H, d, J=1.2 Hz).

MS (ESI) m/z: 503.15930 (M+H)$^+$.

Example 114

(1R)-1-{(4S)-2-[5-(3-{[(2S)-1-Methoxypropan-2-yl]oxy}-5-{[5-(methylsulfonyl)pyrazin-2-yl]oxy}phenyl)-1H-pyrrol-2-yl]-4,5-dihydro-1,3-oxazol-4-yl}ethanol

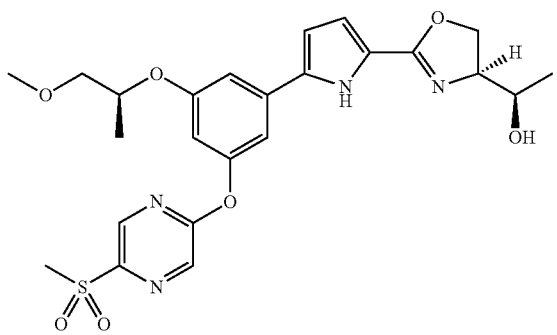

(114a) N-[(2S,3R)-1,3-Dihydroxybutan-2-yl]-5-(3-{[(2S)-1-methoxypropan-2-yl]oxy}-5-[(tripropan-2-ylsilyl)oxy]phenyl)-1H-pyrrole-2-carboxamide 5-{3-[(1S)-2-Methoxy-1-methylethoxy]-5-[(triisopropylsilyl)oxy]phenyl}-1H-pyrrole-2-carboxylic acid (1.63 g, 3.64 mmol) synthesized in Example (106c) was dissolved in methanol (20 mL), and D-allo-threoninol (1.05 g, 9.99 mmol) and 4-(4,6-dimethoxy-1,3,5-triazin-2-yl)-4-methylmorpholinium chloride n hydrate (2.00 g, 7.23 mmol) were added, followed by stirring at room temperature for 1 day under nitrogen atmosphere. After the solvent was distilled off under reduced pressure, a saturated aqueous ammonium chloride solution (50 mL) was added, and extraction was carried out with methylene chloride (80 mL). The organic layer was washed with saturated brine, and subsequently dried over anhydrous magnesium sulfate. The resulting residue was purified using silica gel column chromatography (elution solvent: methanol/methylene chloride=3%-7%) to afford the desired compound (1.70 g, yield 87%) as a white foam.

$^1$H-NMR (CDCl$_3$, 400 MHz): δ 1.07 (18H, d, J=7.0 Hz), 1.17-1.27 (9H, m), 2.01 (1H, br s), 3.37 (3H, s), 3.44 (1H, dd, J=10.0, 4.1 Hz), 3.44 (1H, s), 3.53 (1H, dd, J=10.4, 6.1 Hz), 3.72-3.78 (1H, m), 3.88-3.93 (1H, m), 3.93-3.95 (1H, m), 3.96-4.04 (2H, m), 4.44-4.52 (1H, m), 6.35 (1H, t, J=2.0 Hz), 6.39 (1H, t, J=3.1 Hz), 6.67 (1H, t, J=1.8 Hz), 6.70 (1H, s), 6.72 (1H, s), 6.99 (1H, d, J=7.8 Hz), 10.34 (1H, br s).

(114b) (1R)-1-{(4S)-2-[5-(3-{[(2S)-1-Methoxypropan-2-yl]oxy}-5-[(tripropan-2-ylsilyl)oxy]phenyl)-1H-pyrrol-2-yl]-4,5-dihydro-1,3-oxazol-4-yl}ethanol N-[(2S,3R)-1,3-Dihydroxybutan-2-yl]-5-(3-{[(2S)-1-methoxypropan-2-yl]oxy}-5-[(tripropan-2-ylsilyl)oxy]phenyl)-1H-pyrrole-2-carboxamide (1.70 g, 3.18 mmol) synthesized in Example (114a) was dissolved in tetrahydrofuran (20 mL), and anhydrous methanesulfonic acid (0.78 g, 4.48 mmol) and triethylamine (1.50 mL, 10.76 mmol) were added at 0° C., followed by stirring at the same temperature for 1.5 hours under nitrogen atmosphere, followed by stirring at 50° C. overnight. To the reaction solution, a saturated aqueous ammonium chloride solution (50 mL) was added, and extraction was carried out with methylene chloride (50 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=2%-4%) to afford the desired compound (1.30 g, yield 79%) as a white foam.

$^1$H-NMR (CDCl$_3$, 400 MHz): δ 1.10-1.14 (18H, m), 1.20 (3H, d, J=6.6 Hz), 1.23-1.32 (3H, m), 1.34 (3H, d, J=6.3 Hz), 3.41 (3H, s), 3.48 (1H, dd, J=10.2, 4.3 Hz), 3.59 (1H, dd, J=10.2, 5.9 Hz), 4.20-4.34 (4H, m), 4.53 (1H, br s), 6.33 (1H, d, J=3.9 Hz), 6.40 (1H, t, J=2.0 Hz), 6.44 (1H, br s), 6.74 (1H, t, J=1.8 Hz), 6.78 (1H, t, J=1.8 Hz).

(114c) 3-(5-{(4S)-4-[(1R)-1-Hydroxyethyl]-4,5-dihydro-1,3-oxazol-2-yl}-1H-pyrrol-2-yl)-5-{[(2S)-1-methoxypropan-2-yl]oxy}phenol (1R)-1-{(4S)-2-[5-(3-{[(2S)-1-Methoxypropan-2-yl]oxy}-5-[(tripropan-2-ylsilyl)oxy]phenyl)-1H-pyrrol-2-yl]-4,5-dihydro-1,3-oxazol-4-yl}ethanol (1.30 g, 2.52 mmol) synthesized in Example (114b) was dissolved in tetrahydrofuran (15 mL), and tetrabutylammonium fluoride (1.0 mol/L tetrahydrofuran solution, 4.00 mL, 4.00 mmol) was added at room temperature, followed by stirring at room temperature for 1 hour under nitrogen atmosphere. To this reaction solution, a saturated aqueous ammonium chloride solution (50 mL) was added, and extraction was carried out with methylene chloride (50 mL). The organic layer was washed with saturated brine, and subsequently dried over anhydrous magnesium sulfate. The solvent was distilled off under reduced pressure, and the resulting residue was purified using silica gel column chromatography (elution solvent: methanol/ethyl acetate=8%-12%) to afford the desired compound (766 mg, yield 85%) as a white foam.

$^1$H-NMR (CDCl$_3$, 400 MHz): δ 1.31 (6H, d, J=6.3 Hz), 3.28 (1H, br s), 3.42 (3H, s), 3.47 (1H, dd, J=10.2, 4.3 Hz), 3.61 (1H, dd, J=10.2, 5.9 Hz), 4.23 (1H, br s), 4.35-4.43 (1H, m), 4.47-4.56 (3H, m), 6.46-6.49 (2H, m), 6.72 (1H, s), 6.78 (1H, d, J=3.5 Hz), 7.04 (1H, t, J=1.8 Hz), 11.07 (1H, s).

(114d) (1R)-1-{(4S)-2-[5-(3-{[(2S)-1-Methoxypropan-2-yl]oxy}-5-{[5-(methylsulfonyl)pyrazin-2-yl]oxy}phenyl)-1H-pyrrol-2-yl]-4,5-dihydro-1,3-oxazol-4-yl}ethanol 3-(5-{(4S)-4-[(1R)-1-Hydroxyethyl]-4,5-dihydro-1,3-oxazol-2-yl}-1H-pyrrol-2-yl)-5-{[(2S)-1-methoxypropan-2-yl]oxy}phenol (766 mg, 2.13 mmol) synthesized in Example (114c) was dissolved in acetonitrile (15 mL), and 2-chloro-5-(methylsulfonyl)pyrazine (590 mg, 3.06 mmol) synthesized in Example (97c) and potassium carbonate (870 mg, 6.29 mmol) were added, followed by stirring at room temperature for 4 hours under nitrogen atmosphere. Water (50 mL) was added, and extraction was carried out with methylene chloride (50 mL). The organic layer was washed with saturated brine, and subsequently dried over anhydrous magnesium sulfate. The solvent was distilled off under reduced pressure, and the resulting residue was purified using silica gel column chromatography (elution solvent: methanol/ethyl acetate=5%-8%) to afford the desired compound (890 mg, yield 81%) as a white solid.

$^1$H-NMR (CDCl$_3$, 400 MHz): δ 1.17 (3H, d, J=6.6 Hz), 1.36 (3H, d, J=6.3 Hz), 3.23 (3H, s), 3.42 (3H, s), 3.51 (1H, dd, J=10.4, 4.1 Hz), 3.60 (1H, dd, J=10.2, 5.9 Hz), 4.10-4.26 (2H, m), 4.28-4.35 (2H, m), 4.58 (1H, br s), 6.42 (1H, d, J=3.9 Hz), 6.56 (1H, d, J=3.5 Hz), 6.66 (1H, t, J=2.2 Hz), 6.96 (1H, d, J=1.6 Hz), 7.11 (1H, s), 8.49 (1H, d, J=1.2 Hz), 8.81 (1H, d, J=1.2 Hz).

MS (ESI) m/z: 517.17565 (M+H)$^+$.

Example 115

(2S)-2-[3-(5-{(4S)-4-[(1R)-1-Hydroxyethyl]-4,5-dihydro-1,3-oxazol-2-yl}-1H-pyrrol-2-yl)-5-{[5-(methylsulfonyl)pyrazin-2-yl]oxy}phenoxy]propan-1-ol

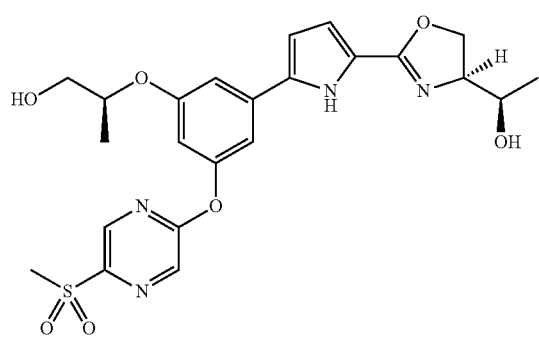

(1R)-1-{(4S)-2-[5-(3-{[(2S)-1-Methoxypropan-2-yl]oxy}-5-{[5-(methylsulfonyl)pyrazin-2-yl]oxy}phenyl)-1H-pyrrol-2-yl]-4,5-dihydro-1,3-oxazol-4-yl}ethanol (213 mg, 0.412 mmol) synthesized in Example (114d) was dissolved in methylene chloride (5.0 mL), and boron tribromide (1.0 mol/L methylene chloride solution, 0.80 mL, 0.80 mmol) was added dropwise at −78° C., followed by stirring at room temperature for 1.5 hours under nitrogen atmosphere. To this reaction solution, a saturated aqueous sodium hydrogencarbonate solution (10 mL) was added, and extraction was carried out with methylene chloride (20 mL). The organic layer was washed with 1N aqueous sodium hydroxide solution (10 mL), and subsequently dried over anhydrous magnesium sulfate. The solvent was distilled off under reduced pressure, and the resulting residue was purified using silica gel column chromatography (elution solvent: methanol/methylene chloride=4%-5%) to afford the desired compound (147 mg, yield 71%) as a white solid.

$^1$H-NMR (CDCl$_3$, 400 MHz): δ 1.18 (3H, d, J=6.3 Hz), 1.33 (3H, d, J=6.3 Hz), 1.61 (2H, br s), 3.23 (3H, s), 3.73-3.82 (2H, m), 4.16-4.26 (2H, m), 4.30-4.36 (2H, m), 4.54-4.61 (1H, m), 6.39 (1H, d, J=3.9 Hz), 6.53 (1H, d, J=3.5 Hz), 6.61 (1H, s), 6.95 (1H, s), 7.07 (1H, s), 8.48 (1H, d, J=1.2 Hz), 8.80 (1H, d, J=1.6 Hz).

MS (ESI) m/z: 503.15973 (M+H)$^+$.

Example 116

1-{[4-(3-[(1S)-2-Methoxy-1-methylethoxy]-5-{5-[(5S)-5-methyl-4,5-dihydro-1,3-oxazol-2-yl]-1H-pyrrol-2-yl}phenoxy)phenyl]sulfonyl}-4-methylpiperazine

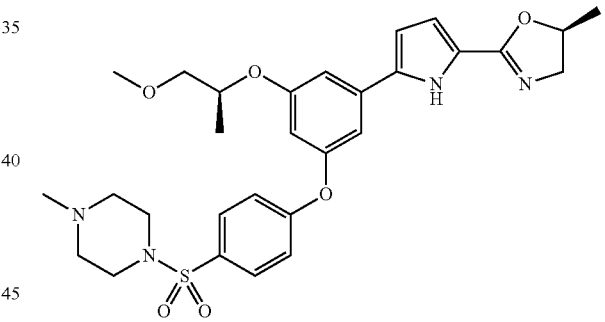

(116a)
1-[(4-Fluorophenypsulfonyl]-4-methylpiperazine

Commercially available 4-fluorobenzenesulfonyl chloride (1.00 g, 5.14 mmol) was suspended in water (15 mL), and N-methylpiperazine (0.68 mL, 6.17 mmol) and potassium carbonate (1.56 g, 11.3 mmol) were added, followed by stirring at room temperature for 14 hours under nitrogen atmosphere. To the reaction solution, water (50 mL) was added, followed by extraction with ethyl acetate (50 mL), and subsequently the organic layer was washed with saturated brine and dried over anhydrous magnesium sulfate. The solvent was distilled off under reduced pressure, and the resulting residue was purified using silica gel column chromatography (elution solvent: ethyl acetate/hexane=50%-90%) to afford the desired compound (491 mg, yield 37%) as a white solid.

$^1$H-NMR (CDCl$_3$, 400 MHz): δ 2.28 (3H, s), 2.49 (4H, t, J=4.9 Hz), 3.04 (4H, br s), 7.21 (2H, dd, J=9.4, 7.8 Hz), 7.76-7.79 (2H, m).

(116b) N-[(2R)-2-Hydroxypropyl]-5-{3-[(1S)-2-methoxy-1-methylethoxy]-5-[(triisopropylsilyl)oxy]phenyl}-1H-pyrrole-2-carboxamide 5-{3-[(1S)-2-Methoxy-1-methylethoxy]-5-[(triisopropylsilyl)oxy]phenyl}-1H-pyrrole-2-carboxylic acid (51.4 g, 115 mmol) synthesized in Example (106c) was dissolved in methanol (600 mL), and (R)-(−)-1-amino-2-propanol (19.9 mL, 253 mmol) and 4-(4,6-dimethoxy-1,3,5-triazin-2-yl)-4-methylmorpholinium chloride n hydrate (63.7 g, 230 mmol) were added, followed by stirring for 15 hours under nitrogen atmosphere. The solvent was distilled off under reduced pressure, and water (500 mL) was added, followed by extraction twice with ethyl acetate (500 mL). Subsequently, the organic layer was washed with saturated brine and dried over anhydrous magnesium sulfate. The solvent was distilled off under reduced pressure, and the resulting residue was purified using silica gel column chromatography (elution solvent: ethyl acetate/hexane=25%-67%) to afford the desired compound (48.7 g, yield 84%) as a white solid.

$^1$H-NMR (CDCl$_3$, 400 MHz): δ 1.12 (18H, d, J=7.8 Hz), 1.27 (3H, q, J=8.3 Hz), 1.32 (3H, d, J=6.3 Hz), 2.60 (1H, s), 3.27-3.33 (1H, m), 3.42 (3H, s), 3.49 (1H, dd, J=10.3, 4.4 Hz), 3.56-3.65 (2H, m), 4.03 (1H, s), 4.53 (1H, td, J=6.1, 4.4 Hz), 6.31 (1H, br s), 6.41 (1H, t, J=2.2 Hz), 6.46 (1H, t, J=3.2 Hz), 6.61 (1H, t, J=3.2 Hz), 6.67 (1H, t, J=1.7 Hz), 6.73 (1H, t, J=2.0 Hz), 9.51 (1H, br s).

(116c) (5S)-2-(5-{3-[(1S)-2-Methoxy-1-methylethoxy]-5-[(triisopropylsilyl)oxy]phenyl}-1H-pyrrol-2-yl)-5-methyl-4,5-dihydro-1,3-oxazole N-[(2R)-2-hydroxypropyl]-5-{3-[(1S)-2-methoxy-1-methylethoxy]-5-[(triisopropylsilyl)oxy]phenyl}-1H-pyrrole-2-carboxamide (48.7 g, 96.5 mmol) synthesized in Example (116b) was dissolved in tetrahydrofuran (600 mL), and anhydrous methanesulfonic acid (33.6 g, 193 mmol) and triethylamine (40.4 mL, 289 mmol) were added, followed by stirring at 50° C. for 3 hours under nitrogen atmosphere. To the reaction solution, a saturated aqueous ammonium chloride solution (500 mL) was added, and extraction was carried out twice with ethyl acetate (500 mL). The organic layer was washed with saturated brine, and subsequently dried over anhydrous magnesium sulfate. The solvent was distilled off under reduced pressure, diisopropylether (300 mL) was added to the resulting residue, and the slurry was stirred to give a white solid, which was filtered off. Under reduced pressure, the solvent in the mother liquor was distilled off, and the resulting residue was purified using silica gel column chromatography (elution solvent: ethyl acetate/hexane=10%-50%). This was vacuum-dried together with the filtered product to afford the desired compound (34.8 g, yield 74%) as a white solid.

$^1$H-NMR (CDCl$_3$, 400 MHz): δ 1.11 (18H, d, J=7.8 Hz), 1.25-1.34 (3H, m), 1.38 (3H, d, J=6.3 Hz), 1.65 (3H, d, J=5.9 Hz), 3.43 (3H, s), 3.58-3.65 (2H, m), 3.76 (1H, dd, J=10.9, 7.8 Hz), 4.28 (1H, dd, J=11.3, 9.8 Hz), 4.81-4.87 (1H, m), 5.28-5.37 (1H, m), 6.51 (1H, t, J=2.2 Hz), 6.62 (1H, d, J=2.0 Hz), 6.91 (1H, s), 7.19 (1H, s), 7.35 (1H, s).

(116d) 3-[(1S)-2-Methoxy-1-methylethoxy]-5-{5-[(5S)-5-methyl-4,5-dihydro-1,3-oxazol-2-yl]-1H-pyrrol-2-yl}phenol (5S)-2-(5-{3-[(1S)-2-Methoxy-1-methylethoxy]-5-[(triisopropylsilyl)oxy]phenyl}-1H-pyrrol-2-yl)-5-methyl-4,5-dihydro-1,3-oxazole (29.5 g, 60.7 mmol) synthesized in Example (116c) was dissolved in tetrahydrofuran (400 mL), and tetrabutylammonium fluoride (1.0 mol/L tetrahydrofuran solution, 66 mL, 66 mmol) was added, followed by stirring for 1 hour under nitrogen atmosphere. The solvent was distilled off under reduced pressure, water (400 mL) was added to the residue, and extraction was carried out twice with ethyl acetate (400 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=10%-50%) to afford the desired compound (16.7 g, yield 83%) as a white solid.

$^1$H-NMR (CDCl$_3$, 400 MHz): δ 1.33 (3H, d, J=6.3 Hz), 1.49 (4H, d, J=6.3 Hz), 3.42 (3H, s), 3.49 (1H, dd, J=10.2, 4.7 Hz), 3.59 (1H, dd, J=10.2, 5.5 Hz), 3.68 (1H, dd, J=13.3, 7.4 Hz), 4.22 (1H, dd, J=13.5, 9.2 Hz), 4.52-4.57 (1H, m), 4.97-4.88 (1H, m), 6.34 (1H, t, J=2.0 Hz), 6.47 (1H, d, J=3.5 Hz), 6.72 (1H, s), 6.76 (1H, d, J=3.5 Hz), 7.10 (1H, s).

(116e) 1-{[4-(3-[(1S)-2-Methoxy-1-methylethoxy]-5-{5-[(5S)-5-methyl-4,5-dihydro-1,3-oxazol-2-yl]-1H-pyrrol-2-yl}phenoxy)phenyl]sulfonyl}-4-methylpiperazine 3-[(1S)-2-Methoxy-1-methylethoxy]-5-{5-[(5S)-5-methyl-4,5-dihydro-1,3-oxazol-2-yl]-1H-pyrrol-2-yl}phenol (40 mg, 0.12 mmol) synthesized in Example (116d) and 1-[(4-fluorophenyl)sulfonyl]-4-methylpiperazine (25 mg, 0.15 mmol) synthesized in Example (116a) were dissolved in N,N-dimethylformamide (2 mL), and potassium carbonate (51 mg, 0.37 mmol) was added, followed by stirring at 100° C. for 1 hour under nitrogen atmosphere. 1-[(4-Fluorophenyl)sulfonyl]-4-methylpiperazine (30 mg) was added again, and the mixture was stirred at 90° C. overnight. The reaction solution was cooled to room temperature, water (10 mL) was added, and extraction was carried out twice with ethyl acetate (10 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=0%-5%) to afford the desired compound (25 mg, yield 35%) as a white solid.

$^1$H-NMR (CDCl$_3$, 400 MHz): δ 1.34 (3H, d, J=5.9 Hz), 1.43 (3H, d, J=6.3 Hz), 2.29 (3H, s), 2.50 (4H, br s), 3.06 (4H, br s), 3.43 (3H, d, J=2.4 Hz), 3.50-3.61 (3H, m), 4.10 (1H, dd, J=14.2, 9.3 Hz), 4.58 (1H, dd, J=10.5, 6.1 Hz), 4.82-4.86 (1H, m), 6.52 (1H, d, J=3.4 Hz), 6.55 (1H, t, J=2.2 Hz), 6.77 (1H, d, J=3.9 Hz), 6.84 (1H, d, J=2.0 Hz), 6.98 (1H, s), 7.09 (2H, d, J=6.8 Hz), 7.71 (2H, d, J=9.3 Hz).

MS (FAB) m/z: 569.2418 (M+H)$^+$.

Example 117

(2S)-2-(3-{5-[(5S)-5-Methyl-4,5-dihydro-1,3-oxazol-2-yl]-1H-pyrrol-2-yl}-5-{4-[(4-methylpiperazin-1-yl)sulfonyl]phenoxy}phenoxy)propan-1-ol

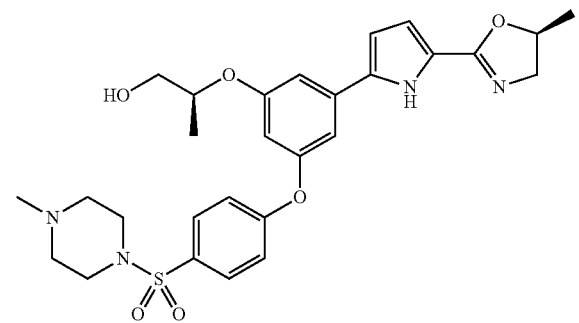

(117a) 3-[(1S)-2-Hydroxy-1-methylethoxy]-5-{5-[(5S)-5-methyl-4,5-dihydro-1,3-oxazol-2-yl]-1H-pyrrol-2-yl}phenol 3-[(1S)-2-Methoxy-1-methylethoxy]-5-{5-[(5S)-5-methyl-4,5-dihydro-1,3-oxazol-2-yl]-1H-pyrrol-2-yl}phenol (60 mg, 0.18 mmol) synthesized in Example (116d) was dissolved in methylene chloride (4 mL), and boron tribromide (1.0 mol/L methylene chloride solution, 0.38 mL, 0.38 mmol) was added at −78° C. under nitrogen atmosphere. Subsequently, the temperature was brought back to room temperature, followed by stirring for 1 hour. To the reaction solution, a saturated aqueous sodium hydrogencarbonate solution was added, and extraction was carried out with ethyl acetate. The organic layer was washed with saturated brine, and subsequently dried over sodium sulfate. The solvent was distilled off under reduced pressure, and the resulting residue was purified using silica gel column chromatography (elution solvent: hexane/ethyl acetate=50%-70%) to afford the desired compound (41 mg, yield 72%) as a white solid.

$^1$H-NMR (CDCl$_3$, 400 MHz) δ 1.29 (3H, d, J=6.3 Hz), 1.49 (3H, d, J=5.9 Hz), 3.66-3.78 (3H, m), 4.23 (1H, dd, J=13.7, 9.3 Hz), 4.52 (1H, ddd, J=14.4, 8.1, 4.6 Hz), 4.93 (1H, dq, J=17.7, 5.0 Hz), 6.32 (1H, t, J=2.0 Hz), 6.48 (1H, d, J=3.9 Hz), 6.71 (1H, s), 6.77 (1H, d, J=3.4 Hz), 7.11 (1H, s), 11.09 (1H, s).

(117b) (2S)-2-(3-{5-[(5S)-5-Methyl-4,5-dihydro-1,3-oxazol-2-yl]-1H-pyrrol-2-yl}-5-{4-[(4-methylpiperazin-1-yl)sulfonyl]phenoxy}phenoxy)propan-1-ol 3-[(1S)-2-Hydroxy-1-methylethoxy]-5-{5-[(5S)-5-methyl-4,5-dihydro-1,3-oxazol-2-yl]-1H-pyrrol-2-yl}phenol (40 mg, 0.13 mmol) synthesized in Example (117a) and 1-[(4-fluorophenyl)sulfonyl]-4-methylpiperazine (49 mg, 0.19 mmol) synthesized in Example (116a) were dissolved in N,N-dimethylformamide (2 mL), and potassium carbonate (52 mg, 0.38 mmol) was added, followed by stirring at 100° C. for 4 hours under nitrogen atmosphere. The reaction solution was cooled to room temperature, water (10 mL) was added, and extraction was carried out twice with ethyl acetate (10 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=0%-5%) to afford the desired compound (17 mg, yield 25%) as a white solid.

$^1$H-NMR (CDCl$_3$, 400 MHz): δ 1.29 (3H, d, J=6.3 Hz), 1.43 (3H, d, J=6.3 Hz), 2.28 (3H, s), 2.48-2.51 (4H, br m), 3.03 (4H, br s), 3.55 (1H, dd, J=13.9, 7.2 Hz), 3.77 (2H, d, J=5.1 Hz), 4.09 (1H, dd, J=14.1, 9.4 Hz), 4.55-4.60 (1H, m), 4.87-4.81 (1H, m), 6.42 (1H, s), 6.50 (1H, d, J=3.9 Hz), 6.76 (1H, d, J=3.5 Hz), 6.83 (1H, s), 6.95 (1H, s), 7.07 (2H, d, J=8.6 Hz), 7.70 (2H, d, J=8.6 Hz).

MS (FAB) m/z: 555.2271 (M+H)$^+$.

Example 118

(2S)-2-(3-{5-[(5S)-5-Methyl-4,5-dihydro-1,3-oxazol-2-yl]-1H-pyrrol-2-yl}-5-{[6-(methylsulfonyl)pyridazin-3-yl]oxy}phenoxy)propan-1-ol

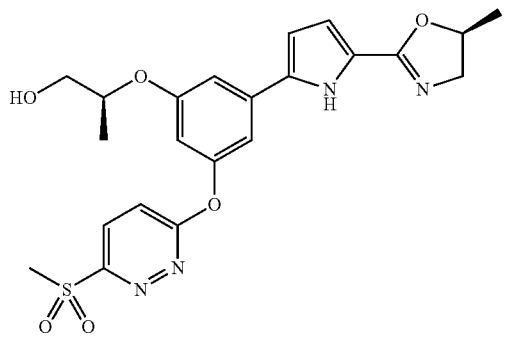

(118a) 6-Chloropyridazine-3-thiol

Under nitrogen atmosphere, dichloropyridazine (1.00 g, 6.71 mmol) was dissolved in methanol (20 mL), and 10-20% aqueous potassium hydrogen sulfide solution (20 mL) was added, followed by heating to reflux for 2 hours. The solvent was distilled off under reduced pressure, and the residue was diluted with water, followed by neutralization with 1N hydrochloric acid. The resulting yellow precipitate was filtered off, washed with water and hexane, and subsequently vacuum-dried to afford the desired compound (500 mg, yield 51%) as a yellow solid.

$^1$H-NMR (CDCl$_3$, 400 MHz) δ 7.00 (1H, d, J=9.4 Hz), 7.60 (1H, d, J=9.4 Hz), 11.68 (1H, br s).

(118b) 3-Chloro-6-(methylthio)pyridazine

6-Chloropyridazine-3-thiol (500 mg, 3.41 mmol) synthesized in Example (118a) was dissolved in methanol (20 mL), and sodium methoxide (203 mg, 3.75 mmol) and iodomethane (234 mL, 3.75 mmol) were added, followed by stirring at 60° C. for 30 minutes under nitrogen atmosphere. The reaction solution was cooled to room temperature, water (50 mL) was added, and extraction was carried out twice with ethyl acetate (50 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=10%-50%) to afford the desired compound (515 mg, yield 94%) as a yellow solid.

$^1$H-NMR (CDCl$_3$, 400 MHz): δ 2.71 (3H, s), 7.25 (1H, d, J=9.6 Hz), 7.30 (1H, d, J=9.0 Hz).

(118c) 3-Chloro-6-(methylsulfonyl)pyridazine

3-Chloro-6-(methylthio)pyridazine (90 mg, 0.50 mmol) synthesized in Example (118b) was dissolved in methylene chloride (10 mL), and m-chloroperbenzoic acid (220 mg, 1.00 mmol) was added, followed by stirring at 0° C. for 30 minutes under nitrogen atmosphere. Water (20 mL) was added to the reaction solution, and extraction was carried out twice with methylene chloride (10 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=10%-100%) to afford the desired compound (77 mg, yield 71%) as a white solid.

$^1$H-NMR (CDCl$_3$, 400 MHz): δ 3.45 (3H, s), 7.81 (1H, d, J=8.2 Hz), 8.16 (1H, d, J=8.4 Hz).

(118d) 3-(3-[(1S)-2-Methoxy-1-methylethoxy]-5-{5-[(5S)-5-methyl-4,5-dihydro-1,3-oxazol-2-yl]-1H-pyrrol-2-yl}phenoxy)-6-(methylsulfonyl)pyridazine 3-Chloro-6-(methylsulfonyl)pyridazine (41 mg, 0.27 mmol) synthesized in Example (118c) and 3-[(1S)-2-methoxy-1-methylethoxy]-5-{5-[(5S)-5-methyl-4,5-dihydro-1,3-oxazol-2-yl]-1H-pyrrol-2-yl}phenol (80 mg, 0.24 mmol) synthesized in Example (116d) were dissolved in acetonitrile (2 mL), and cesium carbonate (158 mg, 0.48 mmol) was added, followed by stirring for 1 hour under nitrogen atmosphere. To the reaction solution, water (10 mL) was added, and extraction was carried out with ethyl acetate (10 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=0%-4%) to afford the desired compound (116 mg, yield 98%) as a white solid.

$^1$H-NMR (CDCl$_3$, 400 MHz): δ 1.34 (3H, d, J=6.3 Hz), 1.42 (3H, d, J=6.3 Hz), 3.40 (3H, s), 3.42 (3H, s), 3.48-3.62 (3H, m), 4.07 (1H, dd, J=13.9, 9.2 Hz), 4.58 (1H, td, J=6.2, 4.4 Hz), 4.82 (1H, dt, J=11.7, 4.6 Hz), 6.50 (1H, d, J=3.5 Hz), 6.69 (1H, t, J=2.2 Hz), 6.74 (1H, d, J=3.9 Hz), 6.99 (1H, q, J=2.0 Hz), 7.09 (1H, t, J=1.8 Hz), 7.40 (1H, d, J=9.0 Hz), 8.17 (1H, d, J=9.0 Hz).

(118e) (2S)-2-(3-{5-[(5S)-5-Methyl-4,5-dihydro-1,3-oxazol-2-yl]-1H-pyrrol-2-yl}-5-{[6-(methylsulfonyl)pyridazin-3-yl]oxy}phenoxy)propan-1-ol 3-(3-[(1S)-2-Methoxy-1-methylethoxy]-5-{5-[(5S)-5-methyl-4,5-dihydro-1,3-oxazol-2-yl]-1H-pyrrol-2-yl}phenoxy)-6-(methylsulfonyl)pyridazine (116 mg, 0.24 mmol) synthesized in Example (118d) was dissolved in methylene chloride (5 mL), and boron tribromide (1.0 mol/L methylene chloride solution, 0.26 mL, 0.26 mmol) was added at −78° C. under nitrogen atmosphere. Subsequently, the temperature was brought back to room temperature, followed by stirring for 4 hours. To the reaction solution, a saturated aqueous sodium hydrogencarbonate solution was added, and extraction was carried out with ethyl acetate. The organic layer was washed with saturated brine, and subsequently dried over sodium sulfate. The solvent was distilled off under reduced pressure, and the resulting residue was purified using silica gel column chromatography (elution solvent: methanol/methylene chloride=0%-5%) to afford the desired compound (100 mg, yield 89%) as a white solid.

$^1$H-NMR (CDCl$_3$, 400 MHz) δ 1.30 (3H, d, J=6.3 Hz), 1.41 (3H, d, J=6.3 Hz), 3.39 (3H, s), 3.53 (1H, dd, J=13.7, 7.4 Hz), 3.76-3.77 (2H, m), 4.07 (1H, dd, J=13.9, 9.2 Hz), 4.56 (1H, dd, J=10.8, 6.1 Hz), 4.82 (1H, dt, J=12.0, 4.6 Hz), 6.47 (1H, d, J=3.5 Hz), 6.61 (1H, t, J=2.2 Hz), 6.74 (1H, d, J=3.9 Hz), 6.99 (1H, t, J=1.6 Hz), 7.03 (1H, t, J=1.6 Hz), 7.39 (1H, d, J=9.4 Hz), 8.16 (1H, d, J=9.4 Hz).

MS (ESI) m/z: 473.15056 (M+H)$^+$.

Example 119

2-(Azetidin-1-ylsulfonyl)-5-(3-[(1S)-2-methoxy-1-methylethoxy]-5-{5-[(5S)-5-methyl-4,5-dihydro-1,3-oxazol-2-yl]-1H-pyrrol-2-yl}phenoxy)-pyridine

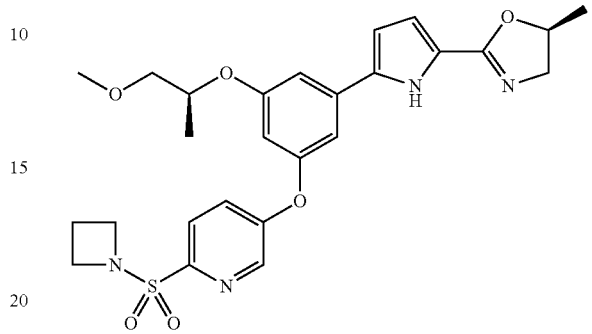

(119a) 5-Chloropyridine-2-thiol

Under nitrogen atmosphere, 2,5-dichloropyridine (5.00 g, 33.8 mmol) was dissolved in dimethyl sulfoxide (35 mL), and sodium disulfide nonahydrate (9.00 g, 37.2 mmol) was added, followed by stirring at 120° C. for 2 hours. The reaction solution was cooled to room temperature, and water (50 mL) was added, followed by neutralization with 5N hydrochloric acid. The resulting precipitate was filtered off, followed by washing with water and hexane, and subsequently the resulting solid was purified using silica gel column chromatography (elution solvent: methanol/methylene chloride=0%-10%) to afford the desired compound (2.28 g, yield 46%) as a yellow solid.

$^1$H-NMR (CDCl$_3$, 400 MHz) δ 2.63 (1H, s), 7.34 (1H, dd, J=9.0, 2.2 Hz), 7.41 (1H, d, J=9.3 Hz), 7.70 (1H, s).

(119b) 2-(Azetidin-1-ylsulfonyl)-5-chloropyridine

5-Chloropyridine-2-thiol (1.00 g, 6.87 mmol) synthesized in Example (119a) was dissolved in methylene chloride (30 mL)/1N hydrochloric acid (30 mL), and cooled to −5° C. To the reaction solution, ice-cooled 7% aqueous sodium perchlorate solution (30 mL) was added dropwise while being kept at 0° C. or below, and stirring was carried out as it is for 15 minutes. The organic layer was extracted with a separatory funnel ice-cooled in advance, and cooled to −78° C., a methylene chloride solution (10 mL) of commercially available azetidine hydrochloride (2.24 mg, 17.7 mmol) and triethylamine (1.8 mL, 12.9 mmol) was added, and the temperature was raised to 0° C., followed by stirring for 30 minutes. To the reaction solution, water (50 mL) was added, and extraction was carried out twice with ethyl acetate (30 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=5%-60%) to afford the desired compound (735 mg, yield 46%) as a white solid.

$^1$H-NMR (CDCl$_3$, 400 MHz): δ 2.19-2.25 (2H, m), 4.10 (4H, t, J=7.8 Hz), 7.91 (1H, dd, J=8.3, 2.0 Hz), 7.95 (1H, d, J=7.8 Hz), 8.72 (1H, d, J=2.0 Hz).

(119c) 2-(Azetidin-1-ylsulfonyl)-5-(3-[(1S)-2-methoxy-1-methylethoxy]-5-{5-[(5S)-5-methyl-4,5-dihydro-1,3-oxazol-2-yl]-1H-pyrrol-2-yl}phenoxy)-pyridine 2-(Azetidin-1-ylsulfonyl)-5-chloropyridine (170 mg, 0.73 mmol) synthesized in Example (119b) and 3-[(1S)-2-methoxy-1-methylethoxy]-5-{5-[(5S)-5-methyl-4,5-dihydro-1,3-oxazol-2-yl]-1H-pyrrol-2-yl}phenol (230 mg, 0.70 mmol) synthesized in Example (116d) were dissolved in N,N-dimethylformamide (3.5 mL), and cesium carbonate (454 mg, 1.39 mmol) was added, followed by stirring at 100° C. for 2 hours under nitrogen atmosphere. The reaction solution was cooled to room temperature, water (20 mL) was added, and extraction was carried out twice with ethyl acetate (20 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=5%-50%) to afford the desired compound (273 mg, yield 75%) as a white solid.

$^1$H-NMR (CDCl$_3$, 400 MHz): δ 1.34 (3H, d, J=6.3 Hz), 1.43 (3H, d, J=6.3 Hz), 2.18-2.24 (2H, m), 3.42 (3H, s), 3.49-3.61 (3H, m), 4.10 (4H, t, J=7.6 Hz), 4.56-4.62 (1H, m), 4.82-4.86 (1H, m), 6.51 (1H, d, J=3.9 Hz), 6.58 (1H, t, J=2.0 Hz), 6.76 (1H, d, J=3.9 Hz), 6.88 (1H, s), 7.04 (1H, s), 7.43 (1H, dd, J=8.8, 2.9 Hz), 7.94 (1H, d, J=8.8 Hz), 8.53 (1H, d, J=2.9 Hz).

MS (ESI) m/z: 527.20527 (M+H)$^+$.

Example 120

5-(3-[(1S)-2-Methoxy-1-methylethoxy]-5-{5-[(5S)-5-methyl-4,5-dihydro-1,3-oxazol-2-yl]-1H-pyrrol-2-yl}phenoxy)pyridine-2-sulfonamide

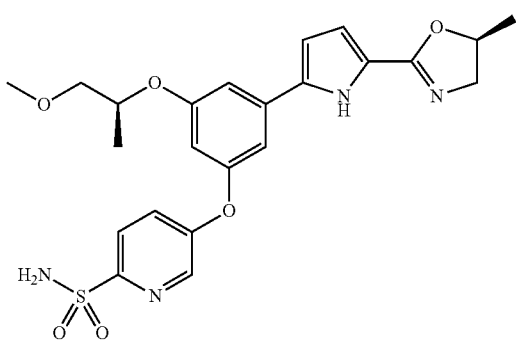

(120a)
5-Chloro-N-(4-methoxybenzyl)pyridine-2-sulfonamide

5-Chloropyridine-2-thiol (1.00 g, 6.87 mmol) synthesized in Example (119a) was dissolved in methylene chloride (30 mL)/1N hydrochloric acid (30 mL), and cooled to −5° C. To the reaction solution, an ice-cooled 7% aqueous sodium perchlorate solution (35 mL) was added dropwise while being kept at 0° C. or below, and stirring was carried out as it is for 15 minutes. The organic layer was extracted with a reparatory funnel ice-cooled in advance, and cooled to −78° C., commercially available 4-methoxybenzylamine (2.24 mL, 17.7 mmol) was added, and the temperature was raised to 0° C., followed by stirring for 30 minutes. To the reaction solution, 0.1N hydrochloric acid (30 mL) was added, and extraction was carried out twice with methylene chloride (30 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=5%-100%) to afford the desired compound (983 mg, yield 46%) as a white solid.

$^1$H-NMR (CDCl$_3$, 400 MHz): δ 3.78 (3H, s), 4.20 (2H, d, J=6.3 Hz), 5.07 (1H, s), 6.79 (2H, dt, J=9.4, 2.5 Hz), 7.14 (2H, d, J=8.6 Hz), 7.83 (1H, dd, J=8.6, 2.3 Hz), 7.90 (1H, d, J=7.8 Hz), 8.60 (1H, dd, J=2.3, 0.8 Hz).

(120b) 5-Chloro-N,N-bis(4-methoxybenzyl)pyridine-2-sulfonamide

5-Chloro-N-(4-methoxybenzyl)pyridine-2-sulfonamide (983 mg, 3.14 mmol) synthesized in Example (120a) was dissolved in N,N-dimethylformamide (5 mL), and sodium hydride (132 mg, 3.30 mmol) was added. After ice cooling, p-methoxybenzyl chloride (1.02 mL, 3.37 mmol) was added, and the temperature was raised to room temperature, followed by stirring for 2 hours. Water (20 mL) was added to the reaction solution, and extraction was carried out twice with ethyl acetate (20 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=10%-100%) to afford the desired compound (1.14 g, yield 84%) as a white solid.

$^1$H-NMR (CDCl$_3$, 400 MHz): δ 3.78 (6H, s), 4.40 (4H, s), 6.75 (4H, dt, J=9.3, 2.5 Hz), 7.05 (4H, dt, J=8.2, 2.0 Hz), 7.78 (1H, dd, J=8.2, 2.3 Hz), 7.84 (1H, d, J=7.8 Hz), 8.55 (1H, d, J=2.7 Hz).

(120c) N,N-Bis(4-methoxybenzyl)-5-(3-[(1S)-2-methoxy-1-methylethoxy]-5-{5-[(5S)-5-methyl-4,5-dihydro-1,3-oxazol-2-yl]-1H-pyrrol-2-yl}phenoxy)pyridine-2-sulfonamide 5-Chloro-N,N-bis(4-methoxybenzyl)pyridine-2-sulfonamide (288 mg, 0.67 mmol) synthesized in Example (120b) and 3-[(1S)-2-methoxy-1-methylethoxy]-5-{5-[(5S)-5-methyl-4,5-dihydro-1,3-oxazol-2-yl]-1H-pyrrol-2-yl}phenol (220 mg, 0.67 mmol) synthesized in Example (116d) were dissolved in N,N-dimethylformamide (3 mL), and cesium carbonate (434 mg, 1.33 mmol) was added, followed by stirring at 100° C. for 1 hour under nitrogen atmosphere. The reaction solution was cooled to room temperature, water (20 mL) was added, and extraction was carried out twice with ethyl acetate (20 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=0.5%-5%) to afford the desired compound (160 mg, yield 33%) as a white solid.

$^1$H-NMR (CDCl$_3$, 400 MHz): δ 1.34 (3H, d, J=5.9 Hz), 1.43 (3H, d, J=6.3 Hz), 3.42 (3H, s), 3.50-3.62 (3H, m), 3.77 (6H, s), 4.09 (1H, dd, J=13.9, 9.0 Hz), 4.41 (4H, s), 4.56-4.63 (1H, m), 4.81-4.86 (1H, m), 6.52 (1H, d, J=3.9 Hz), 6.56 (1H, t, J=2.0 Hz), 6.76 (4H, d, J=8.8 Hz), 7.07 (4H, d, J=8.8 Hz), 7.33 (1H, dd, J=8.5, 2.7 Hz), 7.88 (1H, d, J=8.8 Hz), 8.39 (1H, d, J=2.9 Hz).

(120d) 5-(3-[(1S)-2-Methoxy-1-methylethoxy]-5-{5-[(5S)-5-methyl-4,5-dihydro-1,3-oxazol-2-yl]-1H-pyrrol-2-yl}phenoxy)pyridine-2-sulfonamide N,N-Bis(4-methoxybenzyl)-5-(3-[(1S)-2-methoxy-1-methylethoxy]-5-{5-[(5S)-5-methyl-4,5-dihydro-1,3-oxazol-2-yl]-1H-pyrrol-2-yl}phenoxy)pyridine-2-sulfonamide (160 mg, 0.24 mmol) synthesized in Example (120c) was dissolved in trifluoroacetic acid (2 mL), and stirring was carried out at 40° C. for 8 hours. The solvent was distilled off under reduced pressure, methylene chloride and triethylamine were added in small portions to the residue, and the solvent was distilled off again under reduced pressure. The resulting residue was purified using silica gel column chromatography (elution solvent: methanol/methylene chloride=0%-5%) to afford the desired compound (106 mg, yield 99%) as a white solid.

$^1$H-NMR (CDCl$_3$, 400 MHz) δ 1.33 (3H, d, J=6.3 Hz), 1.42 (3H, d, J=5.9 Hz), 3.42 (3H, s), 3.49-3.53 (2H, m), 3.59 (1H, dd, J=10.3, 5.9 Hz), 4.05 (1H, dd, J=14.2, 9.3 Hz), 4.55-4.61 (1H, m), 4.79-4.86 (1H, m), 5.30 (2H, br s), 6.50 (1H, d, J=3.9 Hz), 6.56 (1H, t, J=2.2 Hz), 6.75 (1H, d, J=3.9 Hz), 6.85 (1H, t, J=1.7 Hz), 7.03 (1H, t, J=1.7 Hz), 7.42 (1H, dd, J=8.5, 2.7 Hz), 7.95 (1H, d, J=8.8 Hz), 8.42 (1H, d, J=2.4 Hz).

MS (ESI) m/z: 487.16619 (M+H)$^+$.

Example 121

5-(3-[(1S)-2-Methoxy-1-methylethoxy]-5-{5-[(5S)-5-methyl-4,5-dihydro-1,3-oxazol-2-yl]-1H-pyrrol-2-yl}phenoxy)-N-methylpyridine-2-sulfonamide

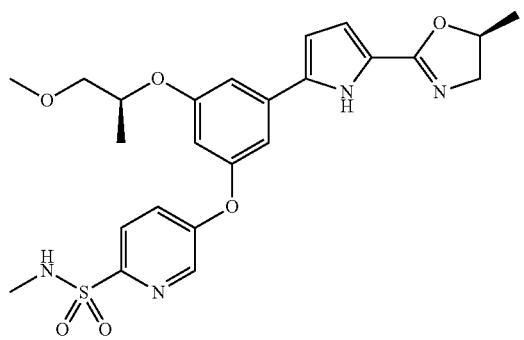

(121a) 5-Chloro-N-methylpyridine-2-sulfonamide

5-Chloropyridine-2-thiol (1.00 g, 6.87 mmol) synthesized in Example (119a) was dissolved in methylene chloride (30 mL)/1N hydrochloric acid (30 mL), and cooled to −5° C. To the reaction solution, an ice-cooled 7% aqueous sodium perchlorate solution (30 mL) was added dropwise while being kept at 0° C. or below, and stirring was carried out as it is for 15 minutes. The organic layer was extracted with a separatory funnel ice-cooled in advance, and cooled to −78° C., a methylene chloride solution (10 mL) of commercially available 40% methylamine/methanol solution (1.33 mL, 17.2 mmol) was added, and the temperature was raised to 0° C., followed by stirring for 2 hours. To the reaction solution, water (50 mL) was added, and extraction was carried out twice with ethyl acetate (30 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=30%-80%) to afford the desired compound (889 mg, yield 63%) as a white solid.

$^1$H-NMR (CDCl$_3$, 400 MHz): δ 2.77 (3H, d, J=4.9 Hz), 4.81 (1H, s), 7.90 (1H, dd, J=8.3, 2.4 Hz), 7.97 (1H, d, J=8.3 Hz), 8.65 (1H, d, J=2.4 Hz).

(121b) 5-Chloro-N-(4-methoxybenzyl)-N-methylpyridine-2-sulfonamide

5-Chloro-N-methylpyridine-2-sulfonamide (889 mg, 4.30 mmol) synthesized in Example (121a) was dissolved in N,N-dimethylformamide (15 mL), and sodium hydride (172 mg, 4.30 mmol) was added. After ice cooling, p-methoxybenzyl chloride (0.70 mL, 5.16 mmol) was added, and the temperature was raised to room temperature, followed by stirring for 3 hours. Water (20 mL) was added to the reaction solution, and extraction was carried out twice with ethyl acetate (20 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=0%-20%) to afford the desired compound (817 mg, yield 58%) as a colorless oil.

$^1$H-NMR (CDCl$_3$, 400 MHz): δ 2.79 (3H, s), 3.81 (3H, s), 4.36 (2H, s), 6.87 (2H, dt, J=9.4, 2.4 Hz), 7.25 (2H, d, J=7.3 Hz), 7.88 (1H, dd, J=8.3, 2.4 Hz), 7.94 (1H, d, J=8.3 Hz), 8.66 (1H, d, J=2.4 Hz).

(121c) N-(4-Methoxybenzyl)-5-(3-[(1S)-2-methoxy-1-methylethoxy]-5-{5-[(5S)-5-methyl-4,5-dihydro-1,3-oxazol-2-yl]-1H-pyrrol-2-yl}phenoxy)-N-methylpyridine-2-sulfonamide 5-Chloro-N-(4-methoxybenzyl)-N-methylpyridine-2-sulfonamide (228 mg, 0.70 mmol) synthesized in Example (121b) and 3-[(1S)-2-methoxy-1-methylethoxy]-5-{5-[(5S)-5-methyl-4,5-dihydro-1,3-oxazol-2-yl]-1H-pyrrol-2-yl}phenol (220 mg, 0.67 mmol) synthesized in Example (116d) were dissolved in N,N-dimethylformamide (3 mL), and cesium carbonate (434 mg, 1.33 mmol) was added, followed by stirring at 100° C. for 3 hours under nitrogen atmosphere. The reaction solution was cooled to room temperature, water (20 mL) was added, and extraction was carried out twice with ethyl acetate (20 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=0.5%-5%) to afford the desired compound (293 mg, yield 71%) as a white solid.

$^1$H-NMR (CDCl$_3$, 400 MHz): δ 1.34 (3H, d, J=6.3 Hz), 1.43 (3H, d, J=5.9 Hz), 2.79 (3H, s), 3.42 (3H, s), 3.49-3.61 (3H, m), 3.81 (3H, s), 4.08 (1H, dd, J=13.7, 9.3 Hz), 4.37 (2H, s), 4.55-4.62 (1H, m), 4.80-4.87 (1H, m), 6.51 (1H, d, J=3.9 Hz), 6.57 (1H, t, J=2.2 Hz), 6.75 (1H, d, J=3.9 Hz), 6.87-6.89 (3H, m), 7.03 (1H, s), 7.28 (2H, d, J=8.8 Hz), 7.41 (1H, dd, J=8.5, 2.7 Hz), 7.94 (1H, d, J=8.3 Hz), 8.47 (1H, d, J=2.4 Hz).

(121d) 5-(3-[(1S)-2-Methoxy-1-methylethoxy]-5-{5-[(5S)-5-methyl-4,5-dihydro-1,3-oxazol-2-yl]-1H-pyrrol-2-yl}phenoxy)-N-methylpyridine-2-sulfonamide N-(4-Methoxybenzyl)-5-(3-[(1S)-2-methoxy-1-methylethoxy]-5-{5-[(5S)-5-methyl-4,5-dihydro-1,3-oxazol-2-yl]-1H-pyrrol-2-yl}phenoxy)-N-methylpyridine-2-sulfonamide (292 mg, 0.47 mmol) synthesized in Example (121c) was dissolved in trifluoroacetic acid (2 mL), and stirring was carried out at 45° C. for 1 hour. The solvent was distilled off under reduced pressure, methylene chloride and triethylamine were added in small portions to the residue, and the solvent was distilled off again under reduced pressure. The resulting residue was purified using silica gel column chromatography (elution solvent: methanol/methylene chloride=0%-4%) to afford the desired compound (208 mg, yield 88%) as a white solid.

$^1$H-NMR (CDCl$_3$, 400 MHz): δ 1.34 (3H, d, J=5.9 Hz), 1.43 (3H, d, J=6.3 Hz), 2.76 (3H, s), 3.41 (3H, s), 3.49-3.61 (3H, m), 4.08 (1H, dd, J=13.9, 9.0 Hz), 4.61-4.55 (1H, m), 4.84 (1H, dd, J=15.1, 7.3 Hz), 6.50 (1H, d, J=3.9 Hz), 6.56 (1H, t, J=2.2 Hz), 6.76 (1H, d, J=3.9 Hz), 6.86 (1H, s), 7.04 (1H, s), 7.41 (1H, dd, J=8.5, 2.7 Hz), 7.96 (1H, d, J=8.8 Hz), 8.45 (1H, d, J=2.4 Hz).

MS (ESI) m/z: 501.18090 (M+H)$^+$.

Example 122

5-(3-[(1S)-2-Hydroxy-1-methylethoxy]-5-{5-[(5S)-5-methyl-4,5-dihydro-1,3-oxazol-2-yl]-1H-pyrrol-2-yl}phenoxy)-N-methylpyridine-2-sulfonamide

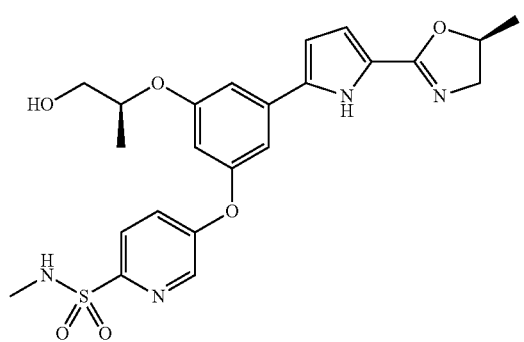

5-(3-[(1S)-2-Methoxy-1-methylethoxy]-5-{5-[(5S)-5-methyl-4,5-dihydro-1,3-oxazol-2-yl]-1H-pyrrol-2-yl}phenoxy)-N-methylpyridine-2-sulfonamide (166 mg, 0.32 mmol) synthesized in Example (121d) was dissolved in methylene chloride (5 mL), and boron tribromide (1.0 mol/L methylene chloride solution, 0.34 mL, 0.34 mmol) was added at −78° C. under nitrogen atmosphere. Subsequently, the temperature was brought back to room temperature, followed by stirring for 1.5 hours. To the reaction solution, a saturated aqueous sodium hydrogencarbonate solution was added, and extraction was carried out with methylene chloride. The organic layer was washed with saturated brine, and subsequently dried over sodium sulfate. The solvent was distilled off under reduced pressure, and the resulting residue was purified using silica gel column chromatography (elution solvent: methanol/methylene chloride=0%-4%) to afford the desired compound (119 mg, yield 78%) as a white solid.

$^1$H-NMR (CDCl$_3$, 400 MHz): δ 1.30 (3H, d, J=6.3 Hz), 1.43 (3H, d, J=6.8 Hz), 2.75 (3H, s), 3.54 (1H, dd, J=13.7, 7.3 Hz), 3.75-3.77 (2H, m), 4.08 (1H, dd, J=9.3, 13.7 Hz), 4.52-4.58 (1H, m), 4.81-4.88 (1H, m), 6.43 (1H, s), 6.47 (1H, d, J=3.9 Hz), 6.75 (1H, d, J=4.4 Hz), 6.83 (1H, s), 7.00 (1H, s), 7.39 (1H, dd, J=8.8, 2.0 Hz), 7.95 (1H, d, J=8.8 Hz), 8.39 (1H, s).

MS (ESI) m/z: 487.16369 (M+H)$^+$.

Example 123

5-(3-[(1S)-2-Hydroxy-1-methylethoxy]-5-{5-[(5S)-5-methyl-4,5-dihydro-1,3-oxazol-2-yl]-1H-pyrrol-2-yl}phenoxy)-N-methylpyridine-2-carboxamide

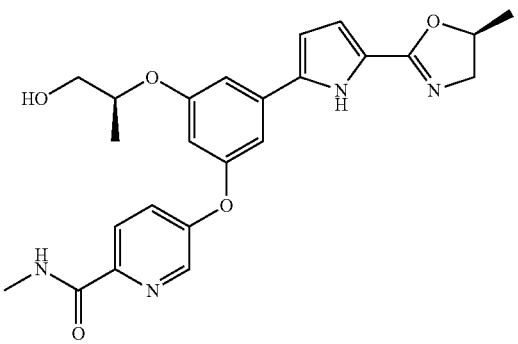

(123a) 5-Fluoro-N-methylpyridine-2-carboxamide

5-Fluoropyridine-2-carboxylic acid (495 mg, 3.51 mmol) was dissolved in methylene chloride (10 mL), and HOBt•H$_2$O (591 mg, 3.86 mmol), WSCI•HCl (1.35 g, 7.02 mmol), triethylamine (2.44 mL, 17.5 mmol) and 40% methylamine/methanol solution (0.82 mL, 10.5 mmol) were added, followed by stirring for 15 hours. To the reaction solution, water (30 mL) was added, and extraction was carried out twice with methylene chloride (30 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=0%-50%) to afford the desired compound (490 mg, yield 91%) as a white solid.

$^1$H-NMR (CDCl$_3$, 400 MHz): δ 3.03 (3H, d, J=5.5 Hz), 7.53 (1H, dt, J=2.7, 8.6 Hz), 7.85 (1H, br s), 8.24 (1H, dd, J=8.2, 4.7 Hz), 8.38 (1H, d, J=2.7 Hz).

(123b) 5-(3-[(1S)-2-Methoxy-1-methylethoxy]-5-{5-[(5S)-5-methyl-4,5-dihydro-1,3-oxazol-2-yl]-1H-pyrrol-2-yl}phenoxy)-N-methylpyridine-2-carboxamide 5-Fluoro-N-methylpyridine-2-carboxamide (122 mg, 0.79 mmol) synthesized in Example (123a) and 3-[(1S)-2-methoxy-1-methylethoxy]-5-{5-[(5S)-5-methyl-4,5-dihydro-1,3-oxazol-2-yl]-1H-pyrrol-2-yl}phenol (275 mg, 0.83 mmol) synthesized in Example (116d) were dissolved in N,N-dimethylformamide (3 mL), and potassium carbonate (219 mg, 1.58 mmol) was added, followed by stirring at 100° C. for 3 hours under nitrogen atmosphere. The reaction solution was cooled to room temperature, water (30 mL) was added, and extraction was carried out twice with ethyl acetate (30 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=0%-5%) to afford the desired compound (283 mg, yield 77%) as a white solid.

$^1$H-NMR (CDCl$_3$, 400 MHz): δ 1.33 (3H, d, J=6.3 Hz), 1.42 (3H, d, J=6.3 Hz), 3.03 (3H, d, J=5.1 Hz), 3.41 (3H, s), 3.48-3.61 (3H, m), 4.08 (1H, dd, J=13.9, 9.2 Hz), 4.53-4.60 (1H, m), 4.80-4.86 (1H, m), 6.49 (1H, d, J=3.9 Hz), 6.53 (1H, t, J=2.2 Hz), 6.74 (1H, d, J=3.5 Hz), 6.83 (1H, d, J=1.6 Hz), 7.00 (1H, s), 7.41 (1H, dd, J=8.6, 2.7 Hz), 7.86 (1H, br s), 8.17 (1H, d, J=8.6 Hz), 8.31 (1H, d, J=2.7 Hz).

(123c) 5-(3-[(1S)-2-Hydroxy-1-methylethoxy]-5-{5-[(5S)-5-methyl-4,5-dihydro-1,3-oxazol-2-yl]-1H-pyrrol-2-yl}phenoxy)-N-methylpyridine-2-carboxamide 5-(3-[(1S)-2-Methoxy-1-methylethoxy]-5-{5-[(5S)-5-methyl-4,5-dihydro-1,3-oxazol-2-yl]-1H-pyrrol-2-yl}phenoxy)-N-methylpyridine-2-carboxamide (176 mg, 0.38 mmol) synthesized in Example (123b) was dissolved in methylene chloride (5 mL), and boron tribromide (1.0 mol/L methylene chloride solution, 0.50 mL, 0.50 mmol) was added at –78° C. Subsequently, the temperature was brought back to room temperature, followed by stirring for 1 hour. To the reaction solution, a saturated aqueous sodium hydrogencarbonate solution was added, and extraction was carried out with methylene chloride. The organic layer was washed with saturated brine, and subsequently dried over sodium sulfate. The solvent was distilled off under reduced pressure, and the resulting residue was purified using silica gel column chromatography (elution solvent: methanol/methylene chloride=0%-5%) to afford the desired compound (118 mg, yield 69%) as a white solid.
$^1$H-NMR (CDCl$_3$, 400 MHz): δ 1.28 (3H, d, J=5.9 Hz), 1.42 (3H, d, J=6.3 Hz), 3.03 (3H, d, J=5.1 Hz), 3.54 (1H, dd, J=13.9, 7.2 Hz), 3.76 (2H, d, J=4.7 Hz), 4.07 (1H, dd, J=13.9, 9.2 Hz), 4.57 (1H, dd, J=11.1, 6.1 Hz), 4.83 (1H, dt, J=11.7, 4.6 Hz), 6.38 (1H, s), 6.45 (1H, d, J=3.5 Hz), 6.73 (1H, d, J=3.9 Hz), 6.80 (1H, s), 6.93 (1H, s), 7.35 (1H, dd, J=8.6, 2.7 Hz), 7.87 (1H, d, J=5.5 Hz), 8.15 (1H, d, J=8.6 Hz), 8.27 (1H, d, J=2.7 Hz).
MS (ESI) m/z: 451.19720 (M+H)$^+$.

Example 124

5-(3-[(1S)-2-Hydroxy-1-methylethoxy]-5-{5-[(5S)-5-methyl-4,5-dihydro-1,3-oxazol-2-yl]-1H-pyrrol-2-yl}phenoxy)-N-methylpyrazine-2-carboxamide

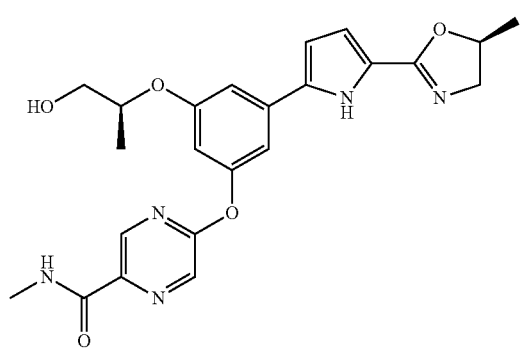

(124a) 5-Chloro-N-methylpyrazine-2-carboxamide

5-Chloropyrazine-2-carboxylic acid (1.99 g, 12.6 mmol) was dissolved in N,N-dimethylformamide (10 mL), and HOBt.H$_2$O (591 mg, 3.86 mmol), WSCI•HCl (1.35 g, 7.02 mmol), N-methylmorpholine (2.76 mL, 25.1 mmol) and 40% methylamine/methanol solution (2.92 mL, 37.6 mmol) were added, followed by stirring for 18 hours. To the reaction solution, water (50 mL) was added, and extraction was carried out twice with ethyl acetate (50 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=0%-75%) to afford the desired compound (585 mg, yield 27%) as a white solid.
$^1$H-NMR (CDCl$_3$, 400 MHz): δ 3.03 (3H, d, J=4.9 Hz), 7.60 (1H, br s), 8.09 (1H, d, J=1.5 Hz), 8.93 (1H, d, J=1.0 Hz).

(124b) 5-(3-[(1S)-2-Hydroxy-1-methylethoxy]-5-{5-[(5S)-5-methyl-4,5-dihydro-1,3-oxazol-2-yl]-1H-pyrrol-2-yl}phenoxy)-N-methylpyrazine-2-carboxamide 5-Chloro-N-methylpyrazine-2-carboxamide (171 mg, 1.00 mmol) synthesized in Example (124a) and 3-[(1S)-2-methoxy-1-methylethoxy]-5-{5-[(5S)-5-methyl-4,5-dihydro-1,3-oxazol-2-yl]-1H-pyrrol-2-yl}phenol (300 mg, 0.91 mmol) synthesized in Example (116d) were dissolved in N,N-dimethylformamide (3 mL), and potassium carbonate (376 mg, 2.72 mmol) was added, followed by stirring at 100° C. for 5 hours under nitrogen atmosphere. To the reaction solution, 5-chloro-N-methylpyrazine-2-carboxamide (110 mg, 0.64 mmol) was added further, and stirring was carried out for 3 hours. The reaction solution was cooled to room temperature, water (30 mL) was added, and extraction was carried out twice with ethyl acetate (30 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=0%-5%) to afford a white solid (206 mg).
This product was dissolved in methylene chloride (5 mL), and boron tribromide (1.0 mol/L methylene chloride solution, 0.57 mL, 0.57 mmol) was added at –78° C. Subsequently, the temperature was brought back to room temperature, followed by stirring for 1.5 hours. The reaction solution was cooled again to –78° C., boron tribromide (1.0 mol/L methylene chloride solution, 1.00 mL, 1.00 mmol) was added, and the temperature was brought back to room temperature, followed by stirring for 3 hours. To the reaction solution, a saturated aqueous sodium hydrogencarbonate solution was added, and extraction was carried out with methylene chloride. The organic layer was washed with saturated brine, and subsequently dried over sodium sulfate. The solvent was distilled off under reduced pressure, and the resulting residue was purified using silica gel column chromatography (elution solvent: methanol/methylene chloride=0%-5%) to afford the desired compound (87.8 mg, yield 21%) as a white solid.
$^1$H-NMR (CDCl$_3$, 400 MHz): δ 1.31 (3H, d, J=5.9 Hz), 1.43 (3H, d, J=6.3 Hz), 3.05 (3H, d, J=5.4 Hz), 3.55 (1H, dd, J=13.9, 7.6 Hz), 3.77 (2H, d, J=5.4 Hz), 4.09 (1H, dd, J=13.9, 9.0 Hz), 4.56 (1H, dd, J=11.2, 5.9 Hz), 4.87-4.80 (1H, m), 6.49 (1H, d, J=3.4 Hz), 6.60 (1H, s), 6.75 (1H, d, J=3.9 Hz), 6.93 (1H, s), 7.00 (1H, s), 7.62 (1H, d, J=4.9 Hz), 8.29 (1H, s), 8.93 (1H, d, J=1.0 Hz).
MS (ESI) m/z: 452.19252 (M+H)$^+$.

Example 125

{(5R)-2-[5-(3-{[6-(Cyclopropylsulfonyl)pyridin-3-yl]oxy}-5-[(1S)-2-methoxy-1-methylethoxy]phenyl)-1H-pyrrol-2-yl]-4,5-dihydro-1,3-oxazol-5-yl}methanol

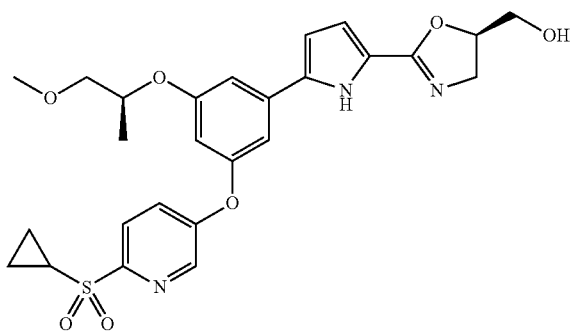

(125a) 5-Chloro-2-[(3-chloropropyl)thio]pyridine

5-Chloropyridine-2-thiol (600 mg, 4.12 mmol) synthesized in Example (119a) was dissolved in methanol (15 mL), and 28% sodium methoxide/methanol solution (0.95 mL, 4.94 mmol) and 1-bromo-3-chloropropane (0.61 mL, 6.18 mmol) were added, followed by stirring at 60° C. for 1.5 hours. The reaction solution was cooled to room temperature, water (40 mL) was added, and extraction was carried out twice with ethyl acetate (40 mL). The organic layer was washed with saturated brine, and subsequently dried over anhydrous magnesium sulfate. The solvent was distilled off under reduced pressure, and vacuum drying was carried out to afford the desired compound (849 mg, yield 92%) as a colorless oil.

$^1$H-NMR (CDCl$_3$, 400 MHz): δ 2.26-2.31 (2H, m), 3.55-3.58 (2H, m), 3.67 (2H, t, J=6.3 Hz), 7.96 (1H, dd, J=8.3, 2.0 Hz), 8.06 (1H, d, J=7.8 Hz), 8.70 (1H, d, J=2.4 Hz).

(125b) 5-Chloro-2-[(3-chloropropyl)sulfonyl]pyridine

5-Chloro-2-[(3-chloropropyl)thio]pyridine (846 mg, 3.80 mmol) synthesized in Example (125a) was dissolved in methylene chloride (20 mL) and ice cooling, and subsequently m-chloroperbenzoic acid (2.02 g, 7.62 mmol) was added, followed by stirring as it is for 1 hour. To the reaction solution, saturated aqueous sodium hydrogencarbonate solution (40 mL) was added, and extraction was carried out twice with methylene chloride (40 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=0%-20%) to afford the desired compound (733 mg, yield 76%) as a colorless oil.

$^1$H-NMR (CDCl$_3$, 400 MHz): δ 2.21-2.14 (2H, m), 3.30 (2H, t, J=6.8 Hz), 3.67 (2H, t, J=6.3 Hz), 7.13 (1H, dd, J=8.6, 0.8 Hz), 7.45 (1H, dd, J=8.6, 2.3 Hz), 8.37 (1H, dd, J=5.1, 3.1 Hz).

(125c) 5-Chloro-2-(cyclopropylsulfonyl)pyridine

5-Chloro-2-[(3-chloropropyl)sulfonyl]pyridine (732 mg, 3.05 mmol) synthesized in Example (125b) was dissolved in tetrahydrofuran (10 mL) and cooled to −30° C., and subsequently potassium-t-butoxide (582 mg, 5.18 mmol) was added, followed by stirring as it is for 30 minutes. To the reaction solution, a saturated aqueous ammonium chloride solution (40 mL) was added, and extraction was carried out twice with methylene chloride (40 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=0%-25%) to afford the desired compound (397 mg, yield 60%).

$^1$H-NMR (CDCl$_3$, 400 MHz): δ 1.07-1.12 (2H, m), 1.37-1.41 (2H, m), 2.76-2.83 (1H, m), 7.91 (1H, dd, J=8.2, 2.3 Hz), 7.98 (1H, d, J=8.2 Hz), 8.71 (1H, dd, J=2.3, 0.8 Hz).

(125d) N-[(2S)-2,3-Dihydroxypropyl]-5-{3-[(1S)-2-methoxy-1-methylethoxy]-5-[(triisopropylsilyl)oxy]phenyl}-1H-pyrrole-2-carboxamide 5-{3-[(1S)-2-Methoxy-1-methylethoxy]-5-[(triisopropylsilyl)oxy]phenyl}-1H-pyrrole-2-carboxylic acid (9.32 g, 20.8 mmol) synthesized in Example (106c) was dissolved in methanol (200 mL), and (S)-(−)-3-amino-1,2-propanediol (5.01 g, 55.0 mmol) and 4-(4,6-dimethoxy-1,3,5-triazin-2-yl)-4-methylmorpholinium chloride n hydrate (10.13 g, 32.3 mmol) were added, followed by stirring at room temperature overnight under nitrogen atmosphere. The solvent was distilled off under reduced pressure, water (300 mL) and ethyl acetate (200 mL) were added to the resulting residue, and the solution was separated. The organic layer was washed with saturated brine, subsequently dried over anhydrous magnesium sulfate, and the solvent was distilled off under reduced pressure. The resulting residue was purified using silica gel column chromatography (elution solvent: ethyl acetate/hexane=70%-100%) to afford the desired product (9.32 g, yield 86%) as a colorless oil.

$^1$H-NMR (CDCl$_3$, 400 Hz): δ 1.11 (18H, d, J=7.0 Hz), 1.22-1.29 (3H, m), 1.31 (3H, d, J=6.3 Hz), 3.07-3.14 (2H, m), 3.42 (3H, s), 3.50 (1H, dd, J=10.2, 4.3 Hz), 3.54-3.66 (5H, m), 3.83-3.90 (1H, m), 4.49-4.57 (1H, m), 6.34 (1H, t, J=6.5 Hz), 6.42 (1H, t, J=2.3 Hz), 6.46 (1H, dd, J=3.9, 2.7 Hz), 6.63 (1H, dd, J=3.9, 2.3 Hz), 6.67 (1H, t, J=1.6 Hz), 6.73 (1H, t, J=1.6 Hz), 9.55 (1H, br s).

(125e) N-{(2S)-2-Hydroxy-3-[(triisopropylsilyl)oxy]propyl}-5-{3-[(1S)-2-methoxy-1-methylethoxy]-5-[(triisopropylsilyl)oxy]phenyl}-1H-pyrrole-2-carboxamide N-[(2S)-2,3-Dihydroxypropyl]-5-{3-[(1S)-2-methoxy-1-methylethoxy]-5-[(triisopropylsilyl)oxy]phenyl}-1H-pyrrole-2-carboxamide (9.30 g, 17.9 mmol) synthesized in Example (125d) was dissolved in methylene chloride (180 mL), and triisopropylsilyl chloride (4.25 mL, 19.9 mmol), triethylamine (7.45 mL, 53.5 mmol) and 4-dimethylaminopyridine (2.20 g, 18.0 mmol) were added, followed by stirring at room temperature for 2.5 hours under nitrogen atmosphere. Water (300 mL) was added to separate the solution, and the organic layer was washed with saturated brine and subsequently dried over anhydrous magnesium sulfate. The solvent was distilled off under reduced pressure, and the resulting residue was purified using silica gel column chromatography (elution solvent: ethyl acetate/hexane=10%-35%) to afford the desired compound (10.56 g, yield 87%) as a colorless oil.

$^1$H-NMR (CDCl$_3$, 400 Hz): δ 1.18-1.06 (39H, m), 1.22-1.30 (3H, m), 1.32 (3H, d, J=6.3 Hz), 3.20 (1H, d, J=4.3 Hz), 3.38-3.44 (1H, m), 3.42 (3H, s), 3.49 (1H, dd, J=10.2, 4.3 Hz), 3.59 (1H, dd, J=10.2, 5.5 Hz), 3.66-3.79 (3H, m), 3.85-3.91 (1H, m), 4.49-4.56 (1H, m), 6.30 (1H, t, J=5.9 Hz), 6.41 (1H, t, J=2.0 Hz), 6.45 (1H, dd, J=3.9, 2.7 Hz), 6.59 (1H, dd, J=3.9, 2.3 Hz), 6.66 (1H, t, J=2.0 Hz), 6.72 (1H, t, J=2.0 Hz), 9.34 (1H, br s).

(125f) (5R)-2-(5-{3-[(1S)-2-Methoxy-1-methylethoxy]-5-[(triisopropylsilyl)oxy]phenyl}-1H-pyrrol-2-yl)-5{[(triisopropylsilyl)oxy]methyl}-4,5-dihydro-1,3-oxazole N-{(2S)-2-Hydroxy-3-[(triisopropylsilyl)oxy]propyl}-5-{3-[(1S)-2-methoxy-1-methylethoxy]-5-[(triisopropylsilyl)oxy]phenyl}-1H-pyrrole-2-carboxamide (10.54 g, 15.6 mmol) synthesized in Example (125e) was dissolved in tetrahydrofuran (160 mL), and anhydrous methanesulfonic acid (5.51 g, 31.6 mmol) and triethylamine (8.70 mL, 62.4 mmol) were added, followed by stirring at room temperature for 3 hours under nitrogen atmosphere, and subsequently the temperature was raised to 60° C., followed by stirring for 3 hours. To the reaction solution, water (200 mL) was added, and extraction was carried out with ethyl acetate (300 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=5%-30%) to afford the desired compound (9.72 g, yield 95%) as a brown oil.

$^1$H-NMR (CDCl$_3$, 400 Hz): δ 1.04-1.14 (39H, m), 1.22-1.29 (3H, m), 1.32 (3H, d, J=6.3 Hz), 3.42 (3H, s), 3.48 (1H, dd, J=10.2, 4.3 Hz), 3.59 (1H, dd, J=10.2, 5.9 Hz), 3.85-3.90 (3H, m), 4.02 (1H, dd, J=14.1, 9.8 Hz), 4.48-4.54 (1H, m), 4.72-4.78 (1H, m), 6.39 (1H, t, J=2.0 Hz), 6.45 (1H, d, J=3.9 Hz), 6.67 (1H, t, J=2.0 Hz), 6.71 (1H, t, J=2.0 Hz), 6.73 (1H, d, J=3.9 Hz).

(125g) 3-{5-[(5R)-5-(Hydroxylmethyl)-4,5-dihydro-1,3-oxazol-2-yl]-1H-pyrrol-2-yl}-5-[(1S)-2-methoxy-1-methylethoxy]phenol (5R)-2-(5-{3-[(1S)-2-Methoxy-1-methylethoxy]-5-[(triisopropylsilyl)oxy]phenyl}-1H-pyrrol-2-yl)-5{[(triisopropylsilyl)oxy]methyl}-4,5-dihydro-1,3-oxazole (9.69 g, 14.7 mmol) synthesized in Example (125f) was dissolved in tetrahydrofuran (150 mL), and tetrabutylammonium fluoride (1 mol/L tetrahydrofuran solution, 30.0 mL, 30 mmol) was added dropwise at 0° C., followed by stirring at 0° C. for 30 minutes. A saturated aqueous ammonium chloride solution (200 mL) was added, and extraction was carried out with ethyl acetate (200 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=3%-7%) to afford the desired compound (6.50 g, yield ~100%) as a pale yellow solid.

$^1$H-NMR (CDCl$_3$, 400 Hz): δ 1.31 (3H, d, J=6.3 Hz), 3.41 (3H, s), 3.48 (1H, dd, J=10.2, 4.3 Hz), 3.58 (1H, dd, J=10.2, 5.9 Hz), 3.78 (1H, dd, J=12.5, 5.5 Hz), 3.92-3.97 (2H, m), 4.12 (1H, dd, J=13.7, 9.8 Hz), 4.51-4.59 (1H, m), 4.88-4.94 (1H, m), 6.39 (1H, t, J=2.0 Hz), 6.47 (1H, d, J=3.5 Hz), 6.72 (1H, s), 6.82 (1H, d, J=3.9 Hz), 7.06 (1H, s), 11.05 (1H, br s).

(125h) {(5R)-2-[5-(3-{[6-(Cyclopropylsulfonyl)pyridin-3-yl]oxy}-5-[(1S)-2-methoxy-1-methylethoxy]phenyl)-1H-pyrrol-2-yl]-4,5-dihydro-1,3-oxazol-5-yl}methanol 5-Chloro-2-(cyclopropylsulfonyl)pyridine (168 mg, 0.77 mmol) synthesized in Example (125c) and 3-{5-[(5R)-5-(Hydroxylmethyl)-4,5-dihydro-1,3-oxazol-2-yl]-1H-pyrrol-2-yl]-5-[(1S)-2-methoxy-1-methylethoxy]phenol (401 mg, 1.16 mmol) synthesized in Example (125g) were dissolved in N,N-dimethylformamide (2 mL), and potassium carbonate (213 mg, 154 mmol) was added, followed by stirring at 100° C. for 3 hours under nitrogen atmosphere. The reaction solution was cooled to room temperature, water (30 mL) was added, and extraction was carried out twice with ethyl acetate (30 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=0.5%-5%) to afford the desired compound (139 mg, yield 34%) as a white solid.

$^1$H-NMR (CDCl$_3$, 400 MHz): δ 1.06-1.11 (2H, m), 1.31 (3H, d, J=6.3 Hz), 1.37-1.41 (2H, m), 2.76-2.83 (1H, m), 3.42 (3H, d, J=2.3 Hz), 3.50 (1H, dd, J=10.2, 3.9 Hz), 3.59 (1H, dd, J=10.2, 6.3 Hz), 3.68-3.79 (2H, m), 3.87 (1H, dd, J=12.3, 2.9 Hz), 4.03 (1H, dd, J=14.1, 9.8 Hz), 4.60-4.53 (1H, m), 4.84-4.77 (1H, m), 6.49 (1H, d, J=3.9 Hz), 6.57 (1H, t, J=2.2 Hz), 6.75 (1H, d, J=3.9 Hz), 6.86 (1H, t, J=1.8 Hz), 7.03 (1H, s), 7.42 (1H, dd, J=8.6, 2.7 Hz), 7.97 (1H, d, J=8.6 Hz), 8.51 (1H, d, J=2.7 Hz).

MS (ESI) m/z: 528.17975 (M+H)$^+$.

Example 126

5-(3-{5-[(5R)-5-(Hydroxymethyl)-4,5-dihydro-1,3-oxazol-2-yl]-1H-pyrrol-2-yl}-5-[(1S)-2-methoxy-1-methylethoxy]phenoxy)-N-methylpyridine-2-carboxamide

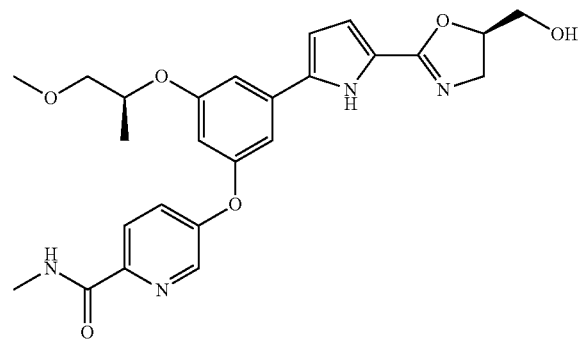

5-Fluoro-N-methylpyridine-2-carboxamide (150 mg, 0.97 mmol) synthesized in Example (123a) and 3-{5-[(5R)-5-(hydroxylmethyl)-4,5-dihydro-1,3-oxazol-2-yl]-1H-pyrrol-2-yl}-5-[(1S)-2-methoxy-1-methylethoxy]phenol (438 mg, 1.27 mmol) synthesized in Example (125g) were dissolved in N,N-dimethylformamide (3 mL), and potassium carbonate (269 mg, 1.95 mmol) was added, followed by stirring at 100° C. for 3 hours under nitrogen atmosphere. The reaction solution was cooled to room temperature, water (30 mL) was added, and extraction was carried out twice with ethyl acetate (30 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=0%-5%) to afford the desired compound (281 mg, yield 60%) as a white solid.

$^1$H-NMR (CDCl$_3$, 400 MHz): δ 1.30 (3H, d, J=6.3 Hz), 3.03 (3H, d, J=4.9 Hz), 3.41 (3H, s), 3.49 (1H, dd, J=10.3, 3.9 Hz), 3.58 (1H, dd, J=10.3, 6.3 Hz), 3.69 (1H, dd, J=11.7, 5.4 Hz), 3.76 (1H, dd, J=13.9, 7.1 Hz), 3.85 (1H, d, J=12.2 Hz), 4.02 (1H, dd, J=14.2, 9.3 Hz), 4.58-4.52 (1H, m), 4.78 (1H, s), 6.47 (1H, d, J=3.9 Hz), 6.54 (1H, t, J=2.2 Hz), 6.73 (1H, d, J=3.4 Hz), 6.83 (1H, t, J=1.7 Hz), 6.98 (1H, s), 7.40 (1H, dd, J=8.8, 2.9 Hz), 7.86 (1H, d, J=4.4 Hz), 8.16 (1H, d, J=8.3 Hz), 8.30 (1H, d, J=2.4 Hz).

MS (ESI) m/z: 481.20954 (M+H)$^+$.

Example 127

5-(3-{5-[(5R)-5-(Hydroxymethyl)-4,5-dihydro-1,3-oxazol-2-yl]-1H-pyrrol-2-yl}-5-[(1S)-2-methoxy-1-methylethoxy]phenoxy)-N-methylpyridine-2-sulfonamide

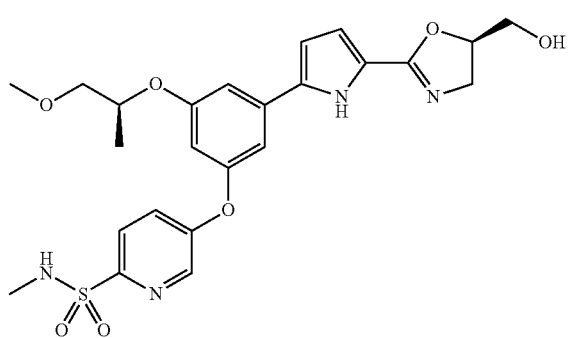

(127a) 5-(3-{5-[(5R)-5-Hydroxymethyl-4,5-dihydro-1,3-oxazol-2-yl]-1H-pyrrol-2-yl}-5-[(1S)-2-methoxy-1-methylethoxy]phenoxy)-N-(4-methoxybenzyl)-N-methylpyridine-2-sulfonamide 5-Chloro-N-(4-methoxybenzyl)-N-methylpyridine-2-sulfonamide (427 mg, 1.31 mmol) synthesized in Example (121b) and 3-{5-[(5R)-5-(hydroxylmethyl)-4,5-dihydro-1,3-oxazol-2-yl]-1H-pyrrol-2-yl}-5-[(1S)-2-methoxy-1-methylethoxy]phenol (568 mg, 1.64 mmol) synthesized in Example (125g) were dissolved in N,N-dimethylformamide (5 mL), and potassium carbonate (361 mg, 2.61 mmol) was added, followed by stirring at 100° C. for 2 hours under nitrogen atmosphere. The reaction solution was cooled to room temperature, water (40 mL) was added, and extraction was carried out twice with ethyl acetate (40 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=0%-3.5%) to afford the desired compound (228 mg, yield 27%) as a white solid.

$^1$H-NMR (CDCl$_3$, 400 MHz): δ 1.31 (3H, d, J=5.9 Hz), 2.79 (3H, s), 3.43 (3H, s), 3.51 (1H, dd, J=10.3, 3.9 Hz), 3.59 (1H, dd, J=10.3, 6.3 Hz), 3.69-3.73 (1H, m), 3.75-3.81 (4H, m), 3.87 (1H, d, J=12.2 Hz), 4.04 (1H, dd, J=14.2, 9.8 Hz), 4.37 (2H, s), 4.55-4.58 (1H, m), 4.79-4.84 (1H, m), 6.50 (1H, d, J=3.9 Hz), 6.58 (1H, t, J=2.2 Hz), 6.76 (1H, d, J=3.9 Hz), 6.85 (1H, s), 6.88 (2H, d, J=8.8 Hz), 6.99 (1H, s), 7.28 (3H, d, J=8.8 Hz), 7.42 (1H, dd, J=8.8, 2.9 Hz), 7.94 (1H, d, J=8.8 Hz), 8.47 (1H, d, J=2.4 Hz).

(127b) 5-(3-{5-[(5R)-5-(Hydroxymethyl)-4,5-dihydro-1,3-oxazol-2-yl]-1H-pyrrol-2-yl}-5-[(1S)-2-methoxy-1-methylethoxy]phenoxy)-N-methylpyridine-2-sulfonamide 5-(3-{5-[(5R)-5-Hydroxymethyl-4,5-dihydro-1,3-oxazol-2-yl]-1H-pyrrol-2-yl}-5-[(1S)-2-methoxy-1-methylethoxy]phenoxy)-N-(4-methoxybenzyl)-N-methylpyridine-2-sulfonamide (292 mg, 0.47 mmol) synthesized in Example (127a) was dissolved in trifluoroacetic acid (2 mL), and stirring was carried out at 45° C. for 6 hours. The solvent was distilled off under reduced pressure, methylene chloride and triethylamine were added in small portions to the residue, and the solvent was distilled off again under reduced pressure. The resulting residue was purified using silica gel column chromatography (elution solvent: methanol/methylene chloride=0%-4%) to afford the desired compound (184 mg, yield 100%) as a white solid.

$^1$H-NMR (CDCl$_3$, 400 MHz): δ 1.34 (3H, d, J=5.9 Hz), 1.43 (3H, d, J=6.3 Hz), 2.76 (3H, s), 3.41 (3H, s), 3.49-3.61 (3H, m), 4.08 (1H, dd, J=13.9, 9.0 Hz), 4.61-4.55 (1H, m), 4.84 (1H, dd, J=15.1, 7.3 Hz), 6.50 (1H, d, J=3.9 Hz), 6.56 (1H, t, J=2.2 Hz), 6.76 (1H, d, J=3.9 Hz), 6.86 (1H, s), 7.04 (1H, s), 7.41 (1H, dd, J=8.5, 2.7 Hz), 7.96 (1H, d, J=8.8 Hz), 8.45 (1H, d, J=2.4 Hz).

MS (ESI) m/z: 517.17549 (M+H)$^+$.

Example 128

5-(3-{5-[(5R)-5-(Hydroxymethyl)-4,5-dihydro-1,3-oxazol-2-yl]-1H-pyrrol-2-yl}-5-[(1S)-2-methoxy-1-methylethoxy]phenoxy)-N-methylpyrazine-2-sulfonamide

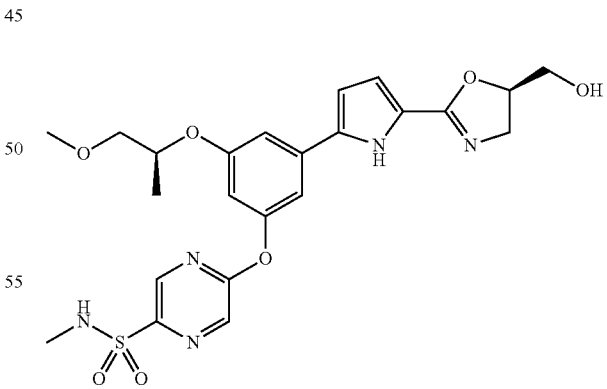

(128a) 5-Bromopyrazine-2-thiol

Under nitrogen atmosphere, 2,5-dibromopyrazine (300 mg, 1.26 mmol) was dissolved in dimethyl sulfoxide (3 mL), and sodium disulfide nonahydrate (454 mg, 1.89 mmol) was added, followed by stirring at 100° C. for 1.5 hours. The reaction solution was cooled to room temperature, and water (30 mL) was added, followed by neutralization with 5N hydrochloric acid. After the resulting precipitate was filtered off and washed with water, the resulting solid was dissolved in diethyl ether/tetrahydrofuran, and the insolubles were filtered off. The solvent was distilled off under reduced pressure, and vacuum drying was carried out to afford the desired compound (163 mg, yield 68%) as an orange solid.

$^1$H-NMR (CDCl$_3$, 400 MHz): δ 3.19 (1H, s), 7.97 (1H, d, J=1.0 Hz), 8.34 (1H, d, J=1.0 Hz).

(128b) 5-Bromo-N-methylpyrazine-2-sulfonamide

5-Bromopyrazine-2-thiol (988 mg, 5.17 mmol) synthesized in Example (128a) was dissolved in methylene chloride (15 mL)/1N hydrochloric acid (15 mL), and cooled to −10° C. To the reaction solution, ice-cooled 7% aqueous sodium perchlorate solution (15 mL) was added dropwise while being kept at −5° C. or below, and stirring was carried out as it is for 1 hour. The organic layer was extracted with a separatory funnel ice-cooled in advance and cooled to 0° C., a commercially available 40% methylamine/methanol solution (1.00 mL, 12.9 mmol) was added, and the temperature was brought back to room temperature, followed by stirring for 17 hours. To the reaction solution, a saturated aqueous ammonium chloride solution (30 mL) was added, and extraction was carried out twice with methylene chloride (30 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=0%-30%) to afford the desired compound (147 mg, yield 11%) as a white solid.

$^1$H-NMR (CDCl$_3$, 400 MHz): δ 2.83 (3H, d, J=5.5 Hz), 4.80 (1H, s), 8.76 (1H, d, J=1.6 Hz), 8.96 (1H, d, J=1.2 Hz).

(128c) 5-(3-{5-[(5R)-5-(Hydroxymethyl)-4,5-dihydro-1,3-oxazol-2-yl]-1H-pyrrol-2-yl}-5-[(1S)-2-methoxy-1-methylethoxy]phenoxy)-N-methylpyrazine-2-sulfonamide 5-Bromo-N-methylpyrazine-2-sulfonamide (147 mg, 0.58 mmol) synthesized in Example (128b) and 3-{5-[(5R)-5-(Hydroxylmethyl)-4,5-dihydro-1,3-oxazol-2-yl]-1H-pyrrol-2-yl}-5-[(1S)-2-methoxy-1-methylethoxy]phenol (262 mg, 0.76 mmol) synthesized in Example (125g) were dissolved in acetonitrile (6 mL), and potassium carbonate (161 mg, 1.17 mmol) was added, followed by stirring for 4 hours under nitrogen atmosphere. Water (20 mL) was added to the reaction solution, and extraction was carried out twice with ethyl acetate (20 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=0%-3.5%) to afford the desired compound (161 mg, yield 54%) as a white solid.

$^1$H-NMR (CDCl$_3$, 400 MHz): δ 1.32 (3H, d, J=6.3 Hz), 2.81 (3H, s), 3.42 (3H, s), 3.51 (1H, dd, J=10.3, 3.9 Hz), 3.60 (1H, dd, J=10.3, 5.9 Hz), 3.68-3.76 (2H, m), 3.85 (1H, dd, J=12.2, 3.4 Hz), 4.00 (1H, dd, J=14.2, 9.8 Hz), 4.60-4.54 (1H, m), 4.76-4.82 (1H, m), 5.23 (1H, s), 6.49 (1H, d, J=3.9 Hz), 6.66 (1H, t, J=2.0 Hz), 6.75 (1H, d, J=3.4 Hz), 6.96 (1H, t, J=1.7 Hz), 7.06 (1H, t, J=2.0 Hz), 8.44 (1H, d, J=1.5 Hz), 8.70 (1H, d, J=1.0 Hz).

MS (ESI) m/z: 518.17036 (M+H)$^+$.

Example 129

1-{[5-(3-[(1S)-2-Methoxy-1-methylethoxy]-5-{5-[(5S)-5-methyl-4,5-dihydro-1,3-oxazol-2-yl]-1H-pyrrol-2-yl}phenoxy)pyridin-2-yl]carbonyl}-4-methylpiperazine

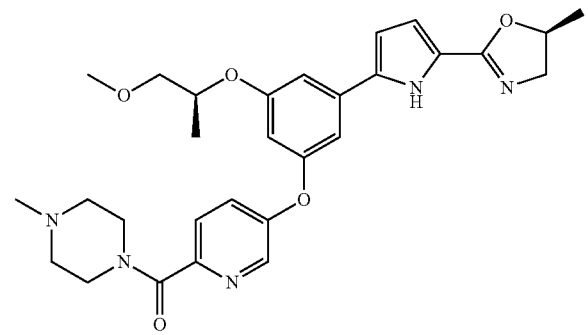

(129a) Methyl 5-fluoro pyridine-2-carboxylate

Commercially available 2-bromo-5-fluoro pyridine (3.80 g, 21.6 mmol) was dissolved in methanol (50 mL) and N,N-dimethylformamide (50 mL), and palladium acetate (484 mg, 2.16 mmol), 1,1-bis(diphenylphosphino)ferrocene (2.39 g, 4.32 mmol) and triethylamine (6.0 mL, 43.2 mmol) were added, followed by stirring at room temperature for 3 days under carbon monoxide atmosphere, and filtering off the insolubles in the reaction solution. Water (100 mL) was added, followed by extraction with ethyl acetate (100 mL), and the organic layer was washed with saturated brine and dried over anhydrous magnesium sulfate. The solvent was distilled off under reduced pressure, and the resulting residue was purified using silica gel column chromatography (elution solvent: ethyl acetate/hexane=0%-50%) to afford the desired compound (2.87 g, yield 86%) as a pale yellow solid.

$^1$H-NMR (CDCl$_3$, 400 MHz): δ 4.01 (3H, s), 7.54 (1H, dt, J=8.6, 3.9 Hz), 8.20 (1H, dd, J=8.6, 4.7 Hz), 8.59 (1H, d, J=2.7 Hz).

(129b) Methyl 5-(3-{5-[(benzyloxy)carbonyl]-1H-pyrrol-2-yl}-5-[(1S)-2-methoxy-1-methylethoxy]phenoxy)pyridine-2-carboxylate 2-Benzyl 1-t-butyl 5-{3-hydroxy-5-[(1S)-2-methoxy-1-methylethoxy]phenyl}-1H-pyrrole-1,2-dicarboxylate (4.08 g, 8.47 mmol) synthesized in Example (78g) and methyl 5-fluoro pyridine-2-carboxylate (1.45 g, 9.32 mmol) synthesized in Example (129a) were dissolved in N,N-dimethylformamide (30 mL), and potassium carbonate (3.51 g, 25.4 mmol) was added, followed by stirring at 100° C. for 3 hours under nitrogen atmosphere. The reaction solution was cooled to room temperature, water (100 mL) was added, and extraction was carried out with ethyl acetate (100 mL). The organic layer was washed with saturated brine, and subsequently dried over anhydrous magnesium sulfate. The solvent was distilled off under reduced pressure, and the resulting residue was purified using silica gel column chromatography (elution solvent: ethyl acetate/hexane=0%-35%).

The resulting yellow solid was dissolved in methylene chloride (5 mL), and trifluoroacetic acid (7.5 mL) was added, followed by stirring at room temperature for 1 hour. To the reaction solution, a saturated aqueous sodium hydrogencarbonate solution (50 mL) was added, and extraction was carried out twice with ethyl acetate (50 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=0%-5%) to afford the desired compound (3.26 g, yield 75%) as a pale yellow solid.

$^1$H-NMR (CDCl$_3$, 400 MHz): δ 1.32 (3H, d, J=6.3 Hz), 3.40 (3H, s), 3.50 (1H, dd, J=10.2, 3.9 Hz), 3.58 (1H, dd, J=10.4, 6.5 Hz), 4.00 (3H, s), 4.52-4.59 (1H, m), 5.32 (2H, s), 6.50 (1H, t, J=2.9 Hz), 6.59 (1H, s), 6.83 (1H, s), 6.99-6.97 (2H, m), 7.34-7.44 (5H, m), 8.12 (1H, d, J=8.6 Hz), 8.52 (1H, d, J=2.7 Hz), 9.22 (1H, s).

(129c) 5-(3-{[6-(Methoxycarbonyl)]pyridin-3-yl]oxy}-5-[(1S)-2-methoxy-1-methylethoxy]phenyl)-1H-pyrrole-2-carboxylic acid Methyl 5-(3-{5-[(benzyloxy)carbonyl]-1H-pyrrol-2-yl}-5-[(1S)-2-methoxy-1-methylethoxy]phenoxy)pyridine-2-carboxylate (3.18 g, 6.16 mmol) synthesized in Example (129b) was dissolved in 5% formic acid/ethanol (200 mL), and a 10% palladium carbon catalyst (2.00 g) was added, followed by stirring for 2 hours under hydrogen atmosphere. The palladium carbon catalyst was removed by Celite filtration, followed by washing with tetrahydrofuran. The solvent was distilled off under reduced pressure, followed by dilution with methylene chloride (100 mL), washing with water, and drying over anhydrous magnesium sulfate. The solvent was distilled off under reduced pressure to afford the desired compound (2.41 g, yield 92%) as a white solid.

$^1$H-NMR (CDCl$_3$, 400 MHz): δ 1.33 (3H, d, J=6.3 Hz), 3.46 (3H, s), 3.54 (1H, dd, J=10.2, 3.9 Hz), 3.66 (1H, dd, J=10.2, 6.6 Hz), 4.00 (3H, s), 4.71 (1H, td, J=6.3, 4.3 Hz), 6.49 (1H, dd, J=3.9, 2.7 Hz), 6.59 (1H, d, J=2.0 Hz), 6.92 (1H, t, J=1.6 Hz), 7.02 (1H, dd, J=3.9, 2.3 Hz), 7.39 (1H, dd, J=8.8, 2.9 Hz), 8.13 (1H, d, J=8.6 Hz), 8.57 (1H, d, J=2.7 Hz), 10.46 (1H, s).

(129d) Methyl 5-(3-{[(2R)-2-hydroxypropyl]carbamoyl}-1H-pyrrol-2-yl)-5-[(1S)-2-methoxy-1-methylethoxy]phenoxyl}pyridine-2-carboxylate 5-(3-{[6-(Methoxycarbonyl)]pyridin-3-yl]oxy}-5-[(1S)-2-methoxy-1-methylethoxy]phenyl)-1H-pyrrole-2-carboxylic acid (800 mg, 1.87 mmol) synthesized in Example (129c) was dissolved in methanol (20 mL), and (R)-(−)-1-amino-2-propanol (339 μL, 4.30 mol) and 4-(4,6-dimethoxy-1,3,5-triazin-2-yl)-4-methylmorpholinium chloride n hydrate (829 mg, 2.99 mmol) were added, followed by stirring at room temperature for 16 hours under nitrogen atmosphere. The solvent was distilled off under reduced pressure, and the resulting residue was purified using silica gel column chromatography (elution solvent: methanol/methylene chloride=0%-5%) to afford the desired compound (726 mg, yield 80%) as a white solid.

$^1$H-NMR (CDCl$_3$, 400 MHz): δ 1.25 (3H, d, J=6.6 Hz), 1.32 (3H, d, J=6.3 Hz), 3.25-3.32 (1H, m), 3.41 (3H, s), 3.51 (1H, dd, J=10.2, 3.9 Hz), 3.57-3.65 (2H, m), 4.05 (3H, s), 4.58 (1H, td, J=6.3, 4.0 Hz), 6.35 (1H, s), 6.48 (1H, d, J=3.9, 3.1 Hz), 6.57 (1H, t, J=2.2 Hz), 6.61 (1H, dd, J=3.9, 2.3 Hz), 6.85 (1H, t, J=1.8 Hz), 7.00 (1H, t, J=1.8 Hz), 7.36 (1H, dd, J=8.8, 2.9 Hz), 8.12 (1H, d, J=9.0 Hz), 8.53 (1H, d, J=2.7 Hz), 9.66 (1H, s).

(129e) Methyl 5-(3-[(1S)-2-methoxy-1-methylethoxy]-5-{5-[(5S)-5-methyl-4,5-dihydro-1,3-oxazol-2-yl]-1H-pyrrol-2-yl}phenoxy)pyridine-2-carboxylate Methyl 5-(3-{[(2R)-2-hydroxypropyl]carbamoyl}-1H-pyrrol-2-yl)-5-[(1S)-2-methoxy-1-methylethoxy]phenoxyl}pyridine-2-carboxylate (726 mg, 1.50 mmol) synthesized in Example (129d) was dissolved in tetrahydrofuran (20 mL), and anhydrous methanesulfonic acid (523 mg, 3.00 mmol) and triethylamine (0.63 mL, 4.50 mmol) were added, followed by stirring at 50° C. for 5 hours under nitrogen atmosphere. To the reaction solution, a saturated aqueous ammonium chloride solution (30 mL) was added, and extraction was carried out with methylene chloride (30 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=0%-7.5%) to afford the desired compound (264 mg, yield 38%) as a pale yellow solid.

$^1$H-NMR (CDCl$_3$, 400 MHz): δ 1.32 (3H, d, J=6.3 Hz), 1.42 (3H, d, J=6.3 Hz), 3.41 (3H, d, J=3.1 Hz), 3.54 (3H, ddt, J=26.4, 11.3, 4.4 Hz), 4.01 (3H, s), 4.04-4.11 (1H, m), 4.60-4.53 (1H, m), 4.87-4.78 (1H, m), 6.49 (1H, d, J=3.9 Hz), 6.55 (1H, t, J=2.0 Hz), 6.75 (1H, d, J=3.9 Hz), 6.83 (1H, t, J=1.8 Hz), 6.99 (1H, t, J=2.0 Hz), 7.35 (1H, dd, J=8.6, 2.7 Hz), 8.12 (1H, d, J=9.0 Hz), 8.53 (1H, d, J=2.7 Hz).

(129f) 5-(3-[(1S)-2-Methoxy-1-methylethoxy]-5-{5-[(5S)-5-methyl-4,5-dihydro-1,3-oxazol-2-yl]-1H-pyrrol-2-yl}phenoxy)pyridine-2-carboxylic acid Methyl 5-(3-[(1S)-2-methoxy-1-methylethoxy]-5-{5-[(5S)-5-methyl-4,5-dihydro-1,3-oxazol-2-yl]-1H-pyrrol-2-yl}phenoxy)pyridine-2-carboxylate (264 mg, 0.57 mmol) synthesized in Example (129e) was dissolved in methanol (20 mL), and water (3 mL) and lithium hydroxide monohydrate (71 mg, 1.70 mmol) were added, followed by stirring at 50° C. for 1 hour under nitrogen atmosphere. To the reaction solution, a saturated aqueous ammonium chloride solution (50 mL) was added, followed by extraction twice with methylene chloride (40 mL), washing with saturated brine, and drying over sodium sulfate. The solvent was distilled off under reduced pressure, and vacuum drying was carried out to afford the desired compound (256 mg, yield 100%) as a pale yellow solid.

$^1$H-NMR (CDCl$_3$, 400 MHz): δ 1.40 (3H, d, J=6.3 Hz), 1.67 (3H, d, J=6.3 Hz), 3.43 (3H, s), 3.58-3.65 (2H, m), 3.78 (1H, dd, J=11.2, 7.8 Hz), 4.29 (1H, t, J=10.3 Hz), 4.84-4.90 (1H, m), 5.30-5.36 (1H, m), 6.65 (1H, d, J=3.9 Hz), 6.69 (1H, t, J=2.2 Hz), 7.21 (2H, s), 7.50 (1H, dd, J=7.3, 3.4 Hz), 7.56 (1H, s), 8.18 (1H, s), 8.39 (1H, d, J=2.4 Hz).

(129g) 1-{[5-(3-[(1S)-2-Methoxy-1-methylethoxy]-5-{5-[(5S)-5-methyl-4,5-dihydro-1,3-oxazol-2-yl]-1H-pyrrol-2-yl}phenoxy)pyridin-2-yl]carbonyl}-4-methylpiperazine 5-(3-[(1S)-2-Methoxy-1-methylethoxy]-5-{5-[(5S)-5-methyl-4,5-dihydro-1,3-oxazol-2-yl]-1H-pyrrol-2-yl}phenoxy)pyridine-2-carboxylic acid (270 mg, 0.60 mmol)

synthesized in Example (129f) was dissolved in tetrahydrofuran (5 mL), and N-methylpiperazine (199 μL, 1.79 mmol), HATU (454 mg, 1.19 mmol) and N,N-diisopropylethylamine (624 μL, 3.58 mmol) were added, followed by stirring at room temperature for 3 days under nitrogen atmosphere. To the reaction solution, saturated brine (15 mL) was added, and extraction was carried out twice with ethyl acetate (15 mL), followed by drying over sodium sulfate. The solvent was distilled off under reduced pressure, and the resulting residue was purified using silica gel column chromatography (elution solvent: methanol/methylene chloride=0%-5%) to afford the desired compound (208 mg, yield 65%) as a pale yellow solid.

$^1$H-NMR (CDCl$_3$, 400 MHz): δ 1.32 (3H, d, J=6.3 Hz), 1.42 (3H, d, J=5.9 Hz), 2.33 (3H, s), 2.44 (2H, t, J=4.9 Hz), 2.52 (2H, t, J=4.9 Hz), 3.41 (3H, d, J=0.8 Hz), 3.48-3.60 (3H, m), 3.73 (2H, br s), 3.84 (2H, br s), 4.08 (1H, dd, J=14.3, 9.2 Hz), 4.56 (1H, dd, J=10.2, 6.3 Hz), 4.83 (1H, dd, J=15.6, 6.6 Hz), 6.49 (1H, d, J=4.3 Hz), 6.54 (1H, t, J=2.0 Hz), 6.75 (1H, d, J=3.9 Hz), 6.81 (1H, t, J=1.8 Hz), 6.95 (1H, t, J=1.8 Hz), 7.38 (1H, dd, J=8.6, 2.7 Hz), 7.69 (1H, d, J=8.6 Hz), 8.36 (1H, d, J=2.7 Hz).

MS (ESI) m/z: 534.27234 (M+H)$^+$.

Example 130

(2S)-2-[3-{5-[(5S)-5-Methyl-4,5-dihydro-1,3-oxazol-2-yl]-1H-pyrrol-2-yl}-5-({6-[(4-methylpiperazin-1-yl)carbonyl]pyridin-3-yl}oxy)phenoxy]propan-1-ol

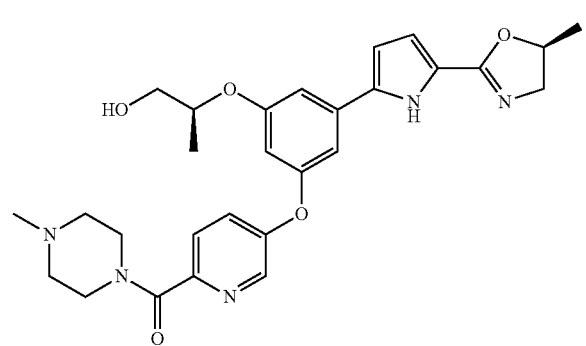

1-{[5-(3-[(1S)-2-Methoxy-1-methylethoxy]-5-{5-[(5S)-5-methyl-4,5-dihydro-1,3-oxazol-2-yl]-1H-pyrrol-2-yl}phenoxy)pyridin-2-yl]carbonyl}-4-methylpiperazine (185 mg, 0.35 mmol) synthesized in Example (129g) was dissolved in methylene chloride (10 mL), and boron tribromide (1.0 mol/L methylene chloride solution, 694 μL, 0.694 mmol) was added at −78° C. Subsequently, the temperature was brought back to room temperature, followed by stirring for 50 minutes. To the reaction solution, a saturated aqueous sodium hydrogencarbonate solution was added, and extraction was carried out with ethyl acetate. The organic layer was washed with saturated brine, and subsequently dried over sodium sulfate. The solvent was distilled off under reduced pressure, and the resulting residue was purified using silica gel column chromatography (elution solvent: methanol/methylene chloride=0%-10%) to afford the desired compound (51 mg, yield 28%) as a white solid.

$^1$H-NMR (CDCl$_3$, 400 MHz): δ 1.28 (3H, d, J=6.3 Hz), 1.43 (3H, d, J=6.3 Hz), 2.34 (3H, s), 2.44 (2H, t, J=4.9 Hz), 2.53 (2H, t, J=4.9 Hz), 3.55 (1H, dd, J=13.9, 7.2 Hz), 3.72 (2H, t, J=4.7 Hz), 3.78 (2H, d, J=5.5 Hz), 3.84 (2H, s), 4.09 (1H, dd, J=13.9, 9.2 Hz), 4.60 (1H, dd, J=11.3, 5.5 Hz), 4.85 (1H, dt, J=11.6, 4.5 Hz), 6.35 (1H, s), 6.46 (1H, d, J=3.9 Hz), 6.75 (1H, d, J=3.9 Hz), 6.79 (1H, t, J=1.8 Hz), 6.90 (1H, s), 7.33 (1H, dd, J=8.6, 2.7 Hz), 7.67 (1H, dd, J=8.6, 0.8 Hz), 8.33 (1H, t, J=1.8 Hz).

MS (ESI) m/z: 520.25784 (M+H)$^+$.

Example 131

2-(3-[(1S)-2-Methoxy-1-methylethoxy]-5-{5-[(5S)-5-methyl-4,5-dihydro-1,3-oxazol-2-yl]-1H-pyrrol-2-yl}phenoxy)-5-[(4-methylpiperazin-1-yl)carbonyl]pyrazine

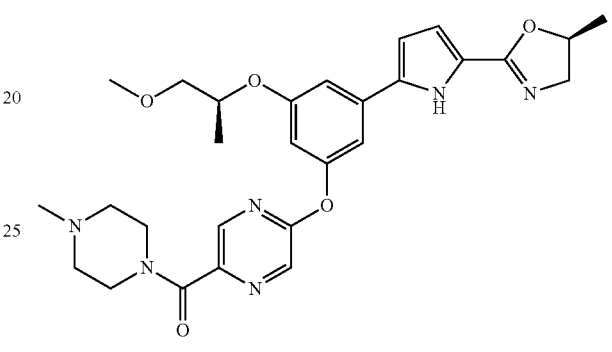

(131a) 2-Chloro-5-[(4-methylpiperazin-1-yl)carbonyl]pyrazine

Commercially available 5-hydroxypyrazine-2-carboxylic acid (5.00 g, 39.0 mmol) was dissolved in thionyl chloride (64 mL), and a few drops of N,N-dimethylformamide were added, followed by heating to reflux for 5 hours under nitrogen atmosphere. The solvent was distilled off under reduced pressure, and the resulting residue was diluted with methylene chloride (50 mL). While being cooled in an ice bath, diisopropylethylamine (18.7 mL, 107 mmol) and 1-methylpiperazine (4.37 mL, 39.2 mmol) were added, and stirring was carried out at room temperature for 3 days under nitrogen atmosphere. To the reaction solution, water (100 mL) was added, and extraction was carried out with methylene chloride (100 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=3%-5%) to afford the desired compound (5.32 g, yield 62%) as a brown solid.

$^1$H-NMR (CDCl$_3$, 400 MHz): δ 2.34 (3H, s), 2.44 (2H, t, J=5.1 Hz), 2.53 (2H, t, J=5.1 Hz), 3.64 (2H, t, J=5.1 Hz), 3.84 (2H, t, J=4.9 Hz), 8.55 (1H, d, J=1.2 Hz), 8.76 (1H, d, J=1.6 Hz).

(131b) Benzyl 5-{3-[(1S)-2-methoxy-1-methylethoxy]-5-({5-[(4-methylpiperazin-1-yl)carbonyl]pyrazin-2-yl}oxy)phenyl}-1H-pyrrole-2-carboxylate 2-Benzyl 1-t-butyl 5-{3-hydroxy-5-[(1S)-2-methoxy-1-methylethoxy]phenyl}-1H-pyrrole-1,2-dicarboxylate (2.00 g, 4.15 mmol) synthesized in Example (78g) and 2-chloro-5-[(4-methylpiperazin-1-yl)carbonyl]pyrazine (1.10 g, 4.57 mmol) synthesized in Example (131a) were dissolved in N,N- dimethylformamide (20 mL), and potassium carbonate (1.72 g, 12.5 mmol) was added, followed by stirring at 80° C. for 4 hours under nitrogen atmosphere. The reaction solution was cooled to room temperature, water (80 mL) was added, and extraction was carried out twice with ethyl acetate (50 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=0%-7.5%) to afford a compound (2.88 g) as a brown oil.

This was dissolved in methylene chloride (5 mL), and trifluoroacetic acid (5 mL) was added, followed by stirring at room temperature for 2 hours. To the reaction solution, a saturated aqueous sodium hydrogencarbonate solution (50 mL) was added, and extraction was carried out twice with methylene chloride (50 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=0%-7.5%) to afford the desired compound (1.96 g, yield 81%) as a pale yellow solid.

$^1$H-NMR (CDCl$_3$, 400 MHz): δ1.34 (3H, d, J=6.3 Hz), 2.34 (3H, s), 2.45 (2H, t, J=4.5 Hz), 2.53 (2H, t, J=4.9 Hz), 3.41 (3H, s), 3.51 (1H, dd, J=10.9, 3.7 Hz), 3.59 (1H, dd, J=9.8, 5.5 Hz), 3.71 (2H, br s), 3.84 (2H, br s), 4.53-4.60 (1H, m), 5.33 (2H, s), 6.51 (1H, dd, J=3.9, 2.7 Hz), 6.69 (1H, t, J=2.0 Hz), 6.93 (1H, s), 6.98 (1H, dd, J=3.7, 2.5 Hz), 7.02 (1H, s), 7.34-7.44 (5H, m), 8.35 (1H, t, J=1.4 Hz), 8.54 (1H, d, J=0.8 Hz), 9.21 (1H, br s).

(131c) N-[(2R)-2-Hydroxypropyl]-5-(3-[(1S)-2-methoxy-1-methylethoxy]-5-({5-[(4-methylpiperazin-1-yl)carbonyl]pyrazin-2-yl}oxy)phenyl}-1H-pyrrole-2-carboxamide Benzyl 5-{3-[(1S)-2-methoxy-1-methylethoxy]-5-({5-[(4-methylpiperazin-1-yl)carbonyl]pyrazin-2-yl}oxy)phenyl}-1H-pyrrole-2-carboxylate (1.94 g, 3.32 mmol) synthesized in Example (131b) was dissolved in methanol (100 mL), and a 10% palladium carbon catalyst (1.20 g) was added, followed by stirring at room temperature for 2.5 hours under hydrogen atmosphere. The palladium carbon catalyst was removed by Celite filtration, followed by washing with tetrahydrofuran. The solvent was distilled off under reduced pressure to afford a white solid (1.45 g).

This white solid (700 mg, 1.41 mmol) and 4-dimethylaminopyridine (86 mg, 0.71 mmol) were dissolved in methylene chloride (30 mL), and WSCI•HCl (625 mg, 2.26 mmol) and (R)-1-amino-2-propanol (256 μL, 3.25 mmol) were added at room temperature, followed by stirring for 3 days under nitrogen atmosphere. The reaction solution was diluted with methylene chloride (60 mL), washed with saturated aqueous sodium hydrogencarbonate solution and saturated brine, and subsequently dried over anhydrous magnesium sulfate. The solvent was distilled off under reduced pressure, and the resulting residue was purified using silica gel column chromatography (elution solvent: methanol/methylene chloride=0%-10%) to afford the desired product (447 mg, 50%) as a white solid.

$^1$H-NMR (CDCl$_3$, 400 MHz): δ 1.23 (3H, d, J=6.3 Hz), 1.33 (3H, d, J=8.0 Hz), 2.34 (3H, s), 2.45 (2H, t, J=4.7 Hz), 2.53 (2H, t, J=4.7 Hz), 3.23-3.30 (1H, m), 3.42 (3H, s), 3.51 (1H, dd, J=10.2, 4.3 Hz), 3.58-3.63 (2H, m), 3.71 (2H, t, J=4.7 Hz), 3.84 (2H, t, J=5.5 Hz), 4.00 (1H, br s), 4.53-4.60 (1H, m), 6.37 (1H, s), 6.49 (1H, t, J=3.3 Hz), 6.61 (1H, dd, J=3.9, 2.3 Hz), 6.66 (1H, s), 6.93 (1H, t, J=1.8 Hz), 7.02 (1H, t, J=2.0 Hz), 8.34 (1H, s), 8.53 (1H, s), 9.66 (1H, br s).

(131d) 2-(3-[(1S)-2-Methoxy-1-methylethoxy]-5-{5-[(5S)-5-methyl-4,5-dihydro-1,3-oxazol-2-yl]-1H-pyrrol-2-yl}phenoxy)-5-[(4-methylpiperazin-1-yl)carbonyl]pyrazine N-[(2R)-2-Hydroxypropyl]-5-(3-[(1S)-2-methoxy-1-methylethoxy]-5-({5-[(4-methylpiperazin-1-yl)carbonyl]pyrazin-2-yl}oxy)phenyl}-1H-pyrrole-2-carboxamide (447 mg, 0.81 mmol) synthesized in Example (131c) was dissolved in tetrahydrofuran (20 mL), and anhydrous methanesulfonic acid (282 mg, 1.62 mmol) and triethylamine (0.34 mL, 2.43 mmol) were added, followed by stirring at 50° C. for 4 hours under nitrogen atmosphere. To the reaction solution, a saturated aqueous ammonium chloride solution (30 mL) was added, and extraction was carried out twice with methylene chloride (30 mL). The organic layer was washed with saturated brine, and subsequently dried over anhydrous magnesium sulfate. The solvent was distilled off under reduced pressure, and the resulting residue was purified using silica gel column chromatography (elution solvent: methanol/methylene chloride=0%-5%) to afford the desired compound (279 mg, yield 65%) as a pale yellow solid.

$^1$H-NMR (CDCl$_3$, 400 MHz): δ 1.34 (3H, d, J=6.3 Hz), 1.42 (3H, d, J=6.3 Hz), 2.34 (3H, s), 2.46 (2H, t, J=4.7 Hz), 2.53 (2H, t, J=4.7 Hz), 3.42 (3H, s), 3.49-3.62 (3H, m), 3.72 (2H, t, J=4.3 Hz), 3.84 (2H, t, J=5.1 Hz), 4.08 (1H, dd, J=14.1, 9.0 Hz), 4.53-4.60 (1H, m), 4.87-4.78 (1H, m), 6.50 (1H, d, J=3.9 Hz), 6.65 (1H, t, J=2.2 Hz), 6.75 (1H, d, J=3.9 Hz), 6.91 (1H, t, J=1.8 Hz), 7.02 (1H, t, J=2.0 Hz), 8.34 (1H, d, J=1.2 Hz), 8.54 (1H, d, J=1.2 Hz).

MS (ESI) m/z: 535.26585 (M+H)$^+$.

Example 132

(2S)-2-[3-{5-[(5S)-5-Methyl-4,5-dihydro-1,3-oxazol-2-yl]-1H-pyrrol-2-yl}-5-({5-[(4-methylpiperazin-1-yl)carbonyl]pyrazin-2-yl}oxy)phenoxy]propan-1-ol

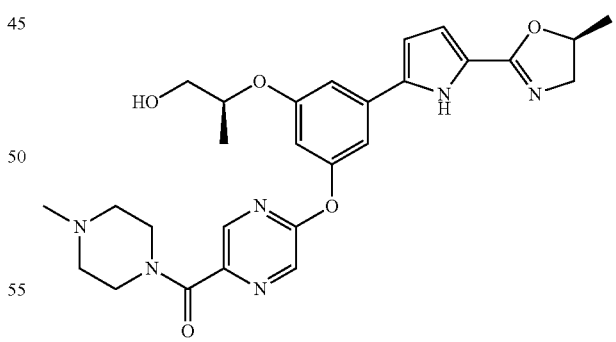

2-(3-[(1S)-2-Methoxy-1-methylethoxy]-5-{5-[(5S)-5-methyl-4,5-dihydro-1,3-oxazol-2-yl]-1H-pyrrol-2-yl}phenoxy)-5-[(4-methylpiperazin-1-yl)carbonyl]pyrazine (259 mg, 0.48 mmol) synthesized in Example (131d) was dissolved in methylene chloride (15 mL), and boron tribromide (1.0 mol/L methylene chloride solution, 0.81 mL, 0.81 mmol) was added at −78° C. Subsequently, the temperature was brought back to room temperature, followed by stirring for 3 hours. To the reaction solution, a saturated aqueous sodium hydrogencarbonate solution was added, and extraction was carried out with ethyl acetate. The organic layer was washed with saturated brine, and subsequently dried over sodium sulfate. The solvent was distilled off under reduced pressure, and the resulting residue was purified using silica gel column chromatography (elution solvent: methanol/methylene chloride=2%-8%) to afford the desired compound (62.4 mg, yield 25%) as a white solid.

$^1$H-NMR (CDCl$_3$, 400 MHz): δ 1.28 (4H, d, J=6.3 Hz), 1.41 (3H, d, J=6.3 Hz), 2.34 (3H, s), 2.45 (2H, t, J=4.5 Hz), 2.52 (2H, t, J=4.7 Hz), 3.53 (1H, dd, J=13.7, 7.4 Hz), 3.71 (2H, t, J=4.7 Hz), 3.77-3.79 (2H, m), 3.83 (2H, t, J=4.7 Hz), 4.07 (1H, dd, J=13.7, 9.4 Hz), 4.59 (1H, td, J=11.5, 5.7 Hz), 4.83 (1H, dq, J=17.8, 5.1 Hz), 6.44 (1H, d, J=3.9 Hz), 6.47 (1H, s), 6.72 (1H, d, J=3.9 Hz), 6.88 (1H, s), 6.94 (1H, s), 8.30 (1H, s), 8.52 (1H, d, J=0.8 Hz).

MS (ESI) m/z: 521.25002 (M+H)$^+$.

Test Example 1

(1) GK Preparation cDNA encoding human pancreatic GK polypeptide (GenBank Accession No. NM_000162, human glucokinase variant 1) was cloned from a human cDNA library by polymerase chain reaction (PCR), and introduced into a glutathione S-transferase (GST)-fused protein expression vector (GEX4T, GE Healthcare Bioscience). The vector was introduced into *Escherichia coli* (such as BL21 or JM109, Invitrogen), and the transformed *E. coli* was cultured overnight at 37° C. followed by recovery of the cells. After freezing and thawing the recovered cells, the cells were suspended in phosphate buffer containing Triton-X at a final concentration of 1% followed by disrupting the cells with an ultrasonic homogenizer. The supernatant obtained by low-speed centrifugation treatment of the homogenate (10,000×g, 30 minutes) was further subjected to high-speed centrifugation (100,000×g, 10 minutes) followed by recovering the supernatant and purifying the fused protein using a GST fused protein purification system (Bulk GST Purification Module, GE Healthcare Bioscience). The GK fused protein was divided into smaller aliquots and stored at −80° C.

(2) GK Activity Test

GK activity was measured using the GK purified in (1) above. More specifically, an enzyme solution was prepared by adding the purified GK of (1) above and glucose-6-phosphate dehydrogenase (Sigma) to solution 1 of a glucose assay kit (D-Glucose UV Method, Roche Diagnostics). The enzyme solution, a test compound diluent and glucose (final concentration: 5 mM) were mixed in a 96-well ELISA plate, and allowed to react for 30 minutes at room temperature. Following completion of the reaction, absorbance at a wavelength of 340 nm was measured using SpectraMax Plus (Molecular Probe). Furthermore, unreacted (when glucose was not added) absorbance was used for the background.

GK activation rates were indicated with values represented by the following numerical formula: (absorbance after reacting for 30 minutes when test compound added)/(absorbance after reacting for 30 minutes when test compound not added). The results for GK activation rates obtained at a test compound concentration of 1 μM are shown in Table 1.

TABLE 1

| Example | GK Activation Rate |
|---|---|
| 1 | 2.0 |
| 2 | 1.9 |
| 3 | 1.9 |
| 15 | 1.6 |
| 20 | 2.0 |
| 21 | 2.0 |
| 25 | 2.0 |
| 26 | 2.3 |
| 29 | 2.0 |
| 31 | 2.0 |
| 32 | 2.0 |
| 33 | 1.7 |
| 35 | 2.1 |
| 41 | 2.1 |
| 47 | 2.0 |
| 60 | 2.0 |
| 64 | 1.9 |
| 65 | 2.4 |
| 67 | 1.7 |
| 68 | 2.0 |
| 69 | 2.2 |
| 70 | 1.9 |
| 73 | 2.0 |
| 74 | 2.0 |
| 75 | 1.8 |
| 76 | 3.0 |
| 77 | 2.6 |
| 81 | 2.2 |
| 82 | 2.7 |
| 84 | 2.7 |
| 85 | 2.9 |
| 86 | 2.5 |
| 88 | 2.4 |
| 89 | 2.3 |
| 91 | 2.6 |
| 93 | 2.4 |
| 95 | 2.5 |
| 98 | 1.9 |
| 100 | 1.9 |
| 101 | 1.9 |
| 103 | 2.1 |
| 107 | 2.0 |
| 108 | 2.0 |
| 109 | 2.2 |
| 110 | 2.4 |
| 112 | 2.4 |
| 114 | 2.2 |
| 122 | 2.5 |
| 123 | 2.6 |
| 126 | 2.6 |
| 127 | 2.4 |

On the basis of the above results, compounds of the present invention have superior GK activating activity, and are useful as a therapeutic and/or preventive of a disease selected from the group consisting of diabetes, impaired glucose tolerance, gestational diabetes, chronic complications of diabetes (including diabetic peripheral neuropathy, diabetic nephropathy, diabetic retinopathy and diabetic macroangiopathy) and metabolic syndrome.

Preparation Example 1

Capsule

| | |
|---|---|
| Compound of Example 1 or 78 | 50 mg |
| Lactose | 128 mg |
| Cornstarch | 70 mg |
| Magnesium stearate | 2 mg |
| | 250 mg |

Powders of the above formulation were mixed and passed through a 60 mesh sieve followed by filling the powders into a 250 mg gelatin capsule to obtain a capsule.

Preparation Example 2

Tablet

| Compound of Example 1 or 78 | 50 mg |
|---|---|
| Lactose | 126 mg |
| Cornstarch | 23 mg |
| Magnesium stearate | 1 mg |
| | 200 mg |

Powders of the above formulation were mixed, granulated using cornstarch paste and dried, followed by forming into tablets with a tableting machine to obtain a 200 mg tablet. This tablet can be provided with a sugar coating as necessary.

Industrial Applicability

A compound represented by general formula (I) of the present invention, or a pharmacologically acceptable salt thereof, has superior GK activating activity, and is useful as a therapeutic or preventive (and particularly a therapeutic) for diabetes, impaired glucose tolerance, gestational diabetes, chronic complications of diabetes (including diabetic peripheral neuropathy, diabetic nephropathy, diabetic retinopathy and diabetic macroangiopathy) or metabolic syndrome (and particularly diabetes or impaired glucose tolerance) for use in warm-blooded animals (and particularly humans).

The invention claimed is:
1. A compound of formula (I), or a pharmacologically acceptable salt thereof:

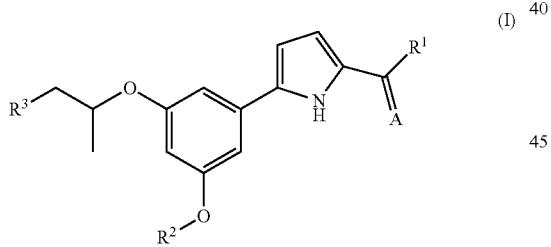

(I)

wherein,
A represents an oxygen atom;
$R^1$ represents a methyl group or a 2-chloroethylamino group; or
A and $R^1$ together with the carbon atom bonded thereto form a heterocyclic group which is a 2-pyridyl group, a 5,6-dihydro-4H-1,3-oxazin-2-yl group, a 1,3-thiazol-2-yl group, a 1,3-oxazol-2-yl group, a 1,3,4-oxadiazol-2-yl group, a 1,3,4-thiadiazol-2-yl group, a 4,5-dihydro-1,3-thiazol-2-yl group, a 4,5-dihydro-1,3-oxazol-2-yl group or a 1,3-benzothiazol-2-yl group optionally substituted with 1 to 3 groups each independently selected from Substituent Group γ,
wherein said Substituent Group γ is a group consisting of a halogen atom, a $C_1$-$C_6$ alkyl group, a $C_1$-$C_6$ halogenated alkyl group, a $C_1$-$C_6$ alkyl group substituted with 1 or 2 hydroxy groups, a $C_1$-$C_6$ alkoxy group, a carboxyl group, a mono-$C_1$-$C_6$ alkylaminocarbonyl group, a di-($C_1$-$C_6$ alkyl)aminocarbonyl group and a hydroxy group;
$R^2$ represents a phenyl group optionally substituted with 1 to 5 groups each independently selected from Substituent Group α or a heterocyclic group optionally substituted with 1 to 3 groups each independently selected from Substituent Group α, wherein, Substituent Group α is a group consisting of a halogen atom, a $C_1$-$C_6$ alkyl group, a $C_1$-$C_6$ halogenated alkyl group, a $C_2$-$C_6$ alkenyl group, a $C_2$-$C_6$ alkynyl group, a hydroxy group, a $C_1$-$C_6$ alkyl group substituted with 1 or 2 hydroxy groups, a $C_1$-$C_6$ alkoxy group, a $C_1$-$C_6$ halogenated alkoxy group, a ($C_1$-$C_6$ alkoxy)-($C_1$-$C_6$ alkyl) group, a ($C_1$-$C_6$ alkoxy)-($C_1$-$C_6$ alkoxy) group, a formyl group, a carboxyl group, a $C_2$-$C_7$ alkylcarbonyl group, a $C_2$-$C_7$ alkoxycarbonyl group, a $C_2$-$C_7$ alkylcarbonyloxy group, a $C_2$-$C_7$ alkoxycarbonyloxy group, a nitro group, an amino group, a mono-$C_1$-$C_6$ alkylamino group, a di-($C_1$-$C_6$ alkyl)amino group, a $C_1$-$C_6$ alkylthio group, a $C_1$-$C_6$ alkylsulfonyl group, a $C_3$-$C_6$ cycloalkylsulfonyl group, a $C_1$-$C_6$ hydroxyalkylsulfonyl group, a ($C_1$-$C_6$ alkoxy)-($C_1$-$C_6$ alkylsulfonyl) group, a group represented by the formula —V—$NR^5R^6$ (wherein V represents a carbonyl group or a sulfonyl group, and $R^5$ and $R^6$ may be the same or different and respectively represent a hydrogen atom or a $C_1$-$C_6$ alkyl group, or $R^5$ and $R^6$ together with the nitrogen atom bonded thereto form a 4- to 6-membered saturated heterocycle optionally substituted with 1 or 2 groups each independently selected from a $C_1$-$C_6$ alkyl group and a hydroxy group, and the 4- to 6-membered saturated heterocycle optionally further comprises one oxygen atom or one additional nitrogen atom), a mono-$C_2$-$C_7$ alkylcarbonylamino group, a mono-$C_1$-$C_6$ alkylaminocarbonyloxy group, a di-($C_1$-$C_6$ alkyl)aminocarbonyloxy group, a mono-$C_2$-$C_7$ alkoxycarbonylamino group, a mono-$C_1$-$C_6$ alkylsulfonylamino group, a cyano group, a 1,3,4-oxadiazol-2-yl group optionally substituted with a $C_1$-$C_6$ alkyl group at the 5-position, a 1,3,4-thiadiazol-2-yl group optionally substituted with a $C_1$-$C_6$ alkyl group at the 5-position, and an oxo group; and
$R^3$ represents a hydroxy group or a methoxy group.
2. The compound or pharmacologically acceptable salt thereof according to claim 1, wherein the formula (I) is formula (Ia);

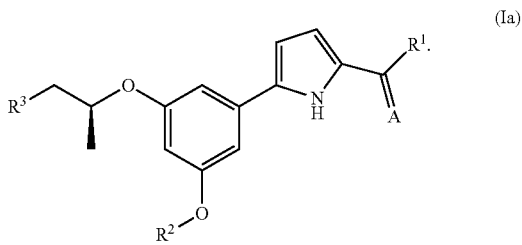

(Ia)

3. The compound or pharmacologically acceptable salt thereof according to claim 1, wherein the heterocyclic group formed by A and $R^1$ together with the carbon atom bonded thereto is a 1,3-thiazol-2-yl group, a 5-methyl-1,3-thiazol-2-yl group, a 5-methyl-1,3,4-oxadiazol-2-yl group, a 4,5-dihydro-1,3-thiazol-2-yl group, a 4,5-dihydro-1,3-oxazol-2-yl group, a (5S)-5-methyl-4,5-dihydro-1,3-oxazol-2-yl group, a (5R)-5-methyl-4,5-dihydro-1,3-oxazol-2-yl group, a 5-hydroxymethyl-4,5-dihydro-1,3-oxazol-2-yl group, a (5R)-5-hydroxymethyl-4,5-dihydro-1,3-oxazol-2-yl group, a (4R)-4-methyl-4,5-dihydro-1,3-oxazol-2-yl group, a (4R)-4-ethyl-4,5-dihydro-1,3-oxazol-2-yl group, a (4R)-4-hydroxymethyl-4,5-dihydro -1,3-oxazol-2-yl group, a (4S)-4-[(1R)-1-hydroxyethyl]-4,5-dihydro-1,3-oxazol-2-yl group, a (4S)-4-[(1S)-1-hydroxyethyl]-4,5-dihydro-1,3-oxazol-2-yl group, a (4R,5S)-4,5-dimethyl-4,5-dihydro-1,3-oxazol-2-yl group, a (5S)-4-hydroxy-5-methyl-4,5-dihydro-1,3-oxazol-2-yl group, a (4R,5S)-4-hydroxymethyl-5-methyl-4,5-dihydro-1,3-oxazol-2-yl group, a (4R,5R)-5-hydroxymethyl-4-methyl-4,5-dihydro-1,3-oxazol-2-yl group, a 5-carboxyl-1,3-thiazol-2-yl group, a 5-dimethylaminocarbonyl-1,3-thiazol-2-yl group, a 5-methyl-1,3,4-thiadiazol-2-yl group or a 5,6-dihydro-4H-1,3-oxazin-2-yl group.

4. The compound or pharmacologically acceptable salt thereof according to claim 1, wherein the heterocyclic group formed by A and R¹ together with the carbon atom bonded thereto is a 4,5-dihydro-1,3-oxazol-2-yl group, a (4R)-4-methyl-4,5-dihydro-1,3-oxazol-2-yl group, a (4R)-4-ethyl-4,5-dihydro-1,3-oxazol-2-yl group, a (5S)-5-methyl-4,5-dihydro-1,3-oxazol-2-yl group, a (4R)-4-hydroxymethyl-4,5-dihydro-1,3-oxazol-2-yl group, a (5R)-5-hydroxymethyl-4,5-dihydro-1,3-oxazol-2-yl group, a (4S)-4-[(1R)-1-hydroxyethyl]-4,5-dihydro-1,3-oxazol-2-yl group, a (4S)-4-[(1S)-1-hydroxyethyl]-4,5-dihydro -1,3-oxazol-2-yl group, a (4R,5S)-4,5-dimethyl-4,5-dihydro-1,3-oxazol-2-yl group, a (4R,5S)-4-hydroxymethyl-5-methyl-4,5-dihydro-1,3-oxazol-2-yl group, a (4R,5R)-5-hydroxymethyl-4-methyl-4,5-dihydro-1,3-oxazol-2-yl group, a 1,3-thiazol-2-yl group, 5-carboxyl-1,3-thiazol-2-yl group, a 5-dimethylaminocarbonyl-1,3-thiazol-2-yl group, a 5-methyl-1,3,4-thiadiazol-2-yl group, a 5-methyl-1,3,4-oxadiazol-2-yl group, a 4,5-dihydro-1,3-thiazol-2-yl group or a 5,6-dihydro-4H-1,3-oxazin-2-yl group.

5. The compound or pharmacologically acceptable salt thereof according to claim 1, wherein the heterocyclic group formed by A and R¹ together with the carbon atom bonded thereto is a 4,5-dihydro-1,3-oxazol-2-yl group, a (4R)-4-methyl-4,5-dihydro-1,3-oxazol-2-yl group, a (4R)-4-ethyl-4,5-dihydro-1,3-oxazol-2-yl group, a (5S)-5-methyl-4,5-dihydro-1,3-oxazol-2-yl group, a (4R)-4-hydroxymethyl-4,5-dihydro-1,3-oxazol-2-yl group, a (5R)-5-hydroxymethyl-4,5-dihydro-1,3-oxazol-2-yl group, a (4S)-4-[(1R)-1-hydroxyethyl]-4,5-dihydro-1,3-oxazol-2-yl group, a (4S)-4-[(1S)-1-hydroxyethyl]-4,5-dihydro -1,3-oxazol-2-yl group, a (4R,5S)-4,5-dimethyl-4,5-dihydro-1,3-oxazol-2-yl group, a (4R,5S)-4-hydroxymethyl-5-methyl-4,5-dihydro-1,3-oxazol-2-yl group or a (4R,5R)-5-hydroxymethyl-4-methyl-4,5-dihydro-1,3-oxazol-2-yl group.

6. The compound or pharmacologically acceptable salt thereof according to claim 1, wherein R² is a phenyl group optionally substituted with 1 to 5 groups each independently selected from Substituent Group δ or a 2-pyridyl group, 3-pyridyl group or 2-pyrazinyl group optionally substituted with 1 to 3 groups each independently selected from Substituent Group δ, wherein
Substituent Group δ is the group consisting of a halogen atom, a $C_1$-$C_6$ alkyl group, a $C_1$-$C_6$ halogenated alkyl group, a $C_1$-$C_6$ alkyl group substituted with 1 or 2 hydroxy groups, a $C_2$-$C_7$ alkylcarbonyl group, a $C_2$-$C_7$ alkoxycarbonyl group, a $C_1$-$C_6$ alkylsulfonyl group, a group represented by the formula —V—NR⁵R⁶ (wherein V represents a carbonyl group or a sulfonyl group, and R⁵ and R⁶ optionally are the same or different and respectively represent a hydrogen atom or a $C_1$-$C_6$ alkyl group, or R⁵ and R⁶ together with the nitrogen atom bonded thereto form a 4- to 6-membered saturated heterocycle optionally substituted with 1 or 2 groups each independently selected from a $C_1$-$C_6$ alkyl group and a hydroxy group, and the 4- to 6-membered saturated heterocycle optionally further comprises one oxygen atom or one additional nitrogen atom), a 1,3,4-oxadiazol-2-yl group optionally substituted with a $C_1$-$C_6$ alkyl group at the 5-position, and a 1,3,4-thiadiazol-2-yl group optionally substituted with a $C_1$-$C_6$ alkyl group at the 5-position.

7. The compound or pharmacologically acceptable salt thereof according to claim 1, wherein R² is a 4-methylsulfonylphenyl group, a 4-(1-azetidinyl)carbonyl-2-fluorophenyl group, a 2-fluoro-4-(1-pyrrolidinyl)carbonylphenyl group, a 5-(1-azetidinyl)carbonyl-3-chloro-2-pyridyl group, a 2-methylsulfonyl-5-pyridyl group, a 5-(4-methyl-1-piperazinyl)carbonyl-2-pyrazinyl group, a 2-methylaminocarbonyl-5-pyridyl group, a 2-methylaminosulfonyl-5-pyridyl group or a 5-methylsulfonyl-2-pyrazinyl group.

8. The compound or pharmacologically acceptable salt thereof according to claim 1, wherein R² is a 4-methylsulfonylphenyl group, a 2-methylsulfonyl-5-pyridyl group, a 5-methylsulfonyl-2-pyrazinyl group or a 5-(1-azetidinyl)carbonyl-3-chloro-2-pyridyl group.

9. The compound or pharmacologically acceptable salt thereof according to claim 1, wherein the compound of formula (I) is:
(2S)-2-{3-[5-(4,5-dihydro-1,3-oxazol-2-yl)-1H-pyrrol-2-yl]-5-[4-(methylsulfonyl)phenoxy]phenoxy}propan-1-ol;
(2S)-2-(3-{5-[(5S)-5-methyl-4,5-dihydro-1,3-oxazol-2-yl]-1H-pyrrol-2-yl}-5-[4-(methylsulfonyl)phenoxy]phenoxy)propan-1-ol;
(2S)-2-(3-{5-[(5S)-5-methyl-4,5-dihydro-1,3-oxazol-2-yl]-1H-pyrrol-2-yl}-5{[6-(methylsulfonyl)pyridin-3-yl]oxy}phenoxy)propan-1-ol;
{(5R)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-5-yl}methanol;
(2S)-2-(3-{5-[(4R)-4-methyl-4,5-dihydro-1,3-oxazol-2-yl]-1H-pyrrol-2-yl}-5-{[6-(methylsulfonyl)pyridin-3-yl]oxy}phenoxy)propan-1-ol;
(2S)-2-(3-{5-[(4R)-4-ethyl-4,5-dihydro-1,3-oxazol-2-yl]-1H-pyrrol-2-yl}-5-{[6-(methylsulfonyl)pyridin-3-yl]oxy}phenoxy)propan-1-ol;
{(4R)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-4-yl}methanol;
(2S)-2-(3-{5-[(4R,5S)-4,5-dimethyl-4,5-dihydro-1,3-oxazol-2-yl]-1H-pyrrol-2-yl}-5-{[6-(methylsulfonyl)pyridin-3-yl]oxy}phenoxy)propan-1-ol;
{(4R,5R)-2-[5-(3-[(1S)-2-methoxy-1-methylethoxy]-5-{[6-(methylsulfonyl)pyridin-3-yl]oxy}phenyl)-1H-pyrrol-2-yl]-4-methyl-4,5-dihydro-1,3-oxazol-5-yl}methanol;
{(4R,5S)-2-[5-(3-[(1S)-2-methoxy-1-methylethoxy]-5-{[6-(methylsulfonyl)pyridin-3-yl]oxy}phenyl)-1H-pyrrol-2-yl]-5-methyl-4,5-dihydro-1,3-oxazol-4-yl}methanol;
(1S)-1-{(4S)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-4-yl}ethanol;
(1R)-1-{(4S)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-4-yl}ethanol;

(2S)-2-(3-{5-[(5S)-5-methyl-4,5-dihydro-1,3-oxazol-2-yl]-1H-pyrrol-2-yl}-5-{[5-(methylsulfonyl)pyrazin-2-yl]oxy}phenoxy)propan-1-ol;

{(5R)-2-[5-(3-[(1S)-2-methoxy-1-methylethoxy]-5-{[5-(methylsulfonyl)pyrazin-2-yl]oxy}phenyl)-1H-pyrrol-2-yl]-4,5-dihydro-1,3-oxazol-5-yl}methanol;

(2S)-2-(3-{5-[(4R)-4-methyl-4,5-dihydro-1,3-oxazol-2-yl]-1H-pyrrol-2-yl}-5-{[5-(methylsulfonyl)pyrazin-2-yl]oxy}phenoxy)propan-1-ol;

(2S)-2-(3-{5-[(4R)-4-ethyl-4,5-dihydro-1,3-oxazol-2-yl]-1H-pyrrol-2-yl}-5-{[5-(methylsulfonyl)pyrazin-2-yl]oxy}phenoxy)propan-1-ol;

(2S)-2-(3-{5-[(4R,5S)-4,5-dimethyl-4,5-dihydro-1,3-oxazol-2-yl]-1H-pyrrol-2-yl}-5-{[5-(methylsulfonyl)pyrazin-2-yl]oxy}phenoxy)propan-1-ol;

{(4R,5S)-2-[5-(3-{[(2S)-1-methoxypropan-2-yl]oxy}-5-{[5-(methylsulfonyl)pyrazin-2-yl]oxy}phenyl)-1H-pyrrol-2-yl]-5-methyl-4,5-dihydro-1,3-oxazol-4-yl}methanol;

(1S)-1-{(4S)-2-[5-(3-{[(2S)-1-methoxypropan-2-yl]oxy}-5-{[5-(methylsulfonyl)pyrazin-2-yl]oxy}phenyl)-1H-pyrrol-2-yl]-4,5-dihydro-1,3-oxazol-4-yl}ethanol; or (1R)-1-{(4S)-2-[5-(3-{[(2S)-1-methoxypropan-2-yl]oxy}-5-{[5-(methylsulfonyl)pyrazin-2-yl]oxy}phenyl)-1H-pyrrol-2-yl]-4,5-dihydro-1,3-oxazol-4-yl}ethanol.

10. The compound or pharmacologically acceptable salt thereof according to claim 1, wherein the compound of formula (I) is (2S)-2-(3-{5-[(5S)-5-methyl-4,5-dihydro-1,3-oxazol-2-yl]-1H-pyrrol-2-yl}-5-{[6-(methylsulfonyl)pyridazin-3 -yl]oxy}phenoxy)propan-1-ol.

11. The compound according to claim 1, wherein the compound of formula (I) is:

(2S)-2-{3-[5-(4,5-dihydro-1,3-oxazol-2-yl)-1H-pyrrol-2-yl]-5-[4-(methylsulfonyl)phenoxy]phenoxy}propan-1-ol;

(2S)-2-(3-{5-[(5S)-5-methyl-4,5-dihydro-1,3-oxazol-2-yl]-1H-pyrrol-2-yl}-5-[4-(methylsulfonyl)phenoxy]phenoxy)propan-1-ol;

(2S)-2-(3-{5-[(5S)-5-methyl-4,5-dihydro-1,3-oxazol-2-yl]-1H-pyrrol-2-yl}-5-{[6-(methylsulfonyl)pyridin-3-yl]oxy}phenoxy)propan-1-ol;

{(5R)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-5-yl}methanol;

(2S)-2-(3-{5-[(4R)-4-methyl-4,5-dihydro-1,3-oxazol-2-yl]-1H-pyrrol-2-yl}-5-{[6-(methylsulfonyl)pyridin-3-yl]oxy}phenoxy)propan-1-ol;

(2S)-2-(3-{5-[(4R)-4-ethyl-4,5-dihydro-1,3-oxazol-2-yl]-1H-pyrrol-2-yl}-5-{[6-(methylsulfonyl)pyridin-3-yl]oxy}phenoxy)propan-1-ol;

{(4R)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-4-yl}methanol;

(2S)-2-(3-{5-[(4R,5S)-4,5-dimethyl-4,5-dihydro-1,3-oxazol-2-yl]-1H-pyrrol-2-yl}-5-{[6-(methylsulfonyl)pyridin-3-yl]oxy}phenoxy)propan-1-ol;

{(4R,5R)-2-[5-(3-[(1S)-2-methoxy-1-methylethoxy]-5-{[6-(methylsulfonyl)pyridin-3-yl]oxy}phenyl)-1H-pyrrol-2-yl]-4-methyl-4,5-dihydro-1,3-oxazol-5-yl}methanol;

{(4R,5S)-2-[5-(3-[(1S)-2-methoxy-1-methylethoxy]-5-{[6-(methylsulfonyl)pyridin-3-yl]oxy}phenyl)-1H-pyrrol-2-yl]-5-methyl-4,5-dihydro-1,3-oxazol-4-yl}methanol;

(1S)-1-{(4S)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-4-yl}ethanol;

(1R)-1-{(4S)-2-[5-(3-[(1S)-2-methoxy-1-methylethoxy]-5-{[6-(methylsulfonyl)pyridin-3-yl]oxy}phenyl)-1H-pyrrol-2-yl]-4,5-dihydro-1,3-oxazol-4-yl}ethanol;

(2S)-2-(3-{5-[(5S)-5-methyl-4,5-dihydro-1,3-oxazol-2-yl]-1H-pyrrol-2-yl}-5-{[5-(methylsulfonyl)pyrazin-2-yl]oxy}phenoxy)propan-1-ol;

{(5R)-2-[5-(3-[(1S)-2-methoxy-1-methylethoxy]-5-{[5-(methylsulfonyl)pyrazin-2-yl]oxy}phenyl)-1H-pyrrol-2-yl]-4,5-dihydro-1,3-oxazol-5-yl}methanol;

(2S)-2-(3-{5-[(4R)-4-methyl-4,5-dihydro-1,3-oxazol-2-yl]-1H-pyrrol-2-yl}-5-{[5-(methylsulfonyl)pyrazin-2-yl]oxy}phenoxy)propan-1-ol;

(2S)-2-(3-{5-[(4R)-4-ethyl-4,5-dihydro-1,3-oxazol-2-yl]-1H-pyrrol-2-yl}-5-{[5-(methylsulfonyl)pyrazin-2-yl]oxy}phenoxy)propan-1-ol;

(2S)-2-(3-{5-[(4R,5S)-4,5-dimethyl-4,5-dihydro-1,3-oxazol-2-yl]-1H-pyrrol-2-yl}-5-{[5-(methylsulfonyl)pyrazin-2-yl]oxy}phenoxy)propan-1-ol;

{(4R,5S)-2-[5-(3-{[(2S)-1-methoxypropan-2-yl]oxy}-5-{[5-(methylsulfonyl)pyrazin-2-yl]oxy}phenyl)-1H-pyrrol-2-yl]-5-methyl-4,5-dihydro-1,3-oxazol-4-yl}methanol;

(1S)-1-{(4S)-2-[5-(3-{[(2S)-1-methoxypropan-2-yl]oxy}-5-{[5-(methylsulfonyl)pyrazin-2-yl]oxy}phenyl)-1H-pyrrol-2-yl]-4,5-dihydro-1,3-oxazol-4-yl}ethanol; or (1R)-1-{(4S)-2-[5-(3-{[(2S)-1-methoxypropan-2-yl]oxy}-5-{[5-(methylsulfonyl)pyrazin-2-yl]oxy}phenyl)-1H-pyrrol-2-yl]-4,5-dihydro-1,3-oxazol-4-yl}ethanol.

12. The compound according to claim 11, wherein the compound is (2S)-2-(3-{5-[(5S)-5-methyl-4,5-dihydro-1,3-oxazol-2-yl]-1H-pyrrol-2-yl}-5-{[6-(methylsulfonyl)pyridin-3-yl]oxy}phenoxy)propan-1-ol.

13. The compound according to claim 11, wherein the compound is {(5R)-2-[5-(3-[(1S)-2-methoxy-1-methylethoxy]-5-{ [6-(methylsulfonyl)pyridin-3-yl]oxy}phenyl)-1H-pyrrol-2-yl]-4,5-dihydro-1,3-oxazol-5-yl}methanol.

14. The compound according to claim 11, wherein the compound is (2S)-2-(3-{5-[(4R)-4-methyl-4,5-dihydro-1,3-oxazol-2-yl]-1H-pyrrol-2-yl}-5-{[6-(methylsulfonyl)pyridin-3-yl]oxy}phenoxy)propan-1-ol.

15. The compound according to claim 11, wherein the compound is {(4R)-2-[5-(3-[(1S)-2-methoxy-1-methylethoxy]-5-{[6-(methylsulfonyl)ppyridin-3-yl]oxy}phenyl)-1H-pyrrol-2-yl]-4,5-dihydro-1,3-oxazol-4-yl}methanol.

16. The compound according to claim 11, wherein the compound is (1S)-1-{(4S)-2-[5-(3-[(1S)-2-methoxy-1-methylethoxy]-5-{[6-(methylsulfonyl)pyridine -3-yl]oxy}phenyl)-1H-pyrrol-2-yl]-4,5-dihydro-1,3-oxazol-4-yl}ethanol.

17. The compound according to claim 11, wherein the compound is (1R)-1-{(4S)-2-[5-(3-[(1S)-2-methoxy-1-methylethoxy]-5{-[6-(methylsulfonyl)pyridin-3 -yl]oxy}phenyl)-1H-pyrrol-2-yl]-4,5-dihydro-1,3-oxazol-4-yl}ethanol.

18. The compound according to claim 11, wherein the compound is (2S)-2-(3-{5-[(5S)-5-methyl-4,5-dihydro-1,3-oxazol-2-yl]-1H-pyrrol-2-yl}-5-{[5-(methylsulfonyl)pyrazin-2-yl]oxy}phenoxy)propan-1-ol.

19. The compound according to claim 11, wherein the compound is (2S)-2-(3-{5-[(4R)-4-methyl-4,5-dihydro-1,3-oxazol-2-yl]-1H-pyrrol-2-yl}-5-{[5-(methylsulfonyl)pyrazin-2-yl]oxy}phenoxy)propan-1-ol.

20. The compound according to claim 1, wherein the compound of formula (I) is (2S)-2-(3-{5-[(5S)-5-methyl-4,5-dihydro-1,3-oxazol-2-yl]-1H-pyrrol-2-yl}-5-{[6-(methylsulfonyl)pyridazin-3-yl]oxy}phenoxy)propan-1-ol.

21. The compound or pharmacologically acceptable salt thereof according to claim 9, wherein the compound is (2S)-2-(3-{5-[(5S)-5-methyl-4,5-dihydro-1,3-oxazol-2-yl]-1H-pyrrol-2-yl}-5-{[5-(methylsulfonyl)pyrazin-2-yl]oxy}phenoxy)propan-1-ol.

22. The pharmacologically acceptable salt according to claim 9, wherein the pharmacologically acceptable salt is a hydrochloride salt of (2S)-2-(3-{5-[(5S)-5-methyl-4,5-dihydro-1,3-oxazol-2-yl]-1H-pyrrol-2-yl}-5-{[5-(methylsulfonyl)pyrazin-2-yl]oxy}phenoxy)propan-1-ol.

23. The pharmacologically acceptable salt according to claim 9, wherein the pharmacologically acceptable salt is a hydrobromide salt of (2S)-2-(3-{5-[(5S)-5-methyl-4,5-dihydro-1,3-oxazol-2-yl]-1H-pyrrol-2-yl}-5-{[5-(methylsulfonyl)pyrazin-2-yl]oxy}phenoxy)propan-1-ol.

24. The pharmacologically acceptable salt according to claim 9, wherein the pharmacologically acceptable salt is a methanesulfonate salt of (2S)-2-(3-{5-[(5S)-5-methyl-4,5-dihydro-1,3-oxazol-2-yl]-1H-pyrrol-2-yl}-5-{[5-(methylsulfonyl)pyrazin-2-yl]oxy}phenoxy)propan-1-ol.

25. The compound or pharmacologically acceptable salt thereof according to claim 9, wherein the compound is (2S)-2-(3-{5-[(4R)-4-methyl-4,5-dihydro-1,3-oxazol-2-yl]-1H-pyrrol-2-yl}-5-{[5-(methylsulfonyl)pyrazin-2-yl]oxy}phenoxy)propan-1-ol.

26. The pharmacologically acceptable salt according to claim 9, wherein the pharmacologically acceptable salt is a hydrochloride salt of (2S)-2-(3-{5-[(4R)-4-methyl-4,5-dihydro-1,3-oxazol-2-yl]-1H-pyrrol-2-yl}-5-{[5-(methylsulfonyl)pyrazin-2-yl]oxy}phenoxy)propan-1-ol.

27. The pharmacologically acceptable salt according to claim 9, wherein the pharmacologically acceptable salt is a hydrobromide salt of (2S)-2-(3-{5-[(4R)-4-methyl-4,5-dihydro-1,3-oxazol-2-yl]-1H-pyrrol-2-yl}-5-{[5-(methylsulfonyl)pyrazin-2-yl]oxy}phenoxy)propan-1-ol.

28. The pharmacologically acceptable salt according to claim 9, wherein the pharmacologically acceptable salt is a methanesulfonate salt of (2S)-2-(3-{5-[(4R)-4-methyl-4,5-dihydro-1,3-oxazol-2-yl]-1H-pyrrol-2-yl}-5-{[5-(methylsulfonyl)pyrazin-2-yl]oxy}phenoxy)propan-1-ol.

29. The pharmacologically acceptable salt according to claim 10, wherein the pharmacologically acceptable salt is a hydrochloride salt of (2S)-2-(3-{5-[(5S)-5-methyl-4,5-dihydro-1,3-oxazol-2-yl]-1H-pyrrol-2-yl}-5-{[6-(methylsulfonyl)pyridazin-3-yl]oxy}phenoxy)propan-1-ol.

30. The pharmacologically acceptable salt according to claim 10, wherein the pharmacologically acceptable salt is a hydrobromide salt of (2S)-2-(3-{5-[(5S)-5-methyl-4,5-dihydro-1,3-oxazol-2-yl]-1H-pyrrol-2-yl}-5-{[6-(methylsulfonyl)pyridazin-3-yl]oxy}phenoxy)propan-1-ol.

31. The pharmacologically acceptable salt according to claim 10, wherein the pharmacologically acceptable salt is a methanesulfonate salt of (2S)-2-(3-{5-[(5S)-5-methyl-4,5-dihydro-1,3-oxazol-2-yl]-1H-pyrrol-2-yl}-5-{[6-(methylsulfonyl)pyridazin-3-yl]oxy}phenoxy)propan-1-ol.

32. A pharmaceutical composition comprising a compound or pharmacologically acceptable salt thereof according to claim 1 and a pharmaceutically acceptable carrier.

33. A pharmaceutical composition comprising a compound or pharmacologically acceptable salt thereof according to claim 9 and a pharmaceutically acceptable carrier.

34. A pharmaceutical composition comprising a compound or pharmacologically acceptable salt thereof according to claim 10 and a pharmaceutically acceptable carrier.

35. A pharmaceutical composition comprising the pharmacologically acceptable salt according to claim 23 and a pharmaceutically acceptable carrier.

36. A pharmaceutical composition comprising the pharmacologically acceptable salt according to claim 24 and a pharmaceutically acceptable carrier.

37. A pharmaceutical composition comprising the pharmacologically acceptable salt according to claim 29 and a pharmaceutically acceptable carrier.

38. A pharmaceutical composition comprising the pharmacologically acceptable salt according to claim 31 and a pharmaceutically acceptable carrier.

39. A method for treating diabetes or impaired glucose tolerance comprising administering a pharmacologically effective amount of a compound or pharmacologically acceptable salt thereof according to claim 1 to a warm-blooded animal.

40. The method according to claim 39, wherein the warm-blooded animal is a human.

41. A method for treating diabetes comprising administering a pharmacologically effective amount of the pharmacologically acceptable salt according to claim 23 to a human.

42. A method for treating impaired glucose tolerance comprising administering a pharmacologically effective amount of the pharmacologically acceptable salt according to claim 23 to a human.

43. A method for treating gestational diabetes comprising administering a pharmacologically effective amount of the pharmacologically acceptable salt according to claim 23 to a human.

44. A method for treating diabetes comprising administering a pharmacologically effective amount of the pharmacologically acceptable salt according to claim 24 to a human.

45. A method for treating impaired glucose tolerance comprising administering a pharmacologically effective amount of the pharmacologically acceptable salt according to claim 24 to a human.

46. A method for treating gestational diabetes comprising administering a pharmacologically effective amount of the pharmacologically acceptable salt according to claim 24 to a human.

47. A method for treating diabetes comprising administering a pharmacologically effective amount of the pharmacologically acceptable salt according to claim 29 to a human.

48. A method for treating impaired glucose tolerance comprising administering a pharmacologically effective amount of the pharmacologically acceptable salt according to claim 29 to a human.

49. A method for treating gestational diabetes comprising administering a pharmacologically effective amount of the pharmacologically acceptable salt according to claim 29 to a human.

50. A method for treating diabetes comprising administering a pharmacologically effective amount of the pharmacologically acceptable salt according to claim 31 to a human.

51. A method for treating impaired glucose tolerance comprising administering a pharmacologically effective amount of the pharmacologically acceptable salt according to claim 31 to a human.

52. A method for treating gestational diabetes comprising administering a pharmacologically effective amount of the pharmacologically acceptable salt according to claim 31 to a human.

* * * * *

UNITED STATES PATENT AND TRADEMARK OFFICE
CERTIFICATE OF CORRECTION

| | | |
|---|---|---|
| PATENT NO. | : 8,017,610 B2 | Page 1 of 1 |
| APPLICATION NO. | : 12/843348 | |
| DATED | : September 13, 2011 | |
| INVENTOR(S) | : Akihiro Furukawa et al. | |

It is certified that error appears in the above-identified patent and that said Letters Patent is hereby corrected as shown below:

In column 246, at line 50-60 (Ia), delete "$R^1$." and insert --$R^1$--

In column 246, at line 62, delete "$R^{1}$" and insert --$R^1$--.

In column 248, at line 36, delete "yl]-1H-pyrrol-2-yl}-5{[6-(methylsulfonyl)pyridin-3-" and insert --yl]-1H-pyrrol-2-yl}-5-{[6-(methylsulfonyl)pyridin-3- --.

In column 250, at line 40, delete "ethoxy]-5-{ [6-(methylsulfonyl)pyridin-3-yl]oxy}phenyl)-" and insert --ethoxy]-5-{[6-(methylsulfonyl)pyridin-3-yl]oxy}phenyl)- --.

In column 250, at line 48, delete "ethoxy]-5-{[6-(methylsulfonyl)ppyridin-3-yl]oxy}phenyl)-" and insert --ethoxy]-5-{[6-(methylsulfonyl)pyridin-3-yl]oxy}phenyl)- --.

In column 250, at line 52, delete "ylethoxy]-5-{[6-(methylsulfonyl)pyridine  -3-yl]" and insert --ylethoxy]-5-{[6-(methylsulfonyl)pyridin-3-yl]--.

In column 250, at line 56, delete "-methoxy-1-me-" and insert -- -methoxy-1-me- --.

In column 250, at line 57, delete "thylethoxy]-5{-[6-(methylsulfonyl)pyridin-3  -yl]" and insert --thylethoxy]-5-{[6-(methylsulfonyl)pyridin-3-yl]--.

Signed and Sealed this

Fourteenth Day of February, 2012

David J. Kappos
*Director of the United States Patent and Trademark Office*